US011209440B2

(12) United States Patent
Kuchroo et al.

(10) Patent No.: US 11,209,440 B2
(45) **Date of Patent: *Dec. 28, 2021**

(54) T CELL BALANCE GENE EXPRESSION, COMPOSITIONS OF MATTERS AND METHODS OF USE THEREOF

(71) Applicants: THE BROAD INSTITUTE, INC., Cambridge, MA (US); THE BRIGHAM AND WOMEN'S HOSPITAL, INC., Boston, MA (US); PRESIDENT AND FELLOWS OF HARVARD COLLEGE, Cambridge, MA (US); MASSACHUSETTS INSTITUTE OF TECHNOLOGY, Cambridge, MA (US)

(72) Inventors: Vijay Kuchroo, Newton, MA (US); Aviv Regev, Cambridge, MA (US); Jellert Gaublomme, Maasmechelen (BE); Youjin Lee, San Francisco, CA (US); Alexander K. Shalek, Lexington, MA (US); Chao Wang, Cambridge, MA (US); Nir Yosef, Richmond, CA (US); Hongkun Park, Cambridge, MA (US)

( * ) Notice: Subject to any disclaimer, the term of this patent is extended or adjusted under 35 U.S.C. 154(b) by 239 days.

This patent is subject to a terminal disclaimer.

(21) Appl. No.: 15/245,748

(22) Filed: Aug. 24, 2016

(65) Prior Publication Data

US 2016/0377631 A1 Dec. 29, 2016

Related U.S. Application Data

(63) Continuation-in-part of application No. PCT/US2015/017826, filed on Feb. 26, 2015.

(60) Provisional application No. 61/945,641, filed on Feb. 27, 2014.

(51) Int. Cl.

| | |
|---|---|
| ***G01N 33/68*** | (2006.01) |
| ***C12Q 1/6883*** | (2018.01) |
| ***A61K 48/00*** | (2006.01) |
| ***C12N 15/68*** | (2006.01) |
| ***C12N 15/86*** | (2006.01) |
| ***C07K 16/28*** | (2006.01) |

(52) U.S. Cl.

CPC ......... *G01N 33/6863* (2013.01); *A61K 48/00* (2013.01); *C07K 16/2866* (2013.01); *C07K 16/2896* (2013.01); *C12N 15/68* (2013.01); *C12N 15/86* (2013.01); *C12Q 1/6883* (2013.01); *C07K 2317/21* (2013.01); *C07K 2317/24* (2013.01); *C07K 2317/75* (2013.01); *C07K 2317/76* (2013.01); *C12Q 2600/112* (2013.01); *C12Q 2600/118* (2013.01); *C12Q 2600/158* (2013.01); *G01N 2800/50* (2013.01); *G01N 2800/52* (2013.01); *G01N 2800/56* (2013.01)

(58) Field of Classification Search

None

See application file for complete search history.

(56) References Cited

U.S. PATENT DOCUMENTS

| | | | |
|---|---|---|---|
| 4,683,195 | A | 7/1987 | Mullis et al. |
| 4,683,202 | A | 7/1987 | Mullis |
| 5,446,603 | A | 8/1995 | Henits et al. |
| 5,545,531 | A | 8/1996 | Rava et al. |
| 5,807,522 | A | 9/1998 | Shalon et al. |
| 5,837,832 | A | 11/1998 | Chee et al. |
| 5,874,219 | A | 2/1999 | Rava et al. |
| 5,989,431 | A | 11/1999 | Evans et al. |
| 6,114,122 | A | 9/2000 | Besemer et al. |
| 6,238,910 | B1 | 5/2001 | Custance et al. |
| 6,365,418 | B1 | 4/2002 | Wagner et al. |
| 6,410,229 | B1 | 6/2002 | Lockhart et al. |
| 6,420,114 | B1 | 7/2002 | Bedilion et al. |
| 6,432,696 | B2 | 8/2002 | Custance et al. |
| 6,475,808 | B1 | 11/2002 | Wagner et al. |
| 6,489,159 | B1 | 12/2002 | Chenchik et al. |
| 6,548,256 | B2 | 4/2003 | Lienau et al. |
| 7,041,481 | B2 | 5/2006 | Anderson et al. |
| 7,708,949 | B2 | 5/2010 | Stone et al. |
| RE41,780 | E | 9/2010 | Anderson et al. |

(Continued)

FOREIGN PATENT DOCUMENTS

| | | | |
|---|---|---|---|
| EP | 2047910 | A2 | 4/2009 |
| EP | 2764103 | A2 | 8/2014 |

(Continued)

OTHER PUBLICATIONS

Whisstock et al., 2003, Quart. Rev. Biophys. vol. 36: 307-340.*

(Continued)

*Primary Examiner* — Amy E Juedes

(74) *Attorney, Agent, or Firm* — Johnson, Marcou, Isaacs & Nix, LLC; F. Brent Nix, Esq.; Michael B. Scher, Esq.

(57) ABSTRACT

This invention relates generally to compositions and methods for identifying the regulatory network that modulates, controls or otherwise influences T cell balance, for example, Th17 cell differentiation, maintenance and/or function, as well compositions and methods for exploiting the regulatory network that modulates, controls or otherwise influences T cell balance in a variety of therapeutic and/or diagnostic indications. This invention also relates generally to identifying and exploiting target genes and/or target gene products that modulate, control or otherwise influence T cell balance in a variety of therapeutic and/or diagnostic indications.

4 Claims, 87 Drawing Sheets

Specification includes a Sequence Listing.

(56) References Cited

U.S. PATENT DOCUMENTS

| | | | |
|---|---|---|---|
| 8,557,746 B2 | 10/2013 | Arthanari et al. | |
| 8,697,359 B1 | 4/2014 | Zhang | |
| 8,771,945 B1 | 7/2014 | Zhang | |
| 8,795,965 B2 | 8/2014 | Zhang | |
| 8,865,406 B2 | 10/2014 | Zhang et al. | |
| 8,871,445 B2 | 10/2014 | Cong et al. | |
| 8,889,356 B2 | 11/2014 | Zhang | |
| 8,889,418 B2 | 11/2014 | Zhang et al. | |
| 8,895,308 B1 | 11/2014 | Zhang et al. | |
| 8,906,616 B2 | 12/2014 | Zhang et al. | |
| 8,932,814 B2 | 1/2015 | Cong et al. | |
| 8,945,839 B2 | 2/2015 | Zhang | |
| 2005/0172476 A1 | 8/2005 | Stone et al. | |
| 2007/0195127 A1 | 8/2007 | Ahn et al. | |
| 2008/0003142 A1 | 1/2008 | Link et al. | |
| 2008/0014589 A1 | 1/2008 | Link et al. | |
| 2010/0002241 A1 | 1/2010 | Hirose | |
| 2010/0022414 A1 | 1/2010 | Link et al. | |
| 2010/0137163 A1 | 6/2010 | Link et al. | |
| 2010/0172803 A1 | 7/2010 | Stone et al. | |
| 2012/0122714 A1 | 5/2012 | Samuels et al. | |
| 2012/0219947 A1 | 8/2012 | Yurkovetsky et al. | |
| 2014/0170753 A1 | 6/2014 | Zhang | |
| 2014/0179006 A1 | 6/2014 | Zhang | |
| 2014/0179770 A1 | 6/2014 | Zhang et al. | |
| 2014/0186843 A1 | 7/2014 | Zhang et al. | |
| 2014/0186919 A1 | 7/2014 | Zhang et al. | |
| 2014/0186958 A1 | 7/2014 | Zhang et al. | |
| 2014/0189896 A1 | 7/2014 | Zhang et al. | |
| 2014/0227787 A1 | 8/2014 | Zhang | |
| 2014/0234972 A1 | 8/2014 | Zhang | |
| 2014/0242664 A1 | 8/2014 | Zhang et al. | |
| 2014/0242699 A1 | 8/2014 | Zhang | |
| 2014/0242700 A1 | 8/2014 | Zhang et al. | |
| 2014/0248702 A1 | 9/2014 | Zhang et al. | |
| 2014/0256046 A1 | 9/2014 | Zhang et al. | |
| 2014/0273231 A1 | 9/2014 | Zhang et al. | |
| 2014/0273232 A1 | 9/2014 | Zhang et al. | |
| 2014/0273234 A1 | 9/2014 | Zhang et al. | |
| 2014/0287938 A1 | 9/2014 | Zhang et al. | |
| 2014/0310830 A1 | 10/2014 | Zhang et al. | |
| 2015/0361396 A1* | 12/2015 | Regev .................. | C12N 5/0636 424/85.1 |

FOREIGN PATENT DOCUMENTS

| | | | |
|---|---|---|---|
| EP | 2771468 | A1 | 9/2014 |
| EP | 2784162 | A1 | 10/2014 |
| WO | 0145843 | A2 | 6/2001 |
| WO | 2004002627 | A2 | 1/2004 |
| WO | 2007089541 | A2 | 8/2007 |
| WO | 2008101354 | A1 | 8/2008 |
| WO | 2013/000870 | A1 | 1/2013 |
| WO | 2013000870 | | 1/2013 |
| WO | 2014018423 | A2 | 1/2014 |
| WO | 2014093595 | A1 | 6/2014 |
| WO | 2014093622 | A2 | 6/2014 |
| WO | 2014093635 | A1 | 6/2014 |
| WO | 2014093655 | A2 | 6/2014 |
| WO | 2014093661 | A2 | 6/2014 |
| WO | 2014093694 | A1 | 6/2014 |
| WO | 2014093701 | A1 | 6/2014 |
| WO | 2014093709 | A1 | 6/2014 |
| WO | 2014093712 | A1 | 6/2014 |
| WO | 2014093718 | A1 | 6/2014 |
| WO | 2014/134351 | A2 | 9/2014 |
| WO | 2014134351 | | 9/2014 |
| WO | 2014204723 | A1 | 12/2014 |
| WO | 2014204724 | A1 | 12/2014 |
| WO | 2014204725 | A1 | 12/2014 |
| WO | 2014204726 | A1 | 12/2014 |
| WO | 2014204727 | A1 | 12/2014 |
| WO | 2014204728 | A1 | 12/2014 |
| WO | 2014204729 | A1 | 12/2014 |
| WO | 2015130968 | A2 | 9/2015 |

OTHER PUBLICATIONS

Wang et al., 2006, BLood, vol. 108: 4071-4077.*

Geary, 2010, Nonpeptide ligands fro peptidergic G protein-coupled receptors, pp. 10-26.*

Stockinger et al., 2017, Nat. Rev. Immunol. vol. 17: 535-544.*

Goncalves et al., 2017, Genet therapy vol. 15: 369-375.*

Lino et al., 2018, Drug Delivery, vol. 25: 1234-1257.*

Freeley et al., 2013, Biochem. vol. 455: 133-147.*

Sheng et al., 2013, Med. Res. Rev. vol. 33: 1119-1173.*

International Search Report dated Aug. 27, 2015, which issued during prosecution of International Application No. PCT/US2015/017826.

Yosef, et al. "Dynamic regulatory network controlling TH17 cell differentiation", Nature, 2013, 496:461-470, doi.10.1038/nature11981.

Zhou, et al. "Transcriptional regulatory networks in TH17 cell differentiation" Current Opinion in Immunology, 2009, 21:146-152, DOI 10.1016/J.COI.2009.03.001.

Korn, et al. "IL-17 and Th17 cells" Annual Review of Immunology, Annual Reviews Inc., 2009, 27:485-517, doi: 10.1146/annurev.immunol.021908.132710.

Wei, et al. "Global Mapping of H3K4me3 and H3k27me3 Reveals Specificity and Plasticity in Lineage Fate Determination of Differentiating CD4+ T Cells" Immunity, 2009, 30:155-167.

Zhou, et al. "TGF-[beta]-induced Foxp3 inhibis TH17 cell differentiation by antagonizing ROR[gamma]t function" Nature, 2008, 453:236-240, doi: 10.1038/nature06878.

Lee, et al. "Induction and molecular signature of pathgenic TH17 cells" Nature Immunology, 2012, 13(10):991-999.

Kyung Lee, et al. "Late Developmental Plasticity in the T Helper 17 Lineage" Immunity, 2009, 30:92-107, DOI: 10.1016/J.IMMUNI.2001.11.005.

Bettelli, et al. "TH-17 cells in the circle of immunity and autoimmunity" Nature Immunology, 2007, 8(4):345-350.

Veldhoen, et al. "The aryl hydrocarbon receptor links TH17-cell-mediated autoimmunity to environmental toxins" Nature, 2008, 453:106-109, doi:10.1038/nature06881.

Gaublomme, et al., "Single-Cell Genomics Unveils Critical Regulartos of Th17 Cell Pathogenicity", Cell, 2015, pp. 1400-1412.

Lee et al., "Induction and Molecular Signature of Pathogenic ThH17 Cells," Nature Immunol., vol. 13, No. 10, Oct. 2012, pp. 991-999.

Miyazaki et al., "Aiming at Metabolic Syndrome—Towards the Development of Novel Therapies for Metabolic Diseases via Apoptosis Inhibitor of Macrophage (AIM)," Circulation Journal, vol. 75, Nov. 2011, pp. 2522-2531.

Sarrias et al., "A Role for Human SP-alpha as a Pattern Recognition Receptor," Journal of Biological Chemistry, vol. 280, No. 42, Oct. 21, 2005, pp. 35391-35398.

Wang, et al., "CD5L/AIM Regulates Lipid Biosynthesis and Restrains Th17 Cell Pathogenicity," Cell, 2015, pp. 1413-1427.

Yosef et al., "Dynamic Regulatory Network Controlling Th17 Cell Differentiation," Nature, vol. 496, 2013, pp. 461-468.

Zhou et al., "Transcriptional Regulatory Networks in Th17 Cell Differentiation," Current Opinion in Immunology, 2009, pp. 146-152.

The Broad Institute, Inc., extended European Search Report for EP 18212362.01, dated Apr. 24, 2019, 7 pages.

The Broad Institute, Inc., "Notice of Reasons for Rejection for JP 2016-554339", dated Dec. 16, 2019, 10 pages.

Quan, et al., "Contribution of Interleukin 17A to the Development and Regulation of Allergic Inflammation in a Murine Allergic Rhinitis Model", Ann Allergy Asthma Immunol., vol. 108, 2012, pp. 342-350.

Jux, et al., "Langerhans cell maturation and contact hypersensitivity are impaired in aryl hydrocarbon receptor-null mice", Journal of immunology (Baltimore, Md.: 1950), vol. 182, No. 11, Jun. 1, 2009, 6709-6717.

(56) References Cited

OTHER PUBLICATIONS

Kleinewietfeld, et al., "The plasticity of human Treg and Th17 cells and its role in autoimmunity", Seminars in Immunology, vol. 25, No. 4, 2013, 305-312.
Konkel, et al., "Balancing acts: the role of TGF-beta in the mucosal immune system", Trends in Molecular Medicine, vol. 17, No. 11, 2011, 668-676.
Korman, et al., "Checkpoint blockade in cancer immunotherapy", Adv Immunol., vol. 90, 2006, 297-339.
Korn, et al., "IL-21 initiates an alternative pathway to induce proinflammatory T(H)17 cells", Nature 448, 2007, pp. 484-487.
Kurokawa, et al., "Macrophage-derived AIM is Endocytosed into Adipocytes and Decreases Lipid Droplets via Inhibition of Fatty Acid Synthase Activity", Cell Metabolism, vol. 11, No. 6, Jun. 9, 2010, 479-492.
Langrish, et al., "IL-23 drives a pathogenic T cell population that induces autoimmune inflammation", The Journal of Experimental Medicine, vol. 201, No. 2, 2005, 233-240.
Laurence, et al., "lnterleukin-2 signaling via STAT5 constrains T helper 17 cell generation", Immunity, vol. 26, No. 3, Mar. 2007, 371-381.
Lee, et al., "Unexpected targets and triggers of autoimmunity", Journal of Clinical Immunology, vol. 34, Suppl 1, 2014, S56-S60.
Leonardi, et al., "Anti-interleukin-17 monoclonal antibody ixekizumab in chronic plaque psoriasis", The New England Journal of Medicine, vol. 366, No. 13, 2012, 1190-1199.
Litvak, et al., "Function of C/EBPdelta in a regulatory circuit that discriminates between transient and persistent TLR4-induced signals", Nat Immunol., vol. 10, No. 4, Apr. 2009, 437-443.
Marson, et al., "Foxp3 occupancy and regulation of key target genes during T-cell stimulation", Nature, vol. 445, No. 7130, Feb. 2007, 931-935.
Martinez, "The macrophage soluble receptor AIM/Api6/CD5L displays a broad pathogen recognition spectrum and is involved in early response to microbial aggression", Cellular & Molecular Immunology, 11, 2014, pp. 343-354.
Martinez-Llordella, et al., "CD28-lnducible Transcription Factor DEC1 is required for Efficient Autoreactive CD4+ T cell R", The Journal of Experimental Medicine, vol. 210, No. 8, Jul. 22, 2013, 1603-1619.
Mathews, et al., "Induction of IL-17A Precedes Development of Airway Hyperresponsiveness during Diet-Induced Obesity and Correlates with Complement Factor D", Frontiers in Immunology, vol. 5, Article 440, 2014, 9 pages.
Matys, et al., "Transfac: transcriptional regulation, from patterns to profiles", Nucleic Acids Res., vol. 31, 2003, 374-378.
Maynard, et al., "Regulatory T cells expressing interleukin 10 develop from Foxp3+ and Foxp3− precursor cells in the absence of interleukin 10", Nature Immunology, vol. 8, No. 9, 2007, 931-941.
McGeachy, et al., "TGF-beta and IL-6 drive the production of IL-17 and IL-10 by T cells and restrain T(H)-17 cell-mediated pathology", Nature Immunology, vol. 8, No. 12, 2007, 1390-1397.
McGeachy, et al., "The interleukin 23 receptor is essential for the terminal differentiation of interleukin 17-producing effector T helper cells in vivo", Nature Immunology, vol. 10, No. 3, 2009, 314-324.
Miaw, et al., "A Repressor of GATA-Mediated Negative Feedback Mechanism of T Cell Activation", J Immunol, 172, 2004, 170-177.
Miaw, et al., "ROG, repressor of GATA, regulates the expression of cytokine genes", Immunity, vol. 12, No. 3, Mar. 2000, 323-333.
Miyazaki, et al., "Increased Susceptibility of Thymocytes to Apoptosis in Mice Lacking AIM, a Novel Murine Macrophage-derived Soluble Factor Belonging to the Scavenger Receptor Cysteine-rich Domain Superfamily", The Journal of Experimental Medicine, vol. 189, No. 2, Jan. 18, 1999, 413-422.
Novershtern, et al., "Densely Interconnected Transcriptional Circuits Control Cell States in Human Hematopoiesis", Cell, vol. 144, No. 2, Jan. 21, 2011, 296-309.
Okamoto, et al., "Mina, an Il4 repressor, controls T helper type 2 bias", Nature Immunology, vol. 10, No. 8, 2009, 872-879.
O'Shea, et al., "Signal transduction and Th17 cell differentiation", Microbes and Infection, vol. 11, No. 5, Apr. 1, 2009, 599-611.
Papp, et al., "Brodalumab, an Anti-Interleukin-17-Receptor Antibody for Psoriasis", The New England Journal of Medicine, vol. 366, No. 13, Mar. 29, 2012, 1181-1189.
Patel, et al., "Effect of IL-17A blockade with secukinumab in autoimmune diseases", Annals of the Rheumatic Diseases, vol. 72, Suppl 2, 2013, ii116-ii123.
Peters, et al., "Th17 Cells Induce Ectopic Lymphoid Follicles in Central Nervous System Tissue Inflammation", Immunity,vol. 35, Issue 6, Dec. 23, 2011, 986-996.
Peters, et al., "The many faces of Th17 cells", Current Opinion in Immunology, vol. 23, No. 6, Dec. 2011, 702-706.
Peters and Yosef, "UnderstandingTh17cellsthroughsystematicgenomicanalyses", CurrentOpinioninImmunology, 28, 2014, pp. 42-48.
Rangachari, et al., "Bat3 promotes T cell responses and autoimmunity by repressing Tim-3-mediated cell death and exhaustion", Nature Medicine, vol. 18, No. 9, Sep. 2012, 1394-1400.
Romani, "Immunity to fungal infections", Nature Reviews Immunology, vol. 11, No. 4, 2004, 275-288.
Sanchez-Tillo, et al., "ZEB1 Represses E-cadherin and Induces an EMT by Recruiting the SWI/SNF Chromatin-Remodeling Protein BRG1", Oncogene ,vol. 29, No. 24, Apr. 2010, 3490-3500.
Sawcer, et al., "Genetic risk and a primary role for cell-mediated immune mechanisms in multiple sclerosis", Nature, vol. 476, No. 7359, Aug. 11, 2011, 214-219.
Schraml, et al., "The AP-1 transcription factor Batf controls T(H)17 differentiation", J. Immunol., Nature, vol. 460, No. 7253, Jul. 16, 2009, 405-409.
Shalek, et al., "Nanowire-Mediated Delivery Enables Functional Interrogation of Primary Immune Cells: Application to the Analysis of Chronic Lymphocytic Leukemia", Nano Letters, vol. 12, No. 12, Dec. 12, 2012, 6498-6504.
Shalek, et al., "Single-cell transcriptomics reveals bimodality in expression and splicing in immune cells", Nature, vol. 498, No. 7453, 2013, 236-240.
Shalek, et al., "Vertical Silicon Nanowires as a Universal Platform for Delivering Biomolecules Into Living Cells", Proceedings of the National Academy of Sciences, vol. 107, No. 5, Feb. 2, 2010, 1870-1875.
Shi, et al., "HIF1alpha-dependent glycolytic pathway orchestrates a metabolic checkpoint for the differentiation of TH17 and Treg cells", The Journal of experimental medicine, vol. 208, No. 7, 2011, 1367-1376.
Soroosh, et al., "Oxysterols are agonist ligands of RORγt and drive Th17 cell differentiation", PNAS, vol. 111, No. 33, Aug. 19, 2014, 12163-12168.
Sundrud, et al., "Halofuginone inhibits TH17 cell differentiation by activating the amino acid starvation response", Science, vol. 324, 2009, 1334-1338.
The Broad Institute, Inc., et al., "Notice of Reasons for Rejection for JP Application No. 2016-554339", dated Feb. 18, 2019, 17 pages.
Valledor, et al., "Activation of liver X receptors and retinoid X receptors prevents bacterial-induced macrophage apoptosis", PNAS, vol. 101, No. 51, Dec. 21, 2004, pp. 17813-17818.
Veldhoen, et al., "TGFbeta in the context of an inflammatory cytokine milieu supports de novo differentiation of IL-17-producing T cells", Immunity, vol. 24, Issue 2, Feb. 2006, 179-189.
Winer, et al., "Obesity predisposes to Th17 bias", European Journal of Immunology, vol. 39, Issue 9, Sep. 2009, 2629-2635.
Wu, et al., "Genome-Wide Binding of the CRISPR Endonuclease Cas9 in Mammalian Cells", Nature Biotechnology, vol. 32, No. 7, Jul. 2014, 670-676.
Wu, et al., "Induction of pathogenic Th17 cells by inducible salt sensing kinase SGK1", Nature, 496(7446), 2013, pp. 513-517.
Xiao, et al., "Retinoic acid increases Foxp3+ regulatory T cells and inhibits development of Th17 cells by enhancing TGF-beta-driven Smad3 signaling and inhibiting IL-6 and IL-23 receptor expression", Journal of Immunology , vol. 181, 2008, 2277-2284.
Xiao, et al., "Small-Molecule RORγt Antagonists Inhibit T Helper 17 Cell Transcriptional Network by Divergent Mechanisms", Immunity, vol. 40, No. 4, Apr. 2014, 477-489.

(56) References Cited

OTHER PUBLICATIONS

Xu, et al., "c-Maf Regulates IL-10 Expression during Th17 Polarization", The Journal of Immunology, vol. 182, No. 10, 2009, 6226-6236.
Yang, et al., "Focused Specificity of Intestinal Th17 Cells towards Commensal Bacterial Antigens", Nature, vol. 510, No. 7503, Jun. 2014, 152-156.
Yang, et al., "Opposing regulation of the locus encoding IL-17 through direct, reciprocal actions of STAT3 and STAT5", Nat. Immunol., vol. 12, No. 3, Mar. 2011, 247-254.
Ye, et al., "The role and regulation of human Th17 cells in tumor immunity", Am J Pathol., vol. 182, No. 1, Jan. 2013, 10-20.
Ying, et al., "Cutting Edge: CTLA-4-B7 Interaction Suppresses Th17 Cell Differentiation", The Journal of Immunology, vol. 185, No. 3, Aug. 2010, 1375-1378.
Yosef, et al., "Dynamic regulatory network controlling Th17 cell differentiation", Nature, vol. 496, Mar. 6, 2013, 461-468.
Zhang, et al., "T helper type 1-specific Brg1 recruitment and remodeling of nucleosomes positioned at the IFN-gamma promoter are State dependent", J. Exp. Med., vol. 203, 2006, 1493-1505.
Zheng, et al., "Genome-wide analysis of Foxp3 target genes in developing and mature regulatory T cells", Nature, vol. 445, 2007, 936-940.
Zielenski, et al., "Pathogen-induced human TH17 cells produce IFN or IL-10 and are regulated by IL", Nature, vol. 484, No. 7395, Apr. 2012, 514-518.
The Broad Institute, Inc., "European Office Action issued in European Application No. 15709048.1 dated Apr. 30, 2018", 8 pages.
The Broad Institute, Inc., "European Office Action issued in European Application No. 15709048.1 dated Feb. 2, 2018", 5 pages.
The Broad Institute, Inc., "International Preliminary Report on Patentability issued in International Application No. PCT/US2015/017826", dated Sep. 9, 2016, 13 pages.
Abadja, et al., "Significance of Th17 immunity in transplantation", Curr Opin Organ Transplant., vol. 17, No. 1, Feb. 2012, 8-14.
Ahmed, et al., "IL-17 in Obesity and Adipogenesis", Cytokine & Growth Factor Reviews, vol. 21, No. 6, Dec. 2010, 449-453.
Amit, et al., "Strategies to Discover Regulatory Circuits of the Mammalian Immune System", Nature Reviews, Immunology, vol. 11, No. 12, Nov. 18, 2011, 873-880.
Amit, et al., "Unbiased Reconstruction of a Mammalian Transcriptional Network Mediating the Differential Response to Pathogens", Science, vol. 326, No. 5950, Oct. 9, 2009, 257-263.
Arai, et al., "Obesity-Associated Autoantibody Production Requires AIM to Retain the Immunoglobulin M Immune Complex on Follicular Dendritic Cells", Cell Reports 3, Apr. 25, 2013, pp. 1187-1198.
Arpaia, et al., "Metabolites produced by commensal bacteria promote peripheral regulatory T-cell generation", Nature, vol. 504, No. 7480, Dec. 2013, 451-455.
Awasthi, et al., "A dominant function for interleukin 27 in generating interleukin 10-producing anti-inflammatory T cells", Nature immunology, vol. 8, No. 12, Dec. 2007, 1380-1389.
Awasthi, et al., "Cutting Edge: IL-23 Receptor GFP Reporter Mice Reveal Distinct Populations of IL-17-Producing Cells1", The Journal of Immunology, vol. 182, Issue 10, Jun. 2009, 5904-5908.
Baeten, et al., "Interleukin-17 and a tale of two autoimmune diseases", Nature Medicine, vol. 19, No. 7, 2013, 824-825.
Barrett, et al., "New IBD genetics: common pathways with other diseases", Gut, 60, 2011, pp. 1739-1753.
Bauquet, et al., "The costimulatory molecule ICOS regulates the expression of c-Maf and IL-21 in the development of follicular T helper cells and TH-17 cells", Nature Immunology, vol. 10, No. 2, 2009, 167-175.
Berod, et al., "De Novo Fatty Acid Synthesis Controls the Fate Between Regulatory T and T helper 17 Cells", Nature Medicine, vol. 20, No. 11, 2014, 1327-1333.
Bettelli, et al., "Reciprocal Developmental Pathways for the Generation of Pathogenic Effector TH17 and Regulatory T Cells", Nature, vol. 441, No. 7090, May 11, 2006, 235-238.
Chaudhry, et al., "Interleukin-10 signaling in regulatory T cells is required for suppression of Th17 cell-mediated inflammation", Immunity, vol. 34, No. 4, Apr. 22, 2011, 566-578.
Chevrier, et al., "Systematic Discovery of TLR Signaling Components Delineates Viral-Sensing Circuits", Cell, vol. 147, No. 4, Nov. 11, 2011, 853-867.
Cho, "The genetics and immunopathogenesis of inflammatory bowel disease", Nature Reviews Immunology, vol. 8, No. 6, Jun. 2008, 458-466.
Choi, et al., "Tsc-22 enhances TGF-beta signaling by associating with Smad4 and induces erythroid cell differentiation", Molecular and Cellular Biochemistry, vol. 271, Issue 1-2, Mar. 2005, 23-28.
Ciofani, et al., "A validated regulatory network for Th 17 cell specification", Cell, vol. 151, No. 2, Oct. 1, 2012, 289-303.
Cortes, et al., "Identification of multiple risk variants for ankylosing spondylitis through high-density genotyping of immune-related loci", Nature Genetics, vol. 45, Jul. 2013, 730-738.
Cua, et al., "Interleukin-23 rather than interleukin-12 is the critical cytokine for autoimmune inflammation of the brain", Mature, vol. 421, No. 6924, Feb. 13, 2003, 744 748.
Dang, et al., "Control of T(H)17/T(reg) balance by hypoxia-inducible factor 1", Cell, vol. 146, No. 5, Sep. 2, 2011, 772-784.
Durant, et al., "Diverse Targets of the Transcription Factor STAT3 Contribute to T Cell Pathogenicity and Homeostasis", Immunity, vol. 32, No. 5, May 28, 2010, 605-615.
Elyaman, et al., "Notch receptors and Smad3 signaling cooperate in the induction of interleukin-9-producing T cells", Immunity, vol. 36, No. 4, Apr. 20, 2012, 623-634.
Esplugues, et al., "Control of TH17 cells occurs in the small intestine", Nature, vol. 475, No. 7357, 2011, 514-518.
Franke, et al., "Genome-wide meta-analysis increases to 71 the No. of confirmed Crohn's disease susceptibility loci", Nature Genetics, vol. 42, No. 12, Dec. 2010, 1118-1125.
Gaffen, et al., "IL-17 Signaling in Host Defense Against Candida albicans", Immunologic Research, vol. 50, No. 2-3, 2011, 181-187.
Garber, et al., "A High Throughput Chromatin Immunoprecipitation Approach Reveals Principles of Dynamic Gene Regulation in Mammals", Molecular Cell, vol. 47, No. 5, Sep. 14, 2012, 810-822.
Genovese, et al., "LY2439821, a humanized anti-interieukin-17 monoclonal antibody, in the treatment of patients with rheumatoid arthritis: A phase I randomized, double-blind, placebo-controlled, proof-of-concept study", Arthritis & Rheumatology, vol. 62, No. 4, 2010, 929-939.
Ghoreschi, et al., "Generation of pathogenic T(H)17 cells in the absence of TGF-beta signaling", Nature, vol. 467, No. 7318, Oct. 21, 2010, 967-971.
Ghoreschi, et al., "T helper 17 cell heterogeneity and pathogenicity in autoimmune disease", Trends in Immunology, vol. 32, Issue 9, Sep. 2011, 395-401.
Glasmacher, et al., "A Genomic Regulatory Element That Directs Assembly and Function of Immune-Specific AP-1-IRF Complexes", Science, vol. 338, No. 6109, Nov. 16, 2012, 975-980.
Griffin, et al., "Protein C anticoagulant and cytoprotective pathways", International Journal of Hematology, vol. 95, No. 4, 2012, 333-345.
Gu, et al., "Disruption of the Endothelial Cell Protein C Receptor Gene in Mice Causes Placental Thrombosis and Early Embryonic Lethality", The Journal of Biological Chemistry, vol. 277, No. 45, Nov. 8, 2002, 43335-43343.
Guglani, et al., "Th17 cytokines in mucosal immunity and inflammation", Current Opinion in HIV and AIDS, vol. 5, No. 2, Mar. 2010, 120-127.
Harrington, et al., "Expanding the effector CD4 T-cell repertoire: the Th17 lineage", Current Opinion in Immunology, 18, 2006, pp. 349-356.
Hill, et al., "Foxp3 transcription-factor-dependent and -independent regulation of the regulatory T cell transcriptional signature", Immunity, vol. 27, No. 5, Nov. 2007, 786-800.
Hu, et al., "Effects of dexamethasone on intracellular expression of Th17 cytokine interleukin 17 in asthmatic mice", Nan Fang Yi Ke Da Xue Xue Bao, vol. 29, No. 6, Jun. 2009, 1185-1188—English abstract.

(56) References Cited

OTHER PUBLICATIONS

Hueber, et al., "Secukinumab, a human anti-IL-17A monoclonal antibody, for moderate to severe Crohn's disease: unexpected results of a randomised, double-blind placebo-controlled trial", Gut, vol. 61, No. 12, 2012, 1693-1700.
Huh, et al., "Digoxin and its derivatives suppress TH17 cell differentiation by antagonizing ROR(gamma)t activity", Nature, vol. 472, No. 7344, Apr. 28, 2011, 486-490.
Ivanov, et al., "Induction of intestinal Th17 cells by segmented filamentous bacteria", Cell, vol. 139, No. 3, 2009, 485-498.
Iwaki, et al., "A cardioprotective role for the endothelial protein C receptor in lipopolysaccharide-induced endotoxemia in the mouse", Blood, vol. 105, No. 6, Mar. 5, 2005, 2364-2371.
Jager, et al., "Th1, Th17, and Th9 effector cells induce experimental autoimmune encephalomyelitis with different pathological phenotypes", The Journal of Immunology, vol. 183, No. 11, 2009, 7169-7177.
Jhun, et al., "Obesity aggravates the joint inflammation in a collagen-induced arthritis model through deviation to Th17 differentiation", Experimental & Molecular Medicine, vol. 44, No. 7, Jul. 2012, 424-431.
Jin, et al., "Structural Basis for Hydroxycholesterols as Natural Ligands of Orphan Nuclear Receptor RORγ", Molecular Endocrinology, vol. 24, No. 5, 2010, 923-929.
Jing, et al., "A mechanistic study on the effect of dexamethasone in moderating cell death in Chinese Hamster Ovary cell cultures", Biotechnology Progress, vol. 28, No. 2, 2012, 490-496.
Jostins, et al., "Host-microbe interactions have shaped the genetic architecture of inflammatory bowel disease", Nature, vol. 491, No. 7422, Nov. 1, 2012, 119-124.
The Broad Institute, Inc., "Communication Pursuant to Article 94(3) EPC for EP 18212362.0", dated Sep. 4, 2020, 4 pages.
Ivanova, et al., "STRA13 Interacts with STAT3 and Modulates Transcription of STAT3-dependent Targets", Journal of Molecular Biology, vol. 340, No. 4, Jul. 16, 2004, 641-653.
Lin, et al., "Bhlhe40 Controls Cytokine Production by T Cells and is Essential for Pathogenicity in Autoimmune Neuroinflammation", Nature Communications, vol. 5, 3551, Apr. 3, 2014, 13 pages.
Miyazaki, et al., "The Role of the Basic Helix-Loop-Helix Transcription Factor Dec1 in the Regulatory T Cells", The Journal of Immunology, vol. 185, No. 12, Nov. 5, 2010, 7330-7339.
Sun, et al., "Defective T Cell Activation and Autoimmune Disorder in Stra13-Deficient Mice", Nature Immunology, vol. 2, No. 11, Oct. 22, 2001, 1040-1047.

* cited by examiner

FIGURE 17A
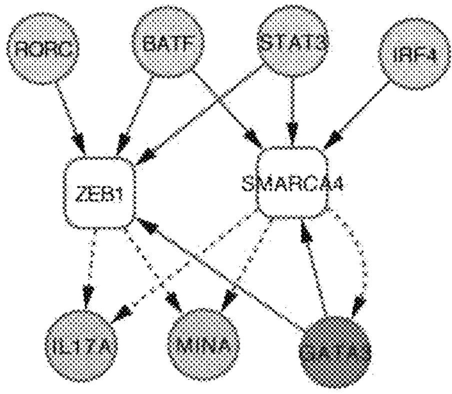
FIGURE 17B
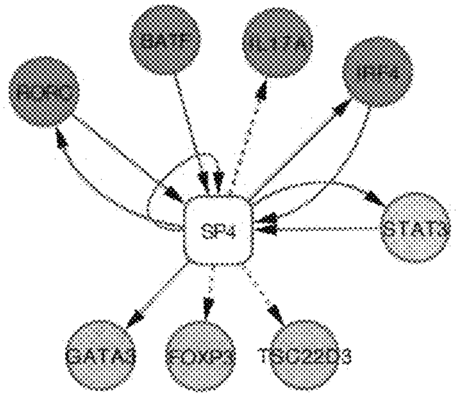
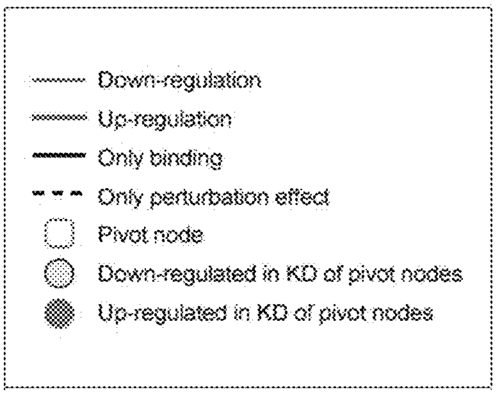

| Higher in T3-IL6 | |
|---|---|
| <5 genes> | <0.3 fold difference |
| CXCL3 | 0.221 |
| GP49A;LILRB4 | 0.24 |
| IL22;ILTIFB | 0.261 |
| TG | 0.278 |
| LUM | 0.282 |

PROCR →

| Higher in T1-IL6 | |
|---|---|
| <16 genes> | >3 fold difference |
| CTLA2A | 3.008 |
| AA467197 | 3.02 |
| PROCR | 3.108 |
| CD38 | 3.224 |
| CTLA2A;CTLA2B | 3.323 |
| TMEM176B | 3.388 |
| KLRD1 | 3.469 |
| AQP3 | 3.532 |
| KCTD14 | 3.549 |
| TMEM176A | 3.558 |
| SGK1 | 3.93 |
| IL9 | 3.959 |
| CTSW | 4.157 |
| IL10 | 4.249 |
| NIPAL1 | 4.32 |
| CTLA2B | 4.673 |

| Group | Group Name | Mice/Group | Mean maximum score | Day of Onset | Dead Mice | Disease incidence |
|---|---|---|---|---|---|---|
| 1 | Ctl_RV | 4 | 2.75+/-0.35 | 20 | 0 | 2/4 (50%) |
| 2 | PROCR_RV | 4 | 0 | - | 0 | 0/4 (0%) |

| | Incidence rate | Day of onset | Mean max score |
|---|---|---|---|
| WT | 15/15 | 8.6±0.7 | 2.6±0.4 |
| CD5L-/- | 12/12 | 8.7±0.9 | 4.0±0.4 |

* No difference in % of Treg or CD11b+ in CNS and periphery

| | Incidence rate | Day of onset | Mean max score |
|---|---|---|---|
| WT | 7/13 | 13.4 ± 1.3 | 1.7 ± 0.6 |
| CD5L-/- | 12/12 | 11.0 ± 0.4 | 4.7 ± 0.1 |

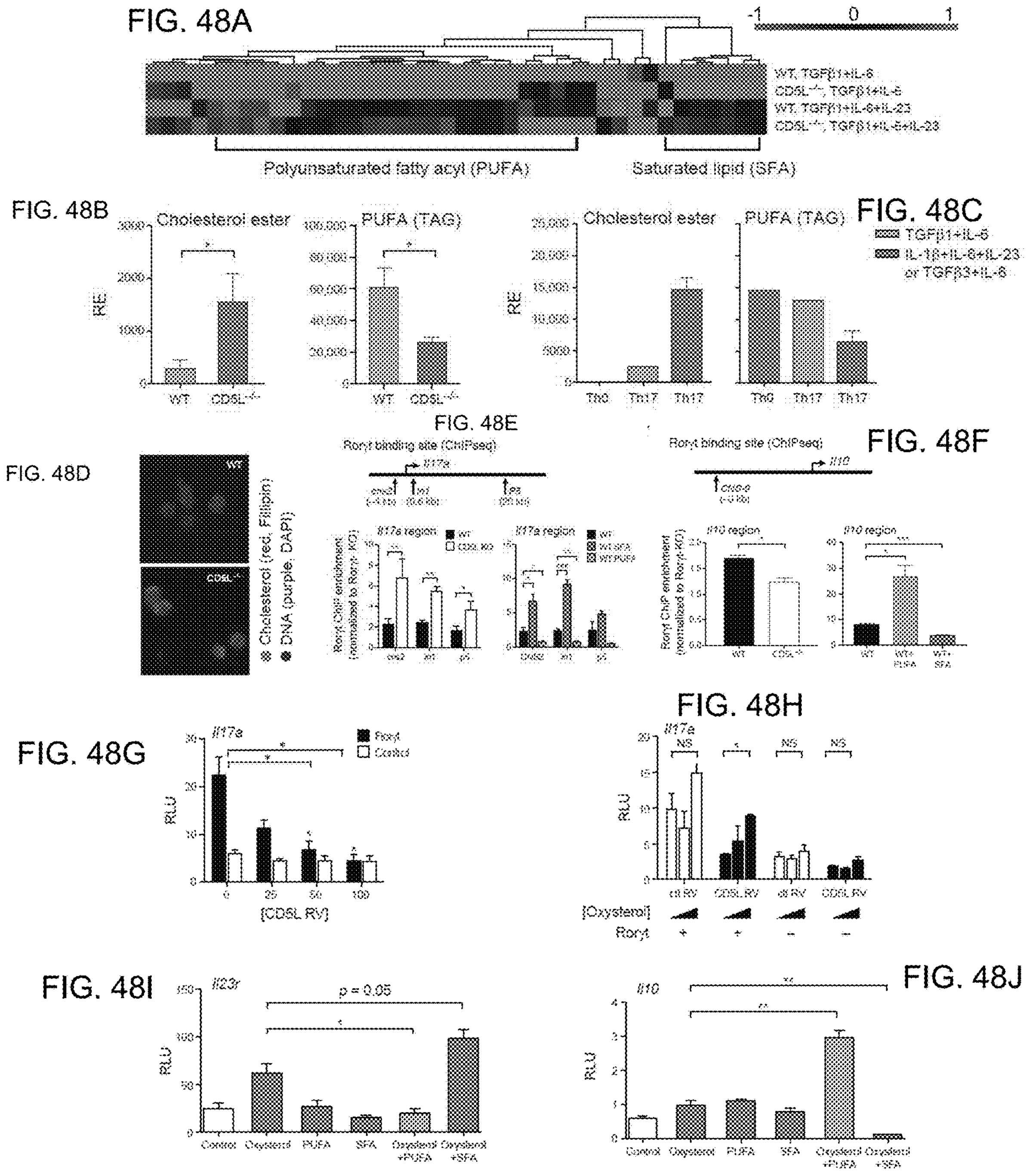
FIG. 48A
-1 0 1
WT, TGFβ1+IL-6
CD5L-/-, TGFβ1+IL-6
WT, TGFβ1+IL-6+IL-23
CD5L-/-, TGFβ1+IL-6+IL-23
Polyunsaturated fatty acyl (PUFA)
Saturated lipid (SFA)
FIG. 48B
Cholesterol ester
PUFA (TAG)
RE
WT CD5L-/-
FIG. 48C
Cholesterol ester
PUFA (TAG)
TGFβ1+IL-6
IL-1β+IL-6+IL-23 or TGFβ3+IL-6
Th0 Th17 Th17
FIG. 48D
WT
CD5L-/-
Cholesterol (red, Fillipin)
DNA (purple, DAPI)
FIG. 48E
Rorγt binding site (ChIPseq)
Il17a
cns2 in1 p5
Il17a region
WT
CD5L KO
WT SFA
WT PUFA
Rorγt ChIP enrichment (normalized to Rorγt-KO)
FIG. 48F
Rorγt binding site (ChIPseq)
Il10
Il10 region
WT CD5L-/-
WT WT+PUFA WT+SFA
FIG. 48G
Il17a
Rorγt
Control
RLU
0 25 50 100
[CD5L RV]
FIG. 48H
Il17a
NS NS NS
RLU
ctl RV CD5L RV ctl RV CD5L RV
[Oxysterol]
Rorγt + + − −
FIG. 48I
Il23r
p = 0.05
RLU
Control Oxysterol PUFA SFA Oxysterol +PUFA Oxysterol +SFA
FIG. 48J
Il10
RLU
Control Oxysterol PUFA SFA Oxysterol +PUFA Oxysterol +SFA FIG. 52A
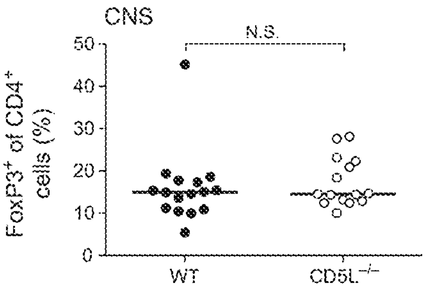
FIG. 52B
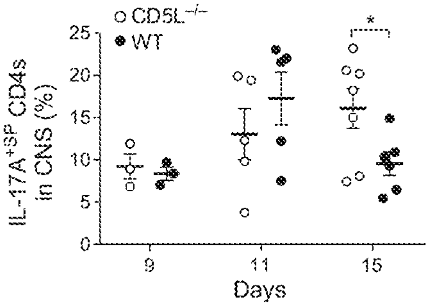
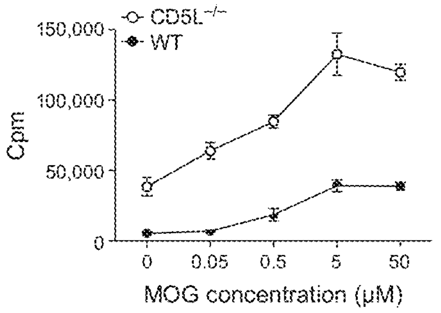
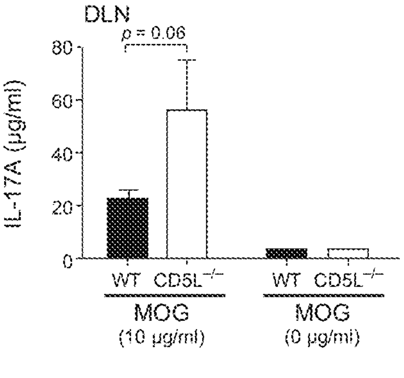
FIG. 52C
FIG. 52D FIG. 53A
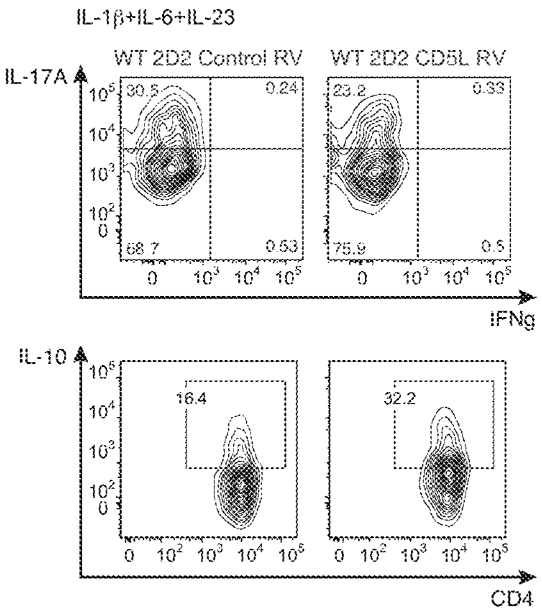
FIG. 53B
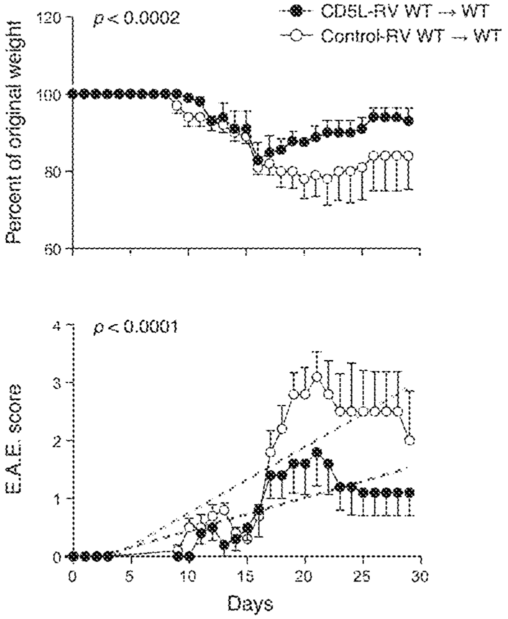
FIG. 53C
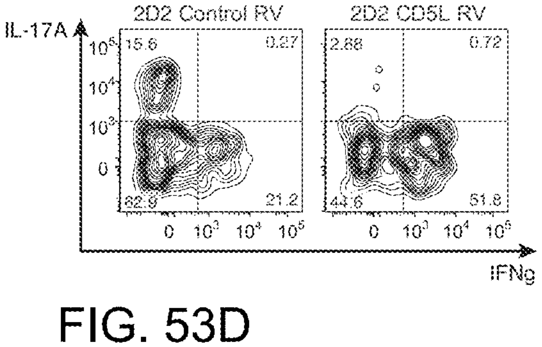
FIG. 53D

SEQUENCE LISTING

<160> NUMBER OF SEQ ID NOS: 1395

<210> SEQ ID NO 1
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1
ggccagagct tgaccatc 18

<210> SEQ ID NO 2
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 2
agcaagccag ccaaacag 18

<210> SEQ ID NO 3
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 3
agccaatttt gaagggca 18

<210> SEQ ID NO 4
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 4
ggaagccctg catttcct 18

<210> SEQ ID NO 5
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 5
tataacccct gggccctc 18

<210> SEQ ID NO 6
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 6
gttgcagccc tcgttgtc 18

<210> SEQ ID NO 7
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 7
gtcgggacat cttgacgg 18

<210> SEQ ID NO 8
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 8
ggaggatgca aaacccct 18

<210> SEQ ID NO 9
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 9
gcatgggtac tgctggct 18

<210> SEQ ID NO 10
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 10
tgaggaggtt cacagccc 18

<210> SEQ ID NO 11
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 11
ggacgcgtga aaggtttg 18

<210> SEQ ID NO 12

<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 12
tgcactatgg ccttatcgg 19

<210> SEQ ID NO 13
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 13
tgcctaagct ccattggc 18

<210> SEQ ID NO 14
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 14
acggcaaggc agcaatac 18

<210> SEQ ID NO 15
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 15
gggtattggg cgtcactg 18

<210> SEQ ID NO 16
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 16
ccacggcaga ctggttct 18

<210> SEQ ID NO 17
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 17
atgcacactc tgggagcc 18

<210> SEQ ID NO 18
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 18
ccaaggacct gcaaagagg 19

<210> SEQ ID NO 19
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 19
agctgccata ccactggc 18

<210> SEQ ID NO 20
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 20
aggcacatgg gatctgga 18

<210> SEQ ID NO 21
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 21
cttcactgca ttcgccct 18

<210> SEQ ID NO 22
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 22
cacaggacaa cggaagca 18

<210> SEQ ID NO 23
<211> LENGTH: 18
<212> TYPE: DNA
<213> ORGANISM: Artificial Sequence
<220> FEATURE:

<221> NAME/KEY: source
<223> OTHER INFORMATION: /note="Description of Artificial Sequence:
Synthetic primer"

<400> SEQUENCE: 23
caccgccatg ggttagag 18

<210> SEQ ID NO 24
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 24
tgggatccgg attcagtg 18

<210> SEQ ID NO 25
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 25
aaggaaaaat gcgagcaaga 20

<210> SEQ ID NO 26
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 26
tctcccgtct catgtcagg 19

<210> SEQ ID NO 27
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 27
atgggggaca gacgaggt 18

<210> SEQ ID NO 28
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 28
tgcctaagcc cttcatgg 18

<210> SEQ ID NO 29
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 29
gatgatggct tggccagt 18

<210> SEQ ID NO 30
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 30
tggccaattg ggttcact 18

<210> SEQ ID NO 31
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 31
catttgggaa atggctcg 18

<210> SEQ ID NO 32
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 32
atgggcccaa cattctga 18

<210> SEQ ID NO 33
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 33
aagctctgcg tgtctgcc 18

<210> SEQ ID NO 34
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 34
accacagctg gcttggag 18

<210> SEQ ID NO 35
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 35
cgtggatcca gccacttc 18

<210> SEQ ID NO 36
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 36
atcattcgct gtggcgtt 18

<210> SEQ ID NO 37
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 37
atctgccgtg cccattta 18

<210> SEQ ID NO 38
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 38
acgagcccat gtccttga 18

<210> SEQ ID NO 39
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 39
ggctcaacag caggaagc 18

<210> SEQ ID NO 40
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 40
ttaatttgaa gacatcatgg ca 22

<210> SEQ ID NO 41
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 41
cccagaagcc acagagga 18

<210> SEQ ID NO 42
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 42
ttccagccct ttccttcc 18

<210> SEQ ID NO 43
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 43
gtgccatttg acacagcg 18

<210> SEQ ID NO 44
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 44
ctggcctacc ctccacct 18

<210> SEQ ID NO 45
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 45
caagccaggc tggaagaa 18

<210> SEQ ID NO 46
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 46
tgggtcgttt ctgctgtg 18

<210> SEQ ID NO 47
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 47
gacacgcttc gggttcac 18

<210> SEQ ID NO 48
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 48
caactgtgat gaggccagc 19

<210> SEQ ID NO 49
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 49
cccagcatta aggctcca 18

<210> SEQ ID NO 50
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 50
aggagcaaca ggggacct 18

<210> SEQ ID NO 51
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 51
cagctttgaa cacagggtct t 21

<210> SEQ ID NO 52
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 52
agctgactga aattcctccc t 21

<210> SEQ ID NO 53
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 53
tcacagtgga catcggga 18

<210> SEQ ID NO 54
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 54
cactcaccct gggcatct 18

<210> SEQ ID NO 55
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 55
ctactgcagg gaggagcg 18

<210> SEQ ID NO 56
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 56
gggtccctct ttagggca 18

<210> SEQ ID NO 57
<211> LENGTH: 18
<212> TYPE: DNA

<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 57
gtccgtgcag tttggctt 18

<210> SEQ ID NO 58
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 58
ggtttgggga caggcttt 18

<210> SEQ ID NO 59
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 59
cctttgcagt gagttggga 19

<210> SEQ ID NO 60
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 60
cgttttgaaa atctgcagag aa 22

<210> SEQ ID NO 61
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 61
gcgggaaaca ctcaaagc 18

<210> SEQ ID NO 62
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 62
tgctgaagat catgccga 18

<210> SEQ ID NO 63
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 63
gccactggag ctgaagga 18

<210> SEQ ID NO 64
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 64
tgacctctcc tgcccgta 18

<210> SEQ ID NO 65
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 65
ccctgctcct gcatctgt 18

<210> SEQ ID NO 66
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 66
aaatcttccg acccagcc 18

<210> SEQ ID NO 67
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 67
tcctgctttt cccatcca 18

<210> SEQ ID NO 68
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic primer"

<400> SEQUENCE: 68
ccagcaacac aagaccagc 19

<210> SEQ ID NO 69
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 69
tccagtctgg gcaagagg 18

<210> SEQ ID NO 70
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 70
ggcagcagag ggtggata 18

<210> SEQ ID NO 71
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 71
atgtcttccc tgcctccc 18

<210> SEQ ID NO 72
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 72
aagcccaaag cacagacg 18

<210> SEQ ID NO 73
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 73
ggaacatcgg ccttcaaa 18

<210> SEQ ID NO 74
<211> LENGTH: 18

<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 74
cattccagcg gcatcata 18

<210> SEQ ID NO 75
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 75
cggcacagct ggaatctt 18

<210> SEQ ID NO 76
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 76
ggttgacggc atagccag 18

<210> SEQ ID NO 77
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 77
ctacccagag gcccagtg 18

<210> SEQ ID NO 78
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 78
aactatccac cccctgcc 18

<210> SEQ ID NO 79
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 79

```
tcctgagggc aaagagga                                                18


<210> SEQ ID NO 80
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 80

gatttggctt gcctggg                                                 17


<210> SEQ ID NO 81
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 81

aactgaatgg ggaggttgg                                               19


<210> SEQ ID NO 82
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 82

ttacagccgc ctttcagg                                                18


<210> SEQ ID NO 83
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 83

ccagccctgg atctcctt                                                18


<210> SEQ ID NO 84
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 84

gccactttca tcaccacca                                               19


<210> SEQ ID NO 85
<211> LENGTH: 16
<212> TYPE: DNA
<213> ORGANISM: Artificial Sequence
<220> FEATURE:
<221> NAME/KEY: source
```

<223> OTHER INFORMATION: /note="Description of Artificial Sequence:
Synthetic primer"

<400> SEQUENCE: 85
tgcaccgagg ggacac 16

<210> SEQ ID NO 86
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 86
aaccccgcag gaacatct 18

<210> SEQ ID NO 87
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 87
tgccgtcatt ttctgcct 18

<210> SEQ ID NO 88
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 88
cgtggcaatg atctcaaca 19

<210> SEQ ID NO 89
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 89
aggaccttga tggagccc 18

<210> SEQ ID NO 90
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 90
ctggcatcca gggtcaac 18

<210> SEQ ID NO 91

```
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 91

catgagggag gatgctgg                                                    18


<210> SEQ ID NO 92
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 92

aaatccctgc tatcaaaaat cc                                               22


<210> SEQ ID NO 93
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 93

gctctctgtc tccaagggc                                                   19


<210> SEQ ID NO 94
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 94

actcacaacc cagaccgc                                                    18


<210> SEQ ID NO 95
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 95

ggcctgatga cctggaga                                                    18


<210> SEQ ID NO 96
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 96
```

```
tccctacttt tgccgcct                                                18


<210> SEQ ID NO 97
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 97

gagggctggg accattg                                                 17


<210> SEQ ID NO 98
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 98

gcagctgccc agaatctt                                                18


<210> SEQ ID NO 99
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 99

gcagcaggct gtttcttacc                                              20


<210> SEQ ID NO 100
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 100

ttcctcccca ctcatcca                                                18


<210> SEQ ID NO 101
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 101

aaggagggca aggaccag                                                18


<210> SEQ ID NO 102
<211> LENGTH: 18
<212> TYPE: DNA
<213> ORGANISM: Artificial Sequence
<220> FEATURE:
```

<221> NAME/KEY: source
<223> OTHER INFORMATION: /note="Description of Artificial Sequence:
Synthetic primer"

<400> SEQUENCE: 102
gagcttgggt cgggattt 18

<210> SEQ ID NO 103
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 103
ggagatggct tgccagaa 18

<210> SEQ ID NO 104
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 104
actcgaattc cgttgcca 18

<210> SEQ ID NO 105
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 105
gccagatcca tgactgacg 19

<210> SEQ ID NO 106
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 106
tttggttgcc tggacgat 18

<210> SEQ ID NO 107
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 107
cagggaacat ccaccagc 18

<210> SEQ ID NO 108
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 108
tagcatcacc ctttgggg 18

<210> SEQ ID NO 109
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 109
cattgtcagt gggcgtca 18

<210> SEQ ID NO 110
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 110
gaatcacagg ctcgccc 17

<210> SEQ ID NO 111
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 111
ccagatctac cgcaggga 18

<210> SEQ ID NO 112
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 112
catgaccaga aggggcag 18

<210> SEQ ID NO 113
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 113
gtcaaccagg gatggcag 18

<210> SEQ ID NO 114
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 114
cagttttccc cagagcga 18

<210> SEQ ID NO 115
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 115
gctgtggatc tgggctgt 18

<210> SEQ ID NO 116
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 116
cccccattca ttttgcag 18

<210> SEQ ID NO 117
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 117
tggaaacacc cagccact 18

<210> SEQ ID NO 118
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 118
ggcaagactc ctggggat 18

<210> SEQ ID NO 119
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 119
tggatggctt cgtctgtg 18

<210> SEQ ID NO 120
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 120
tgcagctgtg ggttgtgt 18

<210> SEQ ID NO 121
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 121
gtgccgacat ctatgccc 18

<210> SEQ ID NO 122
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 122
gcactcccgc atcatctt 18

<210> SEQ ID NO 123
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 123
ggcctcgggt ctttcagt 18

<210> SEQ ID NO 124
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 124
ctaggcagct gggctcac 18

<210> SEQ ID NO 125
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 125
ggaggggtgg ctttcaa 17

<210> SEQ ID NO 126
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 126
aagattctcg gggtccca 18

<210> SEQ ID NO 127
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 127
ggaacagctg ggcaaaga 18

<210> SEQ ID NO 128
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 128
gcctgggtcc acactgaa 18

<210> SEQ ID NO 129
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 129
gtgggtgttt gggactgc 18

<210> SEQ ID NO 130
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 130
atcaagggga tggtggct 18

<210> SEQ ID NO 131
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 131
tgggggtacc acgactgt 18

<210> SEQ ID NO 132
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 132
gggcgtgtag ccttgaga 18

<210> SEQ ID NO 133
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 133
aatcctcctc gactgggg 18

<210> SEQ ID NO 134
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 134
tgacacctgc aatgctgc 18

<210> SEQ ID NO 135
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 135
ccgatagcct gtggatgg 18

<210> SEQ ID NO 136
<211> LENGTH: 18
<212> TYPE: DNA

<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 136
gtcgatgctg atccccac 18

<210> SEQ ID NO 137
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 137
agccttcgcc atgtcaac 18

<210> SEQ ID NO 138
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 138
cgccttcagc gagagaga 18

<210> SEQ ID NO 139
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 139
gcaaatagcc aaccccag 18

<210> SEQ ID NO 140
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 140
gttgcaagac tgaccccg 18

<210> SEQ ID NO 141
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 141
ggagtcccag tcccacct 18

<210> SEQ ID NO 142
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 142
tggaccttct tctccccc 18

<210> SEQ ID NO 143
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 143
tccaaccagg tggagcac 18

<210> SEQ ID NO 144
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 144
tcatctcaga gtccagccg 19

<210> SEQ ID NO 145
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 145
atggcaaact tggacccc 18

<210> SEQ ID NO 146
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 146
caagatctgt gcagggca 18

<210> SEQ ID NO 147
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic primer"

<400> SEQUENCE: 147
cggatttgag cgcttctg 18

<210> SEQ ID NO 148
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 148
agtcactggt gggtggga 18

<210> SEQ ID NO 149
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 149
tggcaagccc tctcactt 18

<210> SEQ ID NO 150
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 150
aaacacacac aaccacgca 19

<210> SEQ ID NO 151
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 151
tgctcaaaat tcacgaggtg 20

<210> SEQ ID NO 152
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 152
cacgggtacg tcatgctg 18

<210> SEQ ID NO 153
<211> LENGTH: 18

<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 153
caccctggtc gcagagtt 18

<210> SEQ ID NO 154
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 154
ggttgtgttg gggcattc 18

<210> SEQ ID NO 155
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 155
ctggctgtgg gcatctg 17

<210> SEQ ID NO 156
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 156
ggagttgtgg tcaagggc 18

<210> SEQ ID NO 157
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 157
tgctggtgta ggcgtcttt 19

<210> SEQ ID NO 158
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 158
tctcagcaat cacagtgcaa 20

<210> SEQ ID NO 159
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 159
tggccttaat gtgcctgtc 19

<210> SEQ ID NO 160
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 160
tgctggcttg ccctttac 18

<210> SEQ ID NO 161
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 161
tggcttgtta catgagcaaa a 21

<210> SEQ ID NO 162
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 162
ccgatgtgtg ctgtgactg 19

<210> SEQ ID NO 163
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 163
ggatacgaat gggactggaa 20

<210> SEQ ID NO 164
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 164
ccaacgcttg aactggct 18

<210> SEQ ID NO 165
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 165
ttccctgcaa tagaagtctg g 21

<210> SEQ ID NO 166
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 166
tgaagtaatc tgtcctcccg a 21

<210> SEQ ID NO 167
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 167
ccggcctact catcctga 18

<210> SEQ ID NO 168
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 168
aactttattg gagcaacaca cg 22

<210> SEQ ID NO 169
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 169
gttgtgatgc caaagggc 18

<210> SEQ ID NO 170

<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 170
caagcgtgca ttggactg 18

<210> SEQ ID NO 171
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 171
tccaatcttg ccaccacc 18

<210> SEQ ID NO 172
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 172
ttccagcact ttgggagc 18

<210> SEQ ID NO 173
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 173
ccaggttttg caccaagg 18

<210> SEQ ID NO 174
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 174
cctcccagac ccctctgt 18

<210> SEQ ID NO 175
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 175
cactgatgtg cctgctgc 18

<210> SEQ ID NO 176
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 176
tgaggcgcag ctttctct 18

<210> SEQ ID NO 177
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 177
taccatccca gggaagca 18

<210> SEQ ID NO 178
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 178
gcaggttggc agcagtct 18

<210> SEQ ID NO 179
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 179
gcttccgaaa tctgccaa 18

<210> SEQ ID NO 180
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 180
cgccatccat ggagttct 18

<210> SEQ ID NO 181
<211> LENGTH: 18
<212> TYPE: DNA
<213> ORGANISM: Artificial Sequence
<220> FEATURE:

<221> NAME/KEY: source
<223> OTHER INFORMATION: /note="Description of Artificial Sequence: Synthetic primer"

<400> SEQUENCE: 181
ggccatcaaa gaagccct 18

<210> SEQ ID NO 182
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 182
gctgtcatgt tcaaggcg 18

<210> SEQ ID NO 183
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 183
gttgaccccg cactgtct 18

<210> SEQ ID NO 184
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 184
attccgagga ggctttgg 18

<210> SEQ ID NO 185
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 185
cctgtggacc cagatgct 18

<210> SEQ ID NO 186
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 186
gacggagttc agctccca 18

<210> SEQ ID NO 187
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 187
gattctgaga aaggagtacg ca 22

<210> SEQ ID NO 188
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 188
gccagtgttc cagttgcc 18

<210> SEQ ID NO 189
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 189
gcgagagagc gagtgagc 18

<210> SEQ ID NO 190
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 190
ccacggaagc tagcctga 18

<210> SEQ ID NO 191
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 191
atggagcaga cgcaatcc 18

<210> SEQ ID NO 192
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 192
aaaggccgaa gttttggg 18

<210> SEQ ID NO 193
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 193
gtgggcatct gtggtggt 18

<210> SEQ ID NO 194
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 194
tggagcggga gcatagtc 18

<210> SEQ ID NO 195
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 195
cagagtccca ctggaccg 18

<210> SEQ ID NO 196
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 196
aggcacaact gtcagggc 18

<210> SEQ ID NO 197
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 197
gcagccaact caaaaggc 18

<210> SEQ ID NO 198
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 198
gtgatgctcc ctggttgg 18

<210> SEQ ID NO 199
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 199
tcagacaggt tccagccc 18

<210> SEQ ID NO 200
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 200
tcttctcgct cagacgca 18

<210> SEQ ID NO 201
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 201
ccttcagccc cagtggta 18

<210> SEQ ID NO 202
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 202
agctcagcct gggttcct 18

<210> SEQ ID NO 203
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 203
aagggacact tcccggag 18

<210> SEQ ID NO 204
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 204
tttcctgcag ttccccag 18

<210> SEQ ID NO 205
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 205
cggtgcggga actatcc 17

<210> SEQ ID NO 206
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 206
catttggtca agaactccct g 21

<210> SEQ ID NO 207
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 207
gaaggagctg tcaggcca 18

<210> SEQ ID NO 208
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 208
gcatccaggg atgtggac 18

<210> SEQ ID NO 209
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 209
gtccttccaa tgaccccc 18

<210> SEQ ID NO 210
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 210
cctccagggc caagaatag 19

<210> SEQ ID NO 211
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 211
gtctgccgga gcatcagt 18

<210> SEQ ID NO 212
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 212
taatgtggag ggaggccc 18

<210> SEQ ID NO 213
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 213
caaggagatg gcgtggat 18

<210> SEQ ID NO 214
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 214
tgggatcagc aactgggt 18

<210> SEQ ID NO 215
<211> LENGTH: 18
<212> TYPE: DNA

<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 215
tggccctctg gtctcaac 18

<210> SEQ ID NO 216
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 216
tttcatactc agcccgacg 19

<210> SEQ ID NO 217
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 217
aagaactttt gggccgct 18

<210> SEQ ID NO 218
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 218
gcactgtggc tgggagtt 18

<210> SEQ ID NO 219
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 219
gctgaaaacc caaaatacga 20

<210> SEQ ID NO 220
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 220
acttcactgc tgtgcccc 18

<210> SEQ ID NO 221
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 221
atcaggacgc gcaaacat 18

<210> SEQ ID NO 222
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 222
gacgtggaac ggttgagg 18

<210> SEQ ID NO 223
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 223
cactgcaagg cagcagg 17

<210> SEQ ID NO 224
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 224
cgtttggttt gttgttgttt tg 22

<210> SEQ ID NO 225
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 225
tcggacggca atttcact 18

<210> SEQ ID NO 226
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic primer"

<400> SEQUENCE: 226
gttgctggag atgctggg 18

<210> SEQ ID NO 227
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 227
actgatcgtc gcgtctcc 18

<210> SEQ ID NO 228
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 228
ttggtctgtc ttccaagtgc t 21

<210> SEQ ID NO 229
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 229
ctgaccaccc gatgcagt 18

<210> SEQ ID NO 230
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 230
tccaggtaac gctgcaca 18

<210> SEQ ID NO 231
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 231
ggctgcagct gaacatca 18

<210> SEQ ID NO 232
<211> LENGTH: 20

<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 232
aagctgagcc attagccaaa 20

<210> SEQ ID NO 233
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 233
aggcaggagg atggcttc 18

<210> SEQ ID NO 234
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 234
tcatgggggt ggaggac 17

<210> SEQ ID NO 235
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 235
ggtttgccca tcaactcg 18

<210> SEQ ID NO 236
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 236
ggatccattt gggccttt 18

<210> SEQ ID NO 237
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 237
gcaaaggaca ggactggg 18

<210> SEQ ID NO 238
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 238
tttgacaccc tccccaaa 18

<210> SEQ ID NO 239
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 239
gcaggcaaat gcctcaac 18

<210> SEQ ID NO 240
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 240
gtggccattg tgcagaca 18

<210> SEQ ID NO 241
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 241
ctcgagcagc tgggacc 17

<210> SEQ ID NO 242
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 242
ccagcaggga ccctcttt 18

<210> SEQ ID NO 243
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 243
tcattcgcta tgcagcca 18

<210> SEQ ID NO 244
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 244
ggcctgttgt gccaattc 18

<210> SEQ ID NO 245
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 245
aagaacccca aagcaggg 18

<210> SEQ ID NO 246
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 246
cagcgatctc tgagggga 18

<210> SEQ ID NO 247
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 247
tctccactct ggccaaca 18

<210> SEQ ID NO 248
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 248
ctgcatccag gtcaggaga 19

<210> SEQ ID NO 249

<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 249
tggcctagtc tccccgat 18

<210> SEQ ID NO 250
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 250
cgagcggttt gcactgt 17

<210> SEQ ID NO 251
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 251
ctgtggaaga tgccaggg 18

<210> SEQ ID NO 252
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 252
gtggttggtg gcagtggt 18

<210> SEQ ID NO 253
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 253
gttcgtggaa ccccagtg 18

<210> SEQ ID NO 254
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 254
tccccttgac tctggctg 18

<210> SEQ ID NO 255
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 255
ggccacagag cttcagga 18

<210> SEQ ID NO 256
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 256
ccagctcact cttgggga 18

<210> SEQ ID NO 257
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 257
tctgactctt gcaggccc 18

<210> SEQ ID NO 258
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 258
tggcacaatc caaagcct 18

<210> SEQ ID NO 259
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 259
actatgcgtg ggctggag 18

<210> SEQ ID NO 260
<211> LENGTH: 18
<212> TYPE: DNA
<213> ORGANISM: Artificial Sequence
<220> FEATURE:

<221> NAME/KEY: source
<223> OTHER INFORMATION: /note="Description of Artificial Sequence:
      Synthetic primer"

<400> SEQUENCE: 260
gcaggagctg gtgcaagt 18

<210> SEQ ID NO 261
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 261
gcctccagcc catcctat 18

<210> SEQ ID NO 262
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 262
tgagggattt attcgggga 19

<210> SEQ ID NO 263
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 263
tacgagtgca cctgccaa 18

<210> SEQ ID NO 264
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 264
gcagcgtcct ggaatgtc 18

<210> SEQ ID NO 265
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 265
atcacgtgac cacagccc 18

```
<210> SEQ ID NO 266
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 266

ctctgatacc ctgccgga                                                18


<210> SEQ ID NO 267
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 267

tctgggcttc tcctcctg                                                18


<210> SEQ ID NO 268
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 268

tccttttgcc agttcctcc                                               19


<210> SEQ ID NO 269
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 269

ggggctgagc tgcagagt                                                18


<210> SEQ ID NO 270
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 270

tggtgttcag ctgcagga                                                18


<210> SEQ ID NO 271
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

<400> SEQUENCE: 271
aaggctggcc tcgaactt 18

<210> SEQ ID NO 272
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 272
gggcagggaa ccaaactt 18

<210> SEQ ID NO 273
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 273
tggtgacata catccttgcc 20

<210> SEQ ID NO 274
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 274
tgtgtggcat tggtcagc 18

<210> SEQ ID NO 275
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 275
gcttcaccca gaacaccg 18

<210> SEQ ID NO 276
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 276
cccatatgtt ggtgccgt 18

<210> SEQ ID NO 277
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 277
tgccgaatac accaagca 18

<210> SEQ ID NO 278
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 278
tccgccggtt ctttacaa 18

<210> SEQ ID NO 279
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 279
ggggcaggta gttgctca 18

<210> SEQ ID NO 280
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 280
tcgggatcaa ggacacaga 19

<210> SEQ ID NO 281
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 281
ccatcttgga gtgcgagaa 19

<210> SEQ ID NO 282
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 282
gctcagtcag gcccttca 18

<210> SEQ ID NO 283
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 283
tgtgctggcc atatccct 18

<210> SEQ ID NO 284
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 284
aggcacagga gcagttgg 18

<210> SEQ ID NO 285
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 285
agctccacgg ctacatgg 18

<210> SEQ ID NO 286
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 286
cgtttcggag cttcagga 18

<210> SEQ ID NO 287
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 287
caagtgattg ccgcagtg 18

<210> SEQ ID NO 288
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 288
cattggtcat acatgcaggg 20

<210> SEQ ID NO 289
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 289
cggccgatca taggatgt 18

<210> SEQ ID NO 290
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 290
ttccctggga gctgtctg 18

<210> SEQ ID NO 291
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 291
cgaaacaaca gcaaatgcc 19

<210> SEQ ID NO 292
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 292
cggtgaaccg tccttgtc 18

<210> SEQ ID NO 293
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 293
acccgaggtc cagtggta 18

<210> SEQ ID NO 294
<211> LENGTH: 18
<212> TYPE: DNA

<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 294
tctcattccg agggctca 18

<210> SEQ ID NO 295
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 295
tgcaagagag gtttccga 18

<210> SEQ ID NO 296
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 296
gttcccaagg aggtggct 18

<210> SEQ ID NO 297
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 297
agcagaagca cccacagg 18

<210> SEQ ID NO 298
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 298
tcctggcact gctcacaa 18

<210> SEQ ID NO 299
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 299
tggaaaattc tgcgagtgtg 20

<210> SEQ ID NO 300
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 300
ttggcccttg aaacttgg 18

<210> SEQ ID NO 301
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 301
ccctccaaaa gggcctaa 18

<210> SEQ ID NO 302
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 302
ggcaaaaaca aagtcccca 19

<210> SEQ ID NO 303
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 303
agtgcacaga agggctgc 18

<210> SEQ ID NO 304
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 304
ccagcaaatg gagaaatgg 19

<210> SEQ ID NO 305
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic primer"

<400> SEQUENCE: 305
aggacgcctg ctctacca 18

<210> SEQ ID NO 306
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 306
gctgcaaatc tgtcccca 18

<210> SEQ ID NO 307
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 307
cggagaagca gaagcacc 18

<210> SEQ ID NO 308
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 308
actttgggcc cactctga 18

<210> SEQ ID NO 309
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 309
gccgcttaga ggctcatc 18

<210> SEQ ID NO 310
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 310
tgctccagct cgacaatg 18

<210> SEQ ID NO 311
<211> LENGTH: 18

<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 311
tggggtgcca tccagtat 18

<210> SEQ ID NO 312
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 312
attccacatg gctttggc 18

<210> SEQ ID NO 313
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 313
tcagccattt caccaggag 19

<210> SEQ ID NO 314
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 314
taacgttttc gctcccca 18

<210> SEQ ID NO 315
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 315
ggggtctagc ccaattcc 18

<210> SEQ ID NO 316
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 316
gccggggaga gaggttag 18

<210> SEQ ID NO 317
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 317
tggtaagctt tccttctttc c 21

<210> SEQ ID NO 318
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 318
tcatcacatc aggaagggc 19

<210> SEQ ID NO 319
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 319
gcaccccatc ctcagcta 18

<210> SEQ ID NO 320
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 320
caagtccagc tcggtggt 18

<210> SEQ ID NO 321
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 321
taagcacggc tgggacat 18

<210> SEQ ID NO 322
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 322
cagcagagct gcccttgt 18

<210> SEQ ID NO 323
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 323
ctccccagcg attgtcat 18

<210> SEQ ID NO 324
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 324
cagcccaaac cagtcagg 18

<210> SEQ ID NO 325
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 325
gagcgggaac tcaggacc 18

<210> SEQ ID NO 326
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 326
gggaaaatga ccactgcg 18

<210> SEQ ID NO 327
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 327
tgccctaggg gacaaaaa 18

<210> SEQ ID NO 328

<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 328
caagcgggtc tcatgctt 18

<210> SEQ ID NO 329
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 329
tggagcatga atccacacc 19

<210> SEQ ID NO 330
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 330
tgagggtccc atgagtgg 18

<210> SEQ ID NO 331
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 331
ctcaggagat ggagcgga 18

<210> SEQ ID NO 332
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 332
cctcgtcact cccgacac 18

<210> SEQ ID NO 333
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 333
cacggtggtg aaggttcc 18

<210> SEQ ID NO 334
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 334
gaaaggaggg agggagga 18

<210> SEQ ID NO 335
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 335
tgcctgtgct tgctctga 18

<210> SEQ ID NO 336
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 336
gaagaagggc cagaaggg 18

<210> SEQ ID NO 337
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 337
ccgaggagcc tcttagcc 18

<210> SEQ ID NO 338
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 338
gtctggatcg ggagatgc 18

<210> SEQ ID NO 339
<211> LENGTH: 18
<212> TYPE: DNA
<213> ORGANISM: Artificial Sequence
<220> FEATURE:

<221> NAME/KEY: source
<223> OTHER INFORMATION: /note="Description of Artificial Sequence:
Synthetic primer"

<400> SEQUENCE: 339
actgccttca gccaggtg 18

<210> SEQ ID NO 340
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 340
cagcttctca cccaggga 18

<210> SEQ ID NO 341
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 341
cctggagtgg tatcatcgc 19

<210> SEQ ID NO 342
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 342
tgcgttggtt ctgattgtg 19

<210> SEQ ID NO 343
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 343
cacaccatgc tgctcctg 18

<210> SEQ ID NO 344
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 344
ctccttggct ttccacga 18

<210> SEQ ID NO 345
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 345
cagagaaacg cattcctgg 19

<210> SEQ ID NO 346
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 346
agtccaccag ctggctttt 19

<210> SEQ ID NO 347
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 347
tattggccgg cagacttt 18

<210> SEQ ID NO 348
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 348
gcctggcact tacaagcc 18

<210> SEQ ID NO 349
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 349
agggaaggaa gacgccac 18

<210> SEQ ID NO 350
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

```
<400> SEQUENCE: 350

tggccatgta aaagccaaa                                                19


<210> SEQ ID NO 351
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 351

gtctccaacg cccagcta                                                 18


<210> SEQ ID NO 352
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 352

atctcttccc tttgccgc                                                 18


<210> SEQ ID NO 353
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 353

actgctaggg gtcctggg                                                 18


<210> SEQ ID NO 354
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 354

tgagccatag gtctgggc                                                 18


<210> SEQ ID NO 355
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 355

gaagctgttt ggcttcgc                                                 18


<210> SEQ ID NO 356
<211> LENGTH: 18
<212> TYPE: DNA
<213> ORGANISM: Artificial Sequence
```

<220> FEATURE:
<221> NAME/KEY: source
<223> OTHER INFORMATION: /note="Description of Artificial Sequence:
Synthetic primer"

<400> SEQUENCE: 356
tcattcctcc cccagaca 18

<210> SEQ ID NO 357
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 357
tcgaggcgct cacataca 18

<210> SEQ ID NO 358
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 358
cggacaacat ctggctga 18

<210> SEQ ID NO 359
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 359
ctcaactgag cgggcaat 18

<210> SEQ ID NO 360
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 360
agggttgagg cacatgga 18

<210> SEQ ID NO 361
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 361
ccttctccag ctccctcc 18

<210> SEQ ID NO 362
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 362
cctcttggca atgttggg 18

<210> SEQ ID NO 363
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 363
gtaaaggccg gctccagt 18

<210> SEQ ID NO 364
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 364
tttccagtgg aggatgtgc 19

<210> SEQ ID NO 365
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 365
aggtctggcc acaacacc 18

<210> SEQ ID NO 366
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 366
ggccacagtc acgttcaa 18

<210> SEQ ID NO 367
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 367
agggcttcca aggtgctt 18

<210> SEQ ID NO 368
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 368
tgctctttag gctttccagg 20

<210> SEQ ID NO 369
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 369
gaggctgagg ctgctgag 18

<210> SEQ ID NO 370
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 370
atcctgggga cacaccct 18

<210> SEQ ID NO 371
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 371
ggtgctttga gcagttctga 20

<210> SEQ ID NO 372
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 372
gccctgcaca agcaaagt 18

<210> SEQ ID NO 373
<211> LENGTH: 18
<212> TYPE: DNA

<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 373
gcctggctat gggaggat 18

<210> SEQ ID NO 374
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 374
ccgtggacct tccttgtc 18

<210> SEQ ID NO 375
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 375
cctgagccct accaccaa 18

<210> SEQ ID NO 376
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 376
gggcagctct atggaggg 18

<210> SEQ ID NO 377
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 377
cgcgcagtag tctggctc 18

<210> SEQ ID NO 378
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 378
aagatgaggg ccttgggt 18

<210> SEQ ID NO 379
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 379
caacaaaggg cagcaagc 18

<210> SEQ ID NO 380
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 380
ttcaacacaa gggcagagg 19

<210> SEQ ID NO 381
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 381
ttagctggat gagcccca 18

<210> SEQ ID NO 382
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 382
atgttgctgc tgtggtgg 18

<210> SEQ ID NO 383
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 383
gccagacggt agtggtgg 18

<210> SEQ ID NO 384
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic primer"

<400> SEQUENCE: 384
cgtgctgtgt atggctcg 18

<210> SEQ ID NO 385
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 385
gatgacggag ggcaaaga 18

<210> SEQ ID NO 386
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 386
ggggttgagg ctggatct 18

<210> SEQ ID NO 387
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 387
accctggcta tgcacctg 18

<210> SEQ ID NO 388
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 388
gggaagctgg attgagca 18

<210> SEQ ID NO 389
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 389
gagagcgagg accgagtg 18

<210> SEQ ID NO 390
<211> LENGTH: 18

<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 390
ccttccacat cacagccc 18

<210> SEQ ID NO 391
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 391
tgcgacaagg tgcagaaa 18

<210> SEQ ID NO 392
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 392
gagctcgcga tcagaagg 18

<210> SEQ ID NO 393
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 393 gcccettccc accattta 18

<210> SEQ ID NO 394
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 394
ctccccctgc tgctacaa 18

<210> SEQ ID NO 395
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 395
ggctaggcac aaggcaga 18

<210> SEQ ID NO 396
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 396
agcgctccct ctggagat 18

<210> SEQ ID NO 397
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 397
acagcctcgt gtggtggt 18

<210> SEQ ID NO 398
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 398
ggccattggc ttctgcta 18

<210> SEQ ID NO 399
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 399
gcctctatgg cctcacca 18

<210> SEQ ID NO 400
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 400
acttccagga gttggccc 18

<210> SEQ ID NO 401
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 401
tgggaagctg agagtcgc 18

<210> SEQ ID NO 402
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 402
gccttctgcc tttccaca 18

<210> SEQ ID NO 403
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 403
tggttagcgt agggcagg 18

<210> SEQ ID NO 404
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 404
cccatgggga tatgcact 18

<210> SEQ ID NO 405
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 405
atctgtgggc gctctgac 18

<210> SEQ ID NO 406
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 406
ggactgtcaa gatggggc 18

<210> SEQ ID NO 407

<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 407
ttctggcagg gacgaaac 18

<210> SEQ ID NO 408
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 408
tttggtcctg tgccttacaa 20

<210> SEQ ID NO 409
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 409
tgctccccaa aattccaa 18

<210> SEQ ID NO 410
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 410
aggaatgccg tatcgggt 18

<210> SEQ ID NO 411
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 411
accaaccagg actgctgc 18

<210> SEQ ID NO 412
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 412
ccctgtggac aggagcac 18

<210> SEQ ID NO 413
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 413
tcacctggag caatgcaa 18

<210> SEQ ID NO 414
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 414
tggtaccatt ggcatccg 18

<210> SEQ ID NO 415
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 415
tttccctctt ggtggcct 18

<210> SEQ ID NO 416
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 416
tccctcccca caccacta 18

<210> SEQ ID NO 417
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 417
ttgttgggcg acttttgc 18

<210> SEQ ID NO 418
<211> LENGTH: 19
<212> TYPE: DNA
<213> ORGANISM: Artificial Sequence
<220> FEATURE:

<221> NAME/KEY: source
<223> OTHER INFORMATION: /note="Description of Artificial Sequence: Synthetic primer"

<400> SEQUENCE: 418
tggagagttg agggacgaa 19

<210> SEQ ID NO 419
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 419
tgggtgaaca ttcctgcc 18

<210> SEQ ID NO 420
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 420
aaacagcaac cctcaccg 18

<210> SEQ ID NO 421
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 421
tgcaggagag cggattct 18

<210> SEQ ID NO 422
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 422
gaactggctg cgtgcttc 18

<210> SEQ ID NO 423
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 423
cctccgctag aagctccc 18

<210> SEQ ID NO 424
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 424
gctcttacac gagaggccc 19

<210> SEQ ID NO 425
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 425
cgcctgagtg gctgtctt 18

<210> SEQ ID NO 426
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 426
atgtcatgga tggtgccc 18

<210> SEQ ID NO 427
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 427
ctgcttgaat atggatcagc a 21

<210> SEQ ID NO 428
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 428
ccaactagtg caccccgt 18

<210> SEQ ID NO 429
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 429
caatggatgc caacgtttc 19

<210> SEQ ID NO 430
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 430
ccttgccagt ccctgtgt 18

<210> SEQ ID NO 431
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 431
ggcccccgtg gactatac 18

<210> SEQ ID NO 432
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 432
cacacacaca cgcacacg 18

<210> SEQ ID NO 433
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 433
ttgagactgt atcccccagc 20

<210> SEQ ID NO 434
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 434
gcagggtctt caaaggtcag 20

<210> SEQ ID NO 435
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 435
tgggtttcca gttgcagtt 19

<210> SEQ ID NO 436
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 436
gcctttatta aacacctccc tg 22

<210> SEQ ID NO 437
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 437
ccctgggtgt gtgcagtc 18

<210> SEQ ID NO 438
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 438
aaggggttga aaggggtg 18

<210> SEQ ID NO 439
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 439
cccaaaagac tgcatcgg 18

<210> SEQ ID NO 440
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 440
tccacagggt aaggctgaa 19

<210> SEQ ID NO 441
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 441
cgacccccaa tgtaagga 18

<210> SEQ ID NO 442
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 442
tagcccaccc tgatggaa 18

<210> SEQ ID NO 443
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 443
ggtcccctgc agtgtctg 18

<210> SEQ ID NO 444
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 444
cttccgtttt cgtggctg 18

<210> SEQ ID NO 445
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 445
ccatgaccac atggacga 18

<210> SEQ ID NO 446
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 446
ccaagctatc acctcggc 18

<210> SEQ ID NO 447
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 447
actcagcgcc cacttcag 18

<210> SEQ ID NO 448
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 448
gctctgcaaa ggcgttgt 18

<210> SEQ ID NO 449
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 449
gccaaagtcc cctggaat 18

<210> SEQ ID NO 450
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 450
aaggaaggca ggaggagg 18

<210> SEQ ID NO 451
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 451
gggagccttc caaggtgt 18

<210> SEQ ID NO 452
<211> LENGTH: 18
<212> TYPE: DNA

<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 452
ggcattatag cccctccg 18

<210> SEQ ID NO 453
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 453
cggtggtcct tcgcc 15

<210> SEQ ID NO 454
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 454
tgcagagcca ttcaacaca 19

<210> SEQ ID NO 455
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 455
ggacctcatc agccaagc 18

<210> SEQ ID NO 456
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 456
gcaggtttga gatgccca 18

<210> SEQ ID NO 457
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 457
cggcaatatt gttatccaga a 21

<210> SEQ ID NO 458
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 458
gggcgtcttc ccactttt 18

<210> SEQ ID NO 459
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 459
tgctgtccca gggatgat 18

<210> SEQ ID NO 460
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 460
caaatagccc aggataccca 20

<210> SEQ ID NO 461
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 461
gctggcttgg catcctt 17

<210> SEQ ID NO 462
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 462
ttgatcttct cgccctcg 18

<210> SEQ ID NO 463
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic primer"

<400> SEQUENCE: 463
gatgtggcag ctgtgtgc 18

<210> SEQ ID NO 464
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 464
ttgaagacat cggggctc 18

<210> SEQ ID NO 465
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 465
ttcttgggca gtgaaccc 18

<210> SEQ ID NO 466
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 466
tcgcgggatc atcaactt 18

<210> SEQ ID NO 467
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 467
ctccatgaag ctcagccaa 19

<210> SEQ ID NO 468
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 468
ttgattacgc aggtgcca 18

<210> SEQ ID NO 469
<211> LENGTH: 18

<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 469
aggacttccc ttcacgcc 18

<210> SEQ ID NO 470
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 470
agccaggatt caactttgtg a 21

<210> SEQ ID NO 471
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 471
tgcttttgcc agtgtgacc 19

<210> SEQ ID NO 472
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 472
acgcccaggg agtttaca 18

<210> SEQ ID NO 473
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 473
tgatgtcagc tctgggca 18

<210> SEQ ID NO 474
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 474
tctgcagcga gaaccaaa 18

<210> SEQ ID NO 475
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 475
ggaaggcacc agggatct 18

<210> SEQ ID NO 476
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 476
ctcgtcgcaa gcctctgt 18

<210> SEQ ID NO 477
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 477
tctgccttgt gcctgaca 18

<210> SEQ ID NO 478
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 478
acgggtgcat cagcctaa 18

<210> SEQ ID NO 479
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 479
aggggacctg gactctgg 18

<210> SEQ ID NO 480
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 480
gacaagttgg ggccaatg 18

<210> SEQ ID NO 481
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 481
gtgaccgctt gatgggg 17

<210> SEQ ID NO 482
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 482
gctgtgtcgg ctgatgaa 18

<210> SEQ ID NO 483
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 483
cctggcctct cagttcca 18

<210> SEQ ID NO 484
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 484
agaggccttt cagcaggc 18

<210> SEQ ID NO 485
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 485
agcagccaag tgcggtag 18

<210> SEQ ID NO 486

<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 486
tgccacaagg agaggtcc 18

<210> SEQ ID NO 487
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 487
cctctgaccc gtctccct 18

<210> SEQ ID NO 488
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 488
gcttccagaa gccagggt 18

<210> SEQ ID NO 489
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 489
atgaaaggct atgccccc 18

<210> SEQ ID NO 490
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 490
gtgcacaatg gtggcctt 18

<210> SEQ ID NO 491
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 491
gaccctgcac ctcattgg 18

<210> SEQ ID NO 492
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 492
gaagccagcc acagcaat 18

<210> SEQ ID NO 493
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 493
aggacccagg agagtcgg 18

<210> SEQ ID NO 494
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 494
atctccacag cctgcacc 18

<210> SEQ ID NO 495
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 495
atggggagtc cttctgcc 18

<210> SEQ ID NO 496
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 496
taggccctgc atcagctc 18

<210> SEQ ID NO 497
<211> LENGTH: 18
<212> TYPE: DNA
<213> ORGANISM: Artificial Sequence
<220> FEATURE:

<221> NAME/KEY: source
<223> OTHER INFORMATION: /note="Description of Artificial Sequence:
Synthetic primer"

<400> SEQUENCE: 497
tctgggattt gccatcca 18

<210> SEQ ID NO 498
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 498
gtgcaggaag agcaggga 18

<210> SEQ ID NO 499
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 499
cgagccatgt gggaaaag 18

<210> SEQ ID NO 500
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 500
gaggctgaga gatgggca 18

<210> SEQ ID NO 501
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 501
ttgtaacgca ctttgagatc c 21

<210> SEQ ID NO 502
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 502
cgtgcctttt tggtagcc 18

-continued

<210> SEQ ID NO 503
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 503
aagcgctgtg tccctttg 18

<210> SEQ ID NO 504
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 504
gtgagatgcc ccagtgct 18

<210> SEQ ID NO 505
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 505
aatttgggtc ctctcggc 18

<210> SEQ ID NO 506
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 506
gctcgagatg ccagtgct 18

<210> SEQ ID NO 507
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 507
cctcccacct gggatagc 18

<210> SEQ ID NO 508
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 508
ccgtcacagg aggaccaa 18

<210> SEQ ID NO 509
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 509
caagcatgca aagtctgagc 20

<210> SEQ ID NO 510
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 510
cgttatgagc ggggtttg 18

<210> SEQ ID NO 511
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 511
gcagcagtgg tctggtca 18

<210> SEQ ID NO 512
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 512
tgtcaccaac aggggctt 18

<210> SEQ ID NO 513
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 513
caaggtgctg gagatgcc 18

<210> SEQ ID NO 514
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 514
gcggcccagg ttagagtt 18

<210> SEQ ID NO 515
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 515
ggtgcgttcc tcataccg 18

<210> SEQ ID NO 516
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 516
aggccaggat gacgatgt 18

<210> SEQ ID NO 517
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 517
gaggtagagg cctgggga 18

<210> SEQ ID NO 518
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 518
tttaagctct gccgcctc 18

<210> SEQ ID NO 519
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 519
cgatgtcgtg gtctccct 18

<210> SEQ ID NO 520
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 520
gtcctgctgc agctcctc 18

<210> SEQ ID NO 521
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 521
ggacccagtc caaaccct 18

<210> SEQ ID NO 522
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 522
cggcaatcag gaccgtat 18

<210> SEQ ID NO 523
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 523
aacaagcctt tcaggggg 18

<210> SEQ ID NO 524
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 524
agagatcttg gcccagcc 18

<210> SEQ ID NO 525
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 525
tgccagtgtg ctccagaa 18

<210> SEQ ID NO 526
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 526
ctgtgcacaa agccatgc 18

<210> SEQ ID NO 527
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 527
cgccaagatt tccgtga 17

<210> SEQ ID NO 528
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 528
tccccgattt cttccaca 18

<210> SEQ ID NO 529
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 529
gcccactggc cttcattt 18

<210> SEQ ID NO 530
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 530
tgggatatca aagaaactgt ca 22

<210> SEQ ID NO 531
<211> LENGTH: 18
<212> TYPE: DNA

<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 531
gccaaaacgt caccatcc 18

<210> SEQ ID NO 532
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 532
acggccacat cgaagaag 18

<210> SEQ ID NO 533
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 533
tcccttaaaa caggagcca 19

<210> SEQ ID NO 534
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 534
cttccccttg acaagcca 18

<210> SEQ ID NO 535
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 535
gcctgagaaa acggtaggg 19

<210> SEQ ID NO 536
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 536
catgtgcctg atggattttt 20

<210> SEQ ID NO 537
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 537
tgagccatca aaggcaaa 18

<210> SEQ ID NO 538
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 538
gcttgttcac ctggccc 17

<210> SEQ ID NO 539
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 539
acgtgcccct gtctgaag 18

<210> SEQ ID NO 540
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 540
gagtggtggg acagggc 17

<210> SEQ ID NO 541
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 541
gcaaccagga acgcagac 18

<210> SEQ ID NO 542
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic primer"

<400> SEQUENCE: 542
tcttcggcaa gaacctgg 18

<210> SEQ ID NO 543
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 543
ggtggaggca gcagagtg 18

<210> SEQ ID NO 544
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 544
catcctcatc tggcaggc 18

<210> SEQ ID NO 545
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 545
cagtctcagt gcgagcca 18

<210> SEQ ID NO 546
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 546
atgtcctccc ggtcatca 18

<210> SEQ ID NO 547
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 547
acgcccccag agaagagt 18

<210> SEQ ID NO 548
<211> LENGTH: 18

<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 548
ctgggtcagg ggaaggag 18

<210> SEQ ID NO 549
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 549
tcgcatgtac agtgaaagaa ga 22

<210> SEQ ID NO 550
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 550
ctttggaaac gcctccct 18

<210> SEQ ID NO 551
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 551
gccttgattg acatgggg 18

<210> SEQ ID NO 552
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 552
aagaaaaagg gaaaaacaac ca 22

<210> SEQ ID NO 553
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 553
tcccaaccct gtgctcat 18

<210> SEQ ID NO 554
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 554
cagtgtgggc agaactgg 18

<210> SEQ ID NO 555
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 555
tggttatgtg gacgcagc 18

<210> SEQ ID NO 556
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 556
ggaagggact tctgggga 18

<210> SEQ ID NO 557
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 557
gcccctctgg gatcaact 18

<210> SEQ ID NO 558
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 558
ggggtgagtc actggtgg 18

<210> SEQ ID NO 559
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 559
aaatcctccc caagtggc 18

<210> SEQ ID NO 560
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 560
tgcagagttc agggaggg 18

<210> SEQ ID NO 561
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 561
ctgggtgcct tggacttg 18

<210> SEQ ID NO 562
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 562
cgcctcatcc aactctgg 18

<210> SEQ ID NO 563
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 563
taccgtgcct cagggaaa 18

<210> SEQ ID NO 564
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 564
ccccggtctt ctgctttt 18

<210> SEQ ID NO 565

<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 565
ttcagcgaga gcagcaaa 18

<210> SEQ ID NO 566
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 566
aaatgcctcc tccttggg 18

<210> SEQ ID NO 567
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 567
tctctcttgc cttgggga 18

<210> SEQ ID NO 568
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 568
ggcccgaaac acctctct 18

<210> SEQ ID NO 569
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 569
gctggacgtt ggaggaaa 18

<210> SEQ ID NO 570
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 570
ctcatccggg gaggagat 18

<210> SEQ ID NO 571
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 571
gtttcccaca ttggctgc 18

<210> SEQ ID NO 572
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 572
agcccgggac tgtctacc 18

<210> SEQ ID NO 573
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 573
tacagagcgc ttgtcccc 18

<210> SEQ ID NO 574
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 574
gccaccatgc catgtttt 18

<210> SEQ ID NO 575
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 575
ccagacgtag ttgggcaga 19

<210> SEQ ID NO 576
<211> LENGTH: 18
<212> TYPE: DNA
<213> ORGANISM: Artificial Sequence
<220> FEATURE:

<221> NAME/KEY: source
<223> OTHER INFORMATION: /note="Description of Artificial Sequence:
Synthetic primer"

<400> SEQUENCE: 576
tgctgctggc agttggta 18

<210> SEQ ID NO 577
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 577
ctgaaagagc ctcacggc 18

<210> SEQ ID NO 578
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 578
ccatcatgca ctctggga 18

<210> SEQ ID NO 579
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 579
ttctggtgct tgtctcactg a 21

<210> SEQ ID NO 580
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 580
cagtatgttc ggcttcccat tc 22

<210> SEQ ID NO 581
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 581
gacgactcct ttcagaccaa gt 22

<210> SEQ ID NO 582
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 582
aaattttctc catcataagc aacc 24

<210> SEQ ID NO 583
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 583
gcatcgcggt caatagtagg 20

<210> SEQ ID NO 584
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 584
caccgttgat caccagctt 19

<210> SEQ ID NO 585
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 585
tcctgtcacg aaacaacagc 20

<210> SEQ ID NO 586
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 586
acggaatcag gatgacttgc 20

<210> SEQ ID NO 587
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 587
tcccatgggc aggaatatag 20

<210> SEQ ID NO 588
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 588
ccattggctt cagaaagagg 20

<210> SEQ ID NO 589
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 589
aagtgtaacc actgcgacag g 21

<210> SEQ ID NO 590
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 590
tcttcatatg gagcgcaaga 20

<210> SEQ ID NO 591
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 591
catggacccc aactgctc 18

<210> SEQ ID NO 592
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 592
agcaggagca gcagcttt 18

<210> SEQ ID NO 593
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 593
ctgctgtgag ggaagtgtat ga 22

<210> SEQ ID NO 594
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 594
cgagcagtct gcctagcttt 20

<210> SEQ ID NO 595
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 595
agccctcctg tggtgtgata 20

<210> SEQ ID NO 596
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 596
tggtcttggg acttccatgt 20

<210> SEQ ID NO 597
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 597
gcttcgggac tggtagcc 18

<210> SEQ ID NO 598
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 598
gcggcttgat atcctcagtg 20

<210> SEQ ID NO 599
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 599
ccagtgcagg acctcatttt 20

<210> SEQ ID NO 600
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 600
ggtctccaac atgcctctct 20

<210> SEQ ID NO 601
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 601
tggagcaaca tgtggaactc 20

<210> SEQ ID NO 602
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 602
cagcagccgg ttaccaag 18

<210> SEQ ID NO 603
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 603
ggcaaattca acggcacagt 20

<210> SEQ ID NO 604
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 604
agatggtgat gggcttccc 19

<210> SEQ ID NO 605
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 605
atgatggctt ggccagtg 18

<210> SEQ ID NO 606
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 606
ccattttctc caacatccaa tc 22

<210> SEQ ID NO 607
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 607
gatactggaa aagtcaagtc atcg 24

<210> SEQ ID NO 608
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 608
aatgggtgga gacaaaaatg a 21

<210> SEQ ID NO 609
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 609
cagagccaca tgctcctaga 20

<210> SEQ ID NO 610
<211> LENGTH: 20
<212> TYPE: DNA

<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 610
gtccagctgg tcctttgttt 20

<210> SEQ ID NO 611
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 611
cgaaactcca gaacccaaga 20

<210> SEQ ID NO 612
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 612
aatggtgaca cttggcaaga c 21

<210> SEQ ID NO 613
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 613
tgcagaatgg gagatgaatt t 21

<210> SEQ ID NO 614
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 614
ggcactattc cggtcatcc 19

<210> SEQ ID NO 615
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 615
cctagtgctg catgaggaga 20

<210> SEQ ID NO 616
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 616
tcttcctcat cttcttgctc ttc 23

<210> SEQ ID NO 617
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 617
cagcattagc ctggctcagt a 21

<210> SEQ ID NO 618
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 618
atggatgggt ctgctctgtt 20

<210> SEQ ID NO 619
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 619
gttcatccat gtggctcaga 20

<210> SEQ ID NO 620
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 620
tcacagccat cagcgtgt 18

<210> SEQ ID NO 621
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic primer”

<400> SEQUENCE: 621
atggcgttgc tgtctctagg 20

<210> SEQ ID NO 622
<211> LENGTH: 19
<212> TYPE: DNA
<213> ORGANISM: Artificial Sequence
<220> FEATURE:
<221> NAME/KEY: source
<223> OTHER INFORMATION: /note=“Description of Artificial Sequence: Synthetic primer”

<400> SEQUENCE: 622
cttcccaacc tggatgagc 19

<210> SEQ ID NO 623
<211> LENGTH: 20
<212> TYPE: DNA
<213> ORGANISM: Artificial Sequence
<220> FEATURE:
<221> NAME/KEY: source
<223> OTHER INFORMATION: /note=“Description of Artificial Sequence: Synthetic primer”

<400> SEQUENCE: 623
gcagcacaac atacggaaaa 20

<210> SEQ ID NO 624
<211> LENGTH: 21
<212> TYPE: DNA
<213> ORGANISM: Artificial Sequence
<220> FEATURE:
<221> NAME/KEY: source
<223> OTHER INFORMATION: /note=“Description of Artificial Sequence: Synthetic primer”

<400> SEQUENCE: 624
tctgtacggg atcttcttgg a 21

<210> SEQ ID NO 625
<211> LENGTH: 22
<212> TYPE: DNA
<213> ORGANISM: Artificial Sequence
<220> FEATURE:
<221> NAME/KEY: source
<223> OTHER INFORMATION: /note=“Description of Artificial Sequence: Synthetic primer”

<400> SEQUENCE: 625
ctcagagcaa gagaaagcac tg 22

<210> SEQ ID NO 626
<211> LENGTH: 23
<212> TYPE: DNA
<213> ORGANISM: Artificial Sequence
<220> FEATURE:
<221> NAME/KEY: source
<223> OTHER INFORMATION: /note=“Description of Artificial Sequence: Synthetic primer”

<400> SEQUENCE: 626
cgttgatgaa ccagttacag acc 23

<210> SEQ ID NO 627
<211> LENGTH: 20

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 627

tccctgaagg atgtgcctac                                                   20


<210> SEQ ID NO 628
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 628

aagggttttc ccgtttgc                                                     18


<210> SEQ ID NO 629
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 629

gccatcaatg gattccctaa                                                   20


<210> SEQ ID NO 630
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 630

catttggacg tgatatagac atgc                                              24


<210> SEQ ID NO 631
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 631

cttcaaggat aagggcgaca                                                   20


<210> SEQ ID NO 632
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 632
```

gacagattgt ggcgaattga 20

<210> SEQ ID NO 633
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 633
ccacagaagg agagtcaagg a 21

<210> SEQ ID NO 634
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 634
gtgttttcct ggggatgct 19

<210> SEQ ID NO 635
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 635
gagctgggcc attcacac 18

<210> SEQ ID NO 636
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 636
tccatgtctt gggatctgg 19

<210> SEQ ID NO 637
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 637
gggaagttta ttcgcttgaa ga 22

<210> SEQ ID NO 638
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 638
atctcccagc ctcccatt 18

<210> SEQ ID NO 639
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 639
tggccttgtt agaccgtga 19

<210> SEQ ID NO 640
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 640
aagtatttct ggcagtcctc ctc 23

<210> SEQ ID NO 641
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 641
gctctttgtt ccccagcat 19

<210> SEQ ID NO 642
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 642
ctaccacgat gaccacgatt t 21

<210> SEQ ID NO 643
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 643
agtcttacgg aaatgaaaaa cga 23

<210> SEQ ID NO 644

<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 644
ccaaccactg cccataagat 20

<210> SEQ ID NO 645
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 645
gaccctggta acaccacagg 20

<210> SEQ ID NO 646
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 646
tcacgacgtc atgccaag 18

<210> SEQ ID NO 647
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 647
ggaaataacg gtgaaggtgc t 21

<210> SEQ ID NO 648
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 648
catgtcaaac gtgagcgact 20

<210> SEQ ID NO 649
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 649
cgttttgcaa tgcagacgta 20

<210> SEQ ID NO 650
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 650
ggaatccacc tccttctcg 19

<210> SEQ ID NO 651
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 651
tcctcctcag accgctttt 19

<210> SEQ ID NO 652
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 652
cctggttcat catcgctaat c 21

<210> SEQ ID NO 653
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 653
gaacttccgc cagcttcc 18

<210> SEQ ID NO 654
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 654
ctggtaaggc gtccagtaat ct 22

<210> SEQ ID NO 655
<211> LENGTH: 20
<212> TYPE: DNA
<213> ORGANISM: Artificial Sequence
<220> FEATURE:

<221> NAME/KEY: source
<223> OTHER INFORMATION: /note="Description of Artificial Sequence:
Synthetic primer"

<400> SEQUENCE: 655
ctgcacacct ctcaatgcag 20

<210> SEQ ID NO 656
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 656
ggaagcggta gtgtacagag gt 22

<210> SEQ ID NO 657
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 657
tgggatctgt catcgtgct 19

<210> SEQ ID NO 658
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 658
atcaccatgt ttctcttgat cg 22

<210> SEQ ID NO 659
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 659
acagcacctt atggctctct g 21

<210> SEQ ID NO 660
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 660
atggggtggc atcatgtagt 20

<210> SEQ ID NO 661
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 661
ccagcaagac attgatgacc 20

<210> SEQ ID NO 662
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 662
gatcttgcct tctccagtgc 20

<210> SEQ ID NO 663
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 663
cctgttccag gctattctgt tc 22

<210> SEQ ID NO 664
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 664
tcatggtctt tcccccaag 19

<210> SEQ ID NO 665
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 665
aggaaccctc cgaagactat g 21

<210> SEQ ID NO 666
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 666
ttcctcctgt atggcttgct 20

<210> SEQ ID NO 667
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 667
ttgcagagat ggatactatg aagc 24

<210> SEQ ID NO 668
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 668
caccgaatac ccaaattttg aa 22

<210> SEQ ID NO 669
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 669
ggagagacct tccatgtgct 20

<210> SEQ ID NO 670
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 670
aagacaaagc tatggtcctg gt 22

<210> SEQ ID NO 671
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 671
aagatcaagc tggggcacta 20

<210> SEQ ID NO 672
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 672
catgggacag cggtcatac 19

<210> SEQ ID NO 673
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 673
ccctacgacc ctaagtcaag c 21

<210> SEQ ID NO 674
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 674
tgtggctgtg catgatagtg 20

<210> SEQ ID NO 675
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 675
tacctgctgg ctggatgg 18

<210> SEQ ID NO 676
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 676
cacagcctcg gcatatttct 20

<210> SEQ ID NO 677
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 677
tgaaatgctt taacgacctc ag 22

<210> SEQ ID NO 678
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 678
gtggcttgaa gtcgacacct 20

<210> SEQ ID NO 679
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 679
gcactagaca aagttcacct gaga 24

<210> SEQ ID NO 680
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 680
cgctatccac atcaaagcaa 20

<210> SEQ ID NO 681
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 681
ggagtgaccc cgtcatctt 19

<210> SEQ ID NO 682
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 682
aggagcagca gcatgtgag 19

<210> SEQ ID NO 683
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 683
gagccagatc ctccctgact 20

<210> SEQ ID NO 684
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 684
ggcatatccg gtcaccagt 19

<210> SEQ ID NO 685
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 685
caaagcgaga gaccagagga 20

<210> SEQ ID NO 686
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 686
aagtggactt tggcttggtg 20

<210> SEQ ID NO 687
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 687
gatcgtaggc aacaccaagg 20

<210> SEQ ID NO 688
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 688
cttcaggatg cctgcaca 18

<210> SEQ ID NO 689
<211> LENGTH: 19
<212> TYPE: DNA

<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 689
catgctctgg caaaaatcc 19

<210> SEQ ID NO 690
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 690
actcgaacac cctggtatgg 20

<210> SEQ ID NO 691
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 691
cccagaccgc agtatccat 19

<210> SEQ ID NO 692
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 692
gctccaggtc tcgcttctt 19

<210> SEQ ID NO 693
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 693
gtgctcccga caaacgtatc 20

<210> SEQ ID NO 694
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 694
cccattcctc agcatctttg 20

<210> SEQ ID NO 695
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 695
cgagctggtc tttcaagtca 20

<210> SEQ ID NO 696
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 696
ctggctgccg tgaacaat 18

<210> SEQ ID NO 697
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 697
tgacgaggtt ccagaggtg 19

<210> SEQ ID NO 698
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 698
tgcagaggtg cacatagtct g 21

<210> SEQ ID NO 699
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 699
acgccactgt cgcttttc 18

<210> SEQ ID NO 700
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic primer"

<400> SEQUENCE: 700
gcaaacagct cgaaggagac 20

<210> SEQ ID NO 701
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 701
tgggatgact aggctggaga 20

<210> SEQ ID NO 702
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 702
agtggatcat gggctttgag 20

<210> SEQ ID NO 703
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 703
cggcagtcaa cacaaacaa 19

<210> SEQ ID NO 704
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 704
tcaggggaac tagtccatgc 20

<210> SEQ ID NO 705
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 705
agaaccagcc accttcacac 20

<210> SEQ ID NO 706
<211> LENGTH: 20

<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 706
gtgttgaaga aagggccagt 20

<210> SEQ ID NO 707
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 707
ctcgacccgt ccttcactc 19

<210> SEQ ID NO 708
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 708
ttgactctcc cttctgaatc ttct 24

<210> SEQ ID NO 709
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 709
tccctcagaa gcacttgacc 20

<210> SEQ ID NO 710
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 710
gagttctgct tgctggggta 20

<210> SEQ ID NO 711
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 711
ggggcagtga aagcctct                                             18

<210> SEQ ID NO 712
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 712
gcttttcact atagcccagg ag                                        22

<210> SEQ ID NO 713
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 713
aatatcaata acgactggcg tgt                                       23

<210> SEQ ID NO 714
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 714
catgtttgcc tctggccta                                            19

<210> SEQ ID NO 715
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 715
ttacgtgtga aggctgcaag                                           20

<210> SEQ ID NO 716
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 716
ggagtaggtg gcattgctct                                           20

<210> SEQ ID NO 717
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 717
gagaaagaga cgtccccaca 20

<210> SEQ ID NO 718
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 718
tcaaagctct tgtaggagta gaagc 25

<210> SEQ ID NO 719
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 719
tctccacgag cttcacattg 20

<210> SEQ ID NO 720
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 720
gaccaccaag ggcagagac 19

<210> SEQ ID NO 721
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 721
gaagatcaca tcagcatctc ca 22

<210> SEQ ID NO 722
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 722
caggattcac acttccaacc t 21

<210> SEQ ID NO 723

<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 723
atccctccac cctatgacaa 20

<210> SEQ ID NO 724
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 724
gccccaggta agcaaactt 19

<210> SEQ ID NO 725
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 725
ctggggttgc tgcttctg 18

<210> SEQ ID NO 726
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 726
agatgtttgg ttgcagtaaa tctg 24

<210> SEQ ID NO 727
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 727
gacagaacca ggcgtcca 18

<210> SEQ ID NO 728
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 728
agctcagaag ggaattcaga tg 22

<210> SEQ ID NO 729
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 729
tgtgctcaca atggagtata agg 23

<210> SEQ ID NO 730
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 730
ctcaggagga ggatgctgat 20

<210> SEQ ID NO 731
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 731
agccaaccat gctcaacttc 20

<210> SEQ ID NO 732
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 732
ggcttttcag aaattagttc catt 24

<210> SEQ ID NO 733
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 733
ttcctctccc gaatttttca 20

<210> SEQ ID NO 734
<211> LENGTH: 20
<212> TYPE: DNA
<213> ORGANISM: Artificial Sequence
<220> FEATURE:

<221> NAME/KEY: source
<223> OTHER INFORMATION: /note="Description of Artificial Sequence:
      Synthetic primer"

<400> SEQUENCE: 734
ccacggagca tttaacaagg 20

<210> SEQ ID NO 735
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 735
catgatggac ttggagttgc 20

<210> SEQ ID NO 736
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 736
cctccaaagg atgtcaatca a 21

<210> SEQ ID NO 737
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 737
acagacttca acttcctcat ggt 23

<210> SEQ ID NO 738
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 738
ctgtcagcaa gcatcacctt 20

<210> SEQ ID NO 739
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 739
ctccgtgcta cccactcact 20

<210> SEQ ID NO 740
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 740
atgacggtga ccagagtgc 19

<210> SEQ ID NO 741
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 741
atggatccca gcagcaag 18

<210> SEQ ID NO 742
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 742
ccagtgttat agccgaactg c 21

<210> SEQ ID NO 743
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 743
tgttggagga cttagaagat ctaacc 26

<210> SEQ ID NO 744
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 744
aggccagctg tactctttgg 20

<210> SEQ ID NO 745
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 745
gccagcagtc atgatgaaaa 20

<210> SEQ ID NO 746
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 746
tatcacaata cgggcaggtg 20

<210> SEQ ID NO 747
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 747
aacagctttc gatgaagcca t 21

<210> SEQ ID NO 748
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 748
tgggtatccg atgtccacaa t 21

<210> SEQ ID NO 749
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 749
acacacctgt gcaagaagca 20

<210> SEQ ID NO 750
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 750
gctcttgttg gttgggaatc 20

<210> SEQ ID NO 751
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 751
tgagagccat gtctgtgacc 20

<210> SEQ ID NO 752
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 752
ctcctgcagc ctcatcttg 19

<210> SEQ ID NO 753
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 753
gagtggagtc ctagcatcac g 21

<210> SEQ ID NO 754
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 754
cagtggaagg cgctgtatc 19

<210> SEQ ID NO 755
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 755
tcccacttga aagcacatca 20

<210> SEQ ID NO 756
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 756
acttcttgca aaacgccact 20

<210> SEQ ID NO 757
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 757
gaatctgagg accggatcg 19

<210> SEQ ID NO 758
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 758
tgggaaagta caacaaatct cca 23

<210> SEQ ID NO 759
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 759
ctggacccca tggacatc 18

<210> SEQ ID NO 760
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 760
aggatgactg cacacattgc 20

<210> SEQ ID NO 761
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 761
tggctaccag tatctccgtg t 21

<210> SEQ ID NO 762
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 762
tggtaaacgc tgctgatgtc 20

<210> SEQ ID NO 763
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 763
ttcaacgacc ttcgattcgt 20

<210> SEQ ID NO 764
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 764
ttggtgaaca cggtgattgt 20

<210> SEQ ID NO 765
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 765
agagaagcag tggctcaagg 20

<210> SEQ ID NO 766
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 766
atttcttctg ccggacctc 19

<210> SEQ ID NO 767
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 767
ttccctcagg gctatgacac 20

<210> SEQ ID NO 768
<211> LENGTH: 19
<212> TYPE: DNA

<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 768
ctgtcgctga cctcctgac 19

<210> SEQ ID NO 769
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 769
ttcacgacac accagatcct 20

<210> SEQ ID NO 770
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 770
tgagcatctt gttacccttg c 21

<210> SEQ ID NO 771
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 771
ttctggtgct tgtctcactg a 21

<210> SEQ ID NO 772
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 772
cagtatgttc ggcttcccat tc 22

<210> SEQ ID NO 773
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 773
ccagagcttg accatcatca g 21

<210> SEQ ID NO 774
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 774
tcctttacaa atcatacagg actgg 25

<210> SEQ ID NO 775
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 775
cccttcaccc tggtcctt 18

<210> SEQ ID NO 776
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 776
cttcctcgaa ttaggccaga 20

<210> SEQ ID NO 777
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 777
ctcaggatca ctttcagaag agc 23

<210> SEQ ID NO 778
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 778
ggcattcatc tttggaatcg 20

<210> SEQ ID NO 779
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic primer"

<400> SEQUENCE: 779
tgatgcaatc cggatcaa 18

<210> SEQ ID NO 780
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 780
cacgtgtgtt gcgtcagtc 19

<210> SEQ ID NO 781
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 781
aagagaggac cagaccagca 20

<210> SEQ ID NO 782
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 782
ctttttggtg acttctgagt agagaat 27

<210> SEQ ID NO 783
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 783
cagccgaagg gtgctctac 19

<210> SEQ ID NO 784
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 784
aaatctggca gaagatgatg g 21

<210> SEQ ID NO 785
<211> LENGTH: 19

<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 785
agggggagac cagagttcc 19

<210> SEQ ID NO 786
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 786
gccattggag caggtcaa 18

<210> SEQ ID NO 787
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 787
agtctcagcg gcaatacgag 20

<210> SEQ ID NO 788
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 788
gcaaactgga actgcaggat 20

<210> SEQ ID NO 789
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 789
cagctgggga agtcattttt 20

<210> SEQ ID NO 790
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 790
ggcaacagca atatggagaa a 21

<210> SEQ ID NO 791
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 791
ccaatgagac cttgaacaaa act 23

<210> SEQ ID NO 792
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 792
gtaggaggca gtgccatttg 20

<210> SEQ ID NO 793
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 793
cggcatctgc tagctcagt 19

<210> SEQ ID NO 794
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 794
tgccatagtt tcattgttag aagc 24

<210> SEQ ID NO 795
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 795
ggcaaattca acggcacagt 20

<210> SEQ ID NO 796
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 796
agatggtgat gggcttccc 19

<210> SEQ ID NO 797
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 797
agagggtggg gaccaaac 18

<210> SEQ ID NO 798
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 798
tgcttcatgt tgattgtctc g 21

<210> SEQ ID NO 799
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 799
gccccaccga cctactct 18

<210> SEQ ID NO 800
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 800
tgtctgtgtc catactttct tgg 23

<210> SEQ ID NO 801
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 801
agaagaaagg ctcgctcaga 20

<210> SEQ ID NO 802

<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 802
ggctccatcg tgtaatccat 20

<210> SEQ ID NO 803
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 803
gaggacgaag acccaggtg 19

<210> SEQ ID NO 804
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 804
cagtgtatcg cttcctcttc ac 22

<210> SEQ ID NO 805
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 805
tgcagacatg ctgtggatct 20

<210> SEQ ID NO 806
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 806
cttaactgtg agccagcaag c 21

<210> SEQ ID NO 807
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 807
cccaggaaga catacttaga agaaa 25

<210> SEQ ID NO 808
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 808
caacagtagc aaagacttga cca 23

<210> SEQ ID NO 809
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 809
tggcaacaat gaagctatcg 20

<210> SEQ ID NO 810
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 810
atgtcgggac cagtaggaca 20

<210> SEQ ID NO 811
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 811
caagaaatta ggcacctgaa gc 22

<210> SEQ ID NO 812
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 812
acacaggaaa cccagggata 20

<210> SEQ ID NO 813
<211> LENGTH: 22
<212> TYPE: DNA
<213> ORGANISM: Artificial Sequence
<220> FEATURE:

<221> NAME/KEY: source
<223> OTHER INFORMATION: /note="Description of Artificial Sequence: Synthetic primer"

<400> SEQUENCE: 813
tgcctgtttg acaactttga gt 22

<210> SEQ ID NO 814
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 814
gtggtctgca cagtatttgt cat 23

<210> SEQ ID NO 815
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 815
acctcttttc acgggagga 19

<210> SEQ ID NO 816
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 816
tcccacatct cccacattg 19

<210> SEQ ID NO 817
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 817
cagctcctca tcgtgttgg 19

<210> SEQ ID NO 818
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 818
cagaggtggc agaaacactg 20

<210> SEQ ID NO 819
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 819
tccctgaagg atgtgcctac 20

<210> SEQ ID NO 820
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 820
aagggttttc ccgtttgc 18

<210> SEQ ID NO 821
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 821
tgcaagcgca gtatcacag 19

<210> SEQ ID NO 822
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 822
tgacgtaatg cctctgcatc 20

<210> SEQ ID NO 823
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 823
agaaagccga cacccttca 19

<210> SEQ ID NO 824
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 824
cggagagctg cgttctgt 18

<210> SEQ ID NO 825
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 825
ccagagatgg gaggcaaac 19

<210> SEQ ID NO 826
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 826
agtgcattgt atacgccttc c 21

<210> SEQ ID NO 827
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 827
tatgacctca cccgctacct 20

<210> SEQ ID NO 828
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 828
gggccccagg tagttcag 18

<210> SEQ ID NO 829
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 829
cgtttcccta tggcaatgtc 20

<210> SEQ ID NO 830
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 830
cccactgctt ggtggtgt 18

<210> SEQ ID NO 831
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 831
ttgacatagt gctttggtac agg 23

<210> SEQ ID NO 832
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 832
tcgtatgtct ttccatctga agc 23

<210> SEQ ID NO 833
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 833
ccagaagatg gtgtggtgtt t 21

<210> SEQ ID NO 834
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 834
ctgaccctct ccccttgc 18

<210> SEQ ID NO 835
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 835
gccaagagtt tgccatgtg 19

<210> SEQ ID NO 836
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 836
cttgcagttc tcacgagtgc 20

<210> SEQ ID NO 837
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 837
tgacgtgtgg aagctgtaaa gt 22

<210> SEQ ID NO 838
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 838
catttcttcc agcacaaagg t 21

<210> SEQ ID NO 839
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 839
ggaacgcggt tattccagt 19

<210> SEQ ID NO 840
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 840
catcttccaa catggacacc t 21

<210> SEQ ID NO 841
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 841
tagcgaaggt tgcggtagac 20

<210> SEQ ID NO 842
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 842
ggtttatgac tttccatctt ggac 24

<210> SEQ ID NO 843
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 843
tcctcctcag accgctttt 19

<210> SEQ ID NO 844
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 844
cctggttcat catcgctaat c 21

<210> SEQ ID NO 845
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 845
tgcacaagga gtggacga 18

<210> SEQ ID NO 846
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 846
aggaagctgg tctggggtat 20

<210> SEQ ID NO 847
<211> LENGTH: 21
<212> TYPE: DNA

<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 847
cacattcaag gcttcctgtt t 21

<210> SEQ ID NO 848
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 848
gtattggatt ggtacagggt gag 23

<210> SEQ ID NO 849
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 849
ccatcctgtt gttcctcatt g 21

<210> SEQ ID NO 850
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 850
tccacatcta gcattctcac ttg 23

<210> SEQ ID NO 851
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 851
tcgcctccat agtgatagcc 20

<210> SEQ ID NO 852
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 852
ctcgctaggc agaggaagc 19

<210> SEQ ID NO 853
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 853
gcaagtgcac agtcacaggt 20

<210> SEQ ID NO 854
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 854
ttgcctgctg cttttgtgt 19

<210> SEQ ID NO 855
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 855
gctgttgatg gacctacagg a 21

<210> SEQ ID NO 856
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 856
ttcaattctg tggcctgctt 20

<210> SEQ ID NO 857
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 857
ctacagcagt tccctcaaac g 21

<210> SEQ ID NO 858
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic primer"

<400> SEQUENCE: 858
tgtctttcct ggggctcat 19

<210> SEQ ID NO 859
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 859
ctttgtcgtg tatcattggg tatt 24

<210> SEQ ID NO 860
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 860
ttggtagctg gagtttgcag 20

<210> SEQ ID NO 861
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 861
aacggtgctg tgttactgag g 21

<210> SEQ ID NO 862
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 862
cagctgggcc atttactacc 20

<210> SEQ ID NO 863
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 863
cggtgcagtg tcagcttc 18

<210> SEQ ID NO 864
<211> LENGTH: 20

<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 864
ctcccgcaaa caacagagtt 20

<210> SEQ ID NO 865
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 865
ccgccggaga gaaaagtt 18

<210> SEQ ID NO 866
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 866
ctggatcagt gccacacct 19

<210> SEQ ID NO 867
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 867
tacctgctgg ctggatgg 18

<210> SEQ ID NO 868
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 868
cacagcctcg gcatatttct 20

<210> SEQ ID NO 869
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 869
caactgcaga gtttggagga 20

<210> SEQ ID NO 870
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 870
tgtgtctgcc tgtcctgact 20

<210> SEQ ID NO 871
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 871
tcccagaggg aactcatcac 20

<210> SEQ ID NO 872
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 872
ccagaccctc gtcttcctc 19

<210> SEQ ID NO 873
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 873
ctggccctca tcagaacaat 20

<210> SEQ ID NO 874
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 874
ggcgactgct ttaccaaaat c 21

<210> SEQ ID NO 875
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 875
gcctcctctg tcagttgctc 20

<210> SEQ ID NO 876
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 876
aagcagagga tgagcaggaa 20

<210> SEQ ID NO 877
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 877
tcaggagccc accagtaca 19

<210> SEQ ID NO 878
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 878
tctgaaggca gagtcaggag a 21

<210> SEQ ID NO 879
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 879
gacattcatc attgacctcg tg 22

<210> SEQ ID NO 880
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 880
tcacaggaag ggcatttagc 20

<210> SEQ ID NO 881

<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 881
aaacggcctg catctaagg 19

<210> SEQ ID NO 882
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 882
agcagcagta agggcacaat 20

<210> SEQ ID NO 883
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 883
gcaacaaagg gcagcaag 18

<210> SEQ ID NO 884
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 884
agacatcttt aggaaaccaa gacc 24

<210> SEQ ID NO 885
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 885
tacaccttgc gagagaccag 20

<210> SEQ ID NO 886
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 886
ggacgttggt ctcactttcc 20

<210> SEQ ID NO 887
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 887
gattgccagc aacacctatg 20

<210> SEQ ID NO 888
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 888
ttgatttgtt gagagggact tg 22

<210> SEQ ID NO 889
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 889
ccctggctta tcccagact 19

<210> SEQ ID NO 890
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 890
agatgccaga ggagttccaa 20

<210> SEQ ID NO 891
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 891
acgccactgt cgcttttc 18

<210> SEQ ID NO 892
<211> LENGTH: 20
<212> TYPE: DNA
<213> ORGANISM: Artificial Sequence
<220> FEATURE:

-continued

<221> NAME/KEY: source
<223> OTHER INFORMATION: /note="Description of Artificial Sequence: Synthetic primer"

<400> SEQUENCE: 892
gcaaacagct cgaaggagac 20

<210> SEQ ID NO 893
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 893
ctggggaccc tcatcctt 18

<210> SEQ ID NO 894
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 894
tggtgaggaa gccaccat 18

<210> SEQ ID NO 895
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 895
gaacaacagc ctgaacatgg 20

<210> SEQ ID NO 896
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 896
tctgagcgtt cacgttgg 18

<210> SEQ ID NO 897
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 897
gccctagaga gccagaaagg 20

<210> SEQ ID NO 898
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 898
tggtacagga agtaagcagt gg 22

<210> SEQ ID NO 899
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 899
ggttcaaccg gagttactgg 20

<210> SEQ ID NO 900
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 900
tgggcaaaga tgctcagac 19

<210> SEQ ID NO 901
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 901
gacagcatgg acagcgact 19

<210> SEQ ID NO 902
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 902
acgaccaggg tacgctcata 20

<210> SEQ ID NO 903
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 903
agttccggta caaggaatgc 20

<210> SEQ ID NO 904
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 904
acaggagtca gcccatctgt 20

<210> SEQ ID NO 905
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 905
tcctgtggca gtctgtgtct 20

<210> SEQ ID NO 906
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 906
ctacgcagaa cgggatgaag 20

<210> SEQ ID NO 907
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 907
ggacaccttc attcgccata 20

<210> SEQ ID NO 908
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 908
ctgccactta accaggaaca t 21

<210> SEQ ID NO 909
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 909
gtcggcgact aggaggact 19

<210> SEQ ID NO 910
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 910
tccaccatct tttgctaata acc 23

<210> SEQ ID NO 911
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 911
tcaagaagac ggggcagtt 19

<210> SEQ ID NO 912
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 912
ccgaccatcc agtgacct 18

<210> SEQ ID NO 913
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 913
gaggatctct tctgtaccct gaaa 24

<210> SEQ ID NO 914
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 914
ttgttgagat gctttgacac ttg 23

<210> SEQ ID NO 915
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 915
atccctccac cctatgacaa 20

<210> SEQ ID NO 916
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 916
gccccaggta agcaaactt 19

<210> SEQ ID NO 917
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 917
gttggtccca tcctcgtg 18

<210> SEQ ID NO 918
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 918
gattgctgca gtagctgtcg 20

<210> SEQ ID NO 919
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 919
ctgcagatgg agcatgttgt 20

<210> SEQ ID NO 920
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 920
gccatttctg cttcactgg 19

<210> SEQ ID NO 921
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 921
gaagccgaat cagcctagc 19

<210> SEQ ID NO 922
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 922
cagcgttact atcccgctct 20

<210> SEQ ID NO 923
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 923
tggaaccgat cagtgtgagt 20

<210> SEQ ID NO 924
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 924
gggcaggaag atcctattga 20

<210> SEQ ID NO 925
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 925
tgccctaatg gagcaaattt ta 22

<210> SEQ ID NO 926
<211> LENGTH: 21
<212> TYPE: DNA

<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 926
ttatatggcc acgttgggta a 21

<210> SEQ ID NO 927
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 927
agcatggggg agaccttc 18

<210> SEQ ID NO 928
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 928
ggggctgaag aaggacaag 19

<210> SEQ ID NO 929
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 929
tcttgtggcc ctactgtgtg 20

<210> SEQ ID NO 930
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 930
gcaatgcaga atccatcaga 20

<210> SEQ ID NO 931
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 931
tggcatgaac atgaggtcag 20

<210> SEQ ID NO 932
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 932
gccaacatct gagcattcaa 20

<210> SEQ ID NO 933
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 933
tggaaacttt tcctagagtt tgaga 25

<210> SEQ ID NO 934
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 934
tttccccctc ggtttgtaa 19

<210> SEQ ID NO 935
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 935
gatgcttcga cagttcacag g 21

<210> SEQ ID NO 936
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 936
ggaaccccgg aagtatgg 18

<210> SEQ ID NO 937
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic primer"

<400> SEQUENCE: 937
gtctggctcc tttctctaca cag 23

<210> SEQ ID NO 938
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 938
agtgatgagg atgacgaggt c 21

<210> SEQ ID NO 939
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 939
aacagctttc gatgaagcca t 21

<210> SEQ ID NO 940
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 940
tgggtatccg atgtccacaa t 21

<210> SEQ ID NO 941
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 941
cagagcagga gccagagc 18

<210> SEQ ID NO 942
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 942
gccaagttca tcatacacgt tc 22

<210> SEQ ID NO 943
<211> LENGTH: 22

<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 943
gaggctgact tcctgtatgc tt 22

<210> SEQ ID NO 944
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 944
aaccacgacc cgtccttt 18

<210> SEQ ID NO 945
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 945
gatattcgcc attgagatag cc 22

<210> SEQ ID NO 946
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 946
tggtaggtgt ccttgtaaaa ctcc 24

<210> SEQ ID NO 947
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 947
gaggggcttt gagagtgct 19

<210> SEQ ID NO 948
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 948
tgtcctgtgt gcctgtcttg 20

<210> SEQ ID NO 949
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 949
acagaaagtg gcagatgcag 20

<210> SEQ ID NO 950
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 950
tctcgctgga acaatgtcag 20

<210> SEQ ID NO 951
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 951
tgaggccacc attagagagg 20

<210> SEQ ID NO 952
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 952
agcagcagcg agtagtctga 20

<210> SEQ ID NO 953
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 953
ggaccaggga gcagaacc 18

<210> SEQ ID NO 954
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 954
gtccggcaca gggtaaatc 19

<210> SEQ ID NO 955
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 955
cctggacctc caactgaaga 20

<210> SEQ ID NO 956
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 956
tcctctgcaa tgtggcaat 19

<210> SEQ ID NO 957
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 957
tccaatttag gagagccaag c 21

<210> SEQ ID NO 958
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 958
gccgacatca gtccacatag 20

<210> SEQ ID NO 959
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 959
ggaacagctg gaacagtggt 20

<210> SEQ ID NO 960

<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 960
gtagctgccg aaggtgga 18

<210> SEQ ID NO 961
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 961
ggagtgagga agttcggaaa 20

<210> SEQ ID NO 962
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 962
tggattcggg agtctccat 19

<210> SEQ ID NO 963
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 963
ttctggtgct tgtctcactg a 21

<210> SEQ ID NO 964
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 964
cagtatgttc ggcttcccat tc 22

<210> SEQ ID NO 965
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 965
gccttggagt actttgcatc a 21

<210> SEQ ID NO 966
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 966
aaatccgcag ggttgttgta 20

<210> SEQ ID NO 967
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 967
gagacatccg ttccccctac 20

<210> SEQ ID NO 968
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 968
gtcggaactg acccttgaaa 20

<210> SEQ ID NO 969
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 969
aggcagcacg agacctga 18

<210> SEQ ID NO 970
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 970
ggcatctagc acttgacgtt c 21

<210> SEQ ID NO 971
<211> LENGTH: 20
<212> TYPE: DNA
<213> ORGANISM: Artificial Sequence
<220> FEATURE:

-continued

<221> NAME/KEY: source
<223> OTHER INFORMATION: /note="Description of Artificial Sequence:
Synthetic primer"

<400> SEQUENCE: 971
agaccatggg caagaacact 20

<210> SEQ ID NO 972
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 972
gccccaggat ctgataagg 19

<210> SEQ ID NO 973
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 973
gctgctcact gtgaaggaag t 21

<210> SEQ ID NO 974
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 974
tggggaatgc attttaccat 20

<210> SEQ ID NO 975
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 975
gctcccattc ctcgtcac 18

<210> SEQ ID NO 976
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 976
aagggcttgg cagttctgt 19

<210> SEQ ID NO 977
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 977
tacatctgcg aatgactctg c 21

<210> SEQ ID NO 978
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 978
ggctgaggtg gtctagaggt t 21

<210> SEQ ID NO 979
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 979
ggattggaat gcattatagt gaaaa 25

<210> SEQ ID NO 980
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 980
tgctctggcc tgataactga g 21

<210> SEQ ID NO 981
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 981
cagaccagcc tgtgtgattg 20

<210> SEQ ID NO 982
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 982
ccaagacaag tgaaacaaaa ggt 23

<210> SEQ ID NO 983
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 983
tccctcttcg ttctgattgg 20

<210> SEQ ID NO 984
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 984
gcttgcgctt cagaccttt 19

<210> SEQ ID NO 985
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 985
cgccaagcta ctggctaaaa 20

<210> SEQ ID NO 986
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 986
cgtacctcag accttgagat aggt 24

<210> SEQ ID NO 987
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 987
ggcaaattca acggcacagt 20

<210> SEQ ID NO 988
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 988
agatggtgat gggcttccc 19

<210> SEQ ID NO 989
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 989
ccctcctgta cttgttccta ctca 24

<210> SEQ ID NO 990
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 990
gcaatggctt caaccctagt 20

<210> SEQ ID NO 991
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 991
ttcgccactc taatcagtag gac 23

<210> SEQ ID NO 992
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 992
tctggtgtag aaagggaagt gg 22

<210> SEQ ID NO 993
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 993
gaatgacgac agaggttcct g 21

<210> SEQ ID NO 994
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 994
gcccaggttg gcttcttat 19

<210> SEQ ID NO 995
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 995
actttaagca cattgccaag c 21

<210> SEQ ID NO 996
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 996
ggagagaaag gttgtgacga a 21

<210> SEQ ID NO 997
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 997
agtgagcaag ctggacgac 19

<210> SEQ ID NO 998
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 998
gaagccaggt actgggtgtg 20

<210> SEQ ID NO 999
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 999
cgcagccgag taatgtacaa g 21

<210> SEQ ID NO 1000
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1000
aacgggaaat ctgcacctc 19

<210> SEQ ID NO 1001
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1001
gcctctgttt tgctcttcag tt 22

<210> SEQ ID NO 1002
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1002
gcattttgac ggtggatca 19

<210> SEQ ID NO 1003
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1003
taggtcagat cgggtcatcc 20

<210> SEQ ID NO 1004
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1004
gtggggtcct ctttcaagg 19

<210> SEQ ID NO 1005
<211> LENGTH: 18
<212> TYPE: DNA

<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1005
tgcggagagg ctccacta 18

<210> SEQ ID NO 1006
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1006
tgggttgctt tccgtttg 18

<210> SEQ ID NO 1007
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1007
atttcgcttc gggactagc 19

<210> SEQ ID NO 1008
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1008
aacttgctgt gggtgaccat 20

<210> SEQ ID NO 1009
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1009
atccagcagc cttccatct 19

<210> SEQ ID NO 1010
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1010
ggcttagggc tgtgattctg 20

<210> SEQ ID NO 1011
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 1011
tccctgaagg atgtgcctac 20

<210> SEQ ID NO 1012
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 1012
aagggttttc ccgtttgc 18

<210> SEQ ID NO 1013
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 1013
tgatgctctt atgaagcagg ac 22

<210> SEQ ID NO 1014
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 1014
cgtctgtccc ccatctctt 19

<210> SEQ ID NO 1015
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 1015
gaggacacat ggatggaatg t 21

<210> SEQ ID NO 1016
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic primer"

<400> SEQUENCE: 1016
acccttgtgt agcacctcca 20

<210> SEQ ID NO 1017
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1017
caggccactg gtctctcc 18

<210> SEQ ID NO 1018
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1018
tccgtcttac acagttcaag ga 22

<210> SEQ ID NO 1019
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1019
cggagactgc agaaagcag 19

<210> SEQ ID NO 1020
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1020
ggtttggctt cgtctacagc 20

<210> SEQ ID NO 1021
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1021
gaggagcttt tgccactgac 20

<210> SEQ ID NO 1022
<211> LENGTH: 18

<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1022
gctcatccat gccctcag 18

<210> SEQ ID NO 1023
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1023
tgtggggtgg agatctcagt 20

<210> SEQ ID NO 1024
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1024
tctccttcct ggacacatga 20

<210> SEQ ID NO 1025
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1025
atcatcacct ttgccgagtc 20

<210> SEQ ID NO 1026
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1026
tcactgcctt ccttggaaat 20

<210> SEQ ID NO 1027
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1027
gacaagcacg cactgagc 18

<210> SEQ ID NO 1028
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1028
cattttcgca gaagatgacc t 21

<210> SEQ ID NO 1029
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1029
atggattctt tggcgttgtc 20

<210> SEQ ID NO 1030
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1030
tgacggtctt ggcttgct 18

<210> SEQ ID NO 1031
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1031
ggaggaaacc agccaagg 18

<210> SEQ ID NO 1032
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1032
tgccagaatc agtcactttc ac 22

<210> SEQ ID NO 1033
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1033
actctgcaaa caacagaaga cg 22

<210> SEQ ID NO 1034
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1034
tctttttccg gaccatatct gt 22

<210> SEQ ID NO 1035
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1035
tcctcctcag accgctttt 19

<210> SEQ ID NO 1036
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1036
cctggttcat catcgctaat c 21

<210> SEQ ID NO 1037
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1037
ggagacgagt tcaacgaaac tt 22

<210> SEQ ID NO 1038
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1038
aacagttgta agataaccat ttgagg 26

<210> SEQ ID NO 1039

<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1039
tcgtctttca caagtgtctt cag 23

<210> SEQ ID NO 1040
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1040
ttgccagtag attcggtctt c 21

<210> SEQ ID NO 1041
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1041
gagcagcagc tcttgcataa 20

<210> SEQ ID NO 1042
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1042
gatgtcgcag tacaaaagca ac 22

<210> SEQ ID NO 1043
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1043
ttatcaagcc caagcgaag 19

<210> SEQ ID NO 1044
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1044
tggtggtggt ctgacagttc 20

<210> SEQ ID NO 1045
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1045
ctattaaccg tgttcaaaac atgaa 25

<210> SEQ ID NO 1046
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1046
cacctgcaat tccaaaatct ta 22

<210> SEQ ID NO 1047
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1047
ccagtgccaa cagtagtgac a 21

<210> SEQ ID NO 1048
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1048
ttgggagaga aagcttctgg 20

<210> SEQ ID NO 1049
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1049
cttcagcact ttcttccgag a 21

<210> SEQ ID NO 1050
<211> LENGTH: 20
<212> TYPE: DNA
<213> ORGANISM: Artificial Sequence
<220> FEATURE:

<221> NAME/KEY: source
<223> OTHER INFORMATION: /note="Description of Artificial Sequence:
Synthetic primer"

<400> SEQUENCE: 1050
tgtagtgtgg tgacccttgc 20

<210> SEQ ID NO 1051
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 1051
tcggaacaag tcggaggt 18

<210> SEQ ID NO 1052
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 1052
tcagcagctg tatgccaaag 20

<210> SEQ ID NO 1053
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 1053
agcgcaagga gaacgtgt 18

<210> SEQ ID NO 1054
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 1054
gggttcagag ccctcctc 18

<210> SEQ ID NO 1055
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 1055
gagctgcgtc atcacctacc 20

<210> SEQ ID NO 1056
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 1056
tgcaggcctt gtacatcttc t 21

<210> SEQ ID NO 1057
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 1057
ggtggcccta gacaacaaga 20

<210> SEQ ID NO 1058
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 1058
tcaagcagct cacgaatctg 20

<210> SEQ ID NO 1059
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 1059
tacctgctgg ctggatgg 18

<210> SEQ ID NO 1060
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 1060
cacagcctcg gcatatttct 20

<210> SEQ ID NO 1061
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 1061
cccactgctg atagggtgac 20

<210> SEQ ID NO 1062
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1062
gcataggtac ataagaatga actgga 26

<210> SEQ ID NO 1063
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1063
tggttctgaa ggtgacagga 20

<210> SEQ ID NO 1064
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1064
caaccagaga gaagagcaac ac 22

<210> SEQ ID NO 1065
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1065
cggtatcatt tagtaaagag gcaaa 25

<210> SEQ ID NO 1066
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1066
gtagagtgta gaggggcaga cc 22

<210> SEQ ID NO 1067
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 1067
tccgagttcg aggacttttg 20

<210> SEQ ID NO 1068
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 1068
gagcggcaca gtgacttct 19

<210> SEQ ID NO 1069
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 1069
tctaaacagg gccttgcag 19

<210> SEQ ID NO 1070
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 1070
gcagagccct ttttgataat gt 22

<210> SEQ ID NO 1071
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 1071
cagggagagc ttcatctgtg t 21

<210> SEQ ID NO 1072
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 1072
gctgagcttt gagggatgat 20

<210> SEQ ID NO 1073
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 1073
ttggtgaagc caggctagag 20

<210> SEQ ID NO 1074
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 1074
cttcagggca ttgaagtcgt 20

<210> SEQ ID NO 1075
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 1075
caccagatct cggaatggac 20

<210> SEQ ID NO 1076
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 1076
aggagcagca gctcttcttg 20

<210> SEQ ID NO 1077
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 1077
cgctctgctg agatgctg 18

<210> SEQ ID NO 1078
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 1078
ctccactgcc atgatggtt 19

<210> SEQ ID NO 1079
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1079
acttcctgtt tatcacctat gagga 25

<210> SEQ ID NO 1080
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1080
aactcacaga tgcgttgcac 20

<210> SEQ ID NO 1081
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1081
ttacacgaag atgagtgcaa atg 23

<210> SEQ ID NO 1082
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1082
caacactgga taggacttta ttcatc 26

<210> SEQ ID NO 1083
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1083
acgccactgt cgcttttc 18

<210> SEQ ID NO 1084
<211> LENGTH: 20
<212> TYPE: DNA

<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1084
gcaaacagct cgaaggagac 20

<210> SEQ ID NO 1085
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1085
tccagacatt cttcagtgtg ga 22

<210> SEQ ID NO 1086
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1086
tctggttcct ccatttccag 20

<210> SEQ ID NO 1087
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1087
ccagccagca tcctctgt 18

<210> SEQ ID NO 1088
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1088
agcaggttcc tggatctcac 20

<210> SEQ ID NO 1089
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1089
ctacccggtg gaagacctc 19

<210> SEQ ID NO 1090
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1090
aatgttgatc atgccatctc c 21

<210> SEQ ID NO 1091
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1091
tcctttgact tcagcctcca 20

<210> SEQ ID NO 1092
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1092
ccatgtctgg gcacctct 18

<210> SEQ ID NO 1093
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1093
tggtctggtc cctgttcaat 20

<210> SEQ ID NO 1094
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1094
ctgggctcca accacatc 18

<210> SEQ ID NO 1095
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic primer"

<400> SEQUENCE: 1095
tgtgccaagt ctggagatga 20

<210> SEQ ID NO 1096
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 1096
ttctttgttc ttgctcagat cagt 24

<210> SEQ ID NO 1097
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 1097
tggaagaccc ggatagca 18

<210> SEQ ID NO 1098
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 1098
gtctagcgct gggtccac 18

<210> SEQ ID NO 1099
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 1099
caaagccaaa gcacacatca 20

<210> SEQ ID NO 1100
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 1100
agtcgccgct ttaaaaacct 20

<210> SEQ ID NO 1101
<211> LENGTH: 19

<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 1101
aaagcaagag gcccaagtg 19

<210> SEQ ID NO 1102
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 1102
tgcattgctg ctagagttcc 20

<210> SEQ ID NO 1103
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 1103
tcaaccagca ccagacagag 20

<210> SEQ ID NO 1104
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 1104
aaacatcctg taatggcttg tg 22

<210> SEQ ID NO 1105
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 1105
gagacttctc ctcctgactt tcc 23

<210> SEQ ID NO 1106
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 1106
ggacttcagt ccccacacc 19

<210> SEQ ID NO 1107
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1107
atccctccac cctatgacaa 20

<210> SEQ ID NO 1108
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1108
gccccaggta agcaaactt 19

<210> SEQ ID NO 1109
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1109
aactgggtga aaagggctgt 20

<210> SEQ ID NO 1110
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1110
gtccaattcc atcccaaaaa 20

<210> SEQ ID NO 1111
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1111
gcatgtagag gccatcaaag a 21

<210> SEQ ID NO 1112
<211> LENGTH: 19
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic primer"

<400> SEQUENCE: 1112

cgggtctgca cacatgtta                                            19


<210> SEQ ID NO 1113
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1113

tgctcaggag cacctaacaa c                                         21


<210> SEQ ID NO 1114
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1114

tggagatgga ccacactctg                                           20


<210> SEQ ID NO 1115
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1115

tggagtcctg gtgtcattcc                                           20


<210> SEQ ID NO 1116
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1116

tgtgtgttct tcacagaagc att                                       23


<210> SEQ ID NO 1117
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1117

atctggagga actggcaaaa                                           20


<210> SEQ ID NO 1118
```

<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 1118
ttcaagactt caaagagtct gaggta 26

<210> SEQ ID NO 1119
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 1119
tttcctgacc aaactcagca 20

<210> SEQ ID NO 1120
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 1120
tctggatgtt ctggtcgtca 20

<210> SEQ ID NO 1121
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 1121
ggagaaactc ggcgtgtact 20

<210> SEQ ID NO 1122
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 1122
cagccattgc atttacagga 20

<210> SEQ ID NO 1123
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 1123
tctacctagg ctgggtctcc t 21

<210> SEQ ID NO 1124
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 1124
ccgacgggtt ctacagtgag 20

<210> SEQ ID NO 1125
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 1125
ggattttctg catgcctctg 20

<210> SEQ ID NO 1126
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 1126
gacaacagtt ctgggatttt cc 22

<210> SEQ ID NO 1127
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 1127
ctcacgttcg gtgctgtg 18

<210> SEQ ID NO 1128
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 1128
tccctcctcc acattgtca 19

<210> SEQ ID NO 1129
<211> LENGTH: 24
<212> TYPE: DNA
<213> ORGANISM: Artificial Sequence
<220> FEATURE:

<221> NAME/KEY: source
<223> OTHER INFORMATION: /note="Description of Artificial Sequence:
Synthetic primer"

<400> SEQUENCE: 1129
tgcatctgtc tctcttagtc tgct 24

<210> SEQ ID NO 1130
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 1130
tctggaaact ccatactgtc ttca 24

<210> SEQ ID NO 1131
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 1131
aacagctttc gatgaagcca t 21

<210> SEQ ID NO 1132
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 1132
tgggtatccg atgtccacaa t 21

<210> SEQ ID NO 1133
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 1133
gccctctctc tcctcttgct 20

<210> SEQ ID NO 1134
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 1134
gagggtcaga gcccattg 18

<210> SEQ ID NO 1135
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1135
gctgccgtca ttttctgc 18

<210> SEQ ID NO 1136
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1136
tctcactggc ccgtcatc 18

<210> SEQ ID NO 1137
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1137
tccctttcgc tgtgagacat 20

<210> SEQ ID NO 1138
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1138
gggcgtgtat gaaattcgtt 20

<210> SEQ ID NO 1139
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1139
tggctaatgg aaattgaggt g 21

<210> SEQ ID NO 1140
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1140
catcaggacc cacatggtct 20

<210> SEQ ID NO 1141
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1141
gcagacatgc acacaccac 19

<210> SEQ ID NO 1142
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1142
tgagagctcc ctctccagat 20

<210> SEQ ID NO 1143
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1143
ccaagtatat tgtgcatgtg aaga 24

<210> SEQ ID NO 1144
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1144
agcttgaggc aagatattgt tgt 23

<210> SEQ ID NO 1145
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1145
ctccgaaaag aggcacaagt 20

<210> SEQ ID NO 1146
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 1146
gcgagaactt tttaaggcag tc 22

<210> SEQ ID NO 1147
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 1147
cgcaccagcc tcttcact 18

<210> SEQ ID NO 1148
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 1148
ttccgaagtc ctcaaaacct t 21

<210> SEQ ID NO 1149
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 1149
ttgggtcaaa aatgagacca g 21

<210> SEQ ID NO 1150
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 1150
ccttgaaata cactgcatta acga 24

<210> SEQ ID NO 1151
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 1151
gagctcggga gaccacag 18

<210> SEQ ID NO 1152
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 1152
tggtcgctac ttagcctcaa t 21

<210> SEQ ID NO 1153
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 1153
ggagaggacg gcgttatttt 20

<210> SEQ ID NO 1154
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 1154
ttttcatacc ccggaggag 19

<210> SEQ ID NO 1155
<211> LENGTH: 19
<212> TYPE: RNA
<213> ORGANISM: Mus musculus

<400> SEQUENCE: 1155
caaagaaucu agucuauga 19

<210> SEQ ID NO 1156
<211> LENGTH: 19
<212> TYPE: RNA
<213> ORGANISM: Mus musculus

<400> SEQUENCE: 1156
ugacaggacu gauuguaua 19

<210> SEQ ID NO 1157
<211> LENGTH: 19
<212> TYPE: RNA
<213> ORGANISM: Mus musculus

<400> SEQUENCE: 1157
gcagaaacau gcaggaaug 19

<210> SEQ ID NO 1158
<211> LENGTH: 19
<212> TYPE: RNA
<213> ORGANISM: Mus musculus

<400> SEQUENCE: 1158
ggcaauaugu guaaugaaa 19

<210> SEQ ID NO 1159
<211> LENGTH: 19
<212> TYPE: RNA
<213> ORGANISM: Mus musculus

<400> SEQUENCE: 1159
ccaaugcacg cuugauuua 19

<210> SEQ ID NO 1160
<211> LENGTH: 19
<212> TYPE: RNA
<213> ORGANISM: Mus musculus

<400> SEQUENCE: 1160
gaaggagagu ucuuguuac 19

<210> SEQ ID NO 1161
<211> LENGTH: 19
<212> TYPE: RNA
<213> ORGANISM: Mus musculus

<400> SEQUENCE: 1161
ccgcaagaug uuauuaaua 19

<210> SEQ ID NO 1162
<211> LENGTH: 19
<212> TYPE: RNA
<213> ORGANISM: Mus musculus

<400> SEQUENCE: 1162
ccaguucucu uaugagugc 19

<210> SEQ ID NO 1163
<211> LENGTH: 19
<212> TYPE: RNA
<213> ORGANISM: Mus musculus

<400> SEQUENCE: 1163
ggaagaacgu guaugauga 19

<210> SEQ ID NO 1164
<211> LENGTH: 19
<212> TYPE: RNA
<213> ORGANISM: Mus musculus

<400> SEQUENCE: 1164
gaagagggau ucgcucaug 19

<210> SEQ ID NO 1165
<211> LENGTH: 19
<212> TYPE: RNA
<213> ORGANISM: Mus musculus

<400> SEQUENCE: 1165
ccucuaaacu ucaccggua 19

<210> SEQ ID NO 1166
<211> LENGTH: 19
<212> TYPE: RNA
<213> ORGANISM: Mus musculus

<400> SEQUENCE: 1166
ggucaucccu gcuuuccca 19

<210> SEQ ID NO 1167
<211> LENGTH: 19
<212> TYPE: RNA
<213> ORGANISM: Mus musculus

<400> SEQUENCE: 1167
gcaucgauau gauagauaa 19

<210> SEQ ID NO 1168
<211> LENGTH: 19
<212> TYPE: RNA
<213> ORGANISM: Mus musculus

<400> SEQUENCE: 1168
caguaaaggu ggaagauaa 19

<210> SEQ ID NO 1169
<211> LENGTH: 19
<212> TYPE: RNA
<213> ORGANISM: Mus musculus

<400> SEQUENCE: 1169
gaaauacggg ugaaaucua 19

<210> SEQ ID NO 1170
<211> LENGTH: 19
<212> TYPE: RNA
<213> ORGANISM: Mus musculus

<400> SEQUENCE: 1170
ugucguagga ugugaccga 19

<210> SEQ ID NO 1171
<211> LENGTH: 19
<212> TYPE: RNA
<213> ORGANISM: Mus musculus

<400> SEQUENCE: 1171
gaacgcagcu cuccgcaaa 19

<210> SEQ ID NO 1172
<211> LENGTH: 19
<212> TYPE: RNA
<213> ORGANISM: Mus musculus

<400> SEQUENCE: 1172
ucaaacagcu caccgagga 19

<210> SEQ ID NO 1173
<211> LENGTH: 19
<212> TYPE: RNA
<213> ORGANISM: Mus musculus

<400> SEQUENCE: 1173
gaggaaaguu cagaggaga 19

<210> SEQ ID NO 1174
<211> LENGTH: 19
<212> TYPE: RNA
<213> ORGANISM: Mus musculus

<400> SEQUENCE: 1174
ucaaguacuu cacaucagu 19

<210> SEQ ID NO 1175
<211> LENGTH: 19
<212> TYPE: RNA
<213> ORGANISM: Mus musculus

<400> SEQUENCE: 1175
ggaguuaucu cucaguguu 19

<210> SEQ ID NO 1176
<211> LENGTH: 19
<212> TYPE: RNA
<213> ORGANISM: Mus musculus

<400> SEQUENCE: 1176
ugaaguuucu acugguuua 19

<210> SEQ ID NO 1177
<211> LENGTH: 19
<212> TYPE: RNA
<213> ORGANISM: Mus musculus

<400> SEQUENCE: 1177
gcuaugacau cgauuaugg 19

<210> SEQ ID NO 1178
<211> LENGTH: 19
<212> TYPE: RNA
<213> ORGANISM: Mus musculus

<400> SEQUENCE: 1178
ugaaacaaau ugcggcuca 19

<210> SEQ ID NO 1179
<211> LENGTH: 19
<212> TYPE: RNA
<213> ORGANISM: Mus musculus

<400> SEQUENCE: 1179
gcacauaugc ggucaacuu 19

<210> SEQ ID NO 1180
<211> LENGTH: 19
<212> TYPE: RNA
<213> ORGANISM: Mus musculus

<400> SEQUENCE: 1180
ccaauugccu acuccuuaa 19

<210> SEQ ID NO 1181
<211> LENGTH: 19
<212> TYPE: RNA
<213> ORGANISM: Mus musculus

<400> SEQUENCE: 1181
gaacggauga uuaugacaa 19

<210> SEQ ID NO 1182
<211> LENGTH: 19
<212> TYPE: RNA

<213> ORGANISM: Mus musculus

<400> SEQUENCE: 1182
uguaugagaa ggaagaaua 19

<210> SEQ ID NO 1183
<211> LENGTH: 19
<212> TYPE: RNA
<213> ORGANISM: Mus musculus

<400> SEQUENCE: 1183
cgacagcagu cccaucuac 19

<210> SEQ ID NO 1184
<211> LENGTH: 19
<212> TYPE: RNA
<213> ORGANISM: Mus musculus

<400> SEQUENCE: 1184
ugacaucgcu cugaauaau 19

<210> SEQ ID NO 1185
<211> LENGTH: 19
<212> TYPE: RNA
<213> ORGANISM: Mus musculus

<400> SEQUENCE: 1185
acuccacuau ccacuauua 19

<210> SEQ ID NO 1186
<211> LENGTH: 19
<212> TYPE: RNA
<213> ORGANISM: Mus musculus

<400> SEQUENCE: 1186
augcguaacu ucagucgua 19

<210> SEQ ID NO 1187
<211> LENGTH: 19
<212> TYPE: RNA
<213> ORGANISM: Mus musculus

<400> SEQUENCE: 1187
gaagguauca ucaauauug 19

<210> SEQ ID NO 1188
<211> LENGTH: 19
<212> TYPE: RNA
<213> ORGANISM: Mus musculus

<400> SEQUENCE: 1188
gaucucccgu auccgagua 19

<210> SEQ ID NO 1189
<211> LENGTH: 19
<212> TYPE: RNA
<213> ORGANISM: Mus musculus

<400> SEQUENCE: 1189
ucucuaccau ccguaauuu 19

<210> SEQ ID NO 1190
<211> LENGTH: 19

<212> TYPE: RNA
<213> ORGANISM: Mus musculus

<400> SEQUENCE: 1190
ugacaugacu ggagagaag 19

<210> SEQ ID NO 1191
<211> LENGTH: 19
<212> TYPE: RNA
<213> ORGANISM: Mus musculus

<400> SEQUENCE: 1191
guagagauca gccgggaga 19

<210> SEQ ID NO 1192
<211> LENGTH: 19
<212> TYPE: RNA
<213> ORGANISM: Mus musculus

<400> SEQUENCE: 1192
gaucagguuu gugaccaau 19

<210> SEQ ID NO 1193
<211> LENGTH: 19
<212> TYPE: RNA
<213> ORGANISM: Mus musculus

<400> SEQUENCE: 1193
ucuuuaaugu ugccaaaug 19

<210> SEQ ID NO 1194
<211> LENGTH: 19
<212> TYPE: RNA
<213> ORGANISM: Mus musculus

<400> SEQUENCE: 1194
ugagauacua uuacgacaa 19

<210> SEQ ID NO 1195
<211> LENGTH: 19
<212> TYPE: RNA
<213> ORGANISM: Mus musculus

<400> SEQUENCE: 1195
gcuuagagau guagcgaug 19

<210> SEQ ID NO 1196
<211> LENGTH: 19
<212> TYPE: RNA
<213> ORGANISM: Mus musculus

<400> SEQUENCE: 1196
ccuguuacac cucggauua 19

<210> SEQ ID NO 1197
<211> LENGTH: 19
<212> TYPE: RNA
<213> ORGANISM: Mus musculus

<400> SEQUENCE: 1197
cagcuacggu aucgagcau 19

<210> SEQ ID NO 1198

-continued

<211> LENGTH: 19
<212> TYPE: RNA
<213> ORGANISM: Mus musculus

<400> SEQUENCE: 1198
ucaaguauga gaacgacua 19

<210> SEQ ID NO 1199
<211> LENGTH: 19
<212> TYPE: RNA
<213> ORGANISM: Mus musculus

<400> SEQUENCE: 1199
gaucaacagc aauacauua 19

<210> SEQ ID NO 1200
<211> LENGTH: 19
<212> TYPE: RNA
<213> ORGANISM: Mus musculus

<400> SEQUENCE: 1200
ugaauuugcu caacaacaa 19

<210> SEQ ID NO 1201
<211> LENGTH: 19
<212> TYPE: RNA
<213> ORGANISM: Mus musculus

<400> SEQUENCE: 1201
uagagcagau gaucaaaga 19

<210> SEQ ID NO 1202
<211> LENGTH: 19
<212> TYPE: RNA
<213> ORGANISM: Mus musculus

<400> SEQUENCE: 1202
gaaugacuuu ggaaucaag 19

<210> SEQ ID NO 1203
<211> LENGTH: 19
<212> TYPE: RNA
<213> ORGANISM: Mus musculus

<400> SEQUENCE: 1203
gaacaaacau gaccuauga 19

<210> SEQ ID NO 1204
<211> LENGTH: 19
<212> TYPE: RNA
<213> ORGANISM: Mus musculus

<400> SEQUENCE: 1204
caaagaggau uuccgcuac 19

<210> SEQ ID NO 1205
<211> LENGTH: 19
<212> TYPE: RNA
<213> ORGANISM: Mus musculus

<400> SEQUENCE: 1205
gcauuaagca ggaacgaau 19

<210> SEQ ID NO 1206
<211> LENGTH: 19
<212> TYPE: RNA
<213> ORGANISM: Mus musculus

<400> SEQUENCE: 1206
cgccacuacu acaaacuaa 19

<210> SEQ ID NO 1207
<211> LENGTH: 19
<212> TYPE: RNA
<213> ORGANISM: Mus musculus

<400> SEQUENCE: 1207
gaguaaauac aucccgaga 19

<210> SEQ ID NO 1208
<211> LENGTH: 19
<212> TYPE: RNA
<213> ORGANISM: Mus musculus

<400> SEQUENCE: 1208
ggaggcgggu ucaugaaac 19

<210> SEQ ID NO 1209
<211> LENGTH: 19
<212> TYPE: RNA
<213> ORGANISM: Mus musculus

<400> SEQUENCE: 1209
cgcagaaccu uagauaaau 19

<210> SEQ ID NO 1210
<211> LENGTH: 19
<212> TYPE: RNA
<213> ORGANISM: Mus musculus

<400> SEQUENCE: 1210
guaccaaucu caugggaag 19

<210> SEQ ID NO 1211
<211> LENGTH: 19
<212> TYPE: RNA
<213> ORGANISM: Mus musculus

<400> SEQUENCE: 1211
gaagacaccu uuacaagug 19

<210> SEQ ID NO 1212
<211> LENGTH: 19
<212> TYPE: RNA
<213> ORGANISM: Mus musculus

<400> SEQUENCE: 1212
ggacaacaac aguaaauuu 19

<210> SEQ ID NO 1213
<211> LENGTH: 19
<212> TYPE: RNA
<213> ORGANISM: Mus musculus

<400> SEQUENCE: 1213
ggagauaccu uggauuuua 19

<210> SEQ ID NO 1214
<211> LENGTH: 19
<212> TYPE: RNA
<213> ORGANISM: Mus musculus

<400> SEQUENCE: 1214
gaaaucagca auccagaaa 19

<210> SEQ ID NO 1215
<211> LENGTH: 19
<212> TYPE: RNA
<213> ORGANISM: Mus musculus

<400> SEQUENCE: 1215
gaagaugucu agcaaaucg 19

<210> SEQ ID NO 1216
<211> LENGTH: 19
<212> TYPE: RNA
<213> ORGANISM: Mus musculus

<400> SEQUENCE: 1216
cggaagaugu cuagcaaau 19

<210> SEQ ID NO 1217
<211> LENGTH: 19
<212> TYPE: RNA
<213> ORGANISM: Mus musculus

<400> SEQUENCE: 1217
guacauggaa gcucaguau 19

<210> SEQ ID NO 1218
<211> LENGTH: 19
<212> TYPE: RNA
<213> ORGANISM: Mus musculus

<400> SEQUENCE: 1218
agaaagagug ccucaagua 19

<210> SEQ ID NO 1219
<211> LENGTH: 19
<212> TYPE: RNA
<213> ORGANISM: Mus musculus

<400> SEQUENCE: 1219
caucugaauu cccuucuga 19

<210> SEQ ID NO 1220
<211> LENGTH: 19
<212> TYPE: RNA
<213> ORGANISM: Mus musculus

<400> SEQUENCE: 1220
gaacacggac aucagcauc 19

<210> SEQ ID NO 1221
<211> LENGTH: 19
<212> TYPE: RNA
<213> ORGANISM: Mus musculus

<400> SEQUENCE: 1221
gucgaaugau agcaaagua 19

<210> SEQ ID NO 1222
<211> LENGTH: 19
<212> TYPE: RNA
<213> ORGANISM: Mus musculus

<400> SEQUENCE: 1222
cggugagguc cguuaggaa 19

<210> SEQ ID NO 1223
<211> LENGTH: 19
<212> TYPE: RNA
<213> ORGANISM: Mus musculus

<400> SEQUENCE: 1223
gauggugccu gacucaaug 19

<210> SEQ ID NO 1224
<211> LENGTH: 19
<212> TYPE: RNA
<213> ORGANISM: Mus musculus

<400> SEQUENCE: 1224
cgacugaacg gccaacuuu 19

<210> SEQ ID NO 1225
<211> LENGTH: 19
<212> TYPE: RNA
<213> ORGANISM: Mus musculus

<400> SEQUENCE: 1225
gugaaggccu uuaagugug 19

<210> SEQ ID NO 1226
<211> LENGTH: 19
<212> TYPE: RNA
<213> ORGANISM: Mus musculus

<400> SEQUENCE: 1226
gaacucacac cugucauca 19

<210> SEQ ID NO 1227
<211> LENGTH: 19
<212> TYPE: RNA
<213> ORGANISM: Mus musculus

<400> SEQUENCE: 1227
ggacagauuu gaggagguu 19

<210> SEQ ID NO 1228
<211> LENGTH: 19
<212> TYPE: RNA
<213> ORGANISM: Mus musculus

<400> SEQUENCE: 1228
gaauaguacu ugucuggau 19

<210> SEQ ID NO 1229
<211> LENGTH: 19
<212> TYPE: RNA
<213> ORGANISM: Mus musculus

<400> SEQUENCE: 1229
ucugggagcu cgagaagaa 19

<210> SEQ ID NO 1230
<211> LENGTH: 19
<212> TYPE: RNA
<213> ORGANISM: Mus musculus

<400> SEQUENCE: 1230
gagagcaacu ccaaaauca 19

<210> SEQ ID NO 1231
<211> LENGTH: 19
<212> TYPE: RNA
<213> ORGANISM: Mus musculus

<400> SEQUENCE: 1231
guccagagau uucacauuu 19

<210> SEQ ID NO 1232
<211> LENGTH: 19
<212> TYPE: RNA
<213> ORGANISM: Mus musculus

<400> SEQUENCE: 1232
agacuuaccu ugaaacaaa 19

<210> SEQ ID NO 1233
<211> LENGTH: 19
<212> TYPE: RNA
<213> ORGANISM: Mus musculus

<400> SEQUENCE: 1233
gaacuucacu gccauuugu 19

<210> SEQ ID NO 1234
<211> LENGTH: 19
<212> TYPE: RNA
<213> ORGANISM: Mus musculus

<400> SEQUENCE: 1234
gcacagagcu gaccgugaa 19

<210> SEQ ID NO 1235
<211> LENGTH: 19
<212> TYPE: RNA
<213> ORGANISM: Mus musculus

<400> SEQUENCE: 1235
ggauuaaacc ugucguaug 19

<210> SEQ ID NO 1236
<211> LENGTH: 19
<212> TYPE: RNA
<213> ORGANISM: Mus musculus

<400> SEQUENCE: 1236
uaagaugccu ggcuagaaa 19

<210> SEQ ID NO 1237
<211> LENGTH: 19
<212> TYPE: RNA
<213> ORGANISM: Mus musculus

<400> SEQUENCE: 1237
gcaaaccgcu cgccugaga 19

<210> SEQ ID NO 1238
<211> LENGTH: 19
<212> TYPE: RNA
<213> ORGANISM: Mus musculus

<400> SEQUENCE: 1238
gaaagucguu uaucgcaaa 19

<210> SEQ ID NO 1239
<211> LENGTH: 19
<212> TYPE: RNA
<213> ORGANISM: Mus musculus

<400> SEQUENCE: 1239
ccauaucaau guccuguga 19

<210> SEQ ID NO 1240
<211> LENGTH: 19
<212> TYPE: RNA
<213> ORGANISM: Mus musculus

<400> SEQUENCE: 1240
cgaguuaccu gaacacguu 19

<210> SEQ ID NO 1241
<211> LENGTH: 19
<212> TYPE: RNA
<213> ORGANISM: Mus musculus

<400> SEQUENCE: 1241
uaucagagcu gcaaguguu 19

<210> SEQ ID NO 1242
<211> LENGTH: 19
<212> TYPE: RNA
<213> ORGANISM: Mus musculus

<400> SEQUENCE: 1242
ggacacaccu augauguua 19

<210> SEQ ID NO 1243
<211> LENGTH: 19
<212> TYPE: RNA
<213> ORGANISM: Mus musculus

<400> SEQUENCE: 1243
ggacauuucu gagccauau 19

<210> SEQ ID NO 1244
<211> LENGTH: 19
<212> TYPE: RNA
<213> ORGANISM: Mus musculus

<400> SEQUENCE: 1244
gagcgaaguu ccugagaug 19

<210> SEQ ID NO 1245
<211> LENGTH: 19
<212> TYPE: RNA
<213> ORGANISM: Mus musculus

<400> SEQUENCE: 1245
gcaagggcgu guucgugaa 19

<210> SEQ ID NO 1246
<211> LENGTH: 19
<212> TYPE: RNA
<213> ORGANISM: Mus musculus

<400> SEQUENCE: 1246
gcaacgcggu ggugugcaa 19

<210> SEQ ID NO 1247
<211> LENGTH: 19
<212> TYPE: RNA
<213> ORGANISM: Mus musculus

<400> SEQUENCE: 1247
gcgaugacug gcagacaua 19

<210> SEQ ID NO 1248
<211> LENGTH: 19
<212> TYPE: RNA
<213> ORGANISM: Mus musculus

<400> SEQUENCE: 1248
gaguggcccu augaaguua 19

<210> SEQ ID NO 1249
<211> LENGTH: 19
<212> TYPE: RNA
<213> ORGANISM: Mus musculus

<400> SEQUENCE: 1249
ggacaauguu cgcgauaaa 19

<210> SEQ ID NO 1250
<211> LENGTH: 19
<212> TYPE: RNA
<213> ORGANISM: Mus musculus

<400> SEQUENCE: 1250
ccagacaccu ccaacauua 19

<210> SEQ ID NO 1251
<211> LENGTH: 19
<212> TYPE: RNA
<213> ORGANISM: Mus musculus

<400> SEQUENCE: 1251
gaacaggugg cacagcuua 19

<210> SEQ ID NO 1252
<211> LENGTH: 19
<212> TYPE: RNA
<213> ORGANISM: Mus musculus

<400> SEQUENCE: 1252
gaaacgaccu ucuacgacg 19

<210> SEQ ID NO 1253
<211> LENGTH: 19
<212> TYPE: RNA
<213> ORGANISM: Mus musculus

<400> SEQUENCE: 1253
ccaagaacgu gaccgacga 19

<210> SEQ ID NO 1254
<211> LENGTH: 19
<212> TYPE: RNA
<213> ORGANISM: Mus musculus

<400> SEQUENCE: 1254
gccaagaacu cggaccuuc 19

<210> SEQ ID NO 1255
<211> LENGTH: 19
<212> TYPE: RNA
<213> ORGANISM: Mus musculus

<400> SEQUENCE: 1255
caaccuggcg gaucccuau 19

<210> SEQ ID NO 1256
<211> LENGTH: 19
<212> TYPE: RNA
<213> ORGANISM: Mus musculus

<400> SEQUENCE: 1256
caacagcaac ggcgugauc 19

<210> SEQ ID NO 1257
<211> LENGTH: 19
<212> TYPE: RNA
<213> ORGANISM: Mus musculus

<400> SEQUENCE: 1257
uggaacagcc uuucuauca 19

<210> SEQ ID NO 1258
<211> LENGTH: 19
<212> TYPE: RNA
<213> ORGANISM: Mus musculus

<400> SEQUENCE: 1258
acaccaaccu cagcaguua 19

<210> SEQ ID NO 1259
<211> LENGTH: 19
<212> TYPE: RNA
<213> ORGANISM: Mus musculus

<400> SEQUENCE: 1259
gcaguaaccu caaaugaac 19

<210> SEQ ID NO 1260
<211> LENGTH: 19
<212> TYPE: RNA
<213> ORGANISM: Mus musculus

<400> SEQUENCE: 1260
ucacauaugc agaugagua 19

<210> SEQ ID NO 1261
<211> LENGTH: 19
<212> TYPE: RNA

<213> ORGANISM: Mus musculus

<400> SEQUENCE: 1261
gaagaaccau ccaaaugcu 19

<210> SEQ ID NO 1262
<211> LENGTH: 19
<212> TYPE: RNA
<213> ORGANISM: Mus musculus

<400> SEQUENCE: 1262
aaacaagccc agauucgaa 19

<210> SEQ ID NO 1263
<211> LENGTH: 19
<212> TYPE: RNA
<213> ORGANISM: Mus musculus

<400> SEQUENCE: 1263
gaagggcucc cguaacaug 19

<210> SEQ ID NO 1264
<211> LENGTH: 19
<212> TYPE: RNA
<213> ORGANISM: Mus musculus

<400> SEQUENCE: 1264
aaagaggccc ugcggcaaa 19

<210> SEQ ID NO 1265
<211> LENGTH: 19
<212> TYPE: RNA
<213> ORGANISM: Mus musculus

<400> SEQUENCE: 1265
gcucgagaga uccggauga 19

<210> SEQ ID NO 1266
<211> LENGTH: 19
<212> TYPE: RNA
<213> ORGANISM: Mus musculus

<400> SEQUENCE: 1266
agacacagua aaugacguu 19

<210> SEQ ID NO 1267
<211> LENGTH: 19
<212> TYPE: RNA
<213> ORGANISM: Mus musculus

<400> SEQUENCE: 1267
guaaacaguu gccaagguu 19

<210> SEQ ID NO 1268
<211> LENGTH: 19
<212> TYPE: RNA
<213> ORGANISM: Mus musculus

<400> SEQUENCE: 1268
gcaccuacca gaacaauuc 19

<210> SEQ ID NO 1269
<211> LENGTH: 19

<212> TYPE: RNA
<213> ORGANISM: Mus musculus

<400> SEQUENCE: 1269
gaaauggaac ggagacgau 19

<210> SEQ ID NO 1270
<211> LENGTH: 19
<212> TYPE: RNA
<213> ORGANISM: Mus musculus

<400> SEQUENCE: 1270
ggucaccaau ucguguuaa 19

<210> SEQ ID NO 1271
<211> LENGTH: 19
<212> TYPE: RNA
<213> ORGANISM: Mus musculus

<400> SEQUENCE: 1271
gacgagaccu ucaucaaga 19

<210> SEQ ID NO 1272
<211> LENGTH: 19
<212> TYPE: RNA
<213> ORGANISM: Mus musculus

<400> SEQUENCE: 1272
gacagcagcu cgcccaaau 19

<210> SEQ ID NO 1273
<211> LENGTH: 19
<212> TYPE: RNA
<213> ORGANISM: Mus musculus

<400> SEQUENCE: 1273
gaauuucuau caccagcaa 19

<210> SEQ ID NO 1274
<211> LENGTH: 19
<212> TYPE: RNA
<213> ORGANISM: Mus musculus

<400> SEQUENCE: 1274
guacagcccu auuucaucu 19

<210> SEQ ID NO 1275
<211> LENGTH: 19
<212> TYPE: RNA
<213> ORGANISM: Mus musculus

<400> SEQUENCE: 1275
gaugauccgg caacuagaa 19

<210> SEQ ID NO 1276
<211> LENGTH: 19
<212> TYPE: RNA
<213> ORGANISM: Mus musculus

<400> SEQUENCE: 1276
guuagaccgu gaggauaua 19

<210> SEQ ID NO 1277

<211> LENGTH: 19
<212> TYPE: RNA
<213> ORGANISM: Mus musculus

<400> SEQUENCE: 1277
cgacugauuc cuauuaaau 19

<210> SEQ ID NO 1278
<211> LENGTH: 19
<212> TYPE: RNA
<213> ORGANISM: Mus musculus

<400> SEQUENCE: 1278
gccuaucgcu guucuugaa 19

<210> SEQ ID NO 1279
<211> LENGTH: 19
<212> TYPE: RNA
<213> ORGANISM: Mus musculus

<400> SEQUENCE: 1279
gaacaugaau ccaaugaug 19

<210> SEQ ID NO 1280
<211> LENGTH: 19
<212> TYPE: RNA
<213> ORGANISM: Mus musculus

<400> SEQUENCE: 1280
gaacauggga ggacaguuu 19

<210> SEQ ID NO 1281
<211> LENGTH: 19
<212> TYPE: RNA
<213> ORGANISM: Mus musculus

<400> SEQUENCE: 1281
ucaagaaucu gcuaccaaa 19

<210> SEQ ID NO 1282
<211> LENGTH: 19
<212> TYPE: RNA
<213> ORGANISM: Mus musculus

<400> SEQUENCE: 1282
ccaagaagau ggugaagau 19

<210> SEQ ID NO 1283
<211> LENGTH: 19
<212> TYPE: RNA
<213> ORGANISM: Mus musculus

<400> SEQUENCE: 1283
gacaugggau uucaggaua 19

<210> SEQ ID NO 1284
<211> LENGTH: 19
<212> TYPE: RNA
<213> ORGANISM: Mus musculus

<400> SEQUENCE: 1284
ggauuucgau uccgcuaug 19

<210> SEQ ID NO 1285
<211> LENGTH: 19
<212> TYPE: RNA
<213> ORGANISM: Mus musculus

<400> SEQUENCE: 1285
cuacggaacu gggcaaaug 19

<210> SEQ ID NO 1286
<211> LENGTH: 19
<212> TYPE: RNA
<213> ORGANISM: Mus musculus

<400> SEQUENCE: 1286
ggaaacgcca gaagcuuau 19

<210> SEQ ID NO 1287
<211> LENGTH: 19
<212> TYPE: RNA
<213> ORGANISM: Mus musculus

<400> SEQUENCE: 1287
gaacaacucc uuccacuuu 19

<210> SEQ ID NO 1288
<211> LENGTH: 19
<212> TYPE: RNA
<213> ORGANISM: Mus musculus

<400> SEQUENCE: 1288
ggaaacaacu gcaagaaug 19

<210> SEQ ID NO 1289
<211> LENGTH: 19
<212> TYPE: RNA
<213> ORGANISM: Mus musculus

<400> SEQUENCE: 1289
gaaccaggcu acacaggaa 19

<210> SEQ ID NO 1290
<211> LENGTH: 19
<212> TYPE: RNA
<213> ORGANISM: Mus musculus

<400> SEQUENCE: 1290
gaagguguau acugugaaa 19

<210> SEQ ID NO 1291
<211> LENGTH: 19
<212> TYPE: RNA
<213> ORGANISM: Mus musculus

<400> SEQUENCE: 1291
gaucgagccu gagguguua 19

<210> SEQ ID NO 1292
<211> LENGTH: 19
<212> TYPE: RNA
<213> ORGANISM: Mus musculus

<400> SEQUENCE: 1292
uuacaaagau ugcagguau 19

<210> SEQ ID NO 1293
<211> LENGTH: 19
<212> TYPE: RNA
<213> ORGANISM: Mus musculus

<400> SEQUENCE: 1293
gccaagaguu auuugauga 19

<210> SEQ ID NO 1294
<211> LENGTH: 19
<212> TYPE: RNA
<213> ORGANISM: Mus musculus

<400> SEQUENCE: 1294
gcauguauga ccaauguaa 19

<210> SEQ ID NO 1295
<211> LENGTH: 19
<212> TYPE: RNA
<213> ORGANISM: Mus musculus

<400> SEQUENCE: 1295
gcgcaagucc aauaucuuc 19

<210> SEQ ID NO 1296
<211> LENGTH: 19
<212> TYPE: RNA
<213> ORGANISM: Mus musculus

<400> SEQUENCE: 1296
agugguaccu caagcauga 19

<210> SEQ ID NO 1297
<211> LENGTH: 19
<212> TYPE: RNA
<213> ORGANISM: Mus musculus

<400> SEQUENCE: 1297
gcgcagacau ugagaagca 19

<210> SEQ ID NO 1298
<211> LENGTH: 19
<212> TYPE: RNA
<213> ORGANISM: Mus musculus

<400> SEQUENCE: 1298
cagcauaucu acuccuuua 19

<210> SEQ ID NO 1299
<211> LENGTH: 19
<212> TYPE: RNA
<213> ORGANISM: Mus musculus

<400> SEQUENCE: 1299
gaagaaagcg uggccauac 19

<210> SEQ ID NO 1300
<211> LENGTH: 19
<212> TYPE: RNA
<213> ORGANISM: Mus musculus

<400> SEQUENCE: 1300
cggaguaugu gucccauga 19

<210> SEQ ID NO 1301
<211> LENGTH: 19
<212> TYPE: RNA
<213> ORGANISM: Mus musculus

<400> SEQUENCE: 1301
ucacuaaugu cacgccaag 19

<210> SEQ ID NO 1302
<211> LENGTH: 19
<212> TYPE: RNA
<213> ORGANISM: Mus musculus

<400> SEQUENCE: 1302
gcaacacgua cgagcucaa 19

<210> SEQ ID NO 1303
<211> LENGTH: 19
<212> TYPE: RNA
<213> ORGANISM: Mus musculus

<400> SEQUENCE: 1303
ggagagaccc accuacaua 19

<210> SEQ ID NO 1304
<211> LENGTH: 19
<212> TYPE: RNA
<213> ORGANISM: Mus musculus

<400> SEQUENCE: 1304
gcaauacagu agugagaaa 19

<210> SEQ ID NO 1305
<211> LENGTH: 19
<212> TYPE: RNA
<213> ORGANISM: Mus musculus

<400> SEQUENCE: 1305
ggaaggacau cuaccguuc 19

<210> SEQ ID NO 1306
<211> LENGTH: 19
<212> TYPE: RNA
<213> ORGANISM: Mus musculus

<400> SEQUENCE: 1306
guacauacau agugaacga 19

<210> SEQ ID NO 1307
<211> LENGTH: 19
<212> TYPE: RNA
<213> ORGANISM: Mus musculus

<400> SEQUENCE: 1307
uaucugaccc aguucgaaa 19

<210> SEQ ID NO 1308
<211> LENGTH: 19
<212> TYPE: RNA
<213> ORGANISM: Mus musculus

<400> SEQUENCE: 1308
uaacuccgau ggcucccaa 19

<210> SEQ ID NO 1309
<211> LENGTH: 19
<212> TYPE: RNA
<213> ORGANISM: Mus musculus

<400> SEQUENCE: 1309
guaaguuucc ggccaaaga 19

<210> SEQ ID NO 1310
<211> LENGTH: 19
<212> TYPE: RNA
<213> ORGANISM: Mus musculus

<400> SEQUENCE: 1310
ccaaacaggu cgcucuuac 19

<210> SEQ ID NO 1311
<211> LENGTH: 19
<212> TYPE: RNA
<213> ORGANISM: Mus musculus

<400> SEQUENCE: 1311
ccaaacgacu cacuaggga 19

<210> SEQ ID NO 1312
<211> LENGTH: 19
<212> TYPE: RNA
<213> ORGANISM: Mus musculus

<400> SEQUENCE: 1312
ucucaacccu gugcguuua 19

<210> SEQ ID NO 1313
<211> LENGTH: 19
<212> TYPE: RNA
<213> ORGANISM: Mus musculus

<400> SEQUENCE: 1313
gcagacggca uuacuggau 19

<210> SEQ ID NO 1314
<211> LENGTH: 19
<212> TYPE: RNA
<213> ORGANISM: Mus musculus

<400> SEQUENCE: 1314
guagaagccg aaacaaugu 19

<210> SEQ ID NO 1315
<211> LENGTH: 19
<212> TYPE: RNA
<213> ORGANISM: Mus musculus

<400> SEQUENCE: 1315
ggaguacccu gaagcuaua 19

<210> SEQ ID NO 1316
<211> LENGTH: 19
<212> TYPE: RNA
<213> ORGANISM: Mus musculus

<400> SEQUENCE: 1316
gaagaagagu ccuuucaau 19

<210> SEQ ID NO 1317
<211> LENGTH: 19
<212> TYPE: RNA
<213> ORGANISM: Mus musculus

<400> SEQUENCE: 1317
uaugagaccu ucaagagua 19

<210> SEQ ID NO 1318
<211> LENGTH: 19
<212> TYPE: RNA
<213> ORGANISM: Mus musculus

<400> SEQUENCE: 1318
gaauccagac caacaauaa 19

<210> SEQ ID NO 1319
<211> LENGTH: 19
<212> TYPE: RNA
<213> ORGANISM: Mus musculus

<400> SEQUENCE: 1319
ugaguauagu ccagaacga 19

<210> SEQ ID NO 1320
<211> LENGTH: 19
<212> TYPE: RNA
<213> ORGANISM: Mus musculus

<400> SEQUENCE: 1320
caauggaagu cguccuagu 19

<210> SEQ ID NO 1321
<211> LENGTH: 19
<212> TYPE: RNA
<213> ORGANISM: Mus musculus

<400> SEQUENCE: 1321
gaguggaaca ucugcaaua 19

<210> SEQ ID NO 1322
<211> LENGTH: 19
<212> TYPE: RNA
<213> ORGANISM: Mus musculus

<400> SEQUENCE: 1322
gcucaucagc uccauauuu 19

<210> SEQ ID NO 1323
<211> LENGTH: 19
<212> TYPE: RNA
<213> ORGANISM: Mus musculus

<400> SEQUENCE: 1323
ugaccacccu ggcgagcua 19

<210> SEQ ID NO 1324
<211> LENGTH: 19
<212> TYPE: RNA
<213> ORGANISM: Mus musculus

<400> SEQUENCE: 1324
gcaacucgcc caccaacau 19

<210> SEQ ID NO 1325
<211> LENGTH: 19
<212> TYPE: RNA
<213> ORGANISM: Mus musculus

<400> SEQUENCE: 1325
gagcuucacu cugaccauc 19

<210> SEQ ID NO 1326
<211> LENGTH: 19
<212> TYPE: RNA
<213> ORGANISM: Mus musculus

<400> SEQUENCE: 1326
acaaauccgc cacaaguug 19

<210> SEQ ID NO 1327
<211> LENGTH: 19
<212> TYPE: RNA
<213> ORGANISM: Mus musculus

<400> SEQUENCE: 1327
caaaggauau gaugguuga 19

<210> SEQ ID NO 1328
<211> LENGTH: 19
<212> TYPE: RNA
<213> ORGANISM: Mus musculus

<400> SEQUENCE: 1328
gaaacgagcc ggaaucuca 19

<210> SEQ ID NO 1329
<211> LENGTH: 19
<212> TYPE: RNA
<213> ORGANISM: Mus musculus

<400> SEQUENCE: 1329
gaagggagca cagacguua 19

<210> SEQ ID NO 1330
<211> LENGTH: 19
<212> TYPE: RNA
<213> ORGANISM: Mus musculus

<400> SEQUENCE: 1330
gcacgcggaa uuuguauug 19

<210> SEQ ID NO 1331
<211> LENGTH: 19
<212> TYPE: RNA
<213> ORGANISM: Mus musculus

<400> SEQUENCE: 1331
gaccaucucu uguuucgug 19

<210> SEQ ID NO 1332
<211> LENGTH: 19
<212> TYPE: RNA
<213> ORGANISM: Mus musculus

<400> SEQUENCE: 1332
ggaaagagau ugagcggcu 19

<210> SEQ ID NO 1333
<211> LENGTH: 19
<212> TYPE: RNA
<213> ORGANISM: Mus musculus

<400> SEQUENCE: 1333
gcugguuccu ccaauaaga 19

<210> SEQ ID NO 1334
<211> LENGTH: 19
<212> TYPE: RNA
<213> ORGANISM: Mus musculus

<400> SEQUENCE: 1334
ugaaggagaa guucgacua 19

<210> SEQ ID NO 1335
<211> LENGTH: 19
<212> TYPE: RNA
<213> ORGANISM: Mus musculus

<400> SEQUENCE: 1335
gaaggacugu ugcagauag 19

<210> SEQ ID NO 1336
<211> LENGTH: 19
<212> TYPE: RNA
<213> ORGANISM: Mus musculus

<400> SEQUENCE: 1336
gcaaaggagu gcaguugga 19

<210> SEQ ID NO 1337
<211> LENGTH: 19
<212> TYPE: RNA
<213> ORGANISM: Mus musculus

<400> SEQUENCE: 1337
gaaguaggac ugcaccaua 19

<210> SEQ ID NO 1338
<211> LENGTH: 19
<212> TYPE: RNA
<213> ORGANISM: Mus musculus

<400> SEQUENCE: 1338
aaagagcaau ugagaguuu 19

<210> SEQ ID NO 1339
<211> LENGTH: 19
<212> TYPE: RNA
<213> ORGANISM: Mus musculus

<400> SEQUENCE: 1339
ggucaacggu guccucaaa 19

<210> SEQ ID NO 1340
<211> LENGTH: 19
<212> TYPE: RNA

<213> ORGANISM: Mus musculus

<400> SEQUENCE: 1340
gauaauggcc uacaagaug 19

<210> SEQ ID NO 1341
<211> LENGTH: 19
<212> TYPE: RNA
<213> ORGANISM: Mus musculus

<400> SEQUENCE: 1341
gagcgaaugc ggaggcuua 19

<210> SEQ ID NO 1342
<211> LENGTH: 19
<212> TYPE: RNA
<213> ORGANISM: Mus musculus

<400> SEQUENCE: 1342
caacgggccu uuccucauc 19

<210> SEQ ID NO 1343
<211> LENGTH: 19
<212> TYPE: RNA
<213> ORGANISM: Mus musculus

<400> SEQUENCE: 1343
gcacagagau gcuucgaca 19

<210> SEQ ID NO 1344
<211> LENGTH: 19
<212> TYPE: RNA
<213> ORGANISM: Mus musculus

<400> SEQUENCE: 1344
ccacgggaau ccuaucuau 19

<210> SEQ ID NO 1345
<211> LENGTH: 19
<212> TYPE: RNA
<213> ORGANISM: Mus musculus

<400> SEQUENCE: 1345
agaauggcgu ggccugcua 19

<210> SEQ ID NO 1346
<211> LENGTH: 19
<212> TYPE: RNA
<213> ORGANISM: Mus musculus

<400> SEQUENCE: 1346
ugaggaauuc agcgauuua 19

<210> SEQ ID NO 1347
<211> LENGTH: 19
<212> TYPE: RNA
<213> ORGANISM: Mus musculus

<400> SEQUENCE: 1347
ggacaacagc agauuauua 19

<210> SEQ ID NO 1348
<211> LENGTH: 19

<212> TYPE: RNA
<213> ORGANISM: Mus musculus

<400> SEQUENCE: 1348
gacaauaggu gcuguuagu 19

<210> SEQ ID NO 1349
<211> LENGTH: 19
<212> TYPE: RNA
<213> ORGANISM: Mus musculus

<400> SEQUENCE: 1349
aauuagaccu ggcguuuca 19

<210> SEQ ID NO 1350
<211> LENGTH: 19
<212> TYPE: RNA
<213> ORGANISM: Mus musculus

<400> SEQUENCE: 1350
ggaguuccag uaacaauca 19

<210> SEQ ID NO 1351
<211> LENGTH: 19
<212> TYPE: RNA
<213> ORGANISM: Mus musculus

<400> SEQUENCE: 1351
gcaaauagca cccagcaac 19

<210> SEQ ID NO 1352
<211> LENGTH: 19
<212> TYPE: RNA
<213> ORGANISM: Mus musculus

<400> SEQUENCE: 1352
caaacgagcg gcagagaug 19

<210> SEQ ID NO 1353
<211> LENGTH: 19
<212> TYPE: RNA
<213> ORGANISM: Mus musculus

<400> SEQUENCE: 1353
ucagugaucu gccauacca 19

<210> SEQ ID NO 1354
<211> LENGTH: 19
<212> TYPE: RNA
<213> ORGANISM: Mus musculus

<400> SEQUENCE: 1354
gccaagauuu cagaagcua 19

<210> SEQ ID NO 1355
<211> LENGTH: 19
<212> TYPE: RNA
<213> ORGANISM: Mus musculus

<400> SEQUENCE: 1355
aaacugaccu gucgagacu 19

<210> SEQ ID NO 1356

<211> LENGTH: 19
<212> TYPE: RNA
<213> ORGANISM: Mus musculus

<400> SEQUENCE: 1356
ccaauacguu caccuagug 19

<210> SEQ ID NO 1357
<211> LENGTH: 19
<212> TYPE: RNA
<213> ORGANISM: Mus musculus

<400> SEQUENCE: 1357
gaucagccua gcucaguua 19

<210> SEQ ID NO 1358
<211> LENGTH: 19
<212> TYPE: RNA
<213> ORGANISM: Mus musculus

<400> SEQUENCE: 1358
gcaagcggcu gauuacaua 19

<210> SEQ ID NO 1359
<211> LENGTH: 19
<212> TYPE: RNA
<213> ORGANISM: Mus musculus

<400> SEQUENCE: 1359
gcaaauggcg gauauguau 19

<210> SEQ ID NO 1360
<211> LENGTH: 19
<212> TYPE: RNA
<213> ORGANISM: Mus musculus

<400> SEQUENCE: 1360
gcgagcagau uauuagaag 19

<210> SEQ ID NO 1361
<211> LENGTH: 19
<212> TYPE: RNA
<213> ORGANISM: Mus musculus

<400> SEQUENCE: 1361
cuacgguucu ggaguaaau 19

<210> SEQ ID NO 1362
<211> LENGTH: 19
<212> TYPE: RNA
<213> ORGANISM: Mus musculus

<400> SEQUENCE: 1362
gaaguucgag agucaaaca 19

<210> SEQ ID NO 1363
<211> LENGTH: 19
<212> TYPE: RNA
<213> ORGANISM: Mus musculus

<400> SEQUENCE: 1363
gugagcugcu ugagaagaa 19

-continued

```
<210> SEQ ID NO 1364
<211> LENGTH: 19
<212> TYPE: RNA
<213> ORGANISM: Mus musculus

<400> SEQUENCE: 1364

cuguacgacu ccaggauuu                                                    19

<210> SEQ ID NO 1365
<211> LENGTH: 19
<212> TYPE: RNA
<213> ORGANISM: Mus musculus

<400> SEQUENCE: 1365

cuauauagcc auaaugcgu                                                    19

<210> SEQ ID NO 1366
<211> LENGTH: 19
<212> TYPE: RNA
<213> ORGANISM: Mus musculus

<400> SEQUENCE: 1366

cagugagccu gucguguca                                                    19

<210> SEQ ID NO 1367
<211> LENGTH: 19
<212> TYPE: RNA
<213> ORGANISM: Mus musculus

<400> SEQUENCE: 1367

cagaaucgau ggaguccca                                                    19

<210> SEQ ID NO 1368
<211> LENGTH: 19
<212> TYPE: RNA
<213> ORGANISM: Mus musculus

<400> SEQUENCE: 1368

gaugguagca uauguuuag                                                    19

<210> SEQ ID NO 1369
<211> LENGTH: 19
<212> TYPE: RNA
<213> ORGANISM: Mus musculus

<400> SEQUENCE: 1369

ggaaugcagu uauauuugg                                                    19

<210> SEQ ID NO 1370
<211> LENGTH: 19
<212> TYPE: RNA
<213> ORGANISM: Mus musculus

<400> SEQUENCE: 1370

gaagagaguu ucggccauu                                                    19

<210> SEQ ID NO 1371
<211> LENGTH: 19
<212> TYPE: RNA
<213> ORGANISM: Mus musculus

<400> SEQUENCE: 1371

ggacuugccu gcuggcuac                                                    19
```

<210> SEQ ID NO 1372
<211> LENGTH: 19
<212> TYPE: RNA
<213> ORGANISM: Mus musculus

<400> SEQUENCE: 1372
ugacacaggu agcgcgagu 19

<210> SEQ ID NO 1373
<211> LENGTH: 19
<212> TYPE: RNA
<213> ORGANISM: Mus musculus

<400> SEQUENCE: 1373
cuacagcaga cuagaacaa 19

<210> SEQ ID NO 1374
<211> LENGTH: 19
<212> TYPE: RNA
<213> ORGANISM: Mus musculus

<400> SEQUENCE: 1374
gcacugaguu ggcccgaca 19

<210> SEQ ID NO 1375
<211> LENGTH: 19
<212> TYPE: RNA
<213> ORGANISM: Mus musculus

<400> SEQUENCE: 1375
ucucaaaccu gcuuucauc 19

<210> SEQ ID NO 1376
<211> LENGTH: 19
<212> TYPE: RNA
<213> ORGANISM: Mus musculus

<400> SEQUENCE: 1376
gagucaaacu aacguggua 19

<210> SEQ ID NO 1377
<211> LENGTH: 19
<212> TYPE: RNA
<213> ORGANISM: Mus musculus

<400> SEQUENCE: 1377
ggaucacccu gaauucauu 19

<210> SEQ ID NO 1378
<211> LENGTH: 19
<212> TYPE: RNA
<213> ORGANISM: Mus musculus

<400> SEQUENCE: 1378
ugacaugucu ucuccacuu 19

<210> SEQ ID NO 1379
<211> LENGTH: 19
<212> TYPE: RNA
<213> ORGANISM: Mus musculus

<400> SEQUENCE: 1379
gaacccagcu ugaacguca 19

<210> SEQ ID NO 1380
<211> LENGTH: 19
<212> TYPE: RNA
<213> ORGANISM: Mus musculus

<400> SEQUENCE: 1380
gaaagagcac uuacggauu 19

<210> SEQ ID NO 1381
<211> LENGTH: 19
<212> TYPE: RNA
<213> ORGANISM: Mus musculus

<400> SEQUENCE: 1381
gguuugguau cucccauaa 19

<210> SEQ ID NO 1382
<211> LENGTH: 19
<212> TYPE: RNA
<213> ORGANISM: Mus musculus

<400> SEQUENCE: 1382
gaaguguauu agcuugaug 19

<210> SEQ ID NO 1383
<211> LENGTH: 19
<212> TYPE: RNA
<213> ORGANISM: Mus musculus

<400> SEQUENCE: 1383
ccuccgcucu gacauauuu 19

<210> SEQ ID NO 1384
<211> LENGTH: 19
<212> TYPE: RNA
<213> ORGANISM: Mus musculus

<400> SEQUENCE: 1384
gauucucggu auccgguuu 19

<210> SEQ ID NO 1385
<211> LENGTH: 19
<212> TYPE: RNA
<213> ORGANISM: Mus musculus

<400> SEQUENCE: 1385
ccgccaagau uuccgugaa 19

<210> SEQ ID NO 1386
<211> LENGTH: 19
<212> TYPE: RNA
<213> ORGANISM: Mus musculus

<400> SEQUENCE: 1386
aaagaccauu ugcguguca 19

<210> SEQ ID NO 1387
<211> LENGTH: 19
<212> TYPE: RNA
<213> ORGANISM: Mus musculus

<400> SEQUENCE: 1387
gcaccaccgc gauguauua 19

<210> SEQ ID NO 1388
<211> LENGTH: 19
<212> TYPE: RNA
<213> ORGANISM: Mus musculus

<400> SEQUENCE: 1388
gaacaacgua ccagauuga 19

<210> SEQ ID NO 1389
<211> LENGTH: 19
<212> TYPE: RNA
<213> ORGANISM: Mus musculus

<400> SEQUENCE: 1389
aagcaaggcc cgauaagua 19

<210> SEQ ID NO 1390
<211> LENGTH: 19
<212> TYPE: RNA
<213> ORGANISM: Mus musculus

<400> SEQUENCE: 1390
gaucaguacu cuggcaaau 19

<210> SEQ ID NO 1391
<211> LENGTH: 19
<212> TYPE: RNA
<213> ORGANISM: Mus musculus

<400> SEQUENCE: 1391
ucaagacgcc ugcccauuu 19

<210> SEQ ID NO 1392
<211> LENGTH: 19
<212> TYPE: RNA
<213> ORGANISM: Mus musculus

<400> SEQUENCE: 1392
ucagcagccu uaaggguga 19

<210> SEQ ID NO 1393
<211> LENGTH: 19
<212> TYPE: RNA
<213> ORGANISM: Mus musculus

<400> SEQUENCE: 1393
ggagcuggcg agccucuuu 19

<210> SEQ ID NO 1394
<211> LENGTH: 19
<212> TYPE: RNA
<213> ORGANISM: Mus musculus

<400> SEQUENCE: 1394 cgaaucccu cacauguuu 19

<210> SEQ ID NO 1395
<211> LENGTH: 21
<212> TYPE: PRT
<213> ORGANISM: Artificial Sequence
<220> FEATURE:
<221> NAME/KEY: source -continued

```
<223> OTHER INFORMATION: /note="Description of Artificial Sequence:
      Synthetic peptide"

<400> SEQUENCE: 1395

Met Glu Val Gly Trp Tyr Arg Ser Pro Phe Ser Arg Val Val His Leu
1               5                   10                  15

Tyr Arg Asn Gly Lys
            20
```

T CELL BALANCE GENE EXPRESSION, COMPOSITIONS OF MATTERS AND METHODS OF USE THEREOF

RELATED APPLICATIONS AND INCORPORATION BY REFERENCE

This application is a Continuation-in-Part of International Application Number PCT/US15/17826 filed on Feb. 26, 2015, which published as PCT Publication Number WO2015/130968 on Sep. 3, 2015. This application claims priority from U.S. provisional patent application 61/945, 641, filed Feb. 27, 2014, incorporated herein by reference. Reference is made to WO/2012/048265; WO/2014/145631; WO/2014/134351. The foregoing applications, and all documents cited therein or during prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. Appln cited documents, herein cited documents, all documents herein referenced or cited, and all documents indicated to be incorporated herein by reference, are incorporated by reference to the same extent as if each individual document was specifically and individually set forth herein in full and indicated to be incorporated by reference when or where cited or referenced.

STATEMENT AS TO FEDERALLY SPONSORED RESEARCH

This invention was made with government support under Grant Numbers OD003958; HG006193; HG005062; OD003893; NS030843; NS045937; AI073748; AI045757; and AI056299 awarded by the National Institutes of Health. The government has certain rights in the invention.

PARTIES TO A JOINT RESEARCH AGREEMENT

The claimed invention was made by, on behalf of, and/or in connection with one or more of the following parties to a joint research agreement: The Broad Institute, Inc., Massachusetts Institute of Technology, President and Fellows of Harvard College, and The Brigham and Women's Hospital, Inc. The joint research agreement was in effect on and before the date the claimed invention was made, and the claimed invention was made as a result of activities undertaken within the scope of the joint research agreement.

SEQUENCE LISTING

The instant application contains a Sequence Listing which has been submitted electronically in ASCII format and is hereby incorporated by references in its entirety. Said ASCII copy, created on Aug. 23, 2016 is named 46783992100_SL.txt and is 324,708 bytes in size.

FIELD OF THE INVENTION

This invention relates generally to compositions and methods for identifying the regulatory network that modulates, controls or otherwise influences T cell balance, for example, Th17 cell differentiation, maintenance and/or function, as well compositions and methods for exploiting the regulatory network that modulates, controls or otherwise influences T cell balance in a variety of therapeutic and/or diagnostic indications. This invention also relates generally to identifying and exploiting target genes and/or target gene products that modulate, control or otherwise influence T cell balance in a variety of therapeutic and/or diagnostic indications.

BACKGROUND OF THE INVENTION

Despite their importance, the molecular circuits that control the balance of T cells, including the differentiation of naïve T cells, remain largely unknown. Recent studies that reconstructed regulatory networks in mammalian cells have focused on short-term responses and relied on perturbation-based approaches that cannot be readily applied to primary T cells. Accordingly, there exists a need for a better understanding of the dynamic regulatory network that modulates, controls, or otherwise influences T cell balance, including Th17 cell differentiation, maintenance and function, and means for exploiting this network in a variety of therapeutic and diagnostic methods. Citations herein are not intended as an admission that anything cited is pertinent or prior art; nor does it constitute any admission as to the contents or date of anything cited.

SUMMARY OF THE INVENTION

The invention has many utilities. The invention pertains to and includes methods and compositions therefrom of Drug Discovery, as well as for detecting patients or subjects who may or may not respond or be responding to a particular treatment, therapy, compound, drug or combination of drugs or compounds; and accordingly ascertaining which drug or combination of drugs may provide a particular treatment or therapy as to a condition or disease or infection or infectious state, as well as methods and compositions for selecting patient populations (e.g., by detecting those who may or may not respond or be responding), or methods and compositions involving personalized treatment—a combination of Drug Discovery and detecting patients or subjects who may not respond or be responding to a particular treatment, therapy, compound, drug or combination of drugs or compounds (e.g., by as to individual(s), so detecting response, nor responding, potential to respond or not, and adjusting particular treatment, therapy, compound, drug or combination of drugs or compounds to be administered or administering a treatment, therapy, compound, drug or combination of drugs or compounds indicated from the detecting).

The invention provides compositions and methods for modulating T cell balance, e.g., Th17 cell differentiation, maintenance and function, and means for exploiting this network in a variety of therapeutic and diagnostic methods. As used herein, the term "modulating" includes up-regulation of, or otherwise increasing, the expression of one or more genes, down-regulation of, or otherwise decreasing, the expression of one or more genes, inhibiting or otherwise decreasing the expression, activity and/or function of one or more gene products, and/or enhancing or otherwise increasing the expression, activity and/or function of one or more gene products.

As used herein, the term "modulating T cell balance" includes the modulation of any of a variety of T cell-related functions and/or activities, including by way of non-limiting example, controlling or otherwise influencing the networks that regulate T cell differentiation; controlling or otherwise influencing the networks that regulate T cell maintenance, for example, over the lifespan of a T cell; controlling or otherwise influencing the networks that regulate T cell function; controlling or otherwise influencing the networks that regulate helper T cell (Th cell) differentiation; controlling or otherwise influencing the networks that regulate Th cell maintenance, for example, over the lifespan of a Th cell; controlling or otherwise influencing the networks that regulate Th cell function; controlling or otherwise influencing the networks that regulate Th17 cell differentiation; controlling or otherwise influencing the networks that regulate Th17 cell maintenance, for example, over the lifespan of a Th17 cell; controlling or otherwise influencing the networks that regulate Th17 cell function; controlling or otherwise influencing the networks that regulate regulatory T cell (Treg) differentiation; controlling or otherwise influencing the networks that regulate Treg cell maintenance, for example, over the lifespan of a Treg cell; controlling or otherwise influencing the networks that regulate Treg cell function; controlling or otherwise influencing the networks that regulate other CD4+ T cell differentiation; controlling or otherwise influencing the networks that regulate other CD4+ T cell maintenance; controlling or otherwise influencing the networks that regulate other CD4+ T cell function; manipulating or otherwise influencing the ratio of T cells such as, for example, manipulating or otherwise influencing the ratio of Th17 cells to other T cell types such as Tregs or other CD4+ T cells; manipulating or otherwise influencing the ratio of different types of Th17 cells such as, for example, pathogenic Th17 cells and non-pathogenic Th17 cells; manipulating or otherwise influencing at least one function or biological activity of a T cell; manipulating or otherwise influencing at least one function or biological activity of Th cell; manipulating or otherwise influencing at least one function or biological activity of a Treg cell; manipulating or otherwise influencing at least one function or biological activity of a Th17 cell; and/or manipulating or otherwise influencing at least one function or biological activity of another CD4+ T cell.

The invention provides T cell modulating agents that modulate T cell balance. For example, in some embodiments, the invention provides T cell modulating agents and methods of using these T cell modulating agents to regulate, influence or otherwise impact the level(s) of and/or balance between T cell types, e.g., between Th17 and other T cell types, for example, regulatory T cells (Tregs), and/or Th17 activity and inflammatory potential. As used herein, terms such as "Th17 cell" and/or "Th17 phenotype" and all grammatical variations thereof refer to a differentiated T helper cell that expresses one or more cytokines selected from the group the consisting of interleukin 17A (IL-17A), interleukin 17F (IL-17F), and interleukin 17A/F heterodimer (IL17-AF). As used herein, terms such as "Th1 cell" and/or "Th1 phenotype" and all grammatical variations thereof refer to a differentiated T helper cell that expresses interferon gamma (IFNγ). As used herein, terms such as "Th2 cell" and/or "Th2 phenotype" and all grammatical variations thereof refer to a differentiated T helper cell that expresses one or more cytokines selected from the group the consisting of interleukin 4 (IL-4), interleukin 5 (IL-5) and interleukin 13 (IL-13). As used herein, terms such as "Treg cell" and/or "Treg phenotype" and all grammatical variations thereof refer to a differentiated T cell that expresses Foxp3.

For example, in some embodiments, the invention provides T cell modulating agents and methods of using these T cell modulating agents to regulate, influence or otherwise impact the level of and/or balance between Th17 phenotypes, and/or Th17 activity and inflammatory potential. Suitable T cell modulating agents include an antibody, a soluble polypeptide, a polypeptide agent, a peptide agent, a nucleic acid agent, a nucleic acid ligand, or a small molecule agent.

For example, in some embodiments, the invention provides T cell modulating agents and methods of using these T cell modulating agents to regulate, influence or otherwise impact the level of and/or balance between Th17 cell types, e.g., between pathogenic and non-pathogenic Th17 cells. For example, in some embodiments, the invention provides T cell modulating agents and methods of using these T cell modulating agents to regulate, influence or otherwise impact the level of and/or balance between pathogenic and non-pathogenic Th17 activity.

For example, in some embodiments, the invention provides T cell modulating agents and methods of using these T cell modulating agents to influence or otherwise impact the differentiation of a population of T cells, for example toward Th17 cells, with or without a specific pathogenic distinction, or away from Th17 cells, with or without a specific pathogenic distinction For example, in some embodiments, the invention provides T cell modulating agents and methods of using these T cell modulating agents to influence or otherwise impact the differentiation of a population of T cells, for example toward a non-Th17 T cell subset or away from a non-Th17 cell subset. For example, in some embodiments, the invention provides T cell modulating agents and methods of using these T cell modulating agents to induce T-cell plasticity, i.e., converting Th17 cells into a different subtype, or into a new state.

For example, in some embodiments, the invention provides T cell modulating agents and methods of using these T cell modulating agents to induce T cell plasticity, e.g., converting Th17 cells into a different subtype, or into a new state.

For example, in some embodiments, the invention provides T cell modulating agents and methods of using these T cell modulating agents to achieve any combination of the above.

In some embodiments, the T cells are naïve T cells. In some embodiments, the T cells are differentiated T cells. In some embodiments, the T cells are partially differentiated T cells. In some embodiments, the T cells are a mixture of naïve T cells and differentiated T cells. In some embodiments, the T cells are mixture of naïve T cells and partially differentiated T cells. In some embodiments, the T cells are mixture of partially differentiated T cells and differentiated T cells. In some embodiments, the T cells are mixture of naïve T cells, partially differentiated T cells, and differentiated T cells.

The T cell modulating agents are used to modulate the expression of one or more target genes or one or more products of one or more target genes that have been identified as genes responsive to Th17-related perturbations. These target genes are identified, for example, contacting a T cell, e.g., naïve T cells, partially differentiated T cells, differentiated T cells and/or combinations thereof, with a T cell modulating agent and monitoring the effect, if any, on the expression of one or more signature genes or one or more products of one or more signature genes. In some embodiments, the one or more signature genes are selected from those listed in Table 1 or Table 2 of the specification.

In some embodiments, the target gene is one or more Th17-associated cytokine(s) or receptor molecule(s) selected from those listed in Table 3 of the specification. In some embodiments, the target gene is one or more Th17-associated transcription regulator(s) selected from those shown in Table 4 of the specification.

In some embodiments, the target gene is one or more Th17-associated transcription regulator(s) selected from those shown in Table 5 of the specification. In some embodiments, the target gene is one or more Th17-associated receptor molecule(s) selected from those listed in Table 6 of the specification. In some embodiments, the target gene is one or more Th17-associated kinase(s) selected from those listed in Table 7 of the specification. In some embodiments, the target gene is one or more Th17-associated signaling molecule(s) selected from those listed in Table 8 of the specification. In some embodiments, the target gene is one or more Th17-associated receptor molecule(s) selected from those listed in Table 9 of the specification.

In some embodiments, the target gene is one or more target genes involved in induction of Th17 differentiation such as, for example, IRF1, IRF8, IRF9, STAT2, STAT3, IRF7, STAT1, ZFP281, IFI35, REL, TBX21, FLI1, BATF, IRF4, one or more of the target genes listed in Table 5 as being associated with the early stage of Th17 differentiation, maintenance and/or function, e.g., AES, AHR, ARID5A, BATF, BCL11B, BCL3, CBFB, CBX4, CHD7, CITED2, CREB1, E2F4, EGR1, EGR2, ELL2, ETS1, ETS2, ETV6, EZH1, FLI1, FOXO1, GATA3, GATAD2B, HIF1A, ID2, IFI35, IKZF4, IRF1, IRF2, IRF3, IRF4, IRF7, IRF9, JMJD1C, JUN, LEF1, LRRFIP1, MAX, NCOA3, NFE2L2, NFIL3, NFKB1, NMI, NOTCH1, NR3C1, PHF21A, PML, PRDM1, REL, RELA, RUNX1, SAP18, SATB1, SMAD2, SMARCA4, SP100, SP4, STAT1, STAT2, STAT3, STAT4, STAT5B, STAT6, TFEB, TP53, TRIM24, and/or ZFP161, or any combination thereof.

In some embodiments, the target gene is one or more target genes involved in onset of Th17 phenotype and amplification of Th17 T cells such as, for example, IRF8, STAT2, STAT3, IRF7, JUN, STAT5B, ZPF2981, CHD7, TBX21, FLI1, SATB1, RUNX1, BATF, RORC, SP4, one or more of the target genes listed in Table 5 as being associated with the intermediate stage of Th17 differentiation, maintenance and/or function, e.g., AES, AHR, ARID3A, ARID5A, ARNTL, ASXL1, BATF, BCL11B, BCL3, BCL6, CBFB, CBX4, CDC5L, CEBPB, CHD7, CREB1, CREB3L2, CREM, E2F4, E2F8, EGR1, EGR2, ELK3, ELL2, ETS1, ETS2, ETV6, EZH1, FLI1, FOSL2, FOXJ2, FOXO1, FUS, HIF1A, HMGB2, ID1, ID2, IFI35, IKZF4, IRF3, IRF4, IRF7, IRF8, IRF9, JUN, JUNB, KAT2B, KLF10, KLF6, KLF9, LEF1, LRRFIP1, MAFF, MAX, MAZ, MINA, MTA3, MYC, MYST4, NCOA1, NCOA3, NFE2L2, NFIL3, NFKB1, NMI, NOTCH1, NR3C1, PHF21A, PML, POU2AF1, POU2F2, PRDM1, RARA, RBPJ, RELA, RORA, RUNX1, SAP18, SATB1, SKI, SKIL, SMAD2, SMAD7, SMARCA4, SMOX, SP1, SP4, SS18, STAT1, STAT2, STAT3, STAT5A, STAT5B, STAT6, SUZ12, TBX21, TFEB, TLE1, TP53, TRIM24, TRIM28, TRPS1, VAV1, ZEB1, ZEB2, ZFP161, ZFP62, ZNF238, ZNF281, and/or ZNF703, or any combination thereof.

In some embodiments, the target gene is one or more target genes involved in stabilization of Th17 cells and/or modulating Th17-associated interleukin 23 (IL-23) signaling such as, for example, STAT2, STAT3, JUN, STAT5B, CHD7, SATB1, RUNX1, BATF, RORC, SP4 IRF4, one or more of the target genes listed in Table 5 as being associated with the late stage of Th17 differentiation, maintenance and/or function, e.g., AES, AHR, ARID3A, ARID5A, ARNTL, ASXL1, ATF3, ATF4, BATF, BATF3, BCL11B, BCL3, BCL6, C21ORF66, CBFB, CBX4, CDC5L, CDYL, CEBPB, CHD7, CHMP1B, CIC, CITED2, CREB1, CREB3L2, CREM, CSDA, DDIT3, E2F1, E2F4, E2F8, EGR1, EGR2, ELK3, ELL2, ETS1, ETS2, EZH1, FLI1, FOSL2, FOXJ2, FOXO1, FUS, GATA3, GATAD2B, HCLS1, HIF1A, ID1, ID2, IFI35, IKZF4, IRF3, IRF4, IRF7, IRF8, IRF9, JARID2, JMJD1C, JUN, JUNB, KAT2B, KLF10, KLF6, KLF7, KLF9, LASS4, LEF1, LRRFIP1, MAFF, MAX, MEN1, MINA, MTA3, MXI1, MYC, MYST4, NCOA1, NCOA3, NFE2L2, NFIL3, NFKB1, NMI, NOTCH1, NR3C1, PHF13, PHF21A, PML, POU2AF1, POU2F2, PRDM1, RARA, RBPJ, REL, RELA, RNF11, RORA, RORC, RUNX1, RUNX2, SAP18, SAP30, SATB1, SERTAD1, SIRT2, SKI, SKIL, SMAD2, SMAD4, SMAD7, SMARCA4, SMOX, SP1, SP100, SP4, SS18, STAT1, STAT3, STAT4, STAT5A, STAT5B, STAT6, SUZ12, TBX21, TFEB, TGIF1, TLE1, TP53, TRIM24, TRPS1, TSC22D3, UBE2B, VAV1, VAX2, XBP1, ZEB1, ZEB2, ZFP161, ZFP36L1, ZFP36L2, ZNF238, ZNF281, ZNF703, ZNRF1, and/or ZNRF2, or any combination thereof.

In some embodiments, the target gene is one or more of the target genes listed in Table 6 as being associated with the early stage of Th17 differentiation, maintenance and/or function, e.g., FAS, CCR5, IL6ST, IL17RA, IL2RA, MYD88, CXCR5, PVR, IL15RA, IL12RB1, or any combination thereof.

In some embodiments, the target gene is one or more of the target genes listed in Table 6 as being associated with the intermediate stage of Th17 differentiation, maintenance and/or function, e.g., IL7R, ITGA3, IL1R1, CCR5, CCR6, ACVR2A, IL6ST, IL17RA, CCR8, DDR1, PROCR, IL2RA, IL12RB2, MYD88, PTPRJ, TNFRSF13B, CXCR3, IL1RN, CXCR5, CCR4, IL4R, IL2RB, TNFRSF12A, CXCR4, KLRD1, IRAK1BP1, PVR, IL12RB1, IL18R1, TRAF3, or any combination thereof.

In some embodiments, the target gene is one or more of the target genes listed in Table 6 as being associated with the late stage of Th17 differentiation, maintenance and/or function, e.g., IL7R, ITGA3, IL1R1, FAS, CCR5, CCR6, ACVR2A, IL6ST, IL17RA, DDR1, PROCR, IL2RA, IL12RB2, MYD88, BMPR1A, PTPRJ, TNFRSF13B, CXCR3, IL1RN, CXCR5, CCR4, IL4R, IL2RB, TNFRSF12A, CXCR4, KLRD1, IRAK1BP1, PVR, IL15RA, TLR1, ACVR1B, IL12RB1, IL18R1, TRAF3, IFNGR1, PLAUR, IL21R, IL23R, or any combination thereof.

In some embodiments, the target gene is one or more of the target genes listed in Table 7 as being associated with the early stage of Th17 differentiation, maintenance and/or function, e.g., EIF2AK2, DUSP22, HK2, RIPK1, RNASEL, TEC, MAP3K8, SGK1, PRKCQ, DUSP16, BMP2K, PIM2, or any combination thereof.

In some embodiments, the target gene is one or more of the target genes listed in Table 7 as being associated with the intermediate stage of Th17 differentiation, maintenance and/or function, e.g., PSTPIP1, PTPN1, ACP5, TXK, RIPK3, PTPRF, NEK4, PPME1, PHACTR2, HK2, GMFG, DAPP1, TEC, GMFB, PIM1, NEK6, ACVR2A, FES, CDK6, ZAK, DUSP14, SGK1, JAK3, ULK2, PTPRJ, SPHK1, TNK2, PCTK1, MAP4K3, TGFBR1, HK1, DDR1, BMP2K, DUSP10, ALPK2, or any combination thereof.

In some embodiments, the target gene is one or more of the target genes listed in Table 7 as being associated with the late stage of Th17 differentiation, maintenance and/or function, e.g., PTPLA, PSTPIP1, TK1, PTEN, BPGM, DCK, PTPRS, PTPN18, MKNK2, PTPN1, PTPRE, SH2D1A, PLK2, DUSP6, CDC25B, SLK, MAP3K5, BMPR1A, ACP5, TXK, RIPK3, PPP3CA, PTPRF, PACSIN1, NEK4, PIP4K2A, PPME1, SRPK2, DUSP2, PHACTR2, DCLK1, PPP2R5A, RIPK1, GK, RNASEL, GMFG, STK4, HINT3, DAPP1, TEC, GMFB, PTPN6, RIPK2, PIM1, NEK6, ACVR2A, AURKB, FES, ACVR1B, CDK6, ZAK, VRK2, MAP3K8, DUSP14, SGK1, PRKCQ, JAK3, ULK2, HIPK2, PTPRJ, INPP1, TNK2, PCTK1, DUSP1, NUDT4, TGFBR1, PTP4A1, HK1, DUSP16, ANP32A, DDR1, ITK, WNK1, NAGK, STK38, BMP2K, BUB1, AAK1, SIK1, DUSP10, PRKCA, PIM2, STK17B, TK2, STK39, ALPK2, MST4, PHLPP1, or any combination thereof.

In some embodiments, the target gene is one or more of the target genes listed in Table 8 as being associated with the early stage of Th17 differentiation, maintenance and/or function, e.g., HK2, CDKN1A, DUT, DUSP1, NADK, LIMK2, DUSP11, TAOK3, PRPS1, PPP2R4, MKNK2, SGK1, BPGM, TEC, MAPK6, PTP4A2, PRPF4B, ACP1, CCRN4L, or any combination thereof.

In some embodiments, the target gene is one or more of the target genes listed in Table 8 as being associated with the intermediate stage of Th17 differentiation, maintenance and/or function, e.g., HK2, ZAP70, NEK6, DUSP14, SH2D1A, ITK, DUT, PPP1R11, DUSP1, PMVK, TK1, TAOK3, GMFG, PRPS1, SGK1, TXK, WNK1, DUSP19, TEC, RPS6KA1, PKM2, PRPF4B, ADRBK1, CKB, ULK2, PLK1, PPP2R5A, PLK2, or any combination thereof.

In some embodiments, the target gene is one or more of the target genes listed in Table 8 as being associated with the late stage of Th17 differentiation, maintenance and/or function, e.g., ZAP70, PFKP, NEK6, DUSP14, SH2D1A, INPP5B, ITK, PFKL, PGK1, CDKN1A, DUT, PPP1R11, DUSP1, PMVK, PTPN22, PSPH, TK1, PGAM1, LIMK2, CLK1, DUSP11, TAOK3, RIOK2, GMFG, UCKL1, PRPS1, PPP2R4, MKNK2, DGKA, SGK1, TXK, WNK1, DUSP19, CHP, BPGM, PIP5K1A, TEC, MAP2K1, MAPK6, RPS6KA1, PTP4A2, PKM2, PRPF4B, ADRBK1, CKB, ACP1, ULK2, CCRN4L, PRKCH, PLK1, PPP2R5A, PLK2, or any combination thereof.

In some embodiments, the target gene is one or more of the target genes listed in Table 9 as being associated with the early stage of Th17 differentiation, maintenance and/or function, e.g., CD200, CD40LG, CD24, CCND2, ADAM17, BSG, ITGAL, FAS, GPR65, SIGMAR1, CAP1, PLAUR, SRPRB, TRPV2, IL2RA, KDELR2, TNFRSF9, or any combination thereof.

In some embodiments, the target gene is one or more of the target genes listed in Table 9 as being associated with the intermediate stage of Th17 differentiation, maintenance and/or function, e.g., CTLA4, CD200, CD24, CD5L, CD9, IL2RB, CD53, CD74, CAST, CCR6, IL2RG, ITGAV, FAS, IL4R, PROCR, GPR65, TNFRSF18, RORA, IL1RN, RORC, CYSLTR1, PNRC2, LOC390243, ADAM10, TNFSF9, CD96, CD82, SLAMF7, CD27, PGRMC1, TRPV2, ADRBK1, TRAF6, IL2RA, THY1, IL12RB2, TNFRSF9, or any combination thereof.

In some embodiments, the target gene is one or more of the target genes listed in Table 9 as being associated with the late stage of Th17 differentiation, maintenance and/or function, e.g., CTLA4, TNFRSF4, CD44, PDCD1, CD200, CD247, CD24, CD5L, CCND2, CD9, IL2RB, CD53, CD74, ADAM17, BSG, CAST, CCR6, IL2RG, CD81, CD6, CD48, ITGAV, TFRC, ICAM2, ATP1B3, FAS, IL4R, CCR7, CD52, PROCR, GPR65, TNFRSF18, FCRL1, RORA, IL1RN, RORC, P2RX4, SSR2, PTPN22, SIGMAR1, CYSLTR1, LOC390243, ADAM10, TNFSF9, CD96, CAP1, CD82, SLAMF7, PLAUR, CD27, SIVA1, PGRMC1, SRPRB, TRPV2, NR1H2, ADRBK1, GABARAPL1, TRAF6, IL2RA, THY1, KDELR2, IL12RB2, TNFRSF9, SCARB1, IFNGR1, or any combination thereof.

In some embodiments, the target gene is one or more target genes that is a promoter of Th17 cell differentiation. In some embodiments, the target gene is GPR65. In some embodiments, the target gene is also a promoter of pathogenic Th17 cell differentiation and is selected from the group consisting of CD5L, DEC1, PLZP and TCF4.

In some embodiments, the target gene is one or more target genes that is a promoter of pathogenic Th17 cell differentiation. In some embodiments, the target gene is selected from the group consisting of CD5L, DEC1, PLZP and TCF4.

The desired gene or combination of target genes is selected, and after determining whether the selected target gene(s) is overexpressed or under-expressed during Th17 differentiation and/or Th17 maintenance, a suitable antagonist or agonist is used depending on the desired differentiation, maintenance and/or function outcome. For example, for target genes that are identified as positive regulators of Th17 differentiation, use of an antagonist that interacts with those target genes will shift differentiation away from the Th17 phenotype, while use of an agonist that interacts with those target genes will shift differentiation toward the Th17 phenotype. For target genes that are identified as negative regulators of Th17 differentiation, use of an antagonist that interacts with those target genes will shift differentiation toward from the Th17 phenotype, while use of an agonist that interacts with those target genes will shift differentiation away the Th17 phenotype. For example, for target genes that are identified as positive regulators of Th17 maintenance, use of an antagonist that interacts with those target genes will reduce the number of cells with the Th17 phenotype, while use of an agonist that interacts with those target genes will increase the number of cells with the Th17 phenotype. For target genes that are identified as negative regulators of Th17 differentiation, use of an antagonist that interacts with those target genes will increase the number of cells with the Th17 phenotype, while use of an agonist that interacts with those target genes will reduce the number of cells with the Th17 phenotype. Suitable T cell modulating agents include an antibody, a soluble polypeptide, a polypeptide agent, a peptide agent, a nucleic acid agent, a nucleic acid ligand, or a small molecule agent.

In some embodiments, the positive regulator of Th17 differentiation is a target gene selected from MINA, TRPS1, MYC, NKFB1, NOTCH, PML, POU2AF1, PROCR, RBPJ, SMARCA4, ZEB1, BATF, CCR5, CCR6, EGR1, EGR2, ETV6, FAS, IL12RB1, IL17RA, IL21R, IRF4, IRF8, ITGA3, and combinations thereof. In some embodiments, the positive regulator of Th17 differentiation is a target gene selected from MINA, PML, POU2AF1, PROCR, SMARCA4, ZEB1, EGR2, CCR6, FAS and combinations thereof.

In some embodiments, the negative regulator of Th17 differentiation is a target gene selected from SP4, ETS2, IKZF4, TSC22D3, IRF1 and combinations thereof. In some embodiments, the negative regulator of Th17 differentiation is a target gene selected from SP4, IKZF4, TSC22D3 and combinations thereof.

In some embodiments, the T cell modulating agent is a soluble Fas polypeptide or a polypeptide derived from FAS. In some embodiments, the T cell modulating agent is an agent that enhances or otherwise increases the expression, activity, and/or function of FAS in Th17 cells. As shown herein, expression of FAS in T cell populations induced or otherwise influenced differentiation toward Th17 cells. In some embodiments, these T cell modulating agents are useful in the treatment of an immune response, for example, an autoimmune response or an inflammatory response. In some embodiments, these T cell modulating agents are useful in the treatment of an infectious disease or other pathogen-based disorders. In some embodiments, the T cell modulating agent is an antibody, a soluble polypeptide, a polypeptide agonist, a peptide agonist, a nucleic acid agonist, a nucleic acid ligand, or a small molecule agonist. In some embodiments, the T cells are naïve T cells. In some embodiments, the T cells are differentiated T cells. In some embodiments, the T cells are partially differentiated T cells. In some embodiments, the T cells are a mixture of naïve T cells and differentiated T cells. In some embodiments, the T cells are mixture of naïve T cells and partially differentiated T cells. In some embodiments, the T cells are mixture of partially differentiated T cells and differentiated T cells. In some embodiments, the T cells are mixture of naïve T cells, partially differentiated T cells, and differentiated T cells.

In some embodiments, the T cell modulating agent is an agent that inhibits the expression, activity and/or function of FAS. Inhibition of FAS expression, activity and/or function in T cell populations repressed or otherwise influenced differentiation away from Th17 cells and/or induced or otherwise influenced differentiation toward regulatory T cells (Tregs) and towards Th1 cells. In some embodiments, these T cell modulating agents are useful in the treatment of an immune response, for example, an autoimmune response or an inflammatory response. In some embodiments, these T cell modulating agents are useful in the treatment of autoimmune diseases such as psoriasis, inflammatory bowel disease (IBD), ankylosing spondylitis, multiple sclerosis, Sjögren's syndrome, uveitis, and rheumatoid arthritis, asthma, systemic lupus erythematosus, transplant rejection including allograft rejection, and combinations thereof. In addition, enhancement of Th17 cells is also useful for clearing fungal infections and extracellular pathogens. In some embodiments, the T cell modulating agent is an antibody, a soluble polypeptide, a polypeptide antagonist, a peptide antagonist, a nucleic acid antagonist, a nucleic acid ligand, or a small molecule antagonist. In some embodiments, the T cells are naïve T cells. In some embodiments, the T cells are differentiated T cells. In some embodiments, the T cells are partially differentiated T cells that express additional cytokines. In some embodiments, the T cells are a mixture of naïve T cells and differentiated T cells. In some embodiments, the T cells are mixture of naïve T cells and partially differentiated T cells. In some embodiments, the T cells are mixture of partially differentiated T cells and differentiated T cells. In some embodiments, the T cells are mixture of naïve T cells, partially differentiated T cells, and differentiated T cells.

In some embodiments, the T cell modulating agent is an agent that inhibits the expression, activity and/or function of CCR5. Inhibition of CCR5 expression, activity and/or function in T cell populations repressed or otherwise influenced differentiation away from Th17 cells and/or induced or otherwise influenced differentiation toward regulatory T cells (Tregs) and towards Th1 cells. In some embodiments, these T cell modulating agents are useful in the treatment of an immune response, for example, an autoimmune response or an inflammatory response. In some embodiments, the T cell modulating agent is an inhibitor or neutralizing agent. In some embodiments, the T cell modulating agent is an antibody, a soluble polypeptide, a polypeptide antagonist, a peptide antagonist, a nucleic acid antagonist, a nucleic acid ligand, or a small molecule antagonist. In some embodiments, the T cells are naïve T cells. In some embodiments, the T cells are differentiated T cells. In some embodiments, the T cells are partially differentiated T cells. In some embodiments, the T cells are a mixture of naïve T cells and differentiated T cells. In some embodiments, the T cells are mixture of naïve T cells and partially differentiated T cells. In some embodiments, the T cells are mixture of partially differentiated T cells and differentiated T cells. In some embodiments, the T cells are mixture of naïve T cells, partially differentiated T cells, and differentiated T cells.

In some embodiments, the T cell modulating agent is an agent that inhibits the expression, activity and/or function of CCR6. Inhibition of CCR6 expression, activity and/or function in T cell populations repressed or otherwise influenced differentiation away from Th17 cells and/or induced or otherwise influenced differentiation toward regulatory T cells (Tregs) and towards Th1 cells. In some embodiments, these T cell modulating agents are useful in the treatment of an immune response, for example, an autoimmune response or an inflammatory response. In some embodiments, the T cell modulating agent is an antibody, a soluble polypeptide, a polypeptide antagonist, a peptide antagonist, a nucleic acid antagonist, a nucleic acid ligand, or a small molecule antagonist. In some embodiments, the T cells are naïve T cells. In some embodiments, the T cells are differentiated T cells. In some embodiments, the T cells are partially differentiated T cells. In some embodiments, the T cells are a mixture of naïve T cells and differentiated T cells. In some embodiments, the T cells are mixture of naïve T cells and partially differentiated T cells. In some embodiments, the T cells are mixture of partially differentiated T cells and differentiated T cells. In some embodiments, the T cells are mixture of naïve T cells, partially differentiated T cells, and differentiated T cells.

In some embodiments, the T cell modulating agent is an agent that inhibits the expression, activity and/or function of EGR1. Inhibition of EGR1 expression, activity and/or function in T cell populations repressed or otherwise influenced differentiation away from Th17 cells and/or induced or otherwise influenced differentiation toward regulatory T cells (Tregs) and towards Th1 cells. In some embodiments, these T cell modulating agents are useful in the treatment of an immune response, for example, an autoimmune response or an inflammatory response. In some embodiments, the T cell modulating agent is an antibody, a soluble polypeptide, a polypeptide antagonist, a peptide antagonist, a nucleic acid antagonist, a nucleic acid ligand, or a small molecule antagonist. In some embodiments, the T cells are naïve T cells. In some embodiments, the T cells are differentiated T cells. In some embodiments, the T cells are partially differentiated T cells. In some embodiments, the T cells are a mixture of naïve T cells and differentiated T cells. In some embodiments, the T cells are mixture of naïve T cells and partially differentiated T cells. In some embodiments, the T cells are mixture of partially differentiated T cells and differentiated T cells. In some embodiments, the T cells are mixture of naïve T cells, partially differentiated T cells, and differentiated T cells.

In some embodiments, the T cell modulating agent is an agent that inhibits the expression, activity and/or function of EGR2. Inhibition of EGR2 expression, activity and/or function in T cell populations repressed or otherwise influenced differentiation away from Th17 cells and/or induced or otherwise influenced differentiation toward regulatory T cells (Tregs) and towards Th1 cells. In some embodiments, these T cell modulating agents are useful in the treatment of an immune response, for example, an autoimmune response or an inflammatory response. In some embodiments, the T cell modulating agent is an antibody, a soluble polypeptide, a polypeptide antagonist, a peptide antagonist, a nucleic acid antagonist, a nucleic acid ligand, or a small molecule antagonist. In some embodiments, the T cells are naïve T cells. In some embodiments, the T cells are differentiated T cells. In some embodiments, the T cells are partially differentiated T cells. In some embodiments, the T cells are a mixture of naïve T cells and differentiated T cells. In some embodiments, the T cells are mixture of naïve T cells and partially differentiated T cells. In some embodiments, the T cells are mixture of partially differentiated T cells and differentiated T cells. In some embodiments, the T cells are mixture of naïve T cells, partially differentiated T cells, and differentiated T cells.

For example, in some embodiments, the invention provides T cell modulating agents and methods of using these T cell modulating agents to regulate, influence or otherwise impact the phenotype of a Th17 cell or population of cells, for example, by influencing a naïve T cell or population of cells to differentiate to a pathogenic or non-pathogenic Th17 cell or population of cells, by causing a pathogenic Th17 cell or population of cells to switch to a non-pathogenic Th17 cell or population of T cells (e.g., populations of naïve T cells, partially differentiated T cells, differentiated T cells and combinations thereof), or by causing a non-pathogenic Th17 cell or population of T cells (e.g., populations of naïve T cells, partially differentiated T cells, differentiated T cells and combinations thereof) to switch to a pathogenic Th17 cell or population of cells.

In some embodiments, the invention comprises a method of drug discovery for the treatment of a disease or condition involving an immune response involving T cell balance in a population of cells or tissue of a target gene comprising the steps of providing a compound or plurality of compounds to be screened for their efficacy in the treatment of said disease or condition, contacting said compound or plurality of compounds with said population of cells or tissue, detecting a first level of expression, activity and/or function of a target gene, comparing the detected level to a control of level of a target gene, and evaluating the difference between the detected level and the control level to determine the immune response elicited by said compound or plurality of compounds. For example, the method contemplates comparing tissue samples which can be inter alia infected tissue, inflamed tissue, healthy tissue, or combinations of tissue samples thereof.

In one embodiment of the invention, the reductase null animals of the present invention may advantageously be used to modulate T cell balance in a tissue or cell specific manner. Such animals may be used for the applications hereinbefore described, where the role of T cell balance in product/drug metabolism, detoxification, normal homeostasis or in disease etiology is to be studied. It is envisaged that this embodiment will also allow other effects, such as drug transporter-mediated effects, to be studied in those tissues or cells in the absence of metabolism, e.g., carbon metabolism. Accordingly the animals of the present invention, in a further aspect of the invention may be used to modulate the functions and antibodies in any of the above cell types to generate a disease model or a model for product/drug discovery or a model to verify or assess functions of T cell balance In another embodiment, the method contemplates use of animal tissues and/or a population of cells derived therefrom of the present invention as an in vitro assay for the study of any one or more of the following events/parameters: (i) role of transporters in product uptake and efflux; (ii) identification of product metabolites produced by T cells; (iii) evaluate whether candidate products are T cells; or (iv) assess drug/drug interactions due to T cell balance.

The terms "pathogenic" or "non-pathogenic" as used herein are not to be construed as implying that one Th17 cell phenotype is more desirable than the other. As described herein, there are instances in which inhibiting the induction of pathogenic Th17 cells or modulating the Th17 phenotype towards the non-pathogenic Th17 phenotype is desirable. Likewise, there are instances where inhibiting the induction of non-pathogenic Th17 cells or modulating the Th17 phenotype towards the pathogenic Th17 phenotype is desirable.

As used herein, terms such as "pathogenic Th17 cell" and/or "pathogenic Th17 phenotype" and all grammatical variations thereof refer to Th17 cells that, when induced in the presence of TGF-β3, express an elevated level of one or more genes selected from Cxcl3, IL22, IL3, Ccl4, Gzmb, Lrmp, Ccl5, Casp1, Csf2, Ccl3, Tbx21, Icos, IL17r, Stat4, Lgals3 and Lag, as compared to the level of expression in a TGF-β3-induced Th17 cells. As used herein, terms such as "non-pathogenic Th17 cell" and/or "non-pathogenic Th17 phenotype" and all grammatical variations thereof refer to Th17 cells that, when induced in the presence of TGF-β3, express a decreased level of one or more genes selected from IL6st, IL1rn, Ikzf3, Maf, Ahr, IL9 and IL10, as compared to the level of expression in a TGF-β3-induced Th17 cells.

In some embodiments, the T cell modulating agent is an agent that enhances or otherwise increases the expression, activity and/or function of Protein C Receptor (PROCR, also called EPCR or CD201) in Th17 cells. As shown herein, expression of PROCR in Th17 cells reduced the pathogenicity of the Th17 cells, for example, by switching Th17 cells from a pathogenic to non-pathogenic signature. Thus, PROCR and/or these agonists of PROCR are useful in the treatment of a variety of indications, particularly in the treatment of aberrant immune response, for example in autoimmune diseases and/or inflammatory disorders. In some embodiments, the T cell modulating agent is an antibody, a soluble polypeptide, a polypeptide agonist, a peptide agonist, a nucleic acid agonist, a nucleic acid ligand, or a small molecule agonist.

In some embodiments, the T cell modulating agent is an agent that inhibits the expression, activity and/or function of the Protein C Receptor (PROCR, also called EPCR or CD201). Inhibition of PROCR expression, activity and/or function in Th17 cells switches non-pathogenic Th17 cells to pathogenic Th17 cells. Thus, these PROCR antagonists are useful in the treatment of a variety of indications, for example, infectious disease and/or other pathogen-based disorders. In some embodiments, the T cell modulating agent is an antibody, a soluble polypeptide, a polypeptide antagonist, a peptide antagonist, a nucleic acid antagonist, a nucleic acid ligand, or a small molecule antagonist. In some embodiments, the T cell modulating agent is a soluble Protein C Receptor (PROCR, also called EPCR or CD201) polypeptide or a polypeptide derived from PROCR.

In some embodiments, the invention provides a method of inhibiting Th17 differentiation, maintenance and/or function in a cell population and/or increasing expression, activity and/or function of one or more non-Th17-associated cytokines, one or more non-Th17 associated receptor molecules, or non-Th17-associated transcription regulators selected from FOXP3, interferon gamma (IFN-γ), GATA3, STAT4 and TBX21, comprising contacting a T cell with an agent that inhibits expression, activity and/or function of MINA, MYC, NKFB1, NOTCH, PML, POU2AF1, PROCR, RBPJ, SMARCA4, ZEB1, BATF, CCR5, CCR6, EGR1, EGR2, ETV6, FAS, IL12RB1, IL17RA, IL21R, IRF4, IRF8, ITGA3 or combinations thereof. In some embodiments, the agent inhibits expression, activity and/or function of at least one of MINA, PML, POU2AF1, PROCR, SMARCA4, ZEB1, EGR2, CCR6, FAS or combinations thereof. In some embodiments, the agent is an antibody, a soluble polypeptide, a polypeptide antagonist, a peptide antagonist, a nucleic acid antagonist, a nucleic acid ligand, or a small molecule antagonist. In some embodiments, the antibody is a monoclonal antibody. In some embodiments, the antibody is a chimeric, humanized or fully human monoclonal antibody. In some embodiments, the T cell is a naïve T cell, and wherein the agent is administered in an amount that is sufficient to modulate the phenotype of the T cell to become and/or produce a desired non-Th17 T cell phenotype, for example, a regulatory T cell (Treg) phenotype or another CD4+ T cell phenotype. In some embodiments, the T cell is a partially differentiated T cell, and wherein the agent is administered in an amount that is sufficient to modulate the phenotype of the partially differentiated T cell to become and/or produce a desired non-Th17 T cell phenotype, for example, a regulatory T cell (Treg) phenotype or another CD4+ T cell phenotype. In some embodiments, the T cell is a Th17 T cell, and wherein the agent is administered in an amount that is sufficient to modulate the phenotype of the Th17 T cell to become and/or produce a CD4+ T cell phenotype other than a Th17 T cell phenotype. In some embodiments, the T cell is a Th17 T cell, and wherein the agent is administered in an amount that is sufficient to modulate the phenotype of the Th17 T cell to become and/or produce a shift in the Th17 T cell phenotype, e.g., between pathogenic or non-pathogenic Th17 cell phenotype.

In some embodiments, the invention provides a method of inhibiting Th17 differentiation in a cell population and/or increasing expression, activity and/or function of one or more non-Th17-associated cytokines, one or more non-Th17-associated receptor molecules, or non-Th17-associated transcription factor selected from FOXP3, interferon gamma (IFN-γ), GATA3, STAT4 and TBX21, comprising contacting a T cell with an agent that enhances expression, activity and/or function of SP4, ETS2, IKZF4, TSC22D3, IRF1 or combinations thereof. In some embodiments, the agent enhances expression, activity and/or function of at least one of SP4, IKZF4, TSC22D3 or combinations thereof. In some embodiments, the agent is an antibody, a soluble polypeptide, a polypeptide agonist, a peptide agonist, a nucleic acid agonist, a nucleic acid ligand, or a small molecule agonist. In some embodiments, the antibody is a monoclonal antibody. In some embodiments, the T cell is a naïve T cell, and wherein the agent is administered in an amount that is sufficient to modulate the phenotype of the T cell to become and/or produce a desired non-Th17 T cell phenotype, for example, a regulatory T cell (Treg) phenotype or another CD4+ T cell phenotype. In some embodiments, the T cell is a partially differentiated T cell, and wherein the agent is administered in an amount that is sufficient to modulate the phenotype of the partially differentiated T cell to become and/or produce a desired non-Th17 T cell phenotype, for example, a regulatory T cell (Treg) phenotype or another CD4+ T cell phenotype. In some embodiments, the T cell is a Th17 T cell, and wherein the agent is administered in an amount that is sufficient to modulate the phenotype of the Th17 T cell to become and/or produce a CD4+ T cell phenotype other than a Th17 T cell phenotype. In some embodiments, the T cell is a Th17 T cell, and wherein the agent is administered in an amount that is sufficient to modulate the phenotype of the Th17 T cell to become and/or produce a shift in the Th17 T cell phenotype, e.g., between pathogenic or non-pathogenic Th17 cell phenotype.

In some embodiments, the invention provides a method of enhancing Th17 differentiation in a cell population increasing expression, activity and/or function of one or more Th17-associated cytokines, one or more Th17-associated receptor molecules, or one or more Th17-associated transcription regulators selected from interleukin 17F (IL-17F), interleukin 17A (IL-17A), STAT3, interleukin 21 (IL-21) and RAR-related orphan receptor C (RORC), and/or decreasing expression, activity and/or function of one or more non-Th17-associated cytokines, one or more Th17-associated receptor molecules, or one or more non-Th17-associated transcription regulators selected from FOXP3, interferon gamma (IFN-γ), GATA3, STAT4 and TBX21, comprising contacting a T cell with an agent that inhibits expression, activity and/or function of SP4, ETS2, IKZF4, TSC22D3, IRF1 or combinations thereof. In some embodiments, the agent inhibits expression, activity and/or function of at least one of SP4, IKZF4, TSC22D3 or combinations thereof. In some embodiments, the agent is an antibody, a soluble polypeptide, a polypeptide antagonist, a peptide antagonist, a nucleic acid antagonist, a nucleic acid ligand, or a small molecule antagonist. In some embodiments, the antibody is a monoclonal antibody. In some embodiments, the antibody is a chimeric, humanized or fully human monoclonal antibody. In some embodiments, the T cell is a naïve T cell, and wherein the agent is administered in an amount that is sufficient to modulate the phenotype of the T cell to become and/or produce a desired Th17 T cell phenotype. In some embodiments, the T cell is a partially differentiated T cell, and wherein the agent is administered in an amount that is sufficient to modulate the phenotype of the partially differentiated T cell to become and/or produce a desired Th17 T cell phenotype. In some embodiments, the T cell is a CD4+ T cell other than a Th17 T cell, and wherein the agent is administered in an amount that is sufficient to modulate the phenotype of the non-Th17 T cell to become and/or produce a Th17 T cell phenotype. In some embodiments, the T cell is a Th17 T cell, and wherein the agent is administered in an amount that is sufficient to modulate the phenotype of the Th17 T cell to become and/or produce a shift in the Th17 T cell phenotype, e.g., between pathogenic or non-pathogenic Th17 cell phenotype.

In some embodiments, the invention provides a method of enhancing Th17 differentiation in a cell population, increasing expression, activity and/or function of one or more Th17-associated cytokines, one or more Th17-associated receptor molecules, and/or one or more Th17-associated transcription regulators selected from interleukin 17F (IL-17F), interleukin 17A (IL-17A), STAT3, interleukin 21 (IL-21) and RAR-related orphan receptor C (RORC), and/or decreasing expression, activity and/or function of one or more non-Th17-associated cytokines, one or more Th17-associated receptor molecules, or one or more non-Th17-associated transcription regulators selected from FOXP3, interferon gamma (IFN-γ), GATA3, STAT4 and TBX21, comprising contacting a T cell with an agent that enhances expression, activity and/or function of MINA, MYC, NKFB1, NOTCH, PML, POU2AF1, PROCR, RBPJ, SMARCA4, ZEB1, BATF, CCR5, CCR6, EGR1, EGR2, ETV6, FAS, IL12RB1, IL17RA, IL21R, IRF4, IRF8, ITGA3 or combinations thereof. In some embodiments, the agent enhances expression, activity and/or function of at least one of MINA, PML, POU2AF1, PROCR, SMARCA4, ZEB1, EGR2, CCR6, FAS or combinations thereof. In some embodiments, the agent is an antibody, a soluble polypeptide, a polypeptide agonist, a peptide agonist, a nucleic acid agonist, a nucleic acid ligand, or a small molecule agonist. In some embodiments, the antibody is a monoclonal antibody. In some embodiments, the antibody is a chimeric, humanized or fully human monoclonal antibody. In some embodiments, the agent is administered in an amount sufficient to inhibit Foxp3, IFN-γ, GATA3, STAT4 and/or TBX21 expression, activity and/or function. In some embodiments, the T cell is a naïve T cell, and wherein the agent is administered in an amount that is sufficient to modulate the phenotype of the T cell to become and/or produce a desired Th17 T cell phenotype. In some embodiments, the T cell is a partially differentiated T cell, and wherein the agent is administered in an amount that is sufficient to modulate the phenotype of the partially differentiated T cell to become and/or produce a desired Th17 T cell phenotype. In some embodiments, the T cell is a CD4+ T cell other than a Th17 T cell, and wherein the agent is administered in an amount that is sufficient to modulate the phenotype of the non-Th17 T cell to become and/or produce a Th17 T cell phenotype. In some embodiments, the T cell is a Th17 T cell, and wherein the agent is administered in an amount that is sufficient to modulate the phenotype of the Th17 T cell to become and/or produce a shift in the Th17 T cell phenotype, e.g., between pathogenic or non-pathogenic Th17 cell phenotype.

In some embodiments, the invention provides a method of identifying genes or genetic elements associated with Th17 differentiation comprising: a) contacting a T cell with an inhibitor of Th17 differentiation or an agent that enhances Th17 differentiation; and b) identifying a gene or genetic element whose expression is modulated by step (a). In some embodiments, the method also comprises c) perturbing expression of the gene or genetic element identified in step b) in a T cell that has been in contact with an inhibitor of Th17 differentiation or an agent that enhances Th17 differentiation; and d) identifying a gene whose expression is modulated by step c). In some embodiments, the inhibitor of Th17 differentiation is an agent that inhibits the expression, activity and/or function of MINA, MYC, NKFB1, NOTCH, PML, POU2AF1, PROCR, RBPJ, SMARCA4, ZEB1, BATF, CCR5, CCR6, EGR1, EGR2, ETV6, FAS, IL12RB1, IL17RA, IL21R, IRF4, IRF8, ITGA3 or combinations thereof. In some embodiments, the agent inhibits expression, activity and/or function of at least one of MINA, PML, POU2AF1, PROCR, SMARCA4, ZEB1, EGR2, CCR6, FAS or combinations thereof. In some embodiments, the inhibitor of Th17 differentiation is an agent that enhances expression, activity and/or function of SP4, ETS2, IKZF4, TSC22D3, IRF1 or combinations thereof. In some embodiments, the agent enhances expression, activity and/or function of at least one of SP4, IKZF4 or TSC22D3. In some embodiments, the agent that enhances Th17 differentiation is an agent that inhibits expression, activity and/or function of SP4, ETS2, IKZF4, TSC22D3, IRF1 or combinations thereof. In some embodiments, wherein the agent that enhances Th17 differentiation is an agent that enhances expression, activity and/or function of MINA, MYC, NKFB1, NOTCH, PML, POU2AF1, PROCR, RBPJ, SMARCA4, ZEB1, BATF, CCR5, CCR6, EGR1, EGR2, ETV6, FAS, IL12RB1, IL17RA, IL21R, IRF4, IRF8, ITGA3 or combinations thereof. In some embodiments, the agent is an antibody, a soluble polypeptide, a polypeptide antagonist, a peptide antagonist, a nucleic acid antagonist, a nucleic acid ligand, or a small molecule antagonist.

In some embodiments, the invention provides a method of modulating induction of Th17 differentiation comprising contacting a T cell with an agent that modulates expression, activity and/or function of one or more target genes or one or more products of one or more target genes selected from IRF1, IRF8, IRF9, STAT2, STAT3, IRF7, STAT1, ZFP281, IFI35, REL, TBX21, FLI1, BATF, IRF4, one or more of the target genes listed in Table 5 as being associated with the early stage of Th17 differentiation, maintenance and/or function, e.g., AES, AHR, ARID5A, BATF, BCL11B, BCL3, CBFB, CBX4, CHD7, CITED2, CREB1, E2F4, EGR1, EGR2, ELL2, ETS1, ETS2, ETV6, EZH1, FLI1, FOXO1, GATA3, GATAD2B, HIF1A, ID2, IFI35, IKZF4, IRF1, IRF2, IRF3, IRF4, IRF7, IRF9, JMJD1C, JUN, LEF1, LRRFIP1, MAX, NCOA3, NFE2L2, NFIL3, NFKB1, NMI, NOTCH1, NR3C1, PHF21A, PML, PRDM1, REL, RELA, RUNX1, SAP18, SATB1, SMAD2, SMARCA4, SP100, SP4, STAT1, STAT2, STAT3, STAT4, STAT5B, STAT6, TFEB, TP53, TRIM24, and/or ZFP161, or any combination thereof.

In some embodiments, the invention provides a method of modulating onset of Th17 phenotype and amplification of Th17 T cells comprising contacting a T cell with an agent that modulates expression, activity and/or function of one or more target genes or one or more products of one or more target genes selected from IRF8, STAT2, STAT3, IRF7, JUN, STAT5B, ZPF2981, CHD7, TBX21, FLI1, SATB1, RUNX1, BATF, RORC, SP4, one or more of the target genes listed in Table 5 as being associated with the intermediate stage of Th17 differentiation, maintenance and/or function, e.g., AES, AHR, ARID3A, ARID5A, ARNTL, ASXL1, BATF, BCL11B, BCL3, BCL6, CBFB, CBX4, CDC5L, CEBPB, CHD7, CREB1, CREB3L2, CREM, E2F4, E2F8, EGR1, EGR2, ELK3, ELL2, ETS1, ETS2, ETV6, EZH1, FLI1, FOSL2, FOXJ2, FOXO1, FUS, HIF1A, HMGB2, ID1, ID2, IFI35, IKZF4, IRF3, IRF4, IRF7, IRF8, IRF9, JUN, JUNB, KAT2B, KLF10, KLF6, KLF9, LEF1, LRRFIP1, MAFF, MAX, MAZ, MINA, MTA3, MYC, MYST4, NCOA1, NCOA3, NFE2L2, NFIL3, NFKB1, NMI, NOTCH1, NR3C1, PHF21A, PML, POU2AF1, POU2F2, PRDM1, RARA, RBPJ, RELA, RORA, RUNX1, SAP18, SATB1, SKI, SKIL, SMAD2, SMAD7, SMARCA4, SMOX, SP1, SP4, SS18, STAT1, STAT2, STAT3, STAT5A, STAT5B, STAT6, SUZ12, TBX21, TFEB, TLE1, TP53, TRIM24, TRIM28, TRPS1, VAV1, ZEB1, ZEB2, ZFP161, ZFP62, ZNF238, ZNF281, and/or ZNF703, or any combination thereof.

In some embodiments, the invention provides a method of modulating stabilization of Th17 cells and/or modulating Th17-associated interleukin 23 (IL-23) signaling comprising contacting a T cell with an agent that modulates expression, activity and/or function of one or more target genes or one or more products of one or more target genes selected from STAT2, STAT3, JUN, STAT5B, CHD7, SATB1, RUNX1, BATF, RORC, SP4 IRF4, one or more of the target genes listed in Table 5 as being associated with the late stage of Th17 differentiation, maintenance and/or function, e.g., AES, AHR, ARID3A, ARID5A, ARNTL, ASXL1, ATF3, ATF4, BATF, BATF3, BCL11B, BCL3, BCL6, C21ORF66, CBFB, CBX4, CDC5L, CDYL, CEBPB, CHD7, CHMP1B, CIC, CITED2, CREB1, CREB3L2, CREM, CSDA, DDIT3, E2F1, E2F4, E2F8, EGR1, EGR2, ELK3, ELL2, ETS1, ETS2, EZH1, FLI1, FOSL2, FOXJ2, FOXO1, FUS, GATA3, GATAD2B, HCLS1, HIF1A, ID1, ID2, IFI35, IKZF4, IRF3, IRF4, IRF7, IRF8, IRF9, JARID2, JMJD1C, JUN, JUNB, KAT2B, KLF10, KLF6, KLF7, KLF9, LASS4, LEF1, LRRFIP1, MAFF, MAX, MEN1, MINA, MTA3, MXI1, MYC, MYST4, NCOA1, NCOA3, NFE2L2, NFIL3, NFKB1, NMI, NOTCH1, NR3C1, PHF13, PHF21A, PML, POU2AF1, POU2F2, PRDM1, RARA, RBPJ, REL, RELA, RNF11, RORA, RORC, RUNX1, RUNX2, SAP18, SAP30, SATB1, SERTAD1, SIRT2, SKI, SKIL, SMAD2, SMAD4, SMAD7, SMARCA4, SMOX, SP1, SP100, SP4, SS18, STAT1, STAT3, STAT4, STAT5A, STAT5B, STAT6, SUZ12, TBX21, TFEB, TGIF1, TLE1, TP53, TRIM24, TRPS1, TSC22D3, UBE2B, VAV1, VAX2, XBP1, ZEB1, ZEB2, ZFP161, ZFP36L1, ZFP36L2, ZNF238, ZNF281, ZNF703, ZNRF1, and/or ZNRF2, or any combination thereof.

In some embodiments, the invention provides a method of modulating one or more of the target genes listed in Table 6 as being associated with the early stage of Th17 differentiation, maintenance and/or function, e.g., FAS, CCR5, IL6ST, IL17RA, IL2RA, MYD88, CXCR5, PVR, IL15RA, IL12RB1, or any combination thereof.

In some embodiments, the invention provides a method of modulating one or more of the target genes listed in Table 6 as being associated with the intermediate stage of Th17 differentiation, maintenance and/or function, e.g., IL7R, ITGA3, IL1R1, CCR5, CCR6, ACVR2A, IL6ST, IL17RA, CCR8, DDR1, PROCR, IL2RA, IL12RB2, MYD88, PTPRJ, TNFRSF13B, CXCR3, IL1RN, CXCR5, CCR4, IL4R, IL2RB, TNFRSF12A, CXCR4, KLRD1, IRAK1BP1, PVR, IL12RB1, IL18R1, TRAF3, or any combination thereof.

In some embodiments, the invention provides a method of modulating one or more of the target genes listed in Table 6 as being associated with the late stage of Th17 differentiation, maintenance and/or function, e.g., IL7R, ITGA3, IL1R1, FAS, CCR5, CCR6, ACVR2A, IL6ST, IL17RA, DDR1, PROCR, IL2RA, IL12RB2, MYD88, BMPR1A, PTPRJ, TNFRSF13B, CXCR3, IL1RN, CXCR5, CCR4, IL4R, IL2RB, TNFRSF12A, CXCR4, KLRD1, IRAK1BP1, PVR, IL15RA, TLR1, ACVR1B, IL12RB1, IL18R1, TRAF3, IFNGR1, PLAUR, IL21R, IL23R, or any combination thereof.

In some embodiments, the invention provides a method of modulating one or more of the target genes listed in Table 7 as being associated with the early stage of Th17 differentiation, maintenance and/or function, e.g., EIF2AK2, DUSP22, HK2, RIPK1, RNASEL, TEC, MAP3K8, SGK1, PRKCQ, DUSP16, BMP2K, PIM2, or any combination thereof.

In some embodiments, the invention provides a method of modulating one or more of the target genes listed in Table 7 as being associated with the intermediate stage of Th17 differentiation, maintenance and/or function, e.g., PSTPIP1, PTPN1, ACP5, TXK, RIPK3, PTPRF, NEK4, PPME1, PHACTR2, HK2, GMFG, DAPP1, TEC, GMFB, PIM1, NEK6, ACVR2A, FES, CDK6, ZAK, DUSP14, SGK1, JAK3, ULK2, PTPRJ, SPHK1, TNK2, PCTK1, MAP4K3, TGFBR1, HK1, DDR1, BMP2K, DUSP10, ALPK2, or any combination thereof.

In some embodiments, the invention provides a method of modulating one or more of the target genes listed in Table 7 as being associated with the late stage of Th17 differentiation, maintenance and/or function, e.g., PTPLA, PSTPIP1, TK1, PTEN, BPGM, DCK, PTPRS, PTPN18, MKNK2, PTPN1, PTPRE, SH2D1A, PLK2, DUSP6, CDC25B, SLK, MAP3K5, BMPR1A, ACP5, TXK, RIPK3, PPP3CA, PTPRF, PACSIN1, NEK4, PIP4K2A, PPME1, SRPK2, DUSP2, PHACTR2, DCLK1, PPP2R5A, RIPK1, GK, RNASEL, GMFG, STK4, HINT3, DAPP1, TEC, GMFB, PTPN6, RIPK2, PIM1, NEK6, ACVR2A, AURKB, FES, ACVR1B, CDK6, ZAK, VRK2, MAP3K8, DUSP14, SGK1, PRKCQ, JAK3, ULK2, HIPK2, PTPRJ, INPP1, TNK2, PCTK1, DUSP1, NUDT4, TGFBR1, PTP4A1, HK1, DUSP16, ANP32A, DDR1, ITK, WNK1, NAGK, STK38, BMP2K, BUB1, AAK1, SIK1, DUSP10, PRKCA, PIM2, STK17B, TK2, STK39, ALPK2, MST4, PHLPP1, or any combination thereof.

In some embodiments, the invention provides a method of modulating is one or more of the target genes listed in Table 8 as being associated with the early stage of Th17 differentiation, maintenance and/or function, e.g., HK2, CDKN1A, DUT, DUSP1, NADK, LIMK2, DUSP11, TAOK3, PRPS1, PPP2R4, MKNK2, SGK1, BPGM, TEC, MAPK6, PTP4A2, PRPF4B, ACP1, CCRN4L, or any combination thereof.

In some embodiments, the invention provides a method of modulating one or more of the target genes listed in Table 8 as being associated with the intermediate stage of Th17 differentiation, maintenance and/or function, e.g., HK2, ZAP70, NEK6, DUSP14, SH2D1A, ITK, DUT, PPP1R11, DUSP1, PMVK, TK1, TAOK3, GMFG, PRPS1, SGK1, TXK, WNK1, DUSP19, TEC, RPS6KA1, PKM2, PRPF4B, ADRBK1, CKB, ULK2, PLK1, PPP2R5A, PLK2, or any combination thereof.

In some embodiments, the invention provides a method of modulating one or more of the target genes listed in Table 8 as being associated with the late stage of Th17 differentiation, maintenance and/or function, e.g., ZAP70, PFKP, NEK6, DUSP14, SH2D1A, INPP5B, ITK, PFKL, PGK1, CDKN1A, DUT, PPP1R11, DUSP1, PMVK, PTPN22, PSPH, TK1, PGAM1, LIMK2, CLK1, DUSP11, TAOK3, RIOK2, GMFG, UCKL1, PRPS1, PPP2R4, MKNK2, DGKA, SGK1, TXK, WNK1, DUSP19, CHP, BPGM, PIP5K1A, TEC, MAP2K1, MAPK6, RPS6KA1, PTP4A2, PKM2, PRPF4B, ADRBK1, CKB, ACP1, ULK2, CCRN4L, PRKCH, PLK1, PPP2R5A, PLK2, or any combination thereof.

In some embodiments, the invention provides a method of modulating one or more of the target genes listed in Table 9 as being associated with the early stage of Th17 differentiation, maintenance and/or function, e.g., CD200, CD40LG, CD24, CCND2, ADAM17, BSG, ITGAL, FAS, GPR65, SIGMAR1, CAP1, PLAUR, SRPRB, TRPV2, IL2RA, KDELR2, TNFRSF9, or any combination thereof.

In some embodiments, the invention provides a method of modulating one or more of the target genes listed in Table 9 as being associated with the intermediate stage of Th17 differentiation, maintenance and/or function, e.g., CTLA4, CD200, CD24, CD5L, CD9, IL2RB, CD53, CD74, CAST, CCR6, IL2RG, ITGAV, FAS, IL4R, PROCR, GPR65, TNFRSF18, RORA, IL1RN, RORC, CYSLTR1, PNRC2, LOC390243, ADAM10, TNFSF9, CD96, CD82, SLAMF7, CD27, PGRMC1, TRPV2, ADRBK1, TRAF6, IL2RA, THY1, IL12RB2, TNFRSF9, or any combination thereof.

In some embodiments, the invention provides a method of modulating one or more of the target genes listed in Table 9 as being associated with the late stage of Th17 differentiation, maintenance and/or function, e.g., CTLA4, TNFRSF4, CD44, PDCD1, CD200, CD247, CD24, CD5L, CCND2, CD9, IL2RB, CD53, CD74, ADAM17, BSG, CAST, CCR6, IL2RG, CD81, CD6, CD48, ITGAV, TFRC, ICAM2, ATP1B3, FAS, IL4R, CCR7, CD52, PROCR, GPR65, TNFRSF18, FCRL1, RORA, IL1RN, RORC, P2RX4, SSR2, PTPN22, SIGMAR1, CYSLTR1, LOC390243, ADAM10, TNFSF9, CD96, CAP1, CD82, SLAMF7, PLAUR, CD27, SIVA1, PGRMC1, SRPRB, TRPV2, NR1H2, ADRBK1, GABARAPL1, TRAF6, IL2RA, THY1, KDELR2, IL12RB2, TNFRSF9, SCARB1, IFNGR1, or any combination thereof.

In some embodiments, the invention provides a method of inhibiting tumor growth in a subject in need thereof by administering to the subject a therapeutically effective amount of an inhibitor of Protein C Receptor (PROCR). In some embodiments, the inhibitor of PROCR is an antibody, a soluble polypeptide, a polypeptide agent, a peptide agent, a nucleic acid agent, a nucleic acid ligand, or a small molecule agent. In some embodiments, the inhibitor of PROCR is one or more agents selected from the group consisting of lipopolysaccharide; cisplatin; fibrinogen; 1, 10-phenanthroline; 5-N-ethylcarboxamido adenosine; cystathionine; hirudin; phospholipid; Drotrecogin alfa; VEGF; Phosphatidylethanolamine; serine; gamma-carboxyglutamic acid; calcium; warfarin; endotoxin; curcumin; lipid; and nitric oxide.

In some embodiments, the invention provides a method of diagnosing an immune response in a subject, comprising detecting a level of expression, activity and/or function of one or more signature genes or one or more products of one or more signature genes selected from those listed in Table 1 or Table 2 and comparing the detected level to a control of level of signature gene or gene product expression, activity and/or function, wherein a difference between the detected level and the control level indicates that the presence of an immune response in the subject. In some embodiments, the immune response is an autoimmune response. In some embodiments, the immune response is an inflammatory response, including inflammatory response(s) associated with an autoimmune response and/or inflammatory response(s) associated with an infectious disease or other pathogen-based disorder.

In some embodiments, the invention provides a method of monitoring an immune response in a subject, comprising detecting a level of expression, activity and/or function of one or more signature genes or one or more products of one or more signature genes, e.g., one or more signature genes selected from those listed in Table 1 or Table 2 at a first time point, detecting a level of expression, activity and/or function of one or more signature genes or one or more products of one or more signature genes, e.g., one or more signature genes selected from those listed in Table 1 or Table 2 at a second time point, and comparing the first detected level of expression, activity and/or function with the second detected level of expression, activity and/or function, wherein a change between the first and second detected levels indicates a change in the immune response in the subject. In some embodiments, the immune response is an autoimmune response. In some embodiments, the immune response is an inflammatory response.

In some embodiments, the invention provides a method of monitoring an immune response in a subject, comprising isolating a population of T cells from the subject at a first time point, determining a first ratio of T cell subtypes within the T cell population at a first time point, isolating a population of T cells from the subject at a second time point, determining a second ratio of T cell subtypes within the T cell population at a second time point, and comparing the first and second ratio of T cell subtypes, wherein a change in the first and second detected ratios indicates a change in the immune response in the subject. In some embodiments, the immune response is an autoimmune response. In some embodiments, the immune response is an inflammatory response.

In some embodiments, the invention provides a method of activating therapeutic immunity by exploiting the blockade of immune checkpoints. The progression of a productive immune response requires that a number of immunological checkpoints be passed. Immunity response is regulated by the counterbalancing of stimulatory and inhibitory signal. The immunoglobulin superfamily occupies a central importance in this coordination of immune responses, and the CD28/cytotoxic T-lymphocyte antigen-4 (CTLA-4):B7.1/B7.2 receptor/ligand grouping represents the archetypal example of these immune regulators (see e.g., Korman A J, Peggs K S, Allison J P, "Checkpoint blockade in cancer immunotherapy." Adv Immunol. 2006; 90:297-339). In part the role of these checkpoints is to guard against the possibility of unwanted and harmful self-directed activities. While this is a necessary function, aiding in the prevention of autoimmunity, it may act as a barrier to successful immunotherapies aimed at targeting malignant self-cells that largely display the same array of surface molecules as the cells from which they derive. The expression of immune-checkpoint proteins can be dysregulated in a disease or disorder and can be an important immune resistance mechanism. Therapies aimed at overcoming these mechanisms of peripheral tolerance, in particular by blocking the inhibitory checkpoints, offer the potential to generate therapeutic activity, either as monotherapies or in synergism with other therapies.

Thus, the present invention relates to a method of engineering T-cells, especially for immunotherapy, comprising modulating T cell balance to inactivate or otherwise inhibit at least one gene or gene product involved in the immune check-point.

Suitable T cell modulating agent(s) for use in any of the compositions and methods provided herein include an antibody, a soluble polypeptide, a polypeptide agent, a peptide agent, a nucleic acid agent, a nucleic acid ligand, or a small molecule agent. By way of non-limiting example, suitable T cell modulating agents or agents for use in combination with one or more T cell modulating agents are shown in Table 10 of the specification.

One skilled in the art will appreciate that the T cell modulating agents have a variety of uses. For example, the T cell modulating agents are used as therapeutic agents as described herein. The T cell modulating agents can be used as reagents in screening assays, diagnostic kits or as diagnostic tools, or these T cell modulating agents can be used in competition assays to generate therapeutic reagents.

In one embodiment, the invention relates to a method of diagnosing, prognosing and/or staging an immune response involving T cell balance, which may comprise detecting a first level of expression, activity and/or function of one or more signature genes or one or more products of one or more signature genes selected from the genes of Table 1 or Table 2 and comparing the detected level to a control of level of signature gene or gene product expression, activity and/or function, wherein a difference in the detected level and the control level indicates that the presence of an immune response in the subject.

In another embodiment, the invention relates to a method of monitoring an immune response in a subject comprising detecting a level of expression, activity and/or function of one or more signature genes or one or more products of one or more signature genes of Table 1 or Table 2 at a first time point, detecting a level of expression, activity and/or function of one or more signature genes or one or more products of one or more signature genes of Table 1 or Table 2 at a second time point, and comparing the first detected level of expression, activity and/or function with the second detected level of expression, activity and/or function, wherein a change in the first and second detected levels indicates a change in the immune response in the subject.

In yet another embodiment, the invention relates to a method of identifying a patient population at risk or suffering from an immune response which may comprise detecting a level of expression, activity and/or function of one or more signature genes or one or more products of one or more signature genes of Table 1 or Table 2 in the patient population and comparing the level of expression, activity and/or function of one or more signature genes or one or more products of one or more signature genes of Table 1 or Table 2 in a patient population not at risk or suffering from an immune response, wherein a difference in the level of expression, activity and/or function of one or more signature genes or one or more products of one or more signature genes of Table 1 or Table 2 in the patient populations identifies the patient population as at risk or suffering from an immune response.

In still another embodiment, the invention relates to a method for monitoring subjects undergoing a treatment or therapy for an aberrant immune response to determine whether the patient is responsive to the treatment or therapy which may comprise detecting a level of expression, activity and/or function of one or more signature genes or one or more products of one or more signature genes of Table 1 or Table 2 in the absence of the treatment or therapy and comparing the level of expression, activity and/or function of one or more signature genes or one or more products of one or more signature genes of Table 1 or Table 2 in the presence of the treatment or therapy, wherein a difference in the level of expression, activity and/or function of one or more signature genes or one or more products of one or more signature genes of Table 1 or Table 2 in the presence of the treatment or therapy indicates whether the patient is responsive to the treatment or therapy.

The invention may also involve a method of modulating T cell balance, the method which may comprise contacting a T cell or a population of T cells with a T cell modulating agent in an amount sufficient to modify differentiation, maintenance and/or function of the T cell or population of T cells by altering balance between Th17 cells, regulatory T cells (Tregs) and other T cell subsets as compared to differentiation, maintenance and/or function of the T cell or population of T cells in the absence of the T cell modulating agent.

The immune response may be an autoimmune response or an inflammatory response. The inflammatory response may be associated with an autoimmune response, an infectious disease and/or a pathogen-based disorder.

The signature genes may be Th17-associated genes.

The treatment or therapy may be an antagonist for GPR65 in an amount sufficient to induce differentiation toward regulatory T cells (Tregs), Th1 cells, or a combination of Tregs and Th1 cells. The treatment or therapy may be an agonist that enhances or increases the expression of GPR65 in an amount sufficient to induce T cell differentiation toward Th17 cells. The treatment or therapy may be specific for a target gene selected from the group consisting of DEC1, PZLP, TCF4 and CD5L. The treatment or therapy may be an antagonist of a target gene selected from the group consisting of DEC1, PZLP, TCF4 and CD5L in an amount sufficient to switch Th17 cells from a pathogenic to non-pathogenic signature. The treatment or therapy may be an agonist that enhances or increases the expression of a target gene selected from the group consisting of DEC1, PZLP, TCF4 and CD5L in an amount sufficient to switch Th17 cells from a non-pathogenic to a pathogenic signature.

The T cell modulating agent may be an antibody, a soluble polypeptide, a polypeptide agent, a peptide agent, a nucleic acid agent, a nucleic acid ligand, or a small molecule agent.

The T cells may be naïve T cells, partially differentiated T cells, differentiated T cells, a combination of naïve T cells and partially differentiated T cells, a combination of naïve T cells and differentiated T cells, a combination of partially differentiated T cells and differentiated T cells, or a combination of naïve T cells, partially differentiated T cells and differentiated T cells.

The invention also involves a method of enhancing Th17 differentiation in a cell population, increasing expression, activity and/or function of one or more Th17-associated cytokines or one or more Th17-associated transcription regulators selected from interleukin 17F (IL-17F), interleukin 17A (IL-17A), STAT3, interleukin 21 (IL-21) and RAR-related orphan receptor C (RORC), and/or decreasing expression, activity and/or function of one or more non-Th17-associated cytokines or non-Th17-associated transcription regulators selected from FOXP3, interferon gamma (IFN-γ), GATA3, STAT4 and TBX21, comprising contacting a T cell with an agent that enhances expression, activity and/or function of CD5L, DEC1, PLZP, TCF4 or combinations thereof. The agent may enhance expression, activity and/or function of at least one of CD5L, DEC1, PLZP, or TCF4. The agent may be an antibody, a soluble polypeptide, a polypeptide agonist, a peptide agonist, a nucleic acid agonist, a nucleic acid ligand, or a small molecule agonist. The antibody may be a monoclonal antibody or a chimeric, humanized or fully human monoclonal antibody.

The present invention also involves the use of an antagonist for GPR65 in an amount sufficient to induce differentiation toward regulatory T cells (Tregs), Th1 cells, or a combination of Tregs and Th1 cells, use of an agonist that enhances or increases the expression of GPR65 in an amount sufficient to induce T cell differentiation toward Th17 cells, use of an antagonist of a target gene selected from the group consisting of DEC1, PZLP, TCF4 and CD5L in an amount sufficient to switch Th17 cells from a pathogenic to non-pathogenic signature, use of an agonist that enhances or increases the expression of a target gene selected from the group consisting of DEC1, PZLP, TCF4 and CD5L in an amount sufficient to switch Th17 cells from a non-pathogenic to a pathogenic signature and Use of T cell modulating agent for treating an aberrant immune response in a patient.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any such subject matter.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention. Nothing herein is to be construed as a promise.

These and other embodiments are disclosed or are obvious from and encompassed by, the following Detailed Description.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1A depicts an overview of approach. FIGS. 1B-1 and 1B-2 depict gene expression profiles during Th17 differentiation. Shown are the differential expression levels for genes (rows) at 18 time points (columns) in Th17 polarizing conditions (TGF-β1 and IL-6; left panel, Z-normalized per row) or Th17 polarizing conditions relative to control activated Th0 cells (right panel, log 2(ratio)). The genes are partitioned into 20 clusters (C1-C20, color bars, right). Right: mean expression (Y axis) and standard deviation (error bar) at each time point (X axis) for genes in representative clusters. Cluster size ("n"), enriched functional annotations ("F"), and representative genes ("M") are denoted. FIG. 1C depicts three major transcriptional phases. Shown is a correlation matrix (red (right side of correlation scale): high; blue (left side of correlation scale): low) between every pair of time points. FIG. 1D depicts transcriptional profiles of key cytokines and receptor molecules. Shown are the differential expression levels (log 2(ratio)) for each gene (column) at each of 18 time points (rows) in Th17 polarizing conditions (TGF-β1 and IL-6; left panel, Z-normalized per row) vs. control activated Th0 cells.

FIG. 2A depicts an overview of computational analysis. FIG. 2B depicts a schematic of temporal network 'snapshots'. Shown are three consecutive cartoon networks (top and matrix columns), with three possible interactions from regulator (A) to targets (B, C & D), shown as edges (top) and matrix rows (A→B—top row; A→C—middle row; A→D—bottom row). FIG. 2C depicts 18 network 'snapshots'. Left: each row corresponds to a TF-target interaction that occurs in at least one network; columns correspond to the network at each time point. A purple entry: interaction is active in that network. The networks are clustered by similarity of active interactions (dendrogram, top), forming three temporally consecutive clusters (early, intermediate, late, bottom). Right: a heatmap denoting edges for selected regulators. FIG. 2D depicts dynamic regulator activity. Shown is, for each regulator (rows), the number of target genes (normalized by its maximum number of targets) in each of the 18 networks (columns, left), and in each of the three canonical networks (middle) obtained by collapsing (arrows). Right: regulators chosen for perturbation (pink), known Th17 regulators (grey), and the maximal number of target genes across the three canonical networks (green, ranging from 0 to 250 targets). FIGS. 2E-1, 2E-2, and 2E-3 depict that at the heart of each network is its 'transcriptional circuit', connecting active TFs to target genes that themselves encode TFs. The transcription factor circuits shown (in each of the 3 canonical networks) are the portions of each of the inferred networks associating transcription regulators to targets that themselves encode transcription regulators. Yellow nodes denote transcription factor genes that are over-expressed (compared to Th0) during the respective time segment. Edge color reflects the data type supporting the regulatory interaction (legend).

FIG. 3A depicts unbiased ranking of perturbation candidates. Shown are the genes ordered from left to right based on their ranking for perturbation (columns, top ranking is leftmost). Two top matrices: criteria for ranking by 'Network Information' (topmost) and 'Gene Expression Information'. Purple entry: gene has the feature (intensity proportional to feature strength; top five features are binary). Bar chart: ranking score. 'Perturbed' row: dark grey: genes successfully perturbed by knockdown followed by high quality mRNA quantification; light grey: genes where an attempt to knockdown was made, but could not achieve or maintain sufficient knockdown or did not obtain enough replicates; Black: genes perturbed by knockout or for which knockout data was already available. Known row: orange entry: a gene was previously associated with Th17 function (this information was not used to rank the genes; FIG. 3B depicts scanning electron micrograph of primary T cells (false colored purple) cultured on vertical silicon nanowires. FIG. 3C depicts delivery by silicon nanowire neither activates nor induces differentiation of naïve T cells and does not affect their response to conventional TCR stimulation with anti-CD3/CD28. FIG. 3D depicts effective knockdown by siRNA delivered on nanowires. Shown is the % of mRNA remaining after knockdown (by qPCR, Y axis: mean±standard error relative to non-targeting siRNA control, n=12, black bar on left) at 48 hrs after introduction of polarizing cytokines. In FIG. 3A and FIG. 3D, the candidate regulators shown are those listed in Table 5. In FIG. 3A, the candidate regulators are listed on the x axis and are, in order from left to right, RORC, SATB1, TRPS1, SMOX, RORA, ARID5A, ETV6, ARNTL, ETS1, UBE2B, BATF, STAT3, STAT1, STAT5A, NR3C1, STAT6, TRIM24, HIF1A, IRF4, IRF8, ETS2, JUN, RUNX1, FLI1, REL, SP4, EGR2, NFKB1, ZFP281, STAT4, RELA, TBX21, STAT5B, IRF7, STAT2, IRF3, XBP1, FOXO1, PRDM1, ATF4, IRF1, GATA3, EGR1, MYC, CREB1, IRF9, IRF2, FOXJ2, SMARCA4, TRP53, SUZ12, POU2AF1, CEBPB, ID2, CREM, MYST4, MXI1, RBPJ, CHD7, CREB3L2, VAX2, KLF10, SKI, ELK3, ZEB1, PML, SERTAD1, NOTCH1, LRRFIP1, AHR, 1810007M14RIK, SAP30, ID1, ZFP238, VAV1, MINA, BATF3, CDYL, IKZF4, NCOA1, BCL3, JUNB, SS18, PHF13, MTA3, ASXL1, LASS4, SKIL, DDIT3, FOSL2, RUNX2, TLE1, ATF3, ELL2, AES, BCL11B, JARID2, KLF9, KAT2B, KLF6, E2F8, BCL6, ZNRF2, TSC22D3, KLF7, HMGB2, FUS, SIRT2, MAFF, CHMP1B, GATAD2B, SMAD7, ZFP703, ZNRF1, JMJD1C, ZFP36L2, TSC22D4, NFE2L2, RNF11, ARID3A, MEN1, RARA, CBX4, ZFP62, CIC, HCLS1, ZFP36L1, TGIF1.

FIG. 4A depicts the impact of perturbed genes on a 275-gene signature. Shown are changes in the expression of 275 signature genes (rows) following knockdown or knockout (KO) of 39 factors (columns) at 48 hr (as well as IL-21r and IL-17ra KO at 60 hours). Blue (left side of Fold change (log 2) scale): decreased expression of target following perturbation of a regulator (compared to a non-targeting control); red (right side of Fold change (log 2) scale): increased expression; Grey: not significant; all color (i.e., non-grey) entries are significant (see Methods in Example 1). 'Perturbed' (left): signature genes that are also perturbed as regulators (black entries). Key signature genes are denoted on right. FIG. 4B depicts two coupled and opposing modules. Shown is the perturbation network associating the 'positive regulators' (blue nodes, left side of x-axis) of Th17 signature genes, the 'negative regulators' (red nodes, right side of x-axis), Th17 signature genes (grey nodes, bottom) and signature genes of other CD4+ T cells (grey nodes, top). A blue edge from node A to B indicates that knockdown of A downregulates B; a red edge indicates that knockdown of A upregulates B. Light grey halos: regulators not previously associated with Th17 differentiation. FIG. 4C depicts how knockdown effects validate edges in network model. Venn diagram: compare the set of targets for a factor in the original model of FIG. 2*a* (pink circle) to the set of genes that respond to that factor's knockdown in an RNA-Seq experiment (yellow circle). Bar chart on bottom: Shown is the −log 10(Pvalue) (Y axis, hypergeometric test) for the significance of this overlap for four factors (X axis). Similar results were obtained with a non-parametric rank-sum test (Mann-Whitney U test, see Methods in Example 1). Red dashed line: P=0.01. FIG. 4D depicts how global knockdown effects are consistent across clusters. Venn diagram: compare the set of genes that respond to a factor's knockdown in an RNA-Seq experiment (yellow circle) to each of the 20 clusters of FIG. 1*b* (purple circle). The knockdown of a 'Th17 positive' regulator was expected to repress genes in induced clusters, and induce genes in repressed clusters (and vice versa for 'Th17 negative' regulators). Heat map: For each regulator knockdown (rows) and each cluster (columns) shown are the significant overlaps (non grey entries) by the test above. Red (right side of Fold enrichment scale): fold enrichment for up-regulation upon knockdown; Blue (left side of Fold enrichment scale): fold enrichment for down regulation upon knockdown. Orange entries in the top row indicate induced clusters.

FIGS. 5A-5D, left: Shown are regulatory network models centered on different pivotal regulators (square nodes): (FIG. 5A) Mina, (FIG. 5B) Fas, (FIG. 5C) Pou2af1, and (FIG. 5D) Tsc22d3. In each network, shown are the targets and regulators (round nodes) connected to the pivotal nodes based on perturbation (red and blue dashed edges), TF binding (black solid edges), or both (red and blue solid edges). Genes affected by perturbing the pivotal nodes are colored (blue: target is down-regulated by knockdown of pivotal node; red: target is up-regulated). (FIGS. 5A-5C, middle and right) Intracellular staining and cytokine assays by ELISA or Cytometric Bead Assays (CBA) on culture supernatants at 72 h of in vitro differentiated cells from respective KO mice activated in vitro with anti-CD3+anti-CD28 with or without Th17 polarizing cytokines (TGF-β+IL-6). (FIG. 5D, middle) ChIP-Seq of Tsc22d3. Shown is the proportion of overlap in bound genes (dark grey) or bound regions (light grey) between Tsc22d3 and a host of Th17 canonical factors (X axis). All results are statistically significant ($P<10^{-6}$; see Methods in Example 1).

FIG. 6A depicts an overview of the time course experiments. Naïve T cells were isolated from WT mice, and treated with IL-6 and TGF-β1. Microarrays were then used to measure global mRNA levels at 18 different time points (0.5 hr-72 hr, see Methods in Example 1). As a control, the same WT naïve T cells under Th0 conditions harvested at the same 18 time points were used. For the last four time points (48 hr-72 hr), cells treated with IL-6, TGF-β1, and IL-23 were also profiled. FIG. 6B depicts generation of Th17 cells by IL-6 and TGF-β1 polarizing conditions. FACS analysis of naïve T cells differentiated with TGF-β1 and IL-6 (right) shows enrichment for IL-17 producing Th17 T cells; these cells are not observed in the Th0 controls. FIG. 6C depicts comparison of the obtained microarray profiles to published data from naïve T-cells and differentiated Th17 cells (Wei et. al, 2009; Langmead, B., Trapnell, C., Pop, M. & Salzberg, S. L. in Genome Biol Vol. 10 R25 (2009)). Shown is the Pearson correlation coefficient (Y axis) between each of the 18 profiles (ordered by time point, X axis) and either the naïve T cell profiles (blue) or the differentiated Th17 profiles (green). The expression profiles gradually transition from a naïve-like state (at t=0.5 hr, r2>0.8, $p<10^{-10}$) to a Th17 differentiated state (at t=72 hr, r2>0.65, $p<10^{-10}$). FIG. 6D depicts expression of key cytokines. Shown are the mRNA levels (Y axis) as measured at each of the 18 time points (X axis) in the Th17 polarizing (blue) and Th0 control (red) conditions for the key Th17 genes RORc (left) and IL-17a (middle), both induced, and for the cytokine IFN-γ, unchanged in the time course.

FIG. 8A depicts transcriptional profiles of key genes. A color version of these figures can be found in Yosef et al., "Dynamic regulatory network controlling Th17 cell differentiation, Nature, vol. 496: 461-468 (2013)/doi: 10.1038/nature11981. Shown are the expression levels (Y axis) of three key genes (IL-22, RORc, IL-4) at each time point (X axis) in Th17 polarizing conditions (blue), Th0 controls (red), and following the addition of IL-23 (beginning at 48 hr post differentiation) to the Th17 polarizing conditions (green). FIG. 8B depicts IL-23-dependent transcriptional clusters. Shown are clusters of differentially expressed genes in the IL-23r$^{-/-}$ time course data (blue) compared to WT cells, both treated with Th17 polarizing cytokines and IL23 (red). For each cluster, shown are the average expression levels (Y axis, ±standard deviation, error bars) at each time point (X axis) in the knockout (blue) and wildtype (red) cells. The cluster size ("n"), enriched functional annotations ("F"), and representative member genes ("M") are denoted on top.

FIG. 9A shows RORγt mRNA levels along the original time course under Th17 polarizing conditions, as measured with microarrays (blue). A sigmoidal fit for the mRNA levels (green) is used as an input for a model (based on Schwanhäusser, B. et al. Global quantification of mammalian gene expression control. Nature 473, 337-342, doi:10.1038/nature10098 (2011)) that predicts the level of RORγt protein at each time point (red). FIG. 9B depicts distribution of measured ROR-γt protein levels (x axis) as determined by FACS analysis in Th17 polarizing conditions (blue) and Th0 conditions (red) at 4, 12, 24, and 48 hr post stimulation.

FIGS. 10A-10B are a series of graphs depicting predictive features for ranking candidates for knockdown. Shown is the fold enrichment (Y axis, in all cases, $p<10^{-3}$, hypergeometric test) in a curated list of known Th17 factors for different (FIG. 10A) network-based features and (FIG. 10B) expression-base features (as used in FIG. 3A).

FIG. 11A depicts how Nanowires do not activate T cells and do not interfere with physiological stimuli. Shown are the levels of mRNA (mean±standard error, n=3) for keygenes, measured 48 hr after activation by qPCR (Y axis, mean and standard error of the mean), in T cells grown in petri dishes (left) or on silicon nanowires (right) without polarizing cytokines ('no cytokines') or in the presence of Th17 polarizing cytokines ('TGF-β1+IL6'). FIG. 11B depicts effective knockdown by siRNA delivered on nanowires. Shown is the % of mRNA remaining after knockdown (by qPCR, Y axis: mean±standard error relative to non-targeting siRNA control, n=12, black bar on left) at 10 hours after introduction of polarizing cytokines. The genes presented are a superset of the 39 genes selected for transcriptional profiling. FIG. 11C. Consistency of NW-based knockdowns and resulting phenotypes. Shown are average target transcript reductions and phenotypic changes (as measured by IL-17f and IL-17a expression) for three different experiments of NW-based knockdown (from at least 2 different cultures) of 9 genes at 48 hours post stimulation. Light blue bars: knockdown level (% remaining relative to siRNA controls); dark grey and light green bars: mRNAs of IL-17f and IL-17a, respectively, relative to siRNA controls.

FIG. 12A depicts a comparison of expression levels measured by Fluidigm (Y axis) and Nanostring (X axis) for the same gene under the same perturbation. Expression values were normalized to control genes as described in Example 1. FIG. 12B depicts how analysis of Fluidigm data recapitulates the partitioning of targeted factors into two modules of positive and negative Th17 regulators. Shown are the changes in transcription of the 82 genes out of the 85 gene signature (rows) that significantly responded to at least one factor knockdown (columns).

FIG. 15A depicts a correlation matrix of knockdown profiles. Shown is the Spearman rank correlation coefficient between the RNA-Seq profiles (fold change relative to NT siRNA controls) of regulators perturbed by knockdowns. Genes that were not significantly differentially expressed in any of the samples were excluded from the profiles. FIG. 15B depicts knockdown effects on known marker genes of different CD4+ T cell lineages. Shown are the expression levels for canonical genes (rows) of different T cell lineages (labeled on right) following knockdown of each of 12 regulators (columns). Red/Blue: increase/decrease in gene expression in knockdown compared to non-targeting control (see Methods in Example 1). Shown are only genes that are significantly differentially expressed in at least one knockdown condition. The experiments are hierarchically clustered, forming distinct clusters for Th17-positive regulators (left) and Th17-negative regulators (right). FIG. 15C depicts knockdown effects on two subclusters of the T-regulatory cell signature, as defined by Hill et al., Foxp3 transcription-factor-dependent and -independent regulation of the regulatory T cell transcriptional signature. Immunity 27, 786-800, doi:S1074-7613(07)00492-X [pii] 10.1016/j.immuni.2007.09.010 (2007). Each cluster (annotated in Hill et al as Clusters 1 and 5) includes genes that are over expressed in Tregs cells compared to conventional T cells. However, genes in Cluster 1 are more correlated to Foxp3 and responsive to Foxp3 transduction. Conversely, genes in cluster 1 are more directly responsive to TCR and IL-2 and less responsive to Foxp3 in Treg cells. Knockdown of Th17-positive regulators strongly induces the expression of genes in the 'Foxp3' Cluster 1. The knockdown profiles are hierarchically clustered, forming distinct clusters for Th17-positive regulators (left) and Th17-negative regulators (right). Red/Blue: increase/decrease in gene expression in knockdown compared to non-targeting control (see Methods in Example 1). Shown are only genes that are significantly differentially expressed in at least one knockdown condition.

(FIG. 16A, left) $Mina^{-/-}$ T cells activated under Th0 controls are controls for the graphs shown in FIG. 5A. (FIG. 16A, right) TNF secretion by $Mina^{-/-}$ and WT cells, as measured by cytometric bead assay showing that $Mina^{-/-}$ T cells produce more TNF when compared to control. FIG. 16B depicts intracellular cytokine staining of $Pou2af1^{-/-}$ and WT cells for IFN-γ and IL-17a as measured by flow cytometry. (FIG. 16C, left) Flow cytometric analysis of $Fas^{-/-}$ and WT cells for Foxp3 and Il-17 expression. (FIG. 16C, right) IL-2 and Tnf secretion by $Fas^{-/-}$ and WT cells, as measured by a cytokine bead assay ELISA. (FIG. 16D, left). Flow cytometry on $Oct1^{-/-}$ and WT cells for IFN-γ and IL-17a, showing an increase in IFN-γ positive cells in the Th0 condition for the Oct1 deficient mouse. (FIG. 16D, right) Il-17a, IFN-γ, IL-2 and TNF production by $Oct1^{-/-}$ and WT cells, as measured by cytokine ELISA and cytometric bead assay. Statistical significance in the ELISA figures is denoted by: *$p<0.05$, $p<0.01$, and *$p<0.001$.

FIGS. 17A-17B are a series of illustrations depicting that Zeb1, Smarca4, and Sp4 are key novel regulators affecting the Th17 differentiation programs. A color version of these figures can be found in Yosef et al., "Dynamic regulatory network controlling Th17 cell differentiation, Nature, vol. 496: 461-468 (2013)/doi: 10.1038/nature11981. Shown are regulatory network models centered on different pivotal regulators (square nodes): (FIG. 17A) Zeb1 and Smarca4, and (FIG. 17B) Sp4. In each network, shown are the targets and regulators (round nodes) connected to the pivotal nodes based on perturbation (red and blue dashed edges), TF binding (black solid edges), or both (red and blue solid edges). Genes affected by perturbing the pivotal nodes are colored (red: target is up-regulated by knockdown of pivotal node; blue: target is down-regulated).

FIG. 19A depicts how PROCR expression level was assessed by the microarray analysis under Th0 and Th17 conditions at 18 different time points. FIG. 19B depicts how kinetic expression of PROCR mRNA was measured by quantitative RT-PCR analysis in Th17 cells differentiated with TGF-β1 and IL-6. FIG. 19C depicts how PROCR mRNA expression was measured by quantitative RT-PCR analysis in different T cell subsets 72 hr after stimulation by each cytokine. FIG. 19D depicts how PROCR protein expression was examined by flow cytometry in different T cell subsets 72 hr after stimulation with each cytokine.

FIG. 20A depicts how naïve CD4+ T cells were differentiated into Th17 cells by anti-CD3/anti-CD28 stimulation in the presence of activated protein C (aPC, 300 nM), the ligand of PROCR. On day 3, cells were stimulated with PMA and Ionomycin for 4 hr, stained intracellularly for IFN-γ and IL-17 and analyzed by flow cytometry. FIG. 20B depicts IL-17 production from Th17 cells (TGF-β+IL-6) differentiated with or without activated protein C (aPC and Ctl, respectively) was assessed by ELISA on Day 3 and 5. FIG. 20C depicts how naïve CD4+ T cells were polarized under Th17 conditions (TGF-β+IL-6), transduced with either GFP control retrovirus (Ctl RV) or PROCR-expressing retrovirus (PROCR RV). Intracellular expression of IFN-γ and IL-17 in GFP+ cells were assessed by flow cytometry. FIG. 20D depicts how naïve CD4+ T cells from EPCR δ/δ mice and control mice were polarized under Th17 conditions with TGF-β1 and IL-6. Intracellular expression of IFN-γ and IL-17 were assessed by flow cytometry.

FIG. 21A depicts how naïve $CD4^+$ T cells were polarized under Th17 conditions (TGF-β+IL-6), transduced with either GFP control retrovirus (Ctl GFP) or PROCR-expressing retrovirus (PROCR RV) and expression of ICOS, CTLA-4, PD-1, Pdp and Tim-3 was analyzed by flow cytometry. FIG. 21B depicts how naïve wild type (WT) or EPCR δ/δ $CD4^+$ T cells were differentiated into Th17 cells by anti-CD3/anti-CD28 stimulation in the presence of TGF-β1 and IL-6. Expression of ICOS, CTLA-4, PD-1, Pdp and Tim-3 was assessed by flow cytometry.

FIG. 22A depicts genes for Th17 cells differentiated with TGF-β3+IL-6 (pathogenic) or TGF-β1+IL-6 (non-pathogenic) and comparison of their expression levels in these two subsets. FIGS. 22B and 22C depict how naïve $CD4^+$ T cells were differentiated with TGF-β1 and IL-6, TGF-β3 and IL-6 or IL-1β and IL-6 and PROCR expression was assessed by (FIG. 22B) quantitative RT-PCR analysis (FIG. 22C) and protein expression was determined by flow cytometry.

FIG. 23A depicts quantitative RT-PCR analysis of mRNA expression of several pathogenic signature genes in Th17 cells differentiated with TGFβ1 and IL-6 in the presence of activated protein C (aPC) for 3 days in vitro. FIG. 23B depicts quantitative RT-PCR analysis of mRNA expression of several pathogenic signature genes in naïve $CD4^+$ T cells polarized under Th17 conditions, transduced with either GFP control retrovirus (Control RV) or PROCR-expressing retrovirus (PROCR RV) for 3 days. FIG. 23C depicts quantitative RT-PCR analysis of mRNA expression of several pathogenic signature genes in Th17 cells from EPCR δ/δ mice and control mice differentiated with TGFβ1 and IL-6 for 3 days in vitro.

FIG. 24A depicts ChIP-Seq of Rorγt. The PROCR genomic region is depicted. FIG. 24B depicts how the binding of Rorγt to the Procr promoter in Th17 cells was assessed by chromatin immunoprecipitation (ChIP). ChIP was performed using digested chromatin from Th17 cells and anti-Rorγt antibody. DNA was analyzed by quantitative RT-PCR analysis. FIG. 24C depicts how naïve CD4+ T cells from Rorγt−/− mice and control mice were polarized under Th17 conditions with TGF-β1 and IL-6 and under Th0 conditions (no cytokines) and PROCR expression was analyzed on day 3 by flow cytometry. FIG. 24D depicts how naïve CD4+ T cells polarized under Th17 conditions were transduced with either GFP control retrovirus (Ctl RV) or Rorγt-expressing retrovirus (Rorγt RV) for 3 days. PROCR mRNA expression was measured by quantitative RT-PCR analysis and PROCR protein expression was assessed by flow cytometry.

FIG. 25A depicts how binding of IRF4 or STAT3 to the Procr promoter was assessed by chromatin immunoprecipitation (ChIP)-PCR. ChIP was performed using digested chromatin from Th17 cells and anti-IRF4 or anti-STAT3 antibody. DNA was analyzed by quantitative RT-PCR analysis. FIG. 25B depicts how naïve CD4+ T cells from $Cd4^{Cre}STAT3^{fl/fl}$ mice (STAT3 KO) and control mice (WT) were polarized under Th17 conditions with TGF-β1 with IL-6 and under Th0 condition with no cytokines. On day 3, PROCR expression was determined by quantitative PCR. FIG. 25C depicts how naïve CD4+ T cells from $Cd4^{Cre}/RF4^{fl/fl}$ mice and control mice were polarized under Th17 conditions with TGF-β1 and IL-6 and under Th0 condition with no cytokines. On day 3, PROCR expression was determined by flow cytometry.

FIG. 26A depicts frequency of CD4+ T cells expressing IL-17 and PROCR isolated from EAE mice 21d after immunization with $MOG_{35-55}$. FIG. 26B depicts how EAE was induced by adoptive transfer of $MOG_{35-55}$-specific 2D2 cells transduced with a control retrovirus (Ctl_GFP) or a PROCR-expression retrovirus (PROCR_RV) and differentiated into Th17 cells. Mean clinical scores and summaries for each group are shown. Results are representative of one of two experiments. FIG. 26C depicts how Rag1−/− mice were reconstituted with either PROCR-deficient (EPCR δ/δ→Rag1−/−) or WT T cells (WT→Rag1−/−) and immunized with $MOG_{35-55}$ to induce EAE. The mean clinical score of each group is shown. Results are representative of one of two experiments. FIG. 26D depicts a schematic representation of PROCR regulation. Rorγt, IRF4, and STAT3 induce PROCR expression. PROCR ligation by activated protein C induces a downregulation of the pathogenic signature genes IL-3, CXCL3, CCL4 and Pdp and reduced pathogenicity in EAE.

FIG. 27C depicts how RNA was extracted and expression of IL17a and Il23r mRNA was determined by quantitative PCR.

FIG. 28C depicts how RNA was extracted and expression of Ifng mRNA was determined by quantitative PCR.

FIG. 30A depicts mean clinical score±s.e.m. of each group as shown. FIG. 30B depicts how on day 14 CNS infiltrating lymphocytes were isolated, re-stimulated with PMA and Ionomycin for 4 hours and stained intracellularly for IL-17, IFN-γ, and Foxp3. Cells were analyzed by flow cytometry.

FIG. 31A depicts a schematic representation of PROCR, its ligand activated protein C and the signaling adapter PAR1. FIG. 31B depicts how naïve CD4+ T cells were differentiated under polarizing conditions for the indicated T helper cell lineages. Expression of PROCR was determined by quantitative PCR on day 3. FIG. 31C depicts how mice were immunized for EAE, cells were isolated at peak of disease, and cytokine production (IL-17) and PROCR expression were analyzed by flow cytometry. FIG. 31D depicts how naïve and memory cells were isolated from WT and PROCRd/d mice and stimulated with anti-CD3/CD28. Naïve cells were cultured under Th17 polarizing conditions as indicated; memory cells were cultured in the presence or absence of IL-23. After 3 days IL-17A levels in supernatants were analyzed by ELISA.

FIG. 32A depicts signature genes of pathogenic and non-pathogenic Th17 cells. Naïve CD4+ T cells were differentiated into non-pathogenic (TGFβ1+IL-6) or pathogenic (TGFβ3+IL-6 or IL-β1+IL-6) Th17 cells and PROCR expression was determined by quantitative PCR. FIG. 32B depicts how naïve WT or PROCRd/d CD4+ T cells were stimulated under Th17 polarizing conditions (TGFβ1+IL-6) in the presence or absence of aPC. Quantitative expression of three pathogenic signature genes was determined on day 3. FIG. 32C depicts how naïve 2D2 T cells were transduced with a retrovirus encoding for PROCR or a control (GFP), differentiated into Th17 cells in vitro, and transferred into naïve recipients. Mice were monitored for EAE. FIG. 32D depicts how naïve 2D2 T cells were differentiated into Th17 cells in vitro with TGFβ1+IL-6+IL-23 and transferred into WT or PD-L1−/− recipients. Mice were monitored for EAE.

FIG. 33A depicts how C57BL/6 or BalbC mice were implanted with B16 melanoma or CT26 colon cancer cells respectively. Tumor Infiltrating Lymphocytes were isolated 3 weeks after tumor implantation, sorted based on PD-1 and Tim3 expression and analyzed for PROCR expression using real time PCR. Effector memory (CD44hiCD62Llo) CD8 T cells were sorted from naïve mice. FIG. 33B) depicts how PROCR, PD-1 and Tim3 expression on antigen-specific CD8 T cells were measured by FACS from acute (Armstrong) and chronic (Clone 13) LCMV infection at different times points as indicated.

FIG. 45E, F, G shows validation of CD5L expression in vitro. Naïve T cells (CD4$^+$CD62L$^+$CD44$^-$CD25$^-$) were sorted and activated by plate-bound anti-CD3 and anti-CD28 antibodies in the presence of various differentiation cytokines as indicated. CD5L expression was measured by qPCR at 48 h (E) and 72 h (F) and intracellularly by flow cytometry at 48 h (G); (F) At 48 h, cells were lifted from plate, washed and replated in fresh media with IL-23 or PBS and cultured for additional 24 h. FIG. 45H shows validation of CD5L expression in vivo. IL-17A.GFP reporter mice were immunized by MOG/CFA (s.c., d1) with pertussis toxin (i.v., d1 and d3). Mice were sacrificed at the peak of disease (score=3) and CD4$^+$GFP$^+$ and CD4$^+$GFP$^-$ cells were sorted from CNS and spleen respectively. Cd5l and Il17a expression are measured by qPCR. Figure shown is representative data of technical replicates from two independent mouse experiments. I. IL-17$^+$ (GFP$^+$) and IL-17$^-$ (GFP$^-$) CD4$^+$ cells were sorted from the gut of naïve mice and the number of RNA transcripts measured by nanostring and normalized based on four house-keeping genes. Figure is summary of two independent experiments.

FIG. 46B, C, D shows naïve T cells (CD4$^+$CD62L$^+$CD44$^-$CD25$^-$) were sorted, activated with plate-bound anti-CD3/anti-CD28 antibodies in the presence of TGFβ1 and IL-6 for 48 h. Cells were restimulated with PMA/ionomycin for 4 hours in the presence of Brefeldin A and cytokine production was measured using FACS (B); Supernatant were used for ELISA analysis of IL-17 and IL-10 (C); and RNA were purified from cells directly and subject to qPCR (D). FIG. 46E, F shows cells were sorted and cultured as in B, at 48 hours, cells were lifted, washed and resuspended in fresh media with no cytokines for an additional 72 h and restimulated. Cytokine production was measured by FACS (E) and mRNA was quantified by qPCR (F). FIG. 46G, H show effector memory T cells (CD4$^+$CD62L$^-$CD44$^+$) (G) or Effector memory Th17 cells (CD4$^+$CD62L$^-$CD44$^+$RorγtGFP$^+$) (H) were sorted directly ex vivo and activated with plate-bound anti-CD3/anti-CD28 antibodies for 48 hours. Cells were harvested and cultured with PMA/ionomycin for 4 hours in the presence of Brefeldin A and subject to FACS. Data are representative of at least 3 independent mouse experiments.

FIG. 48A-48J shows CD5L shifts Th17 cell lipidome balance from saturated to unsaturated lipid, modulating Rorγt ligand availability and function. FIG. 48A, B shows. Lipidome analysis of Th17 cells. (A) WT and $CD5L^{-/-}$ naïve T cells were differentiated as in FIG. 46B in the presence of cytokines as indicated. Cells and supernatant were harvested at 96 hours and subjected to MS/LC. Three independent mouse experiments were performed. Data shown are median expression of each metabolite identified that have at least 1.5 fold differences between and WT and $CD5L^{-/-}$ under the TGFβ1+IL-6 condition. (B) Expression of representative metabolites including a cholesterol ester and a PUFA-containing TAG species. FIG. 48 C, D, E, F-J show as follows: (C) Metabolomic analysis of independent mouse experiments where T cells were differentiated under various cytokine conditions as indicated and harvested at 48 h and 96 h. Summary metabolomics analysis is shown in FIG. 52A. (D,E) Rorγt ChIP from Th17 cells differentiated as described in A. under various conditions as indicated. F-K. Dual luciferase reporter assay was performed in EL4 cells stably transfected with a control vector or Rorγt vector. (F, G) CD5L retroviral vector was cotransfected in F and G at 0, 25, 50 and 100 ng/well. (H-J) 10 μM of either arachidonic acid (PUFA) or 20 μM of palmitic acid (SFA) were used whenever a single dose was indicated and in titration experiments, 20 μM, 4 μM and 0.8 μM for PUFA/SFA and 5 μM, 0.5 μM and 0.05 μM of 7, 27-dihydroxycholesterol were used. All ChIP and luciferase assay are representative of at least 3 independent experiments.

FIG. 52A-52D shows characterization of WT and CD5L−/− mice with EAE. Mice were immunized as in FIG. 46A. (A) 15 days post immunization, lymphocytes from CNS were isolated and directly stained and analyzed with flow cytometry for the expression of FoxP3. (B) Cells from CNS as in A were restimulated with PMA/ionomycin with Brefeldin A for 4 hours and profiled for cytokine production by flow cytometry. (C) Cells were isolated from Inguinal LN of mice 10 days after immunization. 3H Thymidine incorporation assays was used to determine T cell proliferation in response to MOG35-55 peptide; (D) Supernatant from C were harvested amount of IL-17 was determined by ELISA.

FIG. 53A-53D shows CD5L antagonizes pathogenicity of Th17 cells. Passive EAE is induced as described in FIG. 46. Briefly, naïve 2D2 cells were sorted from WT mice and differentiated with IL-1β+IL-6+IL-23. At 24 h, retroviral supernatant containing either CD5L-GFP overexpression- or control-GFP construct were used to infect the activated cells. The expression of CD5L was analyzed at day 3 post-infection. 50% of cells expressed GFP in both groups. (A) Representative flow cytometry analysis of cytokine profile prior to transfer; (B) Weight loss curve after transfer; (C) EAE score; (D) representative flow cytometry data of cytokine profile of CD4+ T cells from CNS at day 30 post transfer.

DETAILED DESCRIPTION

Figure 1A:
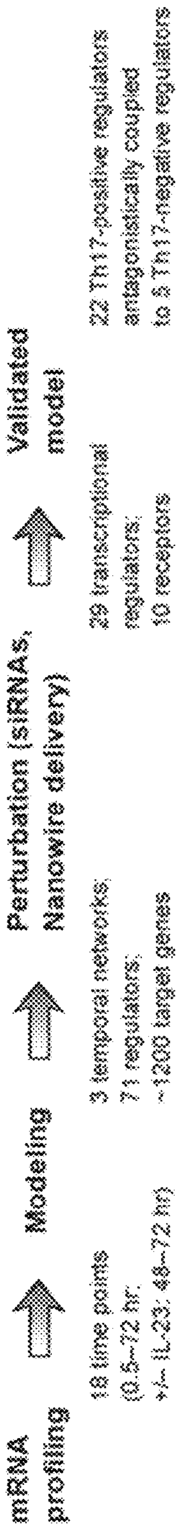
FIGS. 1A-1E are a series of graphs and illustrations depicting genome wide temporal expression profiles of Th17 differentiation.

This invention relates generally to compositions and methods for identifying the regulatory networks that control T cell balance, T cell differentiation, T cell maintenance and/or T cell function, as well compositions and methods for exploiting the regulatory networks that control T cell balance, T cell differentiation, T cell maintenance and/or T cell function in a variety of therapeutic and/or diagnostic indications.

The invention provides compositions and methods for modulating T cell balance. The invention provides T cell modulating agents that modulate T cell balance. For example, in some embodiments, the invention provides T cell modulating agents and methods of using these T cell modulating agents to regulate, influence or otherwise impact the level of and/or balance between T cell types, e.g., between Th17 and other T cell types, for example, regulatory T cells (Tregs). For example, in some embodiments, the invention provides T cell modulating agents and methods of using these T cell modulating agents to regulate, influence or otherwise impact the level of and/or balance between Th17 activity and inflammatory potential. As used herein, terms such as "Th17 cell" and/or "Th17 phenotype" and all grammatical variations thereof refer to a differentiated T helper cell that expresses one or more cytokines selected from the group the consisting of interleukin 17A (IL-17A), interleukin 17F (IL-17F), and interleukin 17A/F heterodimer (IL17-AF). As used herein, terms such as "Th1 cell" and/or "Th1 phenotype" and all grammatical variations thereof refer to a differentiated T helper cell that expresses interferon gamma (IFNγ). As used herein, terms such as "Th2 cell" and/or "Th2 phenotype" and all grammatical variations thereof refer to a differentiated T helper cell that expresses one or more cytokines selected from the group the consisting of interleukin 4 (IL-4), interleukin 5 (IL-5) and interleukin 13 (IL-13). As used herein, terms such as "Treg cell" and/or "Treg phenotype" and all grammatical variations thereof refer to a differentiated T cell that expresses Foxp3.

These compositions and methods use T cell modulating agents to regulate, influence or otherwise impact the level and/or balance between T cell types, e.g., between Th17 and other T cell types, for example, regulatory T cells (Tregs).

The invention provides methods and compositions for modulating T cell differentiation, for example, helper T cell (Th cell) differentiation. The invention provides methods and compositions for modulating T cell maintenance, for example, helper T cell (Th cell) maintenance. The invention provides methods and compositions for modulating T cell function, for example, helper T cell (Th cell) function. These compositions and methods use T cell modulating agents to regulate, influence or otherwise impact the level and/or balance between Th17 cell types, e.g., between pathogenic and non-pathogenic Th17 cells. These compositions and methods use T cell modulating agents to influence or otherwise impact the differentiation of a population of T cells, for example toward the Th17 cell phenotype, with or without a specific pathogenic distinction, or away from the Th17 cell phenotype, with or without a specific pathogenic distinction. These compositions and methods use T cell modulating agents to influence or otherwise impact the maintenance of a population of T cells, for example toward the Th17 cell phenotype, with or without a specific pathogenic distinction, or away from the Th17 cell phenotype, with or without a specific pathogenic distinction. These compositions and methods use T cell modulating agents to influence or otherwise impact the differentiation of a population of Th17 cells, for example toward the pathogenic Th17 cell phenotype or away from the pathogenic Th17 cell phenotype, or toward the non-pathogenic Th17 cell phenotype or away from the non-pathogenic Th17 cell phenotype. These compositions and methods use T cell modulating agents to influence or otherwise impact the maintenance of a population of Th17 cells, for example toward the pathogenic Th17 cell phenotype or away from the pathogenic Th17 cell phenotype, or toward the non-pathogenic Th17 cell phenotype or away from the non-pathogenic Th17 cell phenotype. These compositions and methods use T cell modulating agents to influence or otherwise impact the differentiation of a population of T cells, for example toward a non-Th17 T cell subset or away from a non-Th17 cell subset. These compositions and methods use T cell modulating agents to influence or otherwise impact the maintenance of a population of T cells, for example toward a non-Th17 T cell subset or away from a non-Th17 cell subset.

As used herein, terms such as "pathogenic Th17 cell" and/or "pathogenic Th17 phenotype" and all grammatical variations thereof refer to Th17 cells that, when induced in the presence of TGF-β3, express an elevated level of one or more genes selected from Cxcl3, IL22, IL3, Ccl4, Gzmb, Lrmp, Ccl5, Casp1, Csf2, Ccl3, Tbx21, Icos, IL17r, Stat4, Lgals3 and Lag, as compared to the level of expression in a TGF-β3-induced Th17 cells. As used herein, terms such as "non-pathogenic Th17 cell" and/or "non-pathogenic Th17 phenotype" and all grammatical variations thereof refer to Th17 cells that, when induced in the presence of TGF-β3, express a decreased level of one or more genes selected from IL6st, IL1rn, Ikzf3, Maf, Ahr, IL9 and IL10, as compared to the level of expression in a TGF-β3-induced Th17 cells.

These compositions and methods use T cell modulating agents to influence or otherwise impact the function and/or biological activity of a T cell or T cell population. These compositions and methods use T cell modulating agents to influence or otherwise impact the function and/or biological activity of a helper T cell or helper T cell population. These compositions and methods use T cell modulating agents to influence or otherwise impact the function and/or biological activity of a Th17 cell or Th17 cell population. These compositions and methods use T cell modulating agents to influence or otherwise impact the function and/or biological activity of a non-Th17 T cell or non-Th17 T cell population, such as, for example, a Treg cell or Treg cell population, or another CD4+ T cell or CD4+ T cell population. These compositions and methods use T cell modulating agents to influence or otherwise impact the plasticity of a T cell or T cell population, e.g., by converting Th17 cells into a different subtype, or into a new state.

The methods provided herein combine transcriptional profiling at high temporal resolution, novel computational algorithms, and innovative nanowire-based tools for performing perturbations in primary T cells to systematically derive and experimentally validate a model of the dynamic regulatory network that controls Th17 differentiation. See e.g., Yosef et al., "Dynamic regulatory network controlling Th17 cell differentiation, Nature, vol. 496: 461-468 (2013)/ doi: 10.1038/nature11981, the contents of which are hereby incorporated by reference in their entirety. The network consists of two self-reinforcing, but mutually antagonistic, modules, with novel regulators, whose coupled action may be essential for maintaining the level and/or balance between Th17 and other CD4+ T cell subsets. Overall, 9,159 interactions between 71 regulators and 1,266 genes were active in at least one network; 46 of the 71 are novel. The examples provided herein identify and validate 39 regulatory factors, embedding them within a comprehensive temporal network and reveals its organizational principles, and highlights novel drug targets for controlling Th17 differentiation.

A "Th17-negative" module includes regulators such as SP4, ETS2, IKZF4, TSC22D3 and/or, IRF1. It was found that the transcription factor Tsc22d3, which acts as a negative regulator of a defined subtype of Th17 cells, co-localizes on the genome with key Th17 regulators. The "Th17 positive" module includes regulators such as MINA, PML, POU2AF1, PROCR, SMARCA4, ZEB1, EGR2, CCR6, and/or FAS. Perturbation of the chromatin regulator Mina was found to up-regulate Foxp3 expression, perturbation of the co-activator Pou2af1 was found to up-regulate IFN-γ production in stimulated naïve cells, and perturbation of the TNF receptor Fas was found to up-regulate IL-2 production in stimulated naïve cells. All three factors also control IL-17 production in Th17 cells. Effective coordination of the immune system requires careful balancing of distinct pro-inflammatory and regulatory CD4+ helper T cell populations. Among those, pro-inflammatory IL-17 producing Th17 cells play a key role in the defense against extracellular pathogens and have also been implicated in the induction of several autoimmune diseases (see e.g., Bettelli, E., Oukka, M. & Kuchroo, V. K. T(H)-17 cells in the circle of immunity and autoimmunity. Nat Immunol 8, 345-350, doi:10.1038/ni0407-345 (2007)), including for example, psoriasis, ankylosing spondylitis, multiple sclerosis and inflammatory bowel disease. Th17 differentiation from naïve T-cells can be triggered in vitro by the cytokines TGF-β1 and IL-6. While TGF-β1 alone induces Foxp3+ regulatory T cells (iTreg) (see e.g., Zhou, L. et al. TGF-beta-induced Foxp3 inhibits T(H)17 cell differentiation by antagonizing RORgammat function. Nature 453, 236-240, doi:nature06878 [pii]10.1038/nature06878 (2008)), the presence of IL-6 inhibits iTreg and induces Th17 differentiation (Bettelli et al., Nat Immunol 2007).

While TGF-β1 is required for the induction of Foxp3+ induced Tregs (iTregs), the presence of IL-6 inhibits the generation of iTregs and initiates the Th17 differentiation program. This led to the hypothesis that a reciprocal relationship between pathogenic Th17 cells and Treg cells exists (Bettelli et al., Nat Immunol 2007), which may depend on the balance between the mutually antagonistic master transcription factors (TFs) ROR-γt (in Th17 cells) and Foxp3 (in Treg cells) (Zhou et al., Nature 2008). Other cytokine combinations have also been shown to induce ROR-γt and differentiation into Th17 cells, in particular TGF-β1 and IL-21 or IL-1β, TGF-β3+IL-6, IL-6, and IL-23 (Ghoreschi, K. et al. Generation of pathogenic T(H)17 cells in the absence of TGF-beta signaling. Nature 467, 967-971, doi: 10.1038/nature09447 (2010)). Finally, although a number of cytokine combinations can induce Th17 cells, exposure to IL-23 is critical for both stabilizing the Th17 phenotype and the induction of pathogenic effector functions in Th17 cells.

Much remains unknown about the regulatory network that controls Th17 cells (O'Shea, J. et al. Signal transduction and Th17 cell differentiation. Microbes Infect 11, 599-611 (2009); Zhou, L. & Littman, D. Transcriptional regulatory networks in Th17 cell differentiation. Curr Opin Immunol 21, 146-152 (2009)). Developmentally, as TGF-β is required for both Th17 and iTreg differentiation, it is not understood how balance is achieved between them or how IL-6 biases toward Th17 differentiation (Bettelli et al., Nat Immunol 2007). Functionally, it is unclear how the pro-inflammatory status of Th17 cells is held in check by the immunosuppressive cytokine IL-10 (O'Shea et al., Microbes Infect 2009; Zhou & Littman, Curr Opin Immunol 2009). Finally, many of the key regulators and interactions that drive development of Th17 remain unknown (Korn, T., Bettelli, E., Oukka, M. & Kuchroo, V. K. IL- and Th17 Cells. Annu Rev Immunol 27, 485-517, doi:10.1146/annurev.immunol.021908.13271010.1146/annurev.immunol.021908.132710 [pii] (2009)).

Recent studies have demonstrated the power of coupling systematic profiling with perturbation for deciphering mammalian regulatory circuits (Amit, I. et al. Unbiased reconstruction of a mammalian transcriptional network mediating pathogen responses. Science 326, 257-263, doi:10.1126/science.1179050 (2009); Novershtern, N. et al. Densely interconnected transcriptional circuits control cell states in human hematopoiesis. Cell 144, 296-309, doi:10.1016/j.cell.2011.01.004 (2011); Litvak, V. et al. Function of C/EBPdelta in a regulatory circuit that discriminates between transient and persistent TLR4-induced signals. Nat. Immunol. 10, 437-443, doi:10.1038/ni.1721 (2009); Suzuki, H. et al. The transcriptional network that controls growth arrest and differentiation in a human myeloid leukemia cell line. Nat Genet 41, 553-562 (2009); Amit, I., Regev, A. & Hacohen, N. Strategies to discover regulatory circuits of the mammalian immune system. Nature reviews. Immunology 11, 873-880, doi:10.1038/nri3109 (2011); Chevrier, N. et al. Systematic discovery of TLR signaling components delineates viral-sensing circuits. Cell 147, 853-867, doi:10.1016/j.cell.2011.10.022 (2011); Garber, M. et al. A High-Throughput Chromatin Immunoprecipitation Approach Reveals Principles of Dynamic Gene Regulation in Mammals. Molecular cell, doi:10.1016/j.molcel.2012.07.030 (2012)). Most of these studies have relied upon computational circuit-reconstruction algorithms that assume one 'fixed' network. Th17 differentiation, however, spans several days, during which the components and wiring of the regulatory network likely change. Furthermore, naïve T cells and Th17 cells cannot be transfected effectively in vitro by traditional methods without changing their phenotype or function, thus limiting the effectiveness of perturbation strategies for inhibiting gene expression.

These limitations are addressed in the studies presented herein by combining transcriptional profiling, novel computational methods, and nanowire-based siRNA delivery (Shalek, A. K. et al. Vertical silicon nanowires as a universal platform for delivering biomolecules into living cells. Proc. Natl. Acad. Sci. U.S.A. 107, 1870-1875, doi:10.1073/pnas.0909350107 (2010) (FIG. 1*a*) to construct and validate the transcriptional network of Th17 differentiation. Using genome-wide profiles of mRNA expression levels during differentiation, a model of the dynamic regulatory circuit that controls Th17 differentiation, automatically identifying 25 known regulators and nominating 46 novel regulators that control this system, was built. Silicon nanowires were used to deliver siRNA into naïve T cells (Shalek et al., Proc. Natl. Acad. Sci. U.S.A. 2010) to then perturb and measure the transcriptional effect of 29 candidate transcriptional regulators and 10 candidate receptors on a representative gene signature at two time points during differentiation. Combining this data, a comprehensive validated model of the network was constructed. In particular, the circuit includes 12 novel validated regulators that either suppress or promote Th17 development. The reconstructed model is organized into two coupled, antagonistic, and densely intra-connected modules, one promoting and the other suppressing the Th17 program. The model highlights 12 novel regulators, whose function was further characterized by their effects on global gene expression, DNA binding profiles, or Th17 differentiation in knockout mice. The studies provided herein demonstrate an unbiased systematic and functional approach to understanding the development of the Th17 T cell subset.

The methods provided herein combine a high-resolution transcriptional time course, novel methods to reconstruct regulatory networks, and innovative nanotechnology to perturb T cells, to construct and validate a network model for Th17 differentiation. The model consists of three consecutive, densely intra-connected networks, implicates 71 regulators (46 novel), and suggests substantial rewiring in 3 phases. The 71 regulators significantly overlap with genes genetically associated with inflammatory bowel disease (Jostins, L. et al. Host-microbe interactions have shaped the genetic architecture of inflammatory bowel disease. Nature 491, 119-124, doi:10.1038/nature11582 (2012)) (11 of 71, $p<10^{-9}$). Building on this model, 127 putative regulators (80 novel) were systematically ranked, and top ranking ones were tested experimentally.

It was found that the Th17 regulators are organized into two tightly coupled, self-reinforcing but mutually antagonistic modules, whose coordinated action may explain how the balance between Th17, Treg, and other effector T cell subsets is maintained, and how progressive directional differentiation of Th17 cells is achieved. Within the two modules are 12 novel factors (FIGS. 4 and 5), which were further characterized, highlighting four of the factors (others are in FIG. 17A, 17B). This validated model highlights at least 12 novel regulators that either positively or negatively impact the Th17 program (FIGS. 4 and 5). Remarkably, these and known regulators are organized in two tightly coupled, self-reinforcing and mutually antagonistic modules, whose coordinated action may explain how the balance between Th17, Treg, and other effector T cells is maintained, and how progressive directional differentiation of Th17 cells is achieved while repressing differentiation of other T cell subsets. The function of four of the 12 regulators—Mina, Fas, Pou2af1, and Tsc22d3—was further validated and characterized by undertaking Th17 differentiation of T cells from corresponding knockout mice or with ChIP-Seq binding profiles.

The T cell modulating agents are used to modulate the expression of one or more target genes or one or more products of one or more target genes that have been identified as genes responsive to Th17-related perturbations. These target genes are identified, for example, by contacting a T cell, e.g., naïve T cells, partially differentiated T cells, differentiated T cells and/or combinations thereof, with a T cell modulating agent and monitoring the effect, if any, on the expression of one or more signature genes or one or more products of one or more signature genes. In some embodiments, the one or more signature genes are selected from those listed in Table 1 or Table 2 shown below.

TABLE 1

| Signature Genes | | | |
|---|---|---|---|
| IRF1 | TNFSF9 | PRDM1 | NCF1C |
| CCR6 | SMARCA4 | AHR | NUDT4 |
| SMOX | VAX2 | SLAMF7 | PDCD1LG2 |
| ITGB1 | IL21 | IL1RN | PYCR1 |
| CASP6 | SAP30 | MBNL3 | AQP3 |
| NFKBIE | CD9 | ARID5A | SEMA7A |
| LAMP2 | IL24 | TRIM24 | PRC1 |
| GATA3 | STAT5B | CSF2 | IFIT1 |
| RORA | SKI | NFE2L2 | DNTT |
| SGK1 | BCL6 | IL23R | PMEPA1 |
| IL2RA | ELK3 | KLF6 | GAP43 |
| MT1A | CD74 | ACVR2A | PRICKLE1 |
| JAK3 | STAT6 | NR3C1 | OAS2 |
| IL4R | TNFSF8 | CCR4 | ERRFI1 |
| NAMPT | IL3 | CXCR5 | LAD1 |
| ITGA3 | TGFB1 | SKAP2 | TMEM126A |
| TGFB3 | ETV6 | PLEKHF2 | LILRB1, LILRB2, LILRB3, |
| INHBA | CASP4 | STAT2 | KATNA1 |
| KLF7 | CEBPB | IRF7 | B4GALT1 |
| RUNX3 | TRAF3 | FLI1 | ANXA4 |
| NFKBIZ | TRPS1 | IRF9 | SULT2B1 |
| SERPINE2 | JUN | GFI1 | PHLDA1 |
| RXRA | STAT4 | MXI1 | PRKD3 |
| SERTAD1 | CMTM6 | IFI35 | TAP1 |
| MAF | SOCS3 | MAX | TRIM5 |
| IL10 | TSC22D3 | ZNF238 | FLNA |
| BMPR1A | LIF | CHD7 | GUSB |
| PTPRJ | DAXX | FOXM1 | C14ORF83 |

TABLE 1-continued

| Signature Genes | | | |
|---|---|---|---|
| STAT3 | KLF9 | BCL11B | VAV3 |
| CCR5 | IL6ST | RUNX2 | ARL5A |
| CCL20 | CLCF1 | EMP1 | GRN |
| SPP1 | NFIL3 | PELI2 | PRKCA |
| CD80 | IKZF4 | SEMA4D | PECI |
| RORC | ISG20 | STARD10 | ARMCX2 |
| SERPINB1 | CD86 | TIMP2 | SLC2A1 |
| IL12RB2 | IL2RB | KLF10 | RPP14 |
| IFNGR2 | NCOA1 | CTSW | PSMB9 |
| SMAD3 | NOTCH1 | GEM | CASP3 |
| FOXP3 | TNFRSF12A | TRIM25 | TRAT1 |
| CD24 | CD274 | HLA-A | PLAGL1 |
| CD5L | MAFF | MYST4 | RAD51AP1 |
| CD2 | ATF4 | FRMD4B | NKG7 |
| TNFSF11 | ARNTL | RFK | IFITM2 |
| ICOS | IL1R1 | CD44 | HIP1R |
| IRF8 | FOXO1 | ERCC5 | |

TABLE 2

| Subset of Signature Genes | | | |
|---|---|---|---|
| AHR | HIF1A | IRF4 | REL |
| ARID5A | ICOS | IRF8 | RORA |
| BATF | ID2 | ITGA3 | RORC |
| CASP4 | ID3 | KLF6 | SERPINB1 |
| CASP6 | IFNG | KLRD1 | SGK1 |
| CCL20 | IL10 | LIF | SKAP2 |
| CCL4 | IL10RA | LTA | SKI |
| CCR5 | IL17A | MAF | SMOX |
| CCR6 | IL17F | MAFF | SOCS3 |
| CD24 | IL17RA | MINA | STAT1 |
| CD5L | IL2 | MYC | STAT3 |
| CD80 | IL21 | NFATC2 | STAT4 |
| CEBPB | IL21R | NFE2L2 | TBX21 |
| CLCF1 | IL22 | NFIL3 | TGFBR1 |
| CSF2 | IL23R | NOTCH1 | TGIF1 |
| CXCR3 | IL24 | NUDT4 | TNFRSF25 |
| EGR2 | IL2RA | PML | TNFSF8 |
| ELK3 | IL7R | POU2AF1 | TRIM24 |
| ETV6 | IL9 | PROCR | TRPS1 |
| FAS | INHBA | PSMB9 | TSC22D3 |
| FOXP3 | IRF1 | RBPJ | ZFP36L1 |
| GATA3 | | | |

In some embodiments, the target gene is one or more Th17-associated cytokine(s) or receptor molecule(s) selected from those listed in Table 3. In some embodiments, the target gene is one or more Th17-associated transcription regulator(s) selected from those shown in Table 4.

TABLE 3

| Th17-Associated Receptor Molecules | | | |
|---|---|---|---|
| ACVR1B | CXCR4 | IL6ST | PROCR |
| ACVR2A | CXCR5 | IL7R | PTPRJ |
| BMPR1A | DDR1 | IRAK1BP1 | PVR |
| CCR4 | FAS | ITGA3 | TLR1 |
| CCR5 | IL15RA | KLRD1 | TNFRSF12A |
| CCR6 | IL18R1 | MYD88 | TNFRSF13B |
| CCR8 | IL1RN | PLAUR | TRAF3 |
| CXCR3 | | | |

TABLE 4

| Th17-Associated Transcription Regulators | | | |
|---|---|---|---|
| TRPS1 | SMARCA4 | CDYL | SIRT2 |
| SMOX | ZFP161 | IKZF4 | MAFF |
| ARNTL | TP53 | NCOA1 | CHMP1B |

TABLE 4-continued

| Th17-Associated Transcription Regulators | | | |
|---|---|---|---|
| UBE2B | SUZ12 | SS18 | GATAD2B |
| NR3C1 | POU2AF1 | PHF13 | ZNF703 |
| TRIM24 | MYST4 | MTA3 | ZNRF1 |
| FLI1 | MXI1 | ASXL1 | JMJD1C |
| SP4 | CHD7 | LASS4 | ZFP36L2 |
| EGR2 | CREB3L2 | SKIL | TSC22D4 |
| ZNF281 | VAX2 | FOSL2 | NFE2L2 |
| RELA | KLF10 | RUNX2 | RNF11 |
| IRF7 | SKI | TLE1 | ARID3A |
| STAT2 | ELK3 | ELL2 | MEN1 |
| IRF3 | ZEB1 | BCL11B | CBX4 |
| XBP1 | LRRFIP1 | KAT2B | ZFP62 |
| PRDM1 | PAXBP1 | KLF6 | CIC |
| ATF4 | ID1 | E2F8 | HCLS1 |
| CREB1 | ZNF238 | ZNRF2 | ZFP36L1 |
| IRF9 | VAV1 | TSC22D3 | TGIF1 |

TABLE 4-continued

| Th17-Associated Transcription Regulators | | |
|---|---|---|
| IRF2 | MINA | HMGB2 |
| FOXJ2 | BATF3 | FUS |

In some embodiments, the target gene is one or more Th17-associated transcription regulator(s) selected from those shown in Table 5. In some embodiments, the target gene is one or more Th17-associated receptor molecule(s) selected from those listed in Table 6. In some embodiments, the target gene is one or more Th17-associated kinase(s) selected from those listed in Table 7. In some embodiments, the target gene is one or more Th17-associated signaling molecule(s) selected from those listed in Table 8. In some embodiments, the target gene is one or more Th17-associated receptor molecule(s) selected from those listed in Table 9.

TABLE 5

Candidate Regulators

| Symbol | % Interactions OR differential expression (compared to Th0) Early | Intermediate | Late | IL23R knockout (late) |
|---|---|---|---|---|
| IRF4 | 0.892473118 | 0.841397849 | 1 | UNDER-EXPR |
| IFI35 | 1 | 0.952380952 | 0.904761905 | UNDER-EXPR |
| ETS1 | 1 | 0.636363636 | 0.636363636 | UNDER-EXPR |
| NMI | 1 | 0.857142857 | 0 | UNDER-EXPR |
| SAP18 | 0.785714286 | 0.928571429 | 1 | OVER-EXPR |
| FLI1 | 1 | 0.971590909 | 0.869318182 | |
| SP4 | 1 | 0.710900474 | 0.63507109 | UNDER-EXPR |
| SP100 | 1 | 0 | 0 | UNDER-EXPR |
| TBX21 | 0 | 1 | 0 | OVER-EXPR |
| POU2F2 | 0 | 1 | 0 | OVER-EXPR |
| ZNF281 | 0 | 1 | 0 | UNDER-EXPR |
| NFIL3 | 0.611111111 | 0.611111111 | 1 | |
| SMARCA4 | 0.805825243 | 0.757281553 | 1 | OVER-EXPR |
| CSDA | 0 | 0 | 1 | OVER-EXPR |
| STAT3 | 0.855392157 | 0.970588235 | 1 | UNDER-EXPR |
| FOXO1 | 0.875 | 1 | 0.875 | |
| NCOA3 | 0.875 | 1 | 0.9375 | |
| LEF1 | 0.380952381 | 0.904761905 | 1 | UNDER-EXPR |
| SUZ12 | 0 | 1 | 0 | OVER-EXPR |
| CDC5L | 0 | 1 | 0 | UNDER-EXPR |
| CHD7 | 1 | 0.860465116 | 0.686046512 | UNDER-EXPR |
| HIF1A | 0.733333333 | 0.666666667 | 1 | UNDER-EXPR |
| RELA | 0.928571429 | 1 | 0.880952381 | UNDER-EXPR |
| STAT2 | 1 | 0.821428571 | 0 | |
| STAT5B | 1 | 0.848484848 | 0.515151515 | UNDER-EXPR |
| RORC | 0 | 0 | 1 | UNDER-EXPR |
| STAT1 | 1 | 0.635658915 | 0 | UNDER-EXPR |
| MAZ | 0 | 1 | 0 | |
| LRRFIP1 | 0.9 | 0.8 | 1 | |
| REL | 1 | 0 | 0 | OVER-EXPR |
| CITED2 | 1 | 0 | 0 | UNDER-EXPR |
| RUNX1 | 0.925149701 | 0.925149701 | 1 | UNDER-EXPR |
| ID2 | 0.736842105 | 0.789473684 | 1 | |
| SATB1 | 0.452380952 | 0.5 | 1 | UNDER-EXPR |
| TRIM28 | 0 | 1 | 0 | |
| STAT6 | 0.54 | 0.64 | 1 | OVER-EXPR |
| STAT5A | 0 | 0.642241379 | 1 | UNDER-EXPR |
| BATF | 0.811732606 | 0.761255116 | 1 | UNDER-EXPR |
| EGR1 | 0.857142857 | 1 | 0 | OVER-EXPR |
| EGR2 | 0.896428571 | 0.839285714 | 1 | OVER-EXPR |
| AES | 0.888888889 | 1 | 0.777777778 | |
| IRF8 | 0 | 1 | 0.824786325 | OVER-EXPR |
| SMAD2 | 0.806060606 | 0.781818182 | 1 | |
| NFKB1 | 0.266666667 | 0.706666667 | 1 | UNDER-EXPR |
| PHF21A | 1 | 0.533333333 | 0.933333333 | UNDER-EXPR |
| CBFB | 0.35 | 0.9 | 1 | |
| ZFP161 | 0.818181818 | 0.714876033 | 1 | OVER-EXPR |
| ZEB2 | 0 | 0.411764706 | 1 | |
| SP1 | 0 | 0.740740741 | 1 | |

TABLE 5-continued

| Candidate Regulators | | | | |
|---|---|---|---|---|
| | % Interactions OR differential expression (compared to Th0) | | | |
| Symbol | Early | Intermediate | Late | IL23R knockout (late) |
| FOXJ2 | 0 | 1 | 1 | |
| IRF1 | 1 | 0 | 0 | |
| MYC | 0 | 0.595505618 | 1 | UNDER-EXPR |
| IRF2 | 1 | 0 | 0 | |
| EZH1 | 1 | 0.8 | 0.44 | UNDER-EXPR |
| RUNX2 | 0 | 0 | 1 | |
| JUN | 0.647058824 | 0.647058824 | 1 | OVER-EXPR |
| STAT4 | 1 | 0 | 0 | UNDER-EXPR |
| MAX | 0.947368421 | 0.789473684 | 1 | |
| TP53 | 0.292307692 | 0.615384615 | 1 | UNDER-EXPR |
| IRF3 | 1 | 0.485294118 | 0.235294118 | UNDER-EXPR |
| BCL11B | 0.666666667 | 0.611111111 | 1 | |
| E2F1 | 0 | 0 | 1 | OVER-EXPR |
| IRF9 | 1 | 0.440433213 | 0 | UNDER-EXPR |
| GATA3 | 1 | 0 | 0 | OVER-EXPR |
| TRIM24 | 0.965517241 | 1 | 0.965517241 | UNDER-EXPR |
| E2F4 | 0.083333333 | 0.5 | 1 | |
| NR3C1 | 1 | 1 | 0 | UNDER-EXPR |
| ETS2 | 1 | 0.925925926 | 0.864197531 | OVER-EXPR |
| CREB1 | 0.802197802 | 0.706959707 | 1 | |
| IRF7 | 1 | 0.777777778 | 0 | OVER-EXPR |
| TFEB | 0.8 | 0.6 | 1 | |
| TRPS1 | | OVER-EXPR | | UNDER-EXPR |
| SMOX | | OVER-EXPR | OVER-EXPR | UNDER-EXPR |
| RORA | | OVER-EXPR | OVER-EXPR | UNDER-EXPR |
| ARID5A | OVER-EXPR | OVER-EXPR | OVER-EXPR | OVER-EXPR |
| ETV6 | OVER-EXPR | OVER-EXPR | | |
| ARNTL | | OVER-EXPR | | UNDER-EXPR |
| UBE2B | | | OVER-EXPR | UNDER-EXPR |
| XBP1 | | | OVER-EXPR | |
| PRDM1 | OVER-EXPR | OVER-EXPR | | UNDER-EXPR |
| ATF4 | | | OVER-EXPR | OVER-EXPR |
| POU2AF1 | | OVER-EXPR | | UNDER-EXPR |
| CEBPB | | OVER-EXPR | OVER-EXPR | UNDER-EXPR |
| CREM | | OVER-EXPR | OVER-EXPR | UNDER-EXPR |
| MYST4 | | OVER-EXPR | OVER-EXPR | UNDER-EXPR |
| MXI1 | | | OVER-EXPR | UNDER-EXPR |
| RBPJ | | OVER-EXPR | OVER-EXPR | OVER-EXPR |
| CREB3L2 | | OVER-EXPR | OVER-EXPR | UNDER-EXPR |
| VAX2 | | | OVER-EXPR | OVER-EXPR |
| KLF10 | | OVER-EXPR | OVER-EXPR | |
| SKI | | OVER-EXPR | OVER-EXPR | UNDER-EXPR |
| ELK3 | | OVER-EXPR | | OVER-EXPR |
| ZEB1 | | OVER-EXPR | OVER-EXPR | OVER-EXPR |
| PML | OVER-EXPR | OVER-EXPR | | UNDER-EXPR |
| SERTAD1 | | | OVER-EXPR | UNDER-EXPR |
| NOTCH1 | OVER-EXPR | OVER-EXPR | | OVER-EXPR |
| AHR | OVER-EXPR | OVER-EXPR | OVER-EXPR | UNDER-EXPR |
| C21ORF66 | | | OVER-EXPR | UNDER-EXPR |
| SAP30 | | | OVER-EXPR | OVER-EXPR |
| ID1 | | OVER-EXPR | OVER-EXPR | OVER-EXPR |
| ZNF238 | | OVER-EXPR | OVER-EXPR | |
| VAV1 | | OVER-EXPR | | UNDER-EXPR |
| MINA | | OVER-EXPR | OVER-EXPR | UNDER-EXPR |
| BATF3 | | | OVER-EXPR | OVER-EXPR |
| CDYL | | | | UNDER-EXPR |
| IKZF4 | OVER-EXPR | OVER-EXPR | OVER-EXPR | OVER-EXPR |
| NCOA1 | | OVER-EXPR | | OVER-EXPR |
| BCL3 | OVER-EXPR | OVER-EXPR | OVER-EXPR | UNDER-EXPR |
| JUNB | | OVER-EXPR | | UNDER-EXPR |
| SS18 | | OVER-EXPR | | OVER-EXPR |
| PHF13 | | | | OVER-EXPR |
| MTA3 | | OVER-EXPR | | UNDER-EXPR |
| ASXL1 | | OVER-EXPR | | OVER-EXPR |
| LASS4 | | | OVER-EXPR | UNDER-EXPR |
| SKIL | | OVER-EXPR | OVER-EXPR | OVER-EXPR |
| DDIT3 | | | OVER-EXPR | OVER-EXPR |
| FOSL2 | | OVER-EXPR | OVER-EXPR | |
| TLE1 | | OVER-EXPR | OVER-EXPR | |
| ATF3 | | | | OVER-EXPR |
| ELL2 | OVER-EXPR | OVER-EXPR | | OVER-EXPR |
| JARID2 | | | OVER-EXPR | OVER-EXPR |
| KLF9 | | OVER-EXPR | OVER-EXPR | OVER-EXPR |

TABLE 5-continued

| Candidate Regulators | | | | |
|---|---|---|---|---|
| | % Interactions OR differential expression (compared to Th0) | | | |
| Symbol | Early | Intermediate | Late | IL23R knockout (late) |
| KAT2B | | OVER-EXPR | | UNDER-EXPR |
| KLF6 | | OVER-EXPR | OVER-EXPR | UNDER-EXPR |
| E2F8 | | OVER-EXPR | OVER-EXPR | OVER-EXPR |
| BCL6 | | OVER-EXPR | | UNDER-EXPR |
| ZNRF2 | | | | UNDER-EXPR |
| TSC22D3 | | | OVER-EXPR | UNDER-EXPR |
| KLF7 | | | OVER-EXPR | |
| HMGB2 | | OVER-EXPR | | |
| FUS | | OVER-EXPR | | OVER-EXPR |
| SIRT2 | | | OVER-EXPR | |
| MAFF | | OVER-EXPR | OVER-EXPR | OVER-EXPR |
| CHMP1B | | | OVER-EXPR | UNDER-EXPR |
| GATAD2B | OVER-EXPR | | | OVER-EXPR |
| SMAD7 | | OVER-EXPR | | OVER-EXPR |
| ZNF703 | | OVER-EXPR | | OVER-EXPR |
| ZNRF1 | | | OVER-EXPR | OVER-EXPR |
| JMJD1C | OVER-EXPR | | | UNDER-EXPR |
| ZFP36L2 | | | OVER-EXPR | UNDER-EXPR |
| TSC22D4 | | | | |
| NFE2L2 | OVER-EXPR | OVER-EXPR | OVER-EXPR | UNDER-EXPR |
| RNF11 | | | | OVER-EXPR |
| ARID3A | | OVER-EXPR | OVER-EXPR | UNDER-EXPR |
| MEN1 | | | OVER-EXPR | OVER-EXPR |
| RARA | | OVER-EXPR | OVER-EXPR | UNDER-EXPR |
| CBX4 | OVER-EXPR | OVER-EXPR | | OVER-EXPR |
| ZFP62 | | OVER-EXPR | | |
| CIC | | | OVER-EXPR | |
| HCLS1 | | | | UNDER-EXPR |
| ZFP36L1 | | | | UNDER-EXPR |
| TGIF1 | | | | UNDER-EXPR |
| SMAD4 | | | | OVER-EXPR |
| IL7R | | OVER EXPR | OVER EXPR | UNDER EXPR |
| ITGA3 | | OVER EXPR | OVER EXPR | |
| IL1R1 | | OVER EXPR | OVER EXPR | UNDER EXPR |
| FAS | OVER EXPR | | | UNDER EXPR |
| CCR5 | OVER EXPR | OVER EXPR | OVER EXPR | UNDER EXPR |
| CCR6 | | OVER EXPR | OVER EXPR | |
| ACVR2A | | OVER EXPR | OVER EXPR | UNDER EXPR |
| IL6ST | OVER EXPR | OVER EXPR | | UNDER EXPR |
| IL17RA | OVER EXPR | OVER EXPR | | UNDER EXPR |
| CCR8 | | OVER EXPR | | |
| DDR1 | | OVER EXPR | OVER EXPR | UNDER EXPR |
| PROCR | | OVER EXPR | OVER EXPR | OVER EXPR |
| IL2RA | OVER EXPR | OVER EXPR | OVER EXPR | OVER EXPR |
| IL12RB2 | | OVER EXPR | OVER EXPR | UNDER EXPR |
| MYD88 | OVER EXPR | OVER EXPR | | UNDER EXPR |
| BMPR1A | | | OVER EXPR | UNDER EXPR |
| PTPRJ | | OVER EXPR | OVER EXPR | OVER EXPR |
| TNFRSF13 | | OVER EXPR | OVER EXPR | UNDER EXPR |
| CXCR3 | | OVER EXPR | | UNDER EXPR |
| IL1RN | | OVER EXPR | OVER EXPR | UNDER EXPR |
| CXCR5 | OVER EXPR | OVER EXPR | OVER EXPR | UNDER EXPR |
| CCR4 | | OVER EXPR | OVER EXPR | UNDER EXPR |
| IL4R | | OVER EXPR | OVER EXPR | UNDER EXPR |
| IL2RB | | OVER EXPR | OVER EXPR | |
| TNFRSF12 | | OVER EXPR | OVER EXPR | OVER EXPR |
| CXCR4 | | OVER EXPR | OVER EXPR | UNDER EXPR |
| KLRD1 | | OVER EXPR | OVER EXPR | |
| IRAK1BP1 | | OVER EXPR | | OVER EXPR |
| PVR | OVER EXPR | OVER EXPR | OVER EXPR | UNDER EXPR |
| IL15RA | OVER EXPR | | | OVER EXPR |
| TLR1 | | | | OVER EXPR |
| ACVR1B | | | OVER EXPR | OVER EXPR |
| IL12RB1 | OVER EXPR | OVER EXPR | | OVER EXPR |
| ILI8R1 | | OVER EXPR | | OVER EXPR |
| TRAF3 | | OVER EXPR | | OVER EXPR |
| IFNGR1 | | | OVER EXPR | UNDER EXPR |
| PLAUR | | | OVER EXPR | OVER EXPR |
| IL21R | | | | UNDER EXPR |
| IL23R | | | OVER EXPR | UNDER EXPR |

TABLE 6

Candidate Receptor Molecules

| Symbol | % Differential expression (compared to Th0) Early | Intermediate | Late | IL23R knockout (late) |
|---|---|---|---|---|
| PTPLA | | | | UNDER EXPR |
| PSTPIP1 | | OVER EXPR | OVER EXPR | UNDER EXPR |
| TK1 | | | | UNDER EXPR |
| EIF2AK2 | OVER EXPR | | | |
| PTEN | | | | UNDER EXPR |
| BPGM | | | | UNDER EXPR |
| DCK | | | | OVER EXPR |
| PTPRS | | | | OVER EXPR |
| PTPN18 | | | | OVER EXPR |
| MKNK2 | | | | OVER EXPR |
| PTPN1 | | OVER EXPR | | UNDER EXPR |
| PTPRE | | | | UNDER EXPR |
| SH2D1A | | | | OVER EXPR |
| DUSP22 | OVER EXPR | | | |
| PLK2 | | | | OVER EXPR |
| DUSP6 | | | | UNDER EXPR |
| CDC25B | | | | UNDER EXPR |
| SLK | | | OVER EXPR | UNDER EXPR |
| MAP3K5 | | | | UNDER EXPR |
| BMPR1A | | | OVER EXPR | UNDER EXPR |
| ACP5 | | OVER EXPR | OVER EXPR | UNDER EXPR |
| TXK | | OVER EXPR | OVER EXPR | UNDER EXPR |
| RIPK3 | | OVER EXPR | OVER EXPR | UNDER EXPR |
| PPP3CA | | | | OVER EXPR |
| PTPRF | | OVER EXPR | OVER EXPR | OVER EXPR |
| PACSIN1 | | | | OVER EXPR |
| NEK4 | | OVER EXPR | | UNDER EXPR |
| PIP4K2A | | | | UNDER EXPR |
| PPME1 | | OVER EXPR | OVER EXPR | UNDER EXPR |
| SRPK2 | | | | UNDER EXPR |
| DUSP2 | | | | OVER EXPR |
| PHACTR2 | | OVER EXPR | | OVER EXPR |
| HK2 | OVER EXPR | OVER EXPR | | |
| DCLK1 | | | | OVER EXPR |
| PPP2R5A | | | | UNDER EXPR |
| RIPK1 | OVER EXPR | | | UNDER EXPR |
| GK | | | | OVER EXPR |
| RNASEL | OVER EXPR | | | OVER EXPR |
| GMFG | | OVER EXPR | OVER EXPR | OVER EXPR |
| STK4 | | | | UNDER EXPR |
| HINT3 | | | | OVER EXPR |
| DAPP1 | | OVER EXPR | | UNDER EXPR |
| TEC | OVER EXPR | OVER EXPR | OVER EXPR | UNDER EXPR |
| GMFB | | OVER EXPR | | OVER EXPR |
| PTPN6 | | | | UNDER EXPR |
| RIPK2 | | | | UNDER EXPR |
| PIM1 | | OVER EXPR | OVER EXPR | OVER EXPR |

TABLE 6-continued

Candidate Receptor Molecules

| Symbol | % Differential expression (compared to Th0) Early | Intermediate | Late | IL23R knockout (late) |
|---|---|---|---|---|
| NEK6 | | OVER EXPR | OVER EXPR | UNDER EXPR |
| ACVR2A | | OVER EXPR | OVER EXPR | UNDER EXPR |
| AURKB | | | | UNDER EXPR |
| FES | | OVER EXPR | OVER EXPR | |
| ACVR1B | | | OVER EXPR | OVER EXPR |
| CDK6 | | OVER EXPR | OVER EXPR | UNDER EXPR |
| ZAK | | OVER EXPR | OVER EXPR | UNDER EXPR |
| VRK2 | | | | UNDER EXPR |
| MAP3K8 | OVER EXPR | | | UNDER EXPR |
| DUSP14 | | OVER EXPR | | UNDER EXPR |
| SGK1 | OVER EXPR | OVER EXPR | OVER EXPR | UNDER EXPR |
| PRKCQ | OVER EXPR | | | UNDER EXPR |
| JAK3 | | OVER EXPR | | UNDER EXPR |
| ULK2 | | OVER EXPR | | UNDER EXPR |
| HIPK2 | | | OVER EXPR | OVER EXPR |
| PTPRJ | | OVER EXPR | OVER EXPR | OVER EXPR |
| SPHK1 | | OVER EXPR | | |
| INPP1 | | | | UNDER EXPR |
| TNK2 | | OVER EXPR | OVER EXPR | OVER EXPR |
| PCTK1 | | OVER EXPR | OVER EXPR | OVER EXPR |
| DUSP1 | | | | OVER EXPR |
| NUDT4 | | | | UNDER EXPR |
| MAP4K3 | | OVER EXPR | | |
| TGFBR1 | | OVER EXPR | OVER EXPR | OVER EXPR |
| PTP4A1 | | | | OVER EXPR |
| HK1 | | OVER EXPR | | OVER EXPR |
| DUSP16 | OVER EXPR | | | UNDER EXPR |
| ANP32A | | | | OVER EXPR |
| DDR1 | | OVER EXPR | OVER EXPR | UNDER EXPR |
| ITK | | | | UNDER EXPR |
| WNK1 | | | | UNDER EXPR |
| NAGK | | | OVER EXPR | UNDER EXPR |
| STK38 | | | OVER EXPR | |
| BMP2K | OVER EXPR | OVER EXPR | OVER EXPR | OVER EXPR |
| BUB1 | | | | UNDER EXPR |
| AAK1 | | | | OVER EXPR |
| SIK1 | | | | OVER EXPR |
| DUSP10 | | OVER EXPR | | UNDER EXPR |
| PRKCA | | | | OVER EXPR |
| PIM2 | OVER EXPR | | | UNDER EXPR |
| STK17B | | | OVER EXPR | UNDER EXPR |
| TK2 | | | | UNDER EXPR |
| STK39 | | | | OVER EXPR |
| ALPK2 | | OVER EXPR | OVER EXPR | UNDER EXPR |
| MST4 | | | | OVER EXPR |
| PHLPP1 | | | | UNDER EXPR |

TABLE 7

Candidate Kinases

| Symbol | % Differential expression (compared to Th) Early | Intermediate | Late | IL23R knockout (late) |
|---|---|---|---|---|
| SGK1 | OVER EXPR | OVER EXPR | OVER EXPR | UNDER EXPR |
| HK2 | OVER EXPR | OVER EXPR | OVER EXPR | |
| PRPS1 | | | | UNDER EXPR |
| CAMK4 | | | | |
| ZAP70 | | | | |
| TXK | OVER EXPR | OVER EXPR | OVER EXPR | UNDER EXPR |
| NEK6 | | OVER EXPR | OVER EXPR | |
| MAPKAPK | | | OVER EXPR | |
| MFHAS1 | UNDER EXPR | | | OVER EXPR |
| PDXK | | | | |
| PRKCH | | | OVER EXPR | UNDER EXPR |
| CDK6 | | OVER EXPR | OVER EXPR | |
| ZAK | | OVER EXPR | OVER EXPR | UNDER EXPR |
| PKM2 | | OVER EXPR | | |
| JAK2 | | OVER EXPR | UNDER EXPR | UNDER EXPR |

TABLE 7-continued

| Candidate Kinases | | | | |
|---|---|---|---|---|
| | % Differential expression (compared to Th) | | | |
| Symbol | Early | Intermediate | Late | IL23R knockout (late) |
| STK38 | UNDER EXPR | UNDER EXPR | OVER EXPR | |
| ADRBK1 | | | | |
| PTK2B | UNDER EXPR | | | |
| DGUOK | | UNDER EXPR | UNDER EXPR | |
| DGKA | | | | UNDER EXPR |
| RIPK3 | | OVER EXPR | OVER EXPR | UNDER EXPR |
| PIM1 | | OVER EXPR | OVER EXPR | OVER EXPR |
| CDK5 | | | | |
| STK17B | | | OVER EXPR | |
| CLK3 | | | | |
| CLK1 | | | | |
| ITK | | UNDER EXPR | | |
| AKT1 | | | | UNDER EXPR |
| PGK1 | | | | |
| TWF1 | | | | |
| LIMK2 | | | | |
| RFK | | | | UNDER EXPR |
| WNK1 | | UNDER EXPR | | OVER EXPR |
| HIPK1 | | | | |
| AXL | | OVER EXPR | UNDER EXPR | UNDER EXPR |
| RPS6KB1 | | | | |
| CDC42BPA | | | | |
| STK38L | | | | |
| PRKCD | | | | |
| PDK3 | | | | |
| PI4KA | | | | |
| PNKP | | | | |
| CDKN3 | | | | |
| STK19 | | | | |
| PRPF4B | | | | UNDER EXPR |
| MAP4K2 | | | | |
| PDPK1 | | | | |
| VRK1 | | | | |
| TRRAP | | | | |

TABLE 8

| Candidate Signaling Molecules From Single Cell Analysis | | | | |
|---|---|---|---|---|
| | % Differential expression (compared to Th) | | | |
| Symbol | Early | Intermediate | Late | IL23R knockout (late) |
| CTLA4 | | OVER EXPR | OVER EXPR | UNDER EXPR |
| CD9 | | UNDER EXPR | UNDER EXPR | UNDER EXPR |
| IL2RA | OVER EXPR | OVER EXPR | OVER EXPR | OVER EXPR |
| CD5L | | OVER EXPR | OVER EXPR | OVER EXPR |
| CD24 | | OVER EXPR | OVER EXPR | UNDER EXPR |
| CD200 | OVER EXPR | UNDER EXPR | UNDER EXPR | OVER EXPR |
| CD53 | | UNDER EXPR | OVER EXPR | UNDER EXPR |
| TNFRSF9 | UNDER EXPR | UNDER EXPR | | OVER EXPR |
| CD44 | | | UNDER EXPR | |
| CD96 | | UNDER EXPR | UNDER EXPR | |
| CD83 | | UNDER EXPR | UNDER EXPR | |
| IL27RA | | | | |
| CXCR3 | | OVER EXPR | OVER EXPR | |
| TNFRSF4 | | | UNDER EXPR | |
| IL4R | | OVER EXPR | OVER EXPR | |
| PROCR | | OVER EXPR | OVER EXPR | OVER EXPR |
| LAMP2 | OVER EXPR | OVER EXPR | | UNDER EXPR |
| CD74 | | UNDER EXPR | UNDER EXPR | OVER EXPR |
| TNFRSF13 | | OVER EXPR | OVER EXPR | UNDER EXPR |
| PDCD1 | | | UNDER EXPR | |
| TNFRSF1B | | | | |
| IL21R | | UNDER EXPR | UNDER EXPR | |
| IFNGR1 | | | OVER EXPR | UNDER EXPR |
| ICOS | | | UNDER EXPR | OVER EXPR |
| PTPRC | | | | |
| ADAM17 | | | | |
| FCGR2B | | | | |

TABLE 8-continued

Candidate Signaling Molecules From Single Cell Analysis

| Symbol | % Differential expression (compared to Th) Early | Intermediate | Late | IL23R knockout (late) |
|---|---|---|---|---|
| TNFSF9 | | UNDER EXPR | UNDER EXPR | UNDER EXPR |
| MS4A6A | | UNDER EXPR | UNDER EXPR | UNDER EXPR |
| CCR4 | | OVER EXPR | OVER EXPR | |
| CD226 | | | | |
| CD3G | | UNDER EXPR | UNDER EXPR | |
| ENTPD1 | | | | |
| ADAM10 | | UNDER EXPR | UNDER EXPR | UNDER EXPR |
| CD27 | UNDER EXPR | UNDER EXPR | UNDER EXPR | UNDER EXPR |
| CD84 | | UNDER EXPR | UNDER EXPR | |
| ITGAL | UNDER EXPR | | | |
| CCND2 | | | | UNDER EXPR |
| BSG | | | | UNDER EXPR |
| CD40LG | | | | |
| PTPRCAP | UNDER EXPR | | UNDER EXPR | UNDER EXPR |
| CD68 | | | | |
| CD63 | | | | |
| SLC3A2 | | | | |
| HLA-DQA1 | | OVER EXPR | | |
| CTSD | | | | |
| CSF1R | | | | |
| CD3D | | UNDER EXPR | | |
| CD247 | | | UNDER EXPR | UNDER EXPR |
| CD14 | | | | |
| ITGAV | | | | |
| FCER1G | | | | |
| IL2RG | | OVER EXPR | | UNDER EXPR |

TABLE 9

Candidate Receptor Molecules From Single Cell Analysis

| Symbol | % Differential expression (compared to Th) Early | Intermediate | Late | IL23R knockout (late) |
|---|---|---|---|---|
| PLEK | | OVER EXPR | | |
| BHLH40 | OVER EXPR | OVER EXPR | | |
| ARID5A | OVER EXPR | OVER EXPR | OVER EXPR | OVER EXPR |
| ETS1 | | OVER EXPR | OVER EXPR | UNDER EXPR |
| IRF4 | OVER EXPR | OVER EXPR | OVER EXPR | |
| IKZF3 | | | | |
| RORC | | OVER EXPR | OVER EXPR | UNDER EXPR |
| STAT4 | | UNDER EXPR | UNDER EXPR | UNDER EXPR |
| RORA | | OVER EXPR | OVER EXPR | UNDER EXPR |
| PHF6 | | | | |
| ID3 | UNDER EXPR | UNDER EXPR | UNDER EXPR | OVER EXPR |
| ZBTB32 | | UNDER EXPR | | OVER EXPR |
| IFI35 | OVER EXPR | | | |
| ID2 | OVER EXPR | OVER EXPR | OVER EXPR | UNDER EXPR |
| MDM4 | | | | |
| CHMP2A | | | | |
| ANKHD1 | | | | |
| CHD7 | | OVER EXPR | OVER EXPR | UNDER EXPR |
| STAT5B | | OVER EXPR | OVER EXPR | |
| MAML2 | | | | |
| ID1 | | OVER EXPR | OVER EXPR | OVER EXPR |
| SS18 | | OVER EXPR | | |
| MAF | | | | |
| ETV6 | OVER EXPR | OVER EXPR | | |
| CCRN4L | | OVER EXPR | OVER EXPR | |
| NASP | | | | |
| BLOC1S1 | | | | OVER EXPR |
| XAB2 | | | | |
| STAT5A | | OVER EXPR | | UNDER EXPR |
| IKZF1 | UNDER EXPR | | | |
| JUNB | | OVER EXPR | OVER EXPR | |
| THRAP3 | | | | OVER EXPR |
| SP100 | OVER EXPR | | | |
| PYCR1 | | OVER EXPR | OVER EXPR | OVER EXPR |
| HMGA1 | | | | |

TABLE 9-continued

| Candidate Receptor Molecules From Single Cell Analysis | | | | |
|---|---|---|---|---|
| | % Differential expression (compared to Th) | | | |
| Symbol | Early | Intermediate | Late | IL23R knockout (late) |
| TAF1B | | | | UNDER EXPR |
| CNOT2 | | | | |
| NOC4L | OVER EXPR | | | |
| SKI | UNDER EXPR | OVER EXPR | OVER EXPR | |
| VAV1 | | OVER EXPR | OVER EXPR | |
| NR4A2 | | UNDER EXPR | UNDER EXPR | OVER EXPR |
| LGTN | | | | |
| NFKBIA | | | | UNDER EXPR |
| KDM6B | | | | |
| MAZ | | | | |
| CDC5L | | | | UNDER EXPR |
| HCLS1 | UNDER EXPR | | OVER EXPR | |
| BAZ2B | OVER EXPR | | | |
| MXD3 | | | | |
| BATF | OVER EXPR | OVER EXPR | | |
| E2F4 | | | | |
| NFKBIB | | | | |
| RBPJ | | OVER EXPR | OVER EXPR | OVER EXPR |
| TOX4 | | | | |
| CENPT | | | | |
| CASP8AP2 | | | | |
| ECE2 | | | | |
| MIER1 | | | | |
| AHR | OVER EXPR | OVER EXPR | OVER EXPR | |
| SPOP | | | | UNDER EXPR |
| BTG1 | | | | |
| MATR3 | | | | UNDER EXPR |
| JMJD1C | OVER EXPR | OVER EXPR | | |
| HMGB2 | | OVER EXPR | | |
| CREG1 | | | | OVER EXPR |
| NFATC1 | | | | |
| NFE2L2 | OVER EXPR | OVER EXPR | OVER EXPR | |
| WHSC1L1 | | | | |
| TBPL1 | | | | |
| TRIP12 | | | | |
| BTG2 | | | | |
| HMGN1 | | | | UNDER EXPR |
| ATF2 | | | | |
| NR4A3 | | | | |
| C16ORF80 | | | | |
| MBNL1 | | UNDER EXPR | UNDER EXPR | |
| WDHD1 | | | | |
| LASS6 | | | | |
| CREM | | OVER EXPR | OVER EXPR | |
| CARM1 | | | | |
| RNF5 | | | | UNDER EXPR |
| SMARCA4 | | | | OVER EXPR |
| GATAD1 | | | | |
| TCERG1 | | | | UNDER EXPR |
| CHRAC1 | | | | |
| NFYC | | | | |
| ATF3 | | | OVER EXPR | OVER EXPR |
| ZNF326 | OVER EXPR | | | |
| KLF13 | | | | |
| TFDP1 | | | | |
| LRRFIP1 | | OVER EXPR | OVER EXPR | |
| MORF4L2 | | | | |
| FOXN3 | | | | |
| HDAC8 | | | | |
| MORF4L1 | | | | |
| DNAJC2 | | | | OVER EXPR |
| MAFG | | | | |
| YBX1 | | | | |

Among the novel 'Th17 positive' factors is the zinc finger E-box binding homeobox 1 Zeb1, which is early-induced and sustained in the Th17 time course (FIG. 17*a*), analogous to the expression of many known key Th17 factors. Zeb1 knockdown decreases the expression of Th17 signature cytokines (including IL-17A, IL-17F, and IL-21) and TFs (including Rbpj, Maff, and Mina) and of late induced cytokine and receptor molecule genes ($p<10^{-4}$, cluster C19). It is bound in Th17 cells by ROR-γt, Batf and Stat3, and is down-regulated in cells from Stat3 knockout mice (FIG. 17*a*). Interestingly, Zeb1 is known to interact with the chromatin factor Smarca4/Brg1 to repress the E-cadherin promoter in epithelial cells and induce an epithelial-mesenchymal transition (Sanchez-Tilló, E. et al. ZEB1 represses E-cadherin and induces an EMT by recruiting the SWI/SNF chromatin-remodeling protein BRG1. Oncogene 29, 3490-3500, doi:10.1038/onc.2010.102 (2010)). Smarca4 is a regulator in all three network models (FIG. 2*d,e*) and a member of the 'positive module' (FIG. 4*b*). Although it is not differentially expressed in the Th17 time course, it is bound by Batf, Irf4 and Stat3 (positive regulators of Th17), but also by Gata3 and Stat5 (positive regulators of other lineages, FIG. 17*a*). Chromatin remodeling complexes that contain Smarca4 are known to displace nucleosomes and remodel chromatin at the IFN-γ promoter and promote its expression in Th1 cells (Zhang, F. & Boothby, M. T helper type 1-specific Brg1 recruitment and remodeling of nucleosomes positioned at the IFN-gamma promoter are Stat4 dependent. J. Exp. Med. 203, 1493-1505, doi:10.1084/jem.20060066 (2006)). There are also potential Smarca4 binding DNA sequences within the vicinity of the IL-17a promoter (Matys, V. et al. TRANSFAC: transcriptional regulation, from patterns to profiles. Nucleic Acids Res. 31, 374-378 (2003)). Taken together, this suggests a model where chromatin remodeling by Smarca4, possibly in interaction with Zeb1, positive regulates Th17 cells and is essential for IL-17 expression.

Conversely, among the novel 'Th17 negative' factors is Sp4, an early-induced gene, predicted in the model as a regulator of ROR-γt and as a target of ROR-γt, Batf, Irf4, Stat3 and Smarca4 (FIG. 17*b*). Sp4 knockdown results in an increase in ROR-γt expression at 48 h, and an overall stronger and "cleaner" Th17 differentiation as reflected by an increase in the expression of Th17 signature genes, including IL-17, IL-21 and Irf4, and decrease in the expression of signature genes of other CD4+ cells, including Gata3, Foxp3 and Stat4.

These novel and known regulatory factors act coordinately to orchestrate intra- and intermodules interactions and to promote progressive differentiation of Th17 cells, while limiting modules that inhibit directional differentiation of this subset and promote differentiation of T cells into other T cell subsets. For instance, knockdown of Smarca4 and Zeb1 leads to decrease in Mina (due to all-positive interactions between Th17 'positive regulators'), while knockdown of Smarca4 or Mina leads to increase in Tsc22d3 31 expression, due to negative cross-module interactions. As shown using RNA-seq, these effects extend beyond the expression of regulatory factors in the network and globally affect the Th17 transcriptional program: e.g. knock-down of Mina has substantial effects on the progression of the Th17 differentiation network from the intermediate to the late phase, as some of its affected down-regulated genes significantly overlap the respective temporal clusters ($p<10^{-5}$, e.g., clusters C9, C19). An opposite trend is observed for the negative regulators Tsc22d3 and Sp4. For example, the transcriptional regulator Sp4 represses differentiating Th17 cells from entering into the late phase of differentiation by inhibiting the cytokine signaling (C19; $p<10^{-7}$) and hematopoiesi (C20; $p<10^{-3}$) clusters, which include Ahr, Batf, ROR-γt, etc. These findings emphasize the power of large-scale functional perturbation studies in understanding the action of complex molecular circuits that govern Th17 differentiation.

Figure 18:
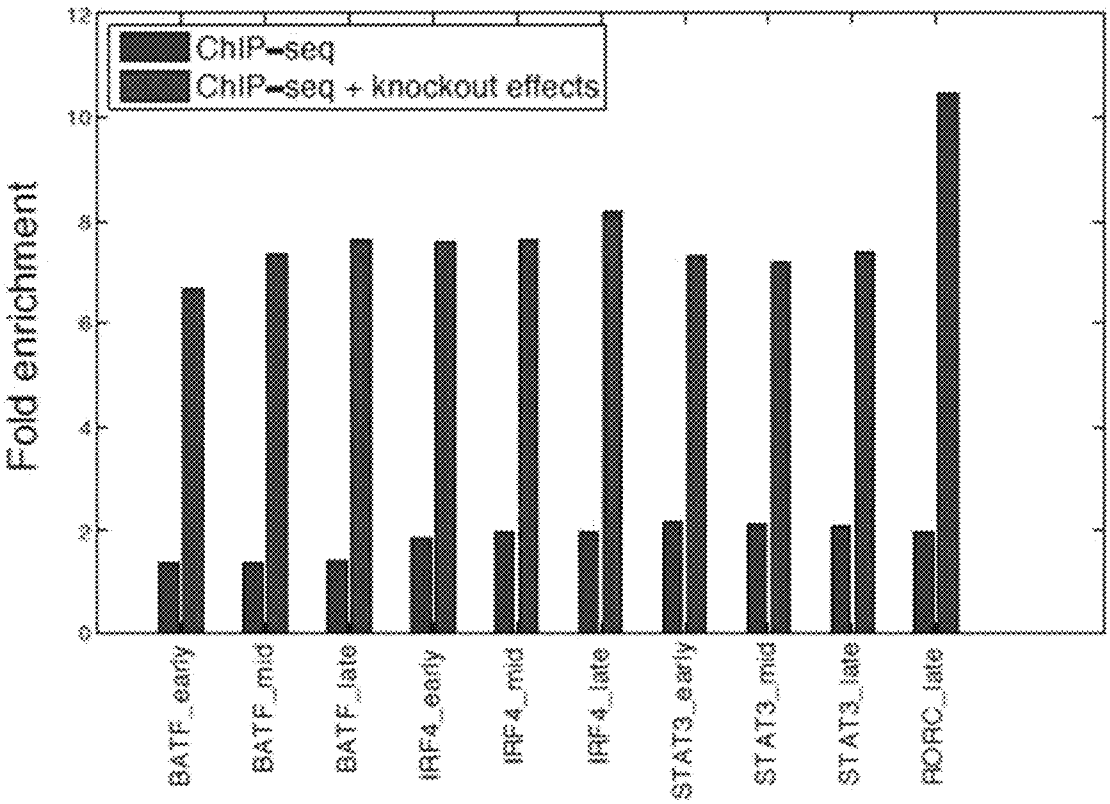
FIG. 18 is a graph depicting the overlap with ChIP-seq and RNA-seq data from Ciofani et al (Cell, 2012). Fold enrichment is shown for the four TF that were studied by Ciofani et al using ChIP-seq and RNA-seq and are predicted as regulators in the three network models (early, intermediate (denoted as "mid"), and late). The results are compared to the ChIP-seq based network of Ciofani et al. (blue) and to their combined ChIP-seq/RNA-seq network (taking a score cutoff of 1.5, as described by the authors; red). In all cases the p-value of the overlap (with ChIP-seq only or with the combined ChIP-seq/RNA-seq network) is below $10^{-10}$ (using Fisher exact test), but the fold enrichment is particularly high in genes that are both bound by a factor and affected by its knockout, the most functional edges.
Figure 19A:
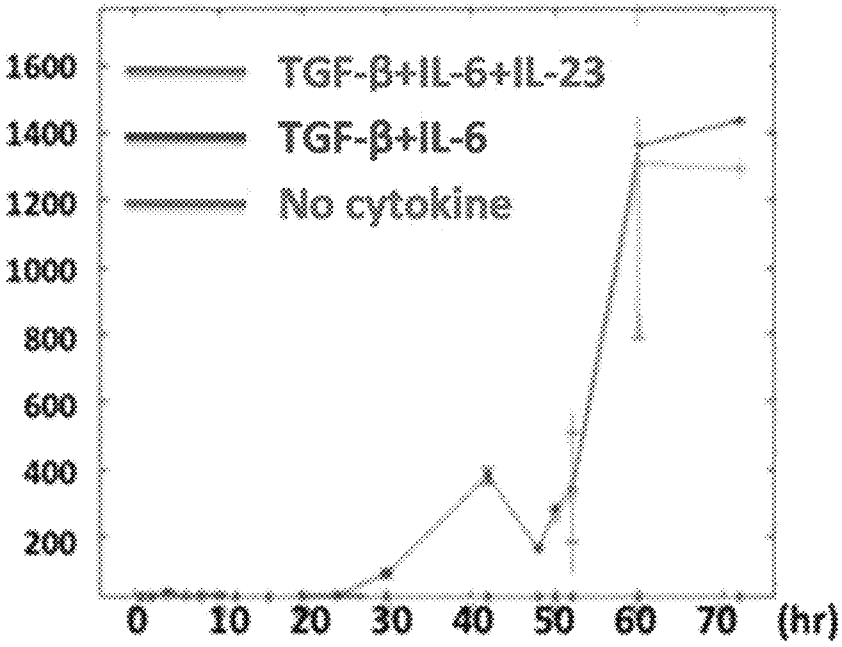
FIGS. 19A-19D are a series of graphs depicting that PROCR is specifically induced in Th17 cells induced by TGF-β1 with IL-6.
Figure 19B:
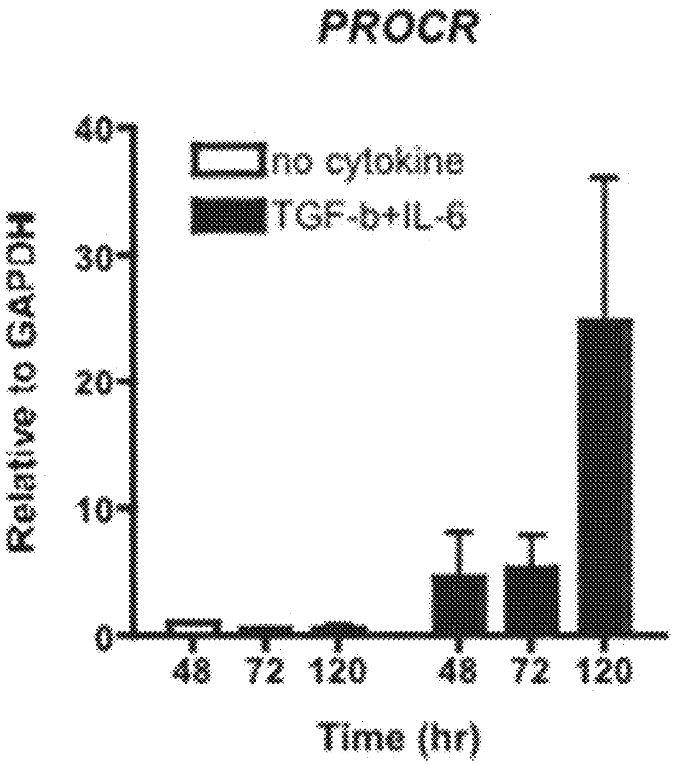
Figure 19C:
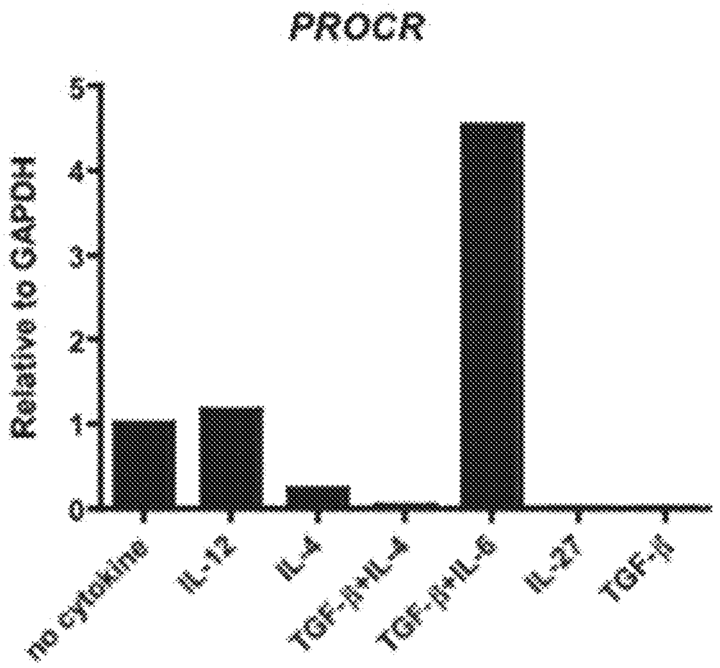
Figure 19D:
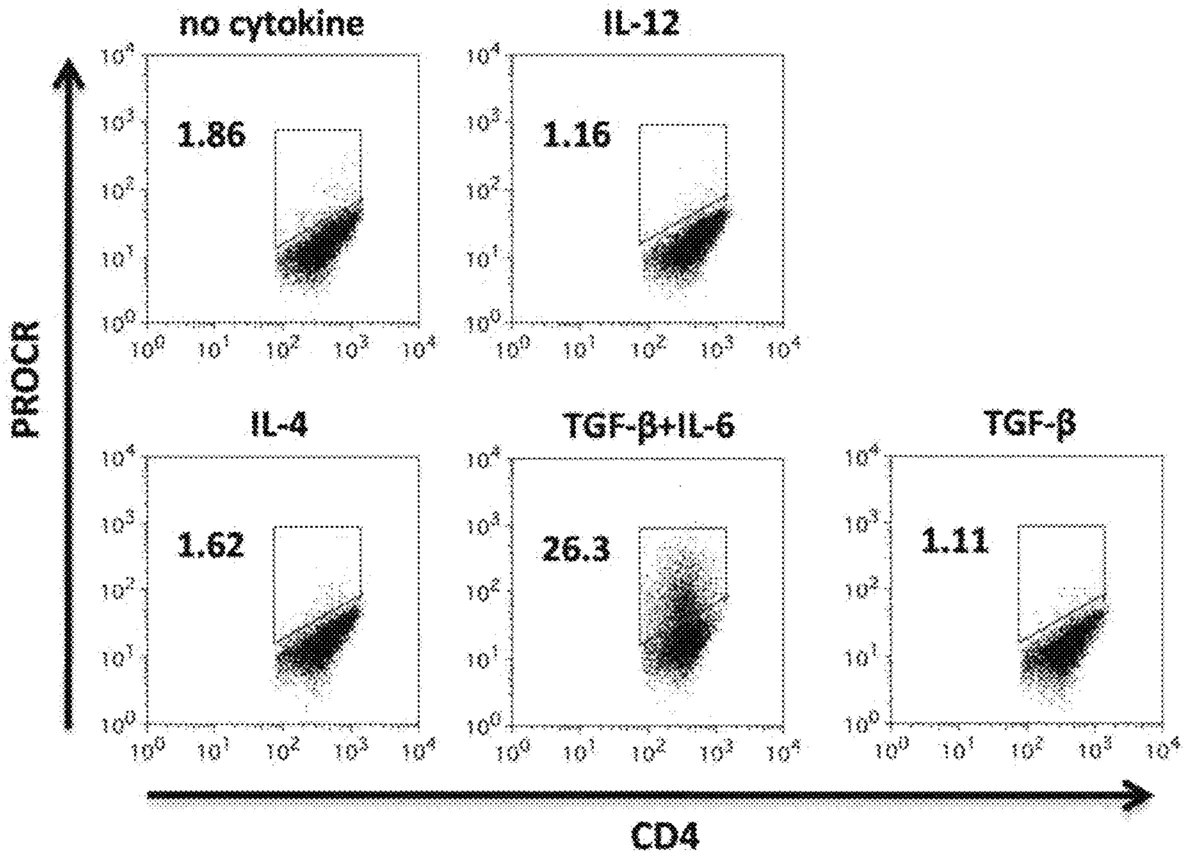
Figure 20A:
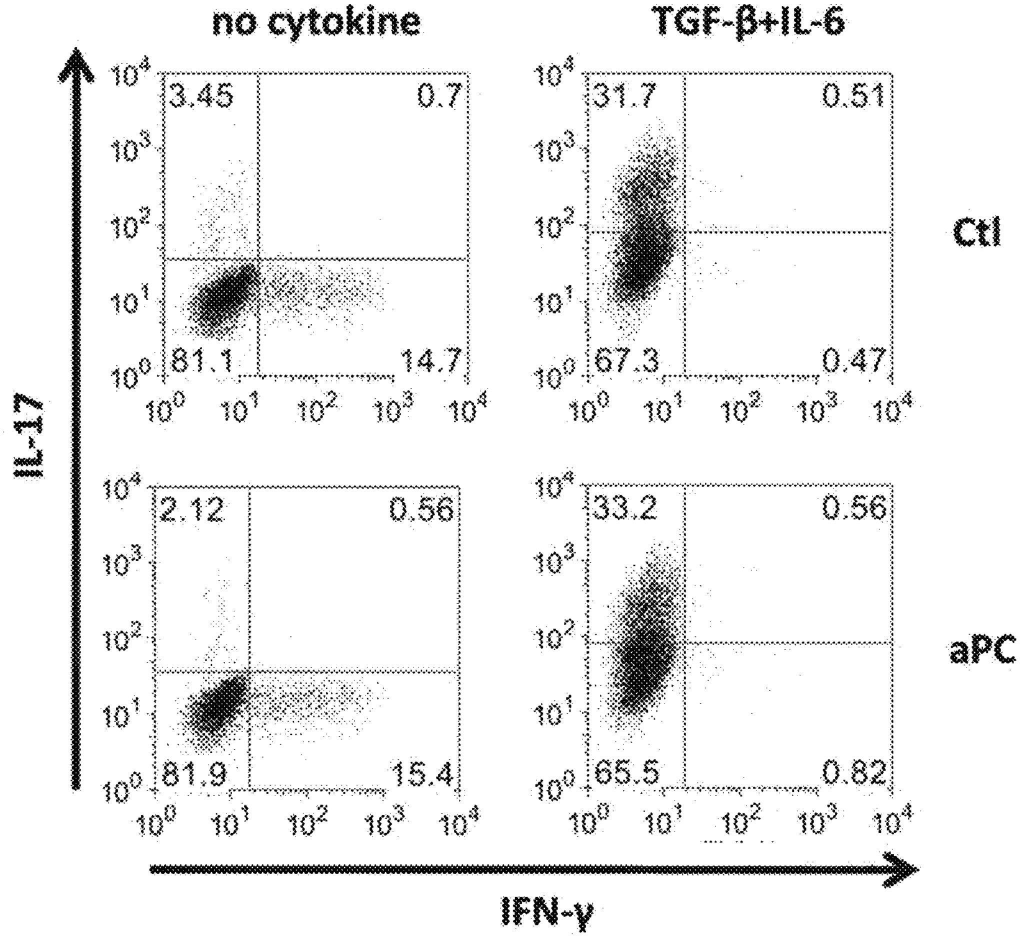
FIGS. 20A-20D are a series of graphs depicting that PROCR stimulation and expression is not essential for cytokine production from Th17 cells.
Figure 20B:
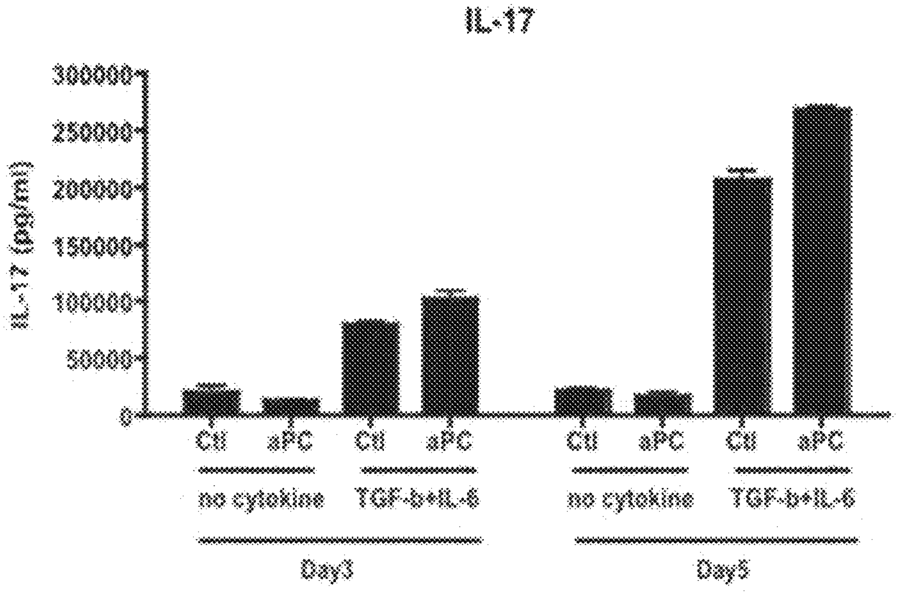
Figure 20C:
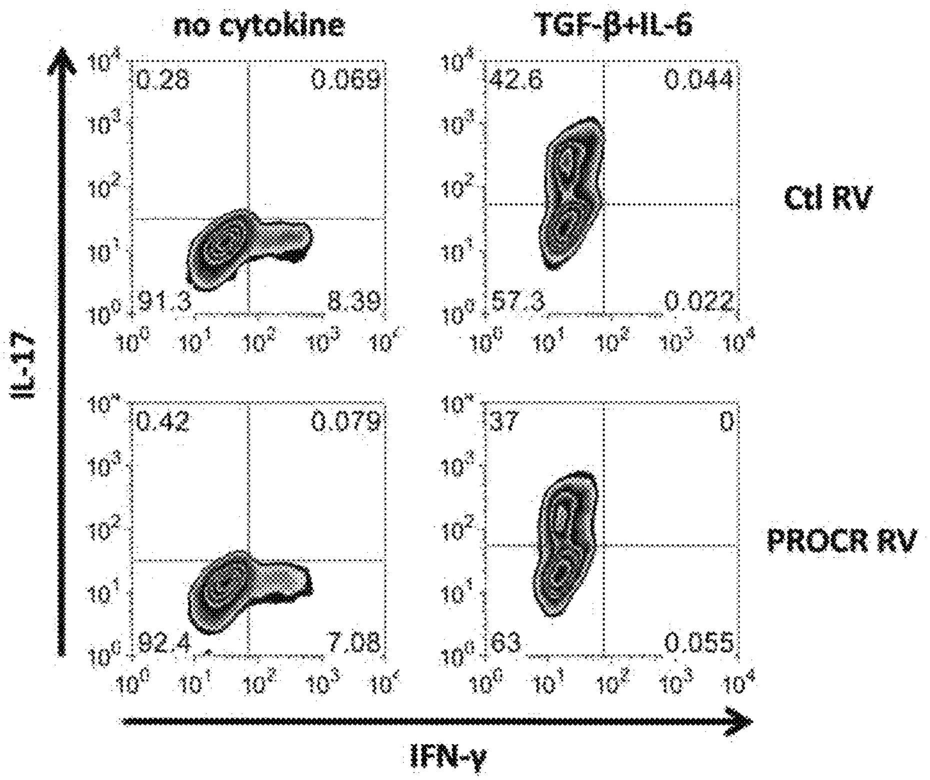
Figure 20D:
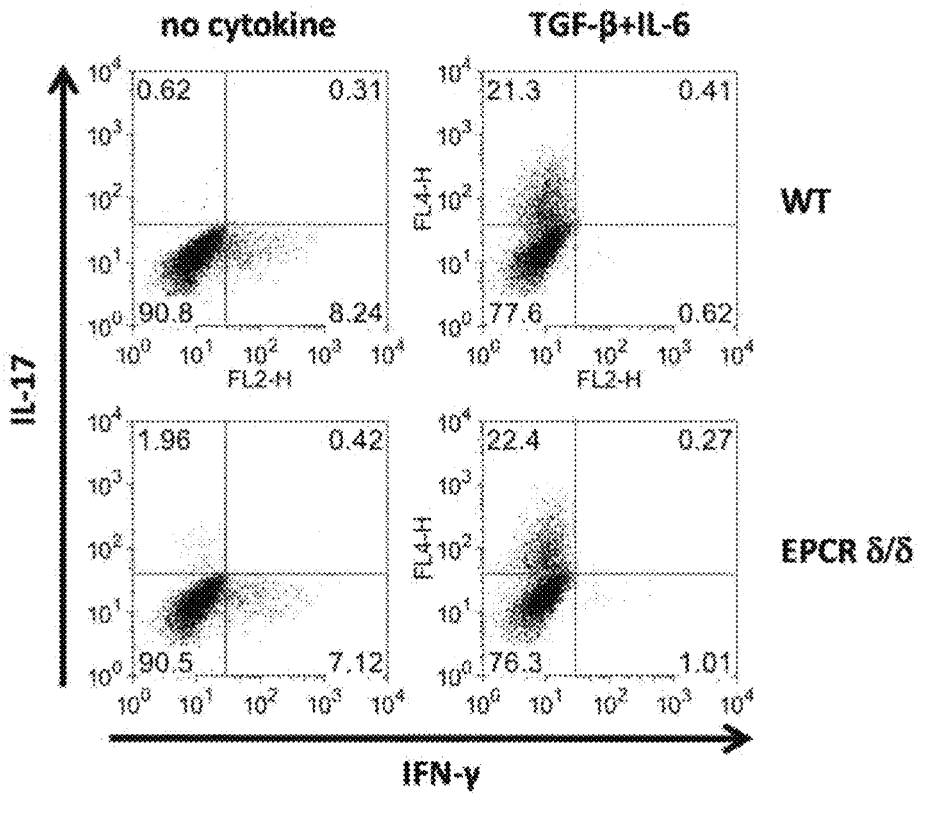
Figure 21A:
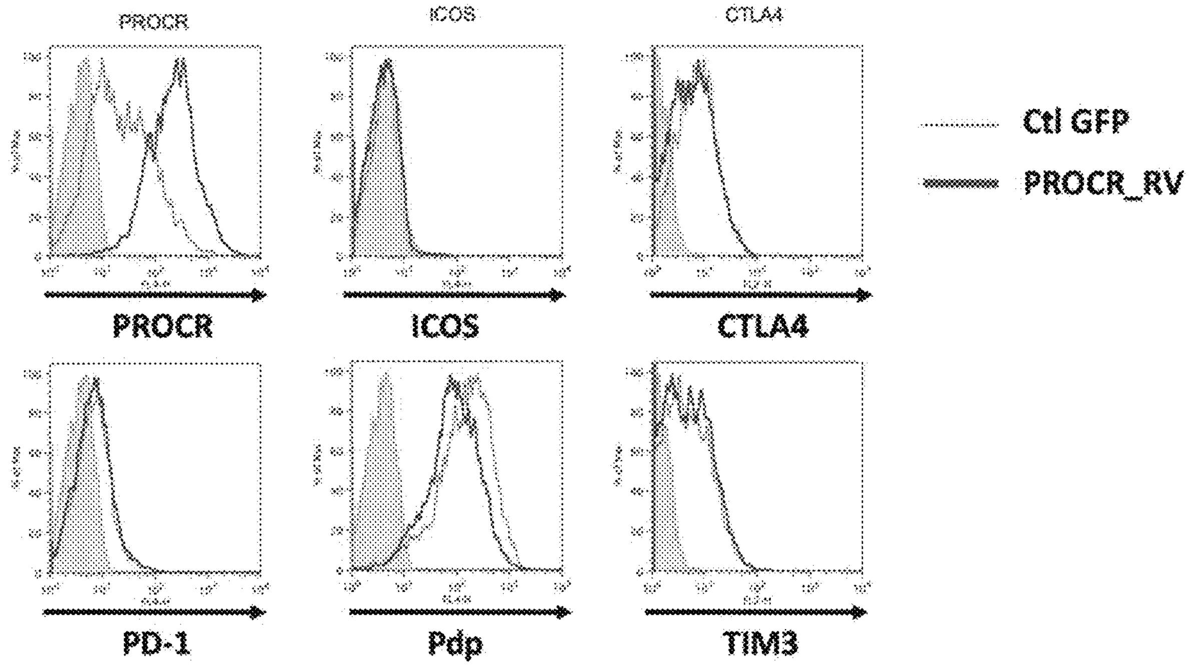
FIGS. 21A-21B are a series of graphs depicting that PROCR expression only induces minor changes in the expression of co-stimulatory molecules on Th17 cells.
Figure 21B:
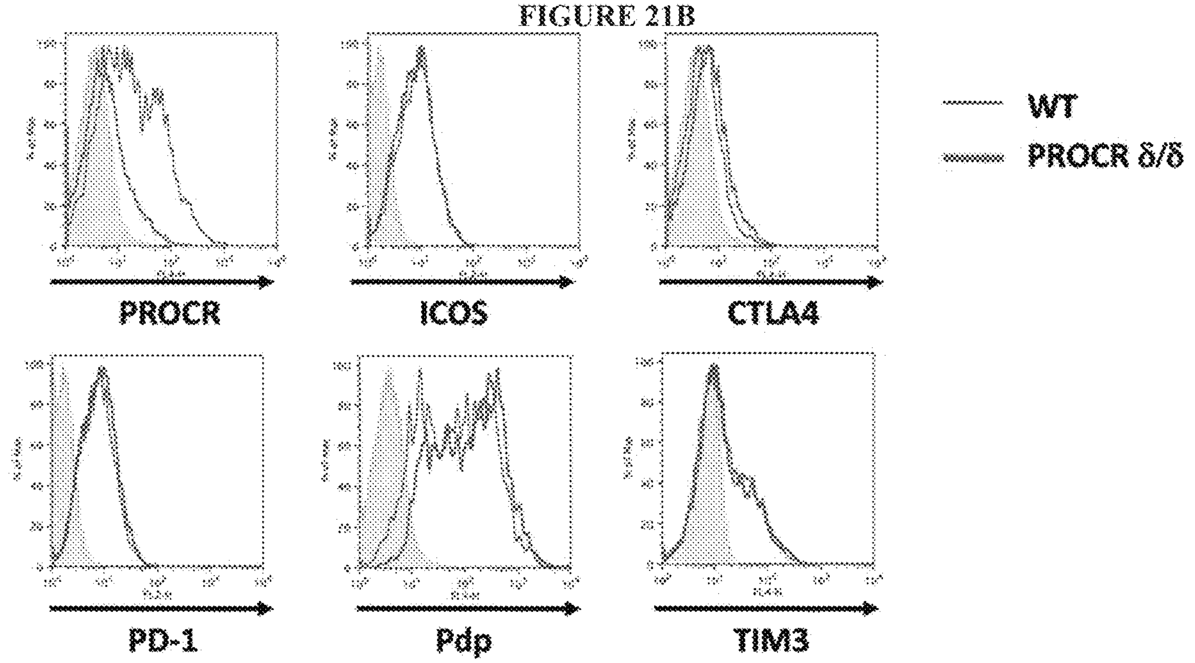
Figure 22A:
FIGS. 22A-22C are a series of graphs depicting that PROCR is expressed in non-pathogenic Th17 cells.
Figure 22B:
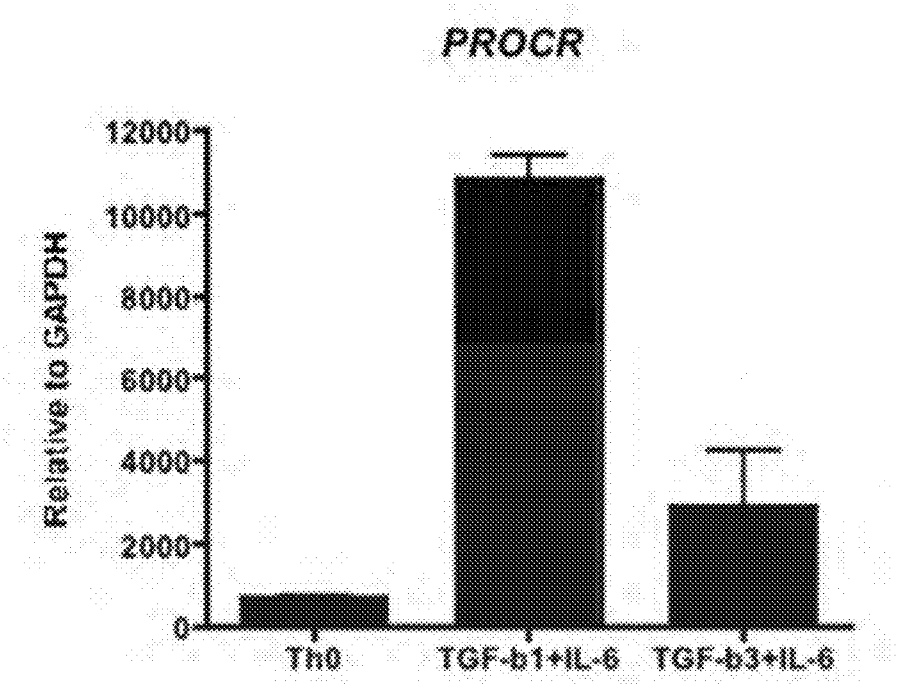
Figure 22C:
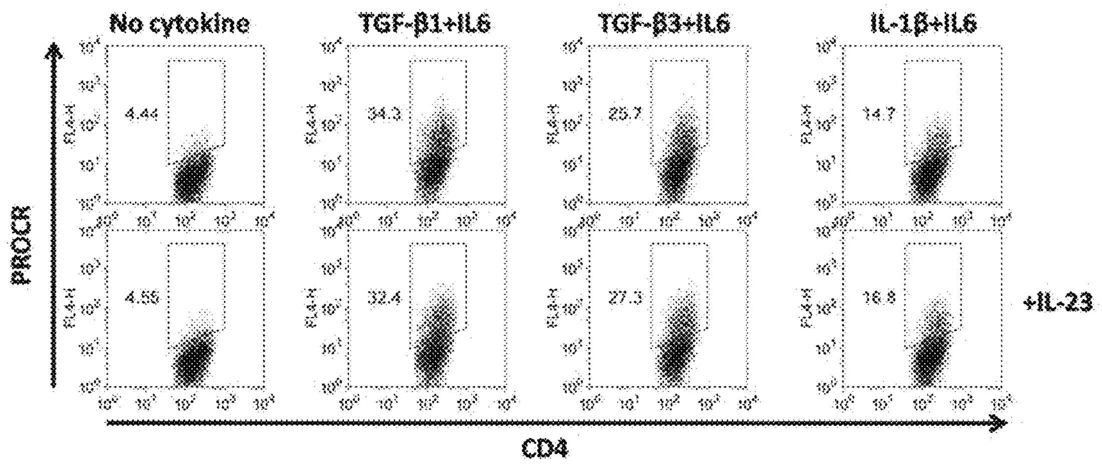
Figure 23A:
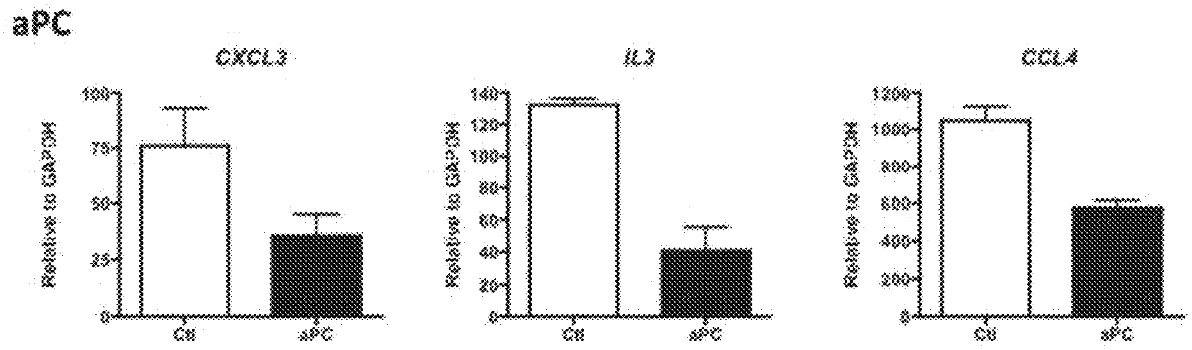
FIGS. 23A-23C are a series of graphs depicting that PROCR stimulation or expression impairs some pathogenic signature genes in Th17 cells.
Figure 23B:
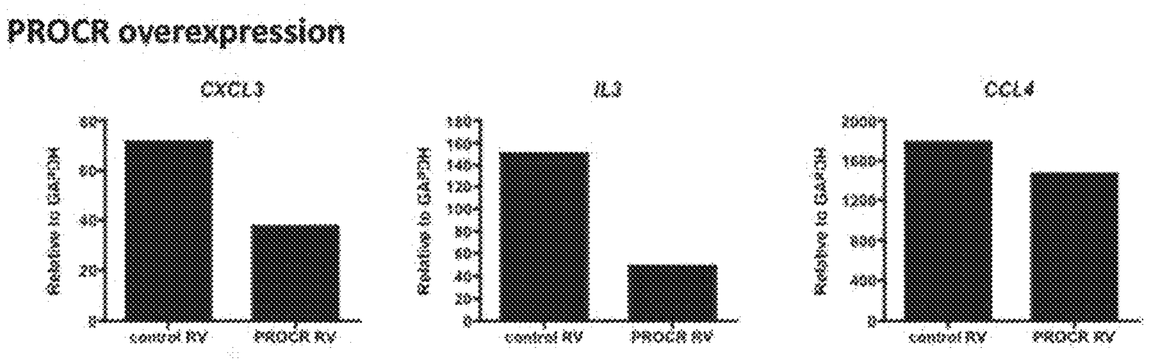
Figure 23C:
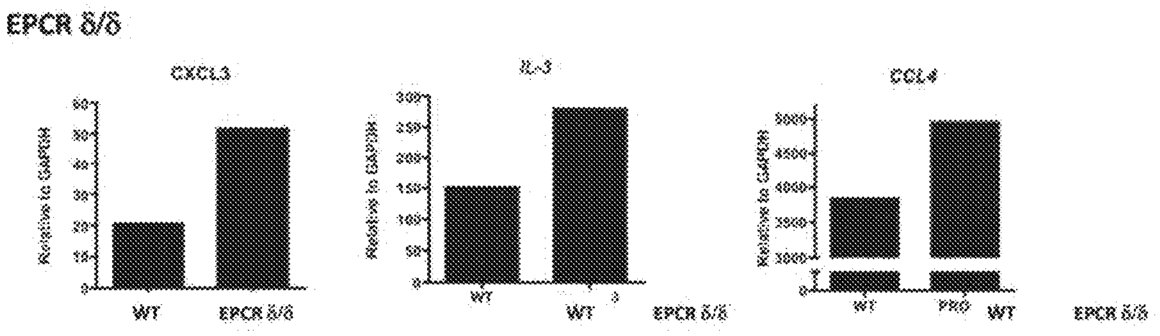
Figure 24A:
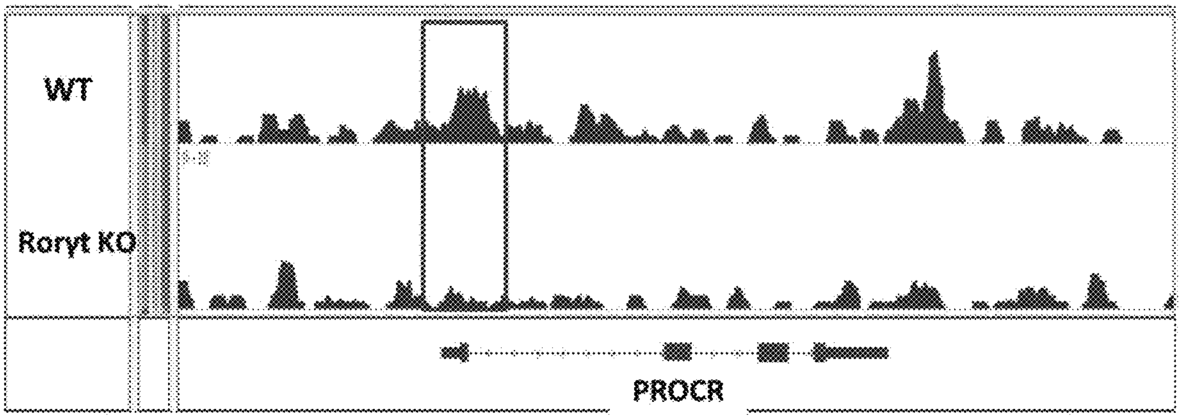
FIGS. 24A-24D are a series of graphs depicting that Rorγt induces PROCR expression under Th17 conditions polarized with TGF-β1 and IL-6.
Figure 24B:
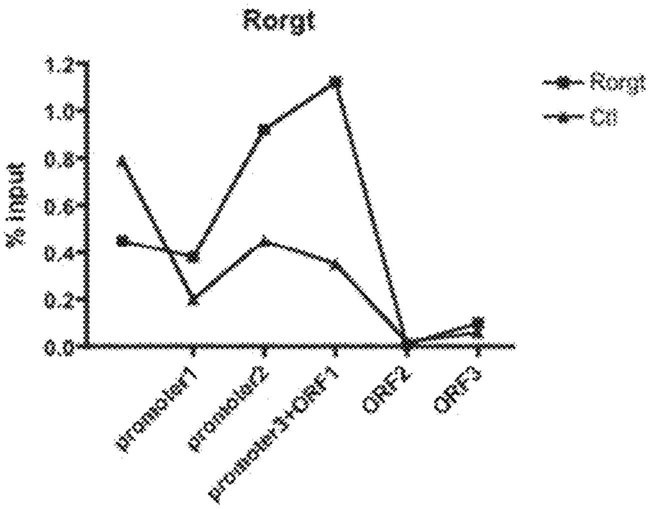
Figure 24C:
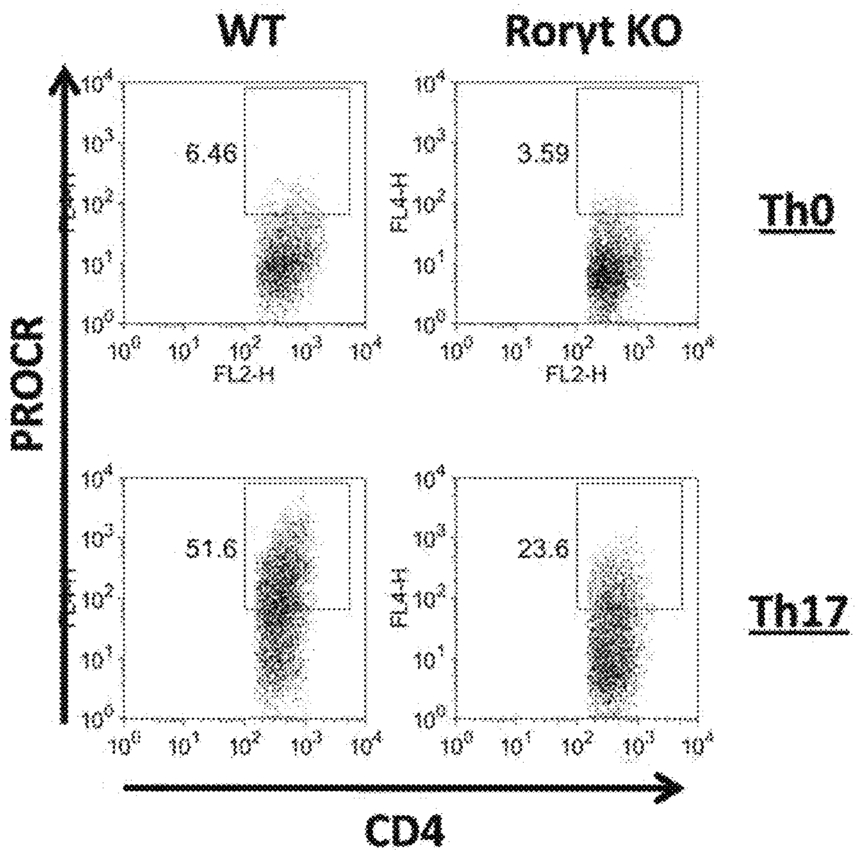
Figure 24D:
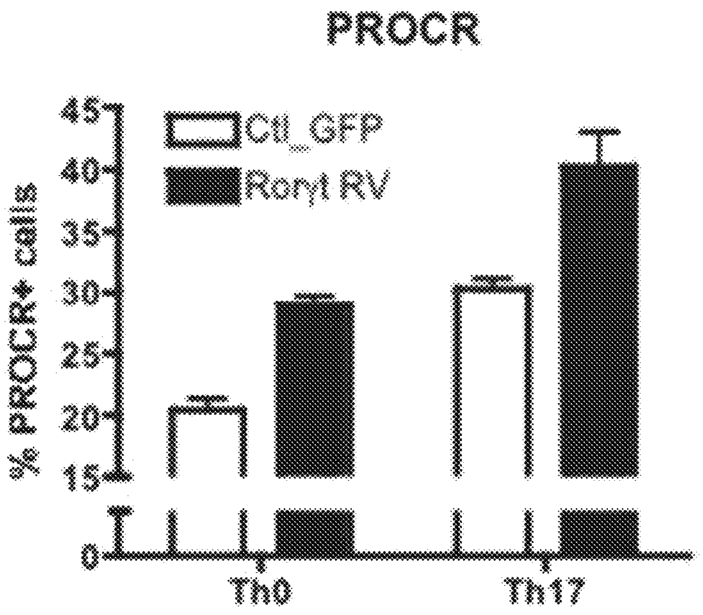
Figure 25A:
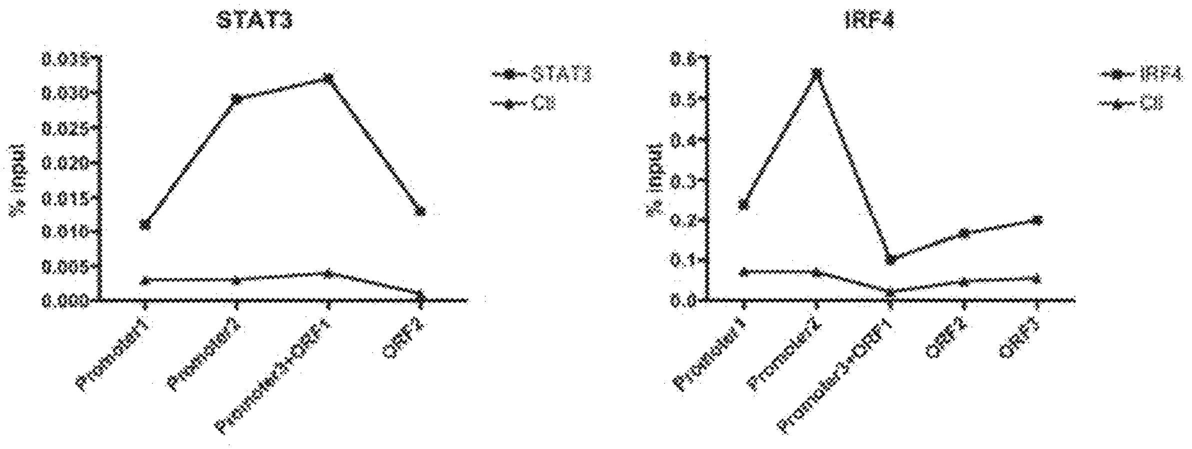
FIGS. 25A-25C are a series of graphs depicting that IRF4 and STAT3 bind to the Procr promoter and induce PROCR expression.
Figure 25B:
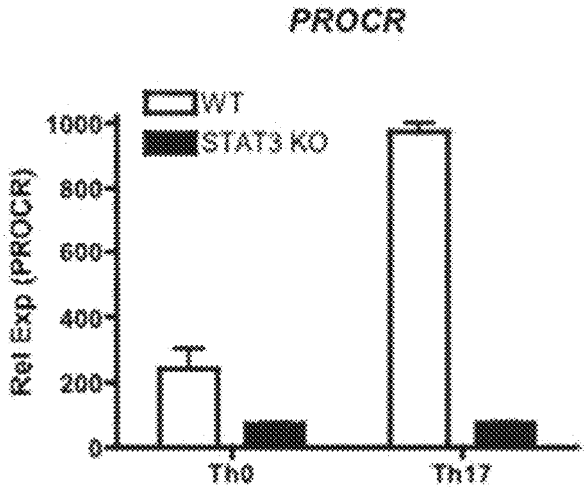
Figure 25C:
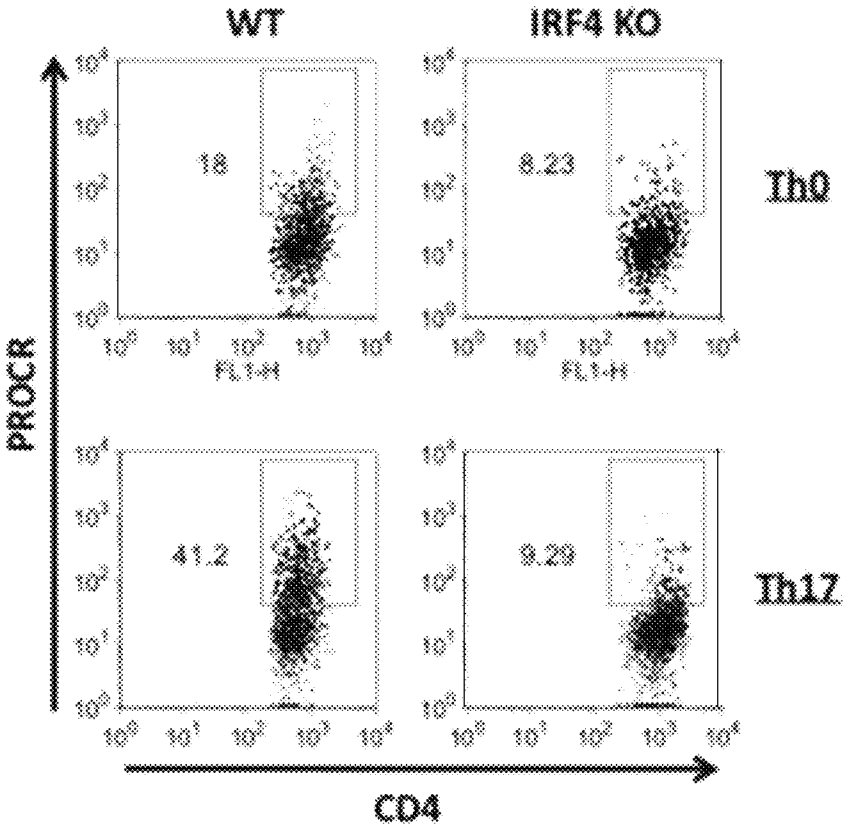
Figure 26A:
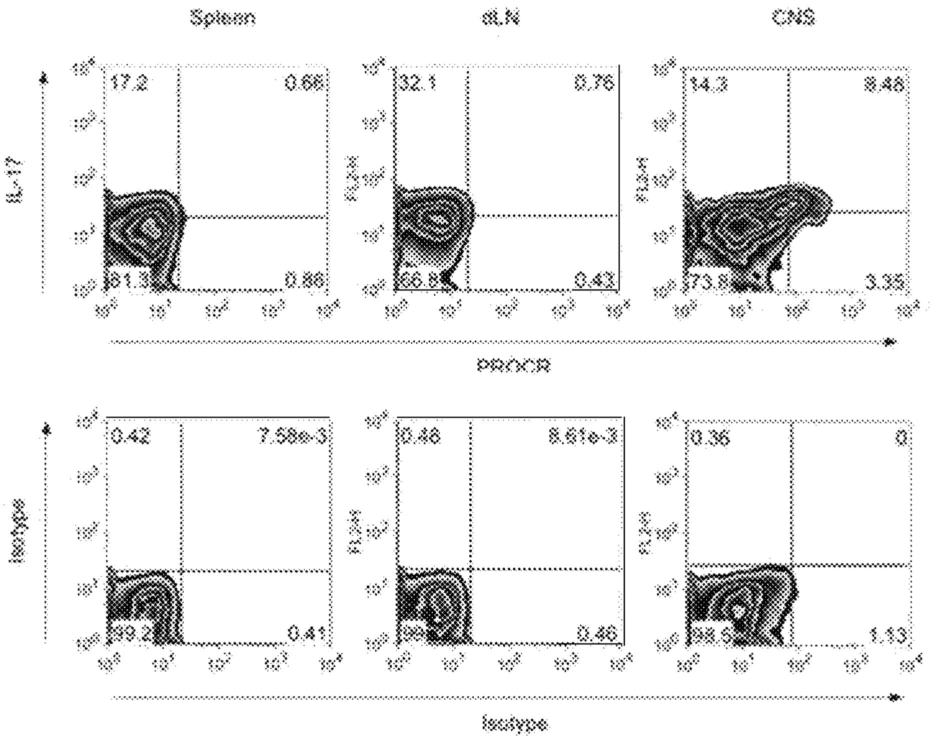
FIGS. 26A-26D are a series of graphs and illustrations depicting that PROCR deficiency exacerbates EAE severity.
Figure 26B:
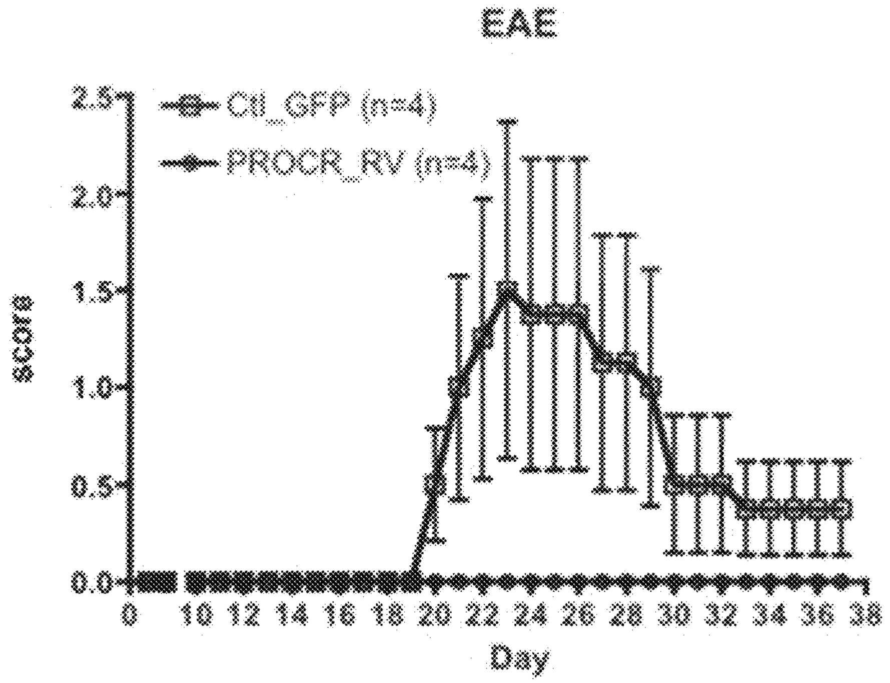
Figure 26C:
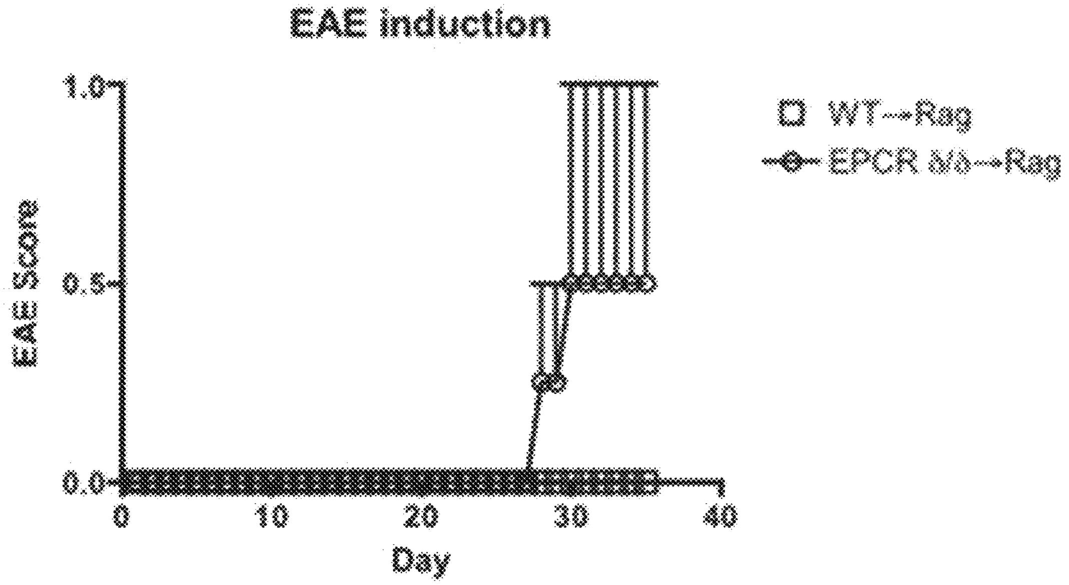
Figure 26D:
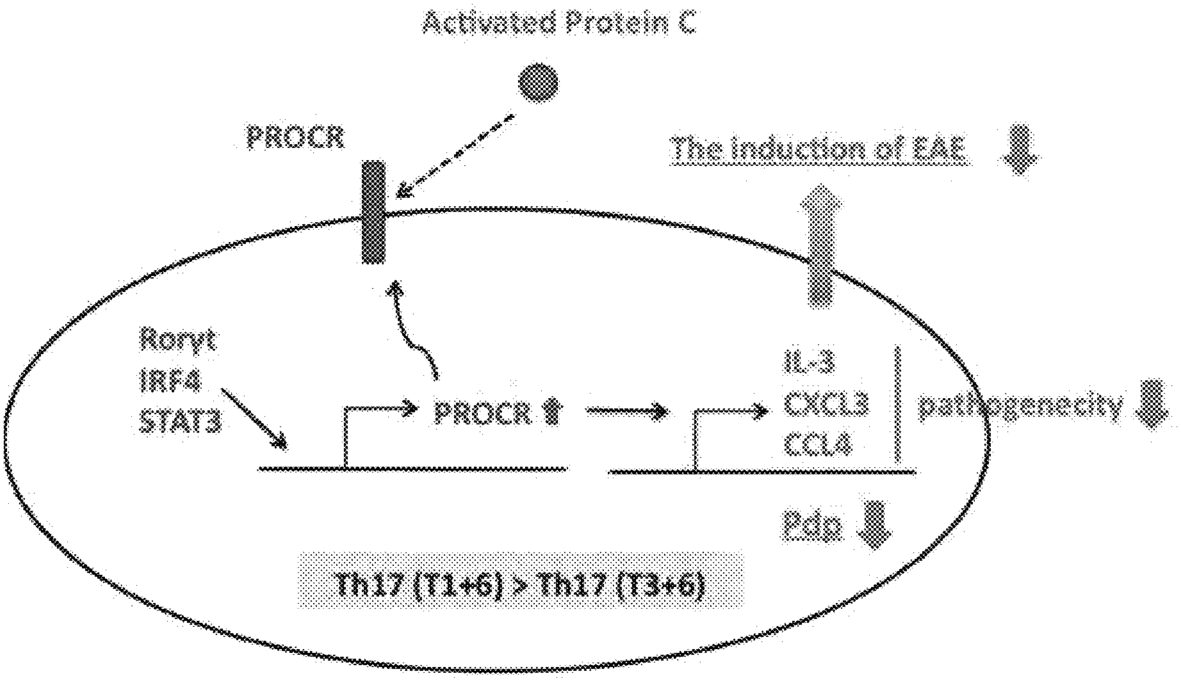
Figure 27A:
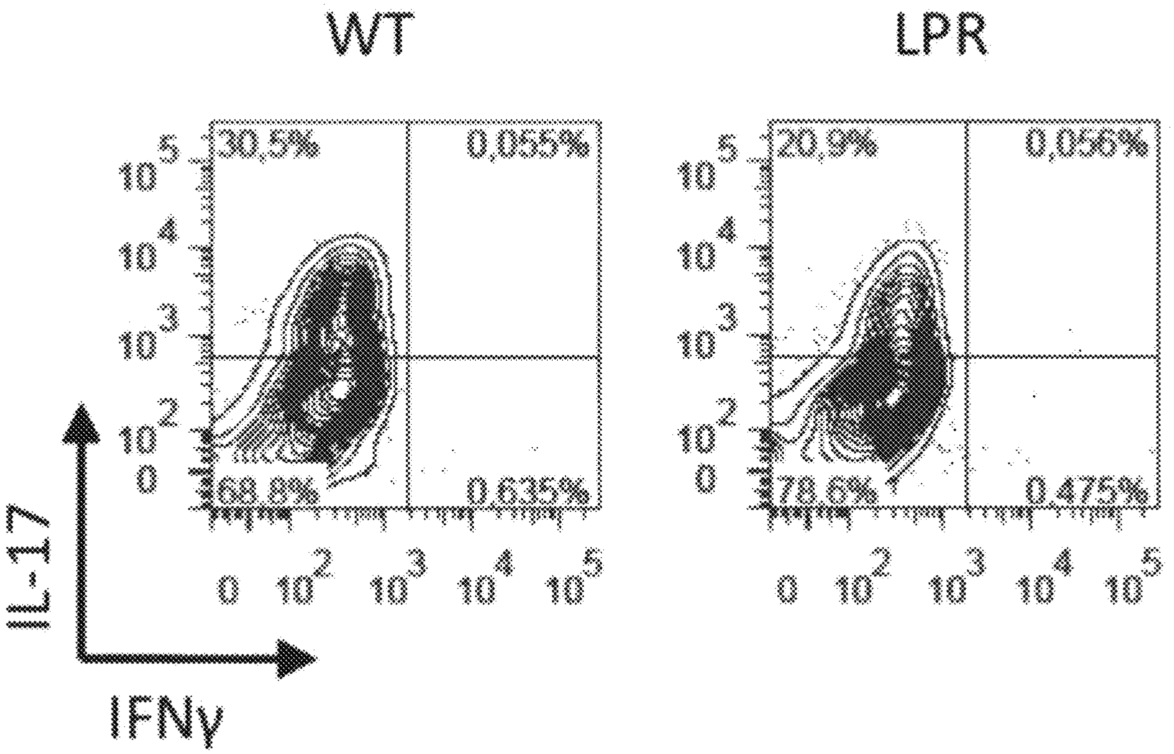
FIGS. 27A-27C are a series of graphs depicting that FAS promotes Th17 differentiation. Naïve $CD4^+$ T cells from wild type (WT) or FAS-deficient (LPR) mice were differentiated into Th17 cells by anti-CD3/anti-CD28 stimulation in the presence of IL-1β, IL-6 and IL-23. On day 4, cells were (FIG. 27A) stimulated with PMA and Ionomycin for 4 hr, stained intracellularly for IFN-γ and IL-17 and analyzed by flow cytometry and (FIG. 27B) IL-17 production was assessed by ELISA.
Figure 27B:
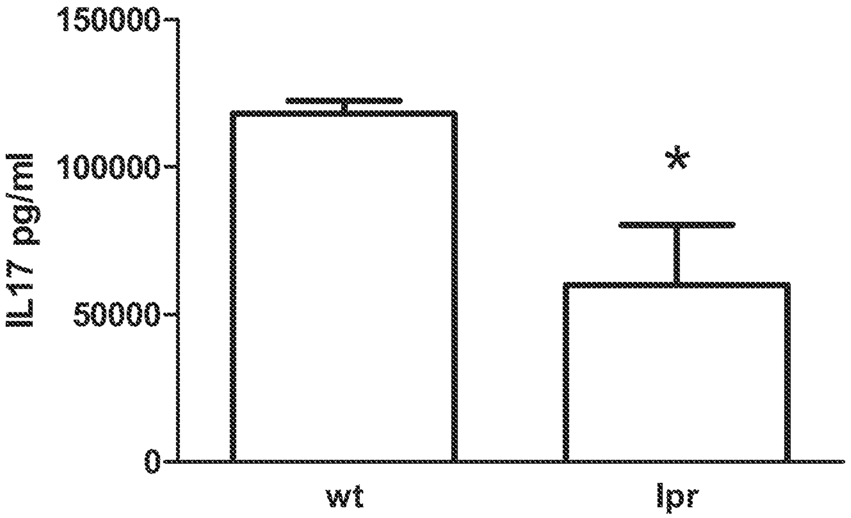
Figure 27C:
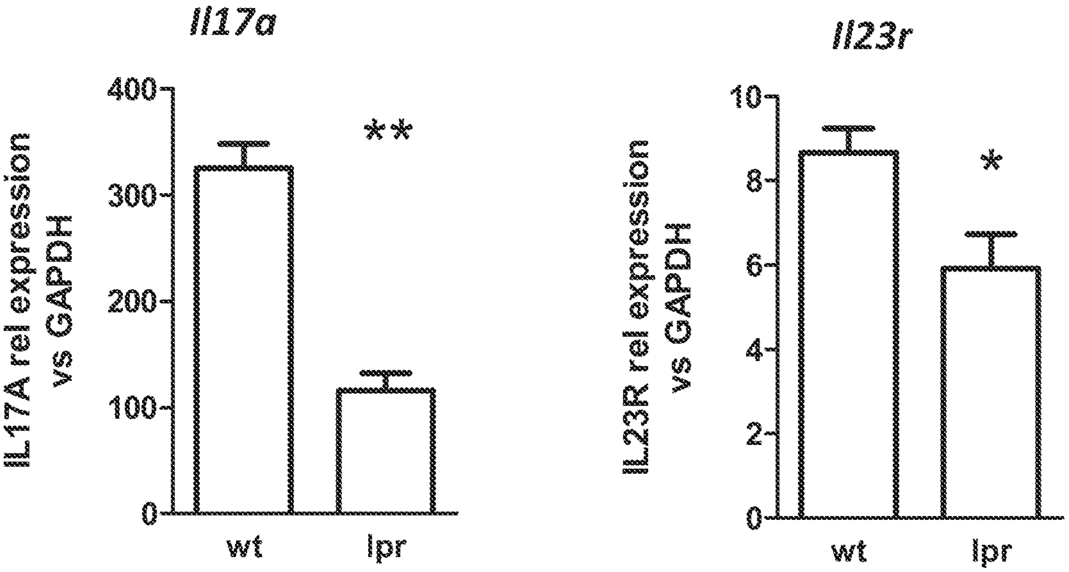
Figure 28A:
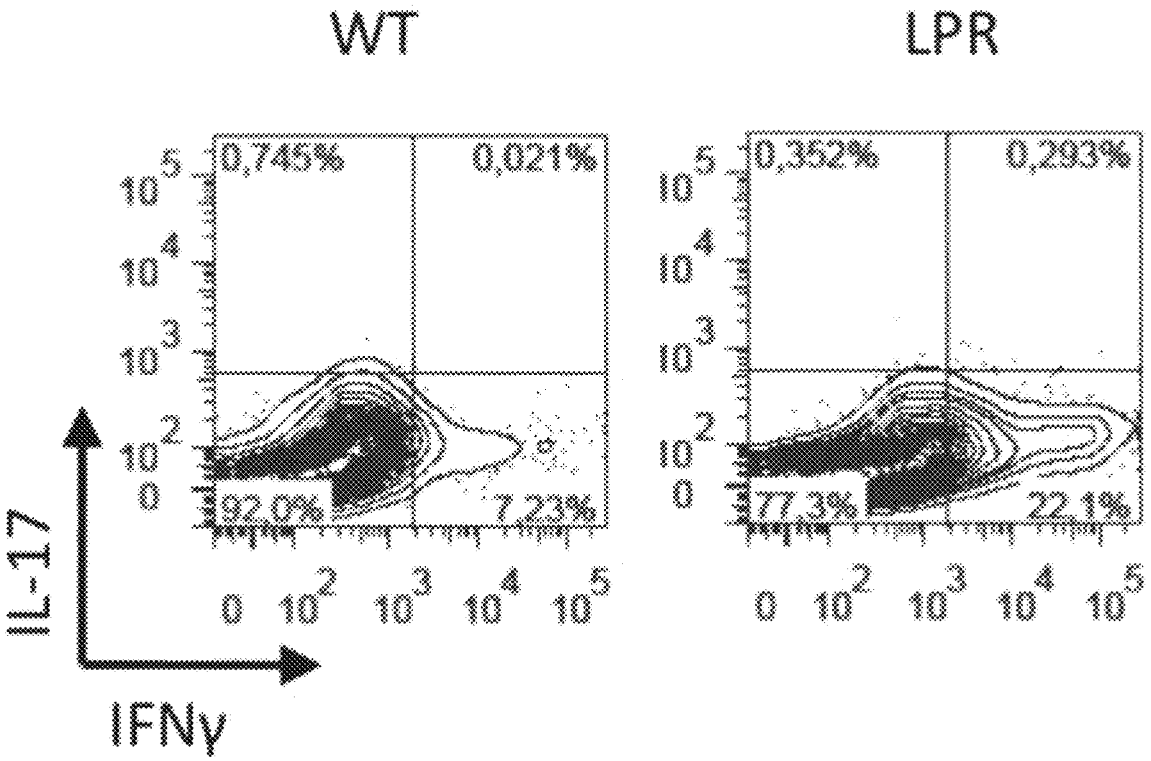
FIGS. 28A-28C are a series of graphs depicting that FAS inhibits Th1 differentiation. Naïve $CD4^+$ T cells from wild type (WT) or FAS-deficient (LPR) mice were differentiated into Th1 cells by anti-CD3/anti-CD28 stimulation in the presence of IL-12 and anti-IL-4. On day 4, cells were (FIG. 28A) stimulated with PMA and Ionomycin for 4 hr, stained intracellularly for IFN-γ and IL-17 and analyzed by flow cytometry and (FIG. 28B) IFN-γ production was assessed by ELISA.
Figure 28B:
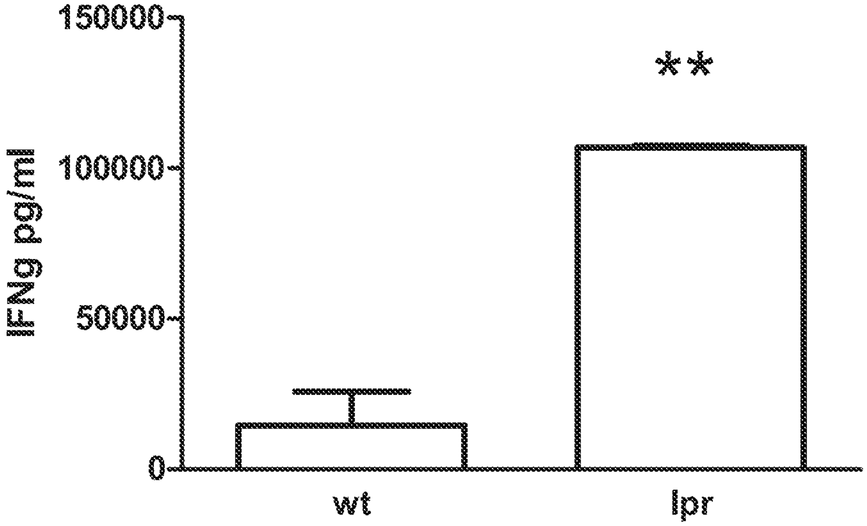
Figure 28C:
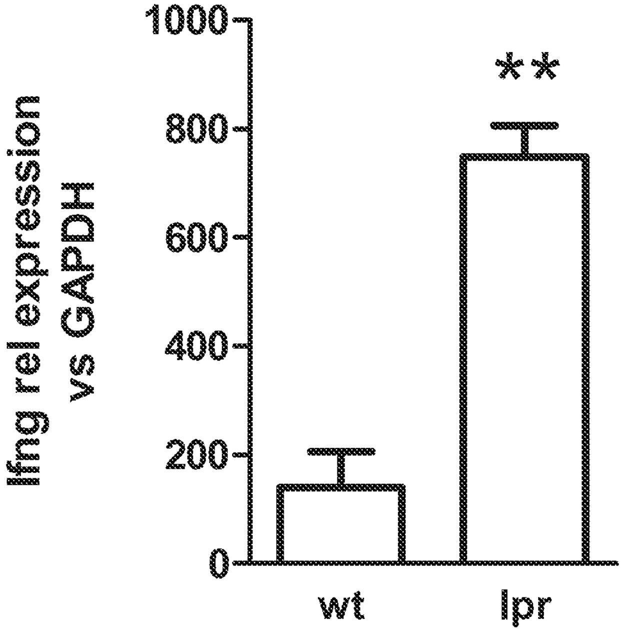
Figure 29A:
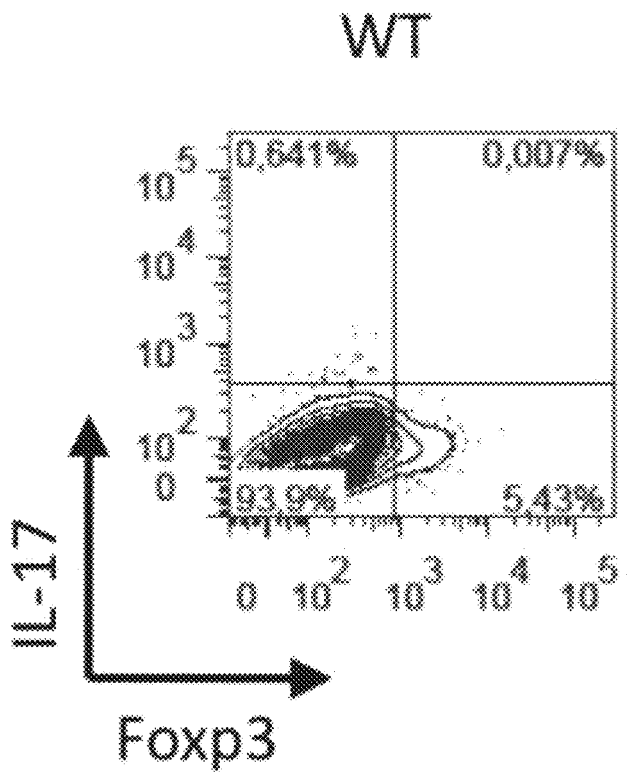
FIGS. 29A-29B are a series of graphs depicting that FAS inhibits Treg differentiation. Naïve $CD4^+$ T cells from wild type (WT) or FAS-deficient (LPR) mice were differentiated into Tregs by anti-CD3/anti-CD28 stimulation in the presence of TGF-β. On day 4, cells were (FIG. 29A) stimulated with PMA and Ionomycin for 4 hr, stained intracellularly for IL-17 and Foxp3 and analyzed by flow cytometry and (FIG. 29B) IL-10 production was assessed by ELISA.
Figure 29B:
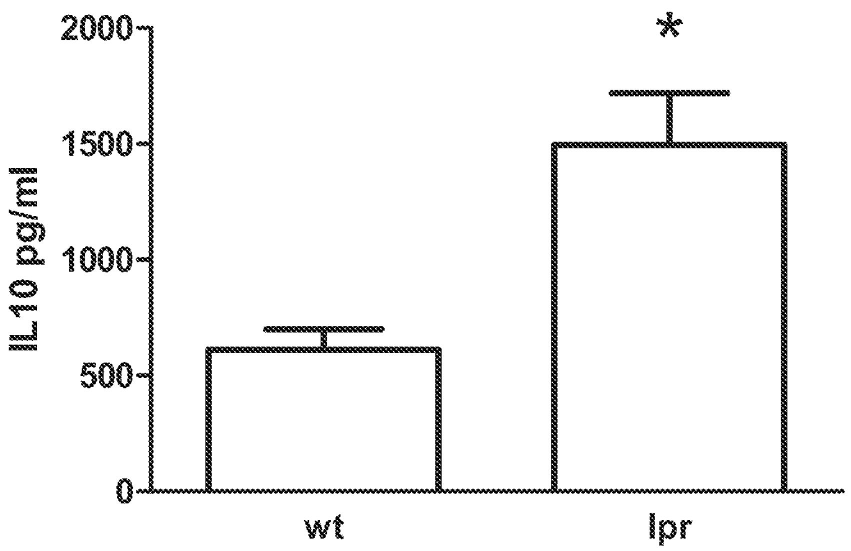

In a recent work, Ciofani et al. (Ciofani, M. et al. A Validated Regulatory Network for Th17 Cell Specification. Cell, doi:10.1016/j.cell.2012.09.016 (2012)) systematically ranked Th17 regulators based on ChIP-seq data for known key factors and transcriptional profiles in wild type and knockout cells. While their network centered on known core Th17 TFs, the complementary approach presented herein perturbed many genes in a physiologically meaningful setting. Reassuringly, their core Th17 network significantly overlaps with the computationally inferred model (FIG. 18).

The wiring of the positive and negative modules (FIGS. 4 and 5) uncovers some of the functional logic of the Th17 program, but likely involve both direct and indirect interactions. The functional model provides an excellent starting point for deciphering the underlying physical interactions with DNA binding profiles (Glasmacher, E. et al. A Genomic Regulatory Element That Directs Assembly and Function of Immune-Specific AP-1-IRF Complexes. Science, doi: 10.1126/science.1228309 (2012)) or protein-protein interactions (Wu, C., Yosef, N. & Thalhamer, T. SGK1 kinase regulates Th17 cells maintenance through IL-23 signaling pathway). The regulators identified are compelling new targets for regulating the Th17/Tregs balance and for switching pathogenic Th17 into non-pathogenic ones.

Automated Procedure for Selection of Signature Genes

The invention also provides methods of determining gene signatures that are useful in various therapeutic and/or diagnostic indications. The goal of these methods is to select a small signature of genes that will be informative with respect to a process of interest. The basic concept is that different types of information can entail different partitions of the "space" of the entire genome (>20 k genes) into subsets of associated genes. This strategy is designed to have the best coverage of these partitions, given the constraint on the signature size. For instance, in some embodiments of this strategy, there are two types of information: (i) temporal expression profiles; and (ii) functional annotations. The first information source partitions the genes into sets of co-expressed genes. The information source partitions the genes into sets of co-functional genes. A small set of genes is then selected such that there are a desired number of representatives from each set, for example, at least 10 representatives from each co-expression set and at least 10 representatives from each co-functional set. The problem of working with multiple sources of information (and thus aiming to "cover" multiple partitions) is known in the theory of computer science as Set-Cover. While this problem cannot be solved to optimality (due to its NP-hardness) it can be approximated to within a small factor. In some embodiments, the desired number of representatives from each set is one or more, at least 2, 5 or more, 10 or more, 15 or more, 20 or more, 25 or more, 30 or more, 35 or more, 40 or more, 50 or more, 60 or more, 70 or more, 80 or more, 90 or more, or 100 or more.

An important feature of this approach is that it can be given either the size of the signature (and then find the best coverage it can under this constraint); or the desired level of coverage (and then select the minimal signature size that can satisfy the coverage demand).

An exemplary embodiment of this procedure is the selection of the 275-gene signature (Table 1), which combined several criteria to reflect as many aspect of the differentiation program as was possible. The following requirements were defined: (1) the signature must include all of the TFs that belong to a Th17 microarray signature (comparing to other CD4+ T cells, see e.g., Wei et al., in Immunity vol. 30 155-167 (2009)), see Methods described herein); that are included as regulators in the network and are at least slightly differentially expressed; or that are strongly differentially expressed; (2) it must include at least 10 representatives from each cluster of genes that have similar expression profiles; (3) it must contain at least 5 representatives from the predicted targets of each TF in the different networks; (4) it must include a minimal number of representatives from each enriched Gene Ontology (GO) category (computed over differentially expressed genes); and, (5) it must include a manually assembled list of ~100 genes that are related to the differentiation process, including the differentially expressed cytokines, receptor molecules and other cell surface molecules. Since these different criteria might generate substantial overlaps, a set-cover algorithm was used to find the smallest subset of genes that satisfies all of five conditions. 18 genes whose expression showed no change (in time or between treatments) in the microarray data were added to this list.

Use of Signature Genes

The invention provides T cell related gene signatures for use in a variety of diagnostic and/or therapeutic indications. For example, the invention provides Th17 related signatures that are useful in a variety of diagnostic and/or therapeutic indications. "Signatures" in the context of the present invention encompasses, without limitation nucleic acids, together with their polymorphisms, mutations, variants, modifications, subunits, fragments, and other analytes or sample-derived measures.

Exemplary signatures are shown in Tables 1 and 2 and are collectively referred to herein as, inter alia, "Th17-associated genes," "Th17-associated nucleic acids," "signature genes," or "signature nucleic acids."

These signatures are useful in methods of diagnosing, prognosing and/or staging an immune response in a subject by detecting a first level of expression, activity and/or function of one or more signature genes or one or more products of one or more signature genes selected from those listed in Table 1 or Table 2 and comparing the detected level to a control of level of signature gene or gene product expression, activity and/or function, wherein a difference in the detected level and the control level indicates that the presence of an immune response in the subject.

These signatures are useful in methods of monitoring an immune response in a subject by detecting a level of expression, activity and/or function of one or more signature genes or one or more products of one or more signature genes selected from those listed in Table 1 or Table 2 at a first time point, detecting a level of expression, activity and/or function of one or more signature genes or one or more products of one or more signature genes selected from those listed in Table 1 or Table 2 at a second time point, and comparing the first detected level of expression, activity and/or function with the second detected level of expression, activity and/or function, wherein a change in the first and second detected levels indicates a change in the immune response in the subject.

These signatures are useful in methods of identifying patient populations at risk or suffering from an immune response based on a detected level of expression, activity and/or function of one or more signature genes or one or more products of one or more signature genes selected from those listed in Table 1 or Table 2. These signatures are also useful in monitoring subjects undergoing treatments and therapies for aberrant immune response(s) to determine efficaciousness of the treatment or therapy. These signatures are also useful in monitoring subjects undergoing treatments and therapies for aberrant immune response(s) to determine whether the patient is responsive to the treatment or therapy. These signatures are also useful for selecting or modifying therapies and treatments that would be efficacious in treating, delaying the progression of or otherwise ameliorating a symptom of an aberrant immune response. The signatures provided herein are useful for selecting a group of patients at a specific state of a disease with accuracy that facilitates selection of treatments.

The present invention also comprises a kit with a detection reagent that binds to one or more signature nucleic acids. Also provided by the invention is an array of detection reagents, e.g., oligonucleotides that can bind to one or more signature nucleic acids. Suitable detection reagents include nucleic acids that specifically identify one or more signature nucleic acids by having homologous nucleic acid sequences, such as oligonucleotide sequences, complementary to a portion of the signature nucleic acids packaged together in the form of a kit. The oligonucleotides can be fragments of the signature genes. For example the oligonucleotides can be 200, 150, 100, 50, 25, 10 or fewer nucleotides in length. The kit may contain in separate container or packaged separately with reagents for binding them to the matrix), control formulations (positive and/or negative), and/or a detectable label such as fluorescein, green fluorescent protein, rhodamine, cyanine dyes, Alexa dyes, luciferase, radiolabels, among others. Instructions (e.g., written, tape, VCR, CD-ROM, etc.) for carrying out the assay may be included in the kit. The assay may for example be in the form of a Northern hybridization or DNA chips or a sandwich ELISA or any other method as known in the art. Alternatively, the kit contains a nucleic acid substrate array comprising one or more nucleic acid sequences.

Use of T Cell Modulating Agents

Suitable T cell modulating agent(s) for use in any of the compositions and methods provided herein include an antibody, a soluble polypeptide, a polypeptide agent, a peptide agent, a nucleic acid agent, a nucleic acid ligand, or a small molecule agent. By way of non-limiting example, suitable T cell modulating agents or agents for use in combination with one or more T cell modulating agents are shown below in Table 10.

TABLE 10

T cell Modulating Agents

| TARGET | AGENT |
|---|---|
| CCR6 | prostaglandin E2, lipopolysaccharide, mip-3alpha, vegf, rantes, calcium, bortezomib, ccl4, larc, tarc, lipid, *E. coli* B5 lipopolysaccharide |
| CCR5 | cholesterol, cyclosporin a, glutamine, methionine, guanine, simvastatin, threonine, indinavir, lipoxin A4, cysteine, prostaglandin E2, zinc, dapta, 17-alpha-ethinylestradiol, polyacrylamide, progesterone, zidovudine, rapamycin, rantes, glutamate, alanine, valine, ccl4, quinine, NSC 651016, methadone, pyrrolidine dithiocarbamate, palmitate, nor-binaltorphimine, interferon beta-1a, vitamin-e, tak779, lipopolysaccharide, cisplatin, albuterol, fluvoxamine, vicriviroc, bevirimat, carbon tetrachloride, galactosylceramide, ATP-gamma-S, cytochalasin d, hemozoin, CP 96345, tyrosine, etravirine, vitamin d, mip 1alpha, ammonium, tyrosine sulfate, isoleucine, isopentenyl diphosphate, Il 10, serine, N-acetyl-L-cysteine, histamine, cocaine, ritonavir, tipranavir, aspartate, atazanavir, tretinoin, ATP, ribavirin, butyrate, N-nitro-L-arginine methyl ester, larc, buthionine sulfoximine, DAPTA, aminooxypentane-rantes, triamcinolone acetonide, shikonin, actinomycin d, bucladesine, aplaviroc, nevirapine, N-formyl-Met-Leu-Phe, cyclosporin A, lipoarabinomannan, nucleoside, sirolimus, morphine, mannose, calcium, heparin, c-d4i, pge2, beta-estradiol, mdms, dextran sulfate, dexamethasone, |

TABLE 10-continued

T cell Modulating Agents

| TARGET | AGENT |
|---|---|
| | arginine, ivig, mcp 2, cyclic amp, U 50488H, N-methyl-D-aspartate, hydrogen peroxide, 8-carboxamidocyclazocine, latex, groalpha, xanthine, ccl3, retinoic acid, Maraviroc, sdf 1, opiate, efavirenz, estrogen, bicyclam, enfuvirtide, filipin, bleomycin, polysaccharide, tarc, pentoxifylline, *E. coli* B5 lipopolysaccharide, methylcellulose, maraviroc |
| ITGA3 | SP600125, paclitaxel, decitabine, e7820, retinoid, U0126, serine, retinoic acid, tyrosine, forskolin, Ca2+ |
| IRF4 | prostaglandin E2, phorbol myristate acetate, lipopolysaccharide, A23187, tacrolimus, trichostatin A, stallimycin, imatinib, cyclosporin A, tretinoin, bromodeoxyuridine, ATP-gamma-S, ionomycin |
| BATF | Cyclic AMP, serine, tacrolimus, beta-estradiol, cyclosporin A, leucine |
| RBPJ | zinc, tretinoin |
| PROCR | lipopolysaccharide, cisplatin, fibrinogen, 1,10-phenanthroline, 5-N-ethylcarboxamido adenosine, cystathionine, hirudin, phospholipid, Drotrecogin alfa, vegf, Phosphatidylethanolamine, serine, gamma-carboxyglutamic acid, calcium, warfarin, endotoxin, curcumin, lipid, nitric oxide |
| ZEB1 | resveratrol, zinc, sulforafan, sorafenib, progesterone, PD-0332991, dihydrotestosterone, silibinin, LY294002, 4-hydroxytamoxifen, valproic acid, beta-estradiol, forskolin, losartan potassium, fulvestrant, vitamin d |
| POU2AF1 | terbutaline, phorbol myristate acetate, bucladesine, tyrosine, ionomycin, KT5720, H89 |
| EGR1 | ghrelin, ly294002, silicone, sodium, propofol, 1, 25 dihydroxy vitamin d3, tetrodotoxin, threonine, cyclopiazonic acid, urea, quercetin, ionomycin, 12-o-tetradecanoylphorbol 13-acetate, fulvestrant, phenylephrine, formaldehyde, cysteine, leukotriene C4, prazosin, LY379196, vegf, rapamycin, leupeptin, pd 98, 059, ruboxistaurin, pCPT-cAMP, methamphetamine, nitroprusside, H-7, Ro31-8220, phosphoinositide, lysophosphatidylcholine, bufalin, calcitriol, leuprolide, isobutylmethylxanthine, potassium chloride, acetic acid, cyclothiazide, quinolinic acid, tyrosine, adenylate, resveratrol, topotecan, genistein, thymidine, D-glucose, mifepristone, lysophosphatidic acid, leukotriene D4, carbon monoxide, poly rI:rC-RNA, sp 600125, agar, cocaine, 4-nitroquinoline-1-oxide, tamoxifen, lead, fibrinogen, tretinoin, atropine, mithramycin, K+, epigallocatechin-gallate, ethylenediaminetetraacetic acid, h2o2, carbachol, sphingosine-1-phosphate, iron, 5-hydroxytryptamine, amphetamine, SP600125, actinomycin d, SB203580, cyclosporin A, norepinephrine, okadaic acid, ornithine, LY294002, pge2, beta-estradiol, glucose, erlotinib, arginine, 1-alpha, 25-dihydroxy vitamin D3, dexamethasone, pranlukast, phorbol myristate acetate, nimodipine, desipramine, cyclic amp, N-methyl-D-aspartate, atipamezole, acadesine, losartan, salvin, methylnitronitrosoguanidine, EGTA, gf 109203x, nitroarginine, 5-N-ethylcarboxamido adenosine, 15-deoxy-delta-12, 14-PGJ 2, dbc-amp, manganese superoxide, di(2-ethylhexyl) phthalate, egcg, mitomycin C, 6,7-dinitroquinoxaline-2,3-dione, GnRH-A, estrogen, ribonucleic acid, imipramine, bapta, L-triiodothyronine, prostaglandin, forskolin, nogalamycin, losartan |

TABLE 10-continued

T cell Modulating Agents

| TARGET | AGENT |
|---|---|
| | potassium, lipid, vincristine, 2-amino-3-phosphonopropionic acid, prostacyclin, methylnitrosourea, cyclosporin a, vitamin K3, thyroid hormone, diethylstilbestrol, D-tubocurarine, tunicamycin, caffeine, phorbol, guanine, bisindolylmaleimide, apomorphine, arachidonic acid, SU6656, prostaglandin E2, zinc, ptx1, progesterone, cyclosporin H, phosphatidylinositol, U0126, hydroxyapatite, epoprostenol, glutamate, 5fluorouracil, indomethacin, 5-fluorouracil, RP 73401, Ca2+, superoxide, trifluoperazine, nitric oxide, lipopolysaccharide, cisplatin, diazoxide, tgf beta1, calmidazolium, anisomycin, paclitaxel, sulindac sulfide, ganciclovir, gemcitabine, testosterone, ag 1478, glutamyl-Se-methyl selenocysteine, doxorubicin, tolbutamide, cytochalasin d, PD98059, leucine, SR 144528, cyclic AMP, matrigel, haloperidol, serine, sb 203580, triiodothyronine, reverse, N-acetyl-L-cysteine, ethanol, s-nitroso-n-acetylpenicillamine, curcumin, l-nmma, H89, tpck, calyculin a, chloramphenicol, A23187, dopamine, platelet activating factor, arsenite, selenomethylselenocysteine, ropinirole, saralasin, methylphenidate, gentamicin, reserpine, triamcinolone acetonide, methyl methanesulfonate, wortmannin, thapsigargin, deferoxamine, calyculin A, peptidoglycan, dihydrotestosterone, calcium, phorbol-12-myristate, ceramide, nmda, 6-cyano-7-nitroquinoxaline-2, 3-dione, hydrogen peroxide, carrageenan, sch 23390, linsidomine, oxygen, clonidine, fluoxetine, retinoid, troglitazone, retinoic acid, epinephrine, n acetylcysteine, KN-62, carbamylcholine, 2-amino-5-phosphonovaleric acid, oligonucleotide, gnrh, rasagiline, 8-bromo-cAMP, muscarine, tacrolimus, kainic acid, chelerythrine, inositol 1, 4, 5 trisphosphate, yohimbine, acetylcholine, atp, 15-deoxy-delta-12, 14-prostaglandin j2, ryanodine, CpG oligonucleotide, cycloheximide, BAPTA-AM, phenylalanine |
| ETV6 | lipopolysaccharide, retinoic acid, prednisolone, valproic acid, tyrosine, cerivastatin, vegf, agar, imatinib, tretinoin |
| IL17RA | rantes, lipopolysaccharide, 17-alpha-ethinylestradiol, camptothecin, *E. coli* B5 lipopolysaccharide |
| EGR2 | phorbol myristate acetate, lipopolysaccharide, platelet activating factor, carrageenan, edratide, 5-N-ethylcarboxamido adenosine, potassium chloride, dbc-amp, tyrosine, PD98059, camptothecin, formaldehyde, prostaglandin E2, leukotriene C4, zinc, cyclic AMP, GnRH-A, bucladesine, thapsigargin, kainic acid, cyclosporin A, mifepristone, leukotriene D4, LY294002, L-triiodothyronine, calcium, beta-estradiol, H89, dexamethasone, cocaine |
| SP4 | betulinic acid, zinc, phorbol myristate acetate, LY294002, methyl 2-cyano-3, 12-dioxoolean-1, 9-dien-28-oate, beta-estradiol, Ca2+ |
| IRF8 | oligonucleotide, chloramphenicol, lipopolysaccharide, estrogen, wortmannin, pirinixic acid, carbon monoxide, retinoic acid, tyrosine |
| NFKB1 | Bay 11-7085, Luteolin, Triflusal, Bay 11-7821, Thalidomide, Caffeic acid phenethyl ester, Pranlukast |
| T5C22D3 | phorbol myristate acetate, prednisolone, sodium, dsip, tretinoin, 3-deazaneplanocin, gaba, PD98059, leucine, triamcinolone acetonide, prostaglandin E2, steroid, norepinephrine, U0126, acth, calcium, ethanol, beta-estradiol, lipid, chloropromazine, arginine, dexamethasone |
| PML | lipopolysaccharide, glutamine, thyroid hormone, cadmium, lysine, tretinoin, bromodeoxyuridine, etoposide, retinoid, pic 1, arsenite, arsenic trioxide, butyrate, retinoic acid, alpha-retinoic acid, h2o2, camptothecin, cysteine, leucine, zinc, actinomycin d, proline, stallimycin, U0126 |
| IL12RB1 | prostaglandin E2, phorbol myristate acetate, lipopolysaccharide, bucladesine, 8-bromo-cAMP, |

TABLE 10-continued

| T cell Modulating Agents | |
|---|---|
| TARGET | AGENT |
| | gp 130, AGN194204, galactosylceramide-alpha, tyrosine, ionomycin, dexamethasone, Il-12 |
| IL21R | azathioprine, lipopolysaccharide, okadaic acid, *E. coli* B5 lipopolysaccharide, calyculin A |
| NOTCH1 | interferon beta-1a, lipopolysaccharide, cisplatin, tretinoin, oxygen, vitamin B12, epigallocatechin-gallate, isobutylmethylxanthine, threonine, apomorphine, matrigel, trichostatin A, vegf, 2-acetylaminofluorene, rapamycin, dihydrotestosterone, poly rI:rC-RNA, hesperetin, valproic acid, asparagine, lipid, curcumin, dexamethasone, glycogen, CpG oligonucleotide, nitric oxide |
| ETS2 | oligonucleotide |
| MINA | phorbol myristate acetate, 4-hydroxytamoxifen |
| SMARCA4 | cyclic amp, cadmium, lysine, tretinoin, latex, androstane, testosterone, sucrose, tyrosine, cysteine, zinc, oligonucleotide, estrogen, steroid, trichostatin A, tpmp, progesterone, histidine, atp, trypsinogen, glucose, agar, lipid, arginine, vancomycin, dihydrofolate |
| FAS | hoechst 33342, ly294002, 2-chlorodeoxyadenosine, glutamine, cd 437, tetrodotoxin, cyclopiazonic acid, arsenic trioxide, phosphatidylserine, niflumic acid, gliadin, ionomycin, safrole oxide, methotrexate, rubitecan, cysteine, propentofylline, vegf, boswellic acids, rapamycin, pd 98, 059, captopril, methamphetamine, vesnarinone, tetrapeptide, oridonin, raltitrexed, pirinixic acid, nitroprusside, H-7, beta-boswellic acid, adriamycin, concanamycin a, etoposide, trastuzumab, cyclophosphamide, ifn-alpha, tyrosine, rituximab, selenodiglutathione, chitosan, omega-N-methylarginine, creatinine, resveratrol, topotecan, genistein, trichostatin A, decitabine, thymidine, D-glucose, mifepristone, tetracycline, Sn50 peptide, poly rI:rC-RNA, actinomycin D, sp 600125, doxifluridine, agar, ascorbic acid, acetaminophen, aspirin, tamoxifen, okt3, edelfosine, sulforafan, aspartate, antide, n, n-dimethylsphingosine, epigallocatechin-gallate, N-nitro-L-arginine methyl ester, h2o2, cerulenin, sphingosine-1-phosphate, SP600125, sodium nitroprusside, glycochenodeoxycholic acid, ceramides, actinomycin d, SB203580, cyclosporin A, morphine, LY294002, n(g)-nitro-l-arginine methyl ester, 4-hydroxynonenal, piceatannol, valproic acid, beta-estradiol, 1-alpha, 25-dihydroxy vitamin D3, arginine, dexamethasone, sulfadoxine, phorbol myristate acetate, beta-lapachone, nitrofurantoin, chlorambucil, methylnitronitrosoguanidine, CD 437, opiate, egcg, mitomycin C, estrogen, ribonucleic acid, fontolizumab, tanshinone iia, recombinant human endostatin, fluoride, L-triiodothyronine, bleomycin, forskolin, nonylphenol, zymosan A, vincristine, daunorubicin, prednisolone, cyclosporin a, vitamin K3, diethylstilbestrol, deoxyribonucleotide, suberoylanilide hydroxamic acid, orlistat, 3-(4,5-dimethylthiazol-2-yl)-2, 5-diphenyltetrazolium bromide, rottlerin, arachidonic acid, ibuprofen, prostaglandin E2, toremifene, depsipeptide, ochratoxin A, (glc)4, phosphatidylinositol, mitomycin c, rantes, sphingosine, indomethacin, 5fluorouracil, phosphatidylcholine, 5-fluorouracil, mg 132, thymidylate, trans-cinnamaldehyde, sterol, polyadenosine diphosphate ribose, nitric oxide, vitamin e succinate, lipopolysaccharide, cisplatin, herbimycin a, 5-aza-2'deoxycytidine, proteasome inhibitor PSI, 2,5-hexanedione, epothilone B, caffeic acid phenethyl ester, glycerol 3-phosphate, tgf beta 1, anisomycin, paclitaxel, gemcitabine, medroxyprogesterone acetate, hymecromone, testosterone, ag 1478, doxorubicin, S-nitroso-N-acetylpenicillamine, adpribose, sulforaphane, vitamin d, annexin-v, lactate, reactive oxygen species, sb 203580, serine, N-acetyl-L-cysteine, dutp, infliximab, ethanol, curcumin, cytarabine, tpck, calyculin a, dopamine, gp 130, bromocriptine, apicidin, fatty acid, citrate, glucocorticoid, arsenite, butyrate, peplomycin, oxaliplatin, camptothecin, benzyloxycarbonyl-Leu-Leu-Leu aldehyde, clofibrate, carbon, wortmannin, fludarabine, N-(3-(aminomethyl)benzyl)acetamidine, sirolimus, peptidoglycan, c2ceramide, dihydrotestosterone, 7-aminoactinomycin d, carmustine, heparin, ceramide, paraffin, mitoxantrone, docosahexaenoic acid, vitamin a, ivig, hydrogen peroxide, 7-ethyl-10-hydroxy-camptothecin, oxygen, pydrin, bortezomib, retinoic acid, 1,4-phenylenebis(methylene)selenocyanate, teriflunomide, epinephrine, n acetylcysteine, noxa, irinotecan, oligonucleotide, d-api, rasagiline, 8-bromo-cAMP, atpo, agarose, fansidar, clobetasol propionate, teniposide, aurintricarboxylic acid, polysaccharide, CpG oligonucleotide, cycloheximide |
| IRF1 | tamoxifen, chloramphenicol, polyinosinic-polycytidylic acid, inosine monophosphate, suberoylanilide hydroxamic acid, butyrate, iron, gliadin, zinc, actinomycin d, deferoxamine, phosphatidylinositol, adenine, ornithine, rantes,calcium, 2',5'-oligoadenylate, pge2, poly(i-c), indoleamine, arginine, estradiol, nitric oxide, etoposide, adriamycin, oxygen, retinoid, guanylate, troglitazone, ifn-alpha, retinoic acid, tyrosine, adenylate, am 580, guanosine, oligonucleotide, estrogen, thymidine, tetracycline, serine, sb 203580, pdtc, lipid, cycloheximide |
| MYC | cd 437, 1, 25 dihydroxy vitamin d3, phenethyl isothiocyanate, threonine, arsenic trioxide, salicylic acid, quercetin, prostaglandin E1, ionomycin, 12-o-tetradecanoylphorbol 13-acetate, fulvestrant, phenylephrine, fisetin, 4-coumaric acid, dihydroartemisinin, 3-deazaadenosine, nitroprusside, pregna-4, 17-diene-3, 16-dione, adriamycin, bromodeoxyuridine, AGN194204, STA-9090, isobutylmethylxanthine, potassium chloride, docetaxel, quinolinic acid, 5,6,7,8-tetrahydrobiopterin, propranolol, delta 7-pga1, topotecan, AVI-4126, trichostatin A, decitabine, thymidine, D-glucose, mifepristone, poly rI:rC-RNA, letrozole, L-threonine, 5-hydroxytryptamine, bucladesine, SB203580, 1'-acetoxychavicol acetate, cyclosporin A, okadaic acid, dfmo, LY294002, hmba, piceatannol, 2',5'-oligoadenylate, 4-hydroxytamoxifen, butylbenzyl phthalate, dexamethasone, ec 109, phosphatidic acid, grape seed extract, phorbol myristate acetate, coumermycin, tosylphenylalanyl chloromethyl ketone, CD 437, di(2-ethylhexyl) phthalate, butyrine, cytidine, sodium arsenite, tanshinone iia, L-triiodothyronine, niacinamide, glycogen, daunorubicin, vincristine, carvedilol, bizelesin, 3-deazaneplanocin, phorbol, neplanocin a, panobinostat, [alcl], phosphatidylinositol, U0126, dichlororibofuranosylbenzimidazole, flavopiridol, 5-fluorouracil, verapamil, cyclopamine, nitric oxide, cisplatin, hrgbeta1, 5,6-dichloro-1-beta-d-ribofuranosylbenzimidazole, amsacrine, gemcitabine, aristeromycin, medroxyprogesterone acetate, |

TABLE 10-continued

| T cell Modulating Agents | |
|---|---|
| TARGET | AGENT |
| | gambogic acid, leucine, alpha-naphthyl acetate, cyclic AMP, reactive oxygen species, PD 180970, curcumin, chloramphenicol, A23187, crocidolite asbestos, 6-hydroxydopamine, cb 33, arsenite, gentamicin, benzyloxycarbonyl-Leu-Leu-Leu aldehyde, clofibrate, wortmannin, sirolimus, ceramide, melphalan, 3M-001, linsidomine, CP-55940, hyaluronic acid, ethionine, clonidine, retinoid, bortezomib, oligonucleotide, methyl 2-cyano-3, 12-dioxoolean-1, 9-dien-28-oate, tacrolimus, embelin, methyl-beta-cyclodextrin, 3M-011, folate, ly294002, PP1, hydroxyurea, aclarubicin, phenylbutyrate, PD 0325901, methotrexate, Cd2+, prazosin, vegf rapamycin, alanine, phenobarbital, pd 98, 059, trapoxin, 4-hydroperoxycyclophosphamide, methamphetamine, s-(1,2-dichlorovinyl)-1-cysteine, aphidicolin, vesnarinone, ADI PEG20, pirinixic acid, wp631, H-7, carbon tetrachloride, bufalin, 2,2-dimethylbutyric acid, etoposide, calcitriol, trastuzumab, cyclophosphamide, harringtonine, tyrosine, N(6)-(3-iodobenzyl)-5'-N-methylcarboxamidoadenosine, resveratrol, thioguanine, genistein, S-nitroso-N-acetyl-DL-penicillamine, zearalenone, lysophosphatidic acid, Sn50 peptide, roscovitine, actinomycin D, propanil, agar, tamoxifen, acetaminophen, imatinib, tretinoin, mithramycin, ATP, epigallocatechin-gallate, ferric ammonium citrate, acyclic retinoid, L-cysteine, nitroblue tetrazolium, actinomycin d, sodium nitroprusside, 1,2-dimethylhydrazine, dibutyl phthalate, ornithine, 4-hydroxynonenal, beta-estradiol, 1-alpha, 25-dihydroxy vitamin D3, cyproterone acetate, nimodipine, nitrofurantoin, temsirolimus, 15-deoxy-delta-12, 14-PGJ 2, estrogen, ribonucleic acid, ciprofibrate, alpha-amanitin, SB 216763, bleomycin, forskolin, prednisolone, cyclosporin a, thyroid hormone, tunicamycin, phosphorothioate, suberoylanilide hydroxamic acid, pga2, 3-(4,5-dimethylthiazol-2-yl)-2, 5-diphenyltetrazolium bromide, benzamide riboside, bisindolylmaleimide, SU6656, prostaglandin E2, depsipeptide, zidovudine, cerivastatin, progesterone, sethoxydim, indomethacin, mg 132, mezerein, pyrrolidine dithiocarbamate, vitamin e succinate, herbimycin a, 5-aza-2'deoxycytidine, lipopolysaccharide, diazoxide, anisomycin, paclitaxel, sodium dodecyl sulfate, nilotinib, oxysterol, doxorubicin, lipofectamine, PD98059, steroid, delta-12-pgj2, serine, H-8, N-acetyl-L-cysteine, ethanol, n-(4-hydroxyphenyl)retinamide, tiazofurin, cytarabine, H89, 10-hydroxycamptothecin, everolimus, lactacystin, n(1), n(12)-bis(ethyl)spermine, silibinin, glucocorticoid, butyrate, camptothecin, triamcinolone acetonide, tocotrienol, n-ethylmaleimide, phorbol 12, 13-didecanoate, thapsigargin, deferoxamine, R59949, bryostatin 1, paraffin, romidepsin, vitamin a, docosahexaenoic acid, hydrogen peroxide, droloxifene, saikosaponin, fluoxetine, retinoic acid, n acetylcysteine, dithiothreitol, cordycepin, agarose, 8-bromo-cAMP, D-galactosamine, tachyplesin i, theophylline, metoprolol, SU6657, 15-deoxy-delta-12, 14-prostaglandin j2, dmso, 2-amino-5-azotoluene, cycloheximide |

It will be appreciated that administration of therapeutic entities in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed, Mack Publishing Company, Easton, Pa. (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol Pharmacol. 32(2):210-8 (2000), Wang W. "Lyophilization and development of solid protein pharmaceuticals." Int. J. Pharm. 203(1-2):1-60 (2000), Charman W N "Lipids, lipophilic drugs, and oral drug delivery-some emerging concepts." J Pharm Sci. 89(8):967-78 (2000), Powell et al. "Compendium of excipients for parenteral formulations" PDA J Pharm Sci Technol. 52:238-311 (1998) and the citations therein for additional information related to formulations, excipients and carriers well known to pharmaceutical chemists.

Therapeutic formulations of the invention, which include a T cell modulating agent, are used to treat or alleviate a symptom associated with an immune-related disorder or an aberrant immune response. The present invention also provides methods of treating or alleviating a symptom associated with an immune-related disorder or an aberrant immune response. A therapeutic regimen is carried out by identifying a subject, e.g., a human patient suffering from (or at risk of developing) an immune-related disorder or aberrant immune response, using standard methods. For example, T cell modulating agents are useful therapeutic tools in the treatment of autoimmune diseases and/or inflammatory disorders. In certain embodiments, the use of T cell modulating agents that modulate, e.g., inhibit, neutralize, or interfere with, Th17 T cell differentiation is contemplated for treating autoimmune diseases and/or inflammatory disorders. In certain embodiments, the use of T cell modulating agents that modulate, e.g., enhance or promote, Th17 T cell differentiation is contemplated for augmenting Th17 responses, for example, against certain pathogens and other infectious diseases. The T cell modulating agents are also useful therapeutic tools in various transplant indications, for example, to prevent, delay or otherwise mitigate transplant rejection and/or prolong survival of a transplant, as it has also been shown that in some cases of transplant rejection, Th17 cells might also play an important role. (See e.g., Abadja F, Sarraj B, Ansari M J., "Significance of T helper 17 immunity in transplantation." Curr Opin Organ Transplant. 2012 February; 17(1):8-14. doi: 10.1097/MOT.0b013e32834ef4e4). The T cell modulating agents are also useful therapeutic tools in cancers and/or anti-tumor immunity, as Th17/Treg balance has also been implicated in these indications. For example, some studies have suggested that IL-23 and Th17 cells play a role in some cancers, such as, by way of non-limiting example, colorectal cancers. (See e.g., Ye J, Livergood R S, Peng G. "The role and regulation of human Th17 cells in tumor immunity." Am J Pathol. 2013 January; 182(1):10-20. doi: 10.1016/j.ajpath.2012.08.041. Epub 2012 Nov. 14). The T cell modulating agents are also useful in patients who have genetic defects that exhibit aberrant Th17 cell production, for example, patients that do not produce Th17 cells naturally.

The T cell modulating agents are also useful in vaccines and/or as vaccine adjuvants against autoimmune disorders, inflammatory diseases, etc. The combination of adjuvants for treatment of these types of disorders are suitable for use in combination with a wide variety of antigens from targeted self-antigens, i.e., autoantigens, involved in autoimmunity, e.g., myelin basic protein; inflammatory self-antigens, e.g., amyloid peptide protein, or transplant antigens, e.g., alloantigens. The antigen may comprise peptides or polypeptides derived from proteins, as well as fragments of any of the following: saccharides, proteins, polynucleotides or oligonucleotides, autoantigens, amyloid peptide protein, transplant antigens, allergens, or other macromolecular components. In some instances, more than one antigen is included in the antigenic composition.

Autoimmune diseases include, for example, Acquired Immunodeficiency Syndrome (AIDS, which is a viral disease with an autoimmune component), alopecia areata, ankylosing spondylitis, antiphospholipid syndrome, autoimmune Addison's disease, autoimmune hemolytic anemia, autoimmune hepatitis, autoimmune inner ear disease (AIED), autoimmune lymphoproliferative syndrome (ALPS), autoimmune thrombocytopenic purpura (ATP), Behcet's disease, cardiomyopathy, celiac sprue-dermatitis herpetiformis; chronic fatigue immune dysfunction syndrome (CFIDS), chronic inflammatory demyelinating polyneuropathy (CIPD), cicatricial pemphigoid, cold agglutinin disease, crest syndrome, Crohn's disease, Degos' disease, dermatomyositis-juvenile, discoid lupus, essential mixed cryoglobulinemia, fibromyalgia-fibromyositis, Graves' disease, Guillain-Barré syndrome, Hashimoto's thyroiditis, idiopathic pulmonary fibrosis, idiopathic thrombocytopenia purpura (ITP), IgA nephropathy, insulin-dependent diabetes mellitus, juvenile chronic arthritis (Still's disease), juvenile rheumatoid arthritis, Ménière's disease, mixed connective tissue disease, multiple sclerosis, myasthenia gravis, pernicious anemia, polyarteritis nodosa, polychondritis, polyglandular syndromes, polymyalgia rheumatica, polymyositis and dermatomyositis, primary agammaglobulinemia, primary biliary cirrhosis, psoriasis, psoriatic arthritis, Raynaud's phenomena, Reiter's syndrome, rheumatic fever, rheumatoid arthritis, sarcoidosis, scleroderma (progressive systemic sclerosis (PSS), also known as systemic sclerosis (SS)), Sjögren's syndrome, stiffman syndrome, systemic lupus erythematosus, Takayasu arteritis, temporal arteritis/giant cell arteritis, ulcerative colitis, uveitis, vitiligo and Wegener's granulomatosis.

In some embodiments, T cell modulating agents are useful in treating, delaying the progression of, or otherwise ameliorating a symptom of an autoimmune disease having an inflammatory component such as an aberrant inflammatory response in a subject. In some embodiments, T cell modulating agents are useful in treating an autoimmune disease that is known to be associated with an aberrant Th17 response, e.g., aberrant IL-17 production, such as, for example, multiple sclerosis (MS), psoriasis, inflammatory bowel disease, ulcerative colitis, Crohn's disease, uveitis, lupus, ankylosing spondylitis, and rheumatoid arthritis.

Inflammatory disorders include, for example, chronic and acute inflammatory disorders. Examples of inflammatory disorders include Alzheimer's disease, asthma, atopic allergy, allergy, atherosclerosis, bronchial asthma, eczema, glomerulonephritis, graft vs. host disease, hemolytic anemias, osteoarthritis, sepsis, stroke, transplantation of tissue and organs, vasculitis, diabetic retinopathy and ventilator induced lung injury.

Symptoms associated with these immune-related disorders include, for example, inflammation, fever, general malaise, fever, pain, often localized to the inflamed area, rapid pulse rate, joint pain or aches (arthralgia), rapid breathing or other abnormal breathing patterns, chills, confusion, disorientation, agitation, dizziness, cough, dyspnea, pulmonary infections, cardiac failure, respiratory failure, edema, weight gain, mucopurulent relapses, cachexia, wheezing, headache, and abdominal symptoms such as, for example, abdominal pain, diarrhea or constipation.

Efficaciousness of treatment is determined in association with any known method for diagnosing or treating the particular immune-related disorder. Alleviation of one or more symptoms of the immune-related disorder indicates that the T cell modulating agent confers a clinical benefit.

Administration of a T cell modulating agent to a patient suffering from an immune-related disorder or aberrant immune response is considered successful if any of a variety of laboratory or clinical objectives is achieved. For example, administration of a T cell modulating agent to a patient is considered successful if one or more of the symptoms associated with the immune-related disorder or aberrant immune response is alleviated, reduced, inhibited or does not progress to a further, i.e., worse, state. Administration of T cell modulating agent to a patient is considered successful if the immune-related disorder or aberrant immune response enters remission or does not progress to a further, i.e., worse, state.

A therapeutically effective amount of a T cell modulating agent relates generally to the amount needed to achieve a therapeutic objective. The amount required to be administered will furthermore depend on the specificity of the T cell modulating agent for its specific target, and will also depend on the rate at which an administered T cell modulating agent is depleted from the free volume other subject to which it is administered.

T cell modulating agents can be administered for the treatment of a variety of diseases and disorders in the form of pharmaceutical compositions. Principles and considerations involved in preparing such compositions, as well as guidance in the choice of components are provided, for example, in Remington: The Science And Practice Of Pharmacy 19th ed. (Alfonso R. Gennaro, et al., editors) Mack Pub. Co., Easton, Pa.: 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York.

Where polypeptide-based T cell modulating agents are used, the smallest fragment that specifically binds to the target and retains therapeutic function is preferred. Such fragments can be synthesized chemically and/or produced by recombinant DNA technology. (See, e.g., Marasco et al., Proc. Natl. Acad. Sci. USA, 90: 7889-7893 (1993)). The formulation can also contain more than one active compound as necessary for the particular indication being treated, preferably those with complementary activities that do not adversely affect each other. Alternatively, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

The invention comprehends a treatment method or Drug Discovery method or method of formulating or preparing a treatment comprising any one of the methods or uses herein discussed.

The present invention also relates to identifying molecules, advantageously small molecules or biologics, that may be involved in inhibiting one or more of the mutations in one or more genes selected from the group consisting of DEC1, PZLP, TCF4 and CD5L. The invention contemplates screening libraries of small molecules or biologics to identify compounds involved in suppressing or inhibiting expression of somatic mutations or alter the cells phenotypically so that the cells with mutations behave more normally in one or more of DEC1, PZLP, TCF4 and CD5L.

High-throughput screening (HTS) is contemplated for identifying small molecules or biologics involved in suppressing or inhibiting expression of somatic mutations in one or more of DEC1, PZLP, TCF4 and CD5L. The flexibility of the process has allowed numerous and disparate areas of biology to engage with an equally diverse palate of chemistry (see, e.g., Inglese et al., Nature Chemical Biology 3, 438-441 (2007)). Diverse sets of chemical libraries, containing more than 200,000 unique small molecules, as well as natural product libraries, can be screened. This includes, for example, the Prestwick library (1,120 chemicals) of off-patent compounds selected for structural diversity, collective coverage of multiple therapeutic areas, and known safety and bioavailability in humans, as well as the NINDS Custom Collection 2 consisting of a 1,040 compound-library of mostly FDA-approved drugs (see, e.g., U.S. Pat. No. 8,557,746) are also contemplated.

The NM's Molecular Libraries Probe Production Centers Network (MLPCN) offers access to thousands of small molecules—chemical compounds that can be used as tools to probe basic biology and advance our understanding of disease. Small molecules can help researchers understand the intricacies of a biological pathway or be starting points for novel therapeutics. The Broad Institute's Probe Development Center (BIPDeC) is part of the MLPCN and offers access to a growing library of over 330,000 compounds for large scale screening and medicinal chemistry. Any of these compounds may be utilized for screening compounds involved in suppressing or inhibiting expression of somatic mutations in one or more of DEC1, PZLP, TCF4 and CD5L.

The phrase "therapeutically effective amount" as used herein refers to a nontoxic but sufficient amount of a drug, agent, or compound to provide a desired therapeutic effect.

As used herein "patient" refers to any human being receiving or who may receive medical treatment.

A "polymorphic site" refers to a polynucleotide that differs from another polynucleotide by one or more single nucleotide changes.

A "somatic mutation" refers to a change in the genetic structure that is not inherited from a parent, and also not passed to offspring.

Therapy or treatment according to the invention may be performed alone or in conjunction with another therapy, and may be provided at home, the doctor's office, a clinic, a hospital's outpatient department, or a hospital. Treatment generally begins at a hospital so that the doctor can observe the therapy's effects closely and make any adjustments that are needed. The duration of the therapy depends on the age and condition of the patient, the stage of the cardiovascular disease, and how the patient responds to the treatment. Additionally, a person having a greater risk of developing a cardiovascular disease (e.g., a person who is genetically predisposed) may receive prophylactic treatment to inhibit or delay symptoms of the disease.

The medicaments of the invention are prepared in a manner known to those skilled in the art, for example, by means of conventional dissolving, lyophilizing, mixing, granulating or confectioning processes. Methods well known in the art for making formulations are found, for example, in Remington: The Science and Practice of Pharmacy, 20th ed., ed. A. R. Gennaro, 2000, Lippincott Williams & Wilkins, Philadelphia, and Encyclopedia of Pharmaceutical Technology, eds. J. Swarbrick and J. C. Boylan, 1988-1999, Marcel Dekker, New York.

Administration of medicaments of the invention may be by any suitable means that results in a compound concentration that is effective for treating or inhibiting (e.g., by delaying) the development of a cardiovascular disease. The compound is admixed with a suitable carrier substance, e.g., a pharmaceutically acceptable excipient that preserves the therapeutic properties of the compound with which it is administered. One exemplary pharmaceutically acceptable excipient is physiological saline. The suitable carrier substance is generally present in an amount of 1-95% by weight of the total weight of the medicament. The medicament may be provided in a dosage form that is suitable for oral, rectal, intravenous, intramuscular, subcutaneous, inhalation, nasal, topical or transdermal, vaginal, or ophthalmic administration. Thus, the medicament may be in form of, e.g., tablets, capsules, pills, powders, granulates, suspensions, emulsions, solutions, gels including hydrogels, pastes, ointments, creams, plasters, drenches, delivery devices, suppositories, enemas, injectables, implants, sprays, or aerosols.

In order to determine the genotype of a patient according to the methods of the present invention, it may be necessary to obtain a sample of genomic DNA from that patient. That sample of genomic DNA may be obtained from a sample of tissue or cells taken from that patient.

The tissue sample may comprise but is not limited to hair (including roots), skin, buccal swabs, blood, or saliva. The tissue sample may be marked with an identifying number or other indicia that relates the sample to the individual patient from which the sample was taken. The identity of the sample advantageously remains constant throughout the methods of the invention thereby guaranteeing the integrity and continuity of the sample during extraction and analysis. Alternatively, the indicia may be changed in a regular fashion that ensures that the data, and any other associated data, can be related back to the patient from whom the data was obtained. The amount/size of sample required is known to those skilled in the art.

Generally, the tissue sample may be placed in a container that is labeled using a numbering system bearing a code corresponding to the patient. Accordingly, the genotype of a particular patient is easily traceable.

In one embodiment of the invention, a sampling device and/or container may be supplied to the physician. The sampling device advantageously takes a consistent and reproducible sample from individual patients while simultaneously avoiding any cross-contamination of tissue. Accordingly, the size and volume of sample tissues derived from individual patients would be consistent.

According to the present invention, a sample of DNA is obtained from the tissue sample of the patient of interest. Whatever source of cells or tissue is used, a sufficient amount of cells must be obtained to provide a sufficient amount of DNA for analysis. This amount will be known or readily determinable by those skilled in the art.

DNA is isolated from the tissue/cells by techniques known to those skilled in the art (see, e.g., U.S. Pat. Nos. 6,548,256 and 5,989,431, Hirota et al., Jinrui Idengaku Zasshi. September 1989; 34(3):217-23 and John et al., Nucleic Acids Res. Jan. 25, 1991; 19(2):408; the disclosures of which are incorporated by reference in their entireties). For example, high molecular weight DNA may be purified from cells or tissue using proteinase K extraction and ethanol precipitation. DNA may be extracted from a patient specimen using any other suitable methods known in the art.

It is an object of the present invention to determine the genotype of a given patient of interest by analyzing the DNA from the patent, in order to identify a patient carrying specific somatic mutations of the invention that are associated with developing a cardiovascular disease. In particular, the kit may have primers or other DNA markers for identifying particular mutations such as, but not limited to, one or more genes selected from the group consisting of DEC1, PZLP, TCF4 and CD5L.

There are many methods known in the art for determining the genotype of a patient and for identifying or analyzing whether a given DNA sample contains a particular somatic mutation. Any method for determining genotype can be used for determining genotypes in the present invention. Such methods include, but are not limited to, amplimer sequencing, DNA sequencing, fluorescence spectroscopy, fluorescence resonance energy transfer (or "FRET")-based hybridization analysis, high throughput screening, mass spectroscopy, nucleic acid hybridization, polymerase chain reaction (PCR), RFLP analysis and size chromatography (e.g., capillary or gel chromatography), all of which are well known to one of skill in the art.

The methods of the present invention, such as whole exome sequencing and targeted amplicon sequencing, have commercial applications in diagnostic kits for the detection of the somatic mutations in patients. A test kit according to the invention may comprise any of the materials necessary for whole exome sequencing and targeted amplicon sequencing, for example, according to the invention. In a particular advantageous embodiment, a diagnostic for the present invention may comprise testing for any of the genes in disclosed herein. The kit further comprises additional means, such as reagents, for detecting or measuring the sequences of the present invention, and also ideally a positive and negative control.

The present invention further encompasses probes according to the present invention that are immobilized on a solid or flexible support, such as paper, nylon or other type of membrane, filter, chip, glass slide, microchips, microbeads, or any other such matrix, all of which are within the scope of this invention. The probe of this form is now called a "DNA chip". These DNA chips can be used for analyzing the somatic mutations of the present invention. The present invention further encompasses arrays or microarrays of nucleic acid molecules that are based on one or more of the sequences described herein. As used herein "arrays" or "microarrays" refers to an array of distinct polynucleotides or oligonucleotides synthesized on a solid or flexible support, such as paper, nylon or other type of membrane, filter, chip, glass slide, or any other suitable solid support. In one embodiment, the microarray is prepared and used according to the methods and devices described in U.S. Pat. Nos. 5,446,603; 5,545,531; 5,807,522; 5,837,832; 5,874,219; 6,114,122; 6,238,910; 6,365,418; 6,410,229; 6,420,114; 6,432,696; 6,475,808 and 6,489,159 and PCT Publication No. WO 01/45843 A2, the disclosures of which are incorporated by reference in their entireties.

EXAMPLES & TECHNOLOGIES AS TO THE INSTANT INVENTION

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

In this regard, mention is made that mutations in cells and also mutated mice for use in or as to the invention can be by way of the CRISPR-Cas system or a Cas9-expressing eukaryotic cell or Cas-9 expressing eukaryote, such as a mouse. The Cas9-expressing eukaryotic cell or eukaryote, e.g., mouse, can have guide RNA delivered or administered thereto, whereby the RNA targets a loci and induces a desired mutation for use in or as to the invention. With respect to general information on CRISPR-Cas Systems, components thereof, and delivery of such components, including methods, materials, delivery vehicles, vectors, particles, and making and using thereof, including as to amounts and formulations, as well as Cas9-expressing eukaryotic cells, Cas-9 expressing eukaryotes, such as a mouse, all useful in or as to the instant invention, reference is made to: U.S. Pat. Nos. 8,697,359, 8,771,945, 8,795,965, 8,865,406, 8,871,445, 8,889,356, 8,889,418, 8,895,308, 8,932,814, 8,945,839, 8,906,616; US Patent Publications US 2014-0310830 (U.S. application Ser. No. 14/105,031), US 2014-0287938 A1 (U.S. application Ser. No. 14/213,991), US 2014-0273234 A1 (U.S. application Ser. No. 14/293,674), US2014-0273232 A1 (U.S. application Ser. No. 14/290,575), US 2014-0273231 (U.S. application Ser. No. 14/259,420), US 2014-0256046 A1 (U.S. application Ser. No. 14/226,274), US 2014-0248702 A1 (U.S. application Ser. No. 14/258,458), US 2014-0242700 A1 (U.S. application Ser. No. 14/222,930), US 2014-0242699 A1 (U.S. application Ser. No. 14/183,512), US 2014-0242664 A1 (U.S. application Ser. No. 14/104,990), US 2014-0234972 A1 (U.S. application Ser. No. 14/183,471), US 2014-0227787 A1 (U.S. application Ser. No. 14/256,912), US 2014-0189896 A1 (U.S. application Ser. No. 14/105,035), US 2014-0186958 (U.S. application Ser. No. 14/105,017), US 2014-0186919 A1 (U.S. application Ser. No. 14/104,977), US 2014-0186843 A1 (U.S. application Ser. No. 14/104,900), US 2014-0179770 A1 (U.S. application Ser. No. 14/104,837) and US 2014-0179006 A1 (U.S. application Ser. No. 14/183,486), US 2014-0170753 (U.S. application Ser. No. 14/183,429); European Patents/Patent Applications: EP 2 771 468 (EP13818570.7), EP 2 764 103 (EP13824232.6), and EP 2 784 162 (EP14170383.5); and PCT Patent Publications WO 2014/093661 (PCT/US2013/074743), WO 2014/093694 (PCT/US2013/074790), WO 2014/093595 (PCT/US2013/074611), WO 2014/093718 (PCT/US2013/074825), WO 2014/093709 (PCT/US2013/074812), WO 2014/093622 (PCT/US2013/074667), WO 2014/093635 (PCT/US2013/074691), WO 2014/093655 (PCT/US2013/074736), WO 2014/093712 (PCT/US2013/074819), WO2014/093701 (PCT/US2013/074800), WO2014/018423 (PCT/US2013/051418), WO 2014/204723 (PCT/US2014/041790), WO 2014/204724 (PCT/US2014/041800), WO 2014/204725 (PCT/US2014/041803), WO 2014/204726 (PCT/US2014/041804), WO 2014/204727 (PCT/US2014/041806), WO 2014/204728 (PCT/US2014/041808), WO 2014/204729 (PCT/US2014/041809), and:

*Multiplex genome engineering using CRISPR/Cas systems*. Cong, L., Ran, F. A., Cox, D., Lin, S., Barretto, R., Habib, N., Hsu, P. D., Wu, X., Jiang, W., Marraffini, L. A., & Zhang, F. *Science* February 15; 339(6121):819-23 (2013);

*RNA-guided editing of bacterial genomes using CRISPR-Cas systems*. Jiang W., Bikard D., Cox D., Zhang F, Marraffini L A. Nat Biotechnol March; 31(3):233-9 (2013);

*One-Step Generation of Mice Carrying Mutations in Multiple Genes by CRISPR/Cas-Mediated Genome Engineering*. Wang H., Yang H., Shivalila C S., Dawlaty M M., Cheng A W., Zhang F., Jaenisch R. Cell May 9; 153(4): 910-8 (2013);

*Optical control of mammalian endogenous transcription and epigenetic states*. Konermann S, Brigham M D, Trevino A E, Hsu P D, Heidenreich M, Cong L, Platt R J, Scott D A, Church G M, Zhang F. Nature. 2013 Aug. 22; 500(7463):472-6. doi: 10.1038/Nature12466. Epub 2013 Aug. 23;

*Double Nicking by RNA-Guided CRISPR Cas9 for Enhanced Genome Editing Specificity*. Ran, F A., Hsu, P D., Lin, C Y., Gootenberg, J S., Konermann, S., Trevino, A E., Scott, D A., Inoue, A., Matoba, S., Zhang, Y., & Zhang, F. *Cell* August 28. pii: S0092-8674(13)01015-5. (2013);

*DNA targeting specificity of RNA guided Cas9 nucleases*. Hsu, P., Scott, D., Weinstein, J., Ran, F A., Konermann, S., Agarwala, V., Li, Y., Fine, E., Wu, X., Shalem, O., Cradick, T J., Marraffini, L A., Bao, G., & Zhang, F. *Nat Biotechnol* doi:10.1038/nbt.2647 (2013);

*Genome engineering using the CRISPR-Cas9 system*. Ran, F A., Hsu, P D., Wright, J., Agarwala, V., Scott, D A., Zhang, F. Nature Protocols November; 8(11):2281-308. (2013);

*Genome-Scale CRISPR-Cas9 Knockout Screening in Human Cells*. Shalem, O., Sanjana, N E., Hartenian, E., Shi, X., Scott, D A., Mikkelson, T., Heckl, D., Ebert, B L., Root, D E., Doench, J G., Zhang, F. *Science* December 12, (2013). [Epub ahead of print];

*Crystal structure of cas9 in complex with guide RNA and target DNA*. Nishimasu, H., Ran, F A., Hsu, P D., Konermann, S., Shehata, S I., Dohmae, N., Ishitani, R., Zhang, F., Nureki, O. *Cell* February 27, (2014). 156(5):935-49;

*Genome-wide binding of the CRISPR endonuclease Cas9 in mammalian cells*. Wu X., Scott D A., Kriz A J., Chiu A C., Hsu P D., Dadon D B., Cheng A W., Trevino A E., Konermann S., Chen S., Jaenisch R., Zhang F., Sharp P A. *Nat Biotechnol*. (2014) April 20. doi: 10.1038/nbt.2889,

*CRISPR-Cas9 Knockin Mice for Genome Editing and Cancer Modeling*, Platt et al., Cell 159(2): 440-455 (2014) DOI: 10.1016/j.cell.2014.09.014,

*Development and Applications of CRISPR-Cas9 for Genome Engineering*, Hsu et al, Cell 157, 1262-1278 (Jun. 5, 2014) (Hsu 2014),

*Genetic screens in human cells using the CRISPR/Cas9 system*, Wang et al., Science. 2014 Jan. 3; 343(6166): 80-84. doi:10.1126/science.1246981,

*Rational design of highly active sgRNAs for CRISPR-Cas9-mediated gene inactivation,* Doench et al., Nature Biotechnology published online 3 Sep. 2014; doi:10.1038/nbt.3026, and

*In vivo interrogation of gene function in the mammalian brain using CRISPR-Cas9*, Swiech et al, Nature Biotechnology; published online 19 Oct. 2014; doi:10.1038/nbt.3055, each of which is incorporated herein by reference.

The invention involves a high-throughput single-cell RNA-Seq and/or targeted nucleic acid profiling (for example, sequencing, quantitative reverse transcription polymerase chain reaction, and the like) where the RNAs from different cells are tagged individually, allowing a single library to be created while retaining the cell identity of each read. In this regard, technology of U.S. provisional patent application Ser. No. 62/048,227 filed Sep. 9, 2014, the disclosure of which is incorporated by reference, may be used in or as to the invention. A combination of molecular barcoding and emulsion-based microfluidics to isolate, lyse, barcode, and prepare nucleic acids from individual cells in high-throughput is used. Microfluidic devices (for example, fabricated in polydimethylsiloxane), sub-nanoliter reverse emulsion droplets. These droplets are used to co-encapsulate nucleic acids with a barcoded capture bead. Each bead, for example, is uniquely barcoded so that each drop and its contents are distinguishable. The nucleic acids may come from any source known in the art, such as for example, those which come from a single cell, a pair of cells, a cellular lysate, or a solution. The cell is lysed as it is encapsulated in the droplet. To load single cells and barcoded beads into these droplets with Poisson statistics, 100,000 to 10 million such beads are needed to barcode ~10,000-100,000 cells. In this regard there can be a single-cell sequencing library which may comprise: merging one uniquely barcoded mRNA capture microbead with a single-cell in an emulsion droplet having a diameter of 75-125 μm; lysing the cell to make its RNA accessible for capturing by hybridization onto RNA capture microbead; performing a reverse transcription either inside or outside the emulsion droplet to convert the cell's mRNA to a first strand cDNA that is covalently linked to the mRNA capture microbead; pooling the cDNA-attached microbeads from all cells; and preparing and sequencing a single composite RNA-Seq library. Accordingly, it is envisioned as to or in the practice of the invention provides that there can be a method for preparing uniquely barcoded mRNA capture microbeads, which has a unique barcode and diameter suitable for microfluidic devices which may comprise: 1) performing reverse phosphoramidite synthesis on the surface of the bead in a pool-and-split fashion, such that in each cycle of synthesis the beads are split into four reactions with one of the four canonical nucleotides (T, C, G, or A) or unique oligonucleotides of length two or more bases; 2) repeating this process a large number of times, at least six, and optimally more than twelve, such that, in the latter, there are more than 16 million unique barcodes on the surface of each bead in the pool. (See http://www.ncbi.nlm.nih.gov/pmc/articles/PMC206447).

Likewise, in or as to the instant invention there can be an apparatus for creating a single-cell sequencing library via a microfluidic system, which may comprise: an oil-surfactant inlet which may comprise a filter and a carrier fluid channel, wherein said carrier fluid channel further may comprise a resistor; an inlet for an analyte which may comprise a filter and a carrier fluid channel, wherein said carrier fluid channel may further comprise a resistor; an inlet for mRNA capture microbeads and lysis reagent which may comprise a filter and a carrier fluid channel, wherein said carrier fluid channel may further comprise a resistor; said carrier fluid channels have a carrier fluid flowing therein at an adjustable or predetermined flow rate; wherein each said carrier fluid channels merge at a junction; and said junction being connected to a mixer, which contains an outlet for drops. Similarly, as to or in the practice of the instant invention there can be a method for creating a single-cell sequencing library which may comprise: merging one uniquely barcoded RNA capture microbead with a single-cell in an emulsion droplet having a diameter of 125 μm lysing the cell thereby capturing the RNA on the RNA capture microbead; performing a reverse transcription either after breakage of the droplets and collection of the microbeads; or inside the emulsion droplet to convert the cell's RNA to a first strand cDNA that is covalently linked to the RNA capture microbead; pooling the cDNA-attached microbeads from all cells; and preparing and sequencing a single composite RNA-Seq library; and, the emulsion droplet can be between 50-210 μm. In a further embodiment, the method wherein the diameter of the mRNA capture microbeads is from 10 μm to 95 μm. Thus, the practice of the instant invention comprehends preparing uniquely barcoded mRNA capture microbeads, which has a unique barcode and diameter suitable for microfluidic devices which may comprise: 1) performing reverse phosphoramidite synthesis on the surface of the bead in a pool-and-split fashion, such that in each cycle of synthesis the beads are split into four reactions with one of the four canonical nucleotides (T, C, G, or A); 2) repeating this process a large number of times, at least six, and optimally more than twelve, such that, in the latter, there are more than 16 million unique barcodes on the surface of each bead in the pool. The covalent bond can be polyethylene glycol. The diameter of the mRNA capture microbeads can be from 10 μm to 95 μm. Accordingly, it is also envisioned as to or in the practice of the invention that there can be a method for preparing uniquely barcoded mRNA capture microbeads, which has a unique barcode and diameter suitable for microfluidic devices which may comprise: 1) performing reverse phosphoramidite synthesis on the surface of the bead in a pool-and-split fashion, such that in each cycle of synthesis the beads are split into four reactions with one of the four canonical nucleotides (T, C, G, or A); 2) repeating this process a large number of times, at least six, and optimally more than twelve, such that, in the latter, there are more than 16 million unique barcodes on the surface of each bead in the pool. And, the diameter of the mRNA capture microbeads can be from 10 μm to 95 μm. Further, as to in the practice of the invention there can be an apparatus for creating a composite single-cell sequencing library via a microfluidic system, which may comprise: an oil-surfactant inlet which may comprise a filter and two carrier fluid channels, wherein said carrier fluid channel further may comprise a resistor; an inlet for an analyte which may comprise a filter and two carrier fluid channels, wherein said carrier fluid channel further may comprise a resistor; an inlet for mRNA capture microbeads and lysis reagent which may comprise a carrier fluid channel; said carrier fluid channels have a carrier fluid flowing therein at an adjustable and predetermined flow rate; wherein each said carrier fluid channels merge at a junction; and said junction being connected to a constriction for droplet pinch-off followed by a mixer, which connects to an outlet for drops. The analyte may comprise a chemical reagent, a genetically perturbed cell, a protein, a drug, an antibody, an enzyme, a nucleic acid, an organelle like the mitochondrion or nucleus, a cell or any combination thereof. In an embodiment of the apparatus the analyte is a cell. In a further embodiment the cell is a brain cell. In an embodiment of the apparatus the lysis reagent may comprise an anionic surfactant such as sodium lauroyl sarcosinate, or a chaotropic salt such as guanidinium thiocyanate. The filter can involve square PDMS posts; e.g., with the filter on the cell channel of such posts with sides ranging between 125-135 μm with a separation of 70-100 mm between the posts. The filter on the oil-surfactant inlet may comprise square posts of two sizes; one with sides ranging between 75-100 μm and a separation of 25-30 μm between them and the other with sides ranging between 40-50 μm and a separation of 10-15 μm. The apparatus can involve a resistor, e.g., a resistor that is serpentine having a length of 7000-9000 μm, width of 50-75 μm and depth of 100-150 mm. The apparatus can have channels having a length of 8000-12,000 μm for oil-surfactant inlet, 5000-7000 for analyte (cell) inlet, and 900-1200 μm for the inlet for microbead and lysis agent; and/or all channels having a width of 125-250 mm, and depth of 100-150 mm. The width of the cell channel can be 125-250 μm and the depth 100-150 μm. The apparatus can include a mixer having a length of 7000-9000 μm, and a width of 110-140 μm with 35-45zig-zigs every 150 μm. The width of the mixer can be about 125 μm. The oil-surfactant can be a PEG Block Polymer, such as BIORAD™ QX200 Droplet Generation Oil. The carrier fluid can be a water-glycerol mixture. In the practice of the invention or as to the invention, a mixture may comprise a plurality of microbeads adorned with combinations of the following elements: bead-specific oligonucleotide barcodes; additional oligonucleotide barcode sequences which vary among the oligonucleotides on an individual bead and can therefore be used to differentiate or help identify those individual oligonucleotide molecules; additional oligonucleotide sequences that create substrates for downstream molecular-biological reactions, such as oligo-dT (for reverse transcription of mature mRNAs), specific sequences (for capturing specific portions of the transcriptome, or priming for DNA polymerases and similar enzymes), or random sequences (for priming throughout the transcriptome or genome). The individual oligonucleotide molecules on the surface of any individual microbead may contain all three of these elements, and the third element may include both oligo-dT and a primer sequence. A mixture may comprise a plurality of microbeads, wherein said microbeads may comprise the following elements: at least one bead-specific oligonucleotide barcode; at least one additional identifier oligonucleotide barcode sequence, which varies among the oligonucleotides on an individual bead, and thereby assisting in the identification and of the bead specific oligonucleotide molecules; optionally at least one additional oligonucleotide sequences, which provide substrates for downstream molecular-biological reactions. A mixture may comprise at least one oligonucleotide sequence(s), which provide for substrates for downstream molecular-biological reactions. In a further embodiment the downstream molecular biological reactions are for reverse transcription of mature mRNAs; capturing specific portions of the transcriptome, priming for DNA polymerases and/or similar enzymes; or priming throughout the transcriptome or genome. The mixture may involve additional oligonucleotide sequence(s) which may comprise a oligo-dT sequence. The mixture further may comprise the additional oligonucleotide sequence which may comprise a primer sequence. The mixture may further comprise the additional oligonucleotide sequence which may comprise a oligo-dT sequence and a primer sequence. Examples of the labeling substance which may be employed include labeling substances known to those skilled in the art, such as fluorescent dyes, enzymes, coenzymes, chemiluminescent substances, and radioactive substances. Specific examples include radioisotopes (e.g., 32P, 14C, 125I, 3H, and 131I), fluorescein, rhodamine, dansyl chloride, umbelliferone, luciferase, peroxidase, alkaline phosphatase, β-galactosidase, β-glucosidase, horseradish peroxidase, glucoamylase, lysozyme, saccharide oxidase, microperoxidase, biotin, and ruthenium. In the case where biotin is employed as a labeling substance, preferably, after addition of a biotin-labeled antibody, streptavidin bound to an enzyme (e.g., peroxidase) is further added. Advantageously, the label is a fluorescent label. Examples of fluorescent labels include, but are not limited to, Atto dyes, 4-acetamido-4'-isothiocyanatostilbene-2,2'disulfonic acid; acridine and derivatives: acridine, acridine isothiocyanate; 5-(2'-aminoethyl)aminonaphthalene-1-sulfonic acid (EDANS); 4-amino-N-[3-vinyl sulfonyl)phenyl]naphthalimide-3,5 disulfonate; N-(4-anilino-1-naphthyl)maleimide; anthranilamide; BODIPY; Brilliant Yellow; coumarin and derivatives; coumarin, 7-amino-4-methylcoumarin (AMC, Coumarin 120), 7-amino-4-trifluoromethylcoumarin (Coumaran 151); cyanine dyes; cyanosine; 4',6-diaminidino-2-phenylindole (DAPI); 5'5"-dibromopyrogallol-sulfonphthaleine (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansylchloride); 4-dimethylaminophenylazophenyl-4'-isothiocyanate (DABITC); eosin and derivatives; eosin, eosin isothiocyanate, erythrosin and derivatives; erythrosin B, erythrosin, isothiocyanate; ethidium; fluorescein and derivatives; 5-carboxyfluorescein (FAM), 5-(4,6-dichlorotriazin-2-yl)aminofluorescein (DTAF), 2',7'-dimethoxy-4'5'-dichloro-6-carboxyfluorescein, fluorescein, fluorescein isothiocyanate, QFITC, (XRITC); fluorescamine; IR144; IR1446; Malachite Green isothiocyanate; 4-methylumbelliferone ortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N' tetramethyl-6-carboxyrhodamine (TAMRA); tetramethyl rhodamine; tetramethyl rhodamine isothiocyanate (TRITC); riboflavin; rosolic acid; terbium chelate derivatives; Cy3; Cy5; Cy5.5; Cy7; IRD 700; IRD 800; La Jolta Blue; phthalo cyanine; and naphthalo cyanine. A fluorescent label may be a fluorescent protein, such as blue fluorescent protein, cyan fluorescent protein, green fluorescent protein, red fluorescent protein, yellow fluorescent protein or any photoconvertible protein. Colorimetric labeling, bioluminescent labeling and/or chemiluminescent labeling may further accomplish labeling. Labeling further may include energy transfer between molecules in the hybridization complex by perturbation analysis, quenching, or electron transport between donor and acceptor molecules, the latter of which may be facilitated by double stranded match hybridization complexes. The fluorescent label may be a perylene or a terylene. In the alternative, the fluorescent label may be a fluorescent bar code. Advantageously, the label may be light sensitive, wherein the label is light-activated and/or light cleaves the one or more linkers to release the molecular cargo. The light-activated molecular cargo may be a major light-harvesting complex (LHCII). In another embodiment, the fluorescent label may induce free radical formation.

Advantageously, agents may be uniquely labeled in a dynamic manner (see, e.g., U.S. provisional patent application Ser. No. 61/703,884 filed Sep. 21, 2012). The unique labels are, at least in part, nucleic acid in nature, and may be generated by sequentially attaching two or more detectable oligonucleotide tags to each other and each unique label may be associated with a separate agent. A detectable oligonucleotide tag may be an oligonucleotide that may be detected by sequencing of its nucleotide sequence and/or by detecting non-nucleic acid detectable moieties to which it may be attached. Oligonucleotide tags may be detectable by virtue of their nucleotide sequence, or by virtue of a non-nucleic acid detectable moiety that is attached to the oligonucleotide such as but not limited to a fluorophore, or by virtue of a combination of their nucleotide sequence and the nonnucleic acid detectable moiety. A detectable oligonucleotide tag may comprise one or more nonoligonucleotide detectable moieties. Examples of detectable moieties may include, but are not limited to, fluorophores, microparticles including quantum dots (Empodocles, et al., Nature 399:126-130, 1999), gold nanoparticles (Reichert et al., Anal. Chem. 72:6025-6029, 2000), microbeads (Lacoste et al., Proc. Natl. Acad. Sci. USA 97(17):9461-9466, 2000), biotin, DNP (dinitrophenyl), fucose, digoxigenin, haptens, and other detectable moieties known to those skilled in the art. In some embodiments, the detectable moieties may be quantum dots. Methods for detecting such moieties are described herein and/or are known in the art. Thus, detectable oligonucleotide tags may be, but are not limited to, oligonucleotides which may comprise unique nucleotide sequences, oligonucleotides which may comprise detectable moieties, and oligonucleotides which may comprise both unique nucleotide sequences and detectable moieties. A unique label may be produced by sequentially attaching two or more detectable oligonucleotide tags to each other. The detectable tags may be present or provided in a plurality of detectable tags. The same or a different plurality of tags may be used as the source of each detectable tag may be part of a unique label. In other words, a plurality of tags may be subdivided into subsets and single subsets may be used as the source for each tag. One or more other species may be associated with the tags. In particular, nucleic acids released by a lysed cell may be ligated to one or more tags. These may include, for example, chromosomal DNA, RNA transcripts, tRNA, mRNA, mitochondrial DNA, or the like. Such nucleic acids may be sequenced, in addition to sequencing the tags themselves, which may yield information about the nucleic acid profile of the cells, which can be associated with the tags, or the conditions that the corresponding droplet or cell was exposed to.

The invention accordingly may involve or be practiced as to high throughput and high resolution delivery of reagents to individual emulsion droplets that may contain cells, organelles, nucleic acids, proteins, etc. through the use of monodisperse aqueous droplets that are generated by a microfluidic device as a water-in-oil emulsion. The droplets are carried in a flowing oil phase and stabilized by a surfactant. In one aspect single cells or single organelles or single molecules (proteins, RNA, DNA) are encapsulated into uniform droplets from an aqueous solution/dispersion. In a related aspect, multiple cells or multiple molecules may take the place of single cells or single molecules. The aqueous droplets of volume ranging from 1 pL to 10 nL work as individual reactors. 104 to 105 single cells in droplets may be processed and analyzed in a single run. To utilize microdroplets for rapid large-scale chemical screening or complex biological library identification, different species of microdroplets, each containing the specific chemical compounds or biological probes cells or molecular barcodes of interest, have to be generated and combined at the preferred conditions, e.g., mixing ratio, concentration, and order of combination. Each species of droplet is introduced at a confluence point in a main microfluidic channel from separate inlet microfluidic channels. Preferably, droplet volumes are chosen by design such that one species is larger than others and moves at a different speed, usually slower than the other species, in the carrier fluid, as disclosed in U.S. Publication No. US 2007/0195127 and International Publication No. WO 2007/089541, each of which are incorporated herein by reference in their entirety. The channel width and length is selected such that faster species of droplets catch up to the slowest species. Size constraints of the channel prevent the faster moving droplets from passing the slower moving droplets resulting in a train of droplets entering a merge zone. Multi-step chemical reactions, biochemical reactions, or assay detection chemistries often require a fixed reaction time before species of different type are added to a reaction. Multi-step reactions are achieved by repeating the process multiple times with a second, third or more confluence points each with a separate merge point. Highly efficient and precise reactions and analysis of reactions are achieved when the frequencies of droplets from the inlet channels are matched to an optimized ratio and the volumes of the species are matched to provide optimized reaction conditions in the combined droplets. Fluidic droplets may be screened or sorted within a fluidic system of the invention by altering the flow of the liquid containing the droplets. For instance, in one set of embodiments, a fluidic droplet may be steered or sorted by directing the liquid surrounding the fluidic droplet into a first channel, a second channel, etc. In another set of embodiments, pressure within a fluidic system, for example, within different channels or within different portions of a channel, can be controlled to direct the flow of fluidic droplets. For example, a droplet can be directed toward a channel junction including multiple options for further direction of flow (e.g., directed toward a branch, or fork, in a channel defining optional downstream flow channels). Pressure within one or more of the optional downstream flow channels can be controlled to direct the droplet selectively into one of the channels, and changes in pressure can be effected on the order of the time required for successive droplets to reach the junction, such that the downstream flow path of each successive droplet can be independently controlled. In one arrangement, the expansion and/or contraction of liquid reservoirs may be used to steer or sort a fluidic droplet into a channel, e.g., by causing directed movement of the liquid containing the fluidic droplet. In another, the expansion and/or contraction of the liquid reservoir may be combined with other flow-controlling devices and methods, e.g., as described herein. Non-limiting examples of devices able to cause the expansion and/or contraction of a liquid reservoir include pistons. Key elements for using microfluidic channels to process droplets include: (1) producing droplet of the correct volume, (2) producing droplets at the correct frequency and (3) bringing together a first stream of sample droplets with a second stream of sample droplets in such a way that the frequency of the first stream of sample droplets matches the frequency of the second stream of sample droplets. Preferably, bringing together a stream of sample droplets with a stream of premade library droplets in such a way that the frequency of the library droplets matches the frequency of the sample droplets. Methods for producing droplets of a uniform volume at a regular frequency are well known in the art. One method is to generate droplets using hydrodynamic focusing of a dispersed phase fluid and immiscible carrier fluid, such as disclosed in U.S. Publication No. US 2005/0172476 and International Publication No. WO 2004/002627. It is desirable for one of the species introduced at the confluence to be a pre-made library of droplets where the library contains a plurality of reaction conditions, e.g., a library may contain plurality of different compounds at a range of concentrations encapsulated as separate library elements for screening their effect on cells or enzymes, alternatively a library could be composed of a plurality of different primer pairs encapsulated as different library elements for targeted amplification of a collection of loci, alternatively a library could contain a plurality of different antibody species encapsulated as different library elements to perform a plurality of binding assays. The introduction of a library of reaction conditions onto a substrate is achieved by pushing a premade collection of library droplets out of a vial with a drive fluid. The drive fluid is a continuous fluid. The drive fluid may comprise the same substance as the carrier fluid (e.g., a fluorocarbon oil). For example, if a library consists of ten pico-liter droplets is driven into an inlet channel on a microfluidic substrate with a drive fluid at a rate of 10,000 pico-liters per second, then nominally the frequency at which the droplets are expected to enter the confluence point is 1000 per second. However, in practice droplets pack with oil between them that slowly drains. Over time the carrier fluid drains from the library droplets and the number density of the droplets (number/mL) increases. Hence, a simple fixed rate of infusion for the drive fluid does not provide a uniform rate of introduction of the droplets into the microfluidic channel in the substrate. Moreover, library-to-library variations in the mean library droplet volume result in a shift in the frequency of droplet introduction at the confluence point. Thus, the lack of uniformity of droplets that results from sample variation and oil drainage provides another problem to be solved. For example if the nominal droplet volume is expected to be 10 pico-liters in the library, but varies from 9 to 11 pico-liters from library-to-library then a 10,000 pico-liter/second infusion rate will nominally produce a range in frequencies from 900 to 1,100 droplet per second. In short, sample to sample variation in the composition of dispersed phase for droplets made on chip, a tendency for the number density of library droplets to increase over time and library-to-library variations in mean droplet volume severely limit the extent to which frequencies of droplets may be reliably matched at a confluence by simply using fixed infusion rates. In addition, these limitations also have an impact on the extent to which volumes may be reproducibly combined. Combined with typical variations in pump flow rate precision and variations in channel dimensions, systems are severely limited without a means to compensate on a run-to-run basis. The foregoing facts not only illustrate a problem to be solved, but also demonstrate a need for a method of instantaneous regulation of microfluidic control over microdroplets within a microfluidic channel. Combinations of surfactant(s) and oils must be developed to facilitate generation, storage, and manipulation of droplets to maintain the unique chemical/biochemical/biological environment within each droplet of a diverse library. Therefore, the surfactant and oil combination must (1) stabilize droplets against uncontrolled coalescence during the drop forming process and subsequent collection and storage, (2) minimize transport of any droplet contents to the oil phase and/or between droplets, and (3) maintain chemical and biological inertness with contents of each droplet (e.g., no adsorption or reaction of encapsulated contents at the oil-water interface, and no adverse effects on biological or chemical constituents in the droplets). In addition to the requirements on the droplet library function and stability, the surfactant-in-oil solution must be coupled with the fluid physics and materials associated with the platform. Specifically, the oil solution must not swell, dissolve, or degrade the materials used to construct the microfluidic chip, and the physical properties of the oil (e.g., viscosity, boiling point, etc.) must be suited for the flow and operating conditions of the platform. Droplets formed in oil without surfactant are not stable to permit coalescence, so surfactants must be dissolved in the oil that is used as the continuous phase for the emulsion library. Surfactant molecules are amphiphilic—part of the molecule is oil soluble, and part of the molecule is water soluble. When a water-oil interface is formed at the nozzle of a microfluidic chip for example in the inlet module described herein, surfactant molecules that are dissolved in the oil phase adsorb to the interface. The hydrophilic portion of the molecule resides inside the droplet and the fluorophilic portion of the molecule decorates the exterior of the droplet. The surface tension of a droplet is reduced when the interface is populated with surfactant, so the stability of an emulsion is improved. In addition to stabilizing the droplets against coalescence, the surfactant should be inert to the contents of each droplet and the surfactant should not promote transport of encapsulated components to the oil or other droplets. A droplet library may be made up of a number of library elements that are pooled together in a single collection (see, e.g., US Patent Publication No. 2010002241). Libraries may vary in complexity from a single library element to 1015 library elements or more. Each library element may be one or more given components at a fixed concentration. The element may be, but is not limited to, cells, organelles, virus, bacteria, yeast, beads, amino acids, proteins, polypeptides, nucleic acids, polynucleotides or small molecule chemical compounds. The element may contain an identifier such as a label. The terms "droplet library" or "droplet libraries" are also referred to herein as an "emulsion library" or "emulsion libraries." These terms are used interchangeably throughout the specification. A cell library element may include, but is not limited to, hybridomas, B-cells, primary cells, cultured cell lines, cancer cells, stem cells, cells obtained from tissue, or any other cell type. Cellular library elements are prepared by encapsulating a number of cells from one to hundreds of thousands in individual droplets. The number of cells encapsulated is usually given by Poisson statistics from the number density of cells and volume of the droplet. However, in some cases the number deviates from Poisson statistics as described in Edd et al., "Controlled encapsulation of single-cells into monodisperse picolitre drops." Lab Chip, 8(8): 1262-1264, 2008. The discrete nature of cells allows for libraries to be prepared in mass with a plurality of cellular variants all present in a single starting media and then that media is broken up into individual droplet capsules that contain at most one cell. These individual droplets capsules are then combined or pooled to form a library consisting of unique library elements. Cell division subsequent to, or in some embodiments following, encapsulation produces a clonal library element. A bead based library element may contain one or more beads, of a given type and may also contain other reagents, such as antibodies, enzymes or other proteins. In the case where all library elements contain different types of beads, but the same surrounding media, the library elements may all be prepared from a single starting fluid or have a variety of starting fluids. In the case of cellular libraries prepared in mass from a collection of variants, such as genomically modified, yeast or bacteria cells, the library elements will be prepared from a variety of starting fluids. Often it is desirable to have exactly one cell per droplet with only a few droplets containing more than one cell when starting with a plurality of cells or yeast or bacteria, engineered to produce variants on a protein. In some cases, variations from Poisson statistics may be achieved to provide an enhanced loading of droplets such that there are more droplets with exactly one cell per droplet and few exceptions of empty droplets or droplets containing more than one cell. Examples of droplet libraries are collections of droplets that have different contents, ranging from beads, cells, small molecules, DNA, primers, antibodies. Smaller droplets may be in the order of femtoliter (fL) volume drops, which are especially contemplated with the droplet dispensers. The volume may range from about 5 to about 600 fL. The larger droplets range in size from roughly 0.5 micron to 500 micron in diameter, which corresponds to about 1 pico liter to 1 nano liter. However, droplets may be as small as 5 microns and as large as 500 microns. Preferably, the droplets are at less than 100 microns, about 1 micron to about 100 microns in diameter. The most preferred size is about 20 to 40 microns in diameter (10 to 100 picoliters). The preferred properties examined of droplet libraries include osmotic pressure balance, uniform size, and size ranges. The droplets within the emulsion libraries of the present invention may be contained within an immiscible oil which may comprise at least one fluorosurfactant. In some embodiments, the fluorosurfactant within the immiscible fluorocarbon oil may be a block copolymer consisting of one or more perfluorinated polyether (PFPE) blocks and one or more polyethylene glycol (PEG) blocks. In other embodiments, the fluorosurfactant is a triblock copolymer consisting of a PEG center block covalently bound to two PFPE blocks by amide linking groups. The presence of the fluorosurfactant (similar to uniform size of the droplets in the library) is critical to maintain the stability and integrity of the droplets and is also essential for the subsequent use of the droplets within the library for the various biological and chemical assays described herein. Fluids (e.g., aqueous fluids, immiscible oils, etc.) and other surfactants that may be utilized in the droplet libraries of the present invention are described in greater detail herein. The present invention can accordingly involve an emulsion library which may comprise a plurality of aqueous droplets within an immiscible oil (e.g., fluorocarbon oil) which may comprise at least one fluorosurfactant, wherein each droplet is uniform in size and may comprise the same aqueous fluid and may comprise a different library element. The present invention also provides a method for forming the emulsion library which may comprise providing a single aqueous fluid which may comprise different library elements, encapsulating each library element into an aqueous droplet within an immiscible fluorocarbon oil which may comprise at least one fluorosurfactant, wherein each droplet is uniform in size and may comprise the same aqueous fluid and may comprise a different library element, and pooling the aqueous droplets within an immiscible fluorocarbon oil which may comprise at least one fluorosurfactant, thereby forming an emulsion library. For example, in one type of emulsion library, all different types of elements (e.g., cells or beads), may be pooled in a single source contained in the same medium. After the initial pooling, the cells or beads are then encapsulated in droplets to generate a library of droplets wherein each droplet with a different type of bead or cell is a different library element. The dilution of the initial solution enables the encapsulation process. In some embodiments, the droplets formed will either contain a single cell or bead or will not contain anything, i.e., be empty. In other embodiments, the droplets formed will contain multiple copies of a library element. The cells or beads being encapsulated are generally variants on the same type of cell or bead. In another example, the emulsion library may comprise a plurality of aqueous droplets within an immiscible fluorocarbon oil, wherein a single molecule may be encapsulated, such that there is a single molecule contained within a droplet for every 20-60 droplets produced (e.g., 20, 25, 30, 35, 40, 45, 50, 55, 60 droplets, or any integer in between). Single molecules may be encapsulated by diluting the solution containing the molecules to such a low concentration that the encapsulation of single molecules is enabled. In one specific example, a LacZ plasmid DNA was encapsulated at a concentration of 20 fM after two hours of incubation such that there was about one gene in 40 droplets, where 10 μm droplets were made at 10 kHz per second. Formation of these libraries rely on limiting dilutions.

The present invention also provides an emulsion library which may comprise at least a first aqueous droplet and at least a second aqueous droplet within a fluorocarbon oil which may comprise at least one fluorosurfactant, wherein the at least first and the at least second droplets are uniform in size and comprise a different aqueous fluid and a different library element. The present invention also provides a method for forming the emulsion library which may comprise providing at least a first aqueous fluid which may comprise at least a first library of elements, providing at least a second aqueous fluid which may comprise at least a second library of elements, encapsulating each element of said at least first library into at least a first aqueous droplet within an immiscible fluorocarbon oil which may comprise at least one fluorosurfactant, encapsulating each element of said at least second library into at least a second aqueous droplet within an immiscible fluorocarbon oil which may comprise at least one fluorosurfactant, wherein the at least first and the at least second droplets are uniform in size and may comprise a different aqueous fluid and a different library element, and pooling the at least first aqueous droplet and the at least second aqueous droplet within an immiscible fluorocarbon oil which may comprise at least one fluorosurfactant thereby forming an emulsion library. One of skill in the art will recognize that methods and systems of the invention are not preferably practiced as to cells, mutations, etc as herein disclosed, but that the invention need not be limited to any particular type of sample, and methods and systems of the invention may be used with any type of organic, inorganic, or biological molecule (see, e.g, US Patent Publication No. 20120122714). In particular embodiments the sample may include nucleic acid target molecules. Nucleic acid molecules may be synthetic or derived from naturally occurring sources. In one embodiment, nucleic acid molecules may be isolated from a biological sample containing a variety of other components, such as proteins, lipids and non-template nucleic acids. Nucleic acid target molecules may be obtained from any cellular material, obtained from an animal, plant, bacterium, fungus, or any other cellular organism. In certain embodiments, the nucleic acid target molecules may be obtained from a single cell. Biological samples for use in the present invention may include viral particles or preparations. Nucleic acid target molecules may be obtained directly from an organism or from a biological sample obtained from an organism, e.g., from blood, urine, cerebrospinal fluid, seminal fluid, saliva, sputum, stool and tissue. Any tissue or body fluid specimen may be used as a source for nucleic acid for use in the invention. Nucleic acid target molecules may also be isolated from cultured cells, such as a primary cell culture or a cell line. The cells or tissues from which target nucleic acids are obtained may be infected with a virus or other intracellular pathogen. A sample may also be total RNA extracted from a biological specimen, a cDNA library, viral, or genomic DNA. Generally, nucleic acid may be extracted from a biological sample by a variety of techniques such as those described by Maniatis, et al., Molecular Cloning: A Laboratory Manual, Cold Spring Harbor, N.Y., pp. 280-281 (1982). Nucleic acid molecules may be single-stranded, double-stranded, or double-stranded with single-stranded regions (for example, stem- and loop-structures). Nucleic acid obtained from biological samples typically may be fragmented to produce suitable fragments for analysis. Target nucleic acids may be fragmented or sheared to desired length, using a variety of mechanical, chemical and/or enzymatic methods. DNA may be randomly sheared via sonication, e.g. Covaris method, brief exposure to a DNase, or using a mixture of one or more restriction enzymes, or a transposase or nicking enzyme. RNA may be fragmented by brief exposure to an RNase, heat plus magnesium, or by shearing. The RNA may be converted to cDNA. If fragmentation is employed, the RNA may be converted to cDNA before or after fragmentation. In one embodiment, nucleic acid from a biological sample is fragmented by sonication. In another embodiment, nucleic acid is fragmented by a hydroshear instrument. Generally, individual nucleic acid target molecules may be from about 40 bases to about 40 kb. Nucleic acid molecules may be single-stranded, double-stranded, or double-stranded with single-stranded regions (for example, stem- and loop-structures). A biological sample as described herein may be homogenized or fractionated in the presence of a detergent or surfactant. The concentration of the detergent in the buffer may be about 0.05% to about 10.0%. The concentration of the detergent may be up to an amount where the detergent remains soluble in the solution. In one embodiment, the concentration of the detergent is between 0.1% to about 2%. The detergent, particularly a mild one that is nondenaturing, may act to solubilize the sample. Detergents may be ionic or nonionic. Examples of nonionic detergents include triton, such as the Triton™ X series (Triton™ X-100 t-Oct-C6H4-(OCH2-CH2)xOH, x=9-10, Triton™ X-100R, Triton™ X-114 x=7-8), octyl glucoside, polyoxyethylene(9)dodecyl ether, digitonin, IGEPAL™ CA630 octylphenyl polyethylene glycol, n-octyl-beta-D-glucopyranoside (betaOG), n-dodecyl-beta, Tween™. 20 polyethylene glycol sorbitan monolaurate, Tween™ 80 polyethylene glycol sorbitan monooleate, polidocanol, n-dodecyl beta-D-maltoside (DDM), NP-40 nonylphenyl polyethylene glycol, C12E8 (octaethylene glycol n-dodecyl monoether), hexaethyleneglycol mono-n-tetradecyl ether (C14E06), octyl-beta-thioglucopyranoside (octyl thioglucoside, OTG), Emulgen, and polyoxyethylene 10 lauryl ether (C12E10). Examples of ionic detergents (anionic or cationic) include deoxycholate, sodium dodecyl sulfate (SDS), N-lauroylsarcosine, and cetyltrimethylammoniumbromide (CTAB). A zwitterionic reagent may also be used in the purification schemes of the present invention, such as Chaps, zwitterion 3-14, and 3-[(3-cholamidopropyl)dimethylammonio]-1-propanesulfonate. It is contemplated also that urea may be added with or without another detergent or surfactant. Lysis or homogenization solutions may further contain other agents, such as reducing agents. Examples of such reducing agents include dithiothreitol (DTT), β-mercaptoethanol, DTE, GSH, cysteine, cysteamine, tricarboxyethyl phosphine (TCEP), or salts of sulfurous acid. Size selection of the nucleic acids may be performed to remove very short fragments or very long fragments. The nucleic acid fragments may be partitioned into fractions which may comprise a desired number of fragments using any suitable method known in the art. Suitable methods to limit the fragment size in each fragment are known in the art. In various embodiments of the invention, the fragment size is limited to between about 10 and about 100 Kb or longer. A sample in or as to the instant invention may include individual target proteins, protein complexes, proteins with translational modifications, and protein/nucleic acid complexes. Protein targets include peptides, and also include enzymes, hormones, structural components such as viral capsid proteins, and antibodies. Protein targets may be synthetic or derived from naturally-occurring sources. The invention protein targets may be isolated from biological samples containing a variety of other components including lipids, non-template nucleic acids, and nucleic acids. Protein targets may be obtained from an animal, bacterium, fungus, cellular organism, and single cells. Protein targets may be obtained directly from an organism or from a biological sample obtained from the organism, including bodily fluids such as blood, urine, cerebrospinal fluid, seminal fluid, saliva, sputum, stool and tissue. Protein targets may also be obtained from cell and tissue lysates and biochemical fractions. An individual protein is an isolated polypeptide chain. A protein complex includes two or polypeptide chains. Samples may include proteins with post translational modifications including but not limited to phosphorylation, methionine oxidation, deamidation, glycosylation, ubiquitination, carbamylation, s-carboxymethylation, acetylation, and methylation. Protein/nucleic acid complexes include cross-linked or stable protein-nucleic acid complexes. Extraction or isolation of individual proteins, protein complexes, proteins with translational modifications, and protein/nucleic acid complexes is performed using methods known in the art.

The invention can thus involve forming sample droplets. The droplets are aqueous droplets that are surrounded by an immiscible carrier fluid. Methods of forming such droplets are shown for example in Link et al. (U.S. patent application numbers 2008/0014589, 2008/0003142, and 2010/0137163), Stone et al. (U.S. Pat. No. 7,708,949 and U.S. patent application number 2010/0172803), Anderson et al. (U.S. Pat. No. 7,041,481 and which reissued as RE41,780) and European publication number EP2047910 to Raindance Technologies Inc. The content of each of which is incorporated by reference herein in its entirety. The present invention may relates to systems and methods for manipulating droplets within a high throughput microfluidic system. A microfluid droplet encapsulates a differentiated cell. The cell is lysed and its mRNA is hybridized onto a capture bead containing barcoded oligo dT primers on the surface, all inside the droplet. The barcode is covalently attached to the capture bead via a flexible multi-atom linker like PEG. In a preferred embodiment, the droplets are broken by addition of a fluorosurfactant (like perfluorooctanol), washed, and collected. A reverse transcription (RT) reaction is then performed to convert each cell's mRNA into a first strand cDNA that is both uniquely barcoded and covalently linked to the mRNA capture bead. Subsequently, a universal primer via a template switching reaction is amended using conventional library preparation protocols to prepare an RNA-Seq library. Since all of the mRNA from any given cell is uniquely barcoded, a single library is sequenced and then computationally resolved to determine which mRNAs came from which cells. In this way, through a single sequencing run, tens of thousands (or more) of distinguishable transcriptomes can be simultaneously obtained. The oligonucleotide sequence may be generated on the bead surface. During these cycles, beads were removed from the synthesis column, pooled, and aliquoted into four equal portions by mass; these bead aliquots were then placed in a separate synthesis column and reacted with either dG, dC, dT, or dA phosphoramidite. In other instances, dinucleotide, trinucleotides, or oligonucleotides that are greater in length are used, in other instances, the oligo-dT tail is replaced by gene specific oligonucleotides to prime specific targets (singular or plural), random sequences of any length for the capture of all or specific RNAs. This process was repeated 12 times for a total of $4^{12}$=16,777,216 unique barcode sequences. Upon completion of these cycles, 8 cycles of degenerate oligonucleotide synthesis were performed on all the beads, followed by 30 cycles of dT addition. In other embodiments, the degenerate synthesis is omitted, shortened (less than 8 cycles), or extended (more than 8 cycles); in others, the 30 cycles of dT addition are replaced with gene specific primers (single target or many targets) or a degenerate sequence. The aforementioned microfluidic system is regarded as the reagent delivery system microfluidic library printer or droplet library printing system of the present invention. Droplets are formed as sample fluid flows from droplet generator which contains lysis reagent and barcodes through microfluidic outlet channel which contains oil, towards junction. Defined volumes of loaded reagent emulsion, corresponding to defined numbers of droplets, are dispensed on-demand into the flow stream of carrier fluid. The sample fluid may typically comprise an aqueous buffer solution, such as ultrapure water (e.g., 18 mega-ohm resistivity, obtained, for example by column chromatography), 10 mM Tris HCl and 1 mM EDTA (TE) buffer, phosphate buffer saline (PBS) or acetate buffer. Any liquid or buffer that is physiologically compatible with nucleic acid molecules can be used. The carrier fluid may include one that is immiscible with the sample fluid. The carrier fluid can be a non-polar solvent, decane (e.g., tetradecane or hexadecane), fluorocarbon oil, silicone oil, an inert oil such as hydrocarbon, or another oil (for example, mineral oil). The carrier fluid may contain one or more additives, such as agents which reduce surface tensions (surfactants). Surfactants can include Tween, Span, fluorosurfactants, and other agents that are soluble in oil relative to water. In some applications, performance is improved by adding a second surfactant to the sample fluid. Surfactants can aid in controlling or optimizing droplet size, flow and uniformity, for example by reducing the shear force needed to extrude or inject droplets into an intersecting channel. This can affect droplet volume and periodicity, or the rate or frequency at which droplets break off into an intersecting channel. Furthermore, the surfactant can serve to stabilize aqueous emulsions in fluorinated oils from coalescing. Droplets may be surrounded by a surfactant which stabilizes the droplets by reducing the surface tension at the aqueous oil interface. Preferred surfactants that may be added to the carrier fluid include, but are not limited to, surfactants such as sorbitan-based carboxylic acid esters (e.g., the "Span" surfactants, Fluka Chemika), including sorbitan monolaurate (Span 20), sorbitan monopalmitate (Span 40), sorbitan monostearate (Span 60) and sorbitan monooleate (Span 80), and perfluorinated polyethers (e.g., DuPont Krytox 157 FSL, FSM, and/or FSH). Other non-limiting examples of non-ionic surfactants which may be used include polyoxyethylenated alkylphenols (for example, nonyl-, p-dodecyl-, and dinonylphenols), polyoxyethylenated straight chain alcohols, polyoxyethylenated polyoxypropylene glycols, polyoxyethylenated mercaptans, long chain carboxylic acid esters (for example, glyceryl and polyglyceryl esters of natural fatty acids, propylene glycol, sorbitol, polyoxyethylenated sorbitol esters, polyoxyethylene glycol esters, etc.) and alkanolamines (e.g., diethanolamine-fatty acid condensates and isopropanolamine-fatty acid condensates). In some cases, an apparatus for creating a single-cell sequencing library via a microfluidic system provides for volume-driven flow, wherein constant volumes are injected over time. The pressure in fluidic channels is a function of injection rate and channel dimensions. In one embodiment, the device provides an oil/surfactant inlet; an inlet for an analyte; a filter, an inlet for mRNA capture microbeads and lysis reagent; a carrier fluid channel which connects the inlets; a resistor; a constriction for droplet pinch-off; a mixer; and an outlet for drops. In an embodiment the invention provides apparatus for creating a single-cell sequencing library via a microfluidic system, which may comprise: an oil-surfactant inlet which may comprise a filter and a carrier fluid channel, wherein said carrier fluid channel may further comprise a resistor; an inlet for an analyte which may comprise a filter and a carrier fluid channel, wherein said carrier fluid channel may further comprise a resistor; an inlet for mRNA capture microbeads and lysis reagent which may comprise a filter and a carrier fluid channel, wherein said carrier fluid channel further may comprise a resistor; said carrier fluid channels have a carrier fluid flowing therein at an adjustable or predetermined flow rate; wherein each said carrier fluid channels merge at a junction; and said junction being connected to a mixer, which contains an outlet for drops. Accordingly, an apparatus for creating a single-cell sequencing library via a microfluidic system microfluidic flow scheme for single-cell RNA-seq is envisioned. Two channels, one carrying cell suspensions, and the other carrying uniquely barcoded mRNA capture bead, lysis buffer and library preparation reagents meet at a junction and is immediately co-encapsulated in an inert carrier oil, at the rate of one cell and one bead per drop. In each drop, using the bead's barcode tagged oligonucleotides as cDNA template, each mRNA is tagged with a unique, cell-specific identifier. The invention also encompasses use of a Drop-Seq library of a mixture of mouse and human cells. The carrier fluid may be caused to flow through the outlet channel so that the surfactant in the carrier fluid coats the channel walls. The fluorosurfactant can be prepared by reacting the perflourinated polyether DuPont Krytox 157 FSL, FSM, or FSH with aqueous ammonium hydroxide in a volatile fluorinated solvent. The solvent and residual water and ammonia can be removed with a rotary evaporator. The surfactant can then be dissolved (e.g., 2.5 wt %) in a fluorinated oil (e.g., Fluorinert (3M)), which then serves as the carrier fluid. Activation of sample fluid reservoirs to produce regent droplets is based on the concept of dynamic reagent delivery (e.g., combinatorial barcoding) via an on demand capability. The on demand feature may be provided by one of a variety of technical capabilities for releasing delivery droplets to a primary droplet, as described herein. From this disclosure and herein cited documents and knowledge in the art, it is within the ambit of the skilled person to develop flow rates, channel lengths, and channel geometries; and establish droplets containing random or specified reagent combinations can be generated on demand and merged with the "reaction chamber" droplets containing the samples/cells/substrates of interest. By incorporating a plurality of unique tags into the additional droplets and joining the tags to a solid support designed to be specific to the primary droplet, the conditions that the primary droplet is exposed to may be encoded and recorded. For example, nucleic acid tags can be sequentially ligated to create a sequence reflecting conditions and order of same. Alternatively, the tags can be added independently appended to solid support. Non-limiting examples of a dynamic labeling system that may be used to bioinformatically record information can be found at US Provisional Patent Application entitled "Compositions and Methods for Unique Labeling of Agents" filed Sep. 21, 2012 and Nov. 29, 2012. In this way, two or more droplets may be exposed to a variety of different conditions, where each time a droplet is exposed to a condition, a nucleic acid encoding the condition is added to the droplet each ligated together or to a unique solid support associated with the droplet such that, even if the droplets with different histories are later combined, the conditions of each of the droplets are remain available through the different nucleic acids. Non-limiting examples of methods to evaluate response to exposure to a plurality of conditions can be found at US Provisional Patent Application entitled "Systems and Methods for Droplet Tagging" filed Sep. 21, 2012. Accordingly, in or as to the invention it is envisioned that there can be the dynamic generation of molecular barcodes (e.g., DNA oligonucleotides, fluorophores, etc.) either independent from or in concert with the controlled delivery of various compounds of interest (drugs, small molecules, siRNA, CRISPR guide RNAs, reagents, etc.). For example, unique molecular barcodes can be created in one array of nozzles while individual compounds or combinations of compounds can be generated by another nozzle array. Barcodes/compounds of interest can then be merged with cell-containing droplets. An electronic record in the form of a computer log file is kept to associate the barcode delivered with the downstream reagent(s) delivered. This methodology makes it possible to efficiently screen a large population of cells for applications such as single-cell drug screening, controlled perturbation of regulatory pathways, etc. The device and techniques of the disclosed invention facilitate efforts to perform studies that require data resolution at the single cell (or single molecule) level and in a cost effective manner. The invention envisions a high throughput and high resolution delivery of reagents to individual emulsion droplets that may contain cells, nucleic acids, proteins, etc. through the use of monodisperse aqueous droplets that are generated one by one in a microfluidic chip as a water-in-oil emulsion. Being able to dynamically track individual cells and droplet treatments/combinations during life cycle experiments, and having an ability to create a library of emulsion droplets on demand with the further capability of manipulating the droplets through the disclosed process(es) are advantageous. In the practice of the invention there can be dynamic tracking of the droplets and create a history of droplet deployment and application in a single cell based environment. Droplet generation and deployment is produced via a dynamic indexing strategy and in a controlled fashion in accordance with disclosed embodiments of the present invention. Microdroplets can be processed, analyzed and sorted at a highly efficient rate of several thousand droplets per second, providing a powerful platform which allows rapid screening of millions of distinct compounds, biological probes, proteins or cells either in cellular models of biological mechanisms of disease, or in biochemical, or pharmacological assays. A plurality of biological assays as well as biological synthesis are contemplated. Polymerase chain reactions (PCR) are contemplated (see, e.g., US Patent Publication No. 20120219947). Methods of the invention may be used for merging sample fluids for conducting any type of chemical reaction or any type of biological assay. There may be merging sample fluids for conducting an amplification reaction in a droplet. Amplification refers to production of additional copies of a nucleic acid sequence and is generally carried out using polymerase chain reaction or other technologies well known in the art (e.g., Dieffenbach and Dveksler, PCR Primer, a Laboratory Manual, Cold Spring Harbor Press, Plainview, N.Y. [1995]). The amplification reaction may be any amplification reaction known in the art that amplifies nucleic acid molecules, such as polymerase chain reaction, nested polymerase chain reaction, polymerase chain reaction-single strand conformation polymorphism, ligase chain reaction (Barany F. (1991) PNAS 88:189-193; Barany F. (1991) PCR Methods and Applications 1:5-16), ligase detection reaction (Barany F. (1991) PNAS 88:189-193), strand displacement amplification and restriction fragments length polymorphism, transcription based amplification system, nucleic acid sequence-based amplification, rolling circle amplification, and hyper-branched rolling circle amplification. In certain embodiments, the amplification reaction is the polymerase chain reaction. Polymerase chain reaction (PCR) refers to methods by K. B. Mullis (U.S. Pat. Nos. 4,683,195 and 4,683,202, hereby incorporated by reference) for increasing concentration of a segment of a target sequence in a mixture of genomic DNA without cloning or purification. The process for amplifying the target sequence includes introducing an excess of oligonucleotide primers to a DNA mixture containing a desired target sequence, followed by a precise sequence of thermal cycling in the presence of a DNA polymerase. The primers are complementary to their respective strands of the double stranded target sequence. To effect amplification, primers are annealed to their complementary sequence within the target molecule. Following annealing, the primers are extended with a polymerase so as to form a new pair of complementary strands. The steps of denaturation, primer annealing and polymerase extension may be repeated many times (i.e., denaturation, annealing and extension constitute one cycle; there may be numerous cycles) to obtain a high concentration of an amplified segment of a desired target sequence. The length of the amplified segment of the desired target sequence is determined by relative positions of the primers with respect to each other, and therefore, this length is a controllable parameter. Methods for performing PCR in droplets are shown for example in Link et al. (U.S. Patent application numbers 2008/0014589, 2008/0003142, and 2010/0137163), Anderson et al. (U.S. Pat. No. 7,041,481 and which reissued as RE41,780) and European publication number EP2047910 to Raindance Technologies Inc. The content of each of which is incorporated by reference herein in its entirety. The first sample fluid contains nucleic acid templates. Droplets of the first sample fluid are formed as described above. Those droplets will include the nucleic acid templates. In certain embodiments, the droplets will include only a single nucleic acid template, and thus digital PCR may be conducted. The second sample fluid contains reagents for the PCR reaction. Such reagents generally include Taq polymerase, deoxynucleotides of type A, C, G and T, magnesium chloride, and forward and reverse primers, all suspended within an aqueous buffer. The second fluid also includes detectably labeled probes for detection of the amplified target nucleic acid, the details of which are discussed below. This type of partitioning of the reagents between the two sample fluids is not the only possibility. In some instances, the first sample fluid will include some or all of the reagents necessary for the PCR whereas the second sample fluid will contain the balance of the reagents necessary for the PCR together with the detection probes. Primers may be prepared by a variety of methods including but not limited to cloning of appropriate sequences and direct chemical synthesis using methods well known in the art (Narang et al., Methods Enzymol., 68:90 (1979); Brown et al., Methods Enzymol., 68:109 (1979)). Primers may also be obtained from commercial sources such as Operon Technologies, Amersham Pharmacia Biotech, Sigma, and Life Technologies. The primers may have an identical melting temperature. The lengths of the primers may be extended or shortened at the 5' end or the 3' end to produce primers with desired melting temperatures. Also, the annealing position of each primer pair may be designed such that the sequence and, length of the primer pairs yield the desired melting temperature. The simplest equation for determining the melting temperature of primers smaller than 25 base pairs is the Wallace Rule (Td=2(A+T)+4(G+C)). Computer programs may also be used to design primers, including but not limited to Array Designer Software (Arrayit Inc.), Oligonucleotide Probe Sequence Design Software for Genetic Analysis (Olympus Optical Co.), NetPrimer, and DNAsis from Hitachi Software Engineering. The TM (melting or annealing temperature) of each primer is calculated using software programs such as Oligo Design, available from Invitrogen Corp.

A droplet containing the nucleic acid is then caused to merge with the PCR reagents in the second fluid according to methods of the invention described above, producing a droplet that includes Taq polymerase, deoxynucleotides of type A, C, G and T, magnesium chloride, forward and reverse primers, detectably labeled probes, and the target nucleic acid. Once mixed droplets have been produced, the droplets are thermal cycled, resulting in amplification of the target nucleic acid in each droplet. Droplets may be flowed through a channel in a serpentine path between heating and cooling lines to amplify the nucleic acid in the droplet. The width and depth of the channel may be adjusted to set the residence time at each temperature, which may be controlled to anywhere between less than a second and minutes. The three temperature zones may be used for the amplification reaction. The three temperature zones are controlled to result in denaturation of double stranded nucleic acid (high temperature zone), annealing of primers (low temperature zones), and amplification of single stranded nucleic acid to produce double stranded nucleic acids (intermediate temperature zones). The temperatures within these zones fall within ranges well known in the art for conducting PCR reactions. See for example, Sambrook et al. (Molecular Cloning, A Laboratory Manual, 3rd edition, Cold Spring Harbor Laboratory Press, Cold Spring Harbor, N.Y., 2001). The three temperature zones can be controlled to have temperatures as follows: 95° C. (TH), 55° C. (TL), 72° C. (TM). The prepared sample droplets flow through the channel at a controlled rate. The sample droplets first pass the initial denaturation zone (TH) before thermal cycling. The initial preheat is an extended zone to ensure that nucleic acids within the sample droplet have denatured successfully before thermal cycling. The requirement for a preheat zone and the length of denaturation time required is dependent on the chemistry being used in the reaction. The samples pass into the high temperature zone, of approximately 95° C., where the sample is first separated into single stranded DNA in a process called denaturation. The sample then flows to the low temperature, of approximately 55° C., where the hybridization process takes place, during which the primers anneal to the complementary sequences of the sample. Finally, as the sample flows through the third medium temperature, of approximately 72° C., the polymerase process occurs when the primers are extended along the single strand of DNA with a thermostable enzyme. The nucleic acids undergo the same thermal cycling and chemical reaction as the droplets pass through each thermal cycle as they flow through the channel. The total number of cycles in the device is easily altered by an extension of thermal zones. The sample undergoes the same thermal cycling and chemical reaction as it passes through N amplification cycles of the complete thermal device. In other aspects, the temperature zones are controlled to achieve two individual temperature zones for a PCR reaction. In certain embodiments, the two temperature zones are controlled to have temperatures as follows: 95° C. (TH) and 60° C. (TL). The sample droplet optionally flows through an initial preheat zone before entering thermal cycling. The preheat zone may be important for some chemistry for activation and also to ensure that double stranded nucleic acid in the droplets is fully denatured before the thermal cycling reaction begins. In an exemplary embodiment, the preheat dwell length results in approximately 10 minutes preheat of the droplets at the higher temperature. The sample droplet continues into the high temperature zone, of approximately 95° C., where the sample is first separated into single stranded DNA in a process called denaturation. The sample then flows through the device to the low temperature zone, of approximately 60° C., where the hybridization process takes place, during which the primers anneal to the complementary sequences of the sample. Finally the polymerase process occurs when the primers are extended along the single strand of DNA with a thermostable enzyme. The sample undergoes the same thermal cycling and chemical reaction as it passes through each thermal cycle of the complete device. The total number of cycles in the device is easily altered by an extension of block length and tubing. After amplification, droplets may be flowed to a detection module for detection of amplification products. The droplets may be individually analyzed and detected using any methods known in the art, such as detecting for the presence or amount of a reporter. Generally, a detection module is in communication with one or more detection apparatuses. Detection apparatuses may be optical or electrical detectors or combinations thereof. Examples of suitable detection apparatuses include optical waveguides, microscopes, diodes, light stimulating devices, (e.g., lasers), photo multiplier tubes, and processors (e.g., computers and software), and combinations thereof, which cooperate to detect a signal representative of a characteristic, marker, or reporter, and to determine and direct the measurement or the sorting action at a sorting module. Further description of detection modules and methods of detecting amplification products in droplets are shown in Link et al. (U.S. patent application numbers 2008/0014589, 2008/0003142, and 2010/0137163) and European publication number EP2047910 to Raindance Technologies Inc.

Examples of assays are also ELISA assays (see, e.g., US Patent Publication No. 20100022414). The present invention provides another emulsion library which may comprise a plurality of aqueous droplets within an immiscible fluorocarbon oil which may comprise at least one fluorosurfactant, wherein each droplet is uniform in size and may comprise at least a first antibody, and a single element linked to at least a second antibody, wherein said first and second antibodies are different. In one example, each library element may comprise a different bead, wherein each bead is attached to a number of antibodies and the bead is encapsulated within a droplet that contains a different antibody in solution. These antibodies may then be allowed to form "ELISA sandwiches," which may be washed and prepared for a ELISA assay. Further, these contents of the droplets may be altered to be specific for the antibody contained therein to maximize the results of the assay. Single-cell assays are also contemplated as part of the present invention (see, e.g., Ryan et al., Biomicrofluidics 5, 021501 (2011) for an overview of applications of microfluidics to assay individual cells). A single-cell assay may be contemplated as an experiment that quantifies a function or property of an individual cell when the interactions of that cell with its environment may be controlled precisely or may be isolated from the function or property under examination. The research and development of single-cell assays is largely predicated on the notion that genetic variation causes disease and that small subpopulations of cells represent the origin of the disease. Methods of assaying compounds secreted from cells, subcellular components, cell-cell or cell-drug interactions as well as methods of patterning individual cells are also contemplated within the present invention.

These and other technologies may be employed in or as to the practice of the instant invention.

Example 1

Materials and Methods

Briefly, gene expression profiles were measured at 18 time points (0.5 hr to 72 days) under Th17 conditions (IL-6, TGF-β1) or control (Th0) using Affymetrix microarrays HT_MG-430A. Differentially expressed genes were detected using a consensus over four inference methods, and cluster the genes using k-means, with an automatically derived k. Temporal regulatory interactions were inferred by looking for significant ($p<5*10^{-5}$ and fold enrichment >1.5) overlaps between the regulator's putative targets (e.g., based on ChIP-seq) and the target gene's cluster (using four clustering schemes). Candidates for perturbation were ordered lexicographically using network-based and expression-based features. Perturbations were done using SiNW for siRNA delivery. These methods are described in more detail below.

Mice: C57BL/6 wild-type (wt), $Mt^{-/-}$, $Irf1^{-/-}$, $Fas^{-/-}$, $Irf4^{-/-}$, and $Cd4^{Cre}$ mice were obtained from Jackson Laboratory (Bar Harbor, Me.). $Stat1^{-/-}$ and 129/Sv control mice were purchased from Taconic (Hudson, N.Y.). IL-$12r\beta1^{-/-}$ mice were provided by Dr. Pahan Kalipada from Rush University Medical Center. IL-$17Ra^{-/-}$ mice were provided by Dr. Jay Kolls from Louisiana State University/University of Pittsburgh. $Irf8^{fl/fl}$ mice were provided by Dr. Keiko Ozato from the National Institute of Health. Both $Irf4^{fl/fl}$ and $Irf8^{fl/fl}$ mice were crossed to $Cd4^{Cre}$ mice to generate $Cd4^{Cre}$x$Irf4^{fl/fl}$ and $Cd4^{Cre}$x$Irf8^{fl/fl}$ mice. All animals were housed and maintained in a conventional pathogen-free facility at the Harvard Institute of Medicine in Boston, Mass. (IUCAC protocols: 0311-031-14 (VKK) and 0609-058015 (AR)). All experiments were performed in accordance to the guidelines outlined by the Harvard Medical Area Standing Committee on Animals at the Harvard Medical School (Boston, Mass.). In addition, spleens from $Mina^{-/-}$ mice were provided by Dr. Mark Bix from St. Jude Children's Research Hospital (IACUC Protocol: 453). $Pou2af1^{-/-}$ mice were obtained from the laboratory of Dr. Robert Roeder (Kim, U. et al. The B-cell-specific transcription coactivator OCA-B/OBF-1/Bob-1 is essential for normal production of immunoglobulin isotypes. Nature 383, 542-547, doi:10.1038/383542a0 (1996)). Wild-type and $Oct1^{-/-}$ fetal livers were obtained at day E12.5 and transplanted into sub-lethally irradiated $Rag1^{-/-}$ mice as previously described (Wang, V. E., Tantin, D., Chen, J. & Sharp, P. A. B cell development and immunoglobulin transcription in Oct-1-deficient mice. Proc. Natl. Acad. Sci. U.S.A. 101, 2005-2010, doi:10.1073/pnas.0307304101 (2004)) (IACUC Protocol: 11-09003).

Cell sorting and in vitro T-cell differentiation in Petri dishes: Cd4+ T cells were purified from spleen and lymph nodes using anti-CD4 microbeads (Miltenyi Biotec) then stained in PBS with 1% FCS for 20 min at room temperature with anti-Cd4-PerCP, anti-Cd62l-APC, and anti-Cd44-PE antibodies (all Biolegend, CA).

Naïve $Cd4^+$ $Cd62l^{high}$ $Cd44^{low}$ T cells were sorted using the BD FACSAria cell sorter. Sorted cells were activated with plate bound anti-Cd3 (2 μg/ml) and anti-Cd28 (2 μg/ml) in the presence of cytokines. For Th17 differentiation: 2 ng/mL rhTGF-β1 (Miltenyi Biotec), 25 ng/mL rmIl-6 (Miltenyi Biotec), 20 ng/ml rmIl-23 (Miltenyi Biotec), and 20 ng/ml rmIL-β1 (Miltenyi Biotec). Cells were cultured for 0.5-72 hours and harvested for RNA, intracellular cytokine staining, and flow cytometry.

Flow cytometry and intracellular cytokine staining (ICC): Sorted naïve T cells were stimulated with phorbol 12-myristate 13-aceate (PMA) (50 ng/ml, Sigma-aldrich, MO), ionomycin (1 μg/ml, Sigma-aldrich, MO) and a protein transport inhibitor containing monensin (Golgistop) (BD Biosciences) for four hours prior to detection by staining with antibodies. Surface markers were stained in PBS with 1% FCS for 20 min at room temperature, then subsequently the cells were fixed in Cytoperm/Cytofix (BD Biosciences), permeabilized with Perm/Wash Buffer (BD Biosciences) and stained with Biolegend conjugated antibodies, i.e. Brilliant Violet 650™ anti-mouse IFN-γ (XMG1.2) and allophycocyanin-anti-IL-17A (TC11-18H10.1), diluted in Perm/Wash buffer as described (Bettelli, E. et al. Reciprocal developmental pathways for the generation of pathogenic effector TH17 and regulatory T cells. Nature 441, 235-238 (2006)) (FIG. 5, FIG. 16). To measure the time-course of RORγt protein expression, a phycoerythrin-conjugated anti-Retinoid-Related Orphan Receptor gamma was used (B2D), also from eBioscience (FIG. 16). FOXP3 staining for cells from knockout mice was performed with the FOXP3 staining kit by eBioscience (00-5523-00) in accordance with their "One step protocol for intracellular (nuclear) proteins". Data was collected using either a FACS Calibur or LSR II (Both BD Biosciences), then analyzed using Flow Jo software (Treestar) (Awasthi, A. et al. A dominant function for interleukin 27 in generating interleukin 10-producing anti-inflammatory T cells. Nature immunology 8, 1380-1389, doi:10.1038/ni1541 (2007); Awasthi, A. et al. Cutting edge: IL-23 receptor gfp reporter mice reveal distinct populations of IL-17-producing cells. J Immunol 182, 5904-5908, doi:10.4049/jimmunol.0900732 (2009)).

Quantification of cytokine secretion using Enzyme-Linked Immunosorbent Assay (ELISA): Naïve T cells from knockout mice and their wild type controls were cultured as described above, their supernatants were collected after 72 h, and cytokine concentrations were determined by ELISA (antibodies for IL-17 and IL-10 from BD Bioscience) or by cytometric bead array for the indicated cytokines (BD Bioscience), according to the manufacturers' instructions (FIG. 5, FIG. 16).

Figure 1B:
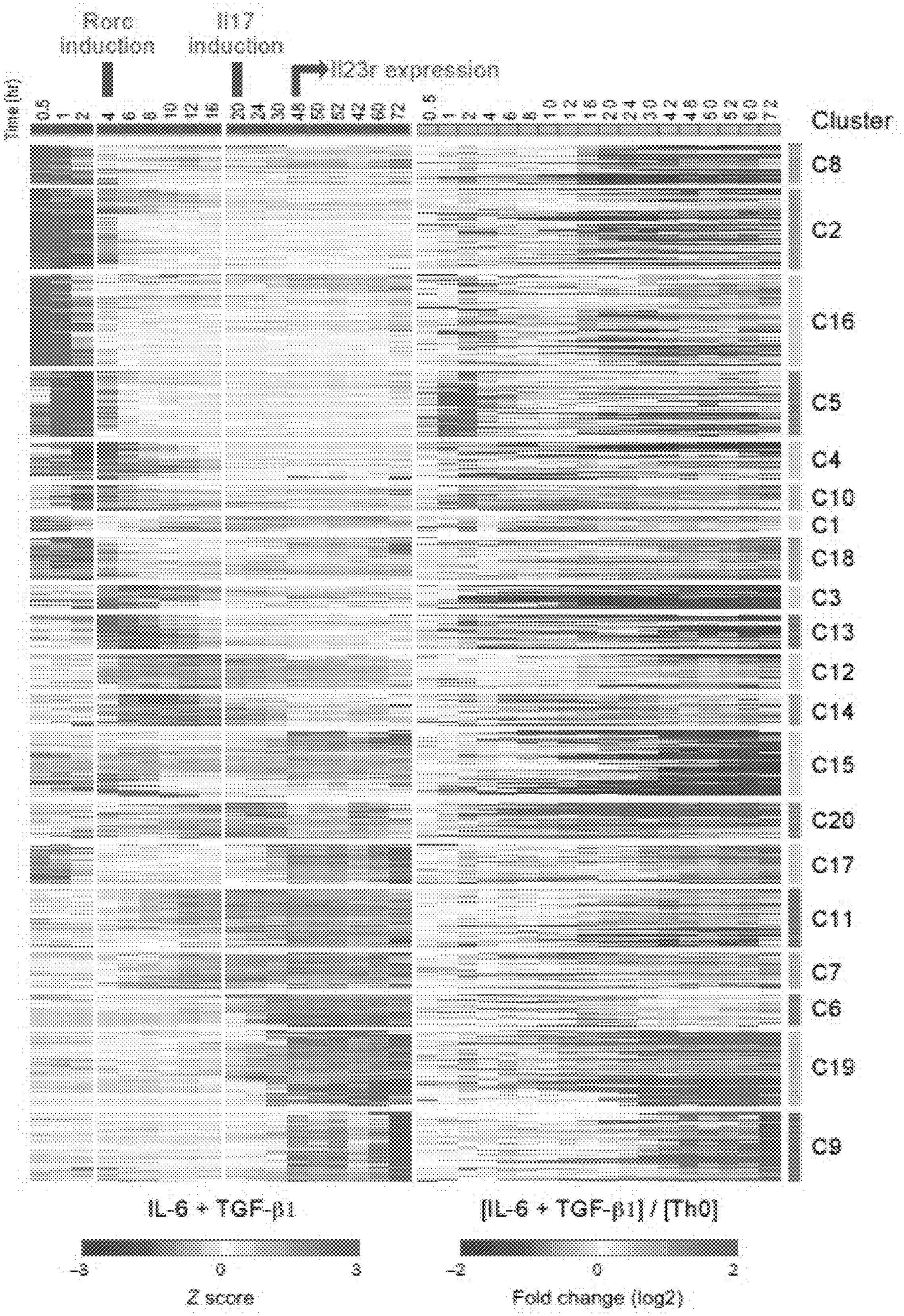
Figure 6A:
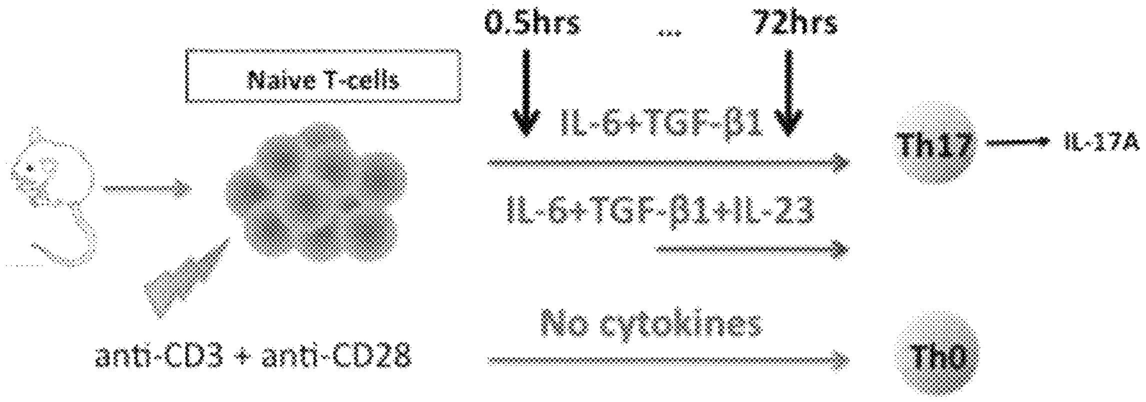
FIGS. 6A-6D are a series of graphs and illustrations depicting treatment of Naïve CD4+ T-cells with TGF-β1 and IL-6 for three days induces the differentiation of Th17 cells. A color version of these figures can be found in Yosef et al., "Dynamic regulatory network controlling Th17 cell differentiation, Nature, vol. 496: 461-468 (2013)/doi: 10.1038/nature11981.
Figure 6B:
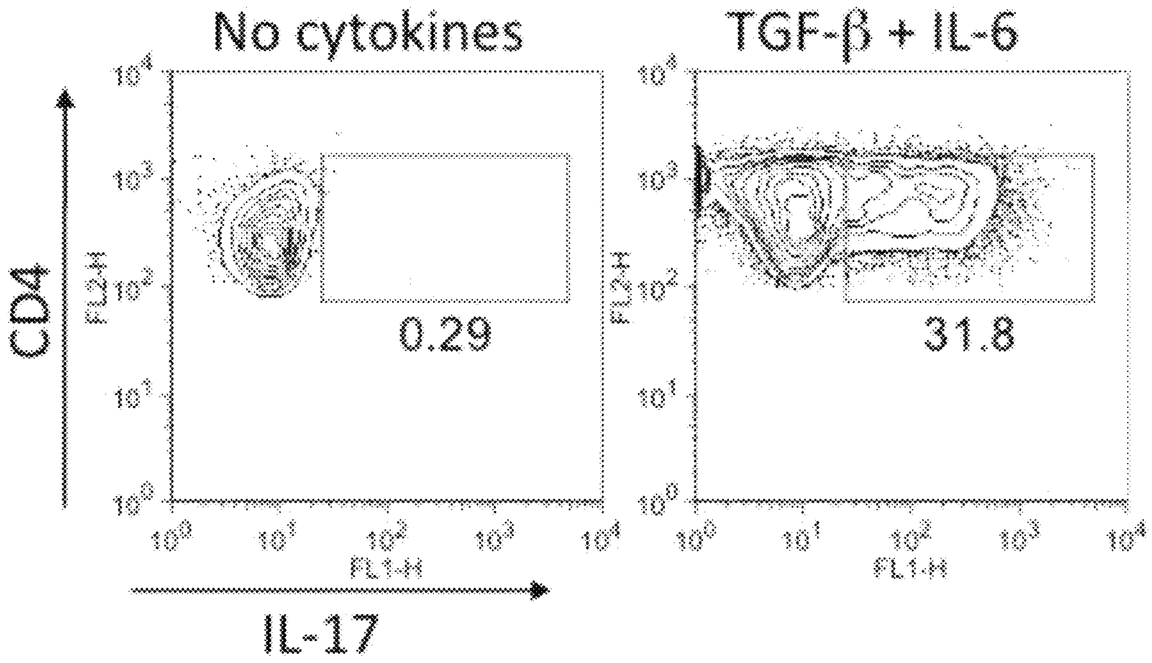
Figure 6C:
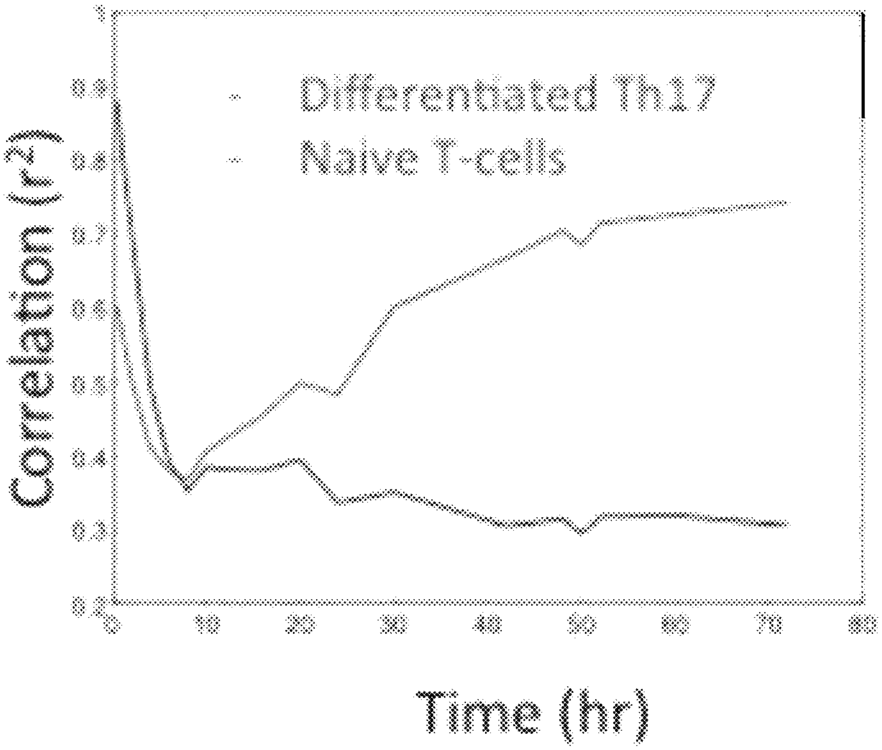

Microarray data: Naïve T cells were isolated from WT mice, and treated with IL-6 and TGF-β1. Affymetrix microarrays HT_MG-430A were used to measure the resulting mRNA levels at 18 different time points (0.5-72 h; FIG. 1*b*). In addition, cells treated initially with IL-6, TGF-β1 and with addition of IL-23 after 48 hr were profiled at five time points (50-72 h). As control, time- and culture-matched WT naïve T cells stimulated under Th0 conditions were used. Biological replicates were measured in eight of the eighteen time points (1 hr, 2 hr, 10 hr, 20 hr, 30 hr, 42 hr, 52 hr, 60 hr) with high reproducibility ($r^2>0.98$). For further validation, the differentiation time course was compared to published microarray data of Th17 cells and naïve T cells (Wei, G. et al. in Immunity Vol. 30 155-167 (2009)) (FIG. 6*c*). In an additional dataset naïve T cells were isolated from WT and $Il23r^{-/-}$ mice, and treated with IL-6, TGF-β1 and IL-23 and profiled at four different time points (49 hr, 54 hr, 65 hr, 72 hr). Expression data was preprocessed using the RMA algorithm followed by quantile normalization (Reich, M. et al. GenePattern 2.0. Nature genetics 38, 500-501, doi:10.1038/ng0506-500 (2006)).

Detecting differentially expressed genes: Differentially expressed genes (comparing to the Th0 control) were found using four methods: (1) Fold change. Requiring a 2-fold change (up or down) during at least two time points. (2) Polynomial fit. The EDGE software (Storey, J., Xiao, W., Leek, J., Tompkins, R. & Davis, R. in Proc. Natl. Acad. Sci. U.S.A. vol. 102 12837 (2005); Leek, J. T., Monsen, E., Dabney, A. R. & Storey, J. D. EDGE: extraction and analysis of differential gene expression. Bioinformatics 22, 507-508, doi:10.1093/bioinformatics/btk005 (2006)), designed to identify differential expression in time course data, was used with a threshold of q-value≤0.01. (3) Sigmoidal fit. An algorithm similar to EDGE while replacing the polynomials with a sigmoid function, which is often more adequate for modeling time course gene expression data (Chechik, G. & Koller, D. Timing of gene expression responses to environmental changes. J Comput Biol 16, 279-290, doi:10.1089/cmb.2008.13TT10.1089/cmb.2008.13TT [pii] (2009)), was used. A threshold of q-value≤0.01. (4) ANOVA was used. Gene expression is modeled by: time (using only time points for which there was more than one replicate) and treatment ("TGF-β1+IL-6" or "Th0"). The model takes into account each variable independently, as well as their interaction. Cases in which the p-value assigned with the treatment parameter or the interaction parameter passed an FDR threshold of 0.01 were reported.

Overall, substantial overlap between the methods (average of 82% between any pair of methods) observed. The differential expression score of a gene was defined as the number of tests that detected it. As differentially expressed genes, cases with differential expression score >3 were reported.

For the $Il23r^{-/-}$ time course (compared to the WT T cells) methods 1.3 (above) were used. Here, a fold change cutoff of 1.5 was used, and genes detected by at least two tests were reported.

Clustering: several ways for grouping the differentially expressed genes were considered, based on their time course expression data: (1) For each time point, two groups were defined: (a) all the genes that are over-expressed and (b) all the genes that are under-expressed relative to Th0 cells (see below); (2) For each time point, two groups were defined: (a) all the genes that are induced and (b) all the genes that are repressed, comparing to the previous time point; (3) K-means clustering using only the Th17 polarizing conditions. The minimal k was used, such that the within-cluster similarity (average Pearson correlation with the cluster's centroid) was higher than 0.75 for all clusters; and, (4) K-means clustering using a concatenation of the Th0 and Th17 profiles.

For methods (1, 2), to decide whether to include a gene, its original mRNA expression profiles (Th0, Th17), and their approximations as sigmoidal functions (Chechik, G. & Koller, D. Timing of gene expression responses to environmental changes. J Comput Biol 16, 279-290, doi:10.1089/cmb.2008.13TT10.1089/cmb.2008.13TT [pii] (2009)) (thus filtering transient fluctuations) were considered. The fold change levels (compared to Th0 (method 1) or to the previous time point (method 2)) were required to pass a cutoff defined as the minimum of the following three values: (1) 1.7; (2) mean+std of the histogram of fold changes across all time points; or (3) the maximum fold change across all time points. The clusters presented in FIG. 1*b* were obtained with method 4.

Regulatory network inference: potential regulators of Th17 differentiation were identified by computing overlaps between their putative targets and sets of differentially expressed genes grouped according to methods 1-4 above. regulator-target associations from several sources were assembled: (1) in vivo DNA binding profiles (typically measured in other cells) of 298 transcriptional regulators (Linhart, C., Halperin, Y. & Shamir, R. Transcription factor and microRNA motif discovery: the Amadeus platform and a compendium of metazoan target sets. Genome research 18, 1180-1189, doi:10.1101/gr.076117.108 (2008); Zheng, G. et al. ITFP: an integrated platform of mammalian transcription factors. Bioinformatics 24, 2416-2417, doi:10.1093/bioinformatics/btn439 (2008); Wilson, N. K. et al. Combinatorial transcriptional control in blood stem/progenitor cells: genome-wide analysis of ten major transcriptional regulators. Cell Stem Cell 7, 532-544, doi:S1934-5909(10) 00440-6 [pii]10.1016/j.stem.2010.07.016 (2010); Lachmann, A. et al. in Bioinformatics Vol. 26 2438-2444 (2010); Liberzon, A. et al. Molecular signatures database (MSigDB) 3.0. Bioinformatics 27, 1739-1740, doi:10.1093/bioinformatics/btr260 (2011); Jiang, C., Xuan, Z., Zhao, F. & Zhang, M. TRED: a transcriptional regulatory element database, new entries and other development. Nucleic Acids Res 35, D137-140 (2007)); (2) transcriptional responses to the knockout of 11 regulatory proteins (Awasthi et al., J. Immunol 2009; Schraml, B. U. et al. The AP-1 transcription factor Batf controls T(H)17 differentiation. Nature 460, 405-409, doi:nature08114 [pii]10.1038/nature08114 (2009); Shi, L. Z. et al. HIF1alpha-dependent glycolytic pathway orchestrates a metabolic checkpoint for the differentiation of TH17 and Treg cells. The Journal of experimental medicine 208, 1367-1376, doi:10.1084/jem.20110278 (2011); Yang, X. P. et al. Opposing regulation of the locus encoding IL-17 through direct, reciprocal actions of STAT3 and STAT5. Nature immunology 12, 247-254, doi:10.1038/ni.1995 (2011); Durant, L. et al. Diverse Targets of the Transcription Factor STAT3 Contribute to T Cell Pathogenicity and Homeostasis. Immunity 32, 605-615, doi:10.1016/j.immuni.2010.05.003 (2010); Jux, B., Kadow, S. & Esser, C. Langerhans cell maturation and contact hypersensitivity are impaired in aryl hydrocarbon receptor-null mice. Journal of immunology (Baltimore, Md.: 1950) 182, 6709-6717, doi:10.4049/jimmunol.0713344 (2009); Amit, I. et al. Unbiased reconstruction of a mammalian transcriptional network mediating pathogen responses. Science 326, 257-263, doi:10.1126/science.1179050 (2009); Xiao, S. et al. Retinoic acid increases Foxp3+ regulatory T cells and inhibits development of Th17 cells by enhancing TGF-beta-driven Smad3 signaling and inhibiting IL-6 and IL-23 receptor expression. J Immunol 181, 2277-2284, doi:181/4/2277 [pii] (2008)); (3) additional potential interactions obtained by applying the Ontogenet algorithm (Jojic et al., under review; regulatory model available at: to data from the mouse ImmGen consortium (January 2010 release (Heng, T. S. & Painter, M. W. The Immunological Genome Project: networks of gene expression in immune cells. Nature immunology 9, 1091-1094, doi:10.1038/ni1008-1091 (2008)), which includes 484 microarray samples from 159 cell subsets from the innate and adaptive immune system of mice; (4) a statistical analysis of cis-regulatory element enrichment in promoter regions (Elkon, R., Linhart, C., Sharan, R., Shamir, R. & Shiloh, Y. in Genome Research Vol. 13 773-780 (2003); Odabasioglu, A., Celik, M. & Pileggi, L. T. in Proceedings of the 1997 IEEE/ACM international conference on Computer-aided design 58-65 (IEEE Computer Society, San Jose, Calif., United States, 1997)); and, (5) the TF enrichment module of the IPA software. For every TF in the database, the statistical significance of the overlap between its putative targets and each of the groups defined above using a Fisher's exact test was computed. Cases where $p<5*10^{-5}$ and the fold enrichment >1.5 were included.

Each edge in the regulatory network was assigned a time stamp based on the expression profiles of its respective regulator and target nodes. For the target node, the time points at which a gene was either differentially expressed or significantly induced or repressed with respect to the previous time point (similarly to grouping methods 1 and 2 above) were considered. A regulator node was defined as 'absent' at a given time point if: (i) it was under expressed compared to Th0; or (ii) the expression is low (<20% of the maximum value in time) and the gene was not over-expressed compared to Th0; or, (iii) up to this point in time the gene was not expressed above a minimal expression value of 100. As an additional constraint, protein expression levels were estimated using the model from Schwanhausser, B. et al. (Global quantification of mammalian gene expression control. Nature 473, 337-342, doi:10.1038/nature10098 (2011)) and using a sigmoidal fit (Chechik & Koller, J Comput Biol 2009) for a continuous representation of the temporal expression profiles, and the ProtParam software (Wilkins, M. R. et al. Protein identification and analysis tools in the ExPASy server. Methods Mol. Biol. 112, 531-552 (1999)) for estimating protein half-lives. It was required that, in a given time point, the predicted protein level be no less than 1.7 fold below the maximum value attained during the time course, and not be less than 1.7 fold below the Th0 levels. The timing assigned to edges inferred based on a time-point specific grouping (grouping methods 1 and 2 above) was limited to that specific time point. For instance, if an edge was inferred based on enrichment in the set of genes induced at 1 hr (grouping method #2), it will be assigned a "1 hr" time stamp. This same edge could then only have additional time stamps if it was revealed by additional tests.

Selection of Nanostring signature genes: The selection of the 275-gene signature (Table 1) combined several criteria to reflect as many aspect of the differentiation program as was possible. The following requirements were defined: (1) the signature must include all of the TFs that belong to a Th17 microarray signature (comparing to other CD4+ T cells (Wei et al., in Immunity vol. 30 155-167 (2009)), see Methods described herein); that are included as regulators in the network and have a differential expression score >1; or that are strongly differentially expressed (differential expression score=4); (2) it must include at least 10 representatives from each cluster of genes that have similar expression profiles (using clustering method (4) above); (3) it must contain at least 5 representatives from the predicted targets of each TF in the different networks; (4) it must include a minimal number of representatives from each enriched Gene Ontology (GO) category (computed across all differentially expressed genes); and, (5) it must include a manually assembled list of ~100 genes that are related to the differentiation process, including the differentially expressed cytokines, receptor molecules and other cell surface molecules. Since these different criteria might generate substantial overlaps, a set-cover algorithm was used to find the smallest subset of genes that satisfies all of five conditions. To this list 18 genes whose expression showed no change (in time or between treatments) in the microarray data were added.

The 85-gene signature (used for the Fluidigm BioMark qPCR assay) is a subset of the 275-gene signature, selected to include all the key regulators and cytokines discussed. To this list 10 control genes (2900064A13RIK, API5, CAND1, CSNK1A1, EIF3E, EIF3H, FIP1L1, GOLGA3, HSBP1, KHDRBS1, MED24, MKLN1, PCBP2, SLC6A6, SUFU, TMED7, UBE3A, ZFP410) were added.

Selection of perturbation targets: an unbiased approach was used to rank candidate regulators—transcription factor or chromatin modifier genes—of Th17 differentiation. The ranking was based on the following features: (a) whether the gene encoding the regulator belonged to the Th17 microarray signature (comparing to other CD4+ T cells (Wei et al., in Immunity vol. 30 155-167 (2009)), see Methods described herein); (b) whether the regulator was predicted to target key Th17 molecules (IL-17, IL-21, IL23r, and ROR-γt); (c) whether the regulator was detected based on both perturbation and physical binding data from the IPA software; (d) whether the regulator was included in the network using a cutoff of at least 10 target genes; (e) whether the gene encoding for the regulator was significantly induced in the Th17 time course. Only cases where the induction happened after 4 hours were considered to exclude non-specific hits; (f) whether the gene encoding the regulator was differentially expressed in response to Th17-related perturbations in previous studies. For this criterion, a database of transcriptional effects in perturbed Th17 cells was assembled, including: knockouts of Batf (Schraml et al., Nature 2009), ROR-γt (Xiao et al., unpublished), Hif1a (Shi et al., J. Exp. Med. (2011)), Stat3 and Stat5 (Yang et al., Nature Immunol (2011); Durant, L. et al. in Immunity Vol. 32 605-615 (2010), Tbx21 (Awasthi et al., unpublished), IL23r (this study), and Ahr (Jux et al., J. Immunol 2009)). Data from the Th17 response to Digoxin (Huh, J. R. et al. Digoxin and its derivatives suppress TH17 cell differentiation by antagonizing RORgammat activity. Nature 472, 486-490, doi: 10.1038/nature09978 (2011)) and Halofuginone (Sundrud, M. S. et al. Halofuginone inhibits TH17 cell differentiation by activating the amino acid starvation response. Science (New York, N.Y.) 324, 1334-1338, doi:10.1126/science.1172638 (2009)), as well as information on direct binding by ROR-γt as inferred from ChIP-seq data (Xiao et al., unpublished) was also included. The analysis of the published expression data sets is described in the Methods described herein. For each regulator, the number of conditions in which it came up as a significant hit (up/down-regulated or bound) was counted; for regulators with 2 to 3 hits (quantiles 3 to 7 out of 10 bins), a score of 1 was then assign; for regulators with more than 3 hits (quantiles 8-10), a score of 2 (a score of 0 is assigned otherwise) was assigned; and, (g) the differential expression score of the gene in the Th17 time course.

The regulators were ordered lexicographically by the above features according to the order: a, b, c, d, (sum of e and f), g—that is, first sort according to a then break ties according to b, and so on. Genes that are not over-expressed during at least one time point were excluded. As an exception, predicted regulators (feature d) that had additional external validation (feature f) were retained. To validate this ranking, a supervised test was used: 74 regulators that were previously associated with Th17 differentiation were manually annotated. All of the features are highly specific for these regulators ($p<10^{-3}$). Moreover, using a supervised learning method (Naive Bayes), the features provided good predictive ability for the annotated regulators (accuracy of 71%, using 5-fold cross validation), and the resulting ranking was highly correlated with the unsupervised lexicographic ordering (Spearman correlation >0.86).

This strategy was adapted for ranking protein receptors. To this end, feature c was excluded and the remaining "protein-level" features (b and d) were replaced with the following definitions: (b) whether the respective ligand is induced during the Th17 time course; and, (d) whether the receptor was included as a target in the network using a cutoff of at least 5 targeting transcriptional regulators.

Figure 11A:
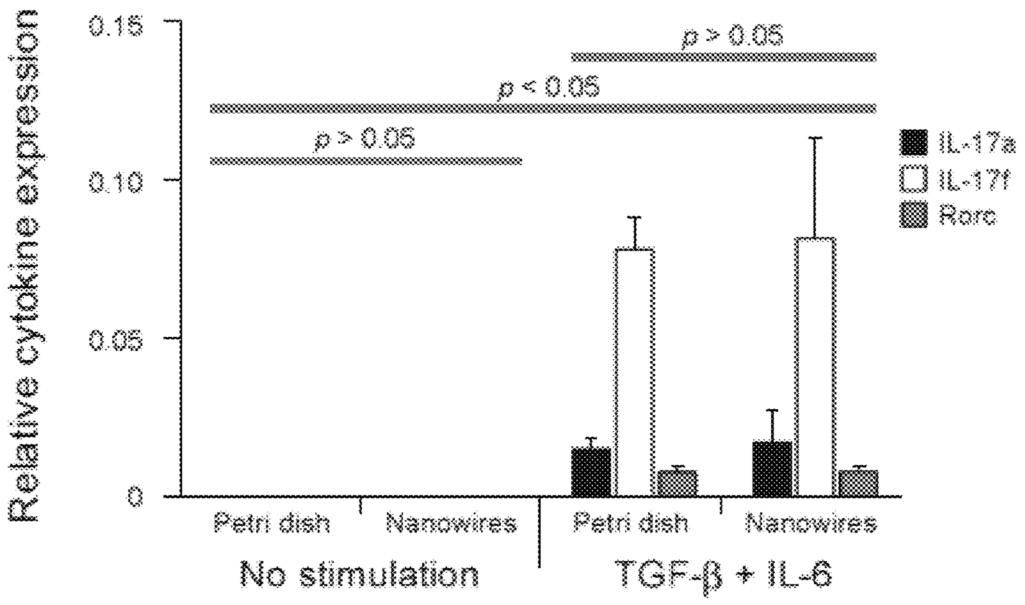
FIGS. 11A-11C are a series of graphs depicting Nanowire activation on T-cells, knockdown at 10 h, and consistency of NW-based knockdowns and resulting phenotypes.
Figure 11B:
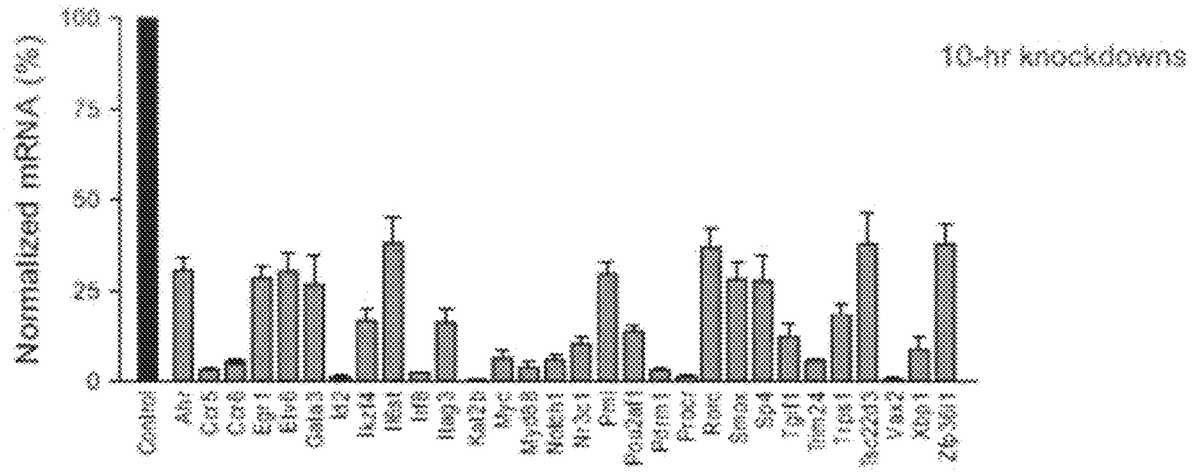
Figure 11C:
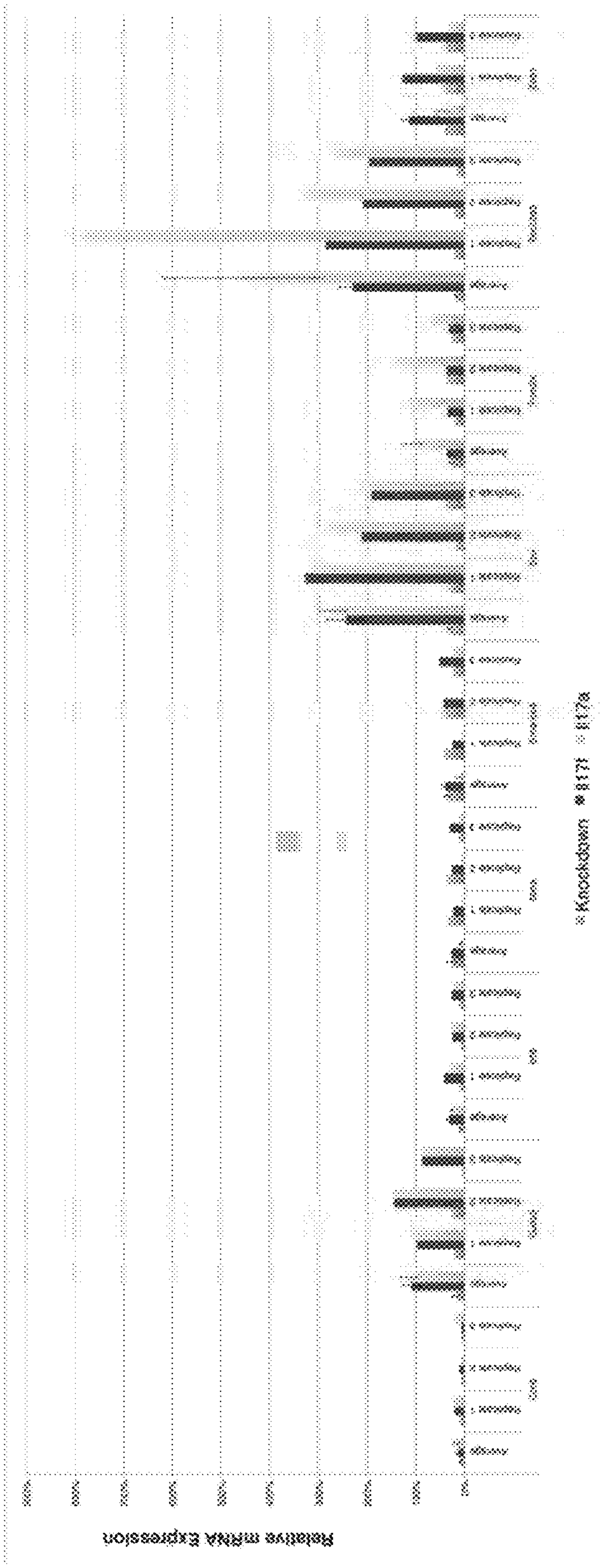

Gene knockdown using silicon nanowires: 4×4 mm silicon nanowire (NW) substrates were prepared and coated with 3 μL of a 50 μM pool of four siGENOME siRNAs (Dharmacon) in 96 well tissue culture plates, as previously described (Shalek, A. K. et al. Vertical silicon nanowires as a universal platform for delivering biomolecules into living cells. Proceedings of the National Academy of Sciences of the United States of America 107, 1870-1875, doi:10.1073/pnas.0909350107 (2010)). Briefly, 150,000 naive T cells were seeded on siRNA-laced NWs in 10 μL of complete media and placed in a cell culture incubator (37° C., 5% $CO_2$) to settle for 45 minutes before full media addition. These samples were left undisturbed for 24 hours to allow target transcript knockdown. Afterward, siRNA-transfected T cells were activated with αCd3/Cd28 dynabeads (Invitrogen), according to the manufacturer's recommendations, under Th17 polarization conditions (TGF-β1 & IL-6, as above). 10 or 48 hr post-activation, culture media was removed from each well and samples were gently washed with 100 μL of PBS before being lysed in 20 μL of buffer TCL (Qiagen) supplemented with 2-mercaptoethanol (1:100 by volume). After mRNA was harvested in Turbocapture plates (Qiagen) and converted to cDNA using Sensiscript RT enzyme (Qiagen), qRT-PCR was used to validate both knockdown levels and phenotypic changes relative to 8-12 non-targeting siRNA control samples, as previously described (Chevrier, N. et al. Systematic discovery of TLR signaling components delineates viral-sensing circuits. Cell 147, 853-867, doi:10.1016/j.cell.2011.10.022 (2011)). A 60% reduction in target mRNA was used as the knockdown threshold. In each knockdown experiment, each individual siRNA pool was run in quadruplicate; each siRNA was tested in at least three separate experiments (FIG. 11).

mRNA measurements in perturbation assays: the nCounter system, presented in full in Geiss et al. (Geiss, G. K. et al. Direct multiplexed measurement of gene expression with color-coded probe pairs. SI. Nature Biotechnology 26, 317-325, doi:10.1038/nbt1385 (2008)), was used to measure a custom CodeSet constructed to detect a total of 293 genes, selected as described above. The Fluidigm BioMark HD system was also used to measure a smaller set of 96 genes. Finally, RNA-Seq was used to follow up and validate 12 of the perturbations.

A custom CodeSet constructed to detect a total of 293 genes, selected as described above, including 18 control genes whose expression remain unaffected during the time course was used. Given the scarcity of input mRNA derived from each NW knockdown, a Nanostring-CodeSet specific, 14 cycle Specific Target Amplification (STA) protocol was performed according to the manufacturer's recommendations by adding 5 μL of TaqMan PreAmp Master Mix (Invitrogen) and 1 μL of pooled mixed primers (500 nM each, see Table S6.1 for primer sequences) to 5 μL of cDNA from a validated knockdown. After amplification, 5 μL of the amplified cDNA product was melted at 95° C. for 2 minutes, snap cooled on ice, and then hybridized with the CodeSet at 65° C. for 16 hours. Finally, the hybridized samples were loaded into the nCounter prep station and product counts were quantified using the nCounter Digital Analyzer following the manufacturer's instructions. Samples that were too concentrated after amplification were diluted and rerun. Serial dilutions (1:1, 1:4, 1:16, & 1:64, pre-STA) of whole spleen and Th17 polarized cDNAs were used to both control for the effects of different amounts of starting input material and check for biases in sample amplification.

Nanostring nCounter data analysis: For each sample, the count values were divided by the sum of counts that were assigned to a set of control genes that showed no change (in time or between treatments) in the microarray data (18 genes altogether). For each condition, a change fold ratio was computed, comparing to at least three different control samples treated with non-targeting (NT) siRNAs. The results of all pairwise comparisons (i.e. AxB pairs for A repeats of the condition and B control (NT) samples) were then pooled together: a substantial fold change (above a threshold value t) in the same direction (up/down regulation) in more than half of the pairwise comparisons was required. The threshold t was determined as max {d1, d2}, where d1 is the mean+std in the absolute log fold change between all pairs of matching NT samples (i.e., form the same batch and the same time point; d1=1.66), and where d2 is the mean+1.645 times the standard deviation in the absolute log fold change shown by the 18 control genes (determined separately for every comparison by taking all the 18×A×B values; corresponding to p=0.05, under assumption of normality). All pairwise comparisons in which both NT and knockdown samples had low counts before normalization (<100) were ignored.

Figure 10A:
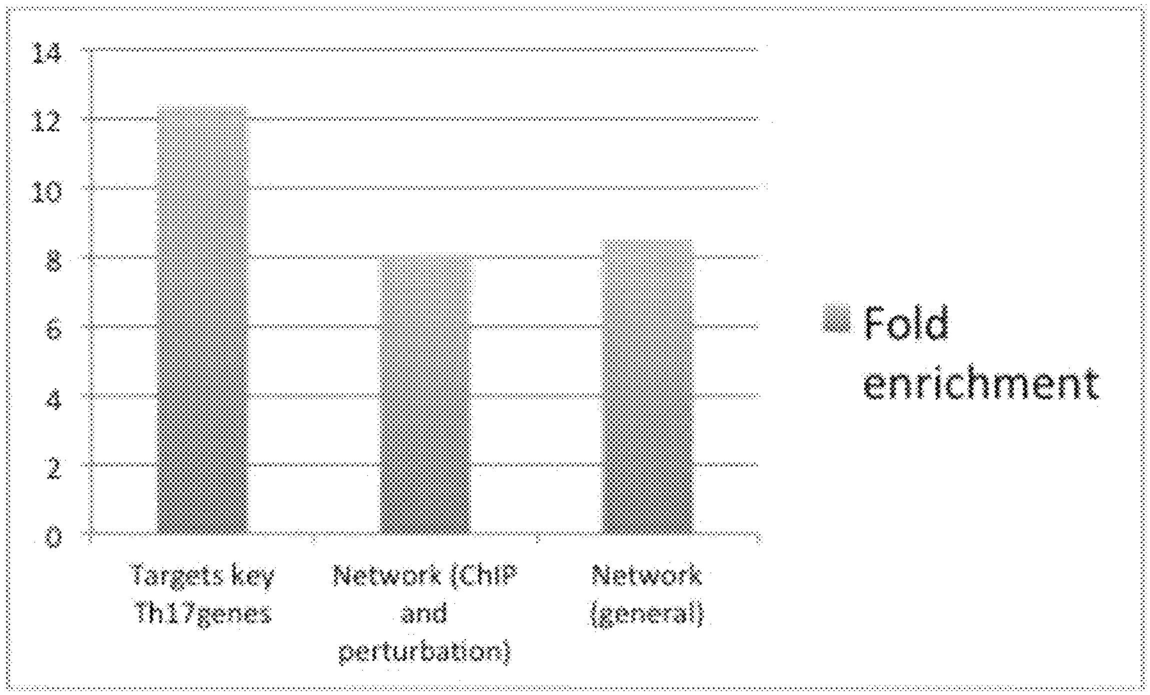
FIG. 10A, 10B).
Figure 10B:
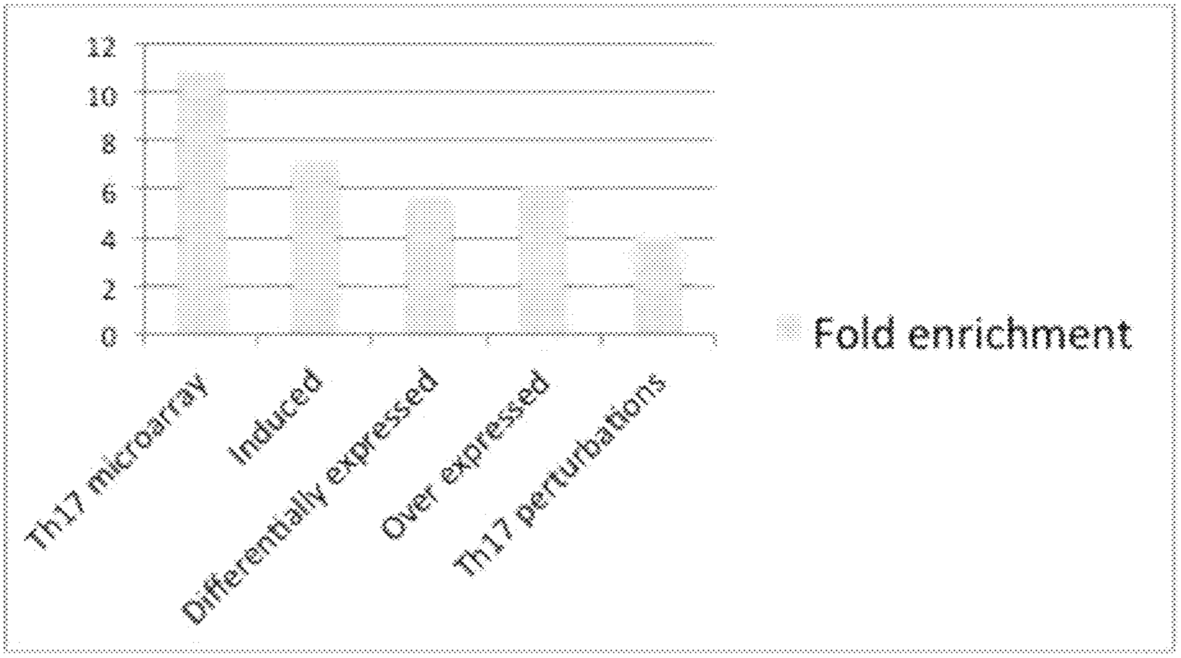

A permutation test was used to evaluate the overlap between the predicted network model (FIG. 2) and the knockdown effects measured in the Nanostring nCounter (FIG. 4, FIG. 10). Two indices were computed for every TF for which predicted target were available: (i) specificity—the percentage of predicted targets that are affected by the respective knockdown (considering only genes measured by nCounter), and (ii) sensitivity—the percentage of genes affected by a given TF knockdown that are also its predicted targets in the model. To avoid circularity, target genes predicted in the original network based on knockout alone were excluded from this analysis. The resulting values (on average, 13.5% and 24.8%, respectively) were combined into an F-score (the harmonic mean of specificity and sensitivity). The calculation of F-score was then repeated in 500 randomized datasets, where the target gene labels in the knockdown result matrix were shuffled. The reported empirical p-value is:

$$P=(1+\#\text{randomized datasets with equal of better } F\text{-score})/(1+\#\text{randomized datasets})$$

mRNA measurements on the Fluidigm BioMark HD: cDNA from validated knockdowns was prepared for quantification on the Fluidigm BioMark HD. Briefly, 5 μL of TaqMan PreAmp Master Mix (Invitrogen), 1 μL of pooled mixed primers (500 nM each, see Table S6.1 for primers), and 1.5 μL of water were added to 2.5 μL of knockdown validated cDNA and 14 cycles of STA were performed according to the manufacturer's recommendations. After the STA, an Exonuclease I digestion (New England Biosystems) was performed to remove unincorporated primers by adding 0.8 μL Exonuclease I, 0.4 μL Exonuclease I Reaction Buffer and 2.8 μL water to each sample, followed by vortexing, centrifuging and heating the sample to 37° C. for 30 minutes. After a 15 minute 80° C. heat inactivation, the amplified sample was diluted 1:5 in Buffer TE. Amplified validated knockdowns and whole spleen and Th17 serial dilution controls (1:1, 1:4, 1:16, & 1:64, pre-STA) were then analyzed using EvaGreen and 96×96 gene expression chips (Fluidigm BioMark HD) (Dalerba, P. et al. Single-cell dissection of transcriptional heterogeneity in human colon tumors. Nat Biotechnol 29, 1120-1127, doi:10.1038/nbt.2038 (2011)).

Fluidigm data analysis: For each sample, the Ct values were subtracted from the geometric mean of the Ct values assigned to a set of four housekeeping genes. For each condition, a fold change ratio was computed, comparing to at least three different control samples treated with non-targeting (NT) siRNAs. The results of all pairwise comparisons (i.e. A×B pairs for A repeats of the condition and B control (NT) samples) were then pooled together: a substantial difference between the normalized Ct values (above a threshold value) in the same direction (up/down regulation) in more than half of the pairwise comparisons was required. The threshold t was determined as max {log 2(1.5), d1(b), d2}, where d1(b) is the mean+std in the delta between all pairs of matching NT samples (i.e., from the same batch and the same time point), over all genes in expression quantile b (1<=b<=10). d2 is the mean+1.645 times the standard deviation in the deltas shown by 10 control genes (the 4 housekeeping genes plus 6 control genes from the Nanostring signature); d2 is determined separately for each comparison by taking all the 10×A×B values; corresponding to p=0.05, under assumption of normality). All pairwise comparisons in which both NT and knockdown samples had low counts before normalization (Ct<21 (taking into account the amplification, this cutoff corresponds to a conventional Ct cutoff of 35)) were ignored.

mRNA measurements using RNA-Seq: Validated single stranded cDNAs from the NW-mediated knockdowns were converted to double stranded DNA using the NEBNext mRNA Second Strand Synthesis Module (New England BioLabs) according to the manufacturer's recommendations. The samples were then cleaned using 0.9×SPRI beads (Beckman Coulter). Libraries were prepared using the Nextera XT DNA Sample Prep Kit (Illumina), quantified, pooled, and then sequenced on the HiSeq 2500 (Illumina) to an average depth 20M reads.

RNA-seq data analysis: a Bowtie index based on the UCSC known Gene transcriptome (Fujita, P. A. et al. The UCSC Genome Browser database: update 2011. Nucleic Acids Res. 39, D876-882, doi:10.1093/nar/gkq963 (2011)) was created, and paired-end reads were aligned directly to this index using Bowtie (Langmead, B., Trapnell, C., Pop, M. & Salzberg, S. L. Ultrafast and memory-efficient alignment of short DNA sequences to the human genome. Genome Biol 10, R25, doi:10.1186/gb-2009-10-3-r25 (2009)). Next, RSEM v1.11 (Li, B. & Dewey, C. N. RSEM: accurate transcript quantification from RNA-Seq data with or without a reference genome. BMC Bioinformatics 12, 323, doi:10.1186/1471-2105-12-323 (2011)) was ran with default parameters on these alignments to estimate expression levels. RSEM's gene level expression estimates (tau) were multiplied by 1,000,000 to obtain transcript per million (TPM) estimates for each gene. Quantile normalization was used to further normalize the TPM values within each batch of samples. For each condition, a fold change ratio was computed, comparing to at least two different control samples treated with nontargeting (NT) siRNAs. The results of all pairwise comparisons (i.e. A×B pairs for A repeats of the condition and B control (NT) samples) were then pooled together: a significant difference between the TPM values in the same direction (up/down regulation) in more than half of the pairwise comparisons was required. The significance cutoff t was determined as max {log 2(1.5), d1(b)}, where d1(b) is the mean+1.645*std in the log fold ratio between all pairs of matching NT samples (i.e., from the same batch and the same time point), over all genes in expression quantile b (1<=b<=20). All pairwise comparisons in which both NT and knockdown samples had low counts (TPM<10) were ignored. To avoid spurious fold levels due to low expression values a small constant, set to the value of the 1st quantile (out of 10) of all TPM values in the respective batch, was add to the expression values.

Figure 4A:
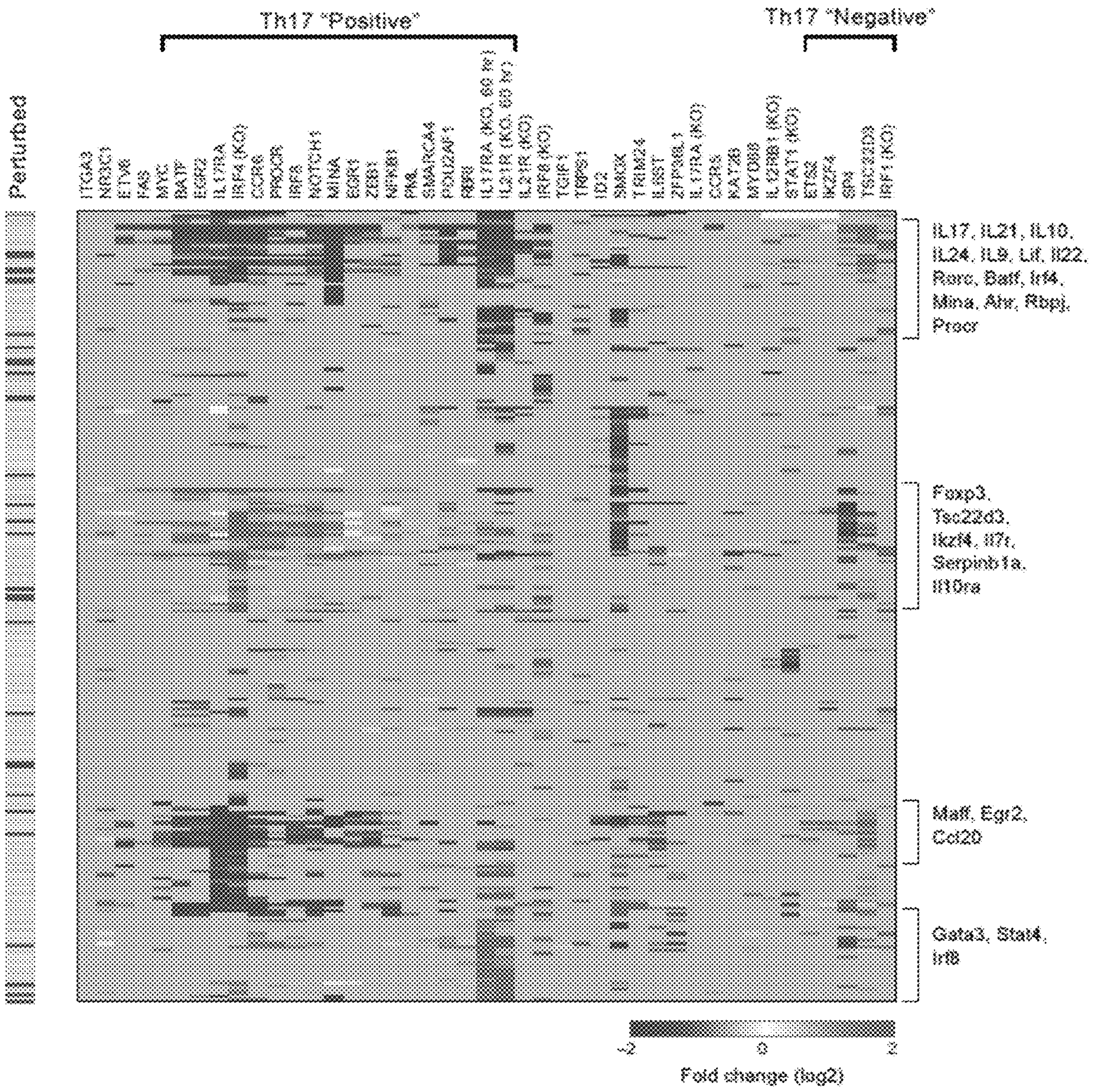
FIGS. 4A-4D are a series of graphs and illustrations depicting coupled and mutually-antagonistic modules in the Th17 network. A color version of these figures can be found in Yosef et al., "Dynamic regulatory network controlling Th17 cell differentiation, Nature, vol. 496: 461-468 (2013)/doi: 10.1038/nature11981.
Figure 4B:
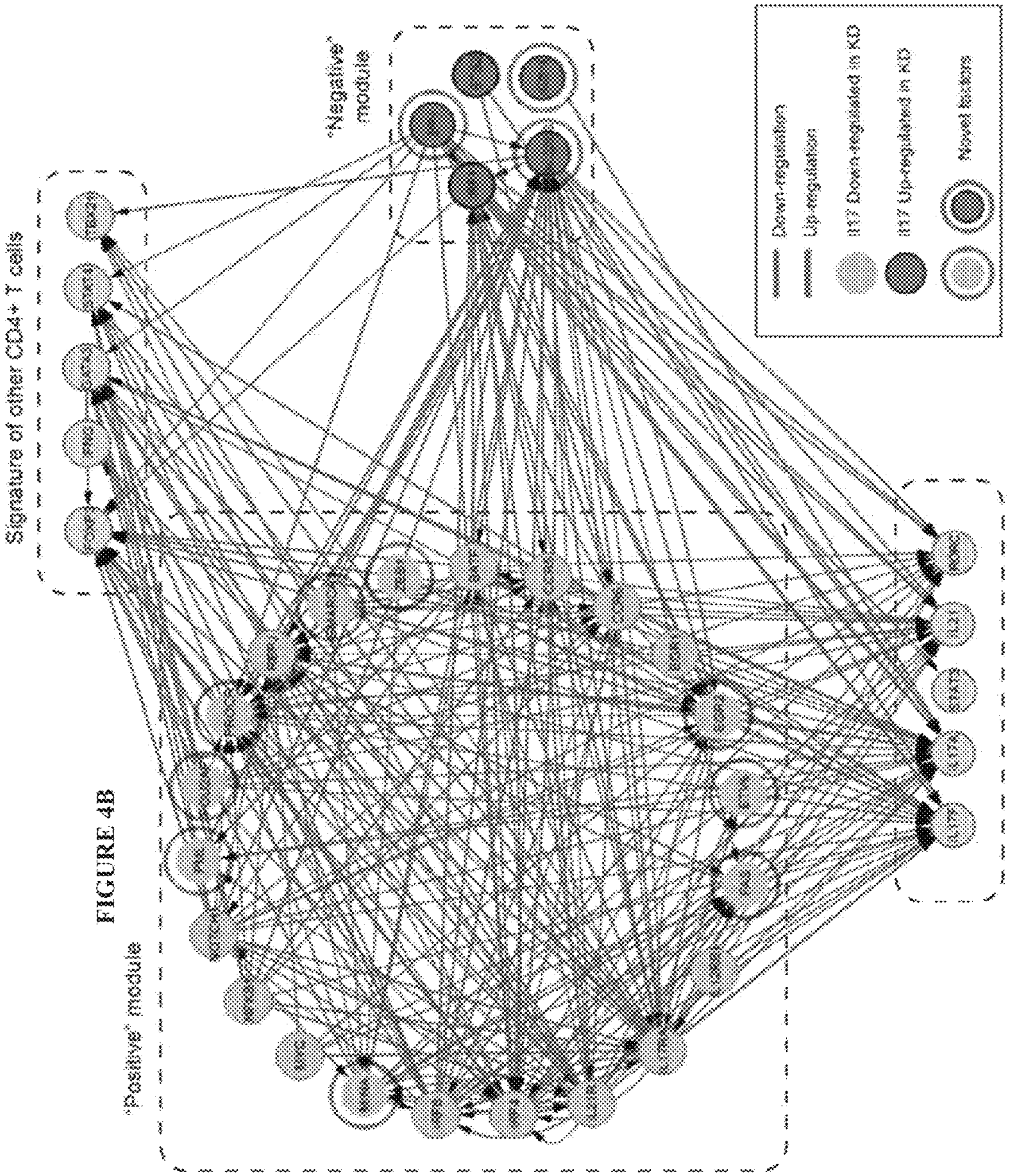
Figure 4C:
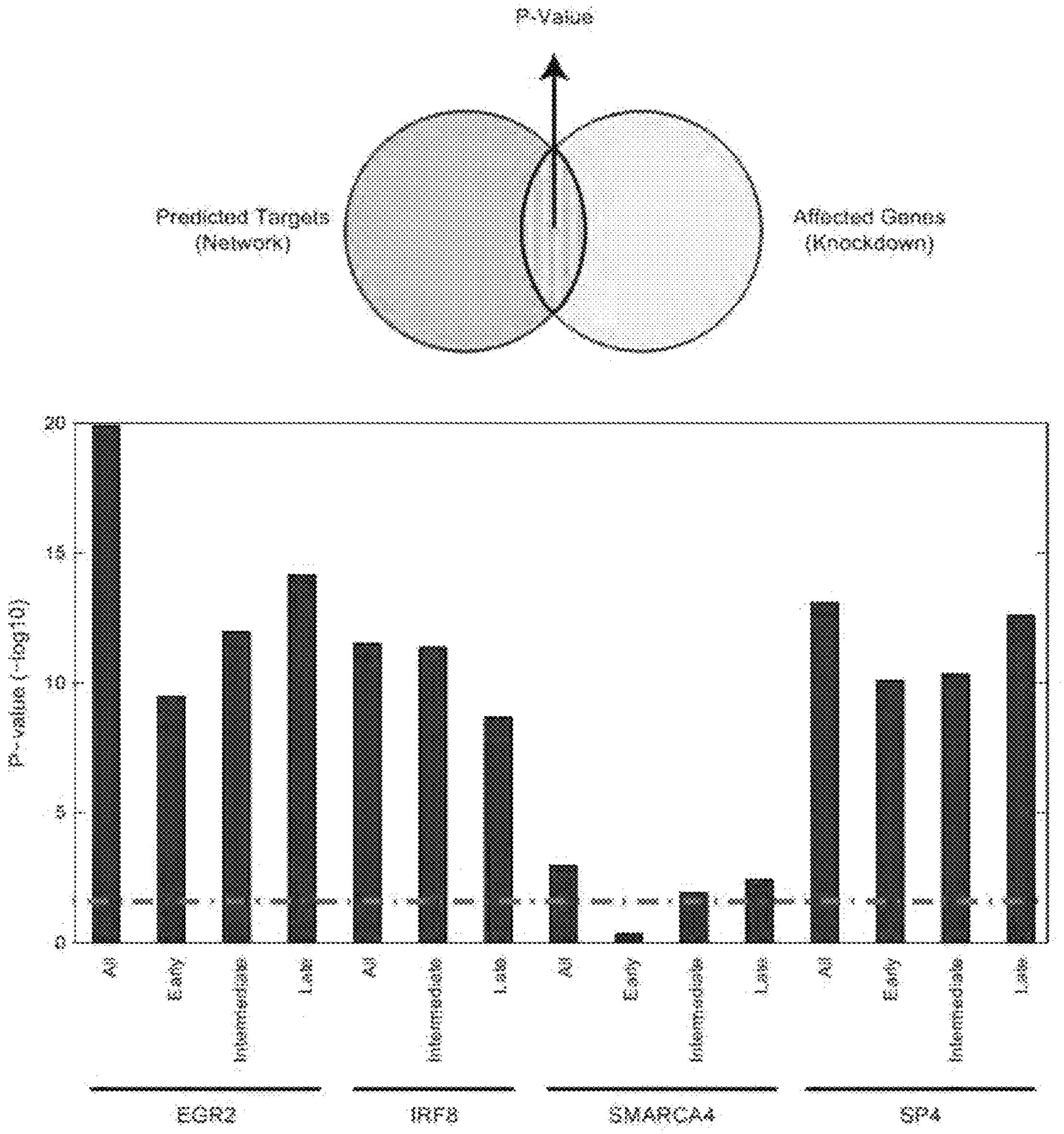
Figure 4D:
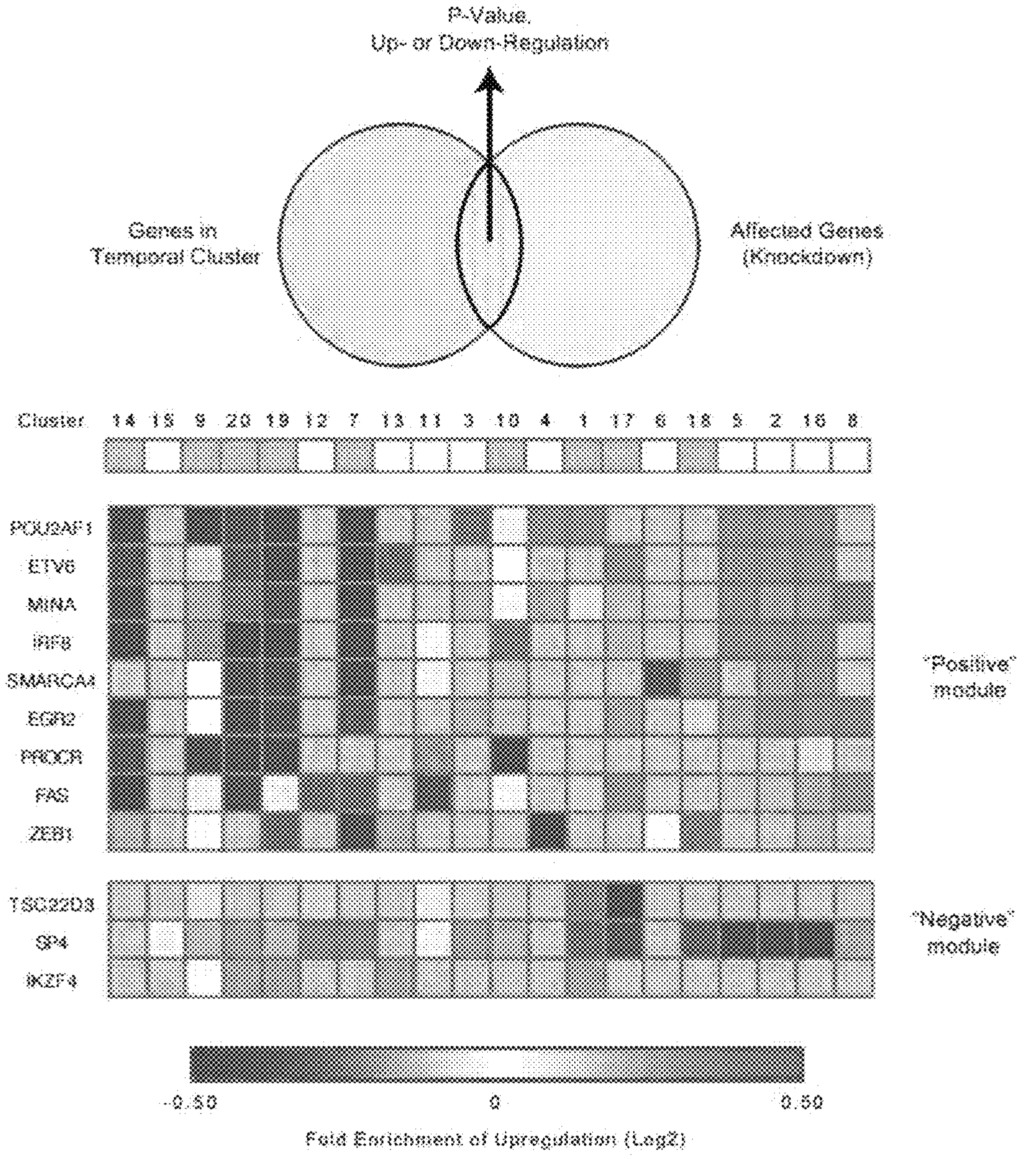

A hypergeometric test was used to evaluate the overlap between the predicted network model (FIG. 2) and the knockdown effects measured by RNA-seq (FIG. 4*d*). As background, all of the genes that appeared in the microarray data (and hence 20 have the potential to be included in the network) were used. As an additional test, the Wilcoxon-Mann-Whitney rank-sum test was used, comparing the absolute log fold-changes of genes in the annotated set to the entire set of genes (using the same background as before). The rank-sum test does not require setting a significance threshold; instead, it considers the fold change values of all the genes. The p-values produced by the rank-sum test were lower (i.e., more significant) than in the hypergeometric test, and therefore, in FIG. 4*c*, only the more stringent (hypergeometric) p-values were reported.

Profiling Tsc22d3 DNA binding using ChIP-seq: ChIP-seq for Tsc22d3 was performed as previously described (Ram, O. et al. Combinatorial Patterning of Chromatin Regulators Uncovered by Genome-wide Location Analysis in Human Cells. Cell 147, 1628-1639 (2011)) using an antibody from Abcam. The analysis of this data was performed as previously described (Ram, O. et al. Combinatorial Patterning of Chromatin Regulators Uncovered by Genome-wide Location Analysis in Human Cells. Cell 147, 1628-1639 (2011)) and is detailed in the Methods described herein.

Analysis of Tsc22d3 ChIP-seq data: ChIP-seq reads were aligned to the NCBI Build 37 (UCSC mm9) of the mouse genome using Bowtie (Langmead, B., Trapnell, C., Pop, M. & Salzberg, S. L. in Genome Biol Vol. 10 R25 (2009)). Enriched binding regions (peaks) were detected using MACS (Zhang, Y. et al. in Genome Biol Vol. 9 R137 (2008)) with a pvalue cutoff of $10^{-8}$. A peak was associated with a gene if it falls in proximity to its 5' end (10 kb upstream and 1 kb downstream from transcription start site) or within the gene's body. The RefSeq transcript annotations for gene's coordinates were used.

The overlap of ChIP-seq peaks with annotated genomic regions was assessed. It was determined that a region A overlap with a peak B if A is within a distance of 50 bp from B's summit (as determined by MACS). The regions used included: (i) regulatory features annotations from the Ensemble database (Flicek, P. et al. Ensembl 2011. Nucleic Acids Res. 39, D800-806, doi:10.1093/nar/gkq1064 (2011)); (ii) regulatory 21 features found by the Oregano algorithm (Smith, R. L. et al. Polymorphisms in the IL-12beta and IL-23R genes are associated with psoriasis of early onset in a UK cohort. J Invest Dermatol 128, 1325-1327, doi:5701140 [pii] 10.1038/sj.jid.5701140 (2008)); (iii) conserved regions annotated by the multiz30way algorithm (here regions with multiz30way score >0.7 were considered); (iv) repeat regions annotated by RepeatMasker; (v) putative promoter regions—taking 10 kb upstream and 1 kb downstream of transcripts annotated in RefSeq (Pruitt, K. D., Tatusova, T. & Maglott, D. R. NCBI reference sequences (RefSeq): a curated non-redundant sequence database of genomes, transcripts and proteins. Nucleic Acids Res. 35, D61-65, doi:10.1093/nar/gkl842 (2007)); (vi) gene body annotations in RefSeq; (vii) 3' proximal regions (taking 1 kb upstream and 5 kb downstream to 3' end); (viii) regions enriched in histone marks H3K4me3 and H3K27me3 in Th17 cells (Wei, G. et al. in Immunity Vol. 30 155-167 (2009)); (ix) regions enriched in binding of Stat3 and Stat5 (Yang, X. P. et al. Opposing regulation of the locus encoding IL-17 through direct, reciprocal actions of STAT3 and STAT5. Nat. Immunol. 12, 247-254, doi:10.1038/ni.1995 (2011)), Irf4 and Batf (Glasmacher, E. et al. A Genomic Regulatory Element That Directs Assembly and Function of Immune-Specific AP-1-IRF Complexes. Science, doi: 10.1126/science.1228309 (2012)), and RORγt (Xiao et al unpublished) in Th17 cells, and Foxp3 in iTreg (Xiao et al., unpublished).

For each set of peaks "x" and each set of genomic regions "y", a binomial pvalue was used to assess their overlap in the genome as described in Mclean, C. Y. et al. in Nature biotechnology Vol. 28 nbt.1630-1639 (2010). The number of hits is defined as the number of x peaks that overlap with y. The background probability in sets (i)-(vii) is set to the overall length of the region (in bp) divided by the overall length of the genome. The background probability in sets (viii)-(ix) is set to the overall length of the region divided by the overall length of annotated genomic regions: this includes annotated regulatory regions (as defined in sets i, and ii), regions annotated as proximal to genes (using the definitions from set v-vii), carry a histone mark in Th17 cells (using the definition from set viii), or bound by transcription regulators in Th17 cells (using the definitions from set ix).

For the transcription regulators (set ix), an additional "gene-level" test was also included: here the overlap between the set of bound genes using a hypergeometric p-value was evaluated. A similar test was used to evaluate the overlap between the bound genes and genes that are differentially expressed in Tsc22d3 knockdown.

The analysis was repeated with a second peak-calling software (Scripture) (Guttman, M. et al. in Nature biotechnology Vol. 28 503-510 (2010); Garber, M. et al. A High-Throughput Chromatin Immunoprecipitation Approach Reveals Principles of Dynamic Gene Regulation in Mammals. Molecular cell, doi:10.1016/j.molcel.2012.07.030 (2012)), and obtained consistent results in all the above tests. Specifically, similar levels of overlap with the Th17 factors tested, both in terms of co-occupied binding sites and in terms of common target genes, was seen.

Estimating statistical significance of monochromatic interactions between modules: The functional network in FIG. 4*b* consists of two modules: positive and negative. Two indices were computed: (1) within-module index: the percentage of positive edges between members of the same module (i.e., down-regulation in knockdown/knockout); and, (2) between-module index: the percentage of negative edges between members of the same module that are negative. The network was shuffled 1,000 times, while maintaining the nodes' out degrees (i.e., number of outgoing edges)

and edges' signs (positive/negative), and re-computed the two indices. The reported p-values were computed using a t-test.

Using literature microarray data for deriving a Th17 signature and for identifying genes responsive to Th17-related perturbations: To define the Th17 signatures genes, the gene expression data from Wei et al., in Immunity, vol. 30 155-167 (2009) was downloaded and analyzed, and the data was preprocessed using the RMA algorithm, followed by quantile normalization using the default parameters in the ExpressionFileCreator module of the 23 GenePattern suite (Reich, M. et al. GenePattern 2.0. Nat. Genet. 38, 500-501, doi:10.1038/ng0506-500 (2006)). This data includes replicate microarray measurements from Th17, Th1, Th2, iTreg, nTreg, and Naïve CD4+ T cells. For each gene, it was evaluated whether it is over-expressed in Th17 cells compared to all other cell subsets using a one-sided t-test. All cases that had a p-value<0.05 were retained. As an additional filtering step, it was required that the expression level of a gene in Th17 cells be at least 1.25 fold higher than its expression in all other cell subsets. To avoid spurious fold levels due to low expression values, a small constant (c=50) was added to the expression values.

To define genes responsive to published Th17-related perturbations, gene expression data from several sources that provided transcriptional profiles of Th17 cells under various conditions (listed above) were downloaded and analyzed. These datasets were preprocessed as above. To find genes that were differentially expressed in a given condition (compared to their respective control), the fold change between the expression levels of each probeset in the case and control conditions was computed. To avoid spurious fold levels due to low expression values, a small constant as above was added to the expression values. Only cases where more than 50% of all of the possible case-control comparisons were above a cutoff of 1.5 fold change were reported. As an additional filter, when duplicates are available, a Z-score was computed as above and only cases with a corresponding p-value<0.05 were reported.

Genes: The abbreviations set forth below in Table 11 are used herein to identify the genes used throughout the disclosure, including but not limited to those shown in Tables 1-9 of the specification.

TABLE 11

Gene Abbreviations, Entrez ID Numbers and Brief Description

| Symbol | Entrez ID | Description |
|---|---|---|
| AAK1 | 22848 | AP2 associated kinase 1 |
| ABCG2 | 9429 | ATP-binding cassette, sub-family G (WHITE), member 2 |
| ACP5 | 54 | acid phosphatase 5, tartrate resistant |
| ACVR1B | 91 | activin A receptor, type 1B |
| ACVR2A | 92 | activin receptor IIA |
| ADAM10 | 102 | a disintegrin and metallopeptidase domain 10 |
| ADAM17 | 6868 | a disintegrin and metallopeptidase domain 17 |
| ADRBK1 | 156 | adrenergic receptor kinase, beta 1 |
| AES | 166 | amino-terminal enhancer of split |
| AHR | 196 | aryl-hydrocarbon receptor |
| AIM1 | 202 | absent in melanoma 1 |
| AKT1 | 207 | thymoma viral proto-oncogene 1 |
| ALPK2 | 115701 | alpha-kinase 2 |
| ANKHD1 | 54882 | ankyrin repeat and KH domain containing 1 |
| ANP32A | 8125 | acidic (leucine-rich) nuclear phosphoprotein 32 family, member A |
| ANXA4 | 307 | annexin A4 |
| AQP3 | 360 | aquaporin 3 |

TABLE 11-continued

Gene Abbreviations, Entrez ID Numbers and Brief Description

| Symbol | Entrez ID | Description |
|---|---|---|
| ARHGEF3 | 50650 | Rho guanine nucleotide exchange factor (GEF) 3 |
| ARID3A | 1820 | AT rich interactive domain 3A (BRIGHT-like) |
| ARID5A | 10865 | AT rich interactive domain 5A (MRF1-like) |
| ARL5A | 26225 | ADP-ribosylation factor-like 5A |
| ARMCX2 | 9823 | armadillo repeat containing, X-linked 2 |
| ARNTL | 406 | aryl hydrocarbon receptor nuclear translocator-like |
| ASXL1 | 171023 | additional sex combs like 1 (*Drosophila*) |
| ATF2 | 1386 | activating transcription factor 2 |
| ATF3 | 467 | activating transcription factor 3 |
| ATF4 | 468 | activating transcription factor 4 |
| AURKB | 9212 | aurora kinase B |
| AXL | 558 | AXL receptor tyrosine kinase |
| B4GALT1 | 2683 | UDP-Gal:betaGlcNAc beta 1,4-galactosyltransferase, polypeptide 1 |
| BATF | 10538 | basic leucine zipper transcription factor, ATF-like |
| BATF3 | 55509 | basic leucine zipper transcription factor, ATF-like 3 |
| BAZ2B | 29994 | bromodomain adjacent to zinc finger domain, 2B |
| BCL11B | 64919 | B-cell leukemia/lymphoma 11B |
| BCL2L11 | 10018 | BCL2-like 11 (apoptosis facilitator) |
| BCL3 | 602 | B-cell leukemia/lymphoma 3 |
| BCL6 | 604 | B-cell leukemia/lymphoma 6 |
| BHLH40 | 8553 | Basic Helix-Loop-Helix Family, Member E40 |
| BLOC1S1 | 2647 | biogenesis of lysosome-related organelles complex-1, subunit 1 |
| BMP2K | 55589 | BMP2 inducible kinase |
| BMPR1A | 657 | bone morphogenetic protein receptor, type 1A |
| BPGM | 669 | 2,3-bisphosphoglycerate mutase |
| BSG | 682 | basigin |
| BTG1 | 694 | B-cell translocation gene 1, anti-proliferative |
| BTG2 | 7832 | B-cell translocation gene 2, anti-proliferative |
| BUB1 | 699 | budding uninhibited by benzimidazoles 1 homolog (*S. cerevisiae*) |
| C14ORF83 | 161145 | RIKEN cDNA 6330442E10 gene |
| C16ORF80 | 29105 | gene trap locus 3 |
| C21ORF66 | 94104 | RIKEN cDNA 1810007M14 gene |
| CAMK4 | 814 | calcium/calmodulin-dependent protein kinase IV |
| CARM1 | 10498 | coactivator-associated arginine methyltransferase 1 |
| CASP1 | 834 | caspase 1 |
| CASP3 | 836 | caspase 3 |
| CASP4 | 837 | caspase 4, apoptosis-related cysteine peptidase |
| CASP6 | 839 | caspase 6 |
| CASP8AP2 | 9994 | caspase 8 associated protein 2 |
| CBFB | 865 | core binding factor beta |
| CBX4 | 8535 | chromobox homolog 4 (*Drosophila* Pc class) |
| CCL1 | 6346 | chemokine (C-C motif) ligand 1 |
| CCL20 | 6364 | chemokine (C-C motif) ligand 20 |
| CCL4 | 6351 | chemokine (C-C motif) ligand 4 |
| CCND2 | 894 | cyclin D2 |
| CCR4 | 1233 | chemokine (C-C motif) receptor 4 |
| CCR5 | 1234 | chemokine (C-C motif) receptor 5 |
| CCR6 | 1235 | chemokine (C-C motif) receptor 6 |
| CCR8 | 1237 | chemokine (C-C motif) receptor 8 |
| CCRN4L | 25819 | CCR4 carbon catabolite repression 4-like (*S. cerevisiae*) |
| CD14 | 929 | CD14 antigen |
| CD2 | 914 | CD2 antigen |
| CD200 | 4345 | CD200 antigen |
| CD226 | 10666 | CD226 antigen |
| CD24 | 934 | CD24a antigen |
| CD247 | 919 | CD247 antigen |
| CD27 | 939 | CD27 antigen |
| CD274 | 29126 | CD274 antigen |
| CD28 | 940 | CD28 antigen |

TABLE 11-continued

| Gene Abbreviations, Entrez ID Numbers and Brief Description | | |
|---|---|---|
| Symbol | Entrez ID | Description |
| CD3D | 915 | CD3 antigen, delta polypeptide |
| CD3G | 917 | CD3 antigen, gamma polypeptide |
| CD4 | 920 | CD4 antigen |
| CD40LG | 959 | CD40 ligand |
| CD44 | 960 | CD44 antigen |
| CD53 | 963 | CD53 antigen |
| CD5L | 922 | CD5 antigen-like |
| CD63 | 967 | CD63 antigen |
| CD68 | 968 | CD68 antigen |
| CD70 | 970 | CD70 antigen |
| CD74 | 972 | CD74 antigen (invariant polypeptide of major histocompatibility complex, cl |
| CD80 | 941 | CD80 antigen |
| CD83 | 9308 | CD83 antigen |
| CD84 | 8832 | CD84 antigen |
| CD86 | 942 | CD86 antigen |
| CD9 | 928 | CD9 antigen |
| CD96 | 10225 | CD96 antigen |
| CDC25B | 994 | cell division cycle 25 homolog B (*S. pombe*) |
| CDC42BPA | 8476 | CDC42 binding protein kinase alpha |
| CDC5L | 988 | cell division cycle 5-like (*S. pombe*) |
| CDK5 | 1020 | cyclin-dependent kinase 5 |
| CDK6 | 1021 | cyclin-dependent kinase 6 |
| CDKN3 | 1033 | cyclin-dependent kinase inhibitor 3 |
| CDYL | 9425 | chromodomain protein, Y chromosome-like |
| CEBPB | 1051 | CCAAT/enhancer binding protein (C/EBP), beta |
| CENPT | 80152 | centromere protein T |
| CHD7 | 55636 | chromodomain helicase DNA binding protein 7 |
| CHMP1B | 57132 | chromatin modifying protein 1B |
| CHMP2A | 27243 | charged multivesicular body protein 2A |
| CHRAC1 | 54108 | chromatin accessibility complex 1 |
| CIC | 23152 | capicua homolog (*Drosophila*) |
| CITED2 | 10370 | Cbp/p300-interacting transactivator, with Glu/Asp-rich carboxy-terminal dom |
| CLCF1 | 23529 | cardiotrophin-like cytokine factor 1 |
| CLK1 | 1195 | CDC-like kinase 1 |
| CLK3 | 1198 | CDC-like kinase 3 |
| CMTM6 | 54918 | CKLF-like MARVEL transmembrane domain containing 6 |
| CNOT2 | 4848 | CCR4-NOT transcription complex, subunit 2 |
| CREB1 | 1385 | cAMP responsive element binding protein 1 |
| CREB3L2 | 64764 | cAMP responsive element binding protein 3-like 2 |
| CREG1 | 8804 | cellular repressor of E1A-stimulated genes 1 |
| CREM | 1390 | cAMP responsive element modulator |
| CSDA | 8531 | cold shock domain protein A |
| CSF1R | 1436 | colony stimulating factor 1 receptor |
| CSF2 | 1437 | colony stimulating factor 2 (granulocyte-macrophage) |
| CTLA4 | 1493 | cytotoxic T-lymphocyte-associated protein 4 |
| CTSD | 1509 | cathepsin D |
| CTSW | 1521 | cathepsin W |
| CXCL10 | 3627 | chemokine (C-X-C motif) ligand 10 |
| CXCR3 | 2833 | chemokine (C-X-C motif) receptor 3 |
| CXCR4 | 7852 | chemokine (C-X-C motif) receptor 4 |
| CXCR5 | 643 | chemochine (C-X-C motif) receptor 5 |
| DAPP1 | 27071 | dual adaptor for phosphotyrosine and 3-phosphoinositides 1 |
| DAXX | 1616 | Fas death domain-associated protein |
| DCK | 1633 | deoxycytidine kinase |
| DCLK1 | 9201 | doublecortin-like kinase 1 |
| DDIT3 | 1649 | DNA-damage inducible transcript 3 |
| DDR1 | 780 | discoidin domain receptor family, member 1 |
| DGKA | 1606 | diacylglycerol kinase, alpha |
| DGUOK | 1716 | deoxyguanosine kinase |
| DNAJC2 | 27000 | DnaJ (Hsp40) homolog, subfamily C, member 2 |
| DNTT | 1791 | deoxynucleotidyltransferase, terminal |
| DPP4 | 1803 | dipeptidylpeptidase 4 |
| DUSP1 | 1843 | dual specificity phosphatase 1 |
| DUSP10 | 11221 | dual specificity phosphatase 10 |

TABLE 11-continued

| Gene Abbreviations, Entrez ID Numbers and Brief Description | | |
|---|---|---|
| Symbol | Entrez ID | Description |
| DUSP14 | 11072 | dual specificity phosphatase 14 |
| DUSP16 | 80824 | dual specificity phosphatase 16 |
| DUSP2 | 1844 | dual specificity phosphatase 2 |
| DUSP22 | 56940 | dual specificity phosphatase 22 |
| DUSP6 | 1848 | dual specificity phosphatase 6 |
| E2F1 | 1869 | E2F transcription factor 1 |
| E2F4 | 1874 | E2F transcription factor 4 |
| E2F8 | 79733 | E2F transcription factor 8 |
| ECE2 | 9718 | endothelin converting enzyme 2 |
| EGR1 | 1958 | early growth response 1 |
| EGR2 | 1959 | early growth response 2 |
| EIF2AK2 | 5610 | eukaryotic translation initiation factor 2-alpha kinase 2 |
| ELK3 | 2004 | ELK3, member of ETS oncogene family |
| ELL2 | 22936 | elongation factor RNA polymerase II 2 |
| EMP1 | 2012 | epithelial membrane protein 1 |
| ENTPD1 | 953 | ectonucleoside triphosphate diphosphohydrolase 1 |
| ERCC5 | 2073 | excision repair cross-complementing rodent repair deficiency, complementati |
| ERRFI1 | 54206 | ERBB receptor feedback inhibitor 1 |
| ETS1 | 2113 | E26 avian leukemia oncogene 1, 5' domain |
| ETS2 | 2114 | E26 avian leukemia oncogene 2, 3' domain |
| ETV6 | 2120 | ets variant gene 6 (TEL oncogene) |
| EZH1 | 2145 | enhancer of zeste homolog 1 (*Drosophila*) |
| FAS | 355 | Fas (TNF receptor superfamily member 6) |
| FASLG | 356 | Fas ligand (TNF superfamily, member 6) |
| FCER1G | 2207 | Fc receptor, IgE, high affinity I, gamma polypeptide |
| FCGR2B | 2213 | Fc receptor, IgG, low affinity IIb |
| FES | 2242 | feline sarcoma oncogene |
| FLI1 | 2313 | Friend leukemia integration 1 |
| FLNA | 2316 | filamin, alpha |
| FOSL2 | 2355 | fos-like antigen 2 |
| FOXJ2 | 55810 | forkhead box J2 |
| FOXM1 | 2305 | forkhead box M1 |
| FOXN3 | 1112 | forkhead box N3 |
| FOX01 | 2308 | forkhead box O1 |
| FOXP1 | 27086 | forkhead box P1 |
| FOXP3 | 50943 | forkhead box P3 |
| FRMD4B | 23150 | FERM domain containing 4B |
| FUS | 2521 | fusion, derived from t(12; 16) malignant liposarcoma (human) |
| FZD7 | 8324 | frizzled homolog 7 (*Drosophila*) |
| GAP43 | 2596 | growth associated protein 43 |
| GATA3 | 2625 | GATA binding protein 3 |
| GATAD1 | 57798 | GATA zinc finger domain containing 1 |
| GATAD2B | 57459 | GATA zinc finger domain containing 2B |
| GEM | 2669 | GTP binding protein (gene overexpressed in skeletal muscle) |
| GFI1 | 2672 | growth factor independent 1 |
| GJA1 | 2697 | gap junction protein, alpha 1 |
| GK | 2710 | glycerol kinase |
| GLIPR1 | 11010 | GLI pathogenesis-related 1 (glioma) |
| GMFB | 2764 | glia maturation factor, beta |
| GMFG | 9535 | glia maturation factor, gamma |
| GRN | 2896 | granulin |
| GUSB | 2990 | glucuronidase, beta |
| HCLS1 | 3059 | hematopoietic cell specific Lyn substrate 1 |
| HDAC8 | 55869 | histone deacetylase 8 |
| HIF1A | 3091 | hypoxia inducible factor 1, alpha subunit |
| HINT3 | 135114 | histidine triad nucleotide binding protein 3 |
| HIP1R | 9026 | huntingtin interacting protein 1 related |
| HIPK1 | 204851 | homeodomain interacting protein kinase 1 |
| HIPK2 | 28996 | homeodomain interacting protein kinase 2 |
| HK1 | 3098 | hexokinase 1 |
| HK2 | 3099 | hexokinase 2 |
| HLA-A | 3105 | major histocompatibility complex, class I, A |
| HLA-DQA1 | 3117 | histocompatibility 2, class II antigen A, alpha |
| HMGA1 | 3159 | high mobility group AT-hook 1 |
| HMGB2 | 3148 | high mobility group box 2 |

TABLE 11-continued

Gene Abbreviations, Entrez ID Numbers and Brief Description

| Symbol | Entrez ID | Description |
|---|---|---|
| HMGN1 | 3150 | high mobility group nucleosomal binding domain 1 |
| ICOS | 29851 | inducible T-cell co-stimulator |
| ID1 | 3397 | inhibitor of DNA binding 1 |
| ID2 | 3398 | inhibitor of DNA binding 2 |
| ID3 | 3399 | inhibitor of DNA binding 3 |
| IER3 | 8870 | immediate early response 3 |
| IFI35 | 3430 | interferon-induced protein 35 |
| IFIH1 | 64135 | interferon induced with helicase C domain 1 |
| IFIT1 | 3434 | interferon-induced protein with tetratricopeptide repeats 1 |
| IFITM2 | 10581 | interferon induced transmembrane protein 2 |
| IFNG | 3458 | interferon gamma |
| IFNGR1 | 3459 | interferon gamma receptor 1 |
| IFNGR2 | 3460 | interferon gamma receptor 2 |
| IKZF1 | 10320 | IKAROS family zinc finger 1 |
| IKZF3 | 22806 | IKAROS family zinc finger 3 |
| IKZF4 | 64375 | IKAROS family zinc finger 4 |
| IL10 | 3586 | interleukin 10 |
| IL10RA | 3587 | interleukin 10 receptor, alpha |
| IL12RB1 | 3594 | interleukin 12 receptor, beta 1 |
| IL12RB2 | 3595 | interleukin 12 receptor, beta 2 |
| IL15RA | 3601 | interleukin 15 receptor, alpha chain |
| IL17A | 3605 | interleukin 17A |
| IL17F | 112744 | interleukin 17F |
| IL17RA | 23765 | interleukin 17 receptor A |
| IL18R1 | 8809 | interleukin 18 receptor 1 |
| IL1R1 | 3554 | interleukin 1 receptor, type I |
| IL1RN | 3557 | interleukin 1 receptor antagonist |
| IL2 | 3558 | interleukin 2 |
| IL21 | 59067 | interleukin 21 |
| IL21R | 50615 | interleukin 21 receptor |
| IL22 | 50616 | interleukin 22 |
| IL23R | 149233 | interleukin 23 receptor |
| IL24 | 11009 | interleukin 24 |
| IL27RA | 9466 | interleukin 27 receptor, alpha |
| IL2RA | 3559 | interleukin 2 receptor, alpha chain |
| IL2RB | 3560 | interleukin 2 receptor, beta chain |
| IL2RG | 3561 | interleukin 2 receptor, gamma chain |
| IL3 | 3562 | interleukin 3 |
| IL4 | 3565 | interleukin 4 |
| IL4R | 3566 | interleukin 4 receptor, alpha |
| IL6ST | 3572 | interleukin 6 signal transducer |
| IL7R | 3575 | interleukin 7 receptor |
| IL9 | 3578 | interleukin 9 |
| INHBA | 3624 | inhibin beta-A |
| INPP1 | 3628 | inositol polyphosphate-1-phosphatase |
| IRAK1BP1 | 134728 | interleukin-1 receptor-associated kinase 1 binding protein 1 |
| IRF1 | 3659 | interferon regulatory factor 1 |
| IRF2 | 3660 | interferon regulatory factor 2 |
| IRF3 | 3661 | interferon regulatory factor 3 |
| IRF4 | 3662 | interferon regulatory factor 4 |
| IRF7 | 3665 | interferon regulatory factor 7 |
| IRF8 | 3394 | interferon regulatory factor 8 |
| IRF9 | 10379 | interferon regulatory factor 9 |
| ISG20 | 3669 | interferon-stimulated protein |
| ITGA3 | 3675 | integrin alpha 3 |
| ITGAL | 3683 | integrin alpha L |
| ITGAV | 3685 | integrin alpha V |
| ITGB1 | 3688 | integrin beta 1 (fibronectin receptor beta) |
| ITK | 3702 | IL2-inducible T-cell kinase |
| JAK2 | 3717 | Janus kinase 2 |
| JAK3 | 3718 | Janus kinase 3 |
| JARID2 | 3720 | jumonji, AT rich interactive domain 2 |
| JMJD1C | 221037 | jumonji domain containing 1C |
| JUN | 3725 | Jun oncogene |
| JUNB | 3726 | Jun-B oncogene |
| KAT2B | 8850 | K(lysine) acetyltransferase 2B |
| KATNA1 | 11104 | katanin p60 (ATPase-containing) subunit A1 |
| KDM6B | 23135 | lysine (K)-specific demethylase 6B |
| KLF10 | 7071 | Kruppel-like factor 10 |
| KLF13 | 51621 | Kruppel-like factor 13 |
| KLF6 | 1316 | Kruppel-like factor 6 |
| KLF7 | 8609 | Kruppel-like factor 7 (ubiquitous) |
| KLF9 | 687 | Kruppel-like factor 9 |

TABLE 11-continued

Gene Abbreviations, Entrez ID Numbers and Brief Description

| Symbol | Entrez ID | Description |
|---|---|---|
| KLRD1 | 3824 | killer cell lectin-like receptor, subfamily D, member 1 |
| LAD1 | 3898 | ladinin |
| LAMP2 | 3920 | lysosomal-associated membrane protein 2 |
| LASS4 | 79603 | LAG1 homolog, ceramide synthase 4 |
| LASS6 | 253782 | LAG1 homolog, ceramide synthase 6 |
| LEF1 | 51176 | lymphoid enhancer binding factor 1 |
| LGALS3BP | 3959 | lectin, galactoside-binding, soluble, 3 binding protein |
| LGTN | 1939 | ligatin |
| LIF | 3976 | leukemia inhibitory factor |
| LILRB1, LILRB2, LILRB3, LILRB4, | 10859, 10288, 11025, 11006, 10990 | leukocyte immunoglobulin-like receptor, subfamily B (with TM and ITIM domains),members 1-5 |
| LIMK2 | 3985 | LIM motif-containing protein kinase 2 |
| LITAF | 9516 | LPS-induced TN factor |
| LMNB1 | 4001 | lamin B1 |
| LRRFIP1 | 9208 | leucine rich repeat (in FLII) interacting protein 1 |
| LSP1 | 4046 | lymphocyte specific 1 |
| LTA | 4049 | lymphotoxin A |
| MAF | 4094 | avian musculoaponeurotic fibrosarcoma (v-maf) AS42 oncogene homolog |
| MAFF | 23764 | v-maf musculoaponeurotic fibrosarcoma oncogene family, protein F (avian) |
| MAFG | 4097 | v-maf musculoaponeurotic fibrosarcoma oncogene family, protein G (avian) |
| MAML2 | 84441 | mastermind like 2 (*Drosophila*) |
| MAP3K5 | 4217 | mitogen-activated protein kinase kinase kinase 5 |
| MAP3K8 | 1326 | mitogen-activated protein kinase kinase kinase 8 |
| MAP4K2 | 5871 | mitogen-activated protein kinase kinase kinase kinase 2 |
| MAP4K3 | 8491 | mitogen-activated protein kinase kinase kinase kinase 3 |
| MAPKAPK2 | 9261 | MAP kinase-activated protein kinase 2 |
| MATR3 | 9782 | matrin 3 |
| MAX | 4149 | Max protein |
| MAZ | 4150 | MYC-associated zinc finger protein (purine-binding transcription factor) |
| MBNL1 | 4154 | muscleblind-like 1 (*Drosophila*) |
| MBNL3 | 55796 | muscleblind-like 3 (*Drosophila*) |
| MDM4 | 4194 | transformed mouse 3T3 cell double minute 4 |
| MEN1 | 4221 | multiple endocrine neoplasia 1 |
| MFHAS1 | 9258 | malignant fibrous histiocytoma amplified sequence 1 |
| MGLL | 11343 | monoglyceride lipase |
| MIER1 | 57708 | mesoderm induction early response 1 homolog (*Xenopus laevis* |
| MINA | 84864 | myc induced nuclear antigen |
| MKNK2 | 2872 | MAP kinase-interacting serine/threonine kinase 2 |
| MORF4L1 | 10933 | mortality factor 4 like 1 |
| MORF4L2 | 9643 | mortality factor 4 like 2 |
| MS4A6A | 64231 | membrane-spanning 4-domains, subfamily A, member 6B |
| MST4 | 51765 | serine/threonine protein kinase MST4 |
| MT1A | 4489 | metallothionein 1 |
| MT2A | 4502 | metallothionein 2 |
| MTA3 | 57504 | metastasis associated 3 |
| MXD3 | 83463 | Max dimerization protein 3 |
| MXI1 | 4601 | Max interacting protein 1 |
| MYC | 4609 | myelocytomatosis oncogene |
| MYD88 | 4615 | myeloid differentiation primary response gene 88 |
| MYST4 | 23522 | MYST histone acetyltransferase monocytic leukemia 4 |
| NAGK | 55577 | N-acetylglucosamine kinase |
| NAMPT | 10135 | nicotinamide phosphoribosyltransferase |

TABLE 11-continued

| Gene Abbreviations, Entrez ID Numbers and Brief Description | | |
|---|---|---|
| Symbol | Entrez ID | Description |
| NASP | 4678 | nuclear autoantigenic sperm protein (histone-binding) |
| NCF1C | 654817 | neutrophil cytosolic factor 1 |
| NCOA1 | 8648 | nuclear receptor coactivator 1 |
| NCOA3 | 8202 | nuclear receptor coactivator 3 |
| NEK4 | 6787 | NIMA (never in mitosis gene a)-related expressed kinase 4 |
| NEK6 | 10783 | NIMA (never in mitosis gene a)-related expressed kinase 6 |
| NFATC1 | 4772 | nuclear factor of activated T-cells, cytoplasmic, calcineurin-dependent 1 |
| NFATC2 | 4773 | nuclear factor of activated T-cells, cytoplasmic, calcineurin-dependent 2 |
| NFE2L2 | 4780 | nuclear factor, erythroid derived 2, like 2 |
| NFIL3 | 4783 | nuclear factor, interleukin 3, regulated |
| NFKB1 | 4790 | nuclear factor of kappa light polypeptide gene enhancer in B-cells 1, p105 |
| NFKBIA | 4792 | nuclear factor of kappa light polypeptide gene enhancer in B-cells inhibito |
| NFKBIB | 4793 | nuclear factor of kappa light polypeptide gene enhancer in B-cells inhibito |
| NFKBIE | 4794 | nuclear factor of kappa light polypeptide gene enhancer in B-cells inhibito |
| NFKBIZ | 64332 | nuclear factor of kappa light polypeptide gene enhancer in B-cells inhibito |
| NFYC | 4802 | nuclear transcription factor-Y gamma |
| NKG7 | 4818 | natural killer cell group 7 sequence |
| NMI | 9111 | N-myc (and STAT) interactor |
| NOC4L | 79050 | nucleolar complex associated 4 homolog (*S. cerevisiae*) |
| NOTCH1 | 4851 | Notch gene homolog 1 (*Drosophila*) |
| NOTCH2 | 4853 | Notch gene homolog 2 (*Drosophila*) |
| NR3C1 | 2908 | nuclear receptor subfamily 3, group C, member 1 |
| NR4A2 | 4929 | nuclear receptor subfamily 4, group A, member 2 |
| NR4A3 | 8013 | nuclear receptor subfamily 4, group A, member 3 |
| NUDT4 | 11163 | nudix (nucleoside diphosphate linked moiety X)-type motif 4 |
| OAS2 | 4939 | 2'-5'oligoadenylate synthetase 2 |
| PACSIN1 | 29993 | protein kinase C and casein kinase substrate in neurons 1 |
| PAXBP1 | 94104 | PAX3 and PAX7 binding protein 1 |
| PCTK1 | 5127 | PCTAIRE-motif protein kinase 1 |
| PDCD1 | 5133 | programmed cell death 1 |
| PDCD1LG2 | 80380 | programmed cell death 1 ligand 2 |
| PDK3 | 5165 | pyruvate dehydrogenase kinase, isoenzyme 3 |
| PDPK1 | 5170 | 3-phosphoinositide dependent protein kinase-1 |
| PDXK | 8566 | pyridoxal (pyridoxine, vitamin B6) kinase |
| PECI | 10455 | peroxisomal delta3, delta2-enoyl-Coenzyme A isomerase |
| PELI2 | 57161 | pellino 2 |
| PGK1 | 5230 | phosphoglycerate kinase 1 |
| PHACTR2 | 9749 | phosphatase and actin regulator 2 |
| PHF13 | 148479 | PHD finger protein 13 |
| PHF21A | 51317 | PHD finger protein 21A |
| PHF6 | 84295 | PHD finger protein 6 |
| PHLDA1 | 22822 | pleckstrin homology-like domain, family A, member 1 |
| PHLPP1 | 23239 | PH domain and leucine rich repeat protein phosphatase 1 |
| PI4KA | 5297 | phosphatidylinositol 4-kinase, catalytic, alpha polypeptide |
| PIM1 | 5292 | proviral integration site 1 |
| PIM2 | 11040 | proviral integration site 2 |

TABLE 11-continued

| Gene Abbreviations, Entrez ID Numbers and Brief Description | | |
|---|---|---|
| Symbol | Entrez ID | Description |
| PIP4K2A | 5305 | phosphatidylinositol-5-phosphate 4-kinase, type II, alpha |
| PKM2 | 5315 | pyruvate kinase, muscle |
| PLAC8 | 51316 | placenta-specific 8 |
| PLAGL1 | 5325 | pleiomorphic adenoma gene-like 1 |
| PLAUR | 5329 | plasminogen activator, urokinase receptor |
| PLEK | 5341 | pleckstrin |
| PLEKHF2 | 79666 | pleckstrin homology domain containing, family F (with FYVE domain) member 2 |
| PLK2 | 10769 | polo-like kinase 2 (*Drosophila*) |
| PMEPA1 | 56937 | prostate transmembrane protein, androgen induced 1 |
| PML | 5371 | promyelocytic leukemia |
| PNKP | 11284 | polynucleotide kinase 3'-phosphatase |
| POU2AF1 | 5450 | POU domain, class 2, associating factor 1 |
| POU2F2 | 5452 | POU domain, class 2, transcription factor 2 |
| PPME1 | 51400 | protein phosphatase methylesterase 1 |
| PPP2R5A | 5525 | protein phosphatase 2, regulatory subunit B (B56), alpha isoform |
| PPP3CA | 5530 | protein phosphatase 3, catalytic subunit, alpha isoform |
| PRC1 | 9055 | protein regulator of cytokinesis 1 |
| PRDM1 | 639 | PR domain containing 1, with ZNF domain |
| PRF1 | 5551 | perforin 1 (pore forming protein) |
| PRICKLE1 | 144165 | prickle like 1 (*Drosophila*) |
| PRKCA | 5578 | protein kinase C, alpha |
| PRKCD | 5580 | protein kinase C, delta |
| PRKCH | 5583 | protein kinase C, eta |
| PRKCQ | 5588 | protein kinase C, theta |
| PRKD3 | 23683 | protein kinase D3 |
| PRNP | 5621 | prion protein |
| PROCR | 10544 | protein C receptor, endothelial |
| PRPF4B | 8899 | PRP4 pre-mRNA processing factor 4 homolog B (yeast) |
| PRPS1 | 5631 | phosphoribosyl pyrophosphate synthetase 1 |
| PSMB9 | 5698 | proteasome (prosome, macropain) subunit, beta type 9 (large multifunctional |
| PSTPIP1 | 9051 | proline-serine-threonine phosphatase-interacting protein 1 |
| PTEN | 5728 | phosphatase and tensin homolog |
| PTK2B | 2185 | PTK2 protein tyrosine kinase 2 beta |
| PTP4A1 | 7803 | protein tyrosine phosphatase 4a1 |
| PTPLA | 9200 | protein tyrosine phosphatase-like (proline instead of catalytic arginine), |
| PTPN1 | 5770 | protein tyrosine phosphatase, non-receptor type 1 |
| PTPN18 | 26469 | protein tyrosine phosphatase, non-receptor type 18 |
| PTPN6 | 5777 | protein tyrosine phosphatase, non-receptor type 6 |
| PTPRC | 5788 | protein tyrosine phosphatase, receptor type, C |
| PTPRCAP | 5790 | protein tyrosine phosphatase, receptor type, C polypeptide-associated prote |
| PTPRE | 5791 | protein tyrosine phosphatase, receptor type, E |
| PTPRF | 5792 | protein tyrosine phosphatase, receptor type, F |
| PTPRJ | 5795 | protein tyrosine phosphatase, receptor type, J |
| PTPRS | 5802 | protein tyrosine phosphatase, receptor type, S |
| PVR | 5817 | poliovirus receptor |
| PYCR1 | 5831 | pyrroline-5-carboxylate reductase 1 |
| RAB33A | 9363 | RAB33A, member of RAS oncogene family |
| RAD51AP1 | 10635 | RAD51 associated protein 1 |
| RARA | 5914 | retinoic acid receptor, alpha |
| RASGRP1 | 10125 | RAS guanyl releasing protein 1 |
| RBPJ | 3516 | recombination signal binding protein for immunoglobulin kappa J region |
| REL | 5966 | reticuloendotheliosis oncogene |
| RELA | 5970 | v-rel reticuloendotheliosis viral oncogene homolog A (avian) |
| RFK | 55312 | riboflavin kinase |
| RIPK1 | 8737 | receptor (TNFRSF)-interacting serine-threonine kinase 1 |

TABLE 11-continued

Gene Abbreviations, Entrez ID Numbers and Brief Description

| Symbol | Entrez ID | Description |
|---|---|---|
| RIPK2 | 8767 | receptor (TNFRSF)-interacting serine-threonine kinase 2 |
| RIPK3 | 11035 | receptor-interacting serine-threonine kinase 3 |
| RNASEL | 6041 | ribonuclease L (2',5'-oligoisoadenylate synthetase-dependent) |
| RNF11 | 26994 | ring finger protein 11 |
| RNF5 | 6048 | ring finger protein 5 |
| RORA | 6095 | RAR-related orphan receptor alpha |
| RORC | 6097 | RAR-related orphan receptor gamma |
| RPP14 | 11102 | ribonuclease P 14 subunit (human) |
| RPS6KB1 | 6198 | ribosomal protein S6 kinase, polypeptide 1 |
| RUNX1 | 861 | runt related transcription factor 1 |
| RUNX2 | 860 | runt related transcription factor 2 |
| RUNX3 | 864 | runt related transcription factor 3 |
| RXRA | 6256 | retinoid X receptor alpha |
| SAP18 | 10284 | Sin3-associated polypeptide 18 |
| SAP30 | 8819 | sin3 associated polypeptide |
| SATB1 | 6304 | special AT-rich sequence binding protein 1 |
| SEMA4D | 10507 | sema domain, immunoglobulin domain (Ig), transmembrane domain (TM) and shor |
| SEMA7A | 8482 | sema domain, immunoglobulin domain (Ig), and GPI membrane anchor, (semaphor |
| SERPINB1 | 1992 | serine (or cysteine) peptidase inhibitor, clade B, member 1a |
| SERPINE2 | 5270 | serine (or cysteine) peptidase inhibitor, clade E, member 2 |
| SERTAD1 | 29950 | SERTA domain containing 1 |
| SGK1 | 6446 | serum/glucocorticoid regulated kinase 1 |
| SH2D1A | 4068 | SH2 domain protein 1A |
| SIK1 | 150094 | salt-inducible kinase 1 |
| SIRT2 | 22933 | sirtuin 2 (silent mating type information regulation 2, homolog) 2 (S. cere |
| SKAP2 | 8935 | src family associated phosphoprotein 2 |
| SKI | 6497 | ski sarcoma viral oncogene homolog (avian) |
| SKIL | 6498 | SKI-like |
| SLAMF7 | 57823 | SLAM family member 7 |
| SLC2A1 | 6513 | solute carrier family 2 (facilitated glucose transporter), member 1 |
| SLC3A2 | 6520 | solute carrier family 3 (activators of dibasic and neutral amino acid trans |
| SLK | 9748 | STE20-like kinase (yeast) |
| SMAD2 | 4087 | MAD homolog 2 (*Drosophila*) |
| SMAD3 | 4088 | MAD homolog 3 (*Drosophila*) |
| SMAD4 | 4089 | MAD homolog 4 (*Drosophila*) |
| SMAD7 | 4092 | MAD homolog 7 (*Drosophila*) |
| SMARCA4 | 6597 | SWI/SNF related, matrix associated, actin dependent regulator of chromatin, |
| SMOX | 54498 | spermine oxidase |
| SOCS3 | 9021 | suppressor of cytokine signaling 3 |
| SP1 | 6667 | trans-acting transcription factor 1 |
| SP100 | 6672 | nuclear antigen Sp100 |
| SP4 | 6671 | trans-acting transcription factor 4 |
| SPHK1 | 8877 | sphingosine kinase 1 |
| SPOP | 8405 | speckle-type POZ protein |
| SPP1 | 6696 | secreted phosphoprotein 1 |
| SPRY1 | 10252 | sprouty homolog 1 (*Drosophila*) |
| SRPK2 | 6733 | serine/arginine-rich protein specific kinase 2 |
| SS18 | 6760 | synovial sarcoma translocation, Chromosome 18 |
| STARD10 | 10809 | START domain containing 10 |
| STAT1 | 6772 | signal transducer and activator of transcription 1 |
| STAT2 | 6773 | signal transducer and activator of transcription 2 |
| STAT3 | 6774 | signal transducer and activator of transcription 3 |
| STAT4 | 6775 | signal transducer and activator of transcription 4 |
| STAT5A | 6776 | signal transducer and activator of transcription 5A |

TABLE 11-continued

Gene Abbreviations, Entrez ID Numbers and Brief Description

| Symbol | Entrez ID | Description |
|---|---|---|
| STAT5B | 6777 | signal transducer and activator of transcription 5B |
| STAT6 | 6778 | signal transducer and activator of transcription 6 |
| STK17B | 9262 | serine/threonine kinase 17b (apoptosis-inducing) |
| STK19 | 8859 | serine/threonine kinase 19 |
| STK38 | 11329 | serine/threonine kinase 38 |
| STK38L | 23012 | serine/threonine kinase 38 like |
| STK39 | 27347 | serine/threonine kinase 39, STE20/SPS1 homolog (yeast) |
| STK4 | 6789 | serine/threonine kinase 4 |
| SULT2B1 | 6820 | sulfotransferase family, cytosolic, 2B, member 1 |
| SUZ12 | 23512 | suppressor of zeste 12 homolog (*Drosophila*) |
| TAF1B | 9014 | TATA box binding protein (Tbp)-associated factor, RNA polymerase I, B |
| TAL2 | 6887 | T-cell acute lymphocytic leukemia 2 |
| TAP1 | 6890 | transporter 1, ATP-binding cassette, sub-family B (MDR/TAP) |
| TBPL1 | 9519 | TATA box binding protein-like 1 |
| TBX21 | 30009 | T-box 21 |
| TCERG1 | 10915 | transcription elongation regulator 1 (CA150) |
| TEC | 7006 | cytoplasmic tyrosine kinase, Dscr28C related (*Drosophila*) |
| TFDP1 | 7027 | transcription factor Dp 1 |
| TFEB | 7942 | transcription factor EB |
| TGFB1 | 7040 | transforming growth factor, beta 1 |
| TGFB3 | 7043 | transforming growth factor, beta 3 |
| TGFBR1 | 7046 | transforming growth factor, beta receptor I |
| TGFBR3 | 7049 | transforming growth factor, beta receptor III |
| TGIF1 | 7050 | TGFB-induced factor homeobox 1 |
| TGM2 | 7052 | transglutaminase 2, C polypeptide |
| THRAP3 | 9967 | thyroid hormone receptor associated protein 3 |
| TIMP2 | 7077 | tissue inhibitor of metalloproteinase 2 |
| TK1 | 7083 | thymidine kinase 1 |
| TK2 | 7084 | thymidine kinase 2, mitochondrial |
| TLE1 | 7088 | transducin-like enhancer of split 1, homolog of *Drosophila* E(spl) |
| TLR1 | 7096 | toll-like receptor 1 |
| TMEM126A | 84233 | transmembrane protein 126A |
| TNFRSF12A | 51330 | tumor necrosis factor receptor superfamily, member 12a |
| TNFRSF13B | 23495 | tumor necrosis factor receptor superfamily, member 13b |
| TNFRSF1B | 7133 | tumor necrosis factor receptor superfamily, member 1b |
| TNFRSF25 | 8718 | tumor necrosis factor receptor superfamily, member 25 |
| TNFRSF4 | 7293 | tumor necrosis factor receptor superfamily, member 4 |
| TNFRSF9 | 3604 | tumor necrosis factor receptor superfamily, member 9 |
| TNFSF11 | 8600 | tumor necrosis factor (ligand) superfamily, member 11 |
| TNFSF8 | 944 | tumor necrosis factor (ligand) superfamily, member 8 |
| TNFSF9 | 8744 | tumor necrosis factor (ligand) superfamily, member 9 |
| TNK2 | 10188 | tyrosine kinase, non-receptor, 2 |
| TOX4 | 9878 | TOX high mobility group box family member 4 |
| TP53 | 7157 | transformation related protein 53 |
| TRAF3 | 7187 | Tnf receptor-associated factor 3 |
| TRAT1 | 50852 | T cell receptor associated transmembrane adaptor 1 |
| TRIM24 | 8805 | tripartite motif-containing 24 |
| TRIM25 | 7706 | tripartite motif-containing 25 |
| TRIM28 | 10155 | tripartite motif-containing 28 |
| TRIM5 | 85363 | tripartite motif containing 5 |
| TRIP12 | 9320 | thyroid hormone receptor interactor 12 |
| TRPS1 | 7227 | trichorhinophalangeal syndrome I (human) |
| TRRAP | 8295 | transformation/transcription domain-associated protein |

TABLE 11-continued

| Gene Abbreviations, Entrez ID Numbers and Brief Description | | |
|---|---|---|
| Symbol | Entrez ID | Description |
| TSC22D3 | 1831 | TSC22 domain family, member 3 |
| TSC22D4 | 81628 | TSC22 domain family, member 4 |
| TWF1 | 5756 | twinfilin, actin-binding protein, homolog 1 (*Drosophila*) |
| TXK | 7294 | TXK tyrosine kinase |
| UBE2B | 7320 | ubiquitin-conjugating enzyme E2B, RAD6 homology (*S. cerevisiae*) |
| UBIAD1 | 29914 | UbiA prenyltransferase domain containing 1 |
| ULK2 | 9706 | Unc-51 like kinase 2 (*C. elegans*) |
| VAV1 | 7409 | vav 1 oncogene |
| VAV3 | 10451 | vav 3 oncogene |
| VAX2 | 25806 | ventral anterior homeobox containing gene 2 |
| VRK1 | 7443 | vaccinia related kinase 1 |
| VRK2 | 7444 | vaccinia related kinase 2 |
| WDHD1 | 11169 | WD repeat and HMG-box DNA binding protein 1 |
| WHSC1L1 | 54904 | Wolf-Hirschhorn syndrome candidate 1-like 1 (human) |
| WNK1 | 65125 | WNK lysine deficient protein kinase 1 |
| XAB2 | 56949 | XPA binding protein 2 |
| XBP1 | 7494 | X-box binding protein 1 |
| XRCC5 | 7520 | X-ray repair complementing defective repair in Chinese hamster cells 5 |

TABLE 11-continued

| Gene Abbreviations, Entrez ID Numbers and Brief Description | | |
|---|---|---|
| Symbol | Entrez ID | Description |
| YBX1 | 4904 | Y box protein 1 |
| ZAK | 51776 | RIKEN cDNA B230120H23 gene |
| ZAP70 | 7535 | zeta-chain (TCR) associated protein kinase |
| ZBTB32 | 27033 | zinc finger and BTB domain containing 32 |
| ZEB1 | 6935 | zinc finger E-box binding homeobox 1 |
| ZEB2 | 9839 | zinc finger E-box binding homeobox 2 |
| ZFP161 | 7541 | zinc finger protein 161 |
| ZFP36L1 | 677 | zinc finger protein 36, C3H type-like 1 |
| ZFP36L2 | 678 | zinc finger protein 36, C3H type-like 2 |
| ZFP62 | 92379 | zinc finger protein 62 |
| ZNF238 | 10472 | zinc finger protein 238 |
| ZNF281 | 23528 | zinc finger protein 281 |
| ZNF326 | 284695 | zinc finger protein 326 |
| ZNF703 | 80139 | zinc finger protein 703 |
| ZNRF1 | 84937 | zinc and ring finger 1 |
| ZNRF2 | 223082 | zinc and ring finger 2 |

Primers for Nanostring STA and qRT-PCR/Fluidigm and siRNA sequences: Table S6.1 presents the sequences for each forward and reverse primer used in the Fluidigm/qRT-PCR experiments and Nanostring nCounter gene expression profiling. Table S6.2 presents the sequences for RNAi used for knockdown analysis.

TABLE S6.1

| Primer Sequences | | | | | |
|---|---|---|---|---|---|
| Assay | Gene Name | SEQ ID NO: | Forward Sequence | SEQ ID NO: | Reverse Sequence |
| Nanostring STA | 1700097 N02Rik | 1 | GGC CAG AGC TTG ACC ATC | 2 | AGC AAG CCA GCC AAA CAG |
| Nanostring STA | Aim1 | 3 | AGC CAA TTT TGA AGG GCA | 4 | GGA AGC CCT GCA TTT CCT |
| Nanostring STA | Arnt1 | 5 | TAT AAC CCC TGG GCC CTC | 6 | GTT GCA GCC CTC GTT GTC |
| Nanostring STA | Bcl6 | 7 | GTC GGG ACA TCT TGA CGG | 8 | GGA GGA TGC AAA ACC CCT |
| Nanostring STA | Ccl20 | 9 | GCA TGG GTA CTG CTG GCT | 10 | TGA GGA GGT TCA CAG CCC |
| Nanostring STA | Cd24a | 11 | GGA CGC GTG AAA GGT TTG | 12 | TGC ACT ATG GCC TTA TCG G |
| Nanostring STA | Cd80 | 13 | TGC CTA AGC TCC ATT GGC | 14 | ACG GCA AGG CAG CAA TAC |
| Nanostring STA | Csnk1a1 | 15 | GGG TAT TGG GCG TCA CTG | 16 | CCA CGG CAG ACT GGT TCT |
| Nanostring STA | Ddr1 | 17 | ATG CAC ACT CTG GGA GCC | 18 | CCA AGG ACC TGC AAA GAG G |
| Nanostring STA | Emp1 | 19 | AGC TGC CAT ACC ACT GGC | 20 | AGG CAC ATG GGA TCT GGA |
| Nanostring STA | Flna | 21 | CTT CAC TGC ATT CGC CCT | 22 | CAC AGG ACA ACG GAA GCA |
| Nanostring STA | Gata3 | 23 | CAC CGC CAT GGG TTA GAG | 24 | TGG GAT CCG GAT TCA GTG |
| Nanostring STA | 2900064 A13Rik | 25 | AAG GAA AAA TGC GAG CAA GA | 26 | TCT CCC GTC TCA TGT CAG G |

TABLE S6.1-continued

| Primer Sequences | | | | | |
|---|---|---|---|---|---|
| Assay | Gene Name | SEQ ID NO: | Forward Sequence | SEQ ID NO: | Reverse Sequence |
| Nanostring STA | Anxa4 | 27 | ATG GGG GAC AGA CGA GGT | 28 | TGC CTA AGC CCT TCA TGG |
| Nanostring STA | Atf4 | 29 | GAT GAT GGC TTG GCC AGT | 30 | TGG CCA ATT GGG TTC ACT |
| Nanostring STA | Bmpr1a | 31 | CAT TTG GGA AAT GGC TCG | 32 | ATG GGC CCA ACA TTC TGA |
| Nanostring STA | Ccl4 | 33 | AAG CTC TGC GTG TCT GCC | 34 | ACC ACA GCT GGC TTG GAG |
| Nanostring STA | Cd274 | 35 | CGT GGA TCC AGC CAC TTC | 36 | ATC ATT CGC TGT GGC GTT |
| Nanostring STA | Cd86 | 37 | ATC TGC CGT GCC CAT TTA | 38 | ACG AGC CCA TGT CCT TGA |
| Nanostring STA | Ct1a2b | 39 | GGC TCA ACA GCA GGA AGC | 40 | TTA ATT TGA AGA CAT CAT GGC A |
| Nanostring STA | Dntt | 41 | CCC AGA AGC CAC AGA GGA | 42 | TTC CAG CCC TTT CCT TCC |
| Nanostring STA | Ercc5 | 43 | GTG CCA TTT GAC ACA GCG | 44 | CTG GCC TAC CCT CCA CCT |
| Nanostring STA | Foxm1 | 45 | CAA GCC AGG CTG GAA GAA | 46 | TGG GTC GTT TCT GCT GTG |
| Nanostring STA | Gem | 47 | GAC ACG CTT CGG GTT CAC | 48 | CAA CTG TGA TGA GGC CAG C |
| Nanostring STA | 6330442 E10Rik | 49 | CCC AGC ATT AAG GCT CCA | 50 | AGG AGC AAC AGG GGA CCT |
| Nanostring STA | Api5 | 51 | CAG CTT TGA ACA CAG GGT CTT | 52 | AGC TGA CTG AAA TTC CTC CCT |
| Nanostring STA | B4galt1 | 53 | TCA CAG TGG ACA TCG GGA | 54 | CAC TCA CCC TGG GCA TCT |
| Nanostring STA | Cand1 | 55 | CTA CTG CAG GGA GGA GCG | 56 | GGG TCC CTC TTT AGG GCA |
| Nanostring STA | Ccr4 | 57 | GTC CGT GCA GTT TGG CTT | 58 | GGT TTG GGG ACA GGC TTT |
| Nanostring STA | Cd28 | 59 | CCT TTG CAG TGA GTT GGG A | 60 | CGT TTT GAA AAT CTG CAG AGA A |
| Nanostring STA | Cd9 | 61 | GCG GGA AAC ACT CAA AGC | 62 | TGC TGA AGA TCA TGC CGA |
| Nanostring STA | Ctsw | 63 | GCC ACT GGA GCT GAA GGA | 64 | TGA CCT CTC CTG CCC GTA |
| Nanostring STA | Dpp4 | 65 | CCC TGC TCC TGC ATC TGT | 66 | AAA TCT TCC GAC CCA GCC |
| Nanostring STA | Errfi1 | 67 | TCC TGC TTT TCC CAT CCA | 68 | CCA GCA ACA CAA GAC CAG C |
| Nanostring STA | Foxo1 | 69 | TCC AGT CTG GGC AAG AGG | 70 | GGC AGC AGA GGG TGG ATA |
| Nanostring STA | Gfi1 | 71 | ATG TCT TCC CTG CCT CCC | 72 | AAG CCC AAA GCA CAG ACG |
| Nanostring STA | Abcg2 | 73 | GGA ACA TCG GCC TTC AAA | 74 | CAT TCC AGC GGC ATC ATA |
| Nanostring STA | Aqp3 | 75 | CGG CAC AGC TGG AAT CTT | 76 | GGT TGA CGG CAT AGC CAG |

TABLE S6.1-continued

| Primer Sequences | | | | | |
|---|---|---|---|---|---|
| Assay | Gene Name | SEQ ID NO: | Forward Sequence | SEQ ID NO: | Reverse Sequence |
| Nanostring STA | Batf | 77 | CTA CCC AGA GGC CCA GTG | 78 | AAC TAT CCA CCC CCT GCC |
| Nanostring STA | Casp1 | 79 | TCC TGA GGG CAA AGA GGA | 80 | GAT TTG GCT TGC CTG GG |
| Nanostring STA | Ccr5 | 81 | AAC TGA ATG GGG AGG TTG G | 82 | TTA CAG CCG CCT TTC AGG |
| Nanostring STA | Cd4 | 83 | CCA GCC CTG GAT CTC CTT | 84 | GCC ACT TTC ATC ACC ACC A |
| Nanostring STA | Cebpb | 85 | TGC ACC GAG GGG ACA C | 86 | AAC CCC GCA GGA ACA TCT |
| Nanostring STA | Cxcl10 | 87 | TGC CGT CAT TTT CTG CCT | 88 | CGT GGC AAT GAT CTC AAC A |
| Nanostring STA | Egr2 | 89 | AGG ACC TTG ATG GAG CCC | 90 | CTG GCA TCC AGG GTC AAC |
| Nanostring STA | Etv6 | 91 | CAT GAG GGA GGA TGC TGG | 92 | AAA TCC CTG CTA TCA AAA ATC C |
| Nanostring STA | Foxp1 | 93 | GCT CTC TGT CTC CAA GGG C | 94 | ACT CAC AAC CCA GAC CGC |
| Nanostring STA | Gja1 | 95 | GGC CTG ATG ACC TGG AGA | 96 | TCC CTA CTT TTG CCG CCT |
| Nanostring STA | Acly | 97 | GAG GGC TGG GAC CAT TG | 98 | GCA GCT GCC CAG AAT CTT |
| Nanostring STA | Arhgef3 | 99 | GCA GCA GGC TGT TTC TTA CC | 100 | TTC CTC CCC ACT CAT CCA |
| Nanostring STA | BC02161 4 | 101 | AAG GAG GGC AAG GAC CAG | 102 | GAG CTT GGG TCG GGA TTT |
| Nanostring STA | Casp3 | 103 | GGA GAT GGC TTG CCA GAA | 104 | ACT CGA ATT CCG TTG CCA |
| Nanostring STA | Ccr6 | 105 | GCC AGA TCC ATG ACT GAC G | 106 | TTT GGT TGC CTG GAC GAT |
| Nanostring STA | Cd44 | 107 | CAG GGA ACA TCC ACC AGC | 108 | TAG CAT CAC CCT TTG GGG |
| Nanostring STA | Chd7 | 109 | CAT TGT CAG TGG GCG TCA | 110 | GAA TCA CAG GCT CGC CC |
| Nanostring STA | Cxcr3 | 111 | CCA GAT CTA CCG CAG GGA | 112 | CAT GAC CAG AAG GGG CAG |
| Nanostring STA | Eif3e | 113 | GTC AAC CAG GGA TGG CAG | 114 | CAG TTT TCC CCA GAG CGA |
| Nanostring STA | Fas | 115 | GCT GTG GAT CTG GGC TGT | 116 | CCC CCA TTC ATT TTG CAG |
| Nanostring STA | Foxp3 | 117 | TGG AAA CAC CCA GCC ACT | 118 | GGC AAG ACT CCT GGG GAT |
| Nanostring STA | Glipr1 | 119 | TGG ATG GCT TCG TCT GTG | 120 | TGC AGC TGT GGG TTG TGT |
| Nanostring STA | Acvr1b | 121 | GTG CCG ACA TCT ATG CCC | 122 | GCA CTC CCG CAT CAT CTT |
| Nanostring STA | Arid5a | 123 | GGC CTC GGG TCT TTC AGT | 124 | CTA GGC AGC TGG GCT CAC |

TABLE S6.1-continued

| Primer Sequences | | | | | |
|---|---|---|---|---|---|
| Assay | Gene Name | SEQ ID NO: | Forward Sequence | SEQ ID NO: | Reverse Sequence |
| Nanostring STA | Bcl11b | 125 | GGA GGG GTG GCT TTC AA | 126 | AAG ATT CTC GGG GTC CCA |
| Nanostring STA | Casp4 | 127 | GGA ACA GCT GGG CAA AGA | 128 | GCC TGG GTC CAC ACT GAA |
| Nanostring STA | Ccr8 | 129 | GTG GGT GTT TGG GAC TGC | 130 | ATC AAG GGG ATG GTG GCT |
| Nanostring STA | Cd51 | 131 | TGG GGG TAC CAC GAC TGT | 132 | GGG CGT GTA GCC TTG AGA |
| Nanostring STA | Clcf1 | 133 | AAT CCT CCT CGA CTG GGG | 134 | TGA CAC CTG CAA TGC TGC |
| Nanostring STA | Cxcr4 | 135 | CCG ATA GCC TGT GGA TGG | 136 | GTC GAT GCT GAT CCC CAC |
| Nanostring STA | Eif3h | 137 | AGC CTT CGC CAT GTC AAC | 138 | CGC CTT CAG CGA GAG AGA |
| Nanostring STA | Fas1 | 139 | GCA AAT AGC CAA CCC CAG | 140 | GTT GCA AGA CTG ACC CCG |
| Nanostring STA | Frmd4b | 141 | GGA GTC CCA GTC CCA CCT | 142 | TGG ACC TTC TTC TCC CCC |
| Nanostring STA | Golga3 | 143 | TCC AAC CAG GTG GAG CAC | 144 | TCA TCT CAG AGT CCA GCC G |
| Nanostring STA | Acvr2a | 145 | ATG GCA AAC TTG GAC CCC | 146 | CAA GAT CTG TGC AGG GCA |
| Nanostring STA | Arl5a | 147 | CGG ATT TGA GCG CTT CTG | 148 | AGT CAC TGG TGG GTG GGA |
| Nanostring STA | Bcl2111 | 149 | TGG CAA GCC CTC TCA CTT | 150 | AAA CAC ACA CAA CCA CGC A |
| Nanostring STA | Casp6 | 151 | TGC TCA AAA TTC ACG AGG TG | 152 | CAC GGG TAC GTC ATG CTG |
| Nanostring STA | Cd2 | 153 | CAC CCT GGT CGC AGA GTT | 154 | GGT TGT GTT GGG GCA TTC |
| Nanostring STA | Cd70 | 155 | CTG GCT GTG GGC ATC TG | 156 | GGA GTT GTG GTC AAG GGC |
| Nanostring STA | Cmtm6 | 157 | TGC TGG TGT AGG CGT CTT T | 158 | TCT CAG CAA TCA CAG TGC AA |
| Nanostring STA | Cxcr5 | 159 | TGG CCT TAA TGT GCC TGT C | 160 | TGC TGG CTT GCC CTT TAC |
| Nanostring STA | Eif3m | 161 | TGG CTT GTT ACA TGA GCA AAA | 162 | CCG ATG TGT GCT GTG ACT G |
| Nanostring STA | Fipl11 | 163 | GGA TAC GAA TGG GAC TGG AA | 164 | CCA ACG CTT GAA CTG GCT |
| Nanostring STA | Fzd7 | 165 | TTC CCT GCA ATA GAA GTC TGG | 166 | TGA AGT AAT CTG TCC TCC CGA |
| Nanostring STA | Grn | 167 | CCG GCC TAC TCA TCC TGA | 168 | AAC TTT ATT GGA GCA ACA CAC G |
| Nanostring STA | Ahr | 169 | GTT GTG ATG CCA AAG GGC | 170 | CAA GCG TGC ATT GGA CTG |
| Nanostring STA | Armcx2 | 171 | TCC AAT CTT GCC ACC ACC | 172 | TTC CAG CAC TTT GGG AGC |

TABLE S6.1-continued

| Primer Sequences | | | | | |
|---|---|---|---|---|---|
| Assay | Gene Name | SEQ ID NO: | Forward Sequence | SEQ ID NO: | Reverse Sequence |
| Nanostring STA | Bcl3 | 173 | CCA GGT TTT GCA CCA AGG | 174 | CCT CCC AGA CCC CTC TGT |
| Nanostring STA | Ccl1 | 175 | CAC TGA TGT GCC TGC TGC | 176 | TGA GGC GCA GCT TTC TCT |
| Nanostring STA | Cd247 | 177 | TAC CAT CCC AGG GAA GCA | 178 | GCA GGT TGG CAG CAG TCT |
| Nanostring STA | Cd74 | 179 | GCT TCC GAA ATC TGC CAA | 180 | CGC CAT CCA TGG AGT TCT |
| Nanostring STA | Csf2 | 181 | GGC CAT CAA AGA AGC CCT | 182 | GCT GTC ATG TTC AAG GCG |
| Nanostring STA | Daxx | 183 | GTT GAC CCC GCA CTG TCT | 184 | ATT CCG AGG AGG CTT TGG |
| Nanostring STA | Elk3 | 185 | CCT GTG GAC CCA GAT GCT | 186 | GAC GGA GTT CAG CTC CCA |
| Nanostring STA | Fli1 | 187 | GAT TCT GAG AAA GGA GTA CGC A | 188 | GCC AGT GTT CCA GTT GCC |
| Nanostring STA | Gap43 | 189 | GCG AGA GAG CGA GTG AGC | 190 | CCA CGG AAG CTA GCC TGA |
| Nanostring STA | Gusb | 191 | ATG GAG CAG ACG CAA TCC | 192 | AAA GGC CGA AGT TTT GGG |
| Nanostring STA | H2-Q10 | 193 | GTG GGC ATC TGT GGT GGT | 194 | TGG AGC GGG AGC ATA GTC |
| Nanostring STA | Ifi35 | 195 | CAG AGT CCC ACT GGA CCG | 196 | AGG CAC AAC TGT CAG GGC |
| Nanostring STA | Il12rb2 | 197 | GCA GCC AAC TCA AAA GGC | 198 | GTG ATG CTC CCT GGT TGG |
| Nanostring STA | Il22 | 199 | TCA GAC AGG TTC CAG CCC | 200 | TCT TCT CGC TCA GAC GCA |
| Nanostring STA | Il4ra | 201 | CCT TCA GCC CCA GTG GTA | 202 | AGC TCA GCC TGG GTT CCT |
| Nanostring STA | Irf8 | 203 | AAG GGA CAC TTC CCG GAG | 204 | TTT CCT GCA GTT CCC CAG |
| Nanostring STA | Katna1 | 205 | CGG TGC GGG AAC TAT CC | 206 | CAT TTG GTC AAG AAC TCC CTG |
| Nanostring STA | Lad1 | 207 | GAA GGA GCT GTC AGG CCA | 208 | GCA TCC AGG GAT GTG GAC |
| Nanostring STA | Ly6c2 | 209 | GTC CTT CCA ATG ACC CCC | 210 | CCT CCA GGG CCA AGA ATA G |
| Nanostring STA | Mina | 211 | GTC TGC CGG AGC ATC AGT | 212 | TAA TGT GGA GGG AGG CCC |
| Nanostring STA | Nampt | 213 | CAA GGA GAT GGC GTG GAT | 214 | TGG GAT CAG CAA CTG GGT |
| Nanostring STA | Nkg7 | 215 | TGG CCC TCT GGT CTC AAC | 216 | TTT CAT ACT CAG CCC GAC G |
| Nanostring STA | Hif1a | 217 | AAG AAC TTT TGG GCC GCT | 218 | GCA CTG TGG CTG GGA GTT |
| Nanostring STA | Ifih1 | 219 | GCT GAA AAC CCA AAA TAC GA | 220 | ACT TCA CTG CTG TGC CCC |
| Nanostring STA | Il17a | 221 | ATC AGG ACG CGC AAA CAT | 222 | GAC GTG GAA CGG TTG AGG |

TABLE S6.1-continued

Primer Sequences

| Assay | Gene Name | SEQ ID NO: | Forward Sequence | SEQ ID NO: | Reverse Sequence |
|---|---|---|---|---|---|
| Nanostring STA | Il23r | 223 | CAC TGC AAG GCA GCA GG | 224 | CGT TTG GTT TGT TGT TGT TTT G |
| Nanostring STA | Il6st | 225 | TCG GAC GGC AAT TTC ACT | 226 | GTT GCT GGA GAT GCT GGG |
| Nanostring STA | Irf9 | 227 | ACT GAT CGT CGC GTC TCC | 228 | TTG GTC TGT CTT CCA AGT GCT |
| Nanostring STA | Kcmf1 | 229 | CTG ACC ACC CGA TGC AGT | 230 | TCC AGG TAA CGC TGC ACA |
| Nanostring STA | Lamp2 | 231 | GGC TGC AGC TGA ACA TCA | 232 | AAG CTG AGC CAT TAG CCA AA |
| Nanostring STA | Maf | 233 | AGG CAG GAG GAT GGC TTC | 234 | TCA TGG GGG TGG AGG AC |
| Nanostring STA | Mkln1 | 235 | GGT TTG CCC ATC AAC TCG | 236 | GGA TCC ATT TGG GCC TTT |
| Nanostring STA | Ncf1 | 237 | GCA AAG GAC AGG ACT GGG | 238 | TTT GAC ACC CTC CCC AAA |
| Nanostring STA | Notch1 | 239 | GCA GGC AAA TGC CTC AAC | 240 | GTG GCC ATT GTG CAG ACA |
| Nanostring STA | Hip1r | 241 | CTC GAG CAG CTG GGA CC | 242 | CCA GCA GGG ACC CTC TTT |
| Nanostring STA | Ifit1 | 243 | TCA TTC GCT ATG CAG CCA | 244 | GGC CTG TTG TGC CAA TTC |
| Nanostring STA | Il17f | 245 | AAG AAC CCC AAA GCA GGG | 246 | CAG CGA TCT CTG AGG GGA |
| Nanostring STA | Il24 | 247 | TCT CCA CTC TGG CCA ACA | 248 | CTG CAT CCA GGT CAG GAG A |
| Nanostring STA | Il7r | 249 | TGG CCT AGT CTC CCC GAT | 250 | CGA GCG GTT TGC ACT GT |
| Nanostring STA | Isg20 | 251 | CTG TGG AAG ATG CCA GGG | 252 | GTG GTT GGT GGC AGT GGT |
| Nanostring STA | Khdrbs1 | 253 | GTT CGT GGA ACC CCA GTG | 254 | TCC CCT TGA CTC TGG CTG |
| Nanostring STA | Lgals3bp | 255 | GGC CAC AGA GCT TCA GGA | 256 | CCA GCT CAC TCT TGG GGA |
| Nanostring STA | Maff | 257 | TCT GAC TCT TGC AGG CCC | 258 | TGG CAC AAT CCA AAG CCT |
| Nanostring STA | Mt1 | 259 | ACT ATG CGT GGG CTG GAG | 260 | GCA GGA GCT GGT GCA AGT |
| Nanostring STA | Ncoa1 | 261 | GCC TCC AGC CCA TCC TAT | 262 | TGA GGG ATT TAT TCG GGG A |
| Nanostring STA | Notch2 | 263 | TAC GAG TGC ACC TGC CAA | 264 | GCA GCG TCC TGG AAT GTC |
| Nanostring STA | Hsbp1 | 265 | ATC ACG TGA CCA CAG CCC | 266 | CTC TGA TAC CCT GCC GGA |
| Nanostring STA | Ifng | 267 | TCT GGG CTT CTC CTC CTG | 268 | TCC TTT TGC CAG TTC CTC C |
| Nanostring STA | Il17ra | 269 | GGG GCT GAG CTG CAG AGT | 270 | TGG TGT TCA GCT GCA GGA |

TABLE S6.1-continued

| Primer Sequences | | | | | |
|---|---|---|---|---|---|
| Assay | Gene Name | SEQ ID NO: | Forward Sequence | SEQ ID NO: | Reverse Sequence |
| Nanostring STA | Il27ra | 271 | AAG GCT GGC CTC GAA CTT | 272 | GGG CAG GGA ACC AAA CTT |
| Nanostring STA | Il9 | 273 | TGG TGA CAT ACA TCC TTG CC | 274 | TGT GTG GCA TTG GTC AGC |
| Nanostring STA | Itga3 | 275 | GCT TCA CCC AGA ACA CCG | 276 | CCC ATA TGT TGG TGC CGT |
| Nanostring STA | Kif2a | 277 | TGC CGA ATA CAC CAA GCA | 278 | TCC GCC GGT TCT TTA CAA |
| Nanostring STA | Lif | 279 | GGG GCA GGT AGT TGC TCA | 280 | TCG GGA TCA AGG ACA CAG A |
| Nanostring STA | Map3k5 | 281 | CCA TCT TGG AGT GCG AGA A | 282 | GCT CAG TCA GGC CCT TCA |
| Nanostring STA | Mt2 | 283 | TGT GCT GGC CAT ATC CCT | 284 | AGG CAC AGG AGC AGT TGG |
| Nanostring STA | Nfatc2 | 285 | AGC TCC ACG GCT ACA TGG | 286 | CGT TTC GGA GCT TCA GGA |
| Nanostring STA | Nr3c1 | 287 | CAA GTG ATT GCC GCA GTG | 288 | CAT TGG TCA TAC ATG CAG GG |
| Nanostring STA | Icos | 289 | CGG CCG ATC ATA GGA TGT | 290 | TTC CCT GGG AGC TGT CTG |
| Nanostring STA | Ifngr2 | 291 | CGA AAC AAC AGC AAA TGC C | 292 | CGG TGA ACC GTC CTT GTC |
| Nanostring STA | Il1r1 | 293 | ACC CGA GGT CCA GTG GTA | 294 | TCT CAT TCC GAG GGC TCA |
| Nanostring STA | Il2ra | 295 | TGC AAG AGA GGT TTC CGA | 296 | GTT CCC AAG GAG GTG GCT |
| Nanostring STA | Inhba | 297 | AGC AGA AGC ACC CAC AGG | 298 | TCC TGG CAC TGC TCA CAA |
| Nanostring STA | Itgb1 | 299 | TGG AAA ATT CTG CGA GTG TG | 300 | TTG GCC CTT GAA ACT TGG |
| Nanostring STA | Klf10 | 301 | CCC TCC AAA AGG GCC TAA | 302 | GGC AAA AAC AAA GTC CCC A |
| Nanostring STA | Litaf | 303 | AGT GCA CAG AAG GGC TGC | 304 | CCA GCA AAT GGA GAA ATG G |
| Nanostring STA | Max | 305 | AGG ACG CCT GCT CTA CCA | 306 | GCT GCA AAT CTG TCC CCA |
| Nanostring STA | Mta3 | 307 | CGG AGA AGC AGA AGC ACC | 308 | ACT TTG GGC CCA CTC TGA |
| Nanostring STA | Nfe2l2 | 309 | GCC GCT TAG AGG CTC ATC | 310 | TGC TCC AGC TCG ACA ATG |
| Nanostring STA | Nudt4 | 311 | TGG GGT GCC ATC CAG TAT | 312 | ATT CCA CAT GGC TTT GGC |
| Nanostring STA | Id2 | 313 | TCA GCC ATT TCA CCA GGA G | 314 | TAA CGT TTT CGC TCC CCA |
| Nanostring STA | Ikzf4 | 315 | GGG GTC TAG CCC AAT TCC | 316 | GCC GGG GAG AGA GGT TAG |
| Nanostring STA | Il1rn | 317 | TGG TAA GCT TTC CTT CTT TCC | 318 | TCA TCA CAT CAG GAA GGG C |
| Nanostring STA | Il2rb | 319 | GCA CCC CAT CCT CAG CTA | 320 | CAA GTC CAG CTC GGT GGT |

TABLE S6.1-continued

| Primer Sequences | | | | | |
|---|---|---|---|---|---|
| Assay | Gene Name | SEQ ID NO: | Forward Sequence | SEQ ID NO: | Reverse Sequence |
| Nanostring STA | Irf1 | 321 | TAA GCA CGG CTG GGA CAT | 322 | CAG CAG AGC TGC CCT TGT |
| Nanostring STA | Jak3 | 323 | CTC CCC AGC GAT TGT CAT | 324 | CAG CCC AAA CCA GTC AGG |
| Nanostring STA | Klf6 | 325 | GAG CGG GAA CTC AGG ACC | 326 | GGG AAA ATG ACC ACT GCG |
| Nanostring STA | Lmnb1 | 327 | TGC CCT AGG GGA CAA AAA | 328 | CAA GCG GGT CTC ATG CTT |
| Nanostring STA | Mbnl3 | 329 | TGG AGC ATG AAT CCA CAC C | 330 | TGA GGG TCC CAT GAG TGG |
| Nanostring STA | Mxi1 | 331 | CTC AGG AGA TGG AGC GGA | 332 | CCT CGT CAC TCC CGA CAC |
| Nanostring STA | Nfil3 | 333 | CAC GGT GGT GAA GGT TCC | 334 | GAA AGG AGG GAG GGA GGA |
| Nanostring STA | Oas2 | 335 | TGC CTG TGC TTG CTC TGA | 336 | GAA GAA GGG CCA GAA GGG |
| Nanostring STA | Id3 | 337 | CCG AGG AGC CTC TTA GCC | 338 | GTC TGG ATC GGG AGA TGC |
| Nanostring STA | Il10 | 339 | ACT GCC TTC AGC CAG GTG | 340 | CAG CTT CTC ACC CAG GGA |
| Nanostring STA | Il21 | 341 | CCT GGA GTG GTA TCA TCG C | 342 | TGC GTT GGT TCT GAT TGT G |
| Nanostring STA | Il3 | 343 | CAC ACC ATG CTG CTC CTG | 344 | CTC CTT GGC TTT CCA CGA |
| Nanostring STA | Irf4 | 345 | CAG AGA AAC GCA TTC CTG G | 346 | AGT CCA CCA GCT GGC TTT T |
| Nanostring STA | Jun | 347 | TAT TGG CCG GCA GAC TTT | 348 | GCC TGG CAC TTA CAA GCC |
| Nanostring STA | Klf9 | 349 | AGG GAA GGA AGA CGC CAC | 350 | TGG CCA TGT AAA AGC CAA A |
| Nanostring STA | Lrrfip1 | 351 | GTC TCC AAC GCC CAG CTA | 352 | ATC TCT TCC CTT TGC CGC |
| Nanostring STA | Med24 | 353 | ACT GCT AGG GGT CCT GGG | 354 | TGA GCC ATA GGT CTG GGC |
| Nanostring STA | Myd88 | 355 | GAA GCT GTT TGG CTT CGC | 356 | TCA TTC CTC CCC CAG ACA |
| Nanostring STA | Nfkbie | 357 | TCG AGG CGC TCA CAT ACA | 358 | CGG ACA ACA TCT GGC TGA |
| Nanostring STA | Pcbp2 | 359 | CTC AAC TGA GCG GGC AAT | 360 | AGG GTT GAG GCA CAT GGA |
| Nanostring STA | Ier3 | 361 | CCT TCT CCA GCT CCC TCC | 362 | CCT CTT GGC AAT GTT GGG |
| Nanostring STA | Il10ra | 363 | GTA AAG GCC GGC TCC AGT | 364 | TTT CCA GTG GAG GAT GTG C |
| Nanostring STA | Il21r | 365 | AGG TCT GGC CAC AAC ACC | 366 | GGC CAC AGT CAC GTT CAA |
| Nanostring STA | Il4 | 367 | AGG GCT TCC AAG GTG CTT | 368 | TGC TCT TTA GGC TTT CCA GG |

TABLE S6.1-continued

| Primer Sequences | | | | | |
|---|---|---|---|---|---|
| Assay | Gene Name | SEQ ID NO: | Forward Sequence | SEQ ID NO: | Reverse Sequence |
| Nanostring STA | Irf7 | 369 | GAG GCT GAG GCT GCT GAG | 370 | ATC CTG GGG ACA CAC CCT |
| Nanostring STA | Kat2b | 371 | GGT GCT TTG AGC AGT TCT GA | 372 | GCC CTG CAC AAG CAA AGT |
| Nanostring STA | Klrd1 | 373 | GCC TGG CTA TGG GAG GAT | 374 | CCG TGG ACC TTC CTT GTC |
| Nanostring STA | Lsp1 | 375 | CCT GAG CCC TAC CAC CAA | 376 | GGG CAG CTC TAT GGA GGG |
| Nanostring STA | Mgl1 | 377 | CGC GCA GTA GTC TGG CTC | 378 | AAG ATG AGG GCC TTG GGT |
| Nanostring STA | Myst4 | 379 | CAA CAA AGG GCA GCA AGC | 380 | TTC AAC ACA AGG GCA GAG G |
| Nanostring STA | Nfkbiz | 381 | TTA GCT GGA TGA GCC CCA | 382 | ATG TTG CTG CTG TGG TGG |
| Nanostring STA | Peli2 | 383 | GCC AGA CGG TAG TGG TGG | 384 | CGT GCT GTG TAT GGC TCG |
| Nanostring STA | Phlda1 | 385 | GAT GAC GGA GGG CAA AGA | 386 | GGG GTT GAG GCT GGA TCT |
| Nanostring STA | Prdm1 | 387 | ACC CTG GCT ATG CAC CTG | 388 | GGG AAG CTG GAT TGA GCA |
| Nanostring STA | Pstpip1 | 389 | GAG AGC GAG GAC CGA GTG | 390 | CCT TCC ACA TCA CAG CCC |
| Nanostring STA | Rela | 391 | TGC GAC AAG GTG CAG AAA | 392 | GAG CTC GCG ATC AGA AGG |
| Nanostring STA | Runx3 | 393 | GCC CCT TCC CAC CAT TTA | 394 | CTC CCC CTG CTG CTA CAA |
| Nanostring STA | Sgk1 | 395 | GGC TAG GCA CAA GGC AGA | 396 | AGC GCT CCC TCT GGA GAT |
| Nanostring STA | Smox | 397 | ACA GCC TCG TGT GGT GGT | 398 | GGC CAT TGG CTT CTG CTA |
| Nanostring STA | Stat4 | 399 | GCC TCT ATG GCC TCA CCA | 400 | ACT TCC AGG AGT TGG CCC |
| Nanostring STA | Tbx21 | 401 | TGG GAA GCT GAG AGT CGC | 402 | GCC TTC TGC CTT TCC ACA |
| Nanostring STA | Tmed7 | 403 | TGG TTA GCG TAG GGC AGG | 404 | CCC ATG GGG ATA TGC ACT |
| Nanostring STA | Traf3 | 405 | ATC TGT GGG CGC TCT GAC | 406 | GGA CTG TCA AGA TGG GGC |
| Nanostring STA | Vav3 | 407 | TTC TGG CAG GGA CGA AAC | 408 | TTT GGT CCT GTG CCT TAC AA |
| Nanostring STA | Plac8 | 409 | TGC TCC CCA AAA TTC CAA | 410 | AGG AAT GCC GTA TCG GGT |
| Nanostring STA | Prf1 | 411 | ACC AAC CAG GAC TGC TGC | 412 | CCC TGT GGA CAG GAG CAC |
| Nanostring STA | Ptprj | 413 | TCA CCT GGA GCA ATG CAA | 414 | TGG TAC CAT TGG CAT CCG |
| Nanostring STA | Rfk | 415 | TTT CCC TCT TGG TGG CCT | 416 | TCC CTC CCC ACA CCA CTA |
| Nanostring STA | Rxra | 417 | TTG TTG GGC GAC TTT TGC | 418 | TGG AGA GTT GAG GGA CGA A |

TABLE S6.1-continued

| Primer Sequences | | | | | |
|---|---|---|---|---|---|
| Assay | Gene Name | SEQ ID NO: | Forward Sequence | SEQ ID NO: | Reverse Sequence |
| Nanostring STA | Skap2 | 419 | TGG GTG AAC ATT CCT GCC | 420 | AAA CAG CAA CCC TCA CCG |
| Nanostring STA | Socs3 | 421 | TGC AGG AGA GCG GAT TCT | 422 | GAA CTG GCT GCG TGC TTC |
| Nanostring STA | Stat5a | 423 | CCT CCG CTA GAA GCT CCC | 424 | GCT CTT ACA CGA GAG GCC C |
| Nanostring STA | Tgfb1 | 425 | CGC CTG AGT GGC TGT CTT | 426 | ATG TCA TGG ATG GTG CCC |
| Nanostring STA | Tmem12 6a | 427 | CTG CTT GAA TAT GGA TCA GCA | 428 | CCA ACT AGT GCA CCC CGT |
| Nanostring STA | Trat1 | 429 | CAA TGG ATG CCA ACG TTT C | 430 | CCT TGC CAG TCC CTG TGT |
| Nanostring STA | Vax2 | 431 | GGC CCC CGT GGA CTA TAC | 432 | CAC ACA CAC ACG CAC ACG |
| Nanostring STA | Plagl1 | 433 | TTG AGA CTG TAT CCC CCA GC | 434 | GCA GGG TCT TCA AAG GTC AG |
| Nanostring STA | Prickle1 | 435 | TGG GTT TCC AGT TGC AGT T | 436 | GCC TTT ATT AAA CAC CTC CCT G |
| Nanostring STA | Pycr1 | 437 | CCC TGG GTG TGT GCA GTC | 438 | AAG GGG TTG AAA GGG GTG |
| Nanostring STA | Rngtt | 439 | CCC AAA AGA CTG CAT CGG | 440 | TCC ACA GGG TAA GGC TGA A |
| Nanostring STA | Sav1 | 441 | CGA CCC CCA ATG TAA GGA | 442 | TAG CCC ACC CTG ATG GAA |
| Nanostring STA | Ski | 443 | GGT CCC CTG CAG TGT CTG | 444 | CTT CCG TTT TCG TGG CTG |
| Nanostring STA | Spp1 | 445 | CCA TGA CCA CAT GGA CGA | 446 | CCA AGC TAT CAC CTC GGC |
| Nanostring STA | Stat5b | 447 | ACT CAG CGC CCA CTT CAG | 448 | GCT CTG CAA AGG CGT TGT |
| Nanostring STA | Tgfb3 | 449 | GCC AAA GTC CCC TGG AAT | 450 | AAG GAA GGC AGG AGG AGG |
| Nanostring STA | Tnfrsf12 a | 451 | GGG AGC CTT CCA AGG TGT | 452 | GGC ATT ATA GCC CCT CCG |
| Nanostring STA | Trim24 | 453 | CGG TGG TCC TTC GCC | 454 | TGC AGA GCC ATT CAA CAC A |
| Nanostring STA | Xbp1 | 455 | GGA CCT CAT CAG CCA AGC | 456 | GCA GGT TTG AGA TGC CCA |
| Nanostring STA | Plekhf2 | 457 | CGG CAA TAT TGT TAT CCA GAA | 458 | GGG CGT CTT CCC ACT TTT |
| Nanostring STA | Prkca | 459 | TGC TGT CCC AGG GAT GAT | 460 | CAA ATA GCC CAG GAT ACC CA |
| Nanostring STA | Rab33a | 461 | GCT GGC TTG GCA TCC TT | 462 | TTG ATC TTC TCG CCC TCG |
| Nanostring STA | Rora | 463 | GAT GTG GCA GCT GTG TGC | 464 | TTG AAG ACA TCG GGG CTC |
| Nanostring STA | Sema4d | 465 | TTC TTG GGC AGT GAA CCC | 466 | TCG CGG GAT CAT CAA CTT |

TABLE S6.1-continued

| Primer Sequences | | | | | |
|---|---|---|---|---|---|
| Assay | Gene Name | SEQ ID NO: | Forward Sequence | SEQ ID NO: | Reverse Sequence |
| Nanostring STA | Slamf7 | 467 | CTC CAT GAA GCT CAG CCA A | 468 | TTG ATT ACG CAG GTG CCA |
| Nanostring STA | Spry1 | 469 | AGG ACT TCC CTT CAC GCC | 470 | AGC CAG GAT TCA ACT TTG TGA |
| Nanostring STA | Stat6 | 471 | TGC TTT TGC CAG TGT GAC C | 472 | ACG CCC AGG GAG TTT ACA |
| Nanostring STA | Tgfbr1 | 473 | TGA TGT CAG CTC TGG GCA | 474 | TCT GCA GCG AGA ACC AAA |
| Nanostring STA | Tnfrsf13 b | 475 | GGA AGG CAC CAG GGA TCT | 476 | CTC GTC GCA AGC CTC TGT |
| Nanostring STA | Trim25 | 477 | TCT GCC TTG TGC CTG ACA | 478 | ACG GGT GCA TCA GCC TAA |
| Nanostring STA | Xrcc5 | 479 | AGG GGA CCT GGA CTC TGG | 480 | GAC AAG TTG GGG CCA ATG |
| Nanostring STA | Pmepa1 | 481 | GTG ACC GCT TGA TGG GG | 482 | GCT GTG TCG GCT GAT GAA |
| Nanostring STA | Prkd3 | 483 | CCT GGC CTC TCA GTT CCA | 484 | AGA GGC CTT TCA GCA GGC |
| Nanostring STA | Rad5 1ap 1 | 485 | AGC AGC CAA GTG CGG TAG | 486 | TGC CAC AAG GAG AGG TCC |
| Nanostring STA | Rorc | 487 | CCT CTG ACC CGT CTC CCT | 488 | GCT TCC AGA AGC CAG GGT |
| Nanostring STA | Sema7a | 489 | ATG AAA GGC TAT GCC CCC | 490 | GTG CAC AAT GGT GGC CTT |
| Nanostring STA | Slc2a1 | 491 | GAC CCT GCA CCT CAT TGG | 492 | GAA GCC AGC CAC AGC AAT |
| Nanostring STA | Stard10 | 493 | AGG ACC CAG GAG AGT CGG | 494 | ATC TCC ACA GCC TGC ACC |
| Nanostring STA | Sufu | 495 | ATG GGG AGT CCT TCT GCC | 496 | TAG GCC CTG CAT CAG CTC |
| Nanostring STA | Tgfbr3 | 497 | TCT GGG ATT TGC CAT CCA | 498 | GTG CAG GAA GAG CAG GGA |
| Nanostring STA | Tnfrsf25 | 499 | CGA GCC ATG TGG GAA AAG | 500 | GAG GCT GAG AGA TGG GCA |
| Nanostring STA | Trps1 | 501 | TTG TAA CGC ACT TTG AGA TCC | 502 | CGT GCC TTT TTG GTA GCC |
| Nanostring STA | Zeb1 | 503 | AAG CGC TGT GTC CCT TTG | 504 | GTG AGA TGC CCC AGT GCT |
| Nanostring STA | Pml | 505 | AAT TTG GGT CCT CTC GGC | 506 | GCT CGA GAT GCC AGT GCT |
| Nanostring STA | Prnp | 507 | CCT CCC ACC TGG GAT AGC | 508 | CCG TCA CAG GAG GAC CAA |
| Nanostring STA | Rasgrp1 | 509 | CAA GCA TGC AAA GTC TGA GC | 510 | CGT TAT GAG CGG GGT TTG |
| Nanostring STA | Rpp14 | 511 | GCA GCA GTG GTC TGG TCA | 512 | TGT CAC CAA CAG GGG CTT |
| Nanostring STA | Serpinb1 a | 513 | CAA GGT GCT GGA GAT GCC | 514 | GCG GCC CAG GTT AGA GTT |
| Nanostring STA | Slc6a6 | 515 | GGT GCG TTC CTC ATA CCG | 516 | AGG CCA GGA TGA CGA TGT |

TABLE S6.1-continued

| Primer Sequences | | | | | |
|---|---|---|---|---|---|
| Assay | Gene Name | SEQ ID NO: | Forward Sequence | SEQ ID NO: | Reverse Sequence |
| Nanostring STA | Stat1 | 517 | GAG GTA GAG GCC TGG GGA | 518 | TTT AAG CTC TGC CGC CTC |
| Nanostring STA | Sult2b1 | 519 | CGA TGT CGT GGT CTC CCT | 520 | GTC CTG CTG CAG CTC CTC |
| Nanostring STA | Tgif1 | 521 | GGA CCC AGT CCA AAC CCT | 522 | CGG CAA TCA GGA CCG TAT |
| Nanostring STA | Tnfsfl 1 | 523 | AAC AAG CCT TTC AGG GGG | 524 | AGA GAT CTT GGC CCA GCC |
| Nanostring STA | Tsc22d3 | 525 | TGC CAG TGT GCT CCA GAA | 526 | CTG TGC ACA AAG CCA TGC |
| Nanostring STA | Zfp161 | 527 | CGC CAA GAT TTC CGT GA | 528 | TCC CCG ATT TCT TCC ACA |
| Nanostring STA | Pou2af1 | 529 | GCC CAC TGG CCT TCA TTT | 530 | TGG GAT ATC AAA GAA ACT GTC A |
| Nanostring STA | Procr | 531 | GCC AAA ACG TCA CCA TCC | 532 | ACG GCC ACA TCG AAG AAG |
| Nanostring STA | Rbpj | 533 | TCC CTT AAA ACA GGA GCC A | 534 | CTT CCC CTT GAC AAG CCA |
| Nanostring STA | Runx1 | 535 | GCC TGA GAA AAC GGT AGG G | 536 | CAT GTG CCT GAT GGA TTT TT |
| Nanostring STA | Serpine2 | 537 | TGA GCC ATC AAA GGC AAA | 538 | GCT TGT TCA CCT GGC CC |
| Nanostring STA | Smad3 | 539 | ACG TGC CCC TGT CTG AAG | 540 | GAG TGG TGG GAC AGG GC |
| Nanostring STA | Stat2 | 541 | GCA ACC AGG AAC GCA GAC | 542 | TCT TCG GCA AGA ACC TGG |
| Nanostring STA | Tal2 | 543 | GGT GGA GGC AGC AGA GTG | 544 | CAT CCT CAT CTG GCA GGC |
| Nanostring STA | Tgm2 | 545 | CAG TCT CAG TGC GAG CCA | 546 | ATG TCC TCC CGG TCA TCA |
| Nanostring STA | Tnfsf8 | 547 | ACG CCC CCA GAG AAG AGT | 548 | CTG GGT CAG GGG AAG GAG |
| Nanostring STA | Ube3a | 549 | TCG CAT GTA CAG TGA AAG AAG A | 550 | CTT TGG AAA CGC CTC CCT |
| Nanostring STA | Zfp238 | 551 | GCC TTG ATT GAC ATG GGG | 552 | AAG AAA AAG GGA AAA ACA ACC A |
| Nanostring STA | Prc1 | 553 | TCC CAA CCC TGT GCT CAT | 554 | CAG TGT GGG CAG AAC TGG |
| Nanostring STA | Psmb9 | 555 | TGG TTA TGT GGA CGC AGC | 556 | GGA AGG GAC TTC TGG GGA |
| Nanostring STA | Rel | 557 | GCC CCT CTG GGA TCA ACT | 558 | GGG GTG AGT CAC TGG TGG |
| Nanostring STA | Runx2 | 559 | AAA TCC TCC CCA AGT GGC | 560 | TGC AGA GTT CAG GGA GGG |
| Nanostring STA | Sertad1 | 561 | CTG GGT GCC TTG GAC TTG | 562 | CGC CTC ATC CAA CTC TGG |
| Nanostring STA | Smarca4 | 563 | TAC CGT GCC TCA GGG AAA | 564 | CCC CGG TCT TCT GCT TTT |

TABLE S6.1-continued

| Primer Sequences | | | | | |
|---|---|---|---|---|---|
| Assay | Gene Name | SEQ ID NO: | Forward Sequence | SEQ ID NO: | Reverse Sequence |
| Nanostring STA | Stat3 | 565 | TTC AGC GAG AGC AGC AAA | 566 | AAA TGC CTC CTC CTT GGG |
| Nanostring STA | Tap1 | 567 | TCT CTC TTG CCT TGG GGA | 568 | GGC CCG AAA CAC CTC TCT |
| Nanostring STA | Timp2 | 569 | GCT GGA CGT TGG AGG AAA | 570 | CTC ATC CGG GGA GGA GAT |
| Nanostring STA | Tnfsf9 | 571 | GTT TCC CAC ATT GGC TGC | 572 | AGC CCG GGA CTG TCT ACC |
| Nanostring STA | Ubiad1 | 573 | TAC AGA GCG CTT GTC CCC | 574 | GCC ACC ATG CCA TGT TTT |
| Nanostring STA | Zfp281 | 575 | CCA GAC GTA GTT GGG CAG A | 576 | TGC TGC TGG CAG TTG GTA |
| Nanostring STA | Zfp410 | 577 | CTG AAA GAG CCT CAC GGC | 578 | CCA TCA TGC ACT CTG GGA |
| Fluidigm & QPCR | B2M | 579 | TTC TGG TGC TTG TCT CAC TGA | 580 | CAG TAT GTT CGG CTT CCC ATT C |
| Fluidigm & QPCR | Aim1 | 581 | GAC GAC TCC TTT CAG ACC AAG T | 582 | AAA TTT TCT CCA TCA TAA GCA ACC |
| Fluidigm & QPCR | Cd44 | 583 | GCA TCG CGG TCA ATA GTA GG | 584 | CAC CGT TGA TCA CCA GCT T |
| Fluidigm & QPCR | Ifngr2 | 585 | TCC TGT CAC GAA ACA ACA GC | 586 | ACG GAA TCA GGA TGA CTT GC |
| Fluidigm & QPCR | Il6st | 587 | TCC CAT GGG CAG GAA TAT AG | 588 | CCA TTG GCT TCA GAA AGA GG |
| Fluidigm & QPCR | Klf7 | 589 | AAG TGT AAC CAC TGC GAC AGG | 590 | TCT TCA TAT GGA GCG CAA GA |
| Fluidigm & QPCR | Mt2 | 591 | CAT GGA CCC CAA CTG CTC | 592 | AGC AGG AGC AGC AGC TTT |
| Fluidigm & QPCR | Nudt4 | 593 | CTG CTG TGA GGG AAG TGT ATG A | 594 | CGA GCA GTC TGC CTA GCT TT |
| Fluidigm & QPCR | Pstpip1 | 595 | AGC CCT CCT GTG GTG TGA TA | 596 | TGG TCT TGG GAC TTC CAT GT |
| Fluidigm & QPCR | Rxra | 597 | GCT TCG GGA CTG GTA GCC | 598 | GCG GCT TGA TAT CCT CAG TG |
| Fluidigm & QPCR | Sod1 | 599 | CCA GTG CAG GAC CTC ATT TT | 600 | GGT CTC CAA CAT GCC TCT CT |
| Fluidigm & QPCR | Tgfb1 | 601 | TGG AGC AAC ATG TGG AAC TC | 602 | CAG CAG CCG GTT ACC AAG |
| Fluidigm & QPCR | GAPDH | 603 | GGC AAA TTC AAC GGC ACA GT | 604 | AGA TGG TGA TGG GCT TCC C |
| Fluidigm & QPCR | Atf4 | 605 | ATG ATG GCT TGG CCA GTG | 606 | CCA TTT TCT CCA ACA TCC AAT C |
| Fluidigm & QPCR | Cmtm6 | 607 | GAT ACT GGA AAA GTC AAG TCA TCG | 608 | AAT GGG TGG AGA CAA AAA TGA |
| Fluidigm & QPCR | Il10 | 609 | CAG AGC CAC ATG CTC CTA GA | 610 | GTC CAG CTG GTC CTT TGT TT |
| Fluidigm & QPCR | Il7r | 611 | CGA AAC TCC AGA ACC CAA GA | 612 | AAT GGT GAC ACT TGG CAA GAC |
| Fluidigm & QPCR | Lamp2 | 613 | TGC AGA ATG GGA GAT GAA TTT | 614 | GGC ACT ATT CCG GTC ATC C |

TABLE S6.1-continued

| Primer Sequences | | | | | |
|---|---|---|---|---|---|
| Assay | Gene Name | SEQ ID NO: | Forward Sequence | SEQ ID NO: | Reverse Sequence |
| Fluidigm & QPCR | Myc | 615 | CCT AGT GCT GCA TGA GGA GA | 616 | TCT TCC TCA TCT TCT TGC TCT TC |
| Fluidigm & QPCR | Pcbp2 | 617 | CAG CAT TAG CCT GGC TCA GTA | 618 | ATG GAT GGG TCT GCT CTG TT |
| Fluidigm & QPCR | Rasgrp1 | 619 | GTT CAT CCA TGT GGC TCA GA | 620 | TCA CAG CCA TCA GCG TGT |
| Fluidigm & QPCR | Satb1 | 621 | ATG GCG TTG CTG TCT CTA GG | 622 | CTT CCC AAC CTG GAT GAG C |
| Fluidigm & QPCR | Stat1 | 623 | GCA GCA CAA CAT ACG GAA AA | 624 | TCT GTA CGG GAT CTT CTT GGA |
| Fluidigm & QPCR | Tgif1 | 625 | CTC AGA GCA AGA GAA AGC ACT G | 626 | CGT TGA TGA ACC AGT TAC AGA CC |
| Fluidigm & QPCR | HMBS | 627 | TCC CTG AAG GAT GTG CCT AC | 628 | AAG GGT TTT CCC GTT TGC |
| Fluidigm & QPCR | B4galt1 | 629 | GCC ATC AAT GGA TTC CCT AA | 630 | CAT TTG GAC GTG ATA TAG ACA TGC |
| Fluidigm & QPCR | Foxo1 | 631 | CTT CAA GGA TAA GGG CGA CA | 632 | GAC AGA TTG TGG CGA ATT GA |
| Fluidigm & QPCR | Il16 | 633 | CCA CAG AAG GAG AGT CAA GGA | 634 | GTG TTT TCC TGG GGA TGC T |
| Fluidigm & QPCR | Irf1 | 635 | GAG CTG GGC CAT TCA CAC | 636 | TCC ATG TCT TGG GAT CTG G |
| Fluidigm & QPCR | Lmnb1 | 637 | GGG AAG TTT ATT CGC TTG AAG A | 638 | ATC TCC CAG CCT CCC ATT |
| Fluidigm & QPCR | Myd88 | 639 | TGG CCT TGT TAG ACC GTG A | 640 | AAG TAT TTC TGG CAG TCC TCC TC |
| Fluidigm & QPCR | Pmepa1 | 641 | GCT CTT TGT TCC CCA GCA T | 642 | CTA CCA CGA TGA CCA CGA TTT |
| Fluidigm & QPCR | Rbpj | 643 | AGT CTT ACG GAA ATG AAA AAC GA | 644 | CCA ACC ACT GCC CAT AAG AT |
| Fluidigm & QPCR | Sema4d | 645 | GAC CCT GGT AAC ACC ACA GG | 646 | TCA CGA CGT CAT GCC AAG |
| Fluidigm & QPCR | Stat3 | 647 | GGA AAT AAC GGT GAA GGT GCT | 648 | CAT GTC AAA CGT GAG CGA CT |
| Fluidigm & QPCR | Timp2 | 649 | CGT TTT GCA ATG CAG ACG TA | 650 | GGA ATC CAC CTC CTT CTC G |
| Fluidigm & QPCR | HPRT | 651 | TCC TCC TCA GAC CGC TTT T | 652 | CCT GGT TCA TCA TCG CTA ATC |
| Fluidigm & QPCR | Cand1 | 653 | GAA CTT CCG CCA GCT TCC | 654 | CTG GTA AGG CGT CCA GTA ATC T |
| Fluidigm & QPCR | Foxp1 | 655 | CTG CAC ACC TCT CAA TGC AG | 656 | GGA AGC GGT AGT GTA CAG AGG T |
| Fluidigm & QPCR | Il17ra | 657 | TGG GAT CTG TCA TCG TGC T | 658 | ATC ACC ATG TTT CTC TTG ATC G |
| Fluidigm & QPCR | Irf4 | 659 | ACA GCA CCT TAT GGC TCT CTG | 660 | ATG GGG TGG CAT CAT GTA GT |
| Fluidigm & QPCR | LOC100 048299 ///Max | 661 | CCA GCA AGA CAT TGA TGA CC | 662 | GAT CTT GCC TTC TCC AGT GC |

TABLE S6.1-continued

Primer Sequences

| Assay | Gene Name | SEQ ID NO: | Forward Sequence | SEQ ID NO: | Reverse Sequence |
|---|---|---|---|---|---|
| Fluidigm & QPCR | Nampt | 663 | CCT GTT CCA GGC TAT TCT GTT C | 664 | TCA TGG TCT TTC CCC CAA G |
| Fluidigm & QPCR | Pml | 665 | AGG AAC CCT CCG AAG ACT ATG | 666 | TTC CTC CTG TAT GGC TTG CT |
| Fluidigm & QPCR | Rel | 667 | TTG CAG AGA TGG ATA CTA TGA AGC | 668 | CAC CGA ATA CCC AAA TTT TGA A |
| Fluidigm & QPCR | Sema7a | 669 | GGA GAG ACC TTC CAT GTG CT | 670 | AAG ACA AAG CTA TGG TCC TGG T |
| Fluidigm & QPCR | Stat5a | 671 | AAG ATC AAG CTG GGG CAC TA | 672 | CAT GGG ACA GCG GTC ATA C |
| Fluidigm & QPCR | Trim25 | 673 | CCC TAC GAC CCT AAG TCA AGC | 674 | TGT GGC TGT GCA TGA TAG TG |
| Fluidigm & QPCR | pgk1 | 675 | TAC CTG CTG GCT GGA TGG | 676 | CAC AGC CTC GGC ATA TTT CT |
| Fluidigm & QPCR | Casp6 | 677 | TGA AAT GCT TTA ACG ACC TCA G | 678 | GTG GCT TGA AGT CGA CAC CT |
| Fluidigm & QPCR | Hif1a | 679 | GCA CTA GAC AAA GTT CAC CTG AGA | 680 | CGC TAT CCA CAT CAA AGC AA |
| Fluidigm & QPCR | Il21r | 681 | GGA GTG ACC CCG TCA TCT T | 682 | AGG AGC AGC AGC ATG TGA G |
| Fluidigm & QPCR | Irf8 | 683 | GAG CCA GAT CCT CCC TGA CT | 684 | GGC ATA TCC GGT CAC CAG T |
| Fluidigm & QPCR | Lsp1 | 685 | CAA AGC GAG AGA CCA GAG GA | 686 | AAG TGG ACT TTG GCT TGG TG |
| Fluidigm & QPCR | Nfatc2 | 687 | GAT CGT AGG CAA CAC CAA GG | 688 | CTT CAG GAT GCC TGC ACA |
| Fluidigm & QPCR | Pou2af1 | 689 | CAT GCT CTG GCA AAA ATC C | 690 | ACT CGA ACA CCC TGG TAT GG |
| Fluidigm & QPCR | Rela | 691 | CCC AGA CCG CAG TAT CCA T | 692 | GCT CCA GGT CTC GCT TCT T |
| Fluidigm & QPCR | Skap2 | 693 | GTG CTC CCG ACA AAC GTA TC | 694 | CCC ATT CCT CAG CAT CTT TG |
| Fluidigm & QPCR | Stat5b | 695 | CGA GCT GGT CTT TCA AGT CA | 696 | CTG GCT GCC GTG AAC AAT |
| Fluidigm & QPCR | Xbp1 | 697 | TGA CGA GGT TCC AGA GGT G | 698 | TGC AGA GGT GCA CAT AGT CTG |
| Fluidigm & QPCR | PPIA | 699 | ACG CCA CTG TCG CTT TTC | 700 | GCA AAC AGC TCG AAG GAG AC |
| Fluidigm & QPCR | Cd2 | 701 | TGG GAT GAC TAG GCT GGA GA | 702 | AGT GGA TCA TGG GCT TTG AG |
| Fluidigm & QPCR | Icos | 703 | CGG CAG TCA ACA CAA ACA A | 704 | TCA GGG GAA CTA GTC CAT GC |
| Fluidigm & QPCR | 1124 | 705 | AGA ACC AGC CAC CTT CAC AC | 706 | GTG TTG AAG AAA GGG CCA GT |
| Fluidigm & QPCR | Khdrbs1 | 707 | CTC GAC CCG TCC TTC ACT C | 708 | TTG ACT CTC CCT TCT GAA TCT TCT |
| Fluidigm & QPCR | Lta | 709 | TCC CTC AGA AGC ACT TGA CC | 710 | GAG TTC TGC TTG CTG GGG TA |
| Fluidigm & QPCR | Nfatc3 | 711 | GGG GCA GTG AAA GCC TCT | 712 | GCT TTT CAC TAT AGC CCA GGA G |

TABLE S6.1-continued

| Primer Sequences | | | | | |
|---|---|---|---|---|---|
| Assay | Gene Name | SEQ ID NO: | Forward Sequence | SEQ ID NO: | Reverse Sequence |
| Fluidigm & QPCR | Prf1 | 713 | AAT ATC AAT AAC GAC TGG CGT GT | 714 | CAT GTT TGC CTC TGG CCT A |
| Fluidigm & QPCR | Rora | 715 | TTA CGT GTG AAG GCT GCA AG | 716 | GGA GTA GGT GGC ATT GCT CT |
| Fluidigm & QPCR | Ski | 717 | GAG AAA GAG ACG TCC CCA CA | 718 | TCA AAG CTC TTG TAG GAG TAG AAG C |
| Fluidigm & QPCR | Stat6 | 719 | TCT CCA CGA GCT TCA CAT TG | 720 | GAC CAC CAA GGG CAG AGA C |
| Fluidigm & QPCR | Xrcc5 | 721 | GAA GAT CAC ATC AGC ATC TCC A | 722 | CAG GAT TCA CAC TTC CAA CCT |
| Fluidigm & QPCR | RPL13A | 723 | ATC CCT CCA CCC TAT GAC AA | 724 | GCC CCA GGT AAG CAA ACT T |
| Fluidigm & QPCR | Cd24a | 725 | CTG GGG TTG CTG CTT CTG | 726 | AGA TGT TTG GTT GCA GTA AAT CTG |
| Fluidigm & QPCR | Id2 | 727 | GAC AGA ACC AGG CGT CCA | 728 | AGC TCA GAA GGG AAT TCA GAT G |
| Fluidigm & QPCR | Il2ra | 729 | TGT GCT CAC AAT GGA GTA TAA GG | 730 | CTC AGG AGG AGG ATG CTG AT |
| Fluidigm & QPCR | Klf10 | 731 | AGC CAA CCA TGC TCA ACT TC | 732 | GGC TTT TCA GAA ATT AGT TCC ATT |
| Fluidigm & QPCR | Maf | 733 | TTC CTC TCC CGA ATT TTT CA | 734 | CCA CGG AGC ATT TAA CAA GG |
| Fluidigm & QPCR | Nfe2l2 | 735 | CAT GAT GGA CTT GGA GTT GC | 736 | CCT CCA AAG GAT GTC AAT CAA |
| Fluidigm & QPCR | Prkca | 737 | ACA GAC TTC AAC TTC CTC ATG GT | 738 | CTG TCA GCA AGC ATC ACC TT |
| Fluidigm & QPCR | Runx1 | 739 | CTC CGT GCT ACC CAC TCA CT | 740 | ATG ACG GTG ACC AGA GTG C |
| Fluidigm & QPCR | Slc2a1 | 741 | ATG GAT CCC AGC AGC AAG | 742 | CCA GTG TTA TAG CCG AAC TGC |
| Fluidigm & QPCR | Sufu | 743 | TGT TGG AGG ACT TAG AAG ATC TAA CC | 744 | AGG CCA GCT GTA CTC TTT GG |
| Fluidigm & QPCR | Zeb1 | 745 | GCC AGC AGT CAT GAT GAA AA | 746 | TAT CAC AAT ACG GGC AGG TG |
| Fluidigm & QPCR | Ywhaz | 747 | AAC AGC TTT CGA TGA AGC CAT | 748 | TGG GTA TCC GAT GTC CAC AAT |
| Fluidigm & QPCR | Cd4 | 749 | ACA CAC CTG TGC AAG AAG CA | 750 | GCT CTT GTT GGT TGG GAA TC |
| Fluidigm & QPCR | Ifi35 | 751 | TGA GAG CCA TGT CTG TGA CC | 752 | CTC CTG CAG CCT CAT CTT G |
| Fluidigm & QPCR | Il4ra | 753 | GAG TGG AGT CCT AGC ATC ACG | 754 | CAG TGG AAG GCG CTG TAT C |
| Fluidigm & QPCR | Klf6 | 755 | TCC CAC TTG AAA GCA CAT CA | 756 | ACT TCT TGC AAA ACG CCA CT |
| Fluidigm & QPCR | Mina | 757 | GAA TCT GAG GAC CGG ATC G | 758 | TGG GAA AGT ACA ACA AAT CTC CA |
| Fluidigm & QPCR | Notch1 | 759 | CTG GAC CCC ATG GAC ATC | 760 | AGG ATG ACT GCA CAC ATT GC |

TABLE S6.1-continued

| Primer Sequences | | | | | |
|---|---|---|---|---|---|
| Assay | Gene Name | SEQ ID NO: | Forward Sequence | SEQ ID NO: | Reverse Sequence |
| Fluidigm & QPCR | Prkd3 | 761 | TGG CTA CCA GTA TCT CCG TGT | 762 | TGG TAA ACG CTG CTG ATG TC |
| Fluidigm & QPCR | Runx3 | 763 | TTC AAC GAC CTT CGA TTC GT | 764 | TTG GTG AAC ACG GTG ATT GT |
| Fluidigm & QPCR | Smarca4 | 765 | AGA GAA GCA GTG GCT CAA GG | 766 | ATT TCT TCT GCC GGA CCT C |
| Fluidigm & QPCR | Tap1 | 767 | TTC CCT CAG GGC TAT GAC AC | 768 | CTG TCG CTG ACC TCC TGA C |
| Fluidigm & QPCR | Zfp36l1 | 769 | TTC ACG ACA CAC CAG ATC CT | 770 | TGA GCA TCT TGT TAC CCT TGC |
| Fluidigm & QPCR | B2M | 771 | TTC TGG TGC TTG TCT CAC TGA | 772 | CAG TAT GTT CGG CTT CCC ATT C |
| Fluidigm & QPCR | 1700097 NO2Rik | 773 | CCA GAG CTT GAC CAT CAT CAG | 774 | TCC TTT ACA AAT CAT ACA GGA CTG G |
| Fluidigm & QPCR | Armcx2 | 775 | CCC TTC ACC CTG GTC CTT | 776 | CTT CCT CGA ATT AGG CCA GA |
| Fluidigm & QPCR | Ccr4 | 777 | CTC AGG ATC ACT TTC AGA AGA GC | 778 | GGC ATT CAT CTT TGG AAT CG |
| Fluidigm & QPCR | Cebpb | 779 | TGA TGC AAT CCG GAT CAA | 780 | CAC GTG TGT TGC GTC AGT C |
| Fluidigm & QPCR | Emp1 | 781 | AAG AGA GGA CCA GAC CAG CA | 782 | CTT TTT GGT GAC TTC TGA GTA GAG AAT |
| Fluidigm & QPCR | Ier3 | 783 | CAG CCG AAG GGT GCT CTA C | 784 | AAA TCT GGC AGA AGA TGA TGG |
| Fluidigm & QPCR | Itga3 | 785 | AGG GGG AGA CCA GAG TTC C | 786 | GCC ATT GGA GCA GGT CAA |
| Fluidigm & QPCR | Lrrfip1 | 787 | AGT CTC AGC GGC AAT ACG AG | 788 | GCA AAC TGG AAC TGC AGG AT |
| Fluidigm & QPCR | Nfkbiz | 789 | CAG CTG GGG AAG TCA TTT TT | 790 | GGC AAC AGC AAT ATG GAG AAA |
| Fluidigm & QPCR | Ptprj | 791 | CCA ATG AGA CCT TGA ACA AAA CT | 792 | GTA GGA GGC AGT GCC ATT TG |
| Fluidigm & QPCR | Stat4 | 793 | CGG CAT CTG CTA GCT CAG T | 794 | TGC CAT AGT TTC ATT GTT AGA AGC |
| Fluidigm & QPCR | GAPDH | 795 | GGC AAA TTC AAC GGC ACA GT | 796 | AGA TGG TGA TGG GCT TCC C |
| Fluidigm & QPCR | Acvr1b | 797 | AGA GGG TGG GGA CCA AAC | 798 | TGC TTC ATG TTG ATT GTC TCG |
| Fluidigm & QPCR | Arnt1 | 799 | GCC CCA CCG ACC TAC TCT | 800 | TGT CTG TGT CCA TAC TTT CTT GG |
| Fluidigm & QPCR | Ccr8 | 801 | AGA AGA AAG GCT CGC TCA GA | 802 | GGC TCC ATC GTG TAA TCC AT |
| Fluidigm & QPCR | Chd7 | 803 | GAG GAC GAA GAC CCA GGT G | 804 | CAG TGT ATC GCT TCC TCT TCA C |
| Fluidigm & QPCR | Fas | 805 | TGC AGA CAT GCT GTG GAT CT | 806 | CTT AAC TGT GAG CCA GCA AGC |
| Fluidigm & QPCR | Il17f | 807 | CCC AGG AAG ACA TAC TTA GAA GAA A | 808 | CAA CAG TAG CAA AGA CTT GAC CA |

TABLE S6.1-continued

| Primer Sequences | | | | | |
|---|---|---|---|---|---|
| Assay | Gene Name | SEQ ID NO: | Forward Sequence | SEQ ID NO: | Reverse Sequence |
| Fluidigm & QPCR | Itgb1 | 809 | TGG CAA CAA TGA AGC TAT CG | 810 | ATG TCG GGA CCA GTA GGA CA |
| Fluidigm & QPCR | Map3k5 | 811 | CAA GAA ATT AGG CAC CTG AAG C | 812 | ACA CAG GAA ACC CAG GGA TA |
| Fluidigm & QPCR | Notch2 | 813 | TGC CTG TTT GAC AAC TTT GAG T | 814 | GTG GTC TGC ACA GTA TTT GTC AT |
| Fluidigm & QPCR | Rorc | 815 | ACC TCT TTT CAC GGG AGG A | 816 | TCC CAC ATC TCC CAC ATT G |
| Fluidigm & QPCR | Tgfbr1 | 817 | CAG CTC CTC ATC GTG TTG G | 818 | CAG AGG TGG CAG AAA CAC TG |
| Fluidigm & QPCR | HMBS | 819 | TCC CTG AAG GAT GTG CCT AC | 820 | AAG GGT TTT CCC GTT TGC |
| Fluidigm & QPCR | Aes | 821 | TGC AAG CGC AGT ATC ACA G | 822 | TGA CGT AAT GCC TCT GCA TC |
| Fluidigm & QPCR | Batf | 823 | AGA AAG CCG ACA CCC TTC A | 824 | CGG AGA GCT GCG TTC TGT |
| Fluidigm & QPCR | Cd247 | 825 | CCA GAG ATG GGA GGC AAA C | 826 | AGT GCA TTG TAT ACG CCT TCC |
| Fluidigm & QPCR | Clcf1 | 827 | TAT GAC CTC ACC CGC TAC CT | 828 | GGG CCC CAG GTA GTT CAG |
| Fluidigm & QPCR | Fip1l1 | 829 | CGT TTC CCT ATG GCA ATG TC | 830 | CCC ACT GCT TGG TGG TGT |
| Fluidigm & QPCR | Il1r1 | 831 | TTG ACA TAG TGC TTT GGT ACA GG | 832 | TCG TAT GTC TTT CCA TCT GAA GC |
| Fluidigm & QPCR | Jun | 833 | CCA GAA GAT GGT GTG GTG TTT | 834 | CTG ACC CTC TCC CCT TGC |
| Fluidigm & QPCR | Mbnl3 | 835 | GCC AAG AGT TTG CCA TGT G | 836 | CTT GCA GTT CTC ACG AGT GC |
| Fluidigm & QPCR | Nr3c1 | 837 | TGA CGT GTG GAA GCT GTA AAG T | 838 | CAT TTC TTC CAG CAC AAA GGT |
| Fluidigm & QPCR | Rpp14 | 839 | GGA ACG CGG TTA TTC CAG T | 840 | CAT CTT CCA ACA TGG ACA CCT |
| Fluidigm & QPCR | Tmem126a | 841 | TAG CGA AGG TTG CGG TAG AC | 842 | GGT TTA TGA CTT TCC ATC TTG GAC |
| Fluidigm & QPCR | HPRT | 843 | TCC TCC TCA GAC CGC TTT T | 844 | CCT GGT TCA TCA TCG CTA ATC |
| Fluidigm & QPCR | Ahr | 845 | TGC ACA AGG AGT GGA CGA | 846 | AGG AAG CTG GTC TGG GGT AT |
| Fluidigm & QPCR | BC021614 | 847 | CAC ATT CAA GGC TTC CTG TTT | 848 | GTA TTG GAT TGG TAC AGG GTG AG |
| Fluidigm & QPCR | Cd274 | 849 | CCA TCC TGT TGT TCC TCA TTG | 850 | TCC ACA TCT AGC ATT CTC ACT TG |
| Fluidigm & QPCR | Cmtm7 | 851 | TCG CCT CCA TAG TGA TAG CC | 852 | CTC GCT AGG CAG AGG AAG C |
| Fluidigm & QPCR | Flna | 853 | GCA AGT GCA CAG TCA CAG GT | 854 | TTG CCT GCT GCT TTT GTG T |
| Fluidigm & QPCR | Il2 | 855 | GCT GTT GAT GGA CCT ACA GGA | 856 | TTC AAT TCT GTG GCC TGC TT |

TABLE S6.1-continued

Primer Sequences

| Assay | Gene Name | SEQ ID NO: | Forward Sequence | SEQ ID NO: | Reverse Sequence |
|---|---|---|---|---|---|
| Fluidigm & QPCR | Lad1 | 857 | CTA CAG CAG TTC CCT CAA ACG | 858 | TGT CTT TCC TGG GGC TCA T |
| Fluidigm & QPCR | Mta3 | 859 | CTT TGT CGT GTA TCA TTG GGT ATT | 860 | TTG GTA GCT GGA GTT TGC AG |
| Fluidigm & QPCR | Peci | 861 | AAC GGT GCT GTG TTA CTG AGG | 862 | CAG CTG GGC CAT TTA CTA CC |
| Fluidigm & QPCR | Sap30 | 863 | CGG TGC AGT GTC AGC TTC | 864 | CTC CCG CAA ACA ACA GAG TT |
| Fluidigm & QPCR | Tnfrsf12 a | 865 | CCG CCG GAG AGA AAA GTT | 866 | CTG GAT CAG TGC CAC ACC T |
| Fluidigm & QPCR | pgk1 | 867 | TAC CTG CTG GCT GGA TGG | 868 | CAC AGC CTC GGC ATA TTT CT |
| Fluidigm & QPCR | A1451617 /// Trim30 | 869 | CAA CTG CAG AGT TTG GAG GA | 870 | TGT GTC TGC CTG TCC TGA CT |
| Fluidigm & QPCR | Bell 1b | 871 | TCC CAG AGG GAA CTC ATC AC | 872 | CCA GAC CCT CGT CTT CCT C |
| Fluidigm & QPCR | Cd28 | 873 | CTG GCC CTC ATC AGA ACA AT | 874 | GGC GAC TGC TTT ACC AAA ATC |
| Fluidigm & QPCR | Ctla2b | 875 | GCC TCC TCT GTC AGT TGC TC | 876 | AAG CAG AGG ATG AGC AGG AA |
| Fluidigm & QPCR | Foxp3 | 877 | TCA GGA GCC CAC CAG TAC A | 878 | TCT GAA GGC AGA GTC AGG AGA |
| Fluidigm & QPCR | Il21 | 879 | GAC ATT CAT CAT TGA CCT CGT G | 880 | TCA CAG GAA GGG CAT TTA GC |
| Fluidigm & QPCR | Lif | 881 | AAA CGG CCT GCA TCT AAG G | 882 | AGC AGC AGT AAG GGC ACA AT |
| Fluidigm & QPCR | Myst4 | 883 | GCA ACA AAG GGC AGC AAG | 884 | AGA CAT CTT TAG GAA ACC AAG ACC |
| Fluidigm & QPCR | Peli2 | 885 | TAC ACC TTG CGA GAG ACC AG | 886 | GGA CGT TGG TCT CAC TTT CC |
| Fluidigm & QPCR | Sgk1 | 887 | GAT TGC CAG CAA CAC CTA TG | 888 | TTG ATT TGT TGA GAG GGA CTT G |
| Fluidigm & QPCR | Tnfrsf25 | 889 | CCC TGG CTT ATC CCA GAC T | 890 | AGA TGC CAG AGG AGT TCC AA |
| Fluidigm & QPCR | PPIA | 891 | ACG CCA CTG TCG CTT TTC | 892 | GCA AAC AGC TCG AAG GAG AC |
| Fluidigm & QPCR | Aqp3 | 893 | CTG GGG ACC CTC ATC CTT | 894 | TGG TGA GGA AGC CAC CAT |
| Fluidigm & QPCR | Bcl3 | 895 | GAA CAA CAG CCT GAA CAT GG | 896 | TCT GAG CGT TCA CGT TGG |
| Fluidigm & QPCR | Cd74 | 897 | GCC CTA GAG AGC CAG AAA GG | 898 | TGG TAC AGG AAG TAA GCA GTG G |
| Fluidigm & QPCR | Ctsw | 899 | GGT TCA ACC GGA GTT ACT GG | 900 | TGG GCA AAG ATG CTC AGA C |
| Fluidigm & QPCR | Gem | 901 | GAC AGC ATG GAC AGC GAC T | 902 | ACG ACC AGG GTA CGC TCA TA |
| Fluidigm & QPCR | Il27ra | 903 | AGT TCC GGT ACA AGG AAT GC | 904 | ACA GGA GTC AGC CCA TCT GT |

TABLE S6.1-continued

| Primer Sequences | | | | | |
|---|---|---|---|---|---|
| Assay | Gene Name | SEQ ID NO: | Forward Sequence | SEQ ID NO: | Reverse Sequence |
| Fluidigm & QPCR | Litaf | 905 | TCC TGT GGC AGT CTG TGT CT | 906 | CTA CGC AGA ACG GGA TGA AG |
| Fluidigm & QPCR | Ncf1 | 907 | GGA CAC CTT CAT TCG CCA TA | 908 | CTG CCA CTT AAC CAG GAA CAT |
| Fluidigm & QPCR | Plekhf2 | 909 | GTC GGC GAC TAG GAG GAC T | 910 | TCC ACC ATC TTT TGC TAA TAA CC |
| Fluidigm & QPCR | Smad3 | 911 | TCA AGA AGA CGG GGC AGT T | 912 | CCG ACC ATC CAG TGA CCT |
| Fluidigm & QPCR | Tnfsf8 | 913 | GAG GAT CTC TTC TGT ACC CTG AAA | 914 | TTG TTG AGA TGC TTT GAC ACT TG |
| Fluidigm & QPCR | RPL13A | 915 | ATC CCT CCA CCC TAT GAC AA | 916 | GCC CCA GGT AAG CAA ACT T |
| Fluidigm & QPCR | Arhgef3 | 917 | GTT GGT CCC ATC CTC GTG | 918 | GAT TGC TGC AGT AGC TGT CG |
| Fluidigm & QPCR | Bcl6 | 919 | CTG CAG ATG GAG CAT GTT GT | 920 | GCC ATT TCT GCT TCA CTG G |
| Fluidigm & QPCR | Cd86 | 921 | GAA GCC GAA TCA GCC TAG C | 922 | CAG CGT TAC TAT CCC GCT CT |
| Fluidigm & QPCR | Cxcr4 | 923 | TGG AAC CGA TCA GTG TGA GT | 924 | GGG CAG GAA GAT CCT ATT GA |
| Fluidigm & QPCR | Glipr1 | 925 | TGC CCT AAT GGA GCA AAT TTT A | 926 | TTA TAT GGC CAC GTT GGG TAA |
| Fluidigm & QPCR | Il2rb | 927 | AGC ATG GGG GAG ACC TTC | 928 | GGG GCT GAA GAA GGA CAA G |
| Fluidigm & QPCR | LOC100 045833 ///Ly6c1 ///Ly6c2 | 929 | TCT TGT GGC CCT ACT GTG TG | 930 | GCA ATG CAG AAT CCA TCA GA |
| Fluidigm & QPCR | Ncoa1 | 931 | TGG CAT GAA CAT GAG GTC AG | 932 | GCC AAC ATC TGA GCA TTC AA |
| Fluidigm & QPCR | Prc1 | 933 | TGG AAA CTT TTC CTA GAG TTT GAG A | 934 | TTT CCC CCT CGG TTT GTA A |
| Fluidigm & QPCR | Smox | 935 | GAT GCT TCG ACA GTT CAC AGG | 936 | GGA ACC CCG GAA GTA TGG |
| Fluidigm & QPCR | Ubiad1 | 937 | GTC TGG CTC CTT TCT CTA CAC AG | 938 | AGT GAT GAG GAT GAC GAG GTC |
| Fluidigm & QPCR | Ywhaz | 939 | AAC AGC TTT CGA TGA AGC CAT | 940 | TGG GTA TCC GAT GTC CAC AAT |
| Fluidigm & QPCR | Arid5a | 941 | CAG AGC AGG AGC CAG AGC | 942 | GCC AAG TTC ATC ATA CAC GTT C |
| Fluidigm & QPCR | Casp3 | 943 | GAG GCT GAC TTC CTG TAT GCT T | 944 | AAC CAC GAC CCG TCC TTT |
| Fluidigm & QPCR | Cd9 | 945 | GAT ATT CGC CAT TGA GAT AGC C | 946 | TGG TAG GTG TCC TTG TAA AAC TCC |
| Fluidigm & QPCR | Elk3 | 947 | GAG GGG CTT TGA GAG TGC T | 948 | TGT CCT GTG TGC CTG TCT TG |
| Fluidigm & QPCR | Golga3 | 949 | ACA GAA AGT GGC AGA TGC AG | 950 | TCT CGC TGG AAC AAT GTC AG |
| Fluidigm & QPCR | Irf9 | 951 | TGA GGC CAC CAT TAG AGA GG | 952 | AGC AGC AGC GAG TAG TCT GA |

TABLE S6.1-continued

Primer Sequences

| Assay | Gene Name | SEQ ID NO: | Forward Sequence | SEQ ID NO: | Reverse Sequence |
|---|---|---|---|---|---|
| Fluidigm & QPCR | LOC100 046232 ///Nfil3 | 953 | GGA CCA GGG AGC AGA ACC | 954 | GTC CGG CAC AGG GTA AAT C |
| Fluidigm & QPCR | Nfkbie | 955 | CCT GGA CCT CCA ACT GAA GA | 956 | TCC TCT GCA ATG TGG CAA T |
| Fluidigm & QPCR | Prnp | 957 | TCC AAT TTA GGA GAG CCA AGC | 958 | GCC GAC ATC AGT CCA CAT AG |
| Fluidigm & QPCR | Stat2 | 959 | GGA ACA GCT GGA ACA GTG GT | 960 | GTA GCT GCC GAA GGT GGA |
| Fluidigm & QPCR | Zfp161 | 961 | GGA GTG AGG AAG TTC GGA AA | 962 | TGG ATT CGG GAG TCT CCA T |
| Fluidigm & QPCR | B2M | 963 | TTC TGG TGC TTG TCT CAC TGA | 964 | CAG TAT GTT CGG CTT CCC ATT C |
| Fluidigm & QPCR | Abcg2 | 965 | GCC TTG GAG TAC TTT GCA TCA | 966 | AAA TCC GCA GGG TTG TTG TA |
| Fluidigm & QPCR | Ccr5 | 967 | GAG ACA TCC GTT CCC CCT AC | 968 | GTC GGA ACT GAC CCT TGA AA |
| Fluidigm & QPCR | Cxcr3 | 969 | AGG CAG CAC GAG ACC TGA | 970 | GGC ATC TAG CAC TTG ACG TTC |
| Fluidigm & QPCR | Fli1 | 971 | AGA CCA TGG GCA AGA ACA CT | 972 | GCC CCA GGA TCT GAT AAG G |
| Fluidigm & QPCR | Gzmb | 973 | GCT GCT CAC TGT GAA GGA AGT | 974 | TGG GGA ATG CAT TTT ACC AT |
| Fluidigm & QPCR | Il10ra | 975 | GCT CCC ATT CCT CGT CAC | 976 | AAG GGC TTG GCA GTT CTG T |
| Fluidigm & QPCR | Il3 | 977 | TAC ATC TGC GAA TGA CTC TGC | 978 | GGC TGA GGT GGT CTA GAG GTT |
| Fluidigm & QPCR | Klrd1 | 979 | GGA TTG GAA TGC ATT ATA GTG AAA A | 980 | TGC TCT GGC CTG ATA ACT GAG |
| Fluidigm & QPCR | Plac8 | 981 | CAG ACC AGC CTG TGT GAT TG | 982 | CCA AGA CAA GTG AAA CAA AAG GT |
| Fluidigm & QPCR | Sertad1 | 983 | TCC CTC TTC GTT CTG ATT GG | 984 | GCT TGC GCT TCA GAC CTT T |
| Fluidigm & QPCR | Tnfsf9 | 985 | CGC CAA GCT ACT GGC TAA AA | 986 | CGT ACC TCA GAC CTT GAG ATA GGT |
| Fluidigm & QPCR | GAPDH | 987 | GGC AAA TTC AAC GGC ACA GT | 988 | AGA TGG TGA TGG GCT TCC C |
| Fluidigm & QPCR | Acvr2a | 989 | CCC TCC TGT ACT TGT TCC TAC TCA | 990 | GCA ATG GCT TCA ACC CTA GT |
| Fluidigm & QPCR | Ccr6 | 991 | TTC GCC ACT CTA ATC AGT AGG AC | 992 | TCT GGT GTA GAA AGG GAA GTG G |
| Fluidigm & QPCR | Cxcr5 | 993 | GAA TGA CGA CAG AGG TTC CTG | 994 | GCC CAG GTT GGC TTC TTA T |
| Fluidigm & QPCR | Foxm1 | 995 | ACT TTA AGC ACA TTG CCA AGC | 996 | GGA GAG AAA GGT TGT GAC GAA |
| Fluidigm & QPCR | Hip1r | 997 | AGT GAG CAA GCT GGA CGA C | 998 | GAA GCC AGG TAC TGG GTG TG |
| Fluidigm & QPCR | Il12rb1 | 999 | CGC AGC CGA GTA ATG TAC AAG | 1000 | AAC GGG AAA TCT GCA CCT C |

TABLE S6.1-continued

Primer Sequences

| Assay | Gene Name | SEQ ID NO: | Forward Sequence | SEQ ID NO: | Reverse Sequence |
|---|---|---|---|---|---|
| Fluidigm & QPCR | Il9 | 1001 | GCC TCT GTT TTG CTC TTC AGT T | 1002 | GCA TTT TGA CGG TGG ATC A |
| Fluidigm & QPCR | LOC100 046643 ///Spry1 | 1003 | TAG GTC AGA TCG GGT CAT CC | 1004 | GTG GGG TCC TCT TTC AAG G |
| Fluidigm & QPCR | Prdm1 | 1005 | TGC GGA GAG GCT CCA CTA | 1006 | TGG GTT GCT TTC CGT TTG |
| Fluidigm & QPCR | Socs3 | 1007 | ATT TCG CTT CGG GAC TAG C | 1008 | AAC TTG CTG TGG GTG ACC AT |
| Fluidigm & QPCR | Trim24 | 1009 | ATC CAG CAG CCT TCC ATC T | 1010 | GGC TTA GGG CTG TGA TTC TG |
| Fluidigm & QPCR | HMBS | 1011 | TCC CTG AAG GAT GTG CCT AC | 1012 | AAG GGT TTT CCC GTT TGC |
| Fluidigm & QPCR | Anxa4 | 1013 | TGA TGC TCT TAT GAA GCA GGA C | 1014 | CGT CTG TCC CCC ATC TCT T |
| Fluidigm & QPCR | Cd51 | 1015 | GAG GAC ACA TGG ATG GAA TGT | 1016 | ACC CTT GTG TAG CAC CTC CA |
| Fluidigm & QPCR | Daxx | 1017 | CAG GCC ACT GGT CTC TCC | 1018 | TCC GTC TTA CAC AGT TCA AGG A |
| Fluidigm & QPCR | Gap43 | 1019 | CGG AGA CTG CAG AAA GCA G | 1020 | GGT TTG GCT TCG TCT ACA GC |
| Fluidigm & QPCR | Id3 | 1021 | GAG GAG CTT TTG CCA CTG AC | 1022 | GCT CAT CCA TGC CCT CAG |
| Fluidigm & QPCR | Il12rb2 | 1023 | TGT GGG GTG GAG ATC TCA GT | 1024 | TCT CCT TCC TGG ACA CAT GA |
| Fluidigm & QPCR | Inhba | 1025 | ATC ATC ACC TTT GCC GAG TC | 1026 | TCA CTG CCT TCC TTG GAA AT |
| Fluidigm & QPCR | Maff | 1027 | GAC AAG CAC GCA CTG AGC | 1028 | CAT TTT CGC AGA AGA TGA CCT |
| Fluidigm & QPCR | Prickle1 | 1029 | ATG GAT TCT TTG GCG TTG TC | 1030 | TGA CGG TCT TGG CTT GCT |
| Fluidigm & QPCR | Spp1 | 1031 | GGA GGA AAC CAG CCA AGG | 1032 | TGC CAG AAT CAG TCA CTT TCA C |
| Fluidigm & QPCR | Trps1 | 1033 | ACT CTG CAA ACA ACA GAA GAC G | 1034 | TCT TTT TCC GGA CCA TAT CTG T |
| Fluidigm & QPCR | HPRT | 1035 | TCC TCC TCA GAC CGC TTT T | 1036 | CCT GGT TCA TCA TCG CTA ATC |
| Fluidigm & QPCR | Bcl2l11 | 1037 | GGA GAC GAG TTC AAC GAA ACT T | 1038 | AAC AGT TGT AAG ATA ACC ATT TGA GG |
| Fluidigm & QPCR | Cd80 | 1039 | TCG TCT TTC ACA AGT GTC TTC AG | 1040 | TTG CCA GTA GAT TCG GTC TTC |
| Fluidigm & QPCR | Dntt | 1041 | GAG CAG CAG CTC TTG CAT AA | 1042 | GAT GTC GCA GTA CAA AAG CAA C |
| Fluidigm & QPCR | Gata3 | 1043 | TTA TCA AGC CCA AGC GAA G | 1044 | TGG TGG TGG TCT GAC AGT TC |
| Fluidigm & QPCR | Ifih1 | 1045 | CTA TTA ACC GTG TTC AAA ACA TGA A | 1046 | CAC CTG CAA TTC CAA AAT CTT A |
| Fluidigm & QPCR | Il15ra | 1047 | CCA GTG CCA ACA GTA GTG ACA | 1048 | TTG GGA GAG AAA GCT TCT GG |

TABLE S6.1-continued

| Primer Sequences | | | | | |
|---|---|---|---|---|---|
| Assay | Gene Name | SEQ ID NO: | Forward Sequence | SEQ ID NO: | Reverse Sequence |
| Fluidigm & QPCR | Irf7 | 1049 | CTT CAG CAC TTT CTT CCG AGA | 1050 | TGT AGT GTG GTG ACC CTT GC |
| Fluidigm & QPCR | Mgl1 | 1051 | TCG GAA CAA GTC GGA GGT | 1052 | TCA GCA GCT GTA TGC CAA AG |
| Fluidigm & QPCR | Procr | 1053 | AGC GCA AGG AGA ACG TGT | 1054 | GGG TTC AGA GCC CTC CTC |
| Fluidigm & QPCR | Stard10 | 1055 | GAG CTG CGT CAT CAC CTA CC | 1056 | TGC AGG CCT TGT ACA TCT TCT |
| Fluidigm & QPCR | Tsc22d3 | 1057 | GGT GGC CCT AGA CAA CAA GA | 1058 | TCA AGC AGC TCA CGA ATC TG |
| Fluidigm & QPCR | pgk1 | 1059 | TAC CTG CTG GCT GGA TGG | 1060 | CAC AGC CTC GGC ATA TTT CT |
| Fluidigm & QPCR | Casp1 | 1061 | CCC ACT GCT GAT AGG GTG AC | 1062 | GCA TAG GTA CAT AAG AAT GAA CTG GA |
| Fluidigm & QPCR | Cd83 | 1063 | TGG TTC TGA AGG TGA CAG GA | 1064 | CAA CCA GAG AGA AGA GCA ACA C |
| Fluidigm & QPCR | Dpp4 | 1065 | CGG TAT CAT TTA GTA AAG AGG CAA A | 1066 | GTA GAG TGT AGA GGG GCA GAC C |
| Fluidigm & QPCR | Gfi1 | 1067 | TCC GAG TTC GAG GAC TTT TG | 1068 | GAG CGG CAC AGT GAC TTC T |
| Fluidigm & QPCR | Ifit1 | 1069 | TCT AAA CAG GGC CTT GCA G | 1070 | GCA GAG CCC TTT TTG ATA ATG T |
| Fluidigm & QPCR | Il17a | 1071 | CAG GGA GAG CTT CAT CTG TGT | 1072 | GCT GAG CTT TGA GGG ATG AT |
| Fluidigm & QPCR | Isg20 | 1073 | TTG GTG AAG CCA GGC TAG AG | 1074 | CTT CAG GGC ATT GAA GTC GT |
| Fluidigm & QPCR | Mt1 | 1075 | CAC CAG ATC TCG GAA TGG AC | 1076 | AGG AGC AGC AGC TCT TCT TG |
| Fluidigm & QPCR | Psmb9 | 1077 | CGC TCT GCT GAG ATG CTG | 1078 | CTC CAC TGC CAT GAT GGT T |
| Fluidigm & QPCR | Sult2b1 | 1079 | ACT TCC TGT TTA TCA CCT ATG AGG A | 1080 | AAC TCA CAG ATG CGT TGC AC |
| Fluidigm & QPCR | Vav3 | 1081 | TTA CAC GAA GAT GAG TGC AAA TG | 1082 | CAA CAC TGG ATA GGA CTT TAT TCA TC |
| Fluidigm & QPCR | PPIA | 1083 | ACG CCA CTG TCG CTT TTC | 1084 | GCA AAC AGC TCG AAG GAG AC |
| Fluidigm QPCR | Casp4 | 1085 | TCC AGA CAT TCT TCA GTG TGG A | 1086 | TCT GGT TCC TCC ATT TCC AG |
| Fluidigm & QPCR | Creb3l2 | 1087 | CCA GCC AGC ATC CTC TGT | 1088 | AGC AGG TTC CTG GAT CTC AC |
| Fluidigm & QPCR | Egr2 | 1089 | CTA CCC GGT GGA AGA CCT C | 1090 | AAT GTT GAT CAT GCC ATC TCC |
| Fluidigm & QPCR | Gja1 | 1091 | TCC TTT GAC TTC AGC CTC CA | 1092 | CCA TGT CTG GGC ACC TCT |
| Fluidigm & QPCR | Ifitm2 | 1093 | TGG TCT GGT CCC TGT TCA AT | 1094 | CTG GGC TCC AAC CAC ATC |
| Fluidigm & QPCR | Il 1rn | 1095 | TGT GCC AAG TCT GGA GAT GA | 1096 | TTC TTT GTT CTT GCT CAG ATC AGT |

TABLE S6.1-continued

| Primer Sequences | | | | | |
|---|---|---|---|---|---|
| Assay | Gene Name | SEQ ID NO: | Forward Sequence | SEQ ID NO: | Reverse Sequence |
| Fluidigm & QPCR | Jak3 | 1097 | TGG AAG ACC CGG ATA GCA | 1098 | GTC TAG CGC TGG GTC CAC |
| Fluidigm QPCR | Mxi1 | 1099 | CAA AGC CAA AGC ACA CAT CA | 1100 | AGT CGC CGC TTT AAA AAC CT |
| Fluidigm & QPCR | Rad51ap 1 | 1101 | AAA GCA AGA GGC CCA AGT G | 1102 | TGC ATT GCT GCT AGA GTT CC |
| Fluidigm & QPCR | Tbx21 | 1103 | TCA ACC AGC ACC AGA CAG AG | 1104 | AAA CAT CCT GTA ATG GCT TGT G |
| Fluidigm & QPCR | Xcl1 | 1105 | GAG ACT TCT CCT CCT GAC TTT CC | 1106 | GGA CTT CAG TCC CCA CAC C |
| Fluidigm & QPCR | RPL13A | 1107 | ATC CCT CCA CCC TAT GAC AA | 1108 | GCC CCA GGT AAG CAA ACT T |
| Fluidigm & QPCR | Ccl20 | 1109 | AAC TGG GTG AAA AGG GCT GT | 1110 | GTC CAA TTC CAT CCC AAA AA |
| Fluidigm & QPCR | Csf2 | 1111 | GCA TGT AGA GGC CAT CAA AGA | 1112 | CGG GTC TGC ACA CAT GTT A |
| Fluidigm & QPCR | Errfi1 | 1113 | TGC TCA GGA GCA CCT AAC AAC | 1114 | TGG AGA TGG ACC ACA CTC TG |
| Fluidigm & QPCR | Gp49a ///Lilrb4 | 1115 | TGG AGT CCT GGT GTC ATT CC | 1116 | TGT GTG TTC TTC ACA GAA GCA TT |
| Fluidigm & QPCR | Ifng | 1117 | ATC TGG AGG AAC TGG CAA AA | 1118 | TTC AAG ACT TCA AAG AGT CTG AGG TA |
| Fluidigm & QPCR | Il22 ///Iltifb | 1119 | TTT CCT GAC CAA ACT CAG CA | 1120 | TCT GGA TGT TCT GGT CGT CA |
| Fluidigm & QPCR | Kat2b | 1121 | GGA GAA ACT CGG CGT GTA CT | 1122 | CAG CCA TTG CAT TTA CAG GA |
| Fluidigm & QPCR | Nkg7 | 1123 | TCT ACC TAG GCT GGG TCT CCT | 1124 | CCG ACG GGT TCT ACA GTG AG |
| Fluidigm & QPCR | Serpinb1 a | 1125 | GGA TTT TCT GCA TGC CTC TG | 1126 | GAC AAC AGT TCT GGG ATT TTC C |
| Fluidigm & QPCR | Tgm2 | 1127 | CTC ACG TTC GGT GCT GTG | 1128 | TCC CTC CTC CAC ATT GTC A |
| Fluidigm & QPCR | Zfp238 | 1129 | TGC ATC TGT CTC TCT TAG TCT GCT | 1130 | TCT GGA AAC TCC ATA CTG TCT TCA |
| Fluidigm & QPCR | Ywhaz | 1131 | AAC AGC TTT CGA TGA AGC CAT | 1132 | TGG GTA TCC GAT GTC CAC AAT |
| Fluidigm & QPCR | Ccl4 | 1133 | GCC CTC TCT CTC CTC TTG CT | 1134 | GAG GGT CAG AGC CCA TTG |
| Fluidigm & QPCR | Cxcl10 | 1135 | GCT GCC GTC ATT TTC TGC | 1136 | TCT CAC TGG CCC GTC ATC |
| Fluidigm & QPCR | Etv6 | 1137 | TCC CTT TCG CTG TGA GAC AT | 1138 | GGG CGT GTA TGA AAT TCG TT |
| Fluidigm & QPCR | Grn | 1139 | TGG CTA ATG GAA ATT GAG GTG | 1140 | CAT CAG GAC CCA CAT GGT CT |
| Fluidigm & QPCR | Ikzf4 | 1141 | GCA GAC ATG CAC ACA CCA C | 1142 | TGA GAG CTC CCT CTC CAG AT |
| Fluidigm & QPCR | Il23r | 1143 | CCA AGT ATA TTG TGC ATG TGA AGA | 1144 | AGC TTG AGG CAA GAT ATT GTT GT |

TABLE S6.1-continued

Primer Sequences

| Assay | Gene Name | SEQ ID NO: | Forward Sequence | SEQ ID NO: | Reverse Sequence |
|---|---|---|---|---|---|
| Fluidigm & QPCR | Klf9 | 1145 | CTC CGA AAA GAG GCA CAA GT | 1146 | GCG AGA ACT TTT TAA GGC AGT C |
| Fluidigm & QPCR | Phlda1 | 1147 | CGC ACC AGC CTC TTC ACT | 1148 | TTC CGA AGT CCT CAA AAC CTT |
| Fluidigm & QPCR | Serpine2 | 1149 | TTG GGT CAA AAA TGA GAC CAG | 1150 | CCT TGA AAT ACA CTG CAT TAA CGA |
| Fluidigm & QPCR | Tnfrsf13 b | 1151 | GAG CTC GGG AGA CCA CAG | 1152 | TGG TCG CTA CTT AGC CTC AAT |
| Fluidigm & QPCR | Zfp281 | 1153 | GGA GAG GAC GGC GTT ATT TT | 1154 | TTT TCA TAC CCC GGA GGA G |

TABLE S6.2

RNAi sequences

| Duplex Catalog Number | Gene Symbol | GENE ID | Gene Accession | SEQ ID NO: | Sequence |
|---|---|---|---|---|---|
| D-040676-01 | Acvr2a | 11480 | NM_007396 | 1155 | CAAAGAAUCUAGUCUAU GA |
| D-040676-02 | Acvr2a | 11480 | NM_007396 | 1156 | UGACAGGACUGAUUGUA UA |
| D-040676-03 | Acvr2a | 11480 | NM_007396 | 1157 | GCAGAAACAUGCAGGAA UG |
| D-040676-04 | Acvr2a | 11480 | NM_007396 | 1158 | GGCAAUAUGUGUAAUGA AA |
| D-044066-01 | Ahr | 11622 | NM_013464 | 1159 | CCAAUGCACGCUUGAUU UA |
| D-044066-02 | Ahr | 11622 | NM_013464 | 1160 | GAAGGAGAGUUCUUGUU AC |
| D-044066-03 | Ahr | 11622 | NM_013464 | 1161 | CCGCAAGAUGUUAUUAA UA |
| D-044066-04 | Ahr | 11622 | NM_013464 | 1162 | CCAGUUCUCUUAUGAGU GC |
| D-054696-01 | Arid5a | 214855 | NM_145996 | 1163 | GGAAGAACGUGUAUGAU GA |
| D-054696-02 | Arid5a | 214855 | NM_145996 | 1164 | GAAGAGGGAUUCGCUCA UG |
| D-054696-03 | Arid5a | 214855 | NM_145996 | 1165 | CCUCUAAACUUCACCGG UA |
| D-054696-04 | Arid5a | 214855 | NM_145996 | 1166 | GGUCAUCCCUGCUUUCC CA |
| D-040483-02 | ARNTL | 11865 | NM_007489 | 1167 | GCAUCGAUAUGAUAGAU AA |
| D-040483-03 | ARNTL | 11865 | NM_007489 | 1168 | CAGUAAAGGUGGAAGAU AA |
| D-040483-04 | ARNTL | 11865 | NM_007489 | 1169 | GAAAUACGGGUGAAAUC UA |
| D-040483-17 | ARNTL | 11865 | NM_007489 | 1170 | UGUCGUAGGAUGUGACC GA |

TABLE S6.2-continued

| RNAi sequences | | | | | |
|---|---|---|---|---|---|
| Duplex Catalog Number | Gene Symbol | GENE ID | Gene Accession | SEQ ID NO: | Sequence |
| D-049093-01 | Batf | 53314 | NM_016767 | 1171 | GAACGCAGCUCUCCGCAAA |
| D-049093-02 | Batf | 53314 | NM_016767 | 1172 | UCAAACAGCUCACCGAGGA |
| D-049093-03 | Batf | 53314 | NM_016767 | 1173 | GAGGAAAGUUCAGAGGAGA |
| D-049093-04 | Batf | 53314 | NM_016767 | 1174 | UCAAGUACUUCACAUCAGU |
| D-058452-01 | CCR5 | 12774 | NM_009917 | 1175 | GGAGUUAUCUCUCAGUGUU |
| D-058452-02 | CCR5 | 12774 | NM_009917 | 1176 | UGAAGUUUCUACUGGUUUA |
| D-058452-03 | CCR5 | 12774 | NM_009917 | 1177 | GCUAUGACAUCGAUUAUGG |
| D-058452-04 | CCR5 | 12774 | NM_009917 | 1178 | UGAAACAAAUUGCGGCUCA |
| D-062489-01 | CCR6 | 12458 | NM_009835 | 1179 | GCACAUAUGCGGUCAACUU |
| D-062489-02 | CCR6 | 12458 | NM_009835 | 1180 | CCAAUUGCCUACUCCUUAA |
| D-062489-03 | CCR6 | 12458 | NM_009835 | 1181 | GAACGGAUGAUUAUGACAA |
| D-062489-04 | CCR6 | 12458 | NM_009835 | 1182 | UGUAUGAGAAGGAAGAAUA |
| D-040286-04 | EGR1 | 13653 | NM_007913 | 1183 | CGACAGCAGUCCCAUCUAC |
| D-040286-01 | EGR1 | 13653 | NM_007913 | 1184 | UGACAUCGCUCUGAAUAAU |
| D-040286-02 | EGR1 | 13653 | NM_007913 | 1185 | ACUCCACUAUCCACUAUUA |
| D-040286-03 | EGR1 | 13653 | NM_007913 | 1186 | AUGCGUAACUUCAGUCGUA |
| D-040303-01 | Egr2 | 13654 | NM_010118 | 1187 | GAAGGUAUCAUCAAUAUUG |
| D-040303-02 | Egr2 | 13654 | NM_010118 | 1188 | GAUCUCCCGUAUCCGAGUA |
| D-040303-03 | Egr2 | 13654 | NM_010118 | 1189 | UCUCUACCAUCCGUAAUUU |
| D-040303-04 | Egr2 | 13654 | NM_010118 | 1190 | UGACAUGACUGGAGAGAAG |
| D-058294-01 | ELK3 | 13713 | NM_013508 | 1191 | GUAGAGAUCAGCCGGGAGA |
| D-058294-02 | ELK3 | 13713 | NM_013508 | 1192 | GAUCAGGUUUGUGACCAAU |
| D-058294-03 | ELK3 | 13713 | NM_013508 | 1193 | UCUUUAAUGUUGCCAAAUG |
| D-058294-04 | ELK3 | 13713 | NM_013508 | 1194 | UGAGAUACUAUUACGACAA |
| D-050997-21 | Ets1 | 23871 | NM_001038642 | 1195 | GCUUAGAGAUGUAGCGAUG |

TABLE S6.2-continued

| RNAi sequences | | | | | |
|---|---|---|---|---|---|
| Duplex Catalog Number | Gene Symbol | GENE ID | Gene Accession | SEQ ID NO: | Sequence |
| D-050997-22 | Ets1 | 23871 | NM_001038642 | 1196 | CCUGUUACACCUCGGAUUA |
| D-050997-23 | Ets1 | 23871 | NM_001038642 | 1197 | CAGCUACGGUAUCGAGCAU |
| D-050997-24 | Ets1 | 23871 | NM_001038642 | 1198 | UCAAGUAUGAGAACGACUA |
| D-040983-01 | ETS2 | 23872 | NM_011809 | 1199 | GAUCAACAGCAAUACAUUA |
| D-040983-02 | ETS2 | 23872 | NM_011809 | 1200 | UGAAUUUGCUCAACAACAA |
| D-040983-03 | ETS2 | 23872 | NM_011809 | 1201 | UAGAGCAGAUGAUCAAAGA |
| D-040983-04 | ETS2 | 23872 | NM_011809 | 1202 | GAAUGACUUUGGAAUCAAG |
| D-058395-01 | Etv6 | 14011 | NM_007961 | 1203 | GAACAAACAUGACCUAUGA |
| D-058395-02 | Etv6 | 14011 | NM_007961 | 1204 | CAAAGAGGAUUUCCGCUAC |
| D-058395-03 | Etv6 | 14011 | NM_007961 | 1205 | GCAUUAAGCAGGAACGAAU |
| D-058395-04 | Etv6 | 14011 | NM_007961 | 1206 | CGCCACUACUACAAACUAA |
| D-045283-04 | Fas | 14102 | NM_007987 | 1207 | GAGUAAAUACAUCCCGAGA |
| D-045283-03 | Fas | 14102 | NM_007987 | 1208 | GGAGGCGGGUUCAUGAAAC |
| D-045283-02 | Fas | 14102 | NM_007987 | 1209 | CGCAGAACCUUAGAUAAAU |
| D-045283-01 | Fas | 14102 | NM_007987 | 1210 | GUACCAAUCUCAUGGGAAG |
| D-041127-01 | Foxo1 | 56458 | NM_019739 | 1211 | GAAGACACCUUUACAAGUG |
| D-041127-02 | Foxo1 | 56458 | NM_019739 | 1212 | GGACAACAACAGUAAAUUU |
| D-041127-03 | Foxo1 | 56458 | NM_019739 | 1213 | GGAGAUACCUUGGAUUUUA |
| D-041127-04 | Foxo1 | 56458 | NM_019739 | 1214 | GAAAUCAGCAAUCCAGAAA |
| D-040670-01 | GATA3 | 14462 | NM_008091 | 1215 | GAAGAUGUCUAGCAAAUCG |
| D-040670-02 | GATA3 | 14462 | NM_008091 | 1216 | CGGAAGAUGUCUAGCAAAU |
| D-040670-03 | GATA3 | 14462 | NM_008091 | 1217 | GUACAUGGAAGCUCAGUAU |
| D-040670-04 | GATA3 | 14462 | NM_008091 | 1218 | AGAAAGAGUGCCUCAAGUA |
| D-060495-01 | Id2 | 15902 | NM_010496 | 1219 | CAUCUGAAUUCCCUUCUGA |

TABLE S6.2-continued

RNAi sequences

| Duplex Catalog Number | Gene Symbol | GENE ID | Gene Accession | SEQ ID NO: | Sequence |
|---|---|---|---|---|---|
| D-060495-02 | Id2 | 15902 | NM_010496 | 1220 | GAACACGGACAUCAGCAUC |
| D-060495-03 | Id2 | 15902 | NM_010496 | 1221 | GUCGAAUGAUAGCAAAGUA |
| D-060495-04 | Id2 | 15902 | NM_010496 | 1222 | CGGUGAGGUCCGUUAGGAA |
| D-051517-01 | Ikzf4 | 22781 | NM_011772 | 1223 | GAUGGUGCCUGACUCAAUG |
| D-051517-02 | Ikzf4 | 22781 | NM_011772 | 1224 | CGACUGAACGGCCAACUUU |
| D-051517-03 | Ikzf4 | 22781 | NM_011772 | 1225 | GUGAAGGCCUUUAAGUGUG |
| D-051517-04 | Ikzf4 | 22781 | NM_011772 | 1226 | GAACUCACACCUGUCAUCA |
| D-040810-01 | IL17RA | 16172 | NM_008359 | 1227 | GGACAGAUUUGAGGAGGUU |
| D-040810-02 | IL17RA | 16172 | NM_008359 | 1228 | GAAUAGUACUUGUCUGGAU |
| D-040810-03 | IL17RA | 16172 | NM_008359 | 1229 | UCUGGGAGCUCGAGAAGAA |
| D-040810-04 | IL17RA | 16172 | NM_008359 | 1230 | GAGAGCAACUCCAAAAUCA |
| D-040007-04 | IL6ST | 16195 | NM_010560 | 1231 | GUCCAGAGAUUUCACAUUU |
| D-040007-03 | IL6ST | 16195 | NM_010560 | 1232 | AGACUUACCUUGAAACAAA |
| D-040007-02 | IL6ST | 16195 | NM_010560 | 1233 | GAACUUCACUGCCAUUUGU |
| D-040007-01 | IL6ST | 16195 | NM_010560 | 1234 | GCACAGAGCUGACCGUGAA |
| D-057981-04 | IL7R | 16197 | NM_008372 | 1235 | GGAUUAAACCUGUCGUAUG |
| D-057981-03 | IL7R | 16197 | NM_008372 | 1236 | UAAGAUGCCUGGCUAGAAA |
| D-057981-02 | IL7R | 16197 | NM_008372 | 1237 | GCAAACCGCUCGCCUGAGA |
| D-057981-01 | IL7R | 16197 | NM_008372 | 1238 | GAAAGUCGUUUAUCGCAAA |
| D-043796-04 | IRF4 | 16364 | NM_013674 | 1239 | CCAUAUCAAUGUCCUGUGA |
| D-043796-03 | IRF4 | 16364 | NM_013674 | 1240 | CGAGUUACCUGAACACGUU |
| D-043796-02 | IRF4 | 16364 | NM_013674 | 1241 | UAUCAGAGCUGCAAGUGUU |
| D-043796-01 | IRF4 | 16364 | NM_013674 | 1242 | GGACACACCUAUGAUGUUA |
| D-040737-01 | Irf8 | 15900 | NM_008320 | 1243 | GGACAUUUCUGAGCCAUAU |
| D-040737-02 | Irf8 | 15900 | NM_008320 | 1244 | GAGCGAAGUUCCUGAGAUG |

TABLE S6.2-continued

RNAi sequences

| Duplex Catalog Number | Gene Symbol | GENE ID | Gene Accession | SEQ ID NO: | Sequence |
|---|---|---|---|---|---|
| D-040737-03 | Irf8 | 15900 | NM_008320 | 1245 | GCAAGGGCGUGUUCGUG AA |
| D-040737-04 | Irf8 | 15900 | NM_008320 | 1246 | GCAACGCGGUGGUGUGC AA |
| D-042246-04 | ITGA3 | 16400 | NM_013565 | 1247 | GCGAUGACUGGCAGACA UA |
| D-042246-03 | ITGA3 | 16400 | NM_013565 | 1248 | GAGUGGCCCUAUGAAGU UA |
| D-042246-02 | ITGA3 | 16400 | NM_013565 | 1249 | GGACAAUGUUCGCGAUA AA |
| D-042246-01 | ITGA3 | 16400 | NM_013565 | 1250 | CCAGACACCUCCAACAU UA |
| D-043776-01 | Jun | 16476 | NM_010591 | 1251 | GAACAGGUGGCACAGCU UA |
| D-043776-02 | Jun | 16476 | NM_010591 | 1252 | GAAACGACCUUCUACGA CG |
| D-043776-03 | Jun | 16476 | NM_010591 | 1253 | CCAAGAACGUGACCGAC GA |
| D-043776-04 | Jun | 16476 | NM_010591 | 1254 | GCCAAGAACUCGGACCU UC |
| D-041158-04 | JUNB | 16477 | NM_008416 | 1255 | CAACCUGGCGGAUCCCU AU |
| D-041158-03 | JUNB | 16477 | NM_008416 | 1256 | CAACAGCAACGGCGUGA UC |
| D-041158-02 | JUNB | 16477 | NM_008416 | 1257 | UGGAACAGCCUUUCUAU CA |
| D-041158-01 | JUNB | 16477 | NM_008416 | 1258 | ACACCAACCUCAGCAGU UA |
| D-049885-01 | Kat2b | 18519 | NM_020005 | 1259 | GCAGUAACCUCAAAUGA AC |
| D-049885-02 | Kat2b | 18519 | NM_020005 | 1260 | UCACAUAUGCAGAUGAG UA |
| D-049885-03 | Kat2b | 18519 | NM_020005 | 1261 | GAAGAACCAUCCAAAUG CU |
| D-049885-04 | Kat2b | 18519 | NM_020005 | 1262 | AAACAAGCCCAGAUUCG AA |
| D-047145-02 | LRRFIP1 | 16978 | NM_001111312 | 1263 | GAAGGGCUCCCGUAACA UG |
| D-047145-17 | LRRFIP1 | 16978 | NM_001111312 | 1264 | AAAGAGGCCCUGCGGCA AA |
| D-047145-18 | LRRFIP1 | 16978 | NM_001111312 | 1265 | GCUCGAGAGAUCCGGAU GA |
| D-047145-19 | LRRFIP1 | 16978 | NM_001111312 | 1266 | AGACACAGUAAAUGACG UU |
| D-063455-01 | Mina | 67014 | NM_025910 | 1267 | GUAAACAGUUGCCAAGG UU |
| D-063455-02 | Mina | 67014 | NM_025910 | 1268 | GCACCUACCAGAACAAU UC |

TABLE S6.2-continued

RNAi sequences

| Duplex Catalog Number | Gene Symbol | GENE ID | Gene Accession | SEQ ID NO: | Sequence |
|---|---|---|---|---|---|
| D-063455-03 | Mina | 67014 | NM_025910 | 1269 | GAAAUGGAACGGAGACGAU |
| D-063455-04 | Mina | 67014 | NM_025910 | 1270 | GGUCACCAAUUCGUGUUAA |
| D-040813-01 | MYC | 17869 | NM_010849 | 1271 | GACGAGACCUUCAUCAAGA |
| D-040813-02 | MYC | 17869 | NM_010849 | 1272 | GACAGCAGCUCGCCCAAAU |
| D-040813-03 | MYC | 17869 | NM_010849 | 1273 | GAAUUUCUAUCACCAGCAA |
| D-040813-04 | MYC | 17869 | NM_010849 | 1274 | GUACAGCCCUAUUUCAUCU |
| D-063057-04 | MYD88 | 17874 | NM_010851 | 1275 | GAUGAUCCGGCAACUAGAA |
| D-063057-03 | MYD88 | 17874 | NM_010851 | 1276 | GUUAGACCGUGAGGAUAUA |
| D-063057-02 | MYD88 | 17874 | NM_010851 | 1277 | CGACUGAUUCCUAUUAAAU |
| D-063057-01 | MYD88 | 17874 | NM_010851 | 1278 | GCCUAUCGCUGUUCUUGAA |
| D-041128-01 | NCOA1 | 17977 | NM_010881 | 1279 | GAACAUGAAUCCAAUGAUG |
| D-041128-02 | NCOA1 | 17977 | NM_010881 | 1280 | GAACAUGGGAGGACAGUUU |
| D-041128-03 | NCOA1 | 17977 | NM_010881 | 1281 | UCAAGAAUCUGCUACCAAA |
| D-041128-04 | NCOA1 | 17977 | NM_010881 | 1282 | CCAAGAAGAUGGUGAAGAU |
| D-047764-01 | Nfkb1 | 18033 | NM_008689 | 1283 | GACAUGGGAUUUCAGGAUA |
| D-047764-02 | Nfkb1 | 18033 | NM_008689 | 1284 | GGAUUUCGAUUCCGCUAUG |
| D-047764-03 | Nfkb1 | 18033 | NM_008689 | 1285 | CUACGGAACUGGGCAAAUG |
| D-047764-04 | Nfkb1 | 18033 | NM_008689 | 1286 | GGAAACGCCAGAAGCUUAU |
| D-041110-01 | NOTCH1 | 18128 | NM_008714 | 1287 | GAACAACUCCUUCCACUUU |
| D-041110-02 | NOTCH1 | 18128 | NM_008714 | 1288 | GGAAACAACUGCAAGAAUG |
| D-041110-03 | NOTCH1 | 18128 | NM_008714 | 1289 | GAACCAGGCUACACAGGAA |
| D-041110-04 | NOTCH1 | 18128 | NM_008714 | 1290 | GAAGGUGUAUACUGUGAAA |
| D-045970-01 | Nr3c1 | 14815 | NM_008173 | 1291 | GAUCGAGCCUGAGGUGUUA |
| D-045970-02 | Nr3c1 | 14815 | NM_008173 | 1292 | UUACAAAGAUUGCAGGUAU |
| D-045970-03 | Nr3c1 | 14815 | NM_008173 | 1293 | GCCAAGAGUUAUUUGAUGA |

TABLE S6.2-continued

RNAi sequences

| Duplex Catalog Number | Gene Symbol | GENE ID | Gene Accession | SEQ ID NO: | Sequence |
|---|---|---|---|---|---|
| D-045970-04 | Nr3c1 | 14815 | NM_08173 | 1294 | GCAUGUAUGACCAAUGUAA |
| D-048514-04 | PML | 18854 | NM_08884 | 1295 | GCGCAAGUCCAAUAUCUUC |
| D-048514-03 | PML | 18854 | NM_08884 | 1296 | AGUGGUACCUCAAGCAUGA |
| D-048514-02 | PML | 18854 | NM_008884 | 1297 | GCGCAGACAUUGAGAAGCA |
| D-048514-01 | PML | 18854 | NM_008884 | 1298 | CAGCAUAUCUACUCCUUUA |
| D-048879-01 | POU2AF1 | 18985 | NM_011136 | 1299 | GAAGAAAGCGUGGCCAUAC |
| D-048879-02 | POU2AF1 | 18985 | NM_011136 | 1300 | CGGAGUAUGUGUCCCAUGA |
| D-048879-03 | POU2AF1 | 18985 | NM_011136 | 1301 | UCACUAAUGUCACGCCAAG |
| D-048879-04 | P0U2AF1 | 18985 | NM_011136 | 1302 | GCAACACGUACGAGCUCAA |
| D-043069-09 | Prdm1 | 12142 | NM_007548 | 1303 | GGAGAGACCCACCUACAUA |
| D-043069-10 | Prdm1 | 12142 | NM_007548 | 1304 | GCAAUACAGUAGUGAGAAA |
| D-043069-11 | Prdm1 | 12142 | NM_007548 | 1305 | GGAAGGACAUCUACCGUUC |
| D-043069-21 | Prdm1 | 12142 | NM_007548 | 1306 | GUACAUACAUAGUGAACGA |
| D-042664-04 | PROCR | 19124 | NM_011171 | 1307 | UAUCUGACCCAGUUCGAAA |
| D-042664-03 | PROCR | 19124 | NM_011171 | 1308 | UAACUCCGAUGGCUCCCAA |
| D-042664-02 | PROCR | 19124 | NM_011171 | 1309 | GUAAGUUUCCGGCCAAAGA |
| D-042664-01 | PROCR | 19124 | NM_011171 | 1310 | CCAAACAGGUCGCUCUUAC |
| D-042742-01 | Rbpj | 19664 | NM_001080928 | 1311 | CCAAACGACUCACUAGGGA |
| D-042742-02 | Rbpj | 19664 | NM_001080928 | 1312 | UCUCAACCCUGUGCGUUUA |
| D-042742-03 | Rbpj | 19664 | NM_001080928 | 1313 | GCAGACGGCAUUACUGGAU |
| D-042742-04 | Rbpj | 19664 | NM_001080928 | 1314 | GUAGAAGCCGAAACAAUGU |
| D-040776-01 | Rela | 19697 | NM_009045 | 1315 | GGAGUACCCUGAAGCUAUA |
| D-040776-02 | Rela | 19697 | NM_009045 | 1316 | GAAGAAGAGUCCUUUCAAU |
| D-040776-03 | Rela | 19697 | NM_009045 | 1317 | UAUGAGACCUUCAAGAGUA |

TABLE S6.2-continued

| RNAi sequences | | | | | |
|---|---|---|---|---|---|
| Duplex Catalog Number | Gene Symbol | GENE ID | Gene Accession | SEQ ID NO: | Sequence |
| D-040776-04 | Rela | 19697 | NM_009045 | 1318 | GAAUCCAGACCAACAAUAA |
| D-042209-01 | Rorc | 19885 | NM_011281 | 1319 | UGAGUAUAGUCCAGAACGA |
| D-042209-02 | Rorc | 19885 | NM_011281 | 1320 | CAAUGGAAGUCGUCCUAGU |
| D-042209-03 | Rorc | 19885 | NM_011281 | 1321 | GAGUGGAACAUCUGCAAUA |
| D-042209-04 | Rorc | 19885 | NM_011281 | 1322 | GCUCAUCAGCUCCAUAUUU |
| D-048982-01 | RUNX1 | 12394 | NM_001111022 | 1323 | UGACCACCCUGGCGAGCUA |
| D-048982-02 | RUNX1 | 12394 | NM_001111022 | 1324 | GCAACUCGCCCACCAACAU |
| D-048982-03 | RUNX1 | 12394 | NM_001111022 | 1325 | GAGCUUCACUCUGACCAUC |
| D-048982-04 | RUNX1 | 12394 | NM_001111022 | 1326 | ACAAAUCCGCCACAAGUUG |
| D-045547-01 | Satb1 | 20230 | NM_009122 | 1327 | CAAAGGAUAUGAUGGUUGA |
| D-045547-02 | Satb1 | 20230 | NM_009122 | 1328 | GAAACGAGCCGGAAUCUCA |
| D-045547-03 | Satb1 | 20230 | NM_009122 | 1329 | GAAGGGAGCACAGACGUUA |
| D-045547-04 | Satb1 | 20230 | NM_009122 | 1330 | GCACGCGGAAUUUGUAUUG |
| D-042265-01 | SKI | 20481 | NM_011385 | 1331 | GACCAUCUCUUGUUUCGUG |
| D-042265-02 | SKI | 20481 | NM_011385 | 1332 | GGAAAGAGAUUGAGCGGCU |
| D-042265-03 | SKI | 20481 | NM_011385 | 1333 | GCUGGUUCCUCCAAUAAGA |
| D-042265-04 | SKI | 20481 | NM_011385 | 1334 | UGAAGGAGAAGUUCGACUA |
| D-040687-04 | SMAD4 | 17128 | NM_008540 | 1335 | GAAGGACUGUUGCAGAUAG |
| D-040687-03 | SMAD4 | 17128 | NM_008540 | 1336 | GCAAAGGAGUGCAGUUGGA |
| D-040687-02 | SMAD4 | 17128 | NM_008540 | 1337 | GAAGUAGGACUGCACCAUA |
| D-040687-01 | SMAD4 | 17128 | NM_008540 | 1338 | AAAGAGCAAUUGAGAGUUU |
| D-041135-01 | Smarca4 | 20586 | NM_011417 | 1339 | GGUCAACGGUGUCCUCAAA |
| D-041135-02 | Smarca4 | 20586 | NM_011417 | 1340 | GAUAAUGGCCUACAAGAUG |
| D-041135-03 | Smarca4 | 20586 | NM_011417 | 1341 | GAGCGAAUGCGGAGGCUUA |
| D-041135-04 | Smarca4 | 20586 | NM_011417 | 1342 | CAACGGGCCUUUCCUCAUC |

TABLE S6.2-continued

| RNAi sequences | | | | | |
|---|---|---|---|---|---|
| Duplex Catalog Number | Gene Symbol | GENE ID | Gene Accession | SEQ ID NO: | Sequence |
| D-051590-01 | SMOX | 228608 | NM_145533 | 1343 | GCACAGAGAUGCUUCGACA |
| D-051590-02 | SMOX | 228608 | NM_145533 | 1344 | CCACGGGAAUCCUAUCUAU |
| D-051590-03 | SMOX | 228608 | NM_145533 | 1345 | AGAAUGGCGUGGCCUGCUA |
| D-051590-04 | SMOX | 228608 | NM_145533 | 1346 | UGAGGAAUUCAGCGAUUUA |
| D-043282-01 | Sp4 | 20688 | NM_009239 | 1347 | GGACAACAGCAGAUUAUUA |
| D-043282-02 | Sp4 | 20688 | NM_009239 | 1348 | GACAAUAGGUGCUGUUAGU |
| D-043282-03 | Sp4 | 20688 | NM_009239 | 1349 | AAUUAGACCUGGCGUUUCA |
| D-043282-04 | Sp4 | 20688 | NM_009239 | 1350 | GGAGUUCCAGUAACAAUCA |
| D-061490-01 | Tgif1 | 21815 | NM_009372 | 1351 | GCAAAUAGCACCCAGCAAC |
| D-061490-02 | Tgif1 | 21815 | NM_009372 | 1352 | CAAACGAGCGGCAGAGAUG |
| D-061490-03 | Tgif1 | 21815 | NM_009372 | 1353 | UCAGUGAUCUGCCAUACCA |
| D-061490-04 | Tgif1 | 21815 | NM_009372 | 1354 | GCCAAGAUUUCAGAAGCUA |
| D-047483-04 | TRIM24 | 21848 | NM_145076 | 1355 | AAACUGACCUGUCGAGACU |
| D-047483-03 | TRIM24 | 21848 | NM_145076 | 1356 | CCAAUACGUUCACCUAGUG |
| D-047483-02 | TRIM24 | 21848 | NM_145076 | 1357 | GAUCAGCCUAGCUCAGUUA |
| D-047483-01 | TRIM24 | 21848 | NM_145076 | 1358 | GCAAGCGGCUGAUUACAUA |
| D-065500-01 | TRPS1 | 83925 | NM_032000 | 1359 | GCAAAUGGCGGAUAUGUAU |
| D-065500-02 | TRPS1 | 83925 | NM_032000 | 1360 | GCGAGCAGAUUAUUAGAAG |
| D-065500-03 | TRPS1 | 83925 | NM_032000 | 1361 | CUACGGUUCUGGAGUAAAU |
| D-065500-04 | TRPS1 | 83925 | NM_032000 | 1362 | GAAGUUCGAGAGUCAAACA |
| D-055209-02 | Tsc22d3 | 14605 | NM_010286 | 1363 | GUGAGCUGCUUGAGAAGAA |
| D-055209-17 | Tsc22d3 | 14605 | NM_010286 | 1364 | CUGUACGACUCCAGGAUUU |
| D-055209-18 | Tsc22d3 | 14605 | NM_010286 | 1365 | CUAUAUAGCCAUAAUGCGU |
| D-055209-19 | Tsc22d3 | 14605 | NM_010286 | 1366 | CAGUGAGCCUGUCGUGUCA |

TABLE S6.2-continued

RNAi sequences

| Duplex Catalog Number | Gene Symbol | GENE ID | Gene Accession | SEQ ID NO: | Sequence |
|---|---|---|---|---|---|
| D-060426-04 | UBE2B | 22210 | NM_009458 | 1367 | CAGAAUCGAUGGAGUCCCA |
| D-060426-03 | UBE2B | 22210 | NM_009458 | 1368 | GAUGGUAGCAUAUGUUUAG |
| D-060426-02 | UBE2B | 22210 | NM_009458 | 1369 | GGAAUGCAGUUAUAUUUGG |
| D-060426-01 | UBE2B | 22210 | NM_009458 | 1370 | GAAGAGAGUUUCGGCCAUU |
| D-047149-02 | VAX2 | 24113 | NM_011912 | 1371 | GGACUUGCCUGCUGGCUAC |
| D-047149-03 | VAX2 | 24113 | NM_011912 | 1372 | UGACACAGGUAGCGCGAGU |
| D-047149-04 | VAX2 | 24113 | NM_011912 | 1373 | CUACAGCAGACUAGAACAA |
| D-047149-17 | VAX2 | 24113 | NM_011912 | 1374 | GCACUGAGUUGGCCCGACA |
| D-040825-04 | XBP1 | 22433 | NM_013842 | 1375 | UCUCAAACCUGCUUUCAUC |
| D-040825-03 | XBP1 | 22433 | NM_013842 | 1376 | GAGUCAAACUAACGUGGUA |
| D-040825-02 | XBP1 | 22433 | NM_013842 | 1377 | GGAUCACCCUGAAUUCAUU |
| D-040825-01 | XBP1 | 22433 | NM_013842 | 1378 | UGACAUGUCUUCUCCACUU |
| D-051513-01 | Zeb1 | 21417 | NM_011546 | 1379 | GAACCCAGCUUGAACGUCA |
| D-051513-02 | Zeb1 | 21417 | NM_011546 | 1380 | GAAAGAGCACUUACGGAUU |
| D-051513-03 | Zeb1 | 21417 | NM_011546 | 1381 | GGUUUGGUAUCUCCCAUAA |
| D-051513-04 | Zeb1 | 21417 | NM_011546 | 1382 | GAAGUGUAUUAGCUUGAUG |
| D-058937-01 | ZFP161 | 22666 | NM_009547 | 1383 | CCUCCGCUCUGACAUAUUU |
| D-058937-02 | ZFP161 | 22666 | NM_009547 | 1384 | GAUUCUCGGUAUCCGGUUU |
| D-058937-03 | ZFP161 | 22666 | NM_009547 | 1385 | CCGCCAAGAUUUCCGUGAA |
| D-058937-04 | ZFP161 | 22666 | NM_009547 | 1386 | AAAGACCAUUUGCGUGUCA |
| D-057818-01 | ZFP281 | 226442 | NM_177643 | 1387 | GCACCACCGCGAUGUAUUA |
| D-057818-02 | ZFP281 | 226442 | NM_177643 | 1388 | GAACAACGUACCAGAUUGA |
| D-057818-03 | ZFP281 | 226442 | NM_177643 | 1389 | AAGCAAGGCCCGAUAAGUA |
| D-057818-04 | ZFP281 | 226442 | NM_177643 | 1390 | GAUCAGUACUCUGGCAAAU |
| D-041703-01 | ZFP36L1 | 12192 | NM_007564 | 1391 | UCAAGACGCCUGCCCAUUU |

TABLE S6.2-continued

| RNAi sequences | | | | | |
|---|---|---|---|---|---|
| Duplex Catalog Number | Gene Symbol | GENE ID | Gene Accession | SEQ ID NO: | Sequence |
| D-041703-02 | ZFP36L1 | 12192 | NM_007564 | 1392 | UCAGCAGCCUUAAGGGUGA |
| D-041703-03 | ZFP36L1 | 12192 | NM_007564 | 1393 | GGAGCUGGCGAGCCUCUUU |
| D-041703-04 | ZFP36L1 | 12192 | NM_007564 | 1394 | CGAAUCCCCUCACAUGUUU |

Example 2

A Transcriptional Time Course of Th17 Differentiation

Figure 1C:
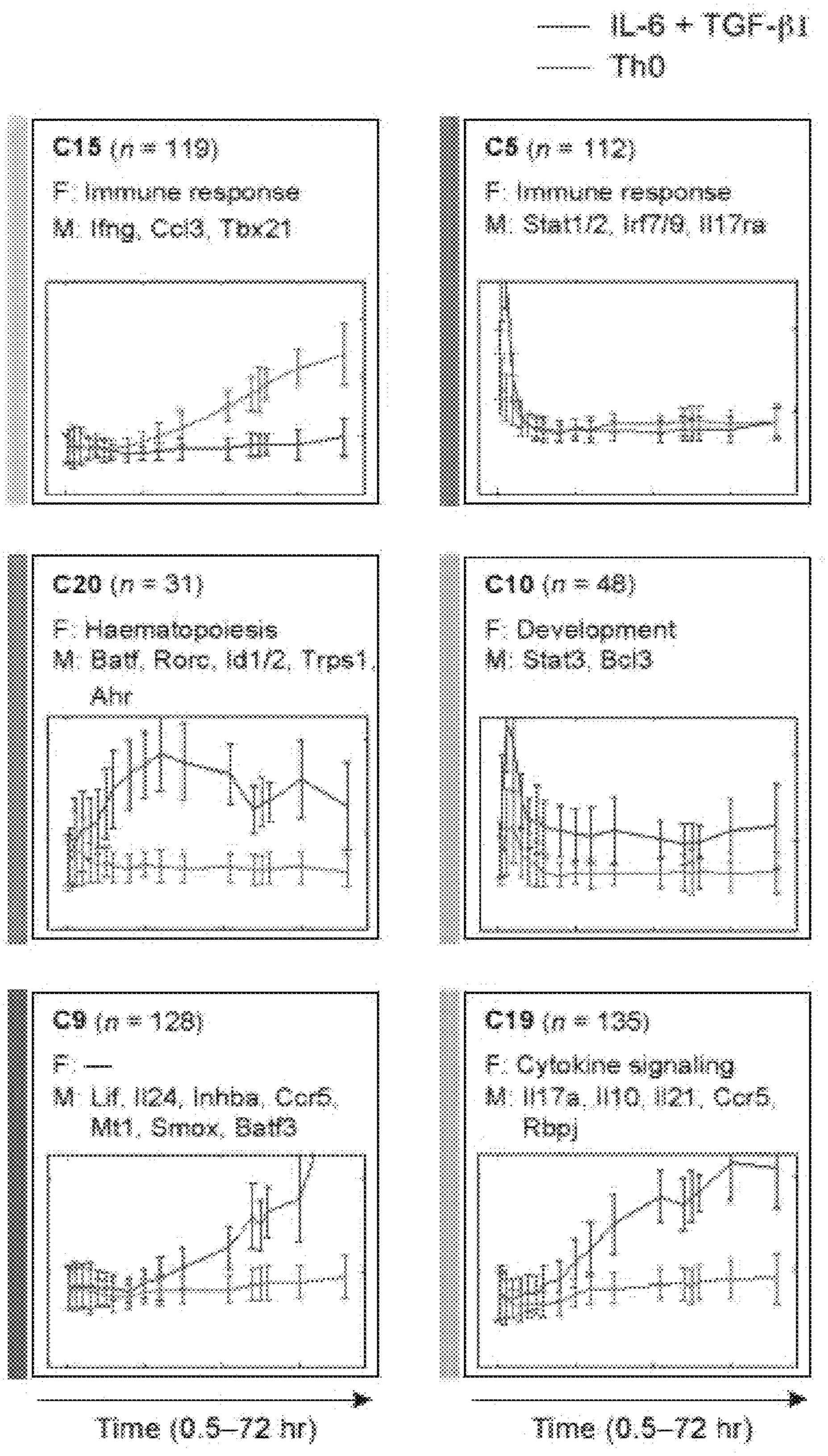
Figure 1D:
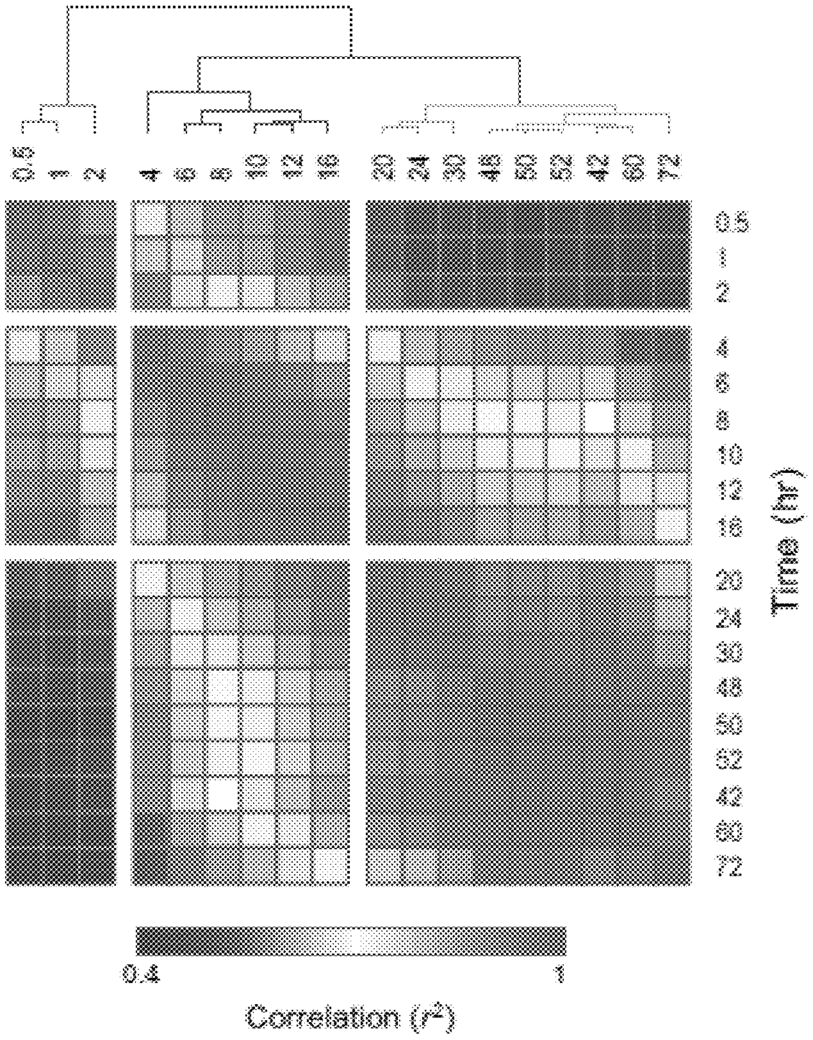
Figure 1E:
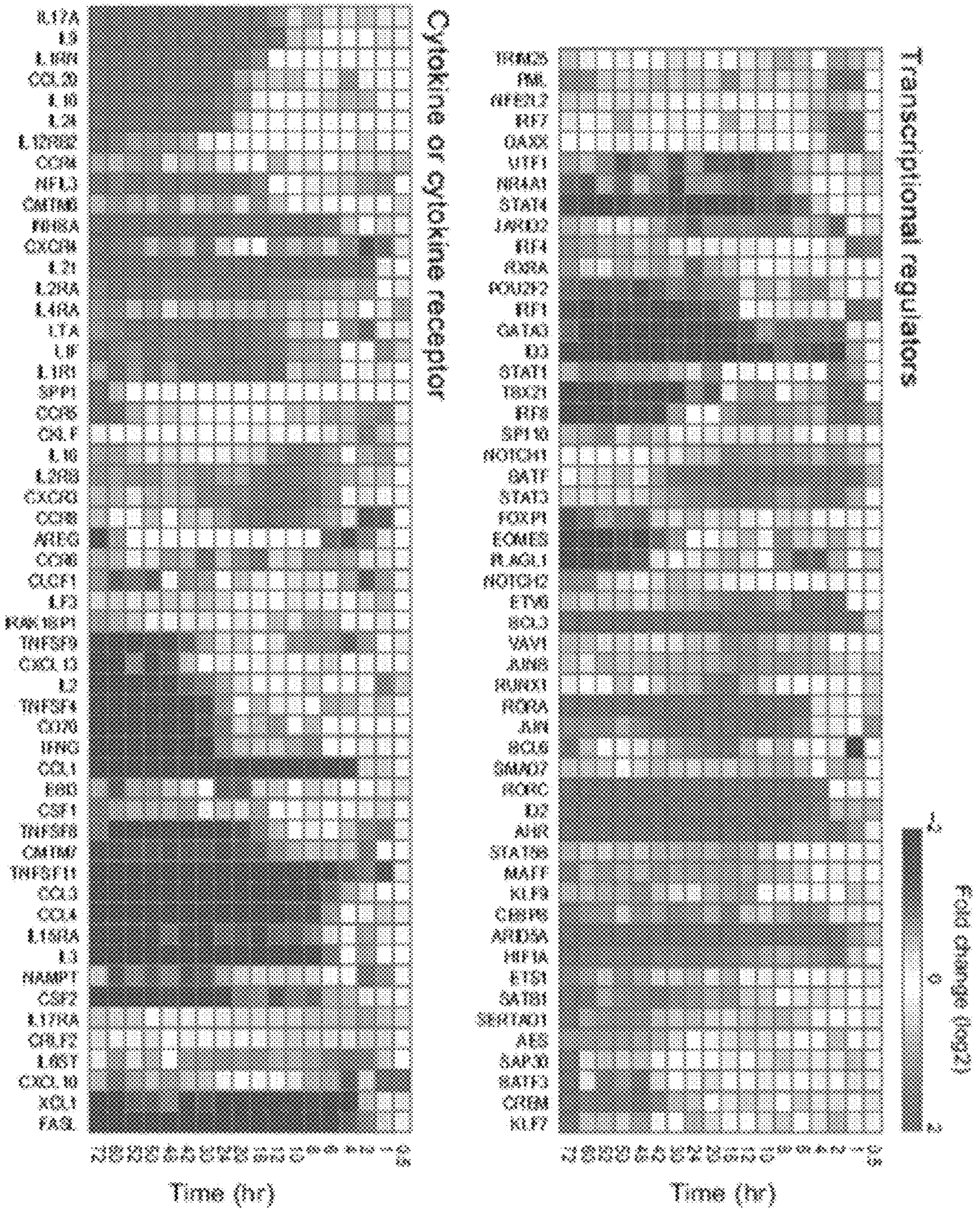
Figure 2A:
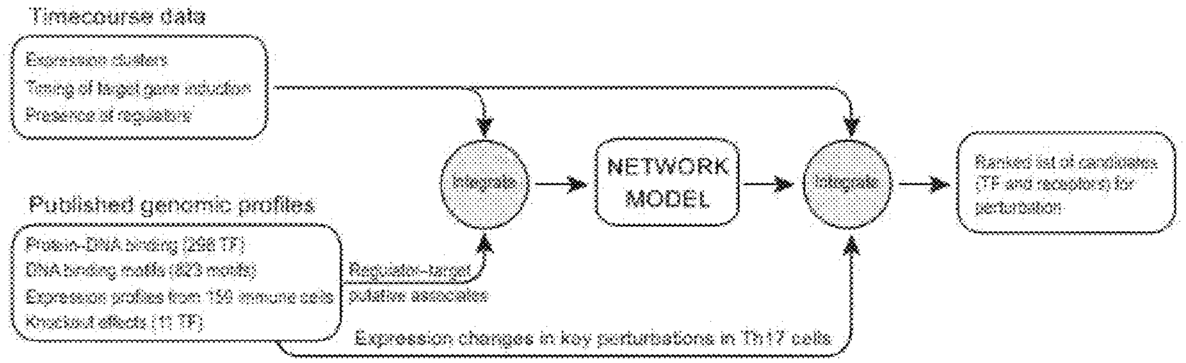
FIGS. 2A-2G are a series of graphs and illustrations depicting a model of the dynamic regulatory network of Th17 differentiation.
Figure 7:
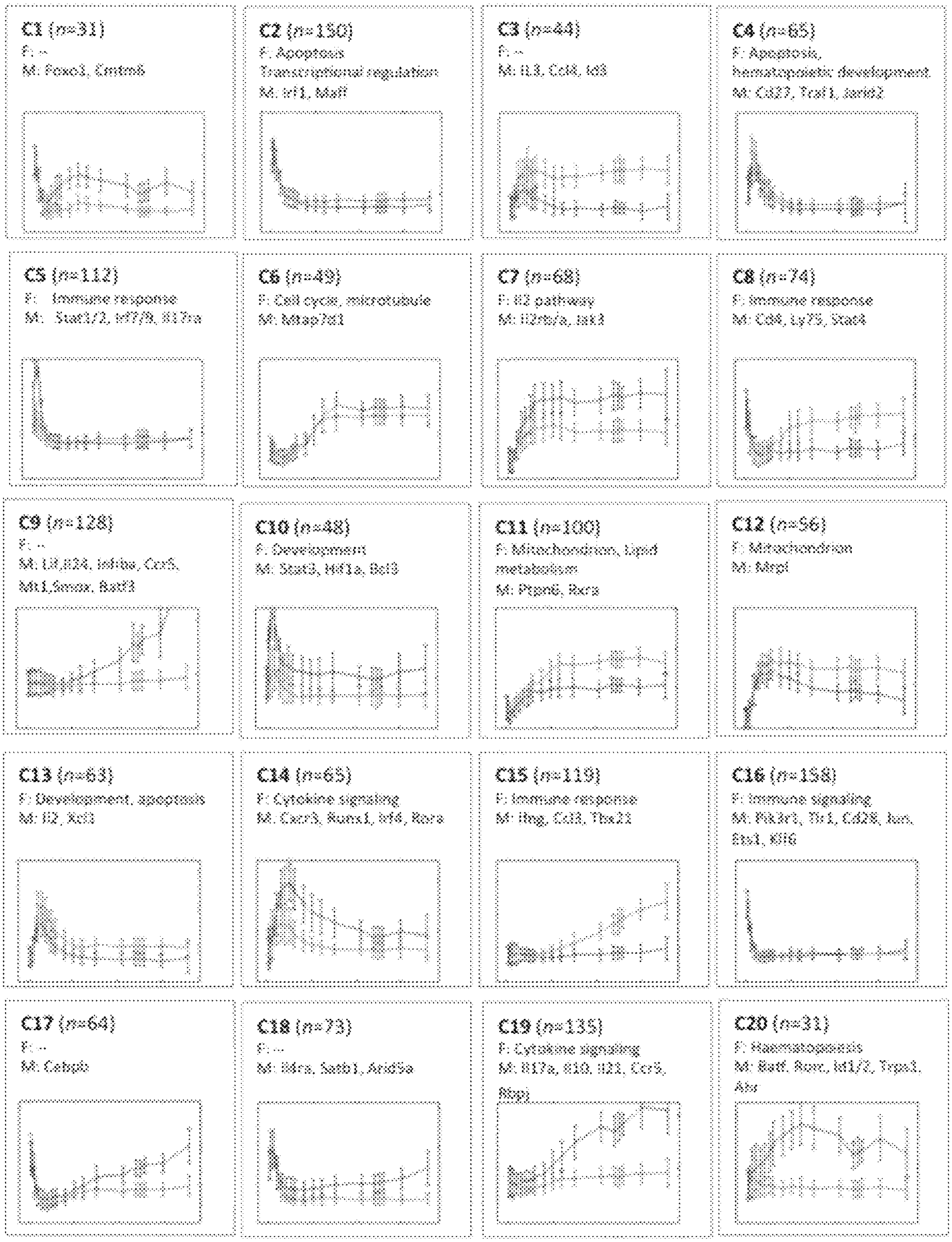
FIG. 7 is a series of graphs depicting clusters of differentially expressed genes in the Th17 time course data. A color version of these figures can be found in Yosef et al., "Dynamic regulatory network controlling Th17 cell differentiation, Nature, vol. 496: 461-468 (2013)/doi: 10.1038/nature11981. For each of the 20 clusters in FIG. 1*b* shown are the average expression levels (Y axis, ±standard deviation, error bars) at each time point (X axis) under Th17 polarizing (blue) and Th0 (red) conditions. The cluster size ("n"), enriched functional annotations ("F"), and representative member genes ("M") are denoted on top.

The differentiation of naïve CD4+ T-cells into Th17 cells was induced using TGF-β1 and IL-6, and measured transcriptional profiles using microarrays at eighteen time points along a 72 hr time course during the differentiation of naïve CD4+ T-cells into Th17 cells, induced by a combination of the anti-inflammatory cytokine TGF-β1 and the proinflammatory cytokine IL-6 (FIG. 1, FIG. 6A, FIG. 6B and FIG. 6C, see Methods in Example 1). As controls, mRNA profiles were measured for cells that were activated without the addition of differentiating cytokines (Th0). 1,291 genes that were differentially expressed specifically during Th17 differentiation were identified by comparing the Th17 differentiating cells to the control cells (see Methods in Example 1) and partitioned into 20 co-expression clusters (k-means clustering, see Methods in Example 1, FIG. 1*b* and FIG. 7) that displayed distinct temporal profiles. These clusters were used to characterize the response and reconstruct a regulatory network model, as described below (FIG. 2*a*).

Three main waves of transcription and differentiation: There are three transcriptional phases as the cells transition from a naïve-like state (t=0.5 hr) to Th17 (t=72 hr; FIG. 1*c* and FIG. 6*c*): early (up to 4 hr), intermediate (4-20 hr), and late (20-72 hr). Each corresponds, respectively, to a differentiation phase (Korn et al., Annu Rev Immunol 2009): (1) induction, (2) onset of phenotype and amplification, and (3) stabilization and IL-23 signaling.

The early phase is characterized by transient induction (e.g., Cluster C5, FIG. 1*b*) of immune response pathways (e.g., IL-6 and TGF-β signaling; FIG. 1*d*). The first transition point (t=4 hr) is marked by a significant increase in the expression level of ROR-γt, which is not detectable at earlier time points. The second transition (t=20 hr) is accompanied by significant changes in cytokine expression, with induction of Th17 signature cytokines (e.g., IL-17) that strengthen the Th17 phenotype and a concomitant decrease in other cytokines (e.g., IFN-γ) that belong to other T cell lineages.

Some early induced genes display sustained expression (e.g., Cluster C10, FIG. 1*b*); these are enriched for transcription regulators (TRs) also referred to herein as transcription factors (TFs), including the key Th17 factors Stat3, Irf4 and Batf, and the cytokine and receptor molecules IL-21, Lif, and Il2ra.

Figure 6D:
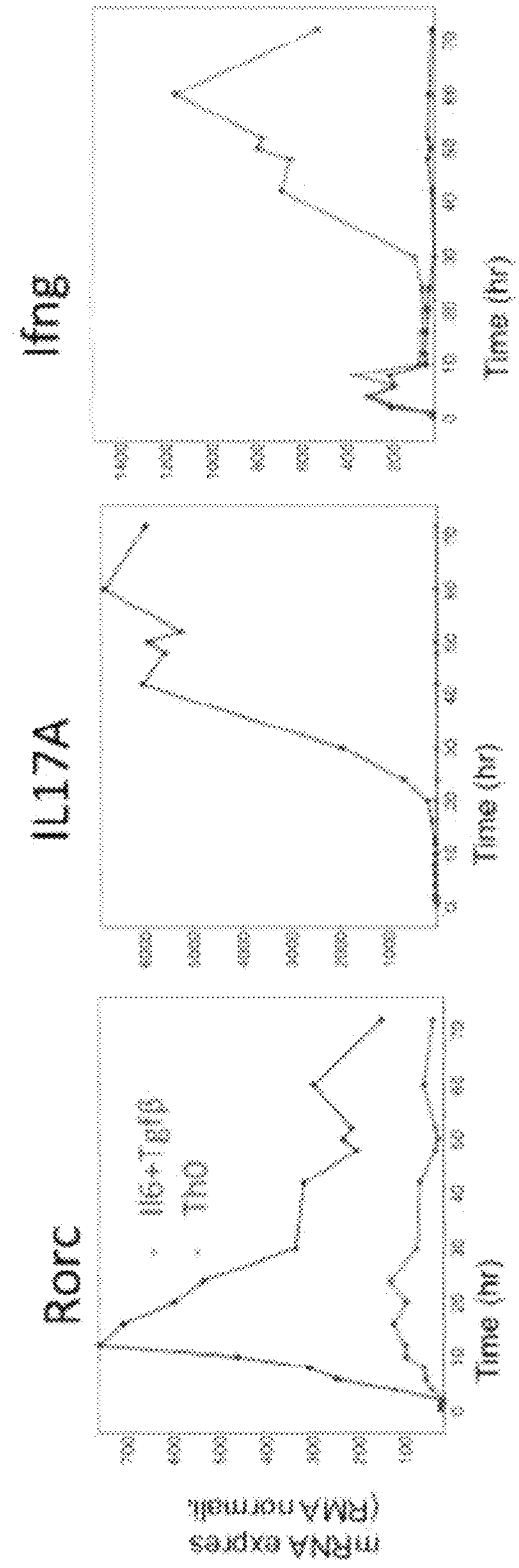

The transition to the intermediate phase (t=4 hr) is marked by induction of ROR-γt (master TF; FIG. 6*d*) and another 12 TFs (Cluster C20, FIG. 1*b*), both known (e.g., Ahr) and novel (e.g., Trps1) to Th17 differentiation. At the 4 hr time point, the expression of ROR-γt, the master TF of Th17 differentiation, significantly increases (FIG. 6*d*)—marking the beginning of the accumulation of differentiation phenotypes ('intermediate phase')—and remains elevated throughout the rest of the time course. Another 12 factors show a similar pattern (Cluster 8 C20, FIG. 1*b*). These include Ahr and Rbpj, as well as a number of factors (e.g., Etv6 and Trps1) not described previously as having roles in Th17 differentiation. Overall, the 585 genes that are induced between 4 and 20 hrs are differentially expressed and substantially distinct from the early response genes (FIG. 1*b*; e.g., clusters C20, C14, and C1).

Figure 8A:
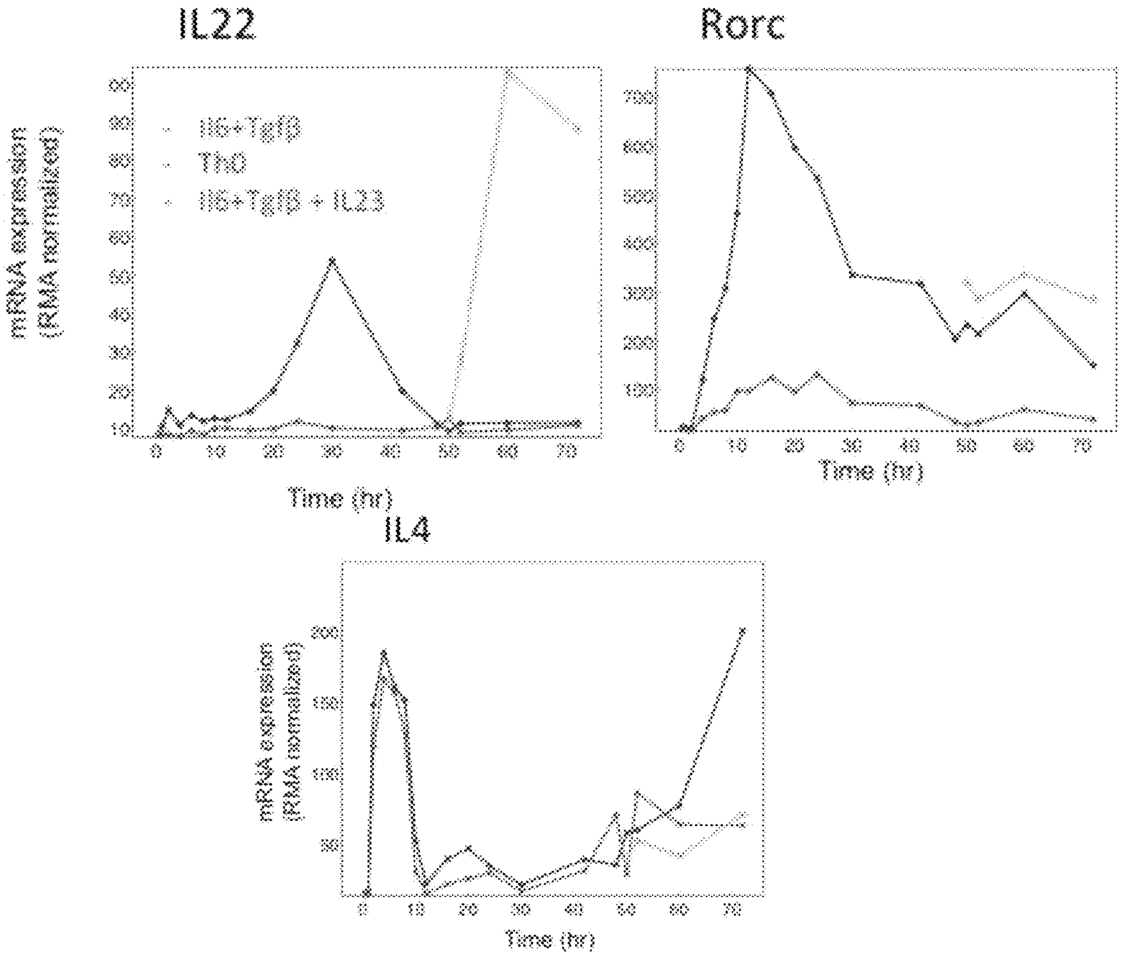
FIGS. 8A-8B are a series of graphs depicting transcriptional effects of IL-23.
Figure 8B:
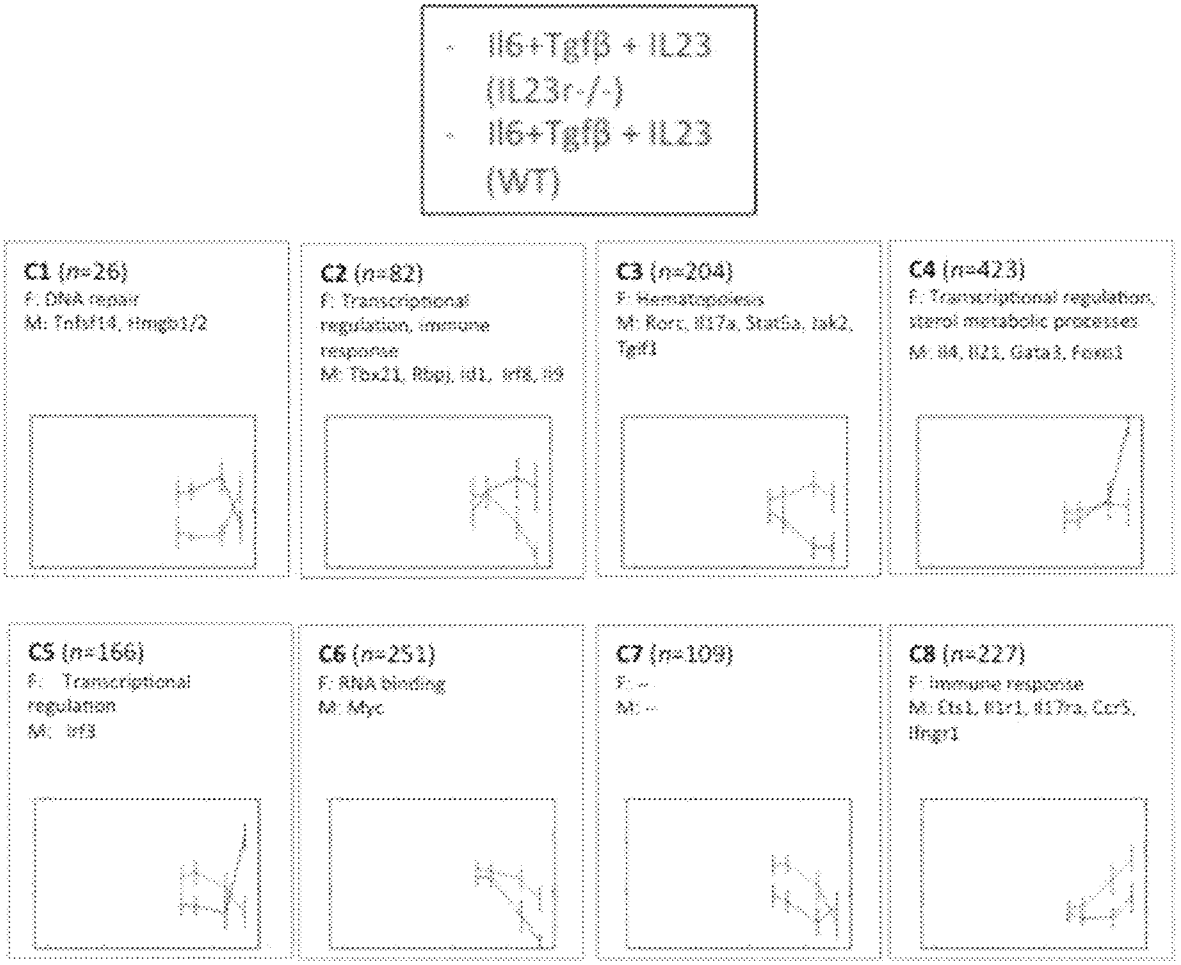

During the transition to the late phase (t=20 hr), mRNAs of Th17 signature cytokines are induced (e.g., IL-17a, IL-9; cluster C19) whereas mRNAs of cytokines that signal other T cell lineages are repressed (e.g., IFN-γ and IL-4). Regulatory cytokines from the IL-10 family are also induced (IL-10, IL-24), possibly as a self-limiting mechanism related to the emergence of 'pathogenic' or 'non-pathogenic' Th17 cells (Lee et al., Induction and Molecular Signature of Pathogenic Th17 Cells, Nature Immunol 13, 991-999; doi: 10.1038/ni.2416). Around 48 hr, the cells induce IL23r (data not shown), which plays an important role in the late phase (FIG. 8A, 8B).

Between 20 and 42 hrs post activation (i.e., starting 16 hrs after the induction of ROR-γt expression), there is a substantial change compared to Th0 in the expression of 821 genes, including many major cytokines (e.g., cluster C19, FIG. 1*b*). The expression of Th17-associated inflammatory cytokines, including IL-17a, IL-24, IL-9 and lymphotoxin alpha LTA (Elyaman, W. et al. Notch receptors and Smad3 signaling cooperate in the induction of interleukin-9-producing T cells. Immunity 36, 623-634, doi:10.1016/j.immuni.2012.01.020 (2012)), is strongly induced (FIG. 1*d*), whereas other cytokines and chemokines are repressed or remain at their low basal level (Clusters C8 and C15, FIG. 1*b* and FIG. 7). These include cytokines that characterize other T-helper cell types, such as IL-2 (Th17 differentiation inhibitor), IL-4 (Th2), and IFN-γ (Th1), and others (Csf1, Tnfsf9/4 and Ccl3). Finally, regulatory cytokines from the IL-10 family are also induced (IL-10, IL-24), possibly as a self-limiting mechanism. Thus, the 20 hr time point might be crucial for the emergence of the proposed 'pathogenic' versus 'nonpathogenic'/regulatory Th17 cells (Lee et al., Nature Immunol 2012).

Most expression changes in the 1,055 genes differentially expressed in the remainder of the time course (>48 hr) are mild, occur in genes that responded during the 20-42 hr period (FIG. 1, e.g., clusters C18, C19, and C20), and typically continue on the same trajectory (up or down). Among the most strongly late-induced genes is the TF Hif1a, previously shown to enhance Th17 development via interaction with ROR-γt (Dang, E. V. et al. Control of T(H)17/T(reg) balance by hypoxia-inducible factor 1. Cell 146, 772-784, doi:10.1016/j.cell.2011.07.033 (2011)). The genes over-expressed at the latest time point (72 hr) are enriched for apoptotic functions ($p<10^{-6}$), consistent with the limited survival of Th17 cells in primary cultures, and include the Th2 cytokine IL-4 (FIG. 8*a*), suggesting that under TGF-β1+IL-6 treatment, the cells might have a less stable phenotype.

The peak of induction of IL-23r mRNA expression occurs at 48 hr and, at this time point one begins to see IL-23r protein on the cell surface (data not shown). The late phase response depends in part on IL-23, as observed when comparing temporal transcriptional profiles between cells stimulated with TGF-β1+IL-6 versus TGF-β1+IL-6+IL-23, or between WT and IL-23r−/− cells treated with TGF-β1+IL-6+IL-23 (FIG. 8). For instance, in IL-23r-deficient Th17 cells, the expression of IL-17ra, IL-1r1, IL-21r, ROR-γt, and Hif1a is decreased, and IL-4 expression is increased. The up-regulated genes in the IL-23r−/− cells are enriched for other CD4+ T cell subsets, suggesting that, in the absence of IL-23 signaling, the cells start to dedifferentiate, thus further supporting the hypothesis that IL-23 may have a role in stabilizing the phenotype of differentiating Th17 cells.

Example 3

Inference of Dynamic Regulatory Interactions

Without wishing to be bound by any one theory, it was hypothesized that each of the clusters (FIG. 1*b*) encompasses genes that share regulators active in the relevant time points. To predict these regulators, a general network of regulator-target associations from published genomics profiles was assembled (Linhart, C., Halperin, Y. & Shamir, R. Transcription factor and microRNA motif discovery: the Amadeus platform and a compendium of metazoan target sets. Genome research 18, 1180-1189, doi:10.1101/gr.076117.108 (2008); Zheng, G. et al. ITFP: an integrated platform of mammalian transcription factors. Bioinformatics 24, 2416-2417, doi:10.1093/bioinformatics/btn439 (2008); Wilson, N. K. et al. Combinatorial transcriptional control in blood stem/progenitor cells: genome-wide analysis of ten major transcriptional regulators. Cell Stem Cell 7, 532-544, doi:10.1016/j.stem.2010.07.016 (2010); Lachmann, A. et al. in Bioinformatics Vol. 26 2438-2444 (2010); Liberzon, A. et al. Molecular signatures database (MSigDB) 3.0. Bioinformatics 27, 1739-1740, doi:10.1093/bioinformatics/btr260 (2011); Jiang, C., Xuan, Z., Zhao, F. & Zhang, M. TRED: a transcriptional regulatory element database, new entries and other development. Nucleic Acids Res 35, D137-140 (2007); Elkon, R., Linhart, C., Sharan, R., Shamir, R. & Shiloh, Y. in Genome Research Vol. 13 773-780 (2003); Heng, T. S. & Painter, M. W. The Immunological Genome Project: networks of gene expression in immune cells. Nat. Immunol. 9, 1091-1094, doi:10.1038/ni1008-1091 (2008)) (FIG. 2*a*, see Methods in Example 1)

The general network of regulator-target associations from published genomics profiles was assembled as follows: in vivo protein-DNA binding profiles for 298 regulators (Linhart, C., Halperin, Y. & Shamir, R. Transcription factor and microRNA motif discovery: the Amadeus platform and a compendium of metazoan target sets. Genome research 18, 1180-1189, doi:10.1101/gr.076117.108 (2008); Zheng, G. et al. ITFP: an integrated platform of mammalian transcription factors. Bioinformatics 24, 2416-2417, doi:10.1093/bioinformatics/btn439 (2008); Wilson, N. K. et al. Combinatorial transcriptional control in blood stem/progenitor cells: genome-wide analysis of ten major transcriptional regulators. Cell Stem Cell 7, 532-544, doi:10.1016/j.stem.2010.07.016 (2010); Lachmann, A. et al. in Bioinformatics Vol. 26 2438-2444 (2010); Liberzon, A. et al. Molecular signatures database (MSigDB) 3.0. Bioinformatics 27, 1739-1740, doi:10.1093/bioinformatics/btr260 (2011); Jiang, C., Xuan, Z., Zhao, F. & Zhang, M. TRED: a transcriptional regulatory element database, new entries and other development. Nucleic Acids Res 35, D137-140 (2007), 825 DNA cis-regulatory elements scored in each gene's promoter (Elkon, R., Linhart, C., Sharan, R., Shamir, R. & Shiloh, Y. Genome-wide in silico identification of transcriptional regulators controlling the cell cycle in human cells. Genome research 13, 773-780, doi:10.1101/gr.947203 (2003)), transcriptional responses to the knockout of 11 regulatory proteins, and regulatory relations inferred from co-expression patterns across 159 immune cell types (Heng, T. S. & Painter, M. W. The Immunological Genome Project: networks of gene expression in immune cells. Nat. Immunol. 9, 1091-1094, doi:10.1038/ni1008-1091 (2008)) (see Methods in Example 1). While most protein-DNA binding profiles were not measured in Th17 cells, DNA-binding profiles in Th17 cells of a number of key TFs, including Irf4 and Batf (Glasmacher, E. et al. A Genomic Regulatory Element That Directs Assembly and Function of Immune-Specific AP-1-IRF Complexes. Science, doi:10.1126/science.1228309 (2012)), Stat3 and Stat5 (Yang, X. P. et al. Opposing regulation of the locus encoding IL-17 through direct, reciprocal actions of STAT3 and STAT5. Nat. Immunol. 12, 247-254, doi:10.1038/ni.1995 (2011)), and Rorc (Xiao et al., unpublished) has been included.

Figure 2B:
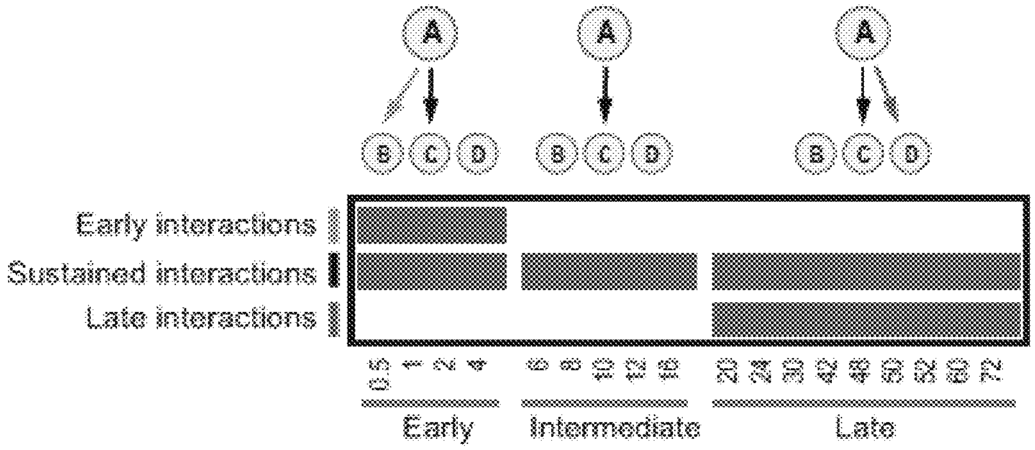
Figure 2C:
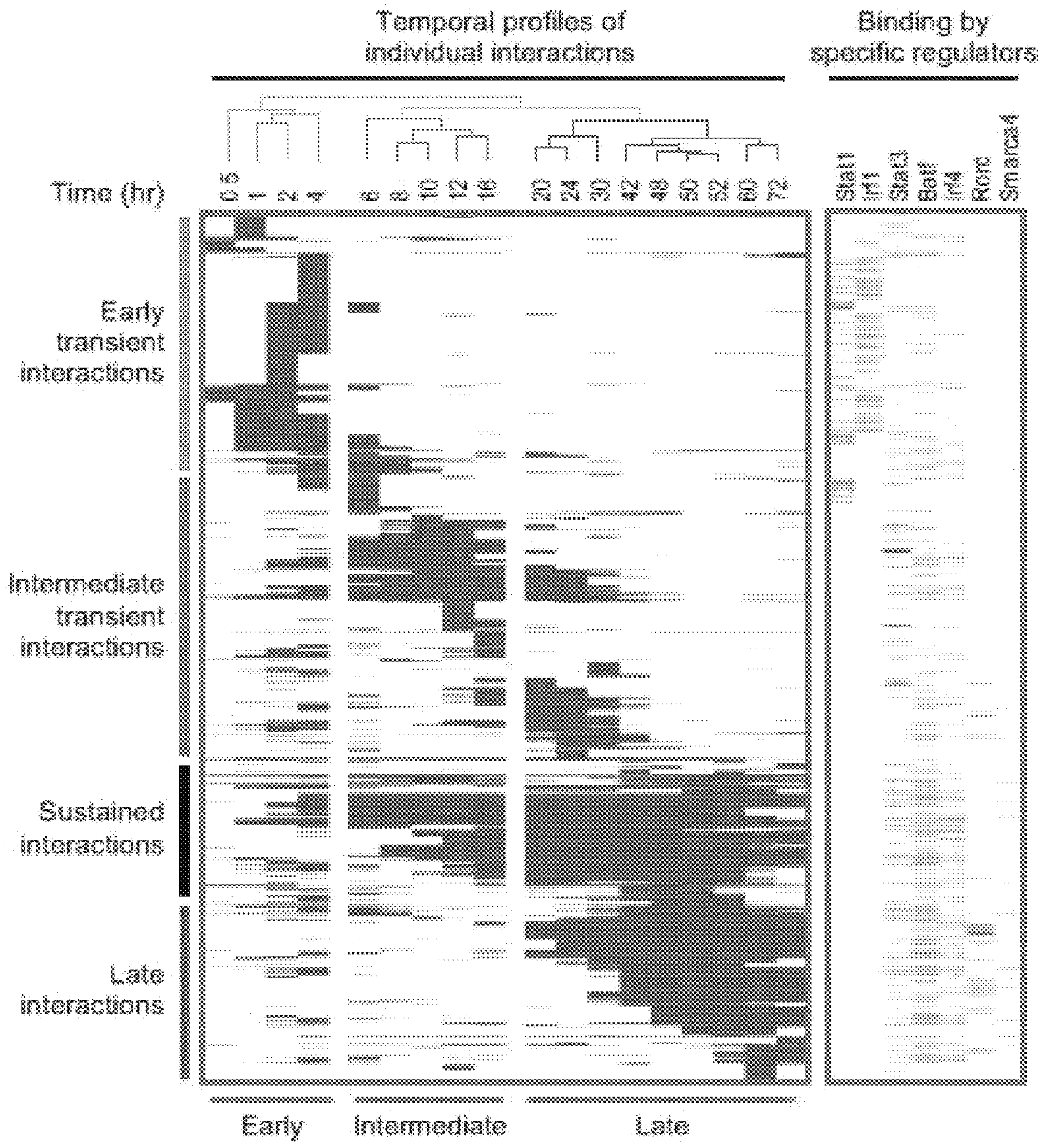
Figure 2D:
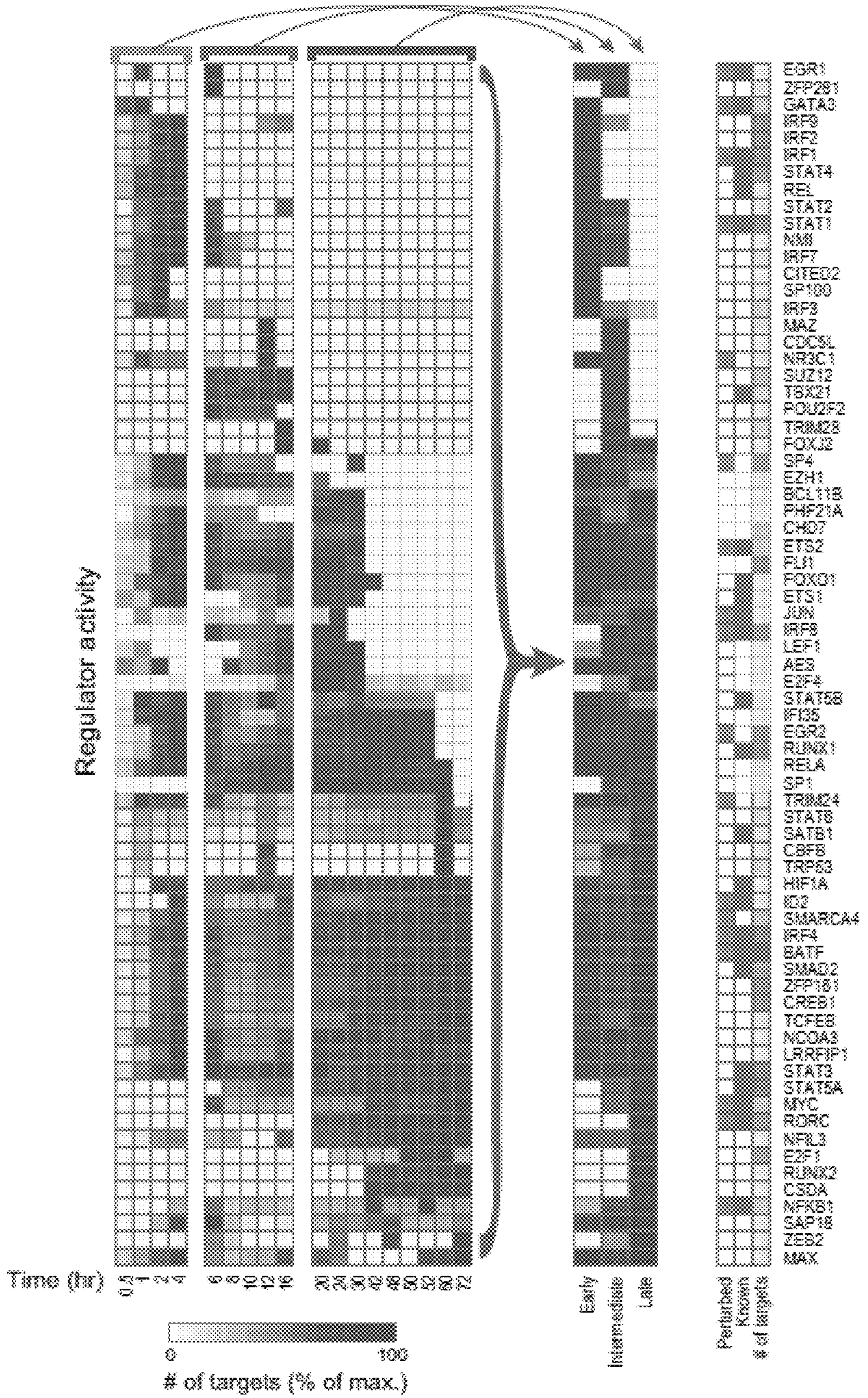

A regulator was then connected to a gene from its set of putative targets only if there was also a significant overlap between the regulator's putative targets and that gene's cluster (see Methods in Example 1). Since different regulators act at different times, the connection between a regulator and its target may be active only within a certain time window. To determine this window, each edge was labeled with a time stamp denoting when both the target gene is regulated (based on its expression profile) and the regulator node is expressed at sufficient levels (based on its mRNA levels and inferred protein levels (Schwanhäusser, B. et al. Global quantification of mammalian gene expression control. Nature 473, 337-342, doi:10.1038/nature10098 (2011)); see Methods in Example 1). For the target gene, the time points in which it is either differentially expressed compared to the Th0 condition or is being induced or repressed compared with preceding time points in the Th17 time course were considered. For the regulator node, only time points where the regulator is sufficiently expressed and not repressed relative to the Th0 condition were included. To this end, the regulator's predicted protein expression level was inferred from its mRNA level using a recently proposed model (Schwanhäusser, B. et al. Global quantification of mammalian gene expression control. Nature 473, 337-342, doi:10.1038/nature10098 (2011)) (see Methods in Example 1). In this way, a network 'snapshot' was derived for each of the 18 time points (FIG. 2*b*-*d*). Overall, 9,159 interactions between 71 regulators and 1,266 genes were inferred in at least one network.

Figure 9A:
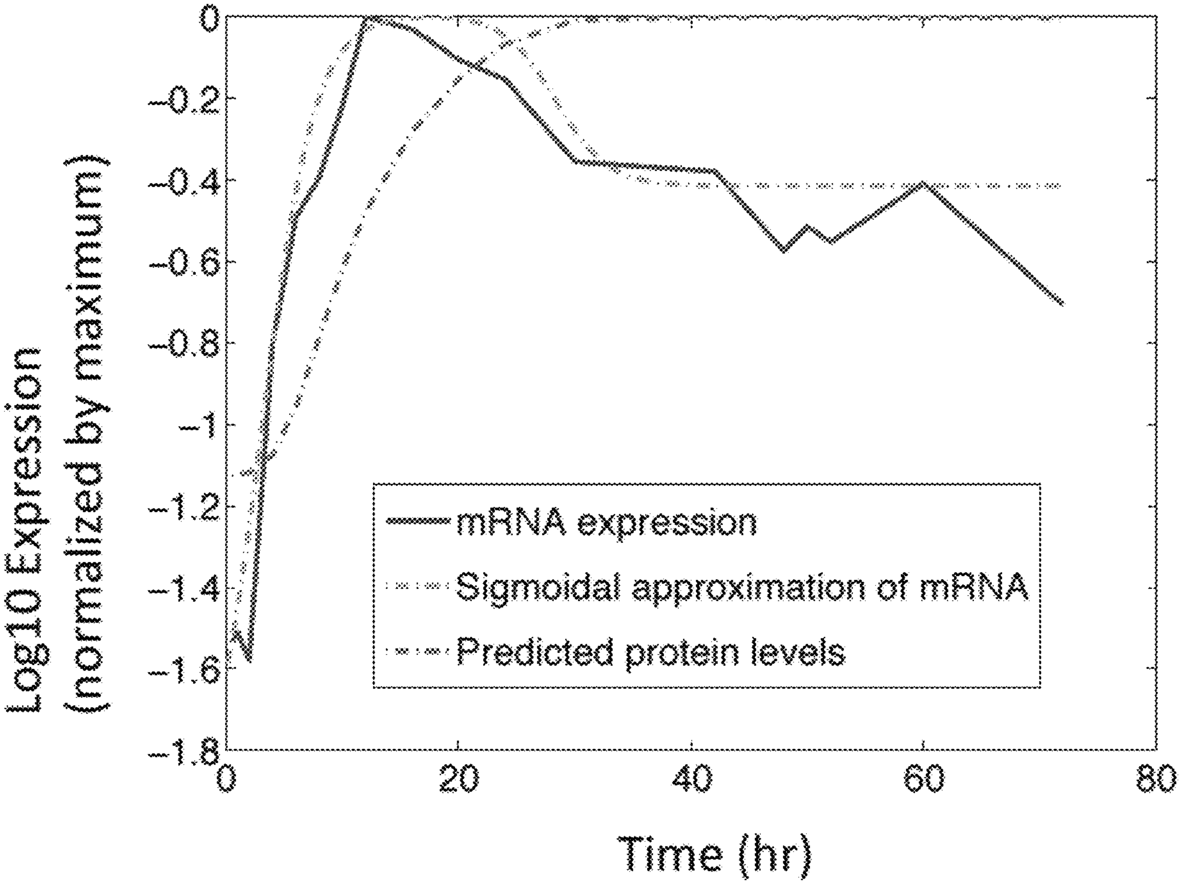
FIGS. 9A-9B are a series of graphs depicting predicted and validated protein levels of ROR-γt during Th17 differentiation. A color version of these figures can be found in Yosef et al., "Dynamic regulatory network controlling Th17 cell differentiation, Nature, vol. 496: 461-468 (2013)/doi: 10.1038/nature11981.
Figure 9B:
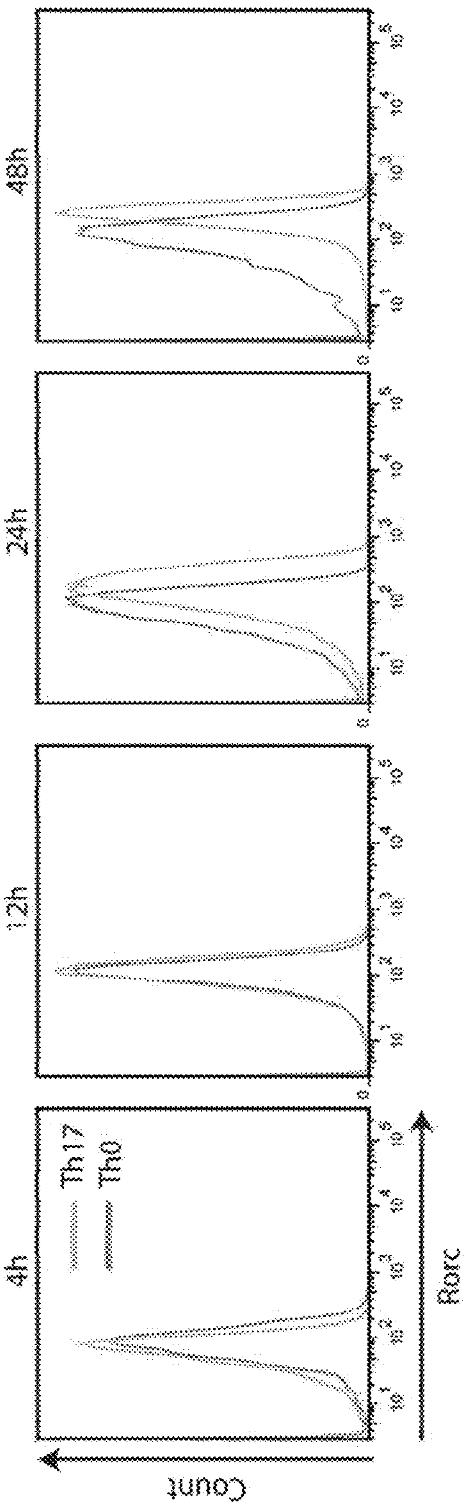

Substantial regulatory re-wiring during differentiation: The active factors and interactions change from one network to the next. The vast majority of interactions are active only at some time window (FIG. 2*c*), even for regulators (e.g., Batf) that participate in all networks. Based on similarity in active interactions, three network classes were identified (FIG. 2*c*), corresponding to the three differentiation phases (FIG. 2*d*). All networks in each phase were collapsed into one model, resulting in three consecutive network models (FIG. 9A, 9B). Among the regulators, 33 are active in all of the networks (e.g. many known master regulators such as Batf1, Irf4, and Stat3), whereas 18 are active in only one (e.g. Stat1 and Irf1 in the early network; ROR-γt in the late network). Indeed, while ROR-γt mRNA levels are induced at ~4 h, ROR-γt protein levels increase at approximately 20 h and further rise over time, consistent with the model (FIG. 9).

Figure 2E:
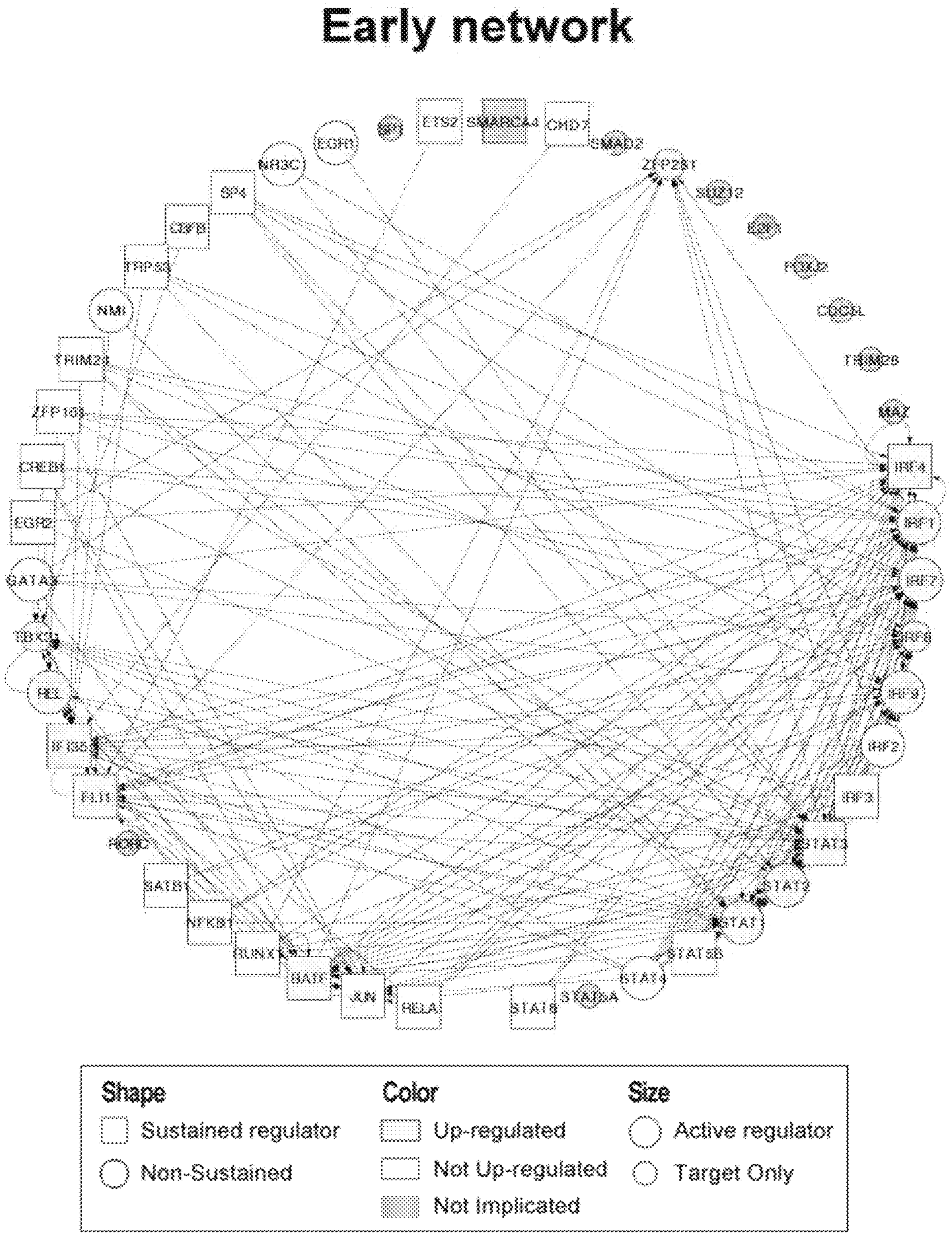
Figure 2F:
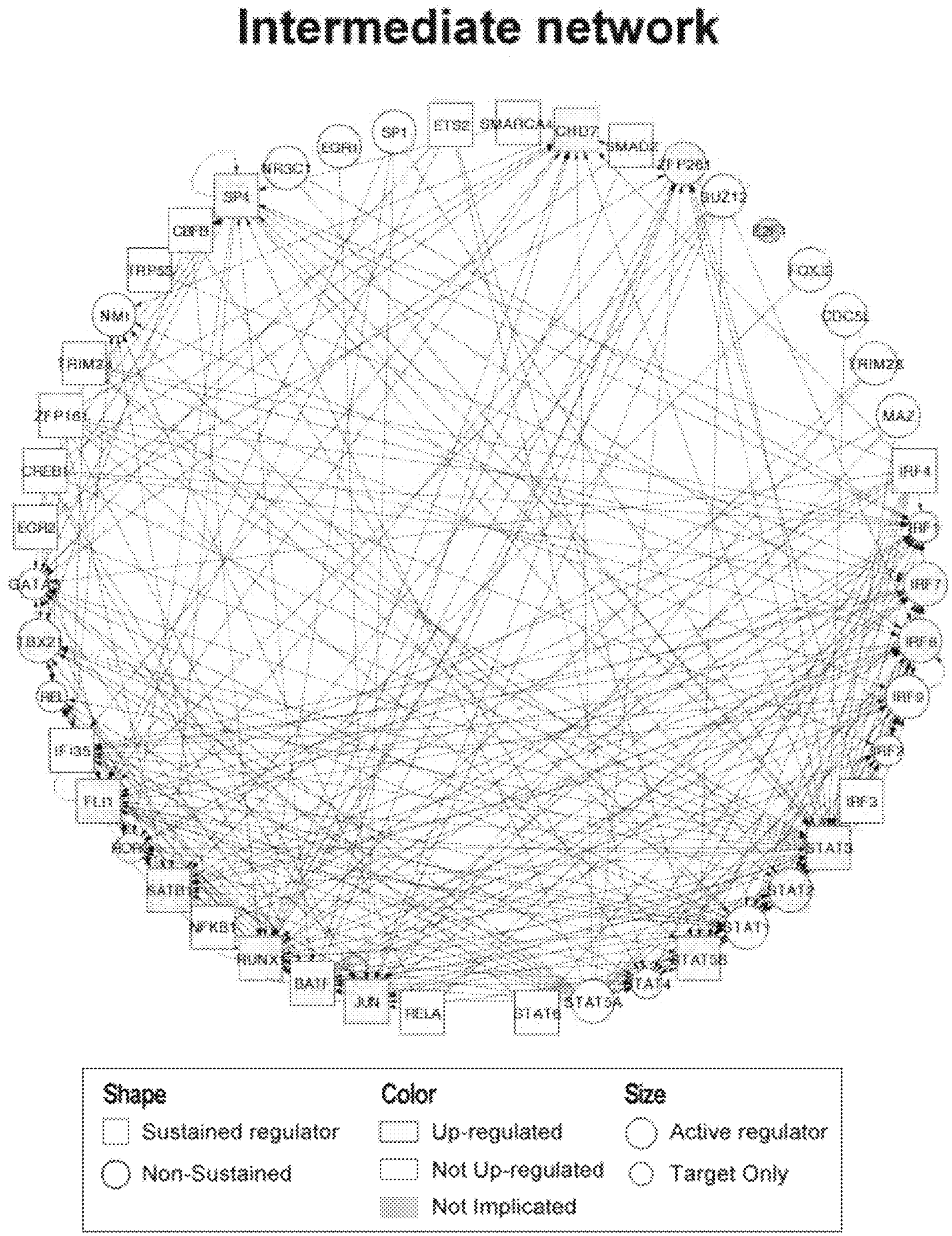
Figure 2G:
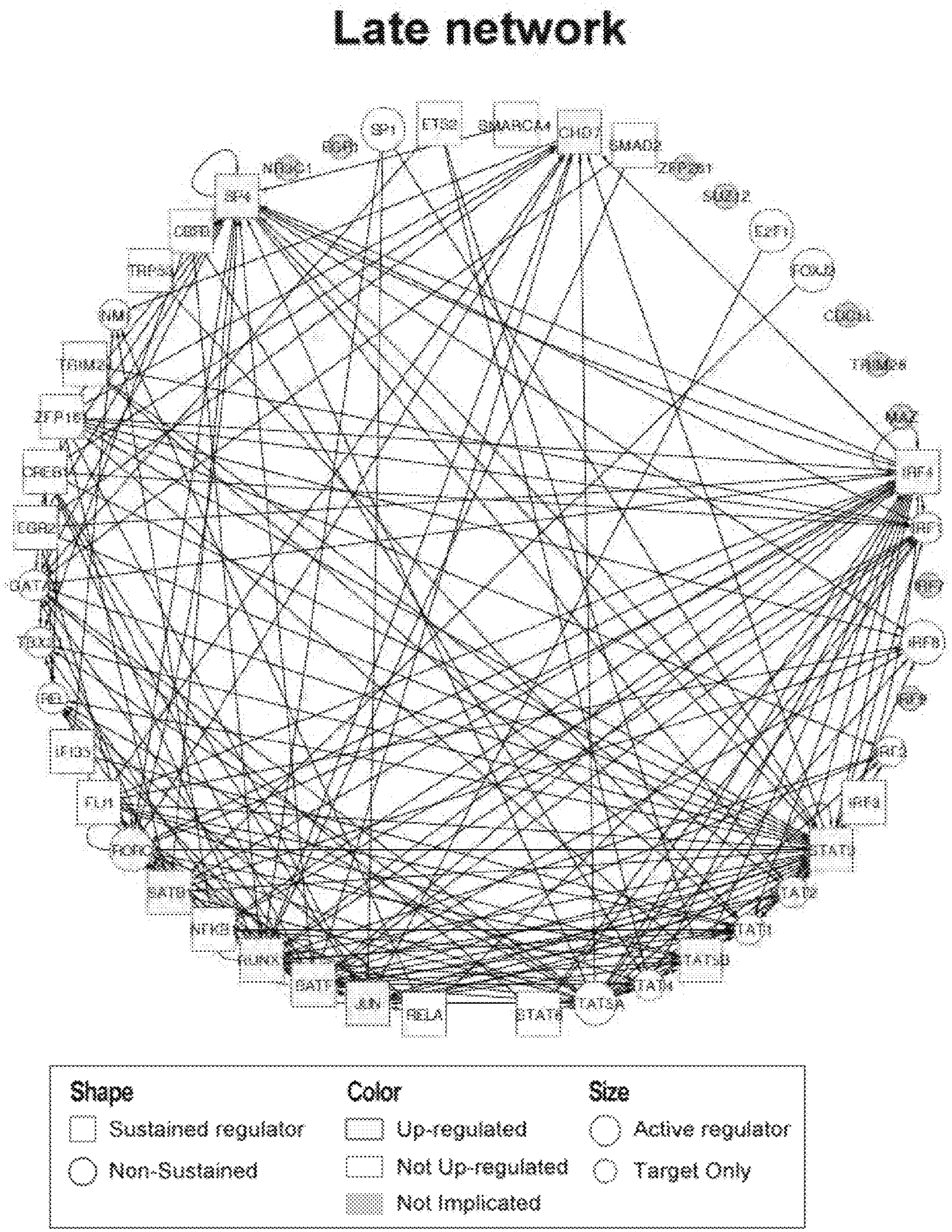

Densely interconnected transcriptional circuits in each network: At the heart of each network is its 'transcriptional circuit', connecting active TFs to target genes that themselves encode TFs. For example, the transcriptional circuit in the early response network connects 48 factors that are predicted to act as regulators to 72 factors whose own transcript is up- or down-regulated during the first four hours (a subset of this model is shown in FIG. 2*e*). The circuit automatically highlights many TFs that were previously implicated in immune signaling and Th17 differentiation, either as positive or negative regulators, including Stat family members, both negative (Stat1, Stat5) and positive (Stat3), the pioneering factor Batf, TFs targeted by TGF-β signaling (Smad2, Runx1, and Irf7), several TFs targeted by TCR signaling (Rel, Nfkb1, and Jun), and several interferon regulatory factors (Irf4 and Irf1), positioned both as regulators and as target genes that are strongly induced. In addition, 34 regulators that were not previously described to have a role in Th17 differentiation were identified (e.g., Sp4, Egr2, and Smarca4). Overall, the circuit is densely intraconnected (Novershtern et al., Cell 2011), with 16 of the 48 regulators themselves transcriptionally controlled (e.g., Stat1, Irf1, Irf4, Batf). This suggests feedback circuitry, some of which may be auto-regulatory (e.g., for Irf4, Stat3 and Stat1).

As in the early network, there is substantial cross-regulation between the 64 TFs in the intermediate and late transcriptional circuits, which include major Th17 regulators such as ROR-γt, Irf4, Batf, Stat3, and Hif1a (FIG. 2*e*).

Ranking novel regulators for systematic perturbation: In addition to known Th17 regulators, the network includes dozens of novel factors as predicted regulators (FIG. 2*d*), induced target genes, or both (FIG. 2E). It also contains receptor genes as induced targets, both previously known in Th17 cells (e.g., IL-1R1, IL-17RA) and novel (e.g., Fas, Itga3). This suggests substantial additional complexity compared to current knowledge, but must be systematically tested to validate the role and characterize the function of each candidate.

Figure 3A:
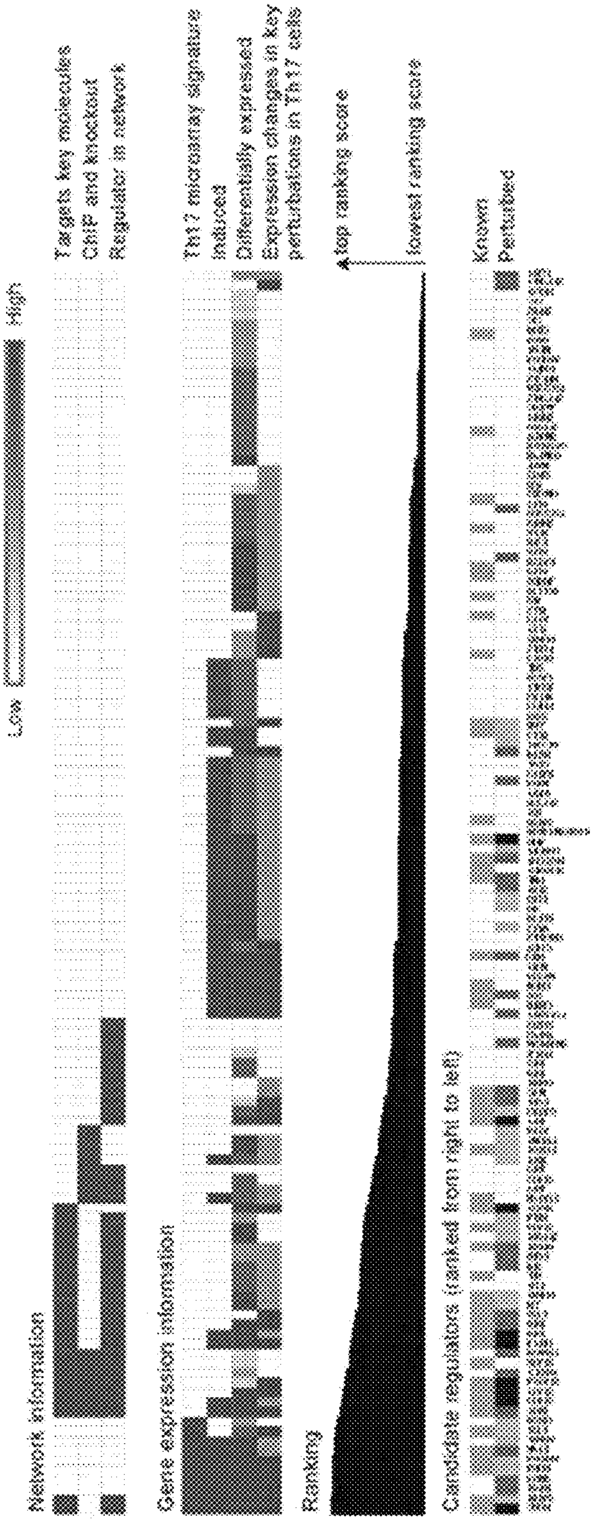
FIGS. 3A-3D are a series of graphs and illustrations depicting knockdown screen in Th17 differentiation using silicon nanowires.

Candidate regulators were ranked for perturbation (FIG. 2*a*, 3*a*, see Methods in Example 1), guided by features that reflect a regulatory role (FIG. 3*a*, "Network Information") and a role as target (FIG. 3*a*, "Gene Expression Information").

To this end, a scoring scheme was devised to rank candidate regulators for perturbation (FIG. 2*a*, FIG. 3*a*, FIG. 10, Methods), guided by protein activity (participation as a regulator node, FIG. 3*a*, "Network Information") and mRNA level (changes in expression as a target, FIG. 3*a*, "Gene Expression Information"; Methods). Under each criterion, several features were considered for selecting genes to perturb (see Methods in Example 1). In "Network Information", it was considered whether the gene acts as regulator in the network, the type of experimental support for this predicted role, and whether it is predicted to target key Th17 genes. In "Gene Expression Information", it was considered changes in mRNA levels of the encoding gene in the time course data (preferring induced genes), under IL23R knockout, or in published data of perturbation in Th17 cells (e.g., Batf knockout (Schraml, B. U. et al. in Nature Vol. 460 405-409 (2009)); See Methods for the complete list); and whether a gene is more highly expressed in Th17 cells as compared to other CD4+ subsets, based on genome wide expression profiles (Wei, G. et al. in Immunity Vol. 30 155-167 (2009)).

The genes were computationally ordered to emphasize certain features (e.g., a predicted regulator of key Th17 genes) over others (e.g., differential expression in the time course data). A similar scheme was used to rank receptor proteins (see Methods in Example 1). Supporting their quality, the top-ranked factors are enriched ($p<10^{-3}$) for manually curated Th17 regulators (FIG. 10), and correlate well (Spearman r>0.86) with a ranking learned by a supervised method (see Methods in Example 1). 65 genes were chose for perturbation: 52 regulators and 13 receptors. These included most of the top 44 regulators and top 9 receptors (excluding a few well-known Th17 genes and/or those for which knockout data already existed), as well as additional representative lower ranking factors.

Example 4

Nanowire-Based Perturbation of Primary T Cells

Figure 3B:
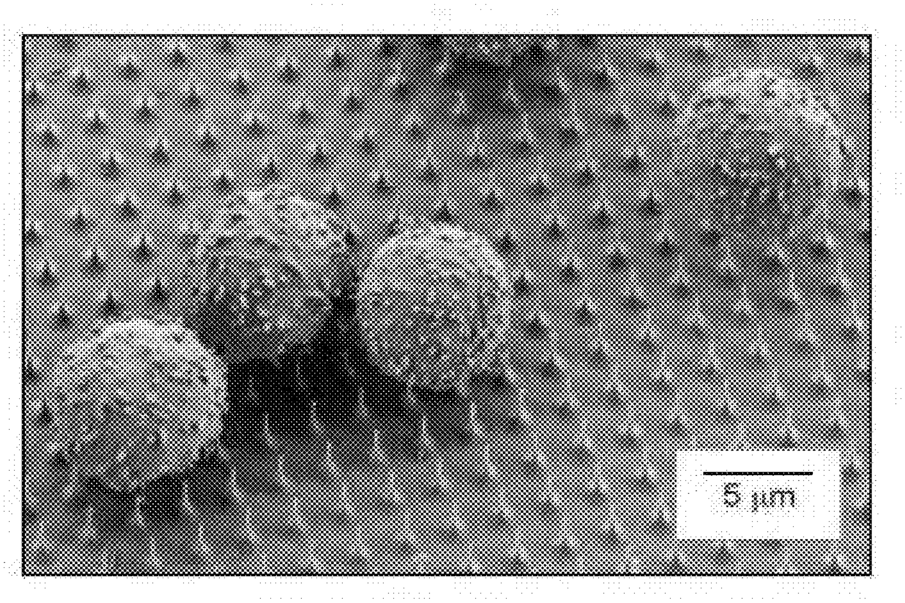

While testing the response of naïve CD4+ T cells from knock-out mice deleted for key factors is a powerful strategy, it is limited by the availability of mouse strains or the ability to generate new ones. In unstimulated primary mouse T cells, viral- or transfection-based siRNA delivery has been nearly impossible because it either alters differentiation or cell viability (Dardalhon, V. et al. Lentivirus-mediated gene transfer in primary T cells is enhanced by a central DNA flap. Gene therapy 8, 190-198 (2001); McManus, M. et al. Small interfering RNA-mediated gene silencing in T lymphocytes. The Journal of Immunology 169, 5754 (2002)). a new delivery technology based on silicon nanowires (NWs) (Shalek et al., Proc Natl Acad Sci U.S.A. 2010; Shalek, A. K. et al. Nanowire-Mediated Delivery Enables Functional Interrogation of Primary Immune Cells: Application to the Analysis of Chronic Lymphocytic Leukemia. Nano Lett. 12, 6498-6504, doi:10.1021/n13042917 (2012)) was, therefore, used, which was optimized to effectively (>95%) deliver siRNA into naïve T cells without activating them (FIGS. 3*b* and *c*) (Shalek et al., Nano Lett 2012).

Figure 3C:
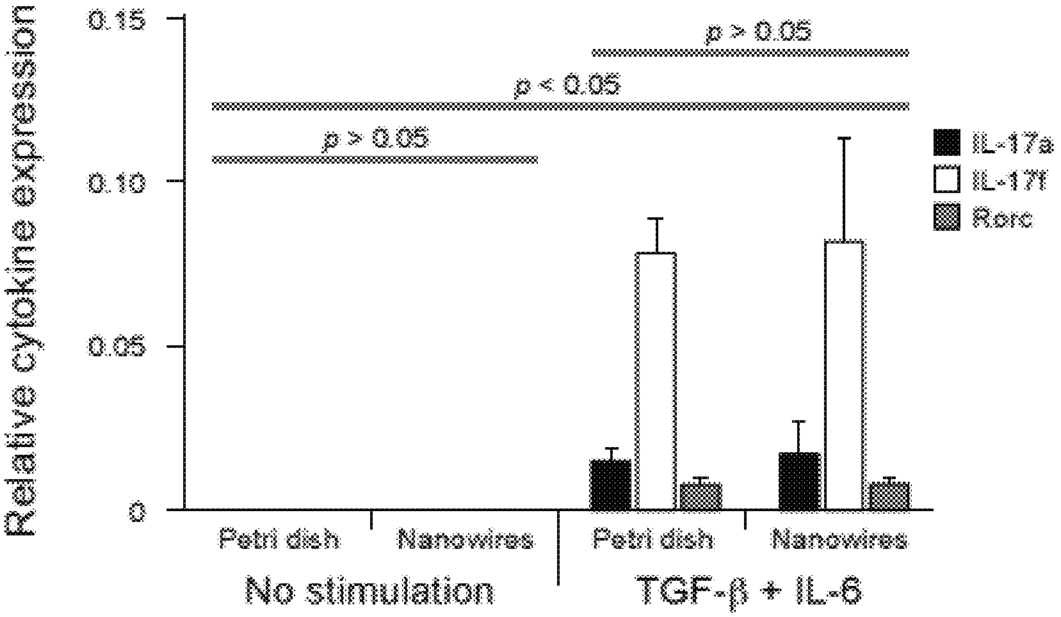

Recently, it was demonstrated that NWs are able to effectively penetrate the membranes of mammalian cells and deliver a broad range of exogenous molecules in aminimally invasive, non-activating fashion (Shalek et al., Proc. Natl. Acad. Sci. U.S.A. 2010; Shalek, et al., Nano Lett. 2012). In particular, the NW-T cell interface (FIG. 3*b*) was optimized to effectively (>95%) deliver siRNAs into naïve murine T cells. This delivery neither activates nor induces differentiation of naïve T cells and does not affect their response to conventional TCR stimulation with anti-CD3/CD28 (FIG. 3*c*) (Shalek, et al., Nano Lett. 2012)). Importantly, NW-delivered siRNAs yielded substantial target transcript knockdowns, prior to and even up to 48 h after anti-CD3/CD28 activation, despite rapid cellular proliferation (FIG. 3*d*).

Figure 3D:
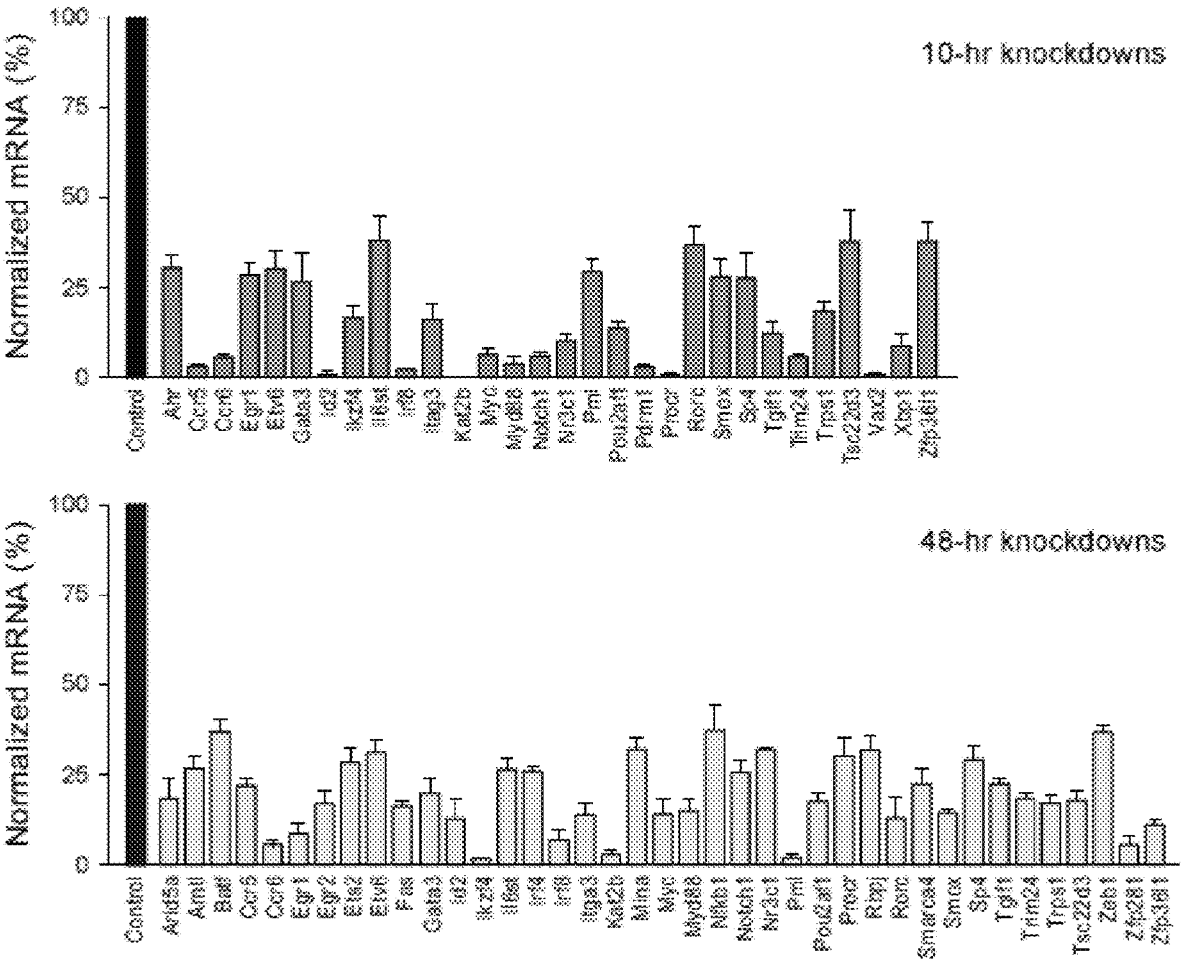

It was then attempted to perturb 60 genes with NW-mediated siRNA delivery and efficient knockdown (<60% transcript remaining at 48 hr post activation) was achieved for 34 genes (FIG. 3*d* and FIG. 11, Table S6.2). Knockout mice were obtained for seven other genes, two of which (Irf8 and Il17ra) were also in the knockdown set. Altogether, 39 of the 65 selected genes were successfully perturbed—29 regulators and 10 receptors—including 21 genes not previously associated with Th17 differentiation.

Nanowire-based screen validates 39 regulators in the Th17 network: the effects of the perturbation on gene expression were profiled at two time points. 28 of the perturbations were profiled at 10 hr after the beginning of differentiation, soon after the induction of ROR-γt (FIG. 6), and all of the perturbations were profiled at 48 hr, when the Th17 phenotype becomes more established (FIG. 1*b*). Two of the perturbations (Il17ra and Il21r knockouts) were also profiled at 60 hr.

In particular, the effects of perturbations at 48 hr post-activation on the expression of 275 signature genes were measured using the Nanostring nCounter system (Il17ra and Il21r knockouts were also measured at 60 hr).

Figure 12A:
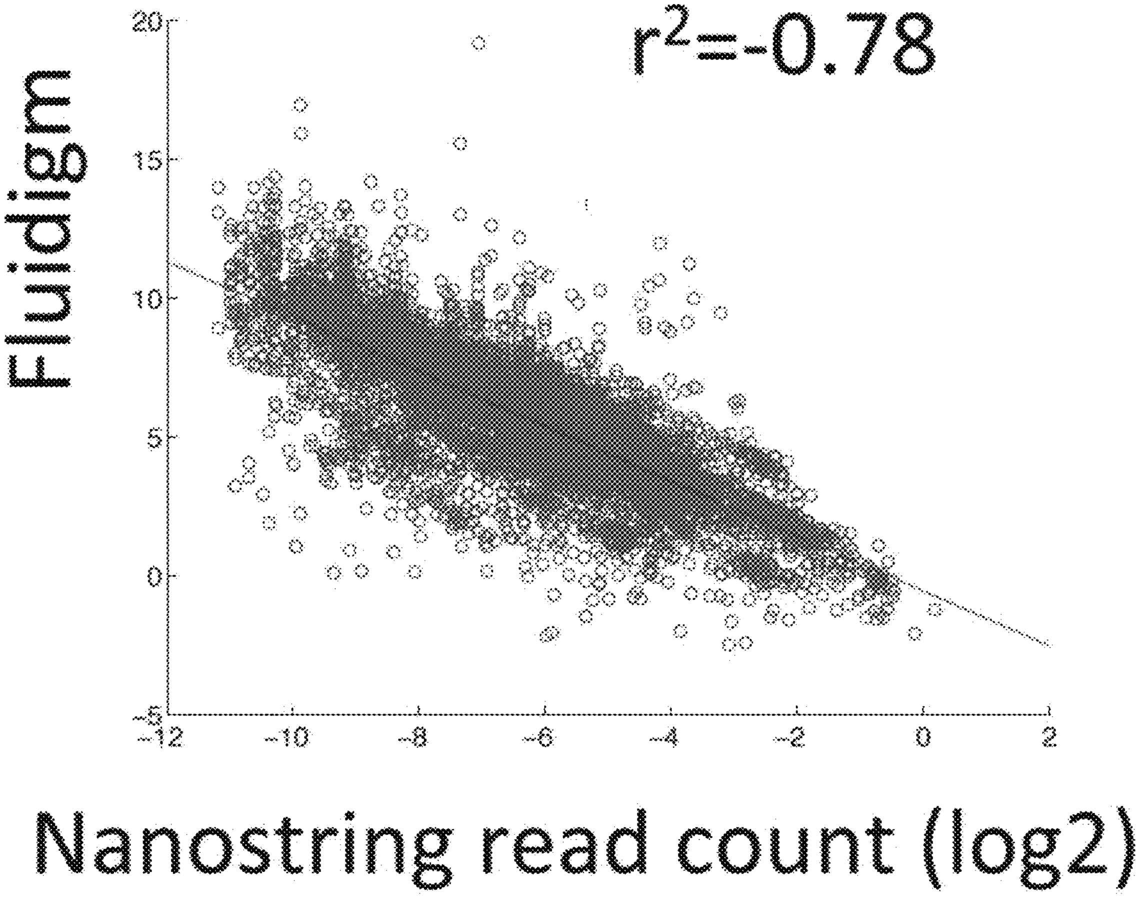
FIGS. 12A-12B are a series of graphs depicting cross-validation of the Nanostring expression profiles for each nanowire-delivered knockdown using Fluidigm 96×96 gene expression chips.
Figure 12B:
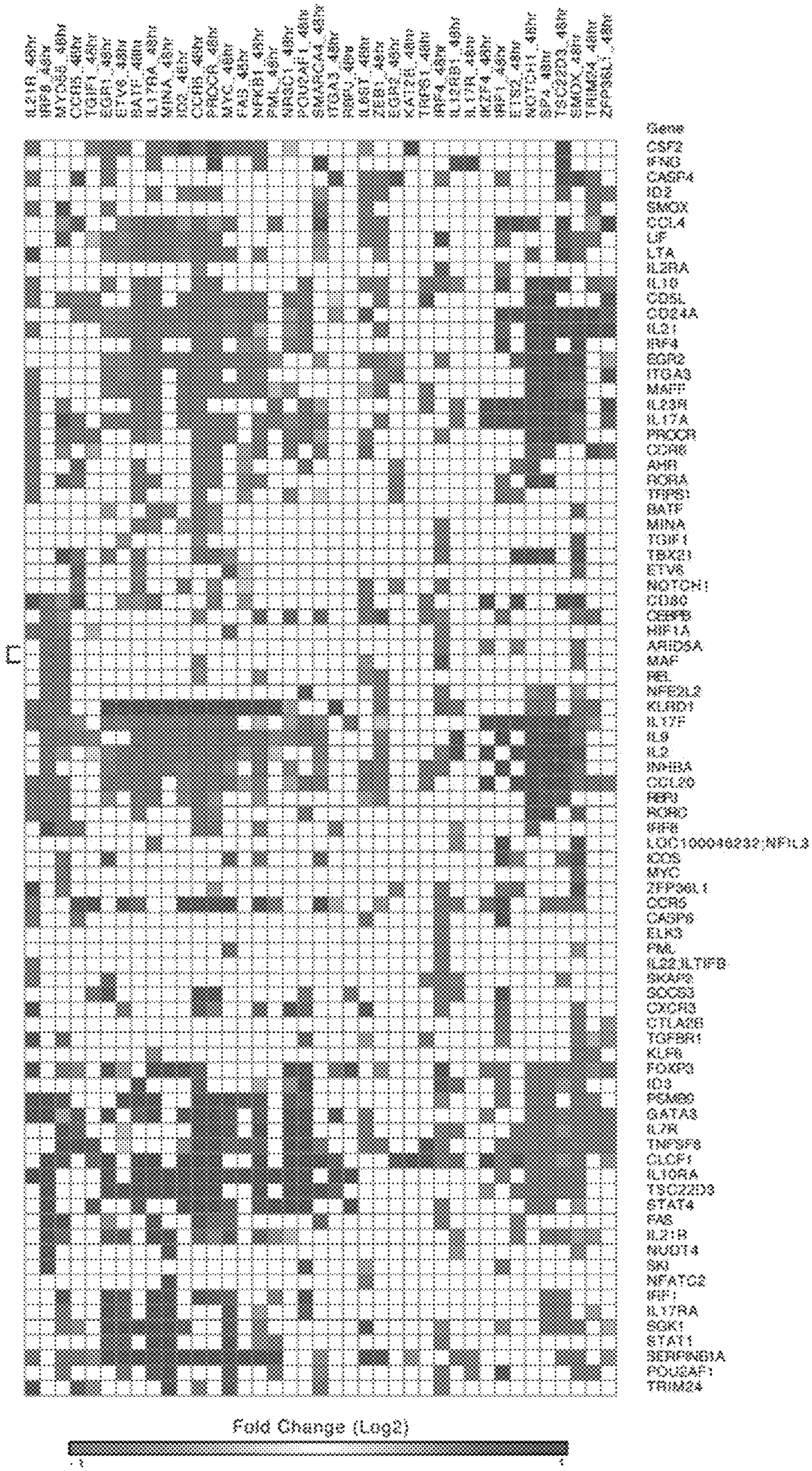

The signature genes were computationally chosen to cover as many aspects of the differentiation process as possible (see Methods in Example 1): they include most differentially expressed cytokines, TFs, and cell surface molecules, as well as representatives from each cluster (FIG. 1*b*), enriched function, and predicted targets in each network. For validation, a signature of 85 genes was profiled using the Fluidigm BioMark system, obtaining highly reproducible results (FIG. 12).

The signature genes for expression analysis were computationally chosen to cover as many aspects of the differentiation process as possible (see Methods in Example 1). They include the majority of the differentially expressed cytokines, TFs, and cell surface genes, as well as representative genes from each expression cluster (FIG. 1*b*), enriched biological function, and predicted targets of the regulators in each network. Importantly, since the signature includes most of the genes encoding the perturbed regulators, the connections between them (FIG. 4*a*, 'perturbed'), including feedback and feed-forward loops, could be determined.

The statistical significance of a perturbation's effect on a signature gene was scored by comparing to non-targeting siRNAs and to 18 control genes that were not differentially expressed (see Methods in Example 1, FIG. 4*a*, all non-grey entries are significant). Perturbation of 26 of the tested regulators had a significant effect on the expression of at least 25 signature genes at the 48 hr time point (10% of signature genes that had any response). On average, a perturbation affected 40 genes, and 80% of the signature genes were affected by at least one regulator. Supporting the original network model (FIG. 2), there is a significant overlap between the genes affected by a regulator's knockdown and its predicted targets ($p \leq 0.01$, permutation test; see Methods in Example 1).

Figure 13:
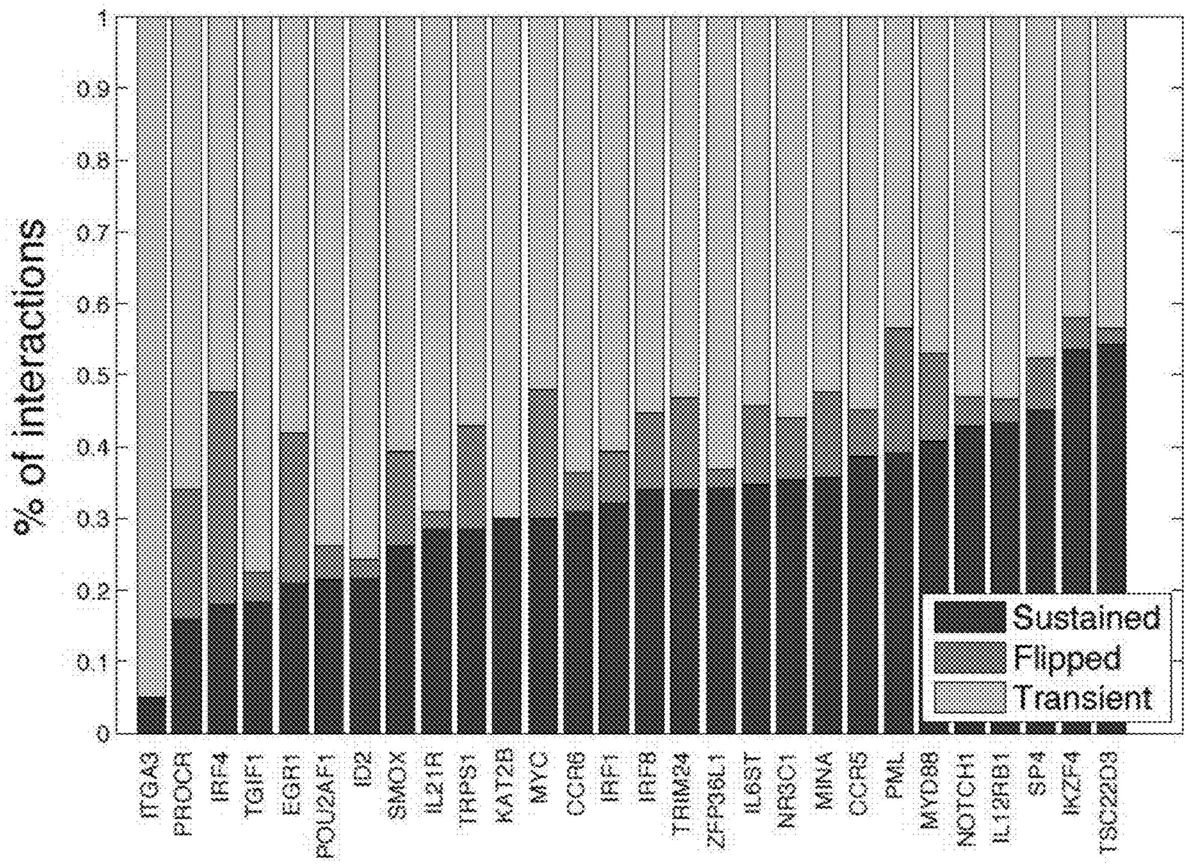
FIG. 13 is a graph depicting rewiring of the Th17 "functional" network between 10 hr to 48 hr post stimulation. For each regulator that was profiled at 10 hr and 48 hr, the percentage of "edges" (i.e., gene A is affected by perturbation of gene B) that either appear in the two time points with the same activation/repression logic (Sustained); appear only in one time point (Transient); or appear in both networks but with a different activation/repression logic (Flipped) were calculated. In the sustained edges, the perturbation effect (fold change) has to be significant in at least one of the time point (see Methods in Example 1), and consistent (in terms of activation/repression) in the other time point (using a more permissive cutoff of 1.25 fold).

To study the network's dynamics, the effect of 28 of the perturbations at 10 hr (shortly after the induction of ROR-γt) was measured using the Fluidigm Biomark system. It was found that 30% of the functional interactions are present with the same activation/repression logic at both 10 hr and 48 hr, whereas the rest are present only in one time point (FIG. 13). This is consistent with the extent of rewiring in the original model (FIG. 2*b*).

Whenever possible, the function of each regulator was classified as either positive or negative for Th17 differentiation. Specifically, at the 48 hr time point, perturbation of 22 of the regulators significantly attenuated IL-17A or IL-17F expression ('Th17 positive regulators', FIG. 4*b*, blue) and perturbation of another five, significantly increased IL-17 levels ('Th17 negative regulators', FIG. 4*b*, red). 12 of these strongly positive or negative regulators were not previously associated with Th17 cells (FIG. 4*b*, light grey halos around blue and red nodes). A color version of these figures can be found in Yosef et al., "Dynamic regulatory network controlling Th17 cell differentiation, Nature, vol. 496: 461-468 (2013)/doi: 10.1038/nature11981. Next, the role of these strong positive and negative regulators in the development of the Th17 phenotype was focused on.

Figure 14:
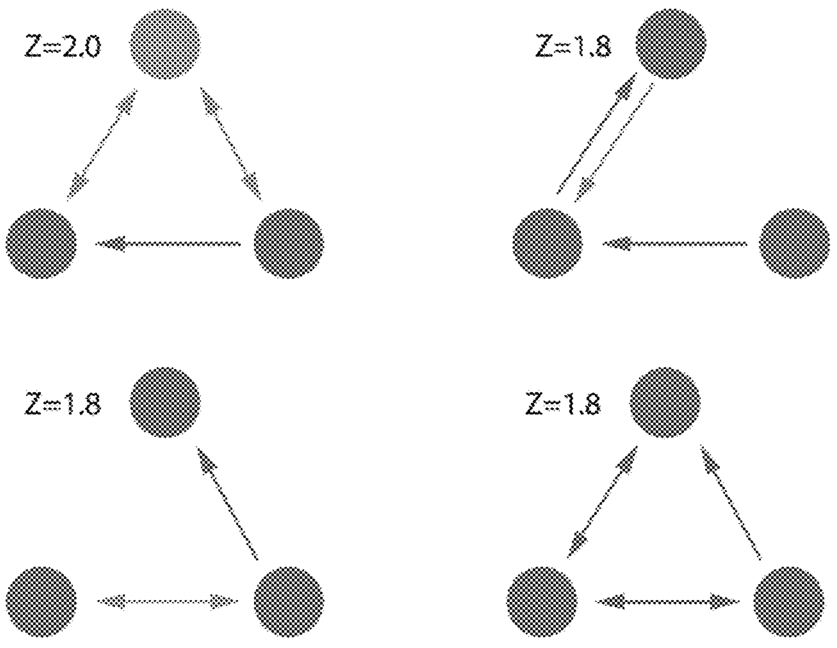
FIG. 14 is an illustration depicting "chromatic" network motifs. A color version of these figures can be found in Yosef et al., "Dynamic regulatory network controlling Th17 cell differentiation, Nature, vol. 496: 461-468 (2013)/doi: 10.1038/nature11981. A 'chromatic' network motif analysis was used to find recurring sub networks with the same topology and the same node and edge colors. Shown are the four significantly enriched motifs ($p<0.05$). Red nodes: positive regulators; blue nodes: negative regulator; red edges from A to B: knockdown of A downregulates B; blue edge: knockdown of A upregulates B. Motifs were found using the FANMOD software (Wernicke, S. & Rasche, F. FANMOD: a tool for fast network motif detection. Bioinformatics 22, 1152-1153, doi:10.1093/bioinformatics/btl038 (2006)).

Two coupled antagonistic circuits in the Th17 network: Characterizing each regulator by its effect on Th17 signature genes (e.g. IL17A, IL17F, FIG. 4*b*, grey nodes, bottom), it was found that at 48 hr the network is organized into two antagonistic modules: a module of 22 'Th17 positive factors' (FIG. 4*b*, blue nodes: 9 novel) whose perturbation decreased the expression of Th17 signature genes (FIG. 4*b*, grey nodes, bottom), and a module of 5 'Th17 negative factors' (FIG. 4*b*, red nodes: 3 novel) whose perturbation did the opposite. A color version of these figures can be found in Yosef et al., "Dynamic regulatory network controlling Th17 cell differentiation, Nature, vol. 496: 461-468 (2013)/ doi: 10.1038/nature11981. Each of the modules is tightly intra-connected through positive, self-reinforcing interactions between its members (70% of the intra-module edges), whereas most (88%) inter-module interactions are negative. This organization, which is statistically significant (empirical p-value$<10^{-3}$; see Methods in Example 1, FIG. 14), is reminiscent to that observed previously in genetic circuits in yeast (Segrè, D., Deluna, A., Church, G. M. & Kishony, R. Modular epistasis in yeast metabolism. Nat. Genet. 37, 77-83, doi:10.1038/ng1489 (2005); Peleg, T., Yosef, N., Ruppin, E. & Sharan, R. Network-free inference of knockout effects in yeast. PLoS Comput Biol 6, e1000635, doi: 10.1371/journal.pcbi.1000635 (2010)). At 10 hrs, the same regulators do not yield this clear pattern ($p>0.5$), suggesting that at that point, the network is still malleable.

The two antagonistic modules may play a key role in maintaining the balance between Th17 and other T cell subsets and in self-limiting the pro-inflammatory status of Th17 cells. Indeed, perturbing Th17 positive factors also induces signature genes of other T cell subsets (e.g., Gata3, FIG. 4*b*, grey nodes, top), whereas perturbing Th17 negative factors suppresses them (e.g., Foxp3, Gata3, Stat4, and Tbx21).

Example 5

Validation and Characterization of Novel Factors

The studies presented herein focused on the role of 12 of the positive or negative factors (including 11 of the 12 novel factors that have not been associated with Th17 cells; FIG. 4*b*, light grey halos). RNA-Seq was used after perturbing each factor to test whether its predicted targets (FIG. 2) were affected by perturbation (FIG. 4*c*, Venn diagram, top). Highly significant overlaps ($p<10^{-5}$) for three of the factors (Egr2, Irf8, and Sp4) that exist in both datasets were found, and a border-line significant overlap for the fourth (Smarca4) was found, validating the quality of the edges in the network.

Figure 15A:
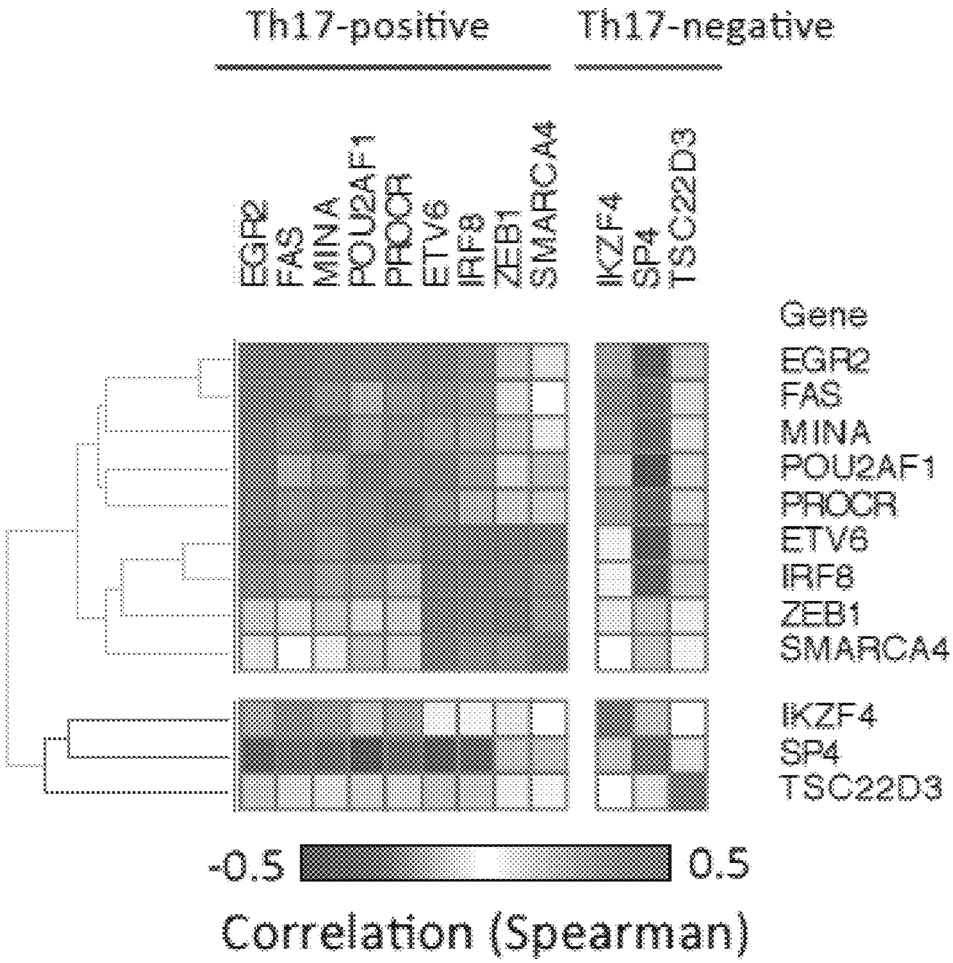
FIGS. 15A-15C are a series of graphs depicting RNA-seq analysis of nanowire-delivered knockdowns. A color version of these figures can be found in Yosef et al., "Dynamic regulatory network controlling Th17 cell differentiation, Nature, vol. 496: 461-468 (2013)/doi: 10.1038/nature11981.

Next, the designation of each of the 12 factors as 'Th17 positive' or 'Th17 negative' was assessed by comparing the set of genes that respond to that factor's knockdown (in RNA-Seq) to each of the 20 clusters (FIG. 1b). Consistent with the original definitions, knockdown of a 'Th17 positive' regulator down-regulated genes in otherwise induced clusters, and up-regulated genes in otherwise repressed or un-induced clusters (and vice versa for 'Th17 negative' regulators; FIG. 4d and FIG. 15a,b). The genes affected by either positive or negative regulators also significantly overlap with those bound by key CD4+ transcription regulators (e.g., Foxp3 (Marson, A. et al. Foxp3 occupancy and regulation of key target genes during T cell stimulation. Nature 445, 931-935, doi:10.1038/nature05478 (2007); Zheng, Y. et al. Genome-wide analysis of Foxp3 target genes in developing and mature regulatory T cells. Nature 445, 936-940, doi:10.1038/nature05563 (2007)), Batf, Irf4, and ROR-γt (Glasmacher, E. et al. A Genomic Regulatory Element That Directs Assembly and Function of Immune-Specific AP-1-IRF Complexes. Science (New York, N.Y.), doi:10.1126/science.1228309 (2012); Ciofani, M. et al. A Validated Regulatory Network for Th17 Cell Specification. Cell, doi: 10.1016/j.cell.2012.09.016 (2012)), Xiao et al., unpublished data). For instance, genes that are down-regulated following knockdown of the 'Th17-positive' regulator Mina are highly enriched ($p<10^{-6}$) in the late induced clusters (e.g., C19, C20). Conversely, genes in the same late induced clusters become even more up-regulated following knockdown of the 'Th17 negative' regulator Sp4.

Figure 5A:
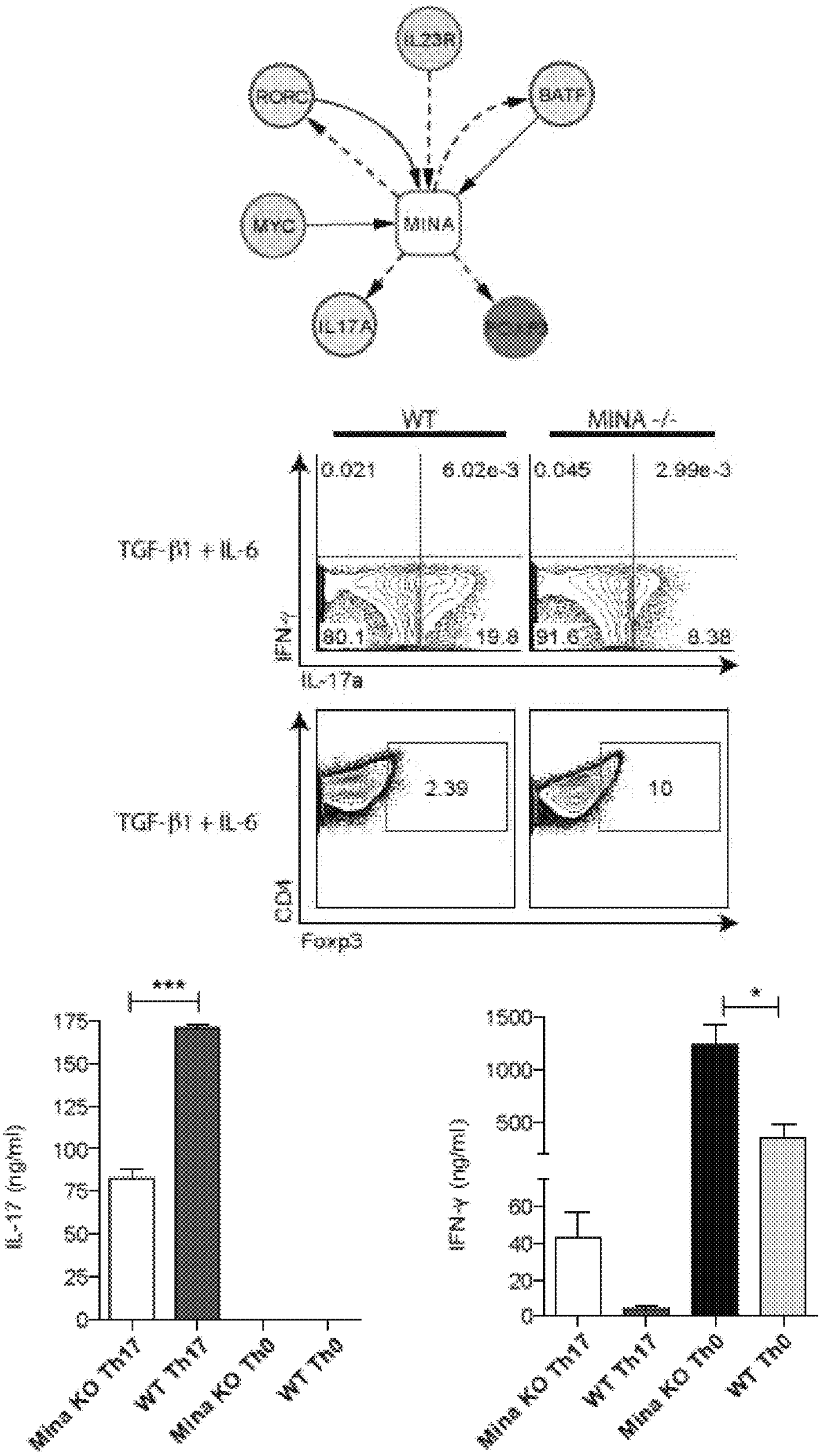
FIGS. 5A-5D are a series of graphs and illustrations depicting that Mina, Fas, Pou2af1, and Tsc22d3 are key novel regulators affecting the Th17 differentiation programs. A color version of these figures can be found in Yosef et al., "Dynamic regulatory network controlling Th17 cell differentiation, Nature, vol. 496: 461-468 (2013)/doi: 10.1038/nature11981.
Figure 15B:
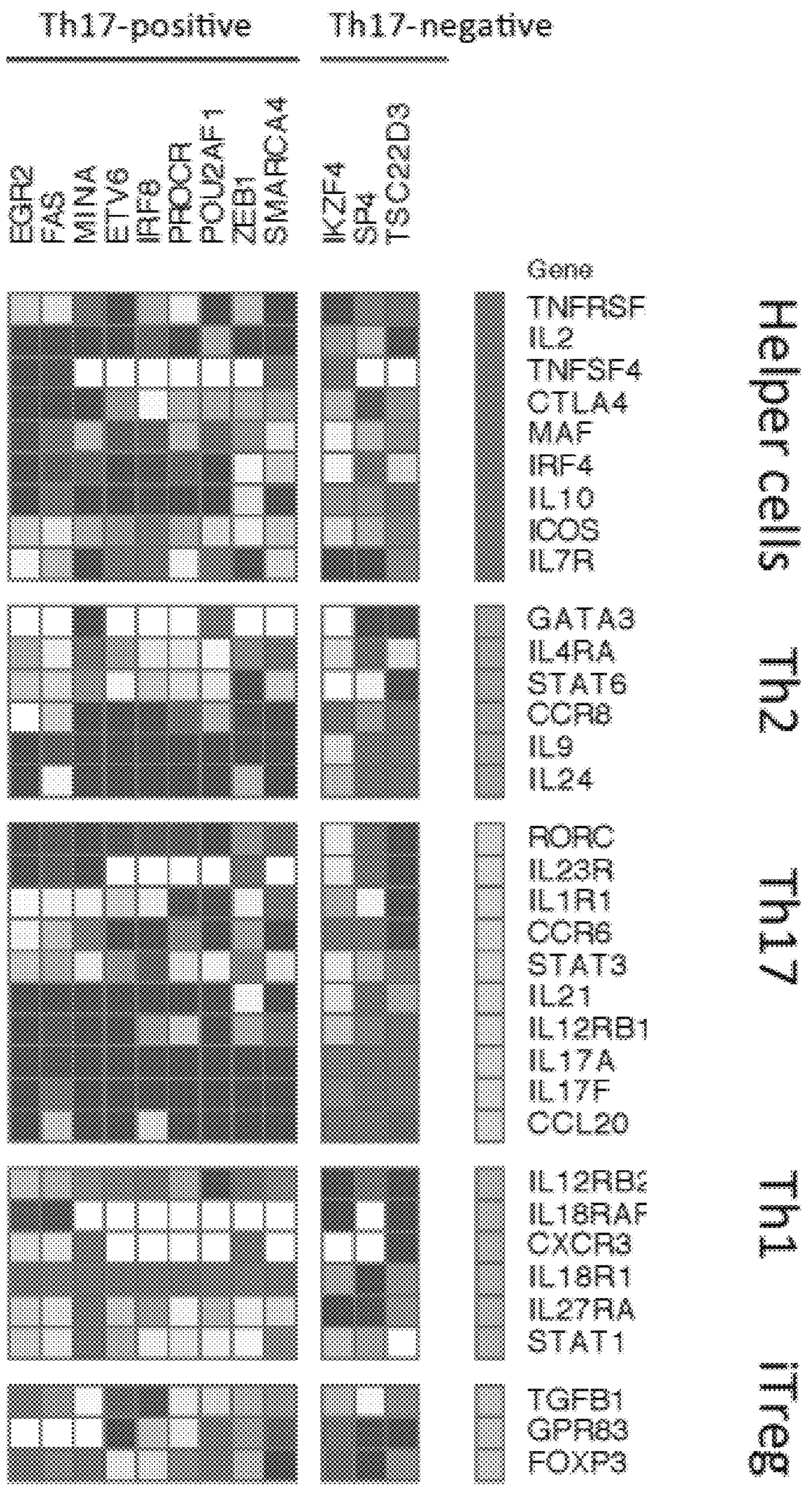
Figure 15C:
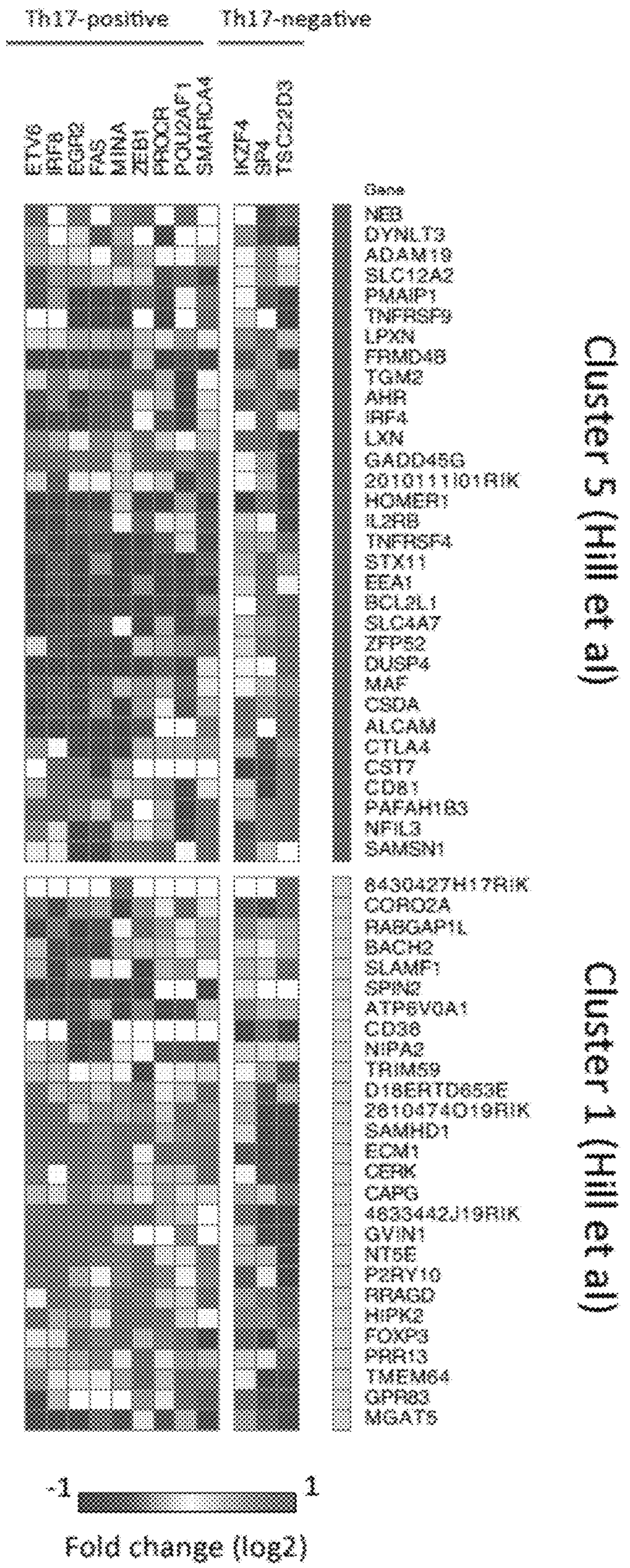

Mina promotes the Th17 program and inhibits the Foxp3 program: Knockdown of Mina, a chromatin regulator from the Jumonji C (JmjC) family, represses the expression of signature Th17 cytokines and TFs (e.g. ROR-γt, Batf, Irf4) and of late-induced genes (clusters C9, C19; $p<10^{-5}$), while increasing the expression of Foxp3, the master TF of Treg cells. Mina is strongly induced during Th17 differentiation (cluster C7), is down-regulated in IL23r−/− Th17 cells, and is a predicted target of Batf (Glasmacher, E. et al. A Genomic Regulatory Element That Directs Assembly and Function of Immune-Specific AP-1-IRF Complexes. Science, doi: 10.1126/science.1228309 (2012)), ROR-γt (Glasmacher et al., Science 2012), and Myc in the model (FIG. 5a). Mina was shown to suppress Th2 bias by interacting with the TF NFAT and repressing the IL-4 promoter (Okamoto, M. et al. Mina, an 114 repressor, controls T helper type 2 bias. Nat. Immunol. 10, 872-879, doi:10.1038/ni.1747 (2009)). However, in the cells, Mina knockdown did not induce Th2 genes, suggesting an alternative mode of action via positive feedback loops between Mina, Batf and ROR-γt (FIG. 5a, left). Consistent with this model, Mina expression is reduced in Th17 cells from ROR-γt-knockout mice, and the Mina promoter was found to be bound by ROR-γt by ChIP-Seq (data not shown). Finally, the genes induced by Mina knockdown significantly overlap with those bound by Foxp3 in Treg cells (Marson et al., Nature 2007; Zheng et al., Nature 2007) ($P<10^{-25}$) and with a cluster previously linked to Foxp3 activity in Treg cells (Hill, J. A. et al. Foxp3 transcription-factor-dependent and -independent regulation of the regulatory T cell transcriptional signature. Immunity 27, 786-800, doi:S1074-7613(07)00492-X [pii]10.1016/j.immuni.2007.09.010 (2007)) (FIG. 15c). When comparing to previously defined transcriptional signatures of Treg cells (compared to conventional T cells, (Hill, J. A. et al. Foxp3 transcription-factor-dependent and -independent regulation of the regulatory T cell transcriptional signature. Immunity 27, 786-800, doi:10.1016/j.immuni.2007.09.010 (2007))), genes that are induced in the Mina knockdown are enriched in a cluster tightly linked to functional activity of FoxP3. Conversely, genes down-regulated in the Mina knockdown are more directly responsive to TCR and IL-2 and less responsive to Foxp3 in Treg cells (FIG. 15c).

Figure 16A:
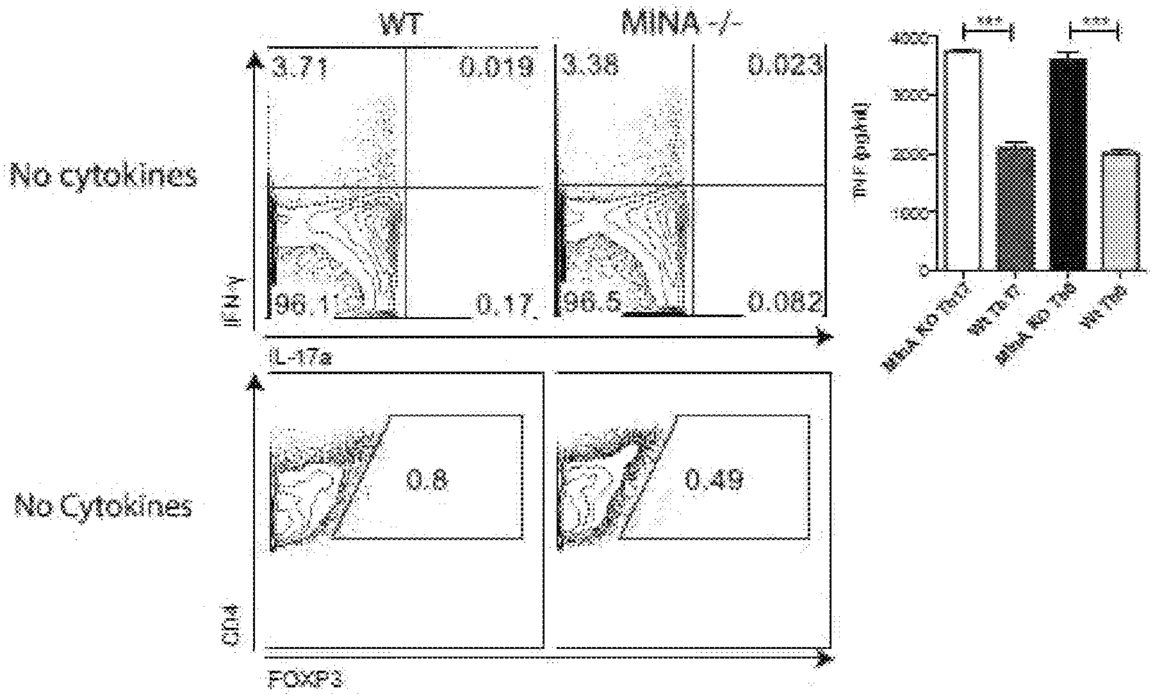
FIGS. 16A-16D are a series of graphs depicting quantification of cytokine production in knockout cells at 72 h of in-vitro differentiation using Flow cytometry and Enzyme-linked immunosorbent assay (ELISA). All flow cytometry figures shown, except for Oct1, are representative of at least 3 repeats, and all ELISA data has at least 3 replicates. For Oct1, only a limited amount of cells were available from reconstituted mice, allowing for only 2 repeats of the Oct1 deficient mouse for flow cytometry and ELISA.

To further analyze the role of Mina, IL-17a and Foxp3 expression was measured following differentiation of naïve T cells from Mina−/− mice. Mina−/− cells had decreased IL-17a and increased Foxp3 compared to wild-type (WT) cells, as detected by intracellular staining (FIG. 5a). Cytokine analysis of the corresponding supernatants confirmed a decrease in IL-17a production and an increase in IFN-γ (FIG. 5a) and TNF-α (FIG. 16a). Under Th17 differentiation conditions, loss of Mina resulted in a decrease in IL-17 expression and increase in FoxP3, as detected by intracellular staining (FIG. 5a). Cytokine analysis of the supernatants from these differentiating cultures confirmed a decrease in IL-17 production with a commensurate increase in IFNγ (FIG. 5a) and TNFα (FIG. 16a).

The reciprocal relationship between Tregs/Th17 cells has been well described (Korn, T. et al. IL-21 initiates an alternative pathway to induce proinflammatory T(H)17 cells. Nature 448, 484-487, doi:10.1038/nature05970 (2007)), and it was assumed that this is achieved by direct binding of the ROR-γt/Foxp3 TFs. However, the analysis suggests a critical role for the regulator Mina in mediating this process. This suggests a model where Mina, induced by ROR-γt and Batf, promotes transcription of ROR-γt, while suppressing induction of Foxp3, thus affecting the reciprocal Tregs/Th17 balance (Korn, et al., Nature 2007)) by favoring rapid Th17 differentiation.

Figure 5B:
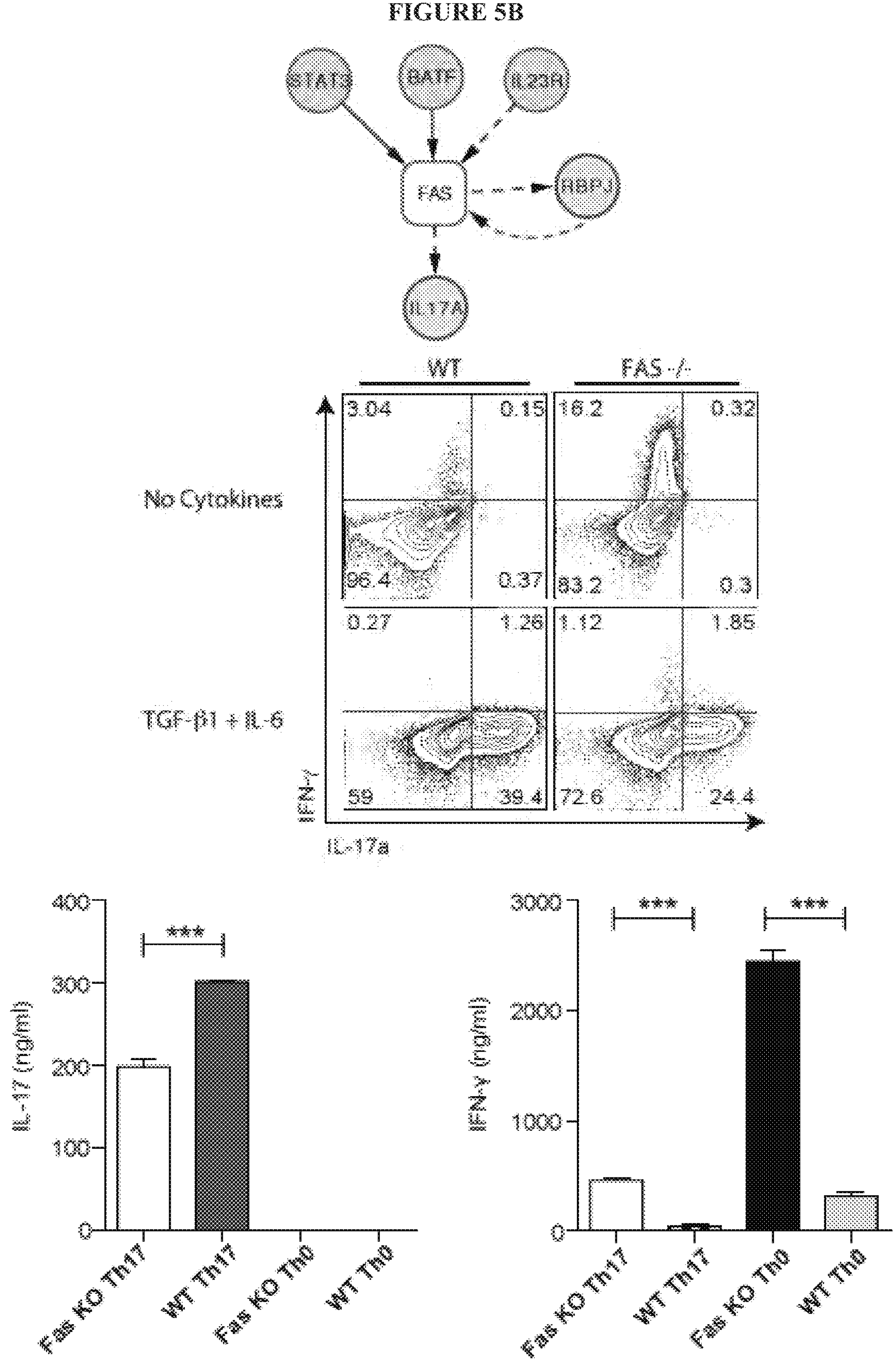

Fas promotes the Th17 program and suppresses IFN-γ expression: Fas, the TNF receptor superfamily member 6, is another Th17 positive regulator (FIG. 5b). Fas is induced early, and is a target of Stat3 and Batf in the model. Fas knockdown represses the expression of key Th17 genes (e.g., IL-17a, IL-17f, Hif1a, Irf4, and Rbpj) and of the induced cluster C14, and promotes the expression of Th1-related genes, including IFN-γ receptor 1 and Klrd1 (Cd94; by RNA-Seq, FIG. 4, FIG. 5b, and FIG. 15). Fas and Fas-ligand deficient mice are resistant to the induction of autoimmune encephalomyelitis (EAE) (Waldner, H., Sobel, R. A., Howard, E. & Kuchroo, V. K. Fas- and FasL-deficient mice are resistant to induction of autoimmune encephalomyelitis. J Immunol 159, 3100-3103 (1997)), but have no defect in IFN-γ or Th1 responses. The mechanism underlying this phenomenon was never studied.

To explore this, T cells from Fas−/− mice (FIG. 5b, FIG. 16c) were differentiated. Consistent with the knockdown analysis, expression of IL-17a was strongly repressed and IFN-γ production was strongly increased under both Th17 and Th0 polarizing conditions (FIG. 5b). These results suggest that besides being a death receptor, Fas may play an important role in controlling the Th1/Th17 balance, and Fas−/− mice may be resistant to EAE due to lack of Th17 cells.

Figure 5C:
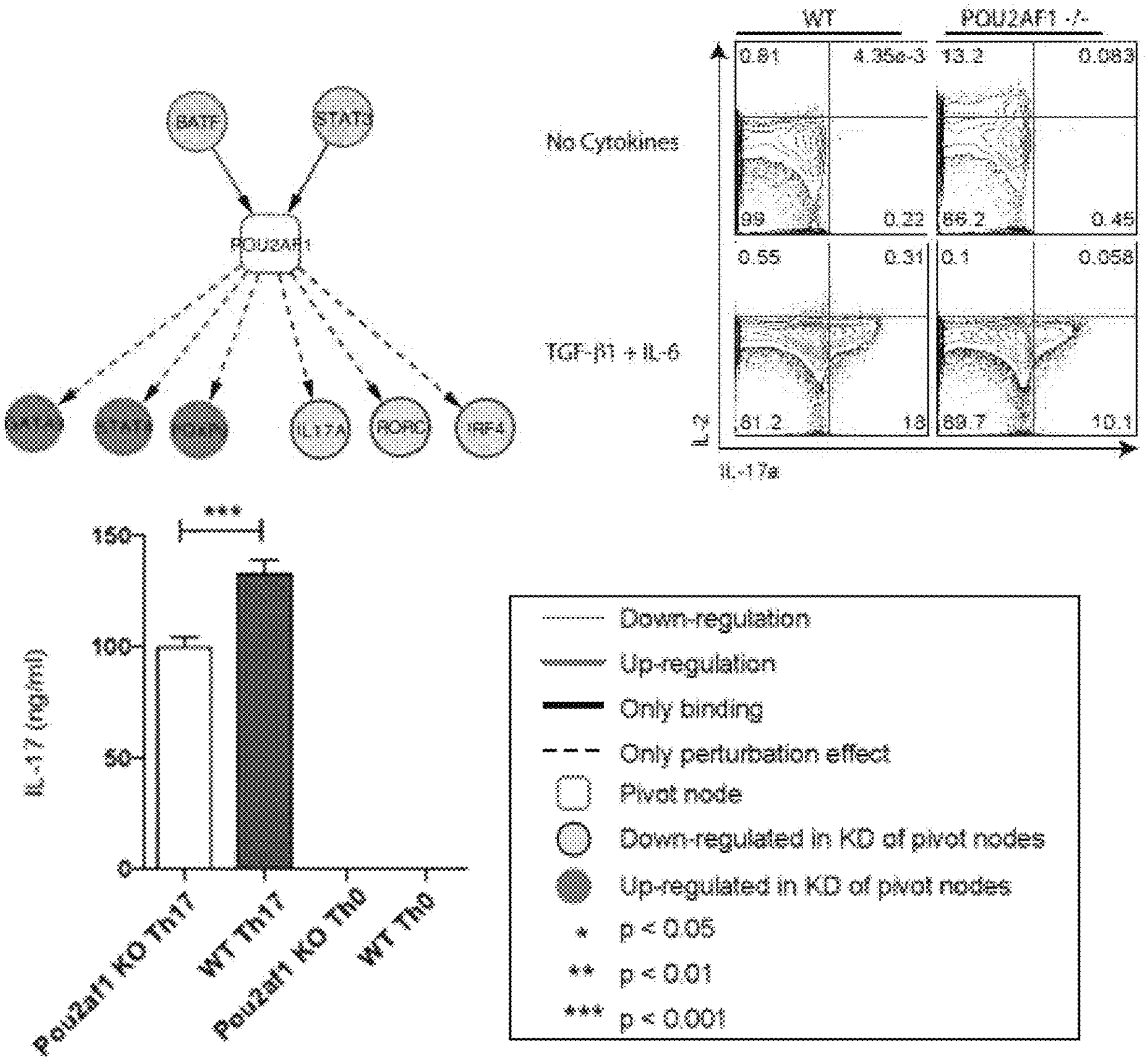
Figure 16B:
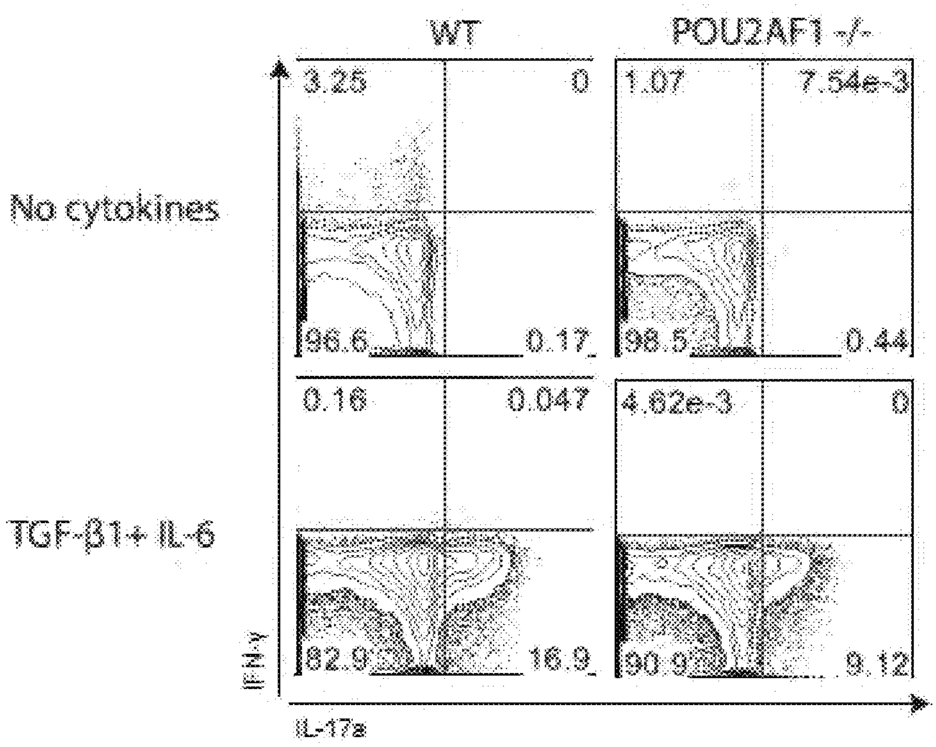
Figure 16C:
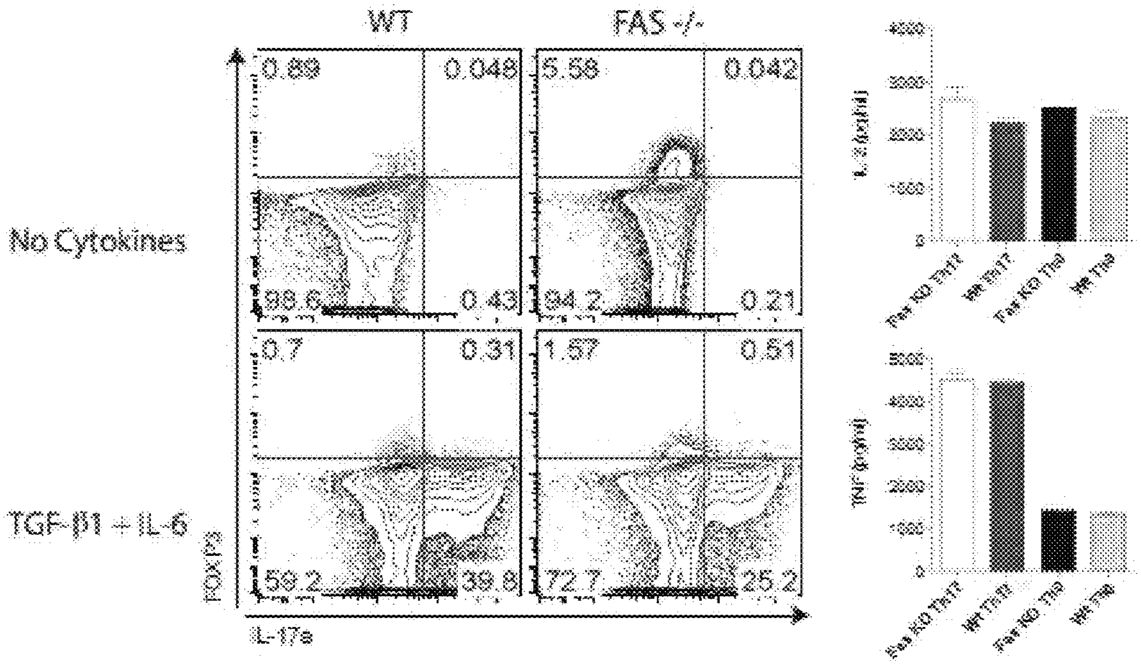
Figure 16D:
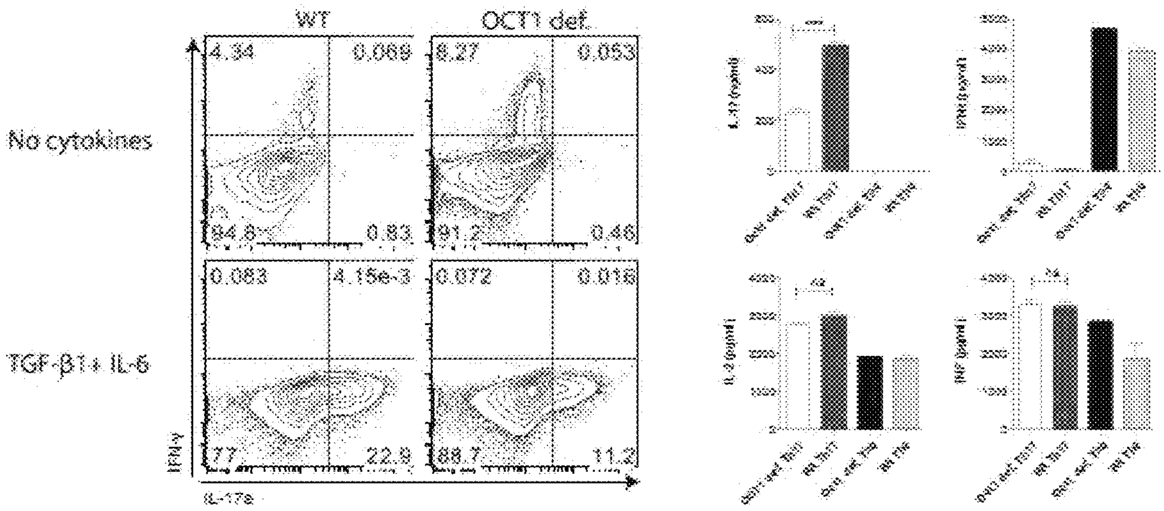

Pou2af1 promotes the Th17 program and suppresses IL-2 expression: Knockdown of Pou2af1 (OBF1) strongly decreases the expression of Th17 signature genes (FIG. 5c) and of intermediate- and late-induced genes (clusters C19 and C20, $p<10^{-7}$), while increasing the expression of regulators of other CD4+ subsets (e.g., Foxp3, Stat4, Gata3) and of genes in non-induced clusters (clusters C2 and C16 $p<10^{-9}$). Pou2af1's role in T cell differentiation has not been explored (Teitell, M. A. OCA-B regulation of B-cell development and function. Trends Immunol 24, 546-553 (2003)). To investigate its effects, T cells from Pou2af1−/− mice were differentiated (FIG. 5c, FIG. 16b). Compared to WT cells, IL-17a production was strongly repressed. Interestingly, IL-2 production was strongly increased in Pou2af1−/− T cells under non-polarizing (Th0) conditions. Thus, Pou2af1 may promote Th17 differentiation by blocking production of IL-2, a known endogenous repressor of Th17 cells (Laurence, A. et al. Interleukin-2 signaling via STAT5 constrains T helper 17 cell generation. Immunity 26, 371-381, doi: S1074-7613(07)00176-8 [pii]10.1016/j.immuni.2007.02.009 (2007)). Pou2af1 acts as a transcriptional co-activator of the TFs OCT1 or OCT2 (Teitell, Trends Immunol 2003). IL-17a production was also strongly repressed in Oct1-deficient cells (FIG. 16*d*), suggesting that Pou2af1 may exert some of its effects through this co-factor.

Figure 5D:
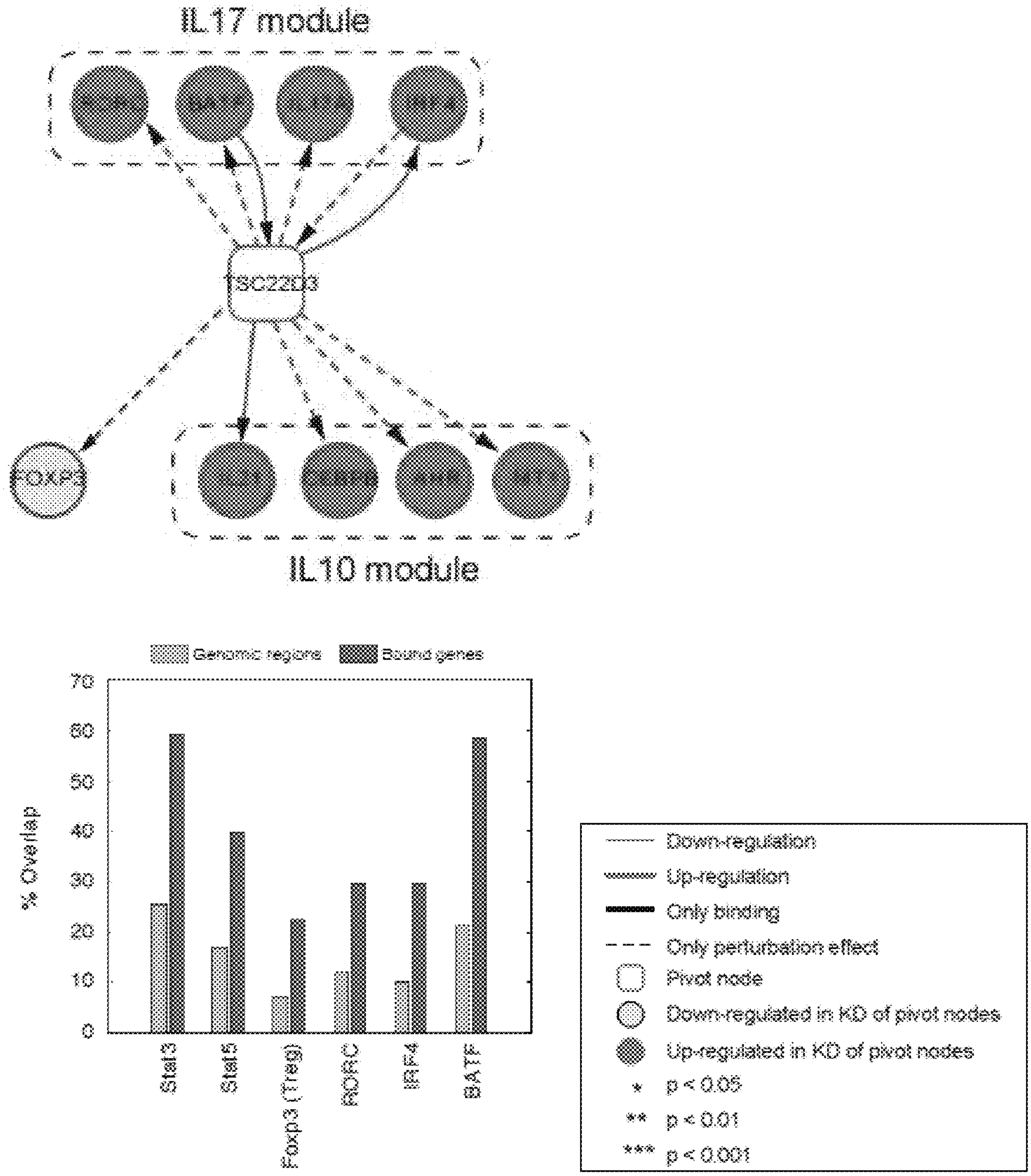

TSC22d3 may limit Th17 differentiation and pro-inflammatory function: Knockdown of the TSC22 domain family protein 3 (Tsc22d3) increases the expression of Th17 cytokines (IL-17a, IL-21) and TFs (ROR-γt, Rbpj, Batf), and reduces Foxp3 expression. Previous studies in macrophages have shown that Tsc22d3 expression is stimulated by glucocorticoids and IL-10, and it plays a key role in their anti-inflammatory and immunosuppressive effects (Choi, S.-J. et al. Tsc-22 enhances TGF-beta signaling by associating with Smad4 and induces erythroid cell differentiation. Mol. Cell. Biochem. 271, 23-28 (2005)). Tsc22d3 knockdown in Th17 cells increased the expression of IL-10 and other key genes that enhance its production (FIG. 5*d*). Although IL-10 production has been shown (Korn et al., Nature 2007; Peters, A., Lee, Y. & Kuchroo, V. K. The many faces of Th17 cells. Curr. Opin. Immunol. 23, 702-706, doi:10.1016/j.coi.2011.08.007 (2011); Chaudhry, A. et al. Interleukin-10 signaling in regulatory T cells is required for suppression of Th17 cell-mediated inflammation. Immunity 34, 566-578, doi:10.1016/j.immuni.2011.03.018 (2011)) to render Th17 cells less pathogenic in autoimmunity, co-production of IL-10 and IL-17a may be the indicated response for clearing certain infections like *Staphylococcus aureus* at mucosal sites (Zielinski, C. E. et al. Pathogen-induced human TH17 cells produce IFN-γ or IL-10 and are regulated by IL-1β. Nature 484, 514-518, doi:10.1038/nature10957 (2012)). This suggests a model where Tsc22d3 is part of a negative feedback loop for the induction of a Th17 cell subtype that coproduce IL-17 and IL-10 and limits their pro-inflammatory capacity. Tsc22d3 is induced in other cells in response to the steroid Dexamethasone (Jing, Y. et al. A mechanistic study on the effect of dexamethasone in moderating cell death in Chinese Hamster Ovary cell cultures. Biotechnol Prog 28, 490-496, doi:10.1002/btpr.747 (2012)), which represses Th17 differentiation and ROR-γt expression (Hu, M., Luo, Y. L., Lai, W. Y. & Chen, P. F. [Effects of dexamethasone on intracellular expression of Th17 cytokine interleukin 17 in asthmatic mice]. Nan Fang Yi Ke Da Xue Xue Bao 29, 1185-1188 (2009)). Thus, Tsc22d3 may mediate this effect of steroids.

To further characterize Tsc22d3's role, ChIP-Seq was used to measure its DNA-binding profile in Th17 cells and RNA-Seq following its knockdown to measure its functional effects. There is a significant overlap between Tsc22d3's functional and physical targets ($P<0.01$, e.g., IL-21, Irf4; see Methods in Example 1). For example, Tsc22d3 binds in proximity to IL-21 and Irf4, which also become up regulated in the Tsc22d3 knockdown. Furthermore, the Tsc22d3 binding sites significantly overlap those of major Th17 factors, including Batf, Stat3, Irf4, and ROR-γt (>5 fold enrichment; FIG. 5*d*, and see Methods in Example 1). This suggests a model where Tsc22d3 exerts its Th17-negative function as a transcriptional repressor that competes with Th17 positive regulators over binding sites, analogous to previous findings in CD4+ regulation (Ciofani et al., Cell 2012; Yang, X. P. et al. Opposing regulation of the locus encoding IL-17 through direct, reciprocal actions of STAT3 and STAT5. Nat. Immunol. 12, 247-254, doi:10.1038/ni.1995 (2011)).

Example 6

Protein C Receptor (PROCR) Regulates Pathogenic Phenotype of Th17 Cells

Th17 cells, a recently identified T cell subset, have been implicated in driving inflammatory autoimmune responses as well as mediating protective responses against certain extracellular pathogens. Based on factors such as molecular signature, Th17 cells are classified as pathogenic or non-pathogenic. (See e.g., Lee et al., "Induction and molecular signature of pathogenic Th17 cells," Nature Immunology, vol. 13(10): 991-999 and online methods).

It should be noted that the terms "pathogenic" or "non-pathogenic" as used herein are not to be construed as implying that one Th17 cell phenotype is more desirable than the other. As will be described herein, there are instances in which inhibiting the induction of pathogenic Th17 cells or modulating the Th17 phenotype towards the non-pathogenic Th17 phenotype or towards another T cell phenotype is desirable. Likewise, there are instances where inhibiting the induction of non-pathogenic Th17 cells or modulating the Th17 phenotype towards the pathogenic Th17 phenotype or towards another T cell phenotype is desirable. For example, pathogenic Th17 cells are believed to be involved in immune responses such as autoimmunity and/or inflammation. Thus, inhibition of pathogenic Th17 cell differentiation or otherwise decreasing the balance of Th17 T cells towards non-pathogenic Th17 cells or towards another T cell phenotype is desirable in therapeutic strategies for treating or otherwise ameliorating a symptom of an immune-related disorder such as an autoimmune disease or an inflammatory disorder. In another example, depending on the infection, non-pathogenic or pathogenic Th17 cells are believed to be desirable in building a protective immune response in infectious diseases and other pathogen-based disorders. Thus, inhibition of non-pathogenic Th17 cell differentiation or otherwise decreasing the balance of Th17 T cells towards pathogenic Th17 cells or towards another T cell phenotype or vice versa is desirable in therapeutic strategies for treating or otherwise ameliorating a symptom of an immune-related disorder such as infectious disease.

Th17 cells are considered to be pathogenic when they exhibit a distinct pathogenic signature where one or more of the following genes or products of these genes is upregulated in TGF-β3-induced Th17 cells as compared to TGF-β1-induced Th17 cells: Cxcl3, Il22, Il3, Ccl4, Gzmb, Lrmp, Ccl5, Casp1, Csf2, Ccl3, Tbx21, Icos, 117r, Stat4, Lgals3 or Lag3. Th17 cells are considered to be non-pathogenic when they exhibit a distinct non-pathogenic signature where one or more of the following genes or products of these genes is down-regulated in TGF-β3-induced Th17 cells as compared to TGF-β1-induced Th17 cells: Il6st, Il1rn, lkzf3, Maf, Ahr, Il9 or Il10.

A temporal microarray analysis of developing Th17 cells was performed to identify cell surface molecules, which are differentially expressed in Th17 cells and regulate the development of Th17 cells. PROCR was identified as a receptor that is differentially expressed in Th17 cells and found its expression to be regulated by Th17-specific transcription regulators.

Protein C receptor (PROCR; also called EPCR or CD201) is primarily expressed on endothelial cells, $CD8^+$ dendritic cells and was also reported to be expressed to lower levels on other hematopoietic and stromal cells. It binds to activated protein C as well as factor VII/VIIa and factor Xa and was shown to have diverse biological functions, including anticoagulant, cytoprotective, anti-apoptotic and anti-inflammatory activity. However, prior to these studies, the function of PROCR in T cells had not been explored.

The biological function of PROCR and its ligand activated protein C in Th17 cells was analyzed, and it was found that it decreased the expression of some of the genes identified as a part of the pathogenic signature of Th17 cells. Furthermore, PROCR expression in Th17 cells reduced the pathogenicity of Th17 cells and ameliorated disease in a mouse model for human multiple sclerosis.

These results imply that PROCR functions as a regulatory gene for the pathogenicity of Th17 cells through the binding of its ligand(s). It is therefore conceivable that the regulation of this pathway might be exploited for therapeutic approaches to inflammatory and autoimmune diseases.

These studies are the first to describe the Th17-specific expression of PROCR and its role in reducing autoimmune Th17 pathogenicity. Thus, activation of PROCR through antibodies or other agonists are useful as a therapeutic strategy in an immune response such as inflammatory autoimmune disorders. In addition, blocking of PROCR through antibodies or other inhibitors could be exploited to augment protective Th17 responses against certain infectious agents and pathogens.

Figure 30A:
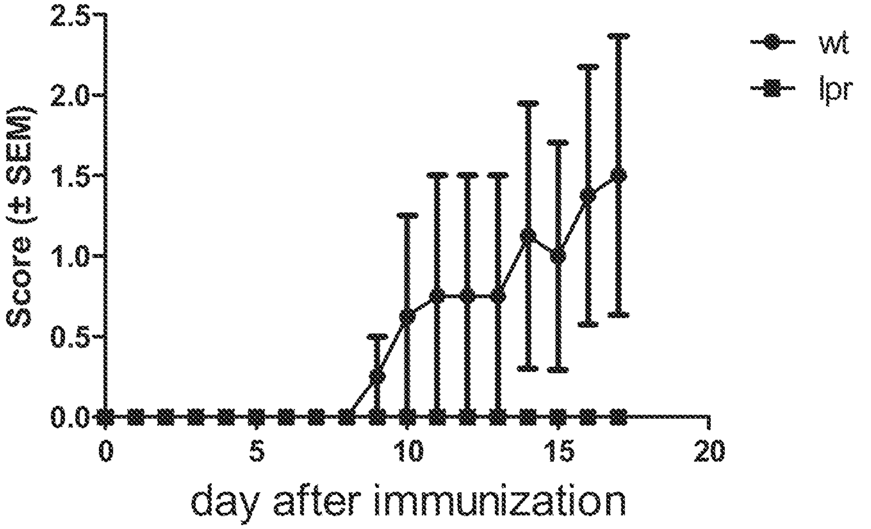
FIGS. 30A-30B are a series of graphs depicting that FAS-deficient mice are resistant to EAE. Wild type (WT) or FAS-deficient (LPR) mice were immunized with 100 μg $MOG_{35-55}$ in CFA s.c. and received pertussis toxin i.v. to induce EAE.
Figure 30B:
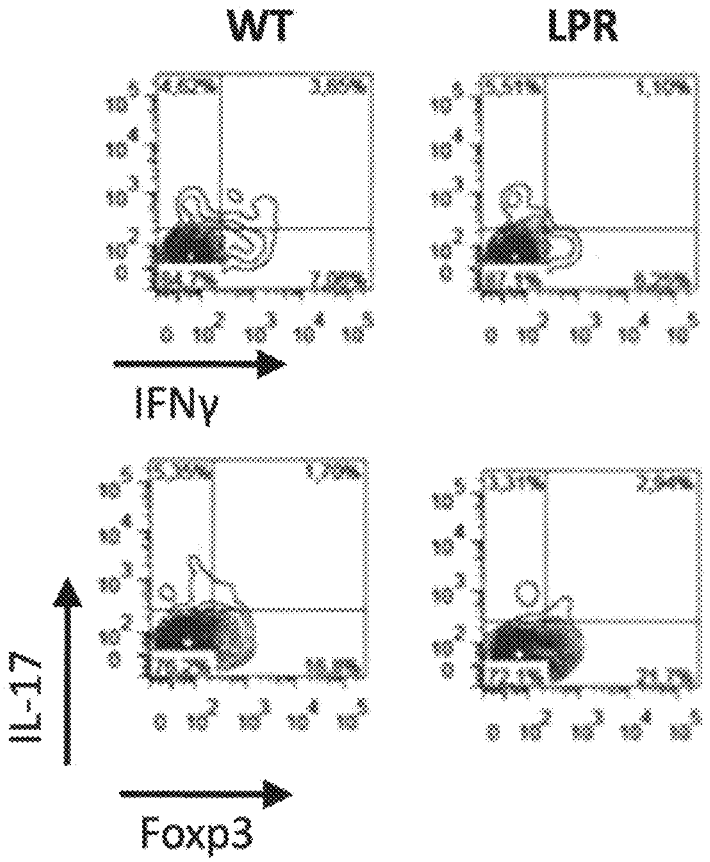
Figure 31A:
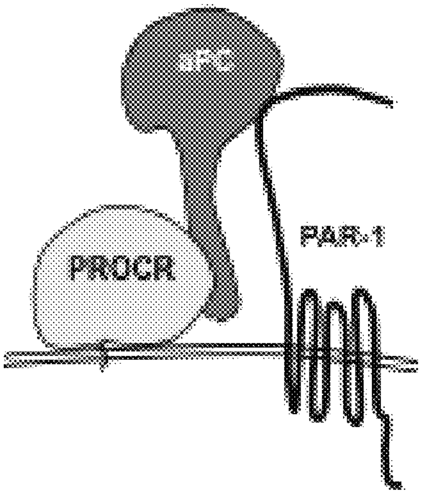
FIGS. 31A-31D are a series of graphs and illustrations depicting that PROCR is expressed on Th17 cells.
Figure 31B:
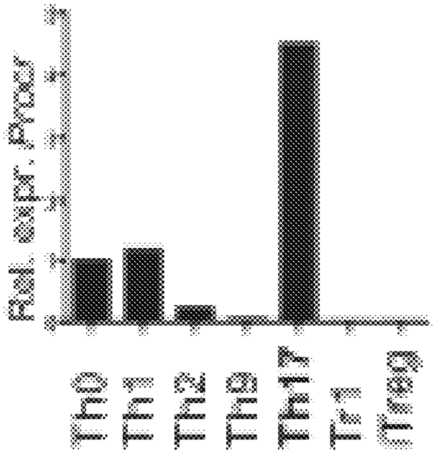
Figure 31C:
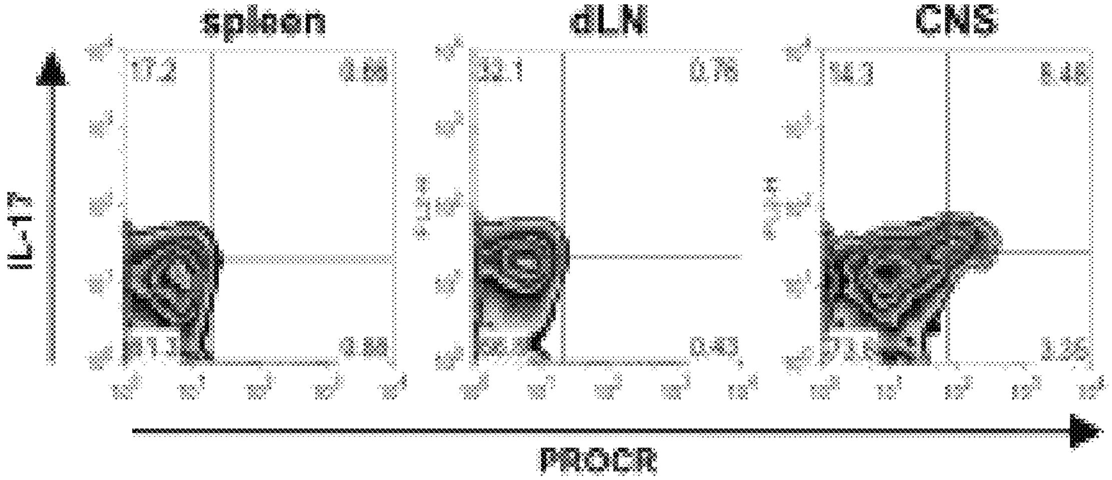
Figure 31D:
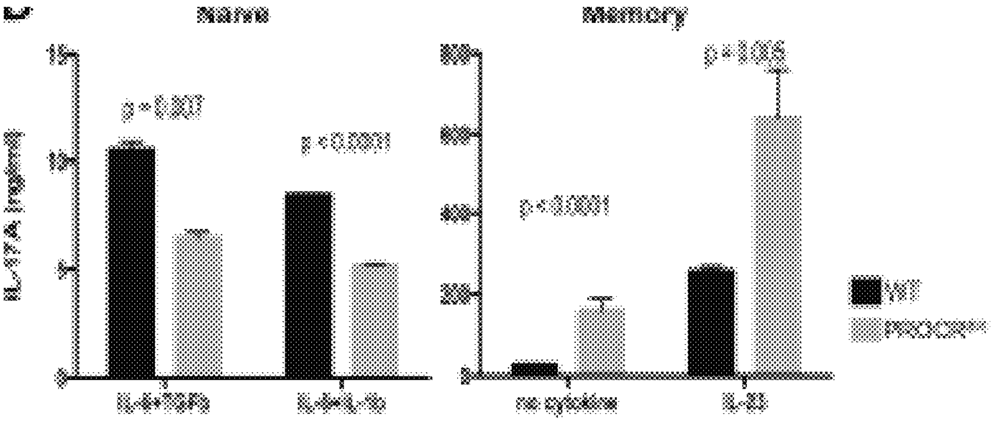

PROCR is expressed in Th17 cells: The membrane receptor PROCR (Protein C receptor; also called EPCR or CD201) is present on epithelial cells, monocytes, macrophages, neutrophils, eosinophils, and natural killer cells but its expression had not previously been reported on T cells (Griffin J H, Zlokovic B V, Mosnier L O. 2012. Protein C anticoagulant and cytoprotective pathways. Int J Hematol 95: 333-45). However, the detailed transcriptomic analysis of Th17 cells described herein has identified PROCR as an important node for Th17 cell differentiation (Yosef N, Shalek A K, Gaublomme J T, Jin H, Lee Y, Awasthi A, Wu C, Karwacz K, Xiao S, Jorgolli M, Gennert D, Satija R, Shakya A, Lu D Y, Trombetta J J, Pillai M R, Ratcliffe P J, Coleman M L, Bix M, Tantin D, Park H, Kuchroo V K, Regev A. 2013. Dynamic regulatory network controlling TH17 cell differentiation. Nature 496: 461-8). PROCR shares structural homologies with the CD1/MHC molecules and binds activated protein C (aPC) as well as blood coagulation factor VII and the Vγ4Vδ5 TCR of γδ T cells. Due to its short cytoplasmic tail PROCR does not signal directly, but rather signals by associating with the G-protein-coupled receptor PAR1 (FIG. 30*a*; (Griffin et al, Int J Hematol 95: 333-45 (2012))). To analyze PROCR expression on Th subsets, CD4+ T cells were differentiated in vitro under polarizing conditions and determined PROCR expression. As indicated by the network analysis of Th17 cells, high levels of PROCR could be detected in cells differentiated under Th17 conditions (FIG. 31*b*). To study expression of PROCR on Th17 cells during an immune response, mice were immunized with MOG/CFA to induce EAE. PROCR was not expressed on T cells in spleen and lymph nodes. In contrast, it could be detected on Th17 cells infiltrating the CNS (FIG. 31*c*). These data indicate that PROCR is expressed on Th17 cells in vitro and in vivo, where it is largely restricted to T cells infiltrating the target organ. To investigate the functions of PROCR in Th17 cells, studies were designed to test how loss of PROCR would affect IL-17 production using T cells from a PROCR hypomorphic mutant (PROCRd/d). PROCR deficiency causes early embryonic lethality (embryonic day 10.5) (Gu J M, Crawley J T, Ferrell G, Zhang F, Li W, Esmon N L, Esmon C T. 2002. Disruption of the endothelial cell protein C receptor gene in mice causes placental thrombosis and early embryonic lethality. J Biol Chem 277: 43335-43), whereas hypomorphic expression of PROCR, which retain only small amounts (<10% of wild-type) of PROCR, is sufficient to completely abolish lethality and mice develop normally under steady state conditions (Castellino F J, Liang Z, Volkir S P, Haalboom E, Martin J A, Sandoval-Cooper M J, Rosen E D. 2002. Mice with a severe deficiency of the endothelial protein C receptor gene develop, survive, and reproduce normally, and do not present with enhanced arterial thrombosis after challenge. Thromb Haemost 88: 462-72). When challenged in a model for septic shock, PROCRd/d mice show compromised survival compared to WT mice (Iwaki T, Cruz D T, Martin J A, Castellino F J. 2005. A cardioprotective role for the endothelial protein C receptor in lipopolysaccharide-induced endotoxemia in the mouse. Blood 105: 2364-71). Naïve CD4+ PROCRd/d T cells differentiated under Th17 conditions produced less IL-17 compared to WT naïve CD4+ T cells (FIG. 31*d*). Effector memory PROCRd/d T cells cultured with IL-23 produced more IL-17 than WT memory T cells. Therefore PROCR, similar to PD-1, promotes generation of Th17 cells from naïve CD4 T cells, but inhibits the function of Th17 effector T cells.

Figure 44:
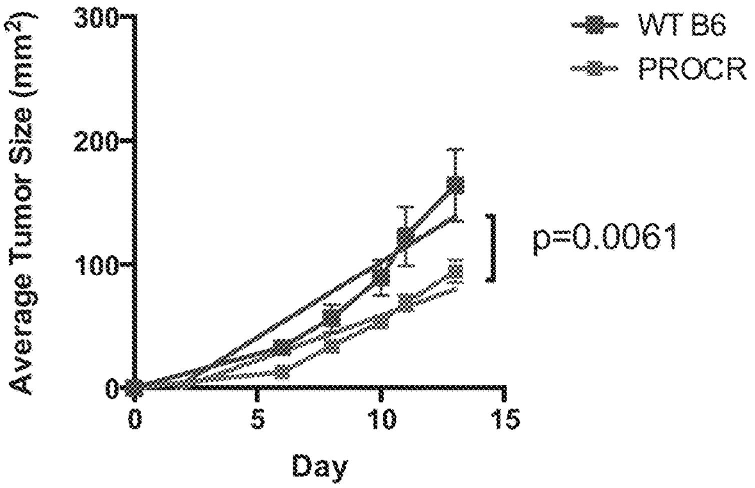
FIG. 44 is a graph depicting B16 tumor inoculation of PROCR mutant mice. 7 week old wild type or PROCR mutant (EPCR delta) C57BL/6 mice were inoculated with $5\times10^5$ B16F10 melanoma cells.

Knockdown Analysis of PROCR in Tumor Model: FIG. 44 is a graph depicting B16 tumor inoculation of PROCR mutant mice. 7 week old wild type or PROCR mutant (EPCR delta) C57BL/6 mice were inoculated with $5\times10^5$ B16F10 melanoma cells. As shown in FIG. 44, inhibition of PROCR slowed tumor growth. Thus, inhibition of PROCR is useful for impeding tumor growth and in other therapeutic applications for treatment of cancer.

PD-1 and PROCR affect Th17 pathogenicity: Th17 cells are very heterogeneous and the pathogenicity of Th17 subsets differs depending on the cytokine environment during their differentiation (Zielinski C E, Mele F, Aschenbrenner D, Jarrossay D, Ronchi F, Gattorno M, Monticelli S, Lanzavecchia A, Sallusto F. 2012. Pathogen-induced human TH17 cells produce IFN-gamma or IL-10 and are regulated by IL-1beta. Nature 484: 514-8; Lee Y, Awasthi A, Yosef N, Quintana F J, Peters A, Xiao S, Kleinewietfeld M, Kunder S, Sobel R A, Regev A, Kuchroo V. 2012. Induction and molecular signature of pathogenic Th17 cells. Nat Immunol In press; and Ghoreschi K, Laurence A, Yang X P, Tato C M, McGeachy M J, Konkel J E, Ramos H L, Wei L, Davidson T S, Bouladoux N, Grainger J R, Chen Q, Kanno Y, Watford W T, Sun H W, Eberl G, Shevach E M, Belkaid Y, Cua D J, Chen W, O'Shea J J. 2010. Generation of pathogenic T(H)17 cells in the absence of TGF-beta signalling. Nature 467: 967-71). In addition to the cytokine milieu, several costimulatory pathways have been implicated in regulating differentiation and function of T helper subsets, including Th17 cells. CTLA-4-B7 interactions inhibit Th17 differentiation (Ying H, Yang L, Qiao G, Li Z, Zhang L, Yin F, Xie D, Zhang J. 2010. Cutting edge: CTLA-4-B7 interaction suppresses Th17 cell differentiation. J Immunol 185: 1375-8). Furthermore, the work described herein revealed that ICOS plays a critical role in the maintenance of Th17 cells (Bauquet A T, Jin H, Paterson A M, Mitsdoerffer M, Ho I C, Sharpe A H, Kuchroo V K. 2009. The costimulatory molecule ICOS regulates the expression of c-Maf and IL-21 in the development of follicular T helper cells and TH-17 cells. Nat Immunol 10: 167-75).

Figure 32A:
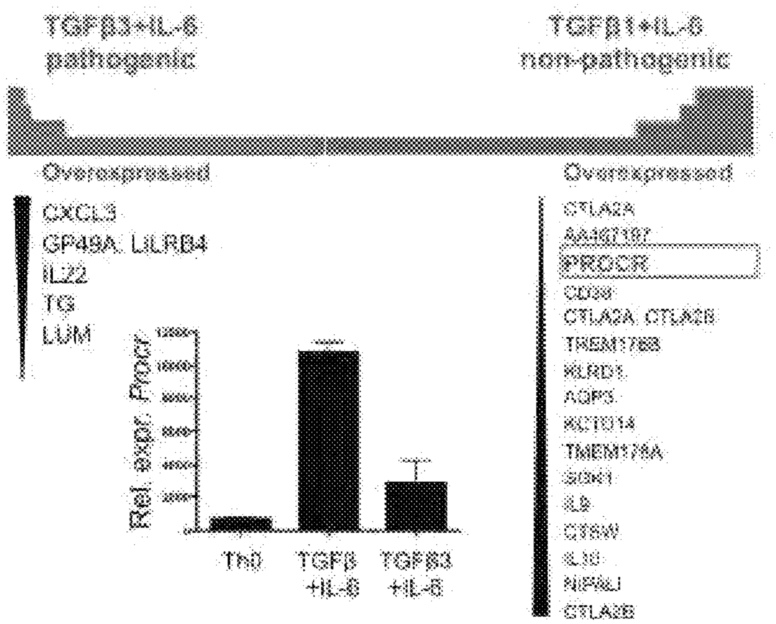
FIGS. 32A-32D are a series of graphs depicting how PROCR and PD-1 expression affects Th17 pathogenicity.
Figure 32B:
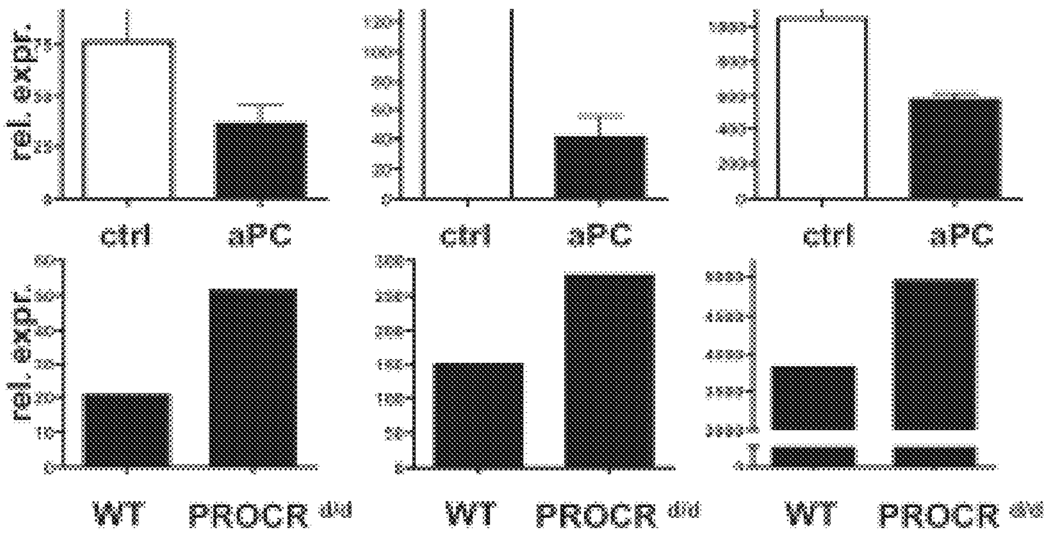
Figure 32C:
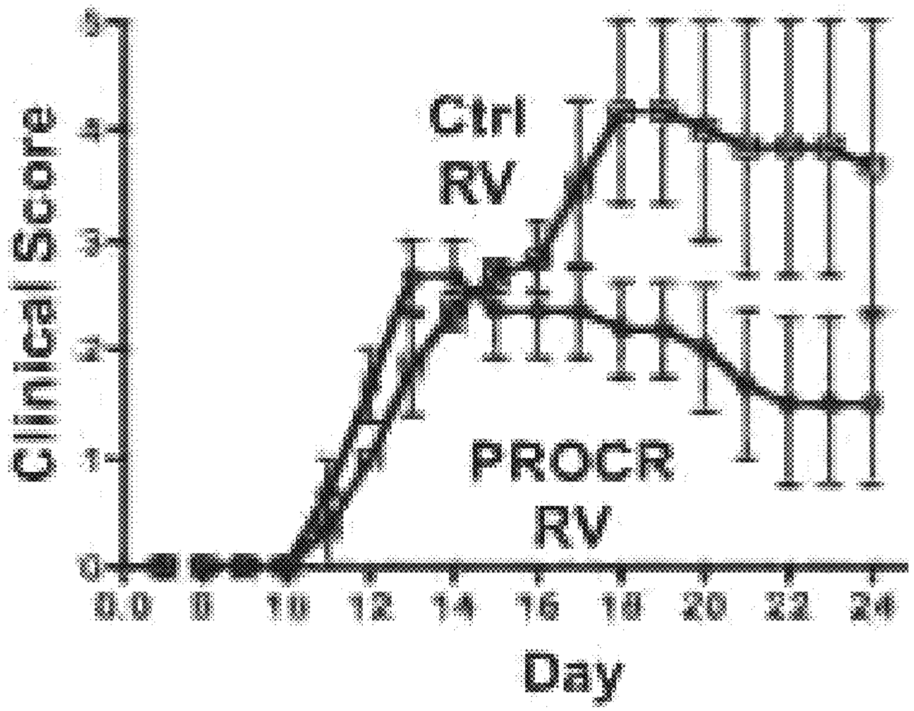
Figure 32D:
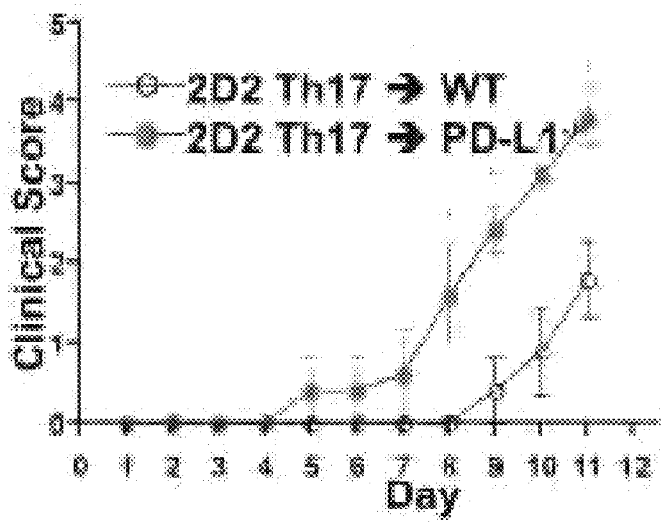

Based on the detailed genomic analysis of pathogenic vs. non-pathogenic Th17 cells herein, it has been determined that the molecular signatures that define pathogenic vs.

non-pathogenic effector Th17 cells in autoimmune disease (Lee Y, Awasthi A, Yosef N, Quintana F J, Peters A, Xiao S, Kleinewietfeld M, Kunder S, Sobel R A, Regev A, Kuchroo V. 2012. Induction and molecular signature of pathogenic Th17 cells. Nat Immunol In press). Interestingly, PROCR is part of the signature for non-pathogenic Th17 cells and its expression is highly increased in non-pathogenic subsets (FIG. 32*a*). Furthermore, PROCR seems to play a functional role in regulating Th17 pathogenicity as engagement of PROCR by its ligand aPC induces some non-pathogenic signature genes, while Th17 cells from PROCRd/d mice show decreased expression of these genes (FIG. 32*b*). To study whether PROCR could also affect pathogenicity of Th17 cells in an in vivo model of autoimmunity, an adoptive transfer model for EAE was used. To induce disease, MOG-specific 2D2 TCR transgenic T cells were differentiated under Th17 conditions and then transferred into naïve recipients. As shown in FIG. 32*c*, forced overexpression of PROCR on Th17 cells ameliorated disease, confirming that PROCR drives conversion of pathogenic towards non-pathogenic Th17 cells. In addition, it was found that PD-1:PD-L1 interactions limit the pathogenicity of effector Th17 cells in vivo. When MOG35-55-specific (2D2) Th17 effector cells were transferred into WT vs. PD-L1−/− mice, PD-L1−/− recipients rapidly developed signs of EAE (as early as day 5 post transfer), and EAE severity was markedly increased with most experiments needed to be terminated due to rapid onset of morbidity in PD-L1−/− recipients (FIG. 32*d*). The number of CNS-infiltrating cells was significantly increased in PD-L1−/− recipients with a greater percentage of 2D2+ IL-17+ in PD-L1−/− recipients compared to WT mice. Therefore both PD-1 and PROCR seem to control pathogenicity of effector Th17 cells.

Figure 33A:
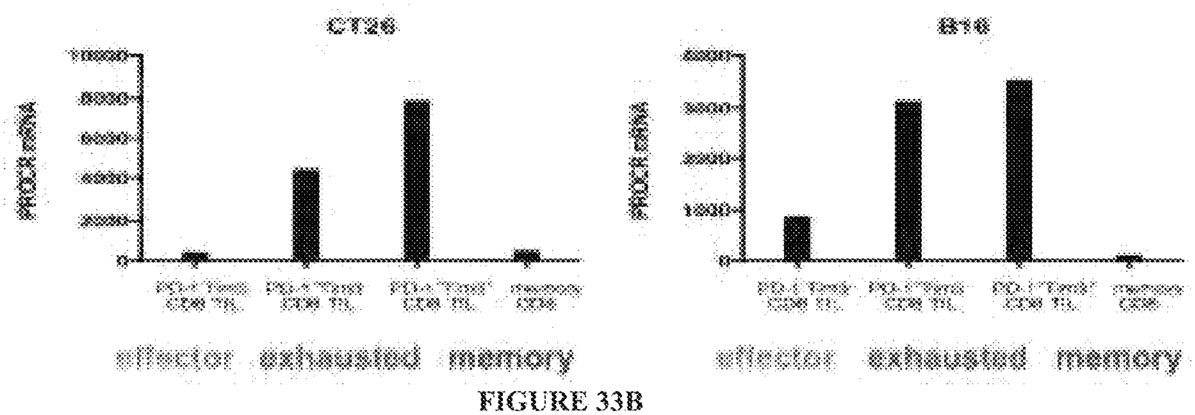
FIGS. 33A-33B are a series of graphs depicting that PROCR expression is enriched in exhausted T cells.
Figure 33B:
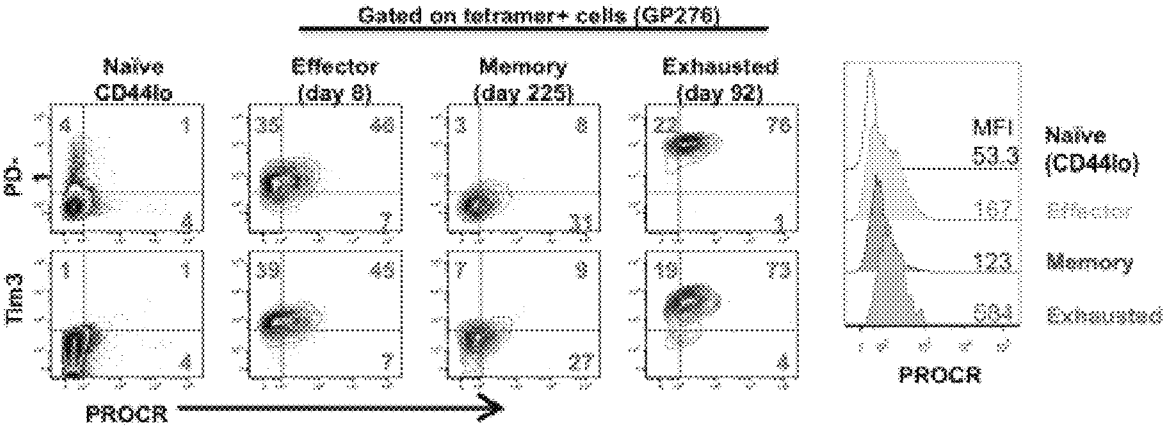

Several co-inhibitory molecules have been implicated in T cell dysfunction during antigen persistence. PD-1 and Tim-3, in particular, have wide implications in cancer and chronic viral infections such as HIV, HCV in human and LCMV in mice. Autoreactive T cell responses in mice and human are characterized with reduced expression of inhibitory molecules. The ability to induce T cell dysfunction in autoimmune settings could be clinically beneficial. MS patients that respond to Copaxone treatment show significantly elevated levels of expression of PROCR and PD-L1. It has been previously demonstrated that increasing Tim-3 expression and promoting T cell exhaustion provides the ability to limit encephalitogenecity of T cells and reduce EAE severity (Rangachari M, Zhu C, Sakuishi K, Xiao S, Karman J, Chen A, Angin M, Wakeham A, Greenfield E A, Sobel R A, Okada H, McKinnon P J, Mak T W, Addo Anderson A C, Kuchroo V K. 2012. Bat3 promotes T cell responses and autoimmunity by repressing Tim-3-mediated cell death and exhaustion. Nat Med 18: 1394-400). Studies were, therefore, designed to determine whether the novel inhibitory molecule PROCR, which is selectively enriched in Th17 cells, could also play a role in T cell exhaustion. It was found that PROCR is expressed in exhausted tumor infiltrating lymphocytes that express both PD-1 and Tim-3 (FIG. 33*a*). Consistent with this observation, it was found that PROCR was most enriched in antigen-specific exhausted CD8 T cells (FIG. 33*b*) during chronic LCMV infection. While T cell exhaustion is detrimental in chronic viral infection and tumor immunity, induction of exhaustion may play a beneficial role in controlling potentially pathogenic effector cells that cause autoimmune diseases. Regulating the expression and/or function of PD-1 and PROCR might provide the avenues to accomplish this task in controlling autoimmunity.

Example 7

Fas in Th Cell Differentiation

Fas, also known as FasR, CD95, APO-1, TNFRSF6, is a member of the TNF receptor superfamily. Binding of FasL leads to FAS trimers that bind FADD (death domains), which activates caspase-8 and leads to apoptosis. Fas also exhibits apoptosis independent effects such as interaction with Akt, STAT3, and NF-κB in liver cells and interaction with NF-κB and MAPK pathways in cancer cells.

Lpr mice are dominant negative for Fas (transposon intron 1), creating a functional knockout (KO). These mice exhibit lymphoproliferative disease (lpr); age dependent >25-fold size increase of LN, Spleen; expansion of Thy1+B220+ CD4-CD8-TCRa/b+ T cells. These mice produce spontaneous anti-dsDNA Ab, systemic autoimmunity, which makes them a model of systemic lupus erythematosus (SLE), but these mice are resistant to experimental autoimmune encephalomyelitis (EAE). Gld mice are dominant negative for FasL. Fas flox mice that are CD4Cre-/CD19Cre-/CD4Cre-CD19Cre-/LckCre-Fasflox exhibit no lymphoproliferation and no expansion of Thy1+B220+CD4-CD8-TCRa/b+ T cells. These mice do exhibit progressive lymphopenia, inflammatory lung fibrosis, and wasting syndrome. Fas flox mice that are MxCre+poly(IC)-Fasflox exhibit an lpr phenotype. Fas flox mice that are MOGCre-Fasflox are resistant to EAE. Fas flox mice that are LysM-Cre-Fasflox exhibit lymphoproliferation and glomerulonephritis.

Although Fas (CD95) has been identified as a receptor mediating apoptosis, the data herein clearly show that Fas is important for Th17 differentiation and development of EAE. The data herein demonstrates that Fas-deficient mice have a defect in Th17 cell differentiation and preferentially differentiate into Th1 and Treg cells. The expansion of Treg cells and inhibition of Th17 cells in Fas-deficient mice might be responsible for disease resistance in EAE.

Fas-deficient cells are impaired in their ability to differentiate into Th17 cells, and they produce significantly lower levels of IL-17 when cultured in vitro under Th17 conditions (IL-1β+IL-6+IL-23). Furthermore, they display reduced levels of IL-23R, which is crucial for Th17 cells as IL-23 is required for Th17 stability and pathogenicity. In contrast, Fas inhibits IFN-γ production and Th1 differentiation, as cells derived from Fas-deficient mice secrete significantly higher levels of IFN-γ. Similarly, Fas-deficient cells more readily differentiate into Foxp3+ Tregs and secrete higher levels of the Treg effector cytokine IL-10. It therefore seems as if Fas suppresses the differentiation into Tregs and IFN-γ-producing Th1 cells while promoting Th17 differentiation. In inflammatory autoimmune disorders, such as EAE, Fas therefore seems to promote disease progression by shifting the balance in T helper cells away from the protective Tregs and from IFN-γ-producing Th1 cells towards pathogenic Th17 cells.

Example 8

Targeting CD5L in Modulation of Th17 Pathogenic State

CD5L (CD5 antigen-like; AIM (apoptosis inhibitor of macrophage)) has been identified as a novel regulator of the Th17 pathogenic state. CD5L is a 54-kD protein belongs to the macrophage scavenger receptor cysteine-rich domain superfamily; other family member include CD5, CD6, CD36, MARCO etc. CD5L is expressed by macrophage and adipocytes and is incorporated into cells through CD36 (Kurokawa J. et al. 2010). CD5L can be induced by activation of RXR/LXR (Valledor A F et al. 2004) and inhibits lipid induced apoptosis of thymocytes and macrophage. CD5L is involved in obesity-associated autoantibody production (Arai S et. al. 2013) and plays a role in lipid metabolism. CD5L promotes lipolysis in adipocytes, potentially preventing obesity onset (Miyazaki T et al. 2011) and inhibits de novo lipid synthesis by inhibiting fatty acid synthase (Kurokawa J. et al. 2010).

Figure 34A:
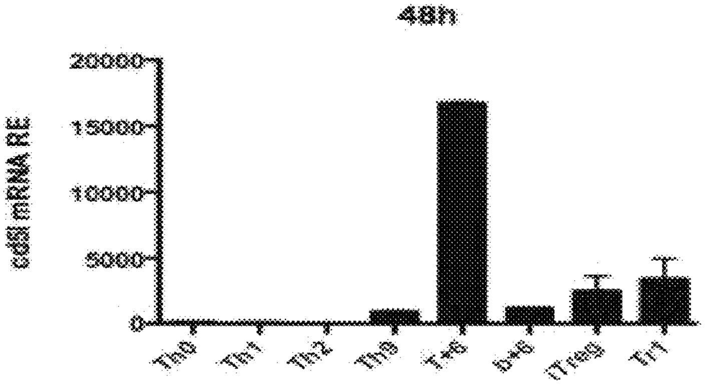
FIGS. 34A-34C are a series of graphs demonstrating the expression of CD5L on Th17 cells.
Figure 34B:
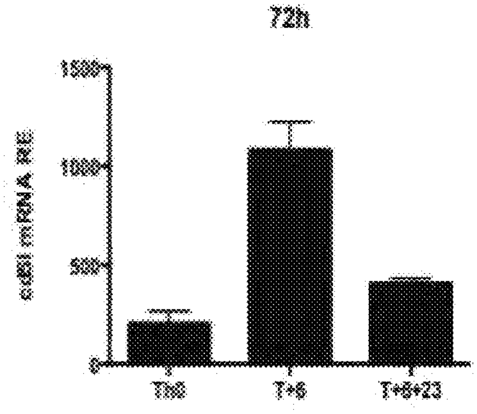
Figure 34C:
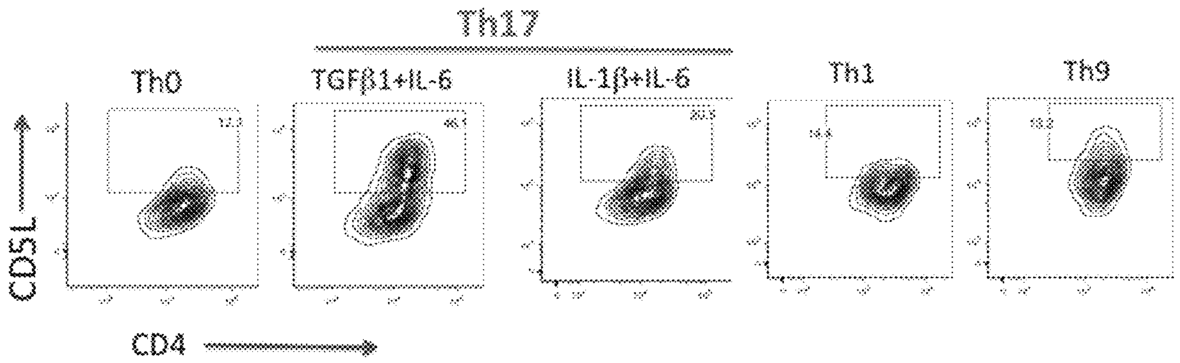
Figure 35A:
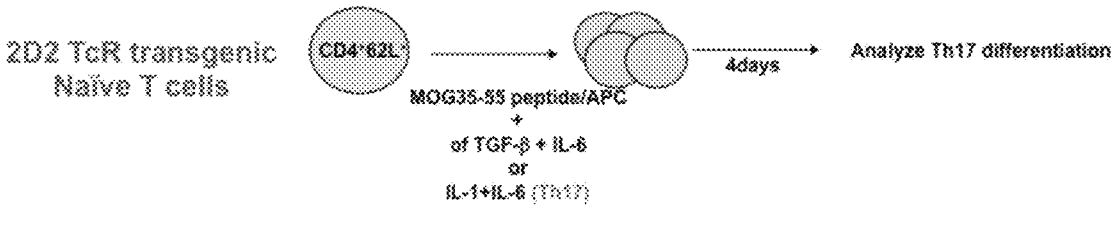
FIGS. 35A-35C are a series of illustrations and graphs depicting how CD5L deficiency does not alter Th17 differentiation.
Figure 35B:
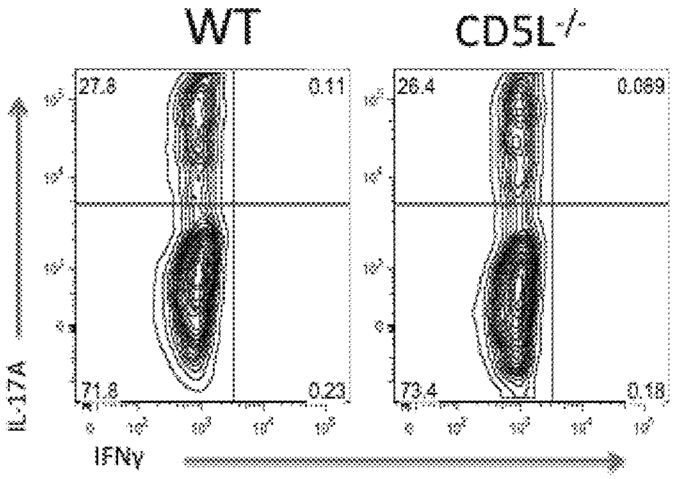
Figure 35C:
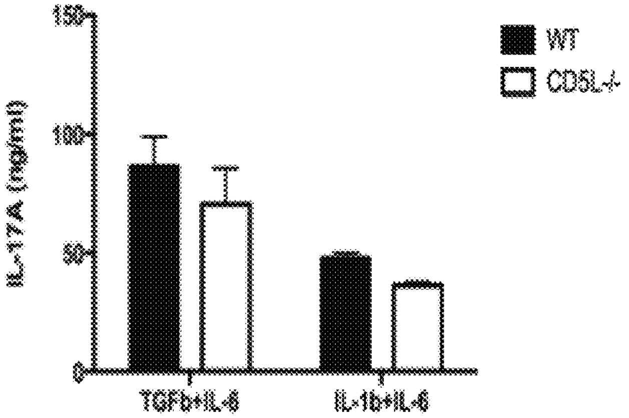
Figure 36A:
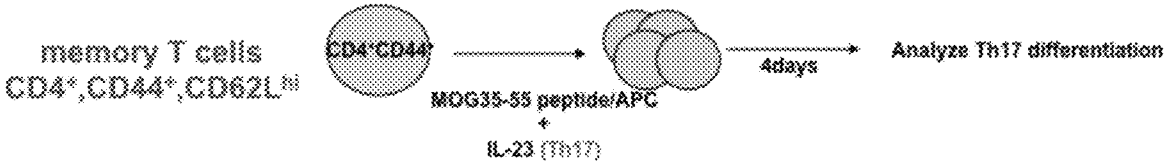
FIGS. 36A-36B are a series of illustrations and graphs depicting how CD5L deficiency alters Th17 memory by affecting survival or stability.
Figure 36B:
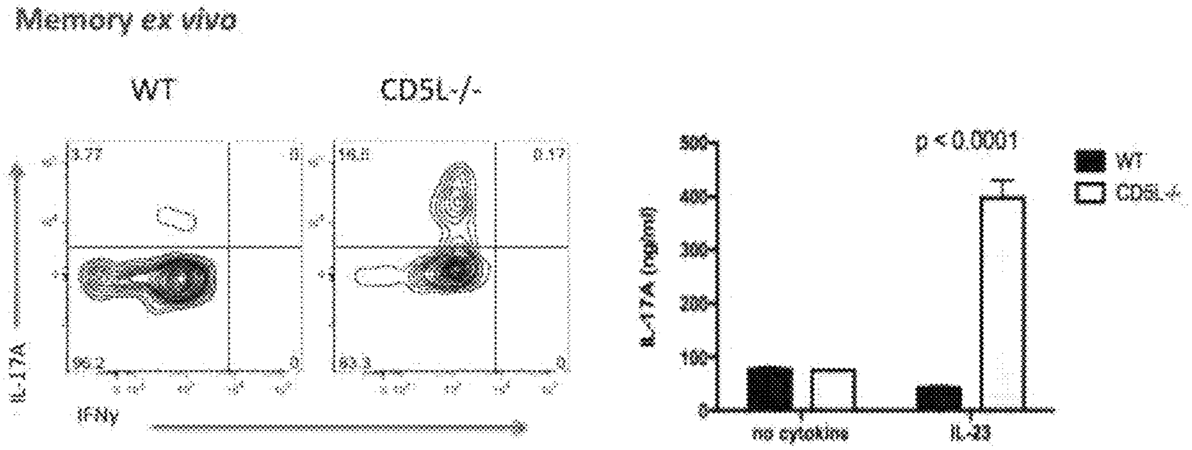

FIGS. 34A-34C are a series of graphs demonstrating the expression of CD5L on Th17 cells. FIGS. 35A-35C are a series of illustrations and graphs depicting how CD5L deficiency does not alter Th17 differentiation. FIGS. 36A-36C are a series of illustrations and graphs depicting how CD5L deficiency alters Th17 memory by affecting survival or stability.

Figure 37A:
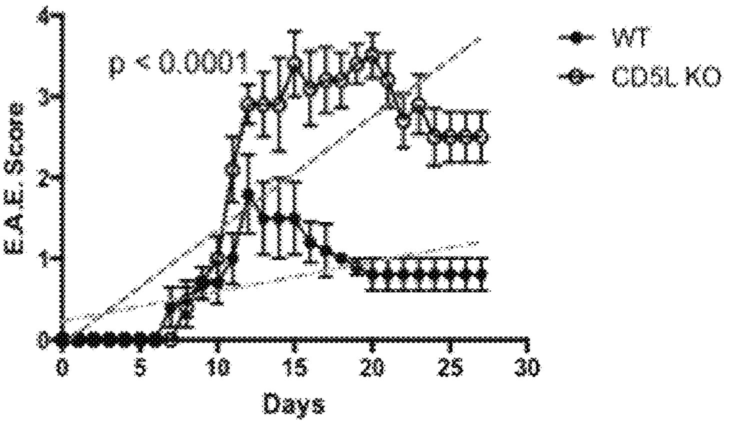
FIGS. 37A-37B are a series of graphs depicting how CD5L deficiency results in more severe and prolonged EAE with higher Th17 responses.
Figure 37B:
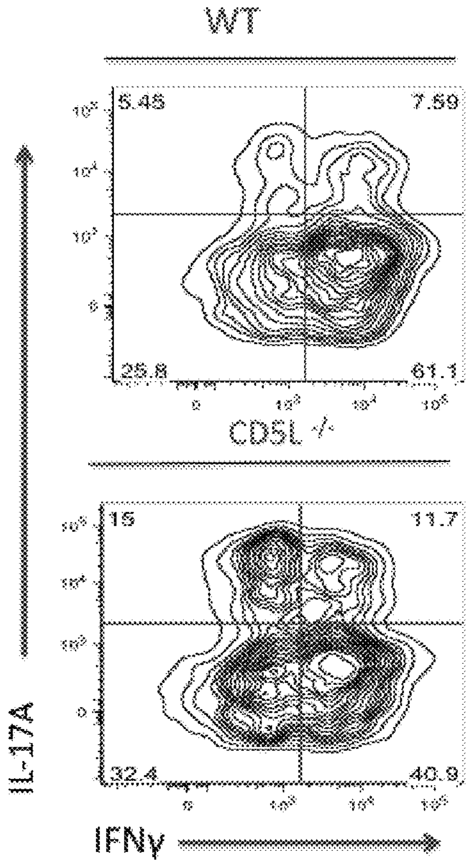
Figure 38A:
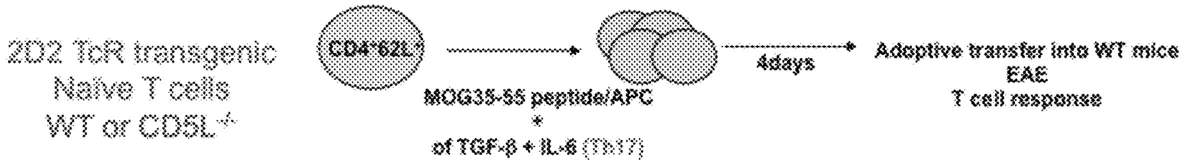
FIGS. 38A-38C are a series of illustrations and graphs depicting how loss of CD5L converts non-pathogenic Th17 cells into pathogenic effector Th17 cells.
Figure 38B:
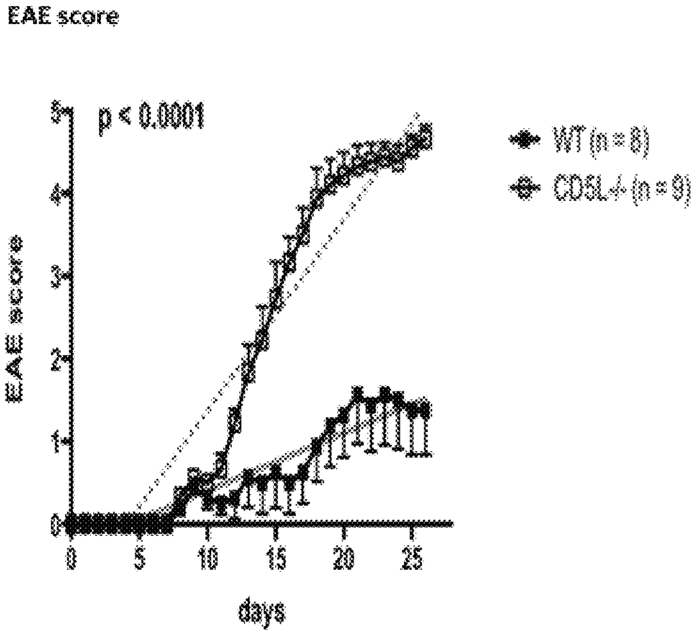
Figure 38C:
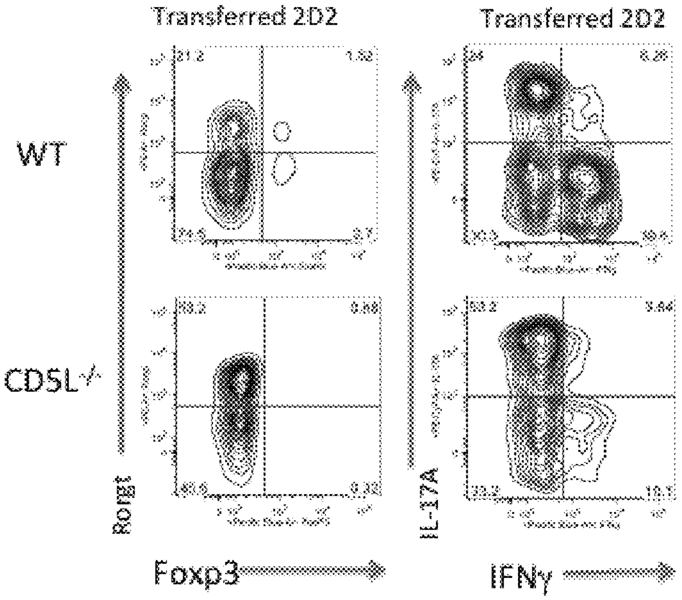
Figure 39A:
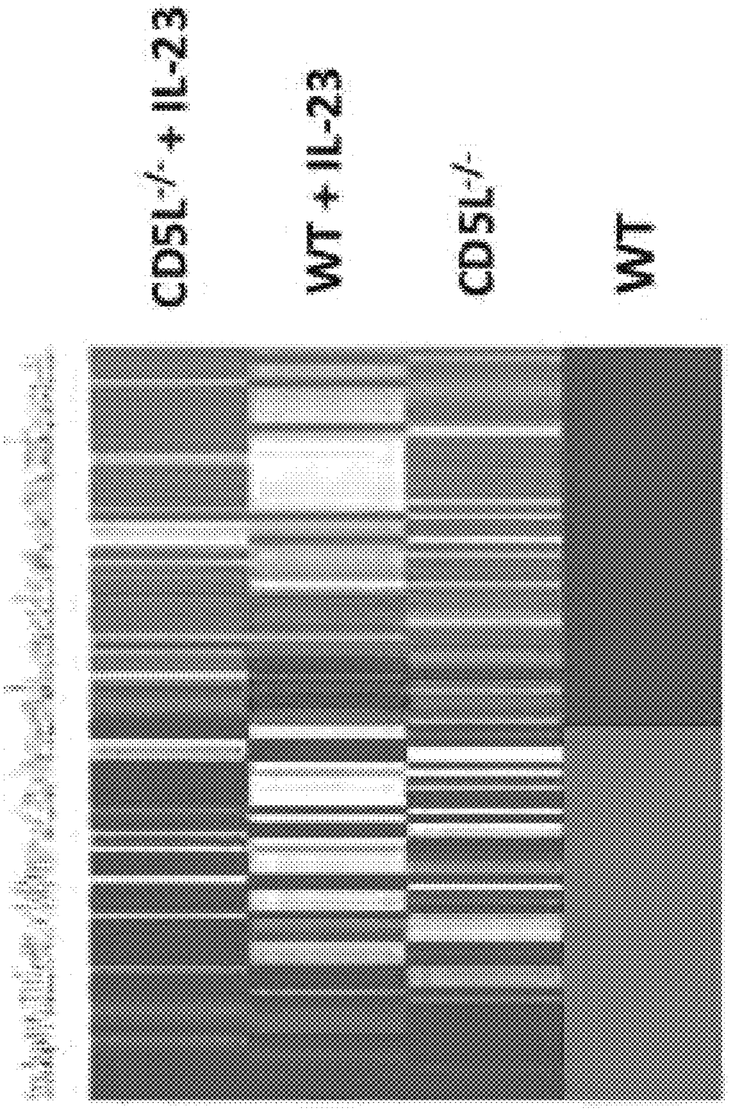
FIGS. 39A-39B are a series of graphs depicting how CD5L-deficient Th17 cells (TGF-β+IL-6) develop a pathogenic phenotype.
Figure 39B:
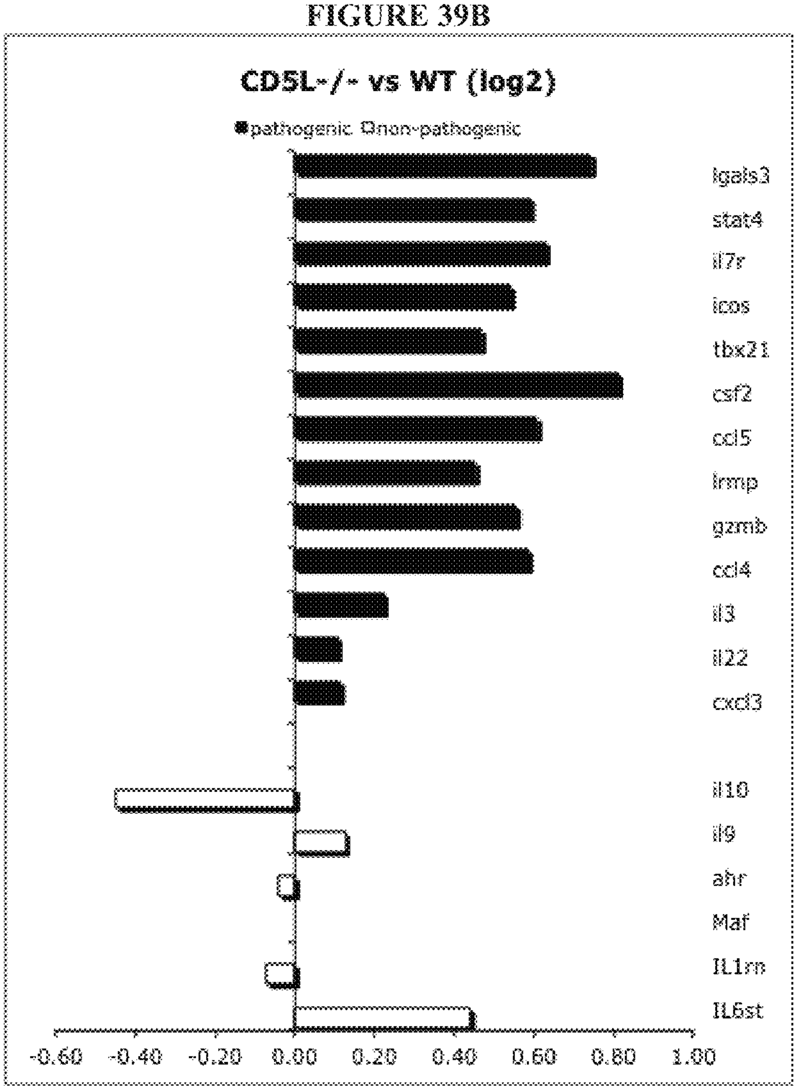

FIGS. 37A-37B are a series of graphs depicting how CD5L deficiency results in more severe and prolonged EAE with higher Th17 responses. FIGS. 38A-38C are a series of illustrations and graphs depicting how loss of CD5L converts non-pathogenic Th17 cells into pathogenic effector Th17 cells. FIGS. 39A-39B are a series of graphs depicting how CD5L-deficient Th17 cells (TGF-β+IL-6) develop a pathogenic phenotype.

Example 9

Single Cell Analysis of Functional Th17 Data

Single cell analysis of target genes that can be exploited for therapeutic and/or diagnostic uses allows for the identification of genes that either cannot be identified at a population level or are not otherwise ready apparent as a suitable target gene at the population level.

Single-cell RNA sequencing provides a unique opportunity to characterize different sub-types of Th17 cells and to gain better understanding of the regulatory mechanisms that underlie their heterogeneity and plasticity. In particular, the studies described herein were designed to identify subpopulations of Th17 cells both in-vitro and in-vivo, and to map the potential divergent mechanisms at play. These results provide important mechanistic insights with the potential for therapeutic relevance in treatment of autoimmune-disease.

Using a microfluidic technology (Fluidigm C1) for preparation of single-cell mRNA SMART-Seq libraries, differentiated Th17 cells (96 cells at a time) were profiled in-vitro under pathogenic and non-pathogenic polarizing conditions at two time points (48 h and 96 h into the differentiation process). In addition, Th17 cells isolated from the central nervous system and lymph nodes were profiled at the peak of disease of mice immunized with experimental autoimmune encephalomyelitis (EAE; a mouse model of multiple sclerosis). A computational pipeline was then developed for processing and analyzing the resulting data set (~1000 cells altogether). The results offer a vantage point into the sources and functional implications of expression patterns observed at the single cell level, expression modality, i.e., map how a gene is expressed across the population, and variability, i.e., how tightly the expression level of a gene is regulated.

For instance, it was found that the signature cytokine IL-17A exhibits one of the highest levels of variability in the cell's transcriptome in-vitro. This variation strongly correlates with an unsupervised partition of the cells into subpopulations, which spans the spectrum between potentially pathogenic cells (high levels of IL-17A and low levels of immunosuppressive cytokines like IL-10) to non-pathogenic cells (opposite expression profiles).

The specific genes that characterize the two extreme states provide appealing target genes and include candidates that were not detected by previous, population-level approaches (Yosef, N. et al. Dynamic regulatory network controlling TH17 cell differentiation. Nature 496, 461-468, doi: 10.1038/nature11981 (2013)). To identify the most promising target genes, a gene prioritization scheme, which combines the single cell RNA-seq results with multiple other sources of information (e.g., transcription factor binding), was developed. High-ranking targets were then further analyzed using the respective knockout mice.

The following provides single cell analysis methods and conditions to induce various T cell phenotypes:

- Condition Th0: cells are activated with CD3/CD28, but no cytokines are added to the media as a control
- Condition T16: CD3/CD28 activation+TGFβ1+IL6 are added to media to produce non-pathogenic Th17 conditions
- Condition T36: CD3/CD28 activation+TGFβ3+IL6 are added to media to produce pathogenic Th17 conditions
- Condition B623: CD3/CD28 activation+IL1β+IL6+IL23 are added to media to produce pathogenic Th17 conditions
- Condition T: CD3/CD28 activation+TGFβ1 are added to media to produce Treg conditions Under condition Th0, proliferation of cell is activated but the cells are not influenced toward a specific outcome. Under conditions T16, T36 and B623, the activated, proliferating cells are influenced toward a specific Th17 cell outcome, as indicated above. Again, the terms "pathogenic" or "non-pathogenic" as used herein are not to be construed as implying that one Th17 cell phenotype is more desirable than the other. They are being used to connote different Th17 cell phenotypes with different identifying characteristics.

The following methods were used in the studies described herein: Mice: C57BL/6 wild-type, CD4−/−(2663). Mice were obtained from Jackson Laboratory. IL-17A-GFP mice were from Biocytogen. In addition, spleens and lymph nodes from GPR65−/− mice were provided by Yang Li. ZBTB32−/− mice were obtained from the laboratory of Pier Paolo Pandolfi. Cell sorting and in vitro T-cell differentiation: CD4+ T cells were purified from spleen and lymph nodes using anti-CD4 microbeads (Miltenyi Biotec) then stained in PBS with 1% FCS for 20 min at room temperature with anti-CD4-PerCP, anti-CD62l-APC and anti-CD44-PE antibodies (all Biolegend). Naive CD4+ CD62lhighCD44low T cells were sorted using the BD FACSAria cell sorter. Sorted cells were activated with plate-bound anti-CD3 (2 μg ml-1) and anti-CD28 (2 μg ml-1) in the presence of cytokines. For TH17 differentiation, the following reagents were used: 2 ng/ml recombinant human TGF-β1 and recombinant human TGF-β3 (Miltenyi Biotec), 25 ng/ml recombinant mouse IL-6 (Miltenyi Biotec), 20 ng/ml recombinant mouse IL-23 (R&D Biosystems) and 20 ng/ml recombinant mouse IL-1β (Miltenyi Biotec). Cells were cultured for 48-96 h and collected for RNA, intracellular cytokine staining, flow-fish.

CyTOF and flow cytometry: Active induction of EAE and disease analysis: For active induction of EAE, mice were immunized by subcutaneous injection of 100 μg MOG (35-55) (MEVGWYRSPFSRVVHLYRNGK) (SEQ ID NO: 1395) in CFA, then received 200 ng pertussis toxin intraperitoneally (List Biological Laboratory) on days 0 and 2. Mice were monitored and were assigned scores daily for development of classical and atypical signs of EAE according to the following criteria: 0, no disease; 1, decreased tail tone or mild balance defects; 2, hind limb weakness, partial paralysis or severe balance defects that cause spontaneous falling over; 3, complete hind limb paralysis or very severe balance defects that prevent walking; 4, front and hind limb paralysis or inability to move body weight into a different position; 5, moribund state (ger, A., Dardalhon, V., Sobel, R. A., Bettelli, E. & Kuchroo, V. K. Th1, Th17, and Th9 effector cells induce experimental autoimmune encephalomyelitis with different pathological phenotypes. Journal of immunology 183, 7169-7177, doi:10.4049/jimmunol.0901906 (2009)).

Isolation of T-cells from EAE mice at the peak of disease: At the peak of disease, mice T-cells were collected from the draining lymph nodes and the CNS. For isolation from the CNS, mice were perfused through the left ventricle of the heart with cold PBS. The brain and the spinal cord were flushed out with PBS by hydrostatic pressure. CNS tissue was minced with a sharp razor blade and digested for 20 min at 37° C. with collagenase D (2.5 mg/ml; Roche Diagnostics) and DNaseI (1 mg/ml; Sigma). Mononuclear cells were isolated by passage of the tissue through a cell strainer (70 μm), followed by centrifugation through a Percoll gradient (37% and 70%). After removal of mononuclear cells, the lymphocytes were washed, stained and sorted for CD3 (Biolegend), CD4 (Biolegend), 7AAD and IL17a-GFP or FOXP3-GFP.

Whole transcriptome amplification: Cell lysis and SMART-Seq (amskold, D. et al. Full-length mRNA-Seq from single-cell levels of RNA and individual circulating tumor cells. Nature Biotechnology 30, 777-782 (2012)) whole transcriptome amplification (WTA) was performed on the C1 chip using the C1 Single-Cell Auto Prep System (C1 System) using the SMARTer Ultra Low RNA Kit for Illumina Sequencing (Clontech) with the following modifications:

Cell Lysis Mix:

| Composition | Stock Conc. | Volume |
|---|---|---|
| C1 Loading Reagent | 20X | 0.60 ul |
| SMARTer Kit RNase Inhibitor | 40 x | 0.30 ul |
| SMARTer Kit 3' SMART CDS Primer II A | 12 μM | 4.20 ul |
| SMARTer Kit Dilution Buffer | 1X | 6.90 ul |

Cycling Conditions I:
a) 72° C., 3 min
b) 4° C., 10 min
c) 25° C., 1 min

Reverse Transcription (RT) Reaction Mix:

| Composition | Stock Conc. | Volume |
|---|---|---|
| C1 Loading Reagent | 20.0 x | 0.45 ul |
| SMARTer Kit 5X First-Strand Buffer (RNase-Free) | 5.0 x | 4.20 ul |
| SMARTer Kit Dithiothreitol | 100 mM | 0.53 ul |
| SMARTer Kit dNTP Mix (dATP, dCTP, dGTP, and dTTP, each at 10 mM) | 10 mM | 2.10 ul |
| SMARTer Kit SMARTer II A Oligonucleotide | 12 uM | 2.10 ul |
| SMARTer Kit RNase Inhibitor | 40 x | 0.53 ul |
| SMARTer Kit SMARTScribe ™ Reverse Transcriptase | 100.0 x | 2.10 ul |

Cycling Conditions II:
a) 42° C., 90 min
b) 70° C., 10 min

PCR Mix:

| Composition | Stock Conc. | Volume |
|---|---|---|
| PCR Water | — | 35.2 ul |
| 10X Advantage 2 PCR Buffer | 10.0 x | 5.6 ul |
| 50X dNTP Mix | 10 mM | 2.2 ul |
| IS PCR primer | 12 uM | 2.2 ul |
| 50X Advantage 2 Polymerase Mix | 50.0 x | 2.2 ul |
| C1 Loading Reagent | 20.0 x | 2.5 ul |

Cycling Conditions III:
a) 95° C., 1 min
b) 5 cycles of:
i) 95° C., 20 s
ii) 58° C., 4 min
ii) 68° C., 6 min
c) 9 cycles of:
i) 95° C., 20 s
ii) 64° C., 30 s
ii) 68° C., 6 min
d) 7 cycles of:
i) 95° C., 30 s
ii) 64° C., 30 s
ii) 68° C., 7 min
e) 72° C., 10 min Library preparation and RNA-Seq: WTA products were harvested from the C1 chip and cDNA libraries were prepared using Nextera XT DNA Sample preparation reagents (Illumina) as per the manufacturer's recommendations, with minor modifications. Specifically, reactions were run at ¼ the recommended volume, the tagmentation step was extended to 10 minutes, and the extension time during the PCR step was increased from 30 s to 60 s. After the PCR step, all 96 samples were pooled without library normalization, cleaned twice with 0.9× AMPure XP SPRI beads (Beckman Coulter), and eluted in buffer TE. The pooled libraries were quantified using Quant-IT DNA High-Sensitivity Assay Kit (Invitrogen) and examined using a high sensitivity DNA chip (Agilent). Finally, samples were sequenced deeply using either a Hi Seq 2000 or a HiSeq 2500 sequencer.

RNA-Seq of population controls: Population controls were generated by extracting total RNA using RNeasy plus Micro RNA kit (Qiagen) according to the manufacturer's recommendations. Subsequently, 1 μL of RNA in water was added to 2 μL of lysis reaction mix, thermocycled using cycling conditions I (as above). Next, 4 μL of the RT Reaction Mix were added and the mixture was thermocycled using cycling conditions II (as above). Finally, 1 μL of the total RT reaction was added to 9 μL of PCR mix and that mixture was thermocycled using cycling conditions III (as above). Products were quantified, diluted to 0.125 ng/μL and libraries were prepared, cleaned, and tested as above.

Flow cytometry and intracellular cytokine staining: Sorted naive T cells were stimulated with phorbol 12-myristate 13-acetate (PMA) (50 ng/ml, Sigma-aldrich), ionomycin (1 μg/ml, Sigma-aldrich) and a protein transport inhibitor containing monensin (Golgistop) (BD Biosciences) for 4 h before detection by staining with antibodies. Surface markers were stained in PBS with 1% FCS for 20 min at room temperature, then subsequently the cells were fixed in Cytoperm/Cytofix (BD Biosciences), permeabilized with Perm/Wash Buffer (BD Biosciences) and stained with Biolegend conjugated antibodies, that is, Brilliant violet 650 anti-mouse IFN-γ (XMG1.2) and allophycocyanin-anti-IL-17A (TC11-18H10.1), diluted in Perm/Wash buffer as described 14. Foxp3 staining was performed with the Foxp3 staining kit by eBioscience (00-5523-00) in accordance with their 'One-step protocol for intracellular (nuclear) proteins'. Data were collected using either a FACS Calibur or LSR II (Both BD Biosciences), then analyzed using Flow Jo software (Treestar).

Quantification of cytokine secretion using ELISA: Naive T cells from knockout mice and their wild-type controls were cultured as described above, their supernatants were collected after 48 h and 96 h, and cytokine concentrations were determined by ELISA (antibodies for IL-17 and IL-10 from BD Bioscience) or by cytometric bead array for the indicated cytokines (BD Bioscience), according to the manufacturers' instructions.

RNA-FlowFish analysis of RNA-expression: Cells prepared under the same conditions as the RNA-seq samples were prepared with the QuantiGene® ViewRNA ISH Cell Assay kit from Affymetrix following the manufacturers protocol. High throughput image acquisition at 60× magnification with an ImageStream X MkII allows for analysis of high-resolution images, including brightfield, of single cells. Genes of interest were targeted by type 1 probes, housekeeping genes by type 4 probes, and nuclei were stained with dapi. Single cells were selected based on cell properties like area, aspect ratio (brightfield images) and nuclear staining. As a negative control, the Bacterial DapB gene (Type 1 probe) was used. Spot counting was performed with the amnis IDEAS software to obtain the expression distributions.

CyTOF analysis of protein-expression: In-vitro differentiated cells were cultured and harvested at 72 h, followed by a 3 h stimulation similar to the flow cytometry protocol described above. Subsequently samples were prepared as described previously 15. In-vivo cells isolated from lymph nodes and CNS from reporter mice were, due to their limited numbers, imbedded in a pool of CD3+ T-cells isolated from a CD4−/− mouse, to allow for proper sample preparation. The cells from the CD4−/− mouse were stained and sorted for CD3+CD4-7AAD-cells to insure that low amounts of CD4+ staining during CyTOF staining would be obtained, and CD4+ cells from LN and CNS could be identified in silico.

RNA-seq profiling of single cells during Th17 differentiation: The mRNA levels of CD4+ naïve T cells differentiated in vitro were profiled under two types of polarizing conditions: Tgfβ1+IL6 and Tgfβ3+IL6. While both treatments lead to IL17-production (Ghoreschi, K., Laurence, A., Yang, X. P., Hirahara, K. & O'Shea, J. J. T helper 17 cell heterogeneity and pathogenicity in autoimmune disease. Trends Immunol 32, 395-401 (2011)), only the latter results in autoimmunity upon adoptive transfer (ostins, L. et al. Host-microbe interactions have shaped the genetic architecture of inflammatory bowel disease. Nature 491, 119-124 (2012)). Microfluidic chips (Fluidigm C1) were used for the preparation of single-cell mRNA SMART-Seq libraries. Each polarizing condition was sampled at 48 hr and 96 hr into the differentiation process. In addition to these single cell RNA-seq libraries, their corresponding bulk populations of at least 10,000 cells, with at least two replicates for each condition and at an average depth of 15 million reads, were also sequenced.

RNA-seq reads were aligned to the NCBI Build 37 (UCSC mm9) of the mouse genome using Top-Hat. The resulting alignments were processed by Cufflinks to evaluate the expression of transcripts. An alternative pipeline based on the RSEM (RNA-Seq by expectation maximization) software for mRNA quantification was also employed. Unless stated otherwise, the results obtained with this alternative pipeline were similar to the ones presented herein.

Library quality metrics, such as genomic alignment rates, ribosomal RNA contamination, and 3' or 5' coverage bias, were computed for each library. Cells that had low values of these parameters were filtered; the remaining cells (~80% of the total profiled cells) had similar quality metrics. As an additional preprocessing step, principal components that significantly ($p<1e-3$) correlated with library quality metrics were subtracted. Finally, unless stated otherwise, genes from each sample that were not appreciably expressed (fragments per kilobase of exon per million (FPKM)>10) in at least 20% of the sample's cells were discarded, retaining on average ~6 k genes for the in vitro samples and ~3 k genes for the in vivo samples.

Although the gene expression levels of population replicates were tightly correlated with one another (Pearson $r>0.97$, log-scale), there were substantial differences in expression between individual cells ($0.72<r<0.82$, mean: 0.78; FIG. 1*b*). Despite this extensive cell-to-cell variation, the average expression across all single cells correlated well with the population data ($r>0.92$).

Single cell profiles reveal IL17-related heterogeneity in vitro: Considering the distribution of the expression from individual genes across cells differentiated with Tgfβ1+IL6, a wide spectrum of behaviors was observed. About 40% of the analyzed genes were constitutively expressed in all cells. Reassuringly, this set of genes is highly enriched for housekeeping genes ($p<x$). However, constitutive expression of TH17 signature cytokines (for example, IL17f, IL9 and IL21) and early-acting transcription factors (e.g. Rorc, Irf4, Batf, Stat3, Hif1a, and Mina) was also seen. The remaining genes exhibit a bimodal expression patterns with high mRNA levels in at least 20% of the cells and a much lower (often undetectable) levels in the remaining cells. Interestingly, the bimodal genes include key TH17 signature cytokines, chemokines and their receptors (for example, IL23r, IL17a, Ccl20). Bimodality was also seen for regulatory cytokines from the IL-10 family (IL10, IL24, IL27ra), as previously observed in population-level data. Finally, a small representation (usually <30% of cells) was seen for transcription factors and cytokines that characterize other T-cell lineages (for example, IL12rb2, Stat4 [Th1], Ccr4, and Gata3 [Th2], and low levels of Foxp3 [iTreg]). Expression of genes from the IL10 module possibly represent a self-limiting mechanism, which is active in a subset of the cells and might play a role in the 'non-pathogenic' effects of TH17 cells differentiated with Tgfβ1. Expression from other T cell subsets may represent a contamination of the sample with non-Th17 cells or, rather reflect a more complex picture of "hybrid" double positive cells.

High-throughput, high resolution, flow RNA-fluorescence in situ hybridization (RNA-FlowFISH), an amplification-free imaging technique, was performed to verify that heterogeneity in the single-cell expression data reflected true biological differences, rather than library preparation biases and technical noise associated with the amplification of small amounts of cellular RNA. For 9 genes, selected to cover a wide range of expression and variation levels, the heterogeneity detected by RNA-FLowFISH closely mirrored the sequencing data. For example, expression of housekeeping genes (such as β-actin (Actb) and β2-microglobulin (B2m)) and key Th17 transcription factors (e.g., Rorc, Irf4, Batf) matched a log-normal distribution in both single-cell RNA-Seq and RNA-FISH measurements. By contrast, other signature genes (e.g., IL17a, IL2) showed significantly greater levels of heterogeneity, recapitulating the RNA-SEQ results.

Identification of cell sub-populations: To quantify this behavior, a model by Shalek et al. (Shalek, et al. "Single-cell transcriptomics reveals bimodality in expression and splicing in immune cells." Nature 2013 May 19. doi: 10.1038/nature1217), describing the distribution of a given gene across cells using three parameters: (alpha)—the % of expressing cells; (sigma): the standard deviation of expression for the expressing cells; and (Mu): the average level of expression for expressing cells, was adapted. In this adapted model, these parameters are inferred by fitting the expression distribution with a mixture-model of two distributions: a log normal distribution for expressing cells and an exponential for non-expressing cells. Interestingly, it was found that the signature cytokine IL17a exhibited one of the highest levels of variability in the cell's transcriptome in-vitro. Additional cytokines, chemokines and their receptors, including Ccl20, IL2, IL10, IL9 and IL24, were among the highly variable genes. While these key genes exhibit strong variability, it was not clear to what extent these patterns are informative for the cell's state. To investigate this, the correlation between signature genes of various CD4+ lineages and all other expressed genes was computed. Clustering this map reveals a clear distinction between regulatory cytokines (IL10 module) and pro-inflammatory molecules (IL17, Rorc). Expression from the IL10 module possibly represents a self-limiting mechanism, which is active in a subset of the cells and plays a role in the 'non-pathogenic' effects of TH17 cells differentiated with Tgfβ1.

To investigate this, principle component analysis was conducted on the space of cells. It was found that the PCA can adequately separate IL17a expressing cells from cells that did not express IL17a. In addition, it was found that the first PC positively correlated with IL17a and negatively correlated with IL10. The depiction of the cells in the space of the first two PC therefore spans the spectrum between potentially pathogenic cells (high levels of IL-17a and low levels of immunosuppressive cytokines like IL-10) to non-pathogenic cells (opposite expression profiles). The PCs were characterized by computing correlations with other cell properties.

GPR65 promotes Th17 differentiation and suppresses IL2: A first set of experiments identified the target gene GPR65, a glycosphingolipid receptor that is genetically associated with autoimmune disorders such as multiple sclerosis, ankylosing spondylitis, inflammatory bowel disease, and Crohn's disease. GPR65 has shown a positive correlation with the module of genes associated with an inflammatory response, referred to herein as the IL17 module, and negatively correlated with the module of genes associated with a regulatory cytokine profile, referred to herein as the IL10. The IL17 module includes genes such as BATF, STAT4, MINA, IL17F, CTLA4, ZBTB32 (PLZP), IL2, IL17A, and RORC. The IL10 module includes genes such as IL10, IRF4, IL9, IL24, and SMAD3. Genes that are known to have a positive correlation with the IL17 module include BATF, HIF1A, RORC, and MINA. Genes that are known to have a negative correlation with the IL17 module include FOXP3, AHR, TRP53, IKZF3, IRF4, IRF1, IL10, IL23, and IL9. As described throughout the disclosure, novel regulators of the IL17 module include DEC1, CD5L, and ZBTB32 (PLZP).

Figure 40A:
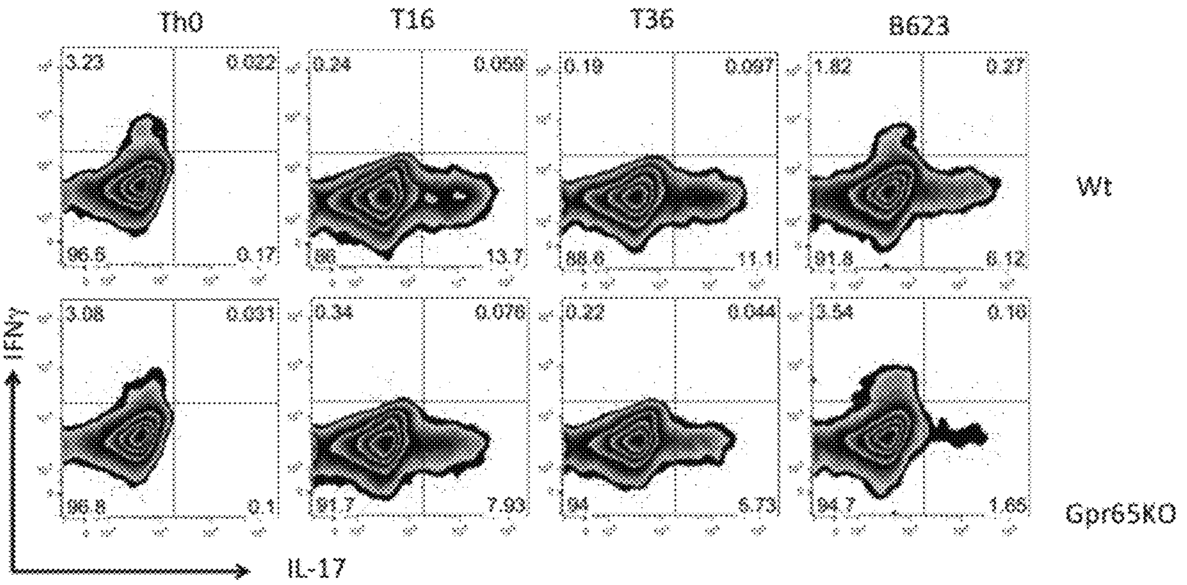
FIGS. 40A-40B are a series of graphs depicting IL17A expression was reduced in GPR65 knock out cells exposed to various T cell conditions (Th0, T16, T36, B623 and T).
Figure 40B:
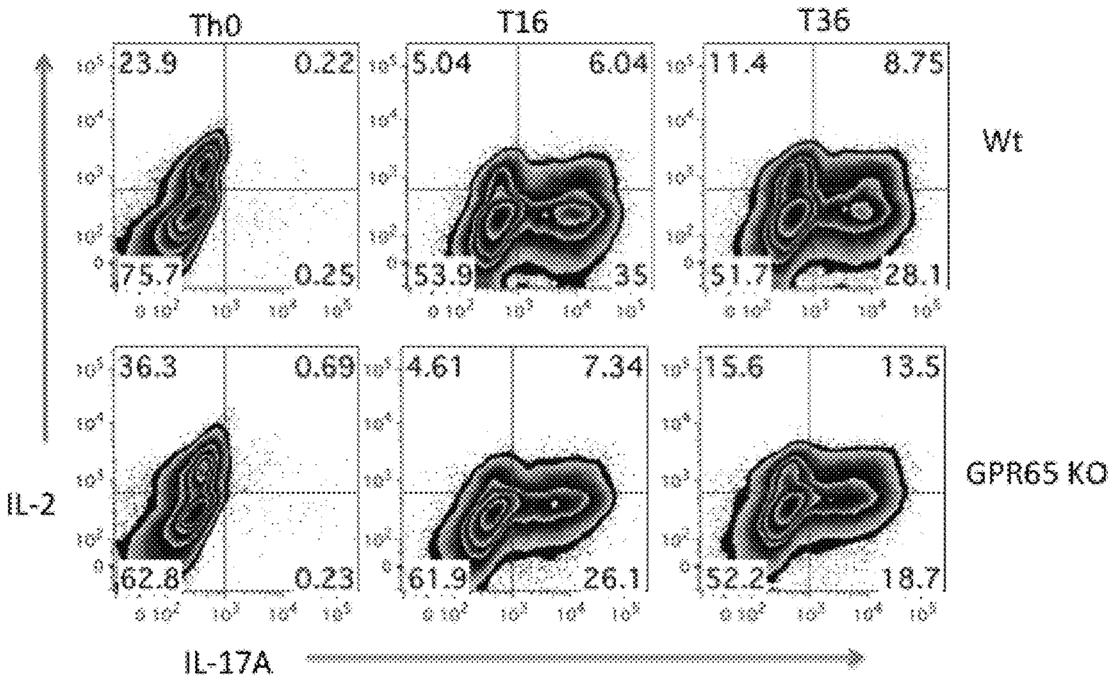

To explore the role of GPR65, GPR65−/− mice were obtained and differentiated naïve T-cells under various T cell conditions (Th0, T16, T36, B623, T). FIGS. 40A and 40B demonstrate that IL17A expression is reduced in GPR65 knock out cells, for example, in FIG. 40A by 42% for T16 condition, by 48% for T36 condition, and by 73% for B623 condition, and in FIG. 40B by 20% in T16 condition and 13% for T36 condition. In addition, the B623 condition showed increased interferon gamma (IFNγ) production, a cytokine that is normally attributed to Th1 cells, and associated with eliciting a severe immune response. These results demonstrate that GPR65 is a regulator of Th17 differentiation. Thus, modulation of GPR65 can be used to influence a population of T cells toward or away from a Th17 phenotype.

A second set of experiments identified the target gene DEC1 also known as Bhlhe40. DEC1 is a basic helix-loop-helix transcription factor that is known to be highly induced in a CD28-dependent manner upon T cell activation (Martinez-Llordella et al. "CD28-inducible transcription factor DEC1 is required for efficient autoreactive CD4+ T cell response." J Exp Med. 2013 Jul. 29; 210(8):1603-19. doi: 10.1084/jem.20122387. Epub 2013 Jul. 22). DEC1 is required for the development of experimental autoimmune encephalomyelitis and plays a critical role in the production of the proinflammatory cytokines GM-CSF, IFNγ, and IL-2 (Bluestone, 2013). Prior to the studies presented herein, DEC1 was not previously known to be associated with T cells generally, or with Th17 cells in particular.

Figure 41A:
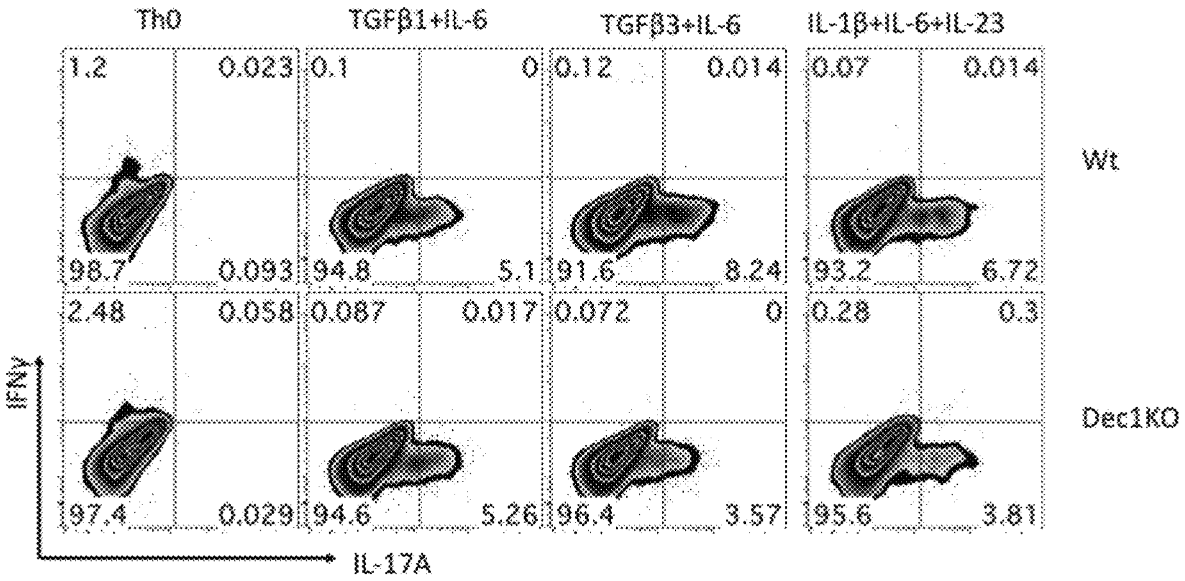
FIGS. 41A-41D are a series of graphs depicting that IL17A expression in DEC1 knock out cells exposed to various T cell conditions (Th0, T16, T36, B623 and T) was unchanged in the non-pathogenic condition (T16), but was reduced in the pathogenic conditions (T36, B623).
Figure 41B:
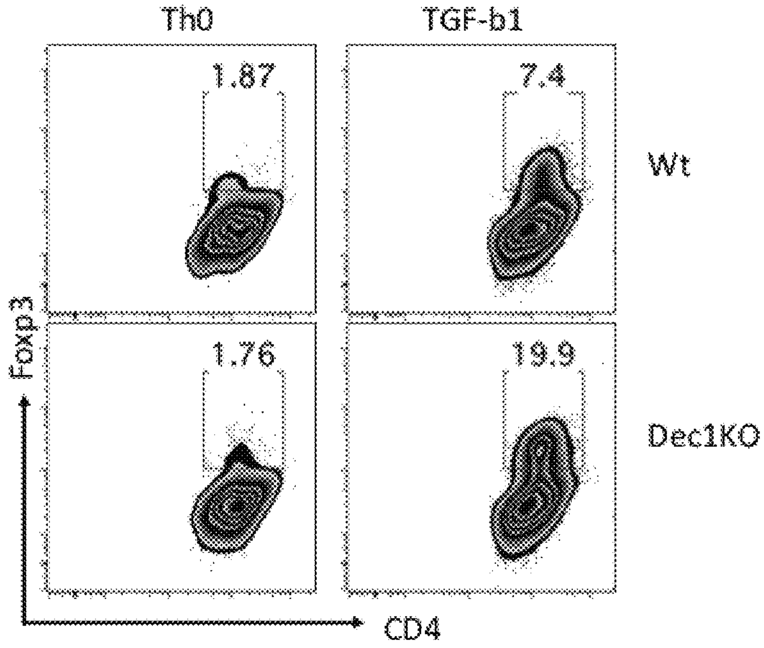
Figure 41C:
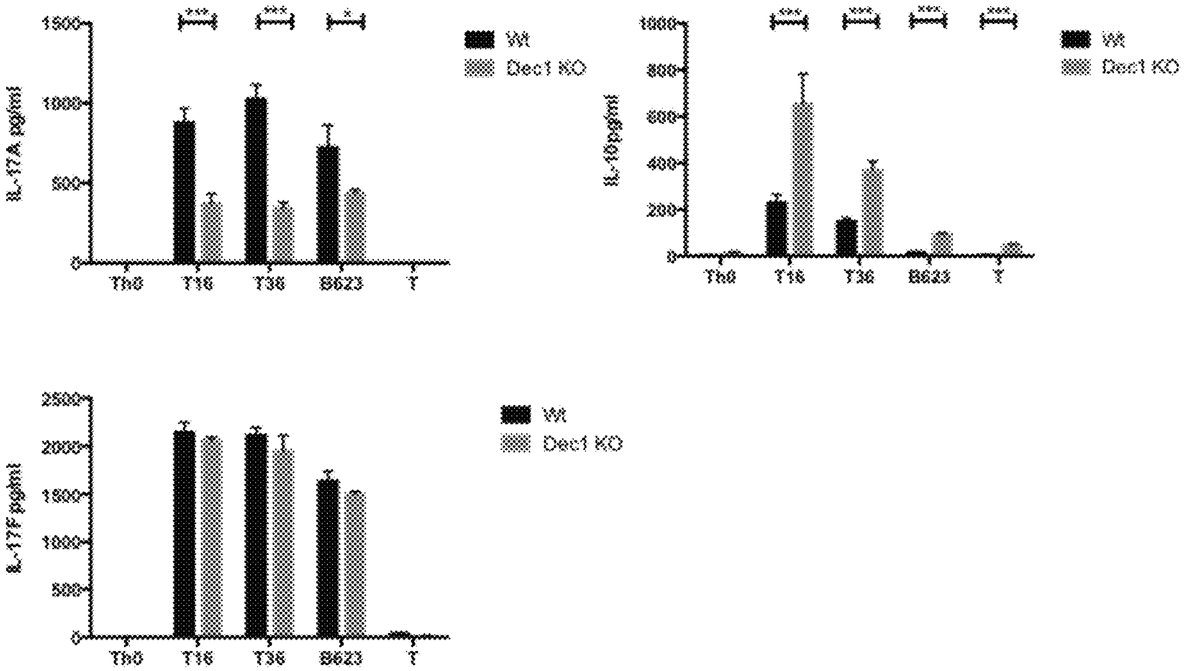
Figure 41D:
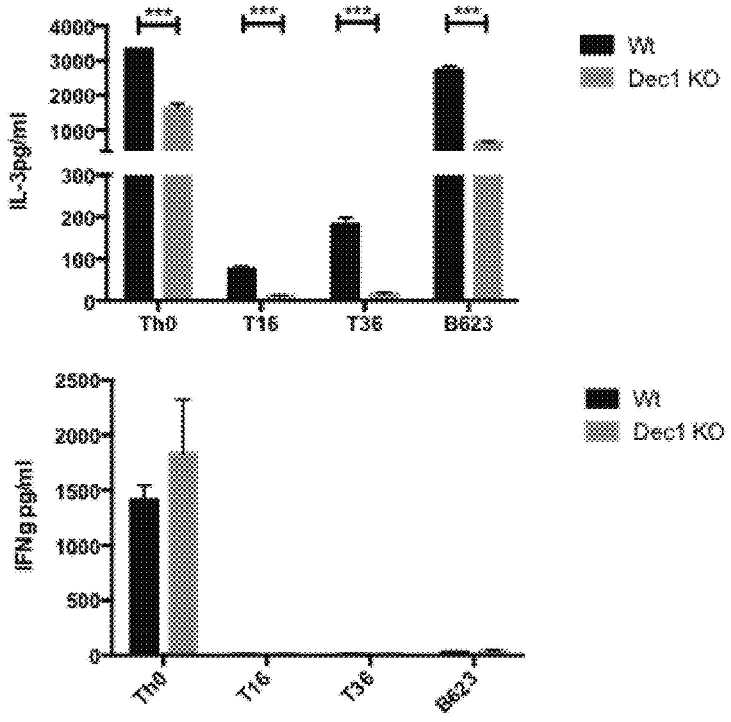

To explore the role of DEC1, DEC1−/− mice were obtained and differentiated naïve T-cells under various T cell conditions (Th0, T16, T36, B623, T). As shown in FIG. 41A, IL-17A expression was unchanged in the non-pathogenic condition, i.e., T16, but expression was reduced in the pathogenic conditions T36 and B623, e.g., about 55% decrease for T36 condition and about 43% decrease for B623 condition. As shown in FIG. 41B, the DEC1 knockout cells also demonstrated an increase in FOXP3 positive cells. FIG. 41C demonstrates that the cytokine secretion assay (CBA) largely supports the ICC data seen in FIG. 41A by demonstrating a decrease for IL17A for all Th17 conditions and an increase in IL-10 production for all Th17 conditions. These results demonstrate that DEC1 is a promoter of pathogenic Th17 differentiation. Thus, modulation of DEC1 can be used to influence a population of T cells toward or away from the Th17 pathogenic phenotype.

A third set of experiments identified the target gene PLZP also known as Zbtb32. PLZP is a transcription factor that is known to be a repressor of GATA-3. PLZP has been shown to negatively regulate T-cell activation (I-Cheng Ho, 2004) and to regulate cytokine expression activation (S C Miaw, 2000).

Figure 42A:
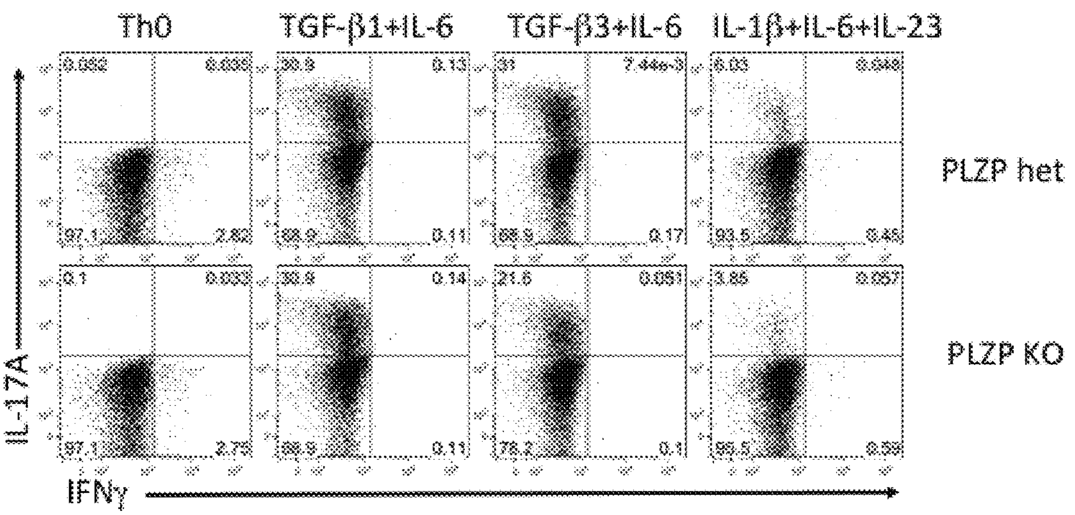
FIGS. 42A-42B are a series of graphs depicting that IL17A expression in PLZP knock out cells exposed to various T cell conditions (Th0, T16, T36, B623 and T) was unchanged in the non-pathogenic condition (T16), but was reduced in the pathogenic conditions (T36, B623).
Figure 42B:
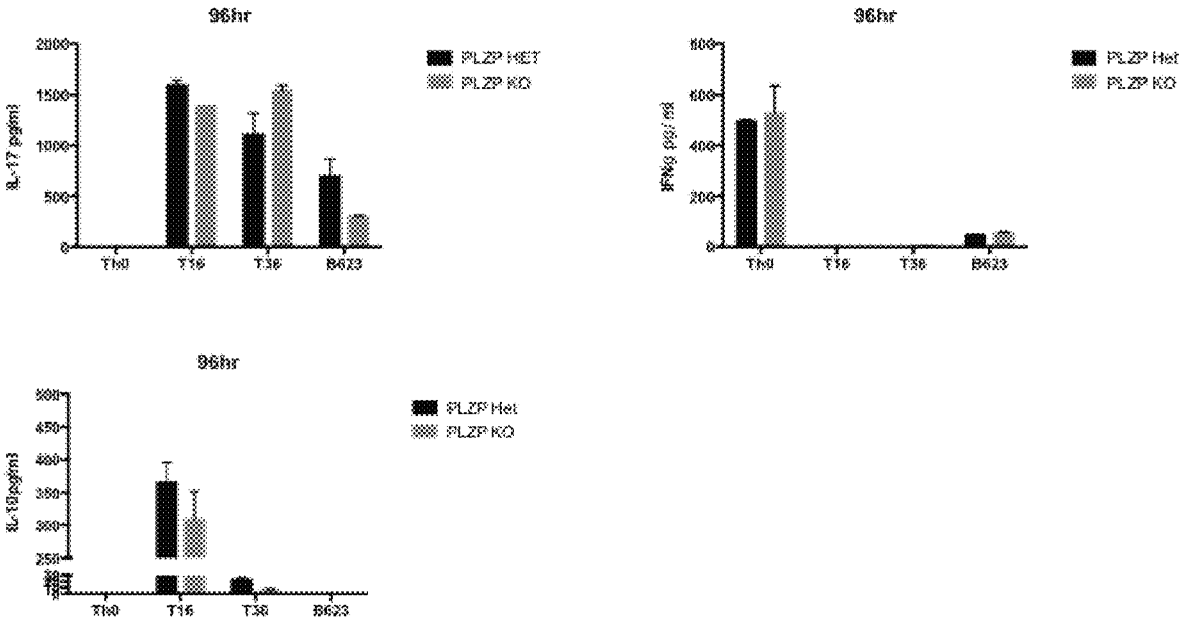

To explore the role of PLZP, PLZP−/− mice were obtained and differentiated naïve T-cells under various T cell conditions (Th0, T16, T36, B623, T). As shown in FIG. 42A, IL-17A production was decreased in the pathogenic Th17 cell conditions T36 and B623. These results demonstrate that PLZP is a promoter of pathogenic Th17 differentiation. Thus, modulation of PLZP can be used to influence a population of T cells toward or away from the Th17 pathogenic phenotype.

A fourth set of experiments identified the target gene TCF4 (transcription factor 4), a basis helix-loop-helix transcription factor. TCF4 is known to be related to superpathways including the MAPK signaling pathway and the myogenesis pathway.

Figure 43:
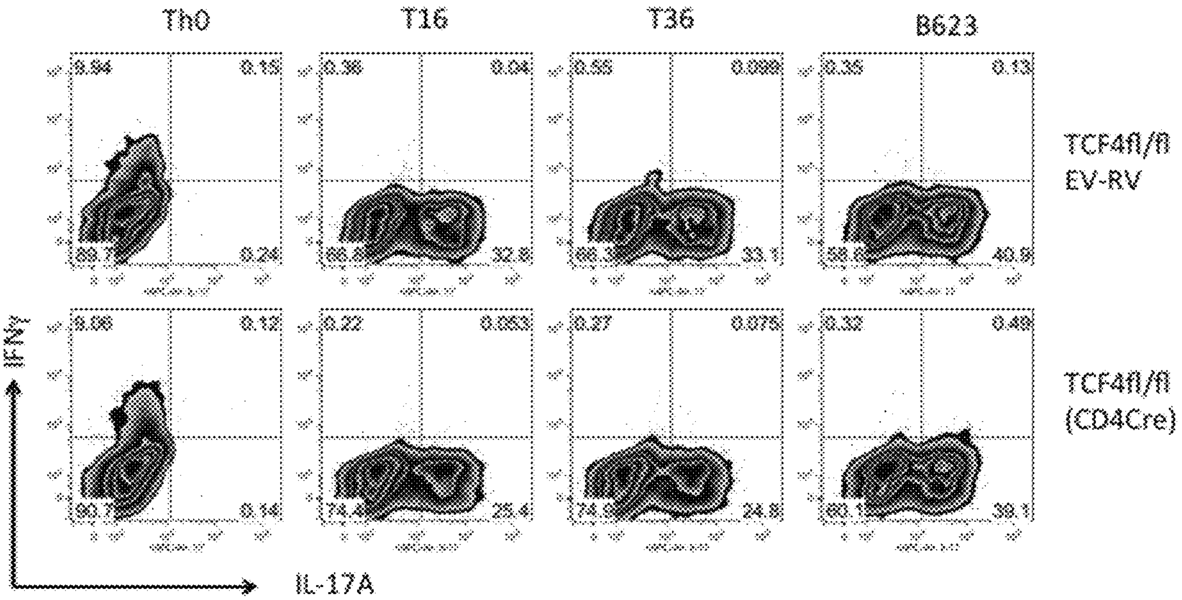
FIG. 43 is a graph depicting IL17A expression in TCF4 knock out cells exposed to various T cell conditions (Th0, T16, T36, B623 and T) was reduced in the pathogenic condition B623.

To explore the role of TCF4, TCF4−/− mice were obtained and differentiated naïve T-cells under various T cell conditions (Th0, T16, T36, B623, T). As shown in FIG. 43, IL-17A production was decreased in the pathogenic Th17 cell condition B623. These results demonstrate that TCF4 can be used as a promoter of pathogenic Th17 differentiation. Thus, modulation of TCF4 can be used to influence a population of T cells toward or away from the Th17 pathogenic phenotype.

Example 10

CD5L, a Regulator of Intracellular Lipid Metabolism, Restrains Pathogenicity of Th17 Cells IL-17-producing Th17 cells are present at the sites of tissue inflammation and have been implicated in the pathogenesis of a number of autoimmune diseases in humans and relevant murine models (Kleinewietfeld and Hafler 2013, Lee, Collins et al. 2014). However, not all IL-17 producing Th17 cells induce autoimmune tissue inflammation and disease ('pathogenic'). Th17 cells that line the normal gut mucosa are thought to play an important role in tissue homeostasis by preventing tissue invasion of gut microflora and promoting epithelial barrier functions (Guglani and Khader 2010). In addition, Th17 cells play a crucial role in host defence against pathogens such as fungi (*Candida albicans*) and extracellular bacteria (*Staphylococcus aureus*) (Gaffen, Hernandez-Santos et al. 2011, Romani 2011). Therefore, Th17 cells show a great degree of diversity in their function: on one hand, they are potent inducers of tissue inflammation and autoimmunity, and on the other hand, they promote tissue homeostasis and barrier function. The extracellular signals and intracellular mechanisms that control these opposing functions of Th17 cells in vivo are only partially known and intensively studied.

Different types of Th17 cells with distinct effector functions can be generated in vitro by different combination of cytokines. It has been shown (Bettelli, Carrier et al. 2006; Veldhoen, Hocking et al. 2006; Harrington et al., 2006) that two cytokines, IL-6 and TGFβ1, can induce differentiation of naïve T cells into Th17 cells in vitro, although these cells are poor inducers of Experimental Autoimmune Encephalomyelitis (EAE), an autoimmune disease model of the central nervous system. Exposure of these cells to the proinflammatory cytokine IL-23 can make them into disease-inducing, pathogenic, cells (McGeachy, Bak-Jensen et al. 2007, Awasthi, Riol-Blanco et al. 2009, Jager, Dardalhon et al. 2009, McGeachy, Chen et al. 2009). Indeed, other combinations of cytokines, such as IL-1β+IL-6+IL-23 (Ghoreschi, Laurence et al. 2010) or TGFβ3+IL-6+IL-23, can induce differentiation of Th17 cells that elicit potent EAE with severe tissue inflammation upon adoptive transfer in vivo. Comparison of gene expression profiles of Th17 cells generated with these distinct in vitro differentiation protocols led to the identification of a gene signature that distinguishes pathogenic from non-pathogenic Th17 cells, consisting of a proinflammatory module of 16 genes expressed in pathogenic Th17 cells (e.g., T-bet, GMCSF and IL-23R) and a regulatory module of 7 genes expressed in non-pathogenic cells (e.g., IL-10). Exposure of non-pathogenic Th17 cells to IL-23 converts them into a pathogenic phenotype, with the diminished expression of the regulatory module and the induced expression of the proinflammatory module, suggesting that IL-23 is a master cytokine that dictates the functional phenotype of Th17 cells.

In humans, two different subtypes of Th17 cells have also been described with specificity for different types of pathogens. Th17 cells that co-produce IL-17 with IFNγ were generated in response to *Candida albicans*, whereas Th17 cells that co-produce IL-17 with IL-10 have specificity for *Staphylococcus aureus* infection (Zielinski, Mele et al.). Both IL-1 and IL-23 contributed to the induction of each of these functionally-distinct subtypes of Th17 cells in response to antigen. Comparison of these human Th17 cell subsets with pathogenic and non-pathogenic Th17 cells in mice suggest that the *C. albicans*-specific Th17 cells may mirror the pathogenic Th17 cells, with expression of the proinflammatory module, whereas *S. aureus*-specific Th17 cells are more similar to the non-pathogenic Th17 cells that has been described in the mouse models of autoimmunity.

Identifying the key molecular switches that drive pathogenic and non-pathogenic Th17 cells will allow selective inhibition of pathogenic Th17 cells, while sparing non-pathogenic, potentially tissue-protective, Th17 cells. To date, the intracellular mechanisms by which IL-23 evokes the pathogenic phenotype in differentiating Th17 cells is not well understood. Genomic approaches provide a compelling unbiased approach to find such candidate mechanisms (Yosef et al. 2014), but it is likely that pathogenic and non-pathogenic cells co-exist in vivo, and co-differentiate in vitro, limiting the power to detect subtler signals. Indeed, previous signature comparing populations of pathogenic and non-pathogenic-derived cells did not find strong candidate regulators, but rather effector molecules. The advent of single cell RNA-Seq opens the way to identify such subtler, yet physiologically important, regulators.

Here, single-cell RNA-Seq profiles of Th17 cells from in vivo autoimmune lesions and from in vitro differentiation were used to identify a novel regulator of Th17 pathogenicity, CD5L (CD5-Like). CD5L is predominantly expressed in non-pathogenic Th17 cells and is down-regulated upon exposure to IL-23. CD5L deficiency converts non-pathogenic Th17 cells into disease-inducing pathogenic Th17 cells, by regulating the Th17 cell lipidome, altering the balance between polyunsaturated fatty acyls (PUFA) and saturated lipids, and in turn affecting the activity and binding of Rorγt, the master transcription factor of Th17 cell differentiation. Thus, CD5L is now identified as a critical regulator that distinguishes Th17 cell functional states, and T-cell lipid metabolism as an integral component of the pathways regulating the pathogenicity of Th17 cells.

Results: Th17 cells play a critical role in host defense against extracellular pathogens and maintenance of gut tissue homeostasis, but have also been implicated in the pathogenic induction of multiple autoimmune diseases. The mechanisms implicated in balancing such 'pathogenic' and 'non-pathogenic' Th17 cell states remain largely unknown. Here, single-cell RNA-Seq was used to identify CD5L (CD5-Like) as one of the novel regulators that is selectively expressed in non-pathogenic but not in pathogenic Th17 cells. While CD5L does not affect Th17 differentiation, it serves as a major functional switch, as loss of CD5L converts 'non-pathogenic' Th17 cells into 'pathogenic' Th17 cells that promote autoimmune disease in mice in vivo. It is shown that CD5L mediates this effect by modulating the intracellular lipidome, such that Th17 cells deficient in CD5L show increased expression of saturated lipids, including cholesterol metabolites, and decreased expression of poly unsaturated fatty acyls (PUFA). This in turn alters the ligand availability to and function of Rorγt, the master transcription factor of Th17 cells, and T cell function. This study identified CD5L as a critical regulator of the functional state of Th17 cells and highlighted the importance of lipid saturation and lipid metabolism in balancing immune protection and disease in T cells.

Single-cell RNA-Seq identifies CD5L as a high-ranking candidate regulator of pathogenicity: To identify candidate regulators of Th17 cell function, single-cell RNA-Seq profiles were analyzed from Th17 cells isolated from the CNS during EAE in vivo or differentiated in vitro under non-pathogenic (TGFβ1+IL-6) and pathogenic (IL-1β+IL-6+IL-23) conditions. Briefly three lines of evidence were used to rank genes for their potential association with pathogenicity: (1) co-variation analysis of a transcript's expression across single Th17 cells differentiated in vitro (in the non-pathogenic conditions), which showed the presence of two anti-correlated modules: a "pro-inflammatory module" (positively correlated with the expression of Il17a) and a "regulatory module" (positively correlated with the expression of Il10); (2) Principle Components Analysis (PCA) of single Th17 cells differentiated under either condition, which showed that cells span a pathogenicity spectrum, such that a cell's location on PC1 is related to the expression of pathogenic genes; and (3) PCA of single Th17 isolated from the CNS and lymph node during EAE in vivo, which showed that cells span a wide functional spectrum along the first PC (from effector to memory to exhausted state) and the second PC (from a naïve-like to terminally differentiated state).

Figure 45A:
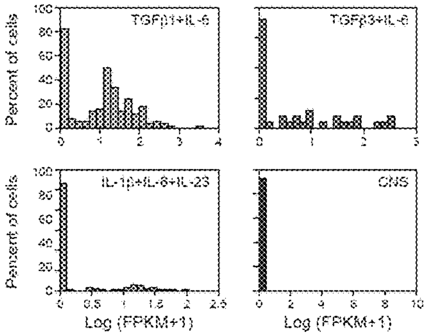
FIG. 45A-45H show Single-cell RNA-seq identifies Cd5l as a novel regulator associated with Th17 cell pathogenicity and expressed only by non-pathogenic Th17 cells. Single-cells were sorted from in-vitro Th17 cells differentiated with TGFβ1+IL-6 (A,B), IL-1β+IL-6+IL-23 (C), TGFβ3+IL-6 (D) and in-vivo Th17 cells from CNS of mice at the peak of EAE (score=3) (D). IL-17A.GFP$^+$ CD4$^+$ T cells were sorted in all panels in D. (A) Correlation of CD5L expression in non-pathogenic Th17 cells with the pathogenic signature (Lee, Awasthi et al.). (B) Principal Component Analysis of CD5L expression where the direction of PC1 correlates with pathogenicity. (C, D) Histogram of CD5L expression in single-cell from conditions as indicated. CD5L expression in vitro is validated by qPCR (E, F) and flow cytometry (G).
Figure 45B:
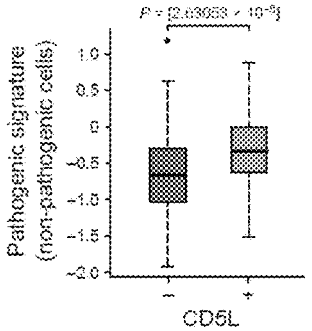
Figure 45C:
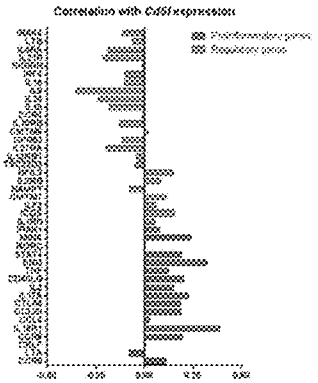
Figure 45D:
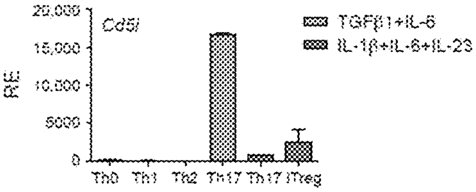

Cd5l (Cd5-like) was one of the high-ranking genes by single-cell analysis of potential regulators, showing a surprising combination of two key features: (1) it is only expressed in vitro in Th17 cells derived under non-pathogenic conditions (FIG. 45D); but (2) in those non-pathogenic cells, it was expressed as a member in co-variance with the other genes in the proinflammatory module in Th17 cells. First, the vast majority (~80%) of Th17 cells derived under the pathogenic condition (IL-1β+IL-6+IL-23) lacked Cd5l expression, whereas Th17 cells differentiated under the non-pathogenic (TGF-b1+IL-6) condition predominantly expressed Cd5l (FIG. 45C). Furthermore, most of sorted IL-17A$^+$ (GFP$^+$, where GFP is under the control of IL-17 promoter) cells differentiated under the non-pathogenic condition (TGFβ1+IL-6) expressed Cd5l (FIG. 45D, top left panel), consistent with its original association with the IL17 module (in non-sorted cells; below). In contrast, Th17 cells differentiated under two different pathogenic conditions (IL-1□+IL-6+IL-23 or TGFβ3+IL-6) lacked Cd5l expression in a majority of the T cells. Similarly, none of the encephalitogenic Th17 cells (CD4$^+$ IL-17A.GFP$^+$) sorted from the central nervous system (CNS) of mice undergoing active EAE expressed any Cd5l at the single-cell level (FIG. 45D, lower right panel). Second, CD5L is highly positively correlated with the defining signature of the pro-inflammatory module, and negatively correlated with the regulatory module. In particular, it is among the top 5 genes in the proinflammatory module whose expression is also most strongly correlated with the expression of previously-defined pathogenic gene signature (FIG. 45A, empirical p-value<0.05). Furthermore, non-pathogenic Th17 cells expressing higher levels of Cd5l also have lower scores for the aforementioned PC1, as does the pathogenicity signature (FIG. 45B, Pearson correlation of 0.44; $p<10^{-7}$).

CD5L is a member of the scavenger receptor cysteine rich superfamily (Sarrias M R et al. 2004). Its expression was previously reported in macrophages (Miyazaki, Hirokami et al. 1999), and it has been shown to bind to cytosolic fatty acid synthase in adipocytes following endocytosis. It has also been reported to be a receptor for Pathogen Associated Molecular Patterns (PAMPs), and may have a function in regulating innate immune responses (Martinez V G et al. 2014). However, it has not been reported to be expressed in T cell and therefore it's role in T cell function has not been identified.

CD5L expression is specifically associated with non-pathogenic Th17 cells in vitro and in vivo: It was hypothesized that CD5L's exclusive expression in Th17 cells differentiated under non-pathogenic conditions but in association with the IL17 inflammatory module, may indicate a unique role in regulating the transition between a non-pathogenic and pathogenic state. While co-expression with the inflammatory module and correlation with a pathogenicity signature (FIG. 45A,B) per se could have suggested a function as a positive regulator of pathogenicity, the apparent absent of CD5L from Th17 cell differentiated in vitro under pathogenic conditions or isolated from lesions in the CNS (FIG. 45C,D) suggest a more nuanced role. In particular, it was hypothesized that CD5L may be a negative regulator of pathogenicity, explaining its absence from truly pathogenic cells. Notably, mRNAs of negative regulators of state-changes in cells are often co-regulated with the modules that they negatively regulate in eukaryotes from yeast (Segal et al., Nature Genetics 2003; Pe'er et al. *Bioinformatics* 2002) to human (Amit et al Nature Genetics 2007).

Figure 45E:
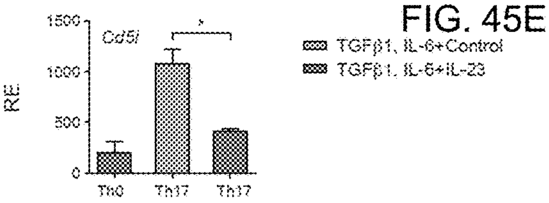
Figure 45F:
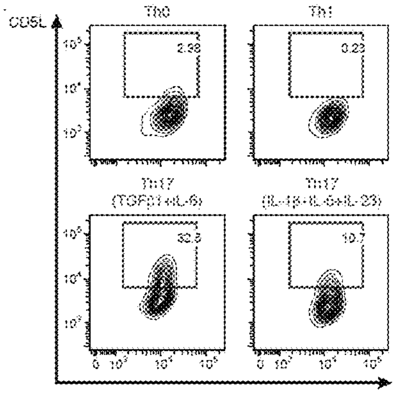
Figure 45G:
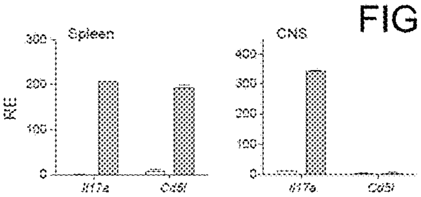

To test this hypothesis, the initial finding that CD5L is uniquely expressed in non-pathogenic Th17 cells both in vitro and in vivo with qPCR (FIG. 45E, F) and protein expression analyses (FIG. 45G) of naïve CD4 T cells cultured under various differentiation conditions was first validated and extended. At the mRNA level, little to no Cd5l expression was found in Th0, Th1 or Th2 helper T cells (FIG. 45E), high expression in Th17 cells differentiated with TGFβ1+IL-6, but little to no expression in Th17 cells differentiated IL-1β+IL-6+IL-23 or in iTregs (FIG. 45E). Importantly, similar patterns are observed for CD5L protein expression by flow cytometry (FIG. 45G).

Figure 45H:
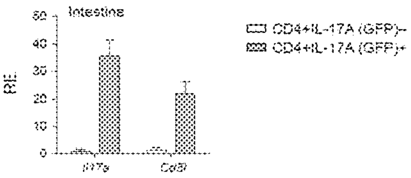

Next, it was explored whether CD5L expression is associated with less pathogenic Th17 cells in vivo. First, Cd5l expression was analyzed in Th17 cells isolated from mice following immunization with myelin oligodendrocyte glycoprotein ($MOG_{35-55}$) in complete Freund's adjuvant (CFA). Th17 cells (CD3$^+$CD4$^+$IL-17.GFP$^+$) were sorted from the periphery (spleen) and it was found that Cd5l was only expressed in IL-17$^+$ but not IL-17$^-$ T cells (FIG. 45H, left panel). In striking contrast, Cd5l was not expressed in Th17 cells from the CNS despite significant expression of Il17 (FIG. 45H, right panel), consistent with the single-cell RNA-seq data (FIG. 45D). Next, Cd5l expression was analyzed on Th17 cells isolated from naïve mice that line the gut mucosa and are not associated with inflammation. IL-17A.GFP$^+$ and IL-17A.GFP$^-$ CD4 T cells were isolated from the mesenteric lymph node (mLN) and the lamina propria (LP) of naïve mice, where Th17 cells are thought to contribute to tissue homeostasis and mucosal barrier function. IL-17$^+$ but not IL-17$^-$ T cells harvested from mLN and LP of normal gut mucosa expressed high levels of Cd5l (FIG. 45I and data not shown). Thus, CD5L is a gene expressed in non-pathogenic (but not in pathogenic) Th17 cells in vivo.

Finally, it was tested whether IL-23 exposure, known to make Th17 cells more pathogenic, can directly regulate Cd5l expression. It was hypothesized that if CD5L is a positive regulator of IL23-dependent pathogenicity its expression will be increased by IL23, whereas if it is a negative regulator, its expression will be suppressed. As IL-23R is induced after 48 hours of T-cell activation, naïve T cells were differentiated with TGFβ1+IL-6 for 48 h and then expanded with or without IL-23 in fresh media. The addition of IL-23 significantly suppressed Cd5l expression as compared to PBS control (FIG. 45F), consistent with these cells acquiring a pro-inflammatory module and becoming pathogenic Th17 cells, and with the hypothetical assignment of CD5L as a negative regulator of pathogenicity.

Figure 46A:
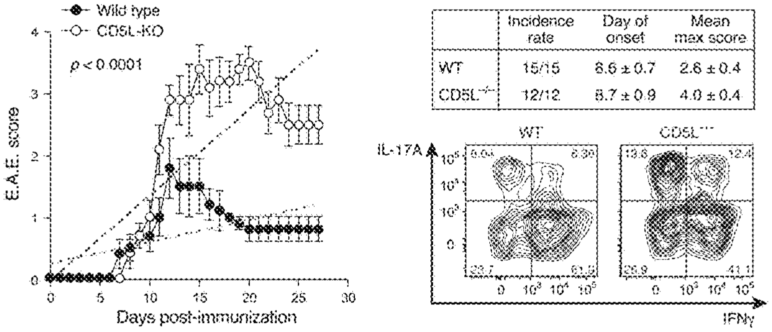
FIG. 46A-46H shows CD5L regulates Th17 cell effector function. (A) WT and CD5L$^{-/-}$ mice were immunized with 40 μg MOG/CFA with pertussis toxin injection (iv) on day 1 and day 3. EAE was scored as previously published (Jager, Dardalhon et al. 2009). Upper panel is pooled results from 3 independent mice experiments; Lower panel is representative FACS plot showing cytokine production from CD4 T cells isolated from CNS at day 15 post immunization after 4 hours of restimulation with PMA/ionomycin. Summary data is shown in FIG. 50B.
Figure 50A:
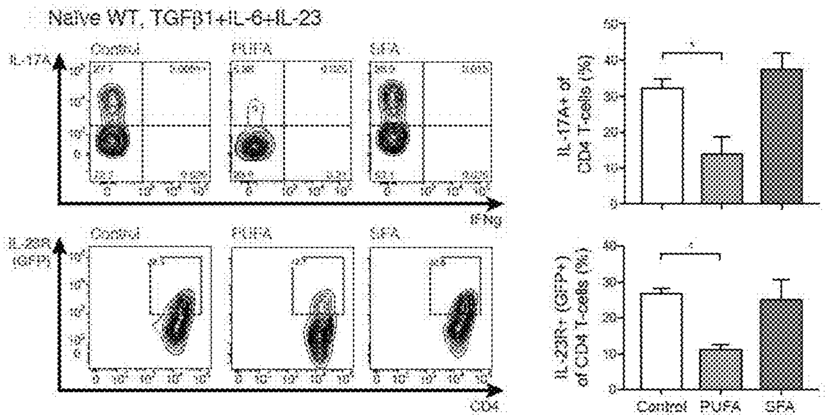
FIG. 50A-50E PUFA and SFA can regulate Th17 cell function and contribute to CD5L-dependent regulation of Th17 cells. (A) Naïve T cells were sorted from either WT or IL-23RGFP reporter mice, activated with plate-bound anti-CD3/anti-CD28 and differentiated with TGFβ1+IL-6 for 48 hours. At 48 h, cells were cultured with IL-23 in fresh media in the presence of either 10 uM arachidonic acid (PUFA) or 20 uM of palmitic acid (SFA) for another 48 hours and harvested for PMA/ionomycin restimulation and FACS. The concentration of FFA was predetermined in titration experiments (data not shown). (B) Cells from WT and $Rorc^{-/-}$ mice were sorted, differentiated and treated with FFA as in A. Cells were harvested for RNA purification and qPCR. (C) Naïve WT and $CD5L^{-/-}$ T cells were differentiated as in A. Cells were then lifted, washed and replated in fresh media with no addition of cytokines and in the presence of control or 5 uM of arachidonic acid (PUFA). Cytokine profile of T cells were measured after PMA/ionomycin restimulation. Data are representative of at least 3 independent differentiation experiments. DE. naïve T cells were sorted and differentiated with TGFβ1+IL-6 as in A. At 48 h, cells were then lifted, washed and replated in fresh media with no addition of cytokines and in the presence of control or 5 uM arachidonic acid (PUFA) for CD5L−/− T cells; and control or 25 uM palmitic acid (SFA) for WT T cells. Another 48 hours later, cells were harvested for nanostring analysis (D) or qPCR (E).
Figure 50B:
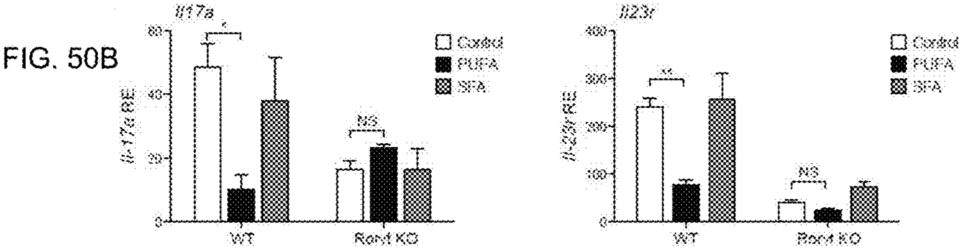
Figure 50C:
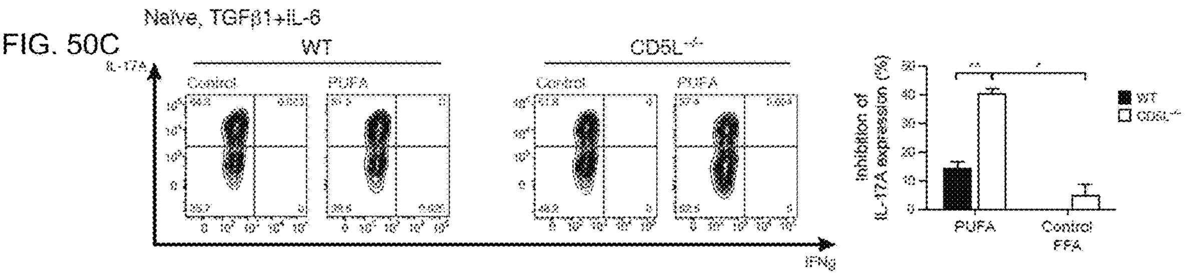
Figure 50D:
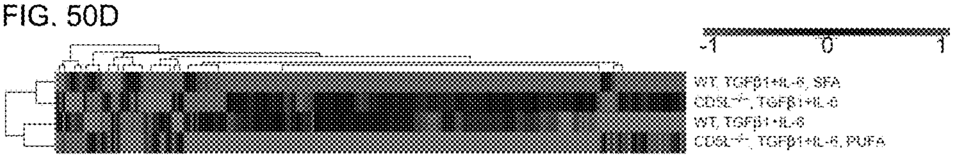
Figure 50E:
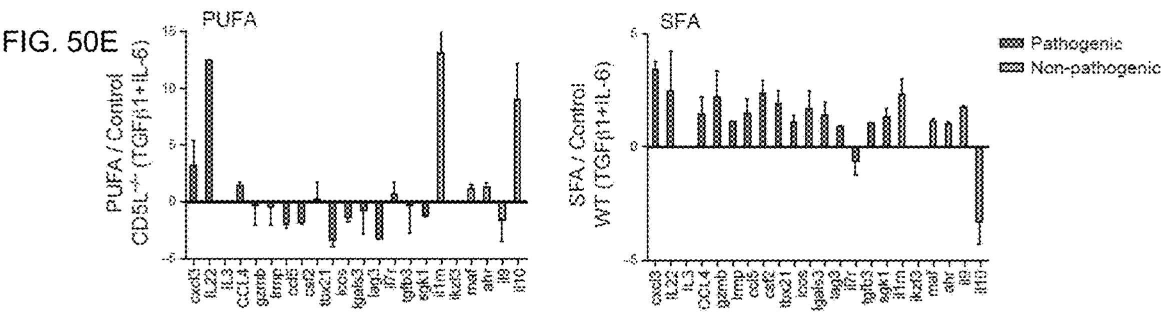
Figure 51A:
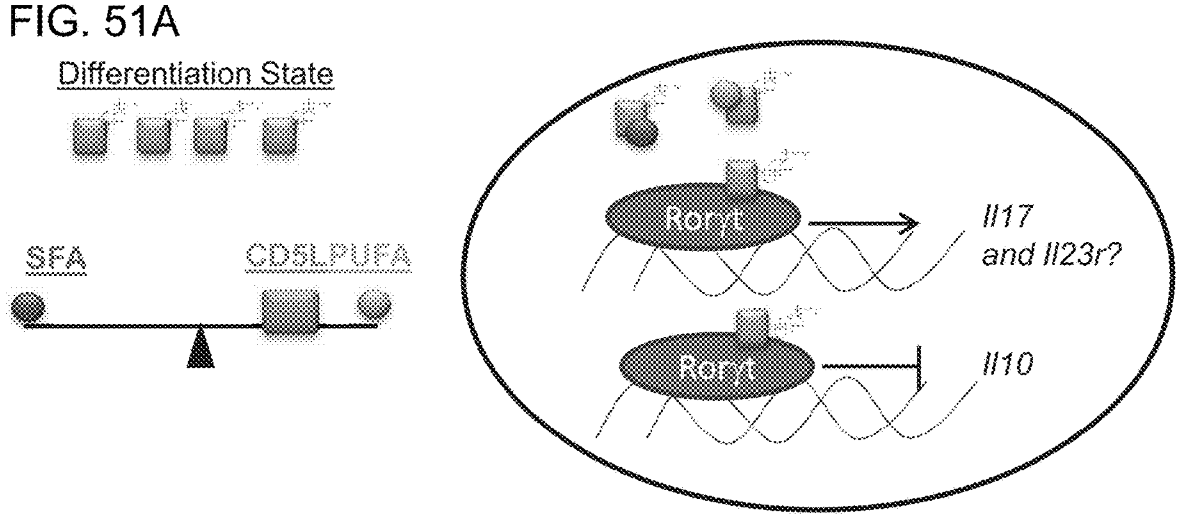
FIG. 51A-51C Model for action of PUFA and CD5L. During differentiation (A) abundant Rorγt ligand are synthesized, limiting the specific impact of PUFA/SFA; once Th17 cells are differentiated (B,C), however, ligand synthesis is substantially reduced due to decreased glucose metabolism, allowing PUFA to have a more pronounced effect. The extent of this effect depends on whether CD5L is present (B) or absent (C), resulting in less or more pathogenic cells, respectively.
Figure 51B:
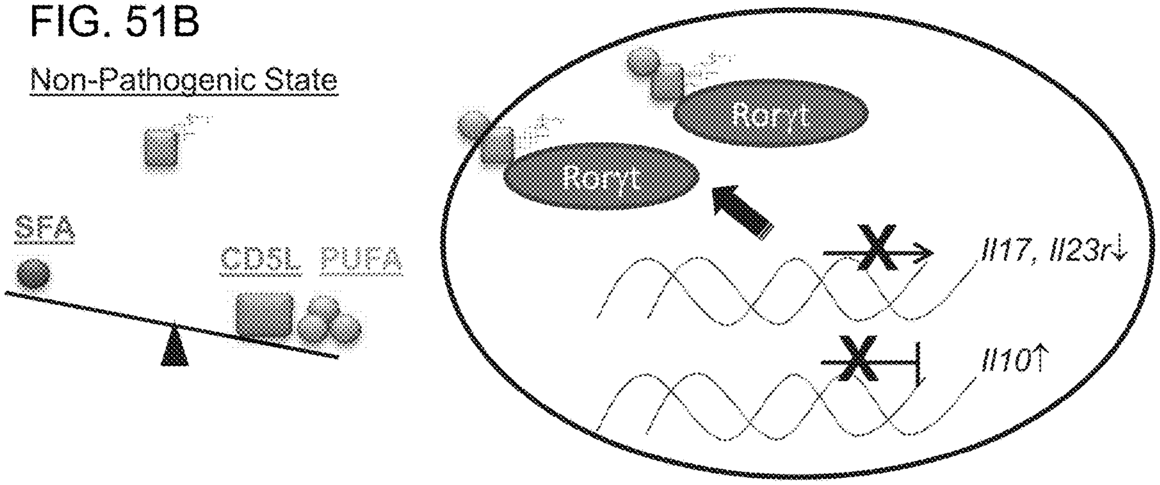
Figure 51C:
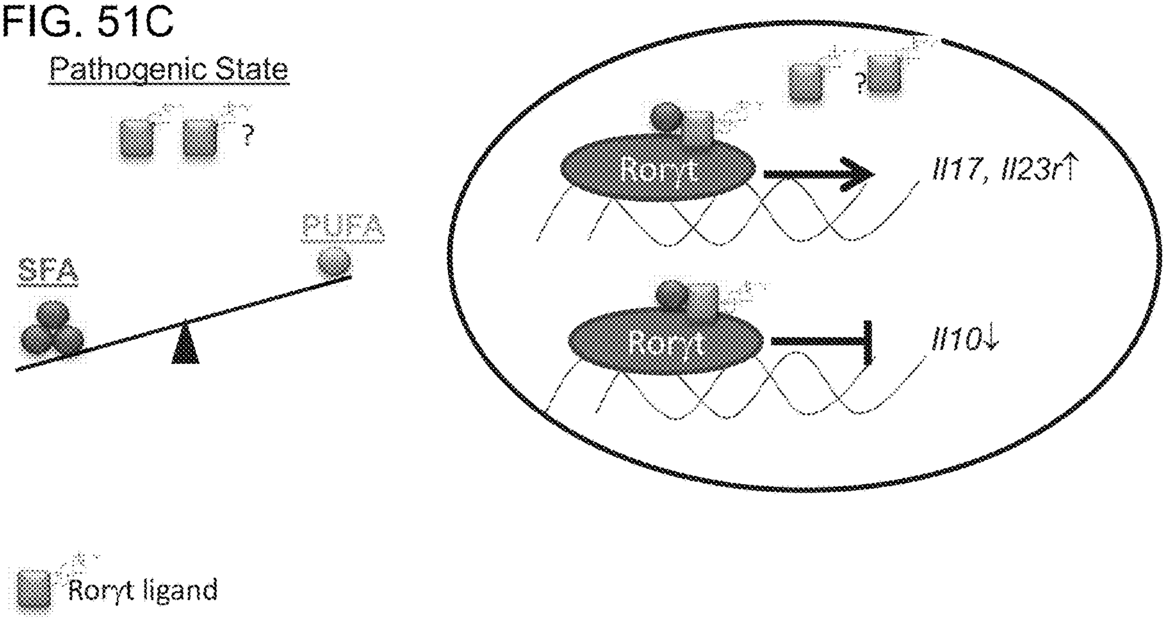
Figures 54A, 54B, 54C, 54D:
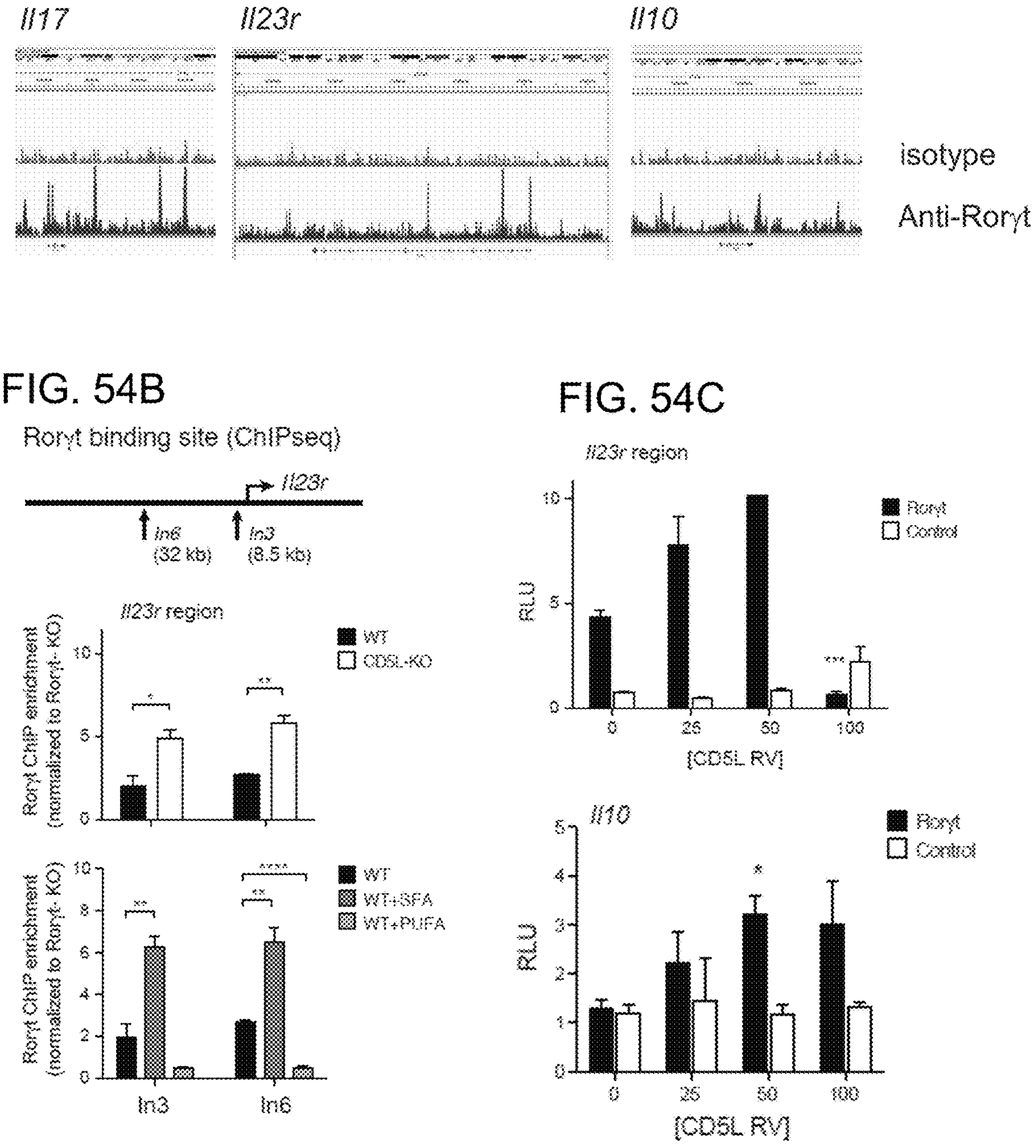
FIG. 54A-54D CD5L regulate lipid metabolism in Th17 cells and modulate Rorγt function. (A) Rorγt binding sites in the Il17, Il23r and Il10 regions as identified from Rorγt ChIP-seq (Xiao, Yosef et al. 2014). Top row is isotype control (red) and bottom role shows Rorγt ChIP-seq results from anti-Rorγt antibody (Experimental Procedures) (B) ChIP-PCR of Rorγt in the genomic region of Il23r as in FIG. 48E. (C,D) Rorγt transcriptional activity was measured with respect to Il23r (C) and Il10 (D) in the presence of retroviral vector expressing Cd5l as in FIG. 48G.

CD5L represses/dampens Th17 cell effector function without affecting Th17 differentiation of naïve T cells: To analyze whether CD5L plays any functional role in vivo, wildtype (WT) and Cd5l deficient mice were immunized with $MOG_{35-55}$/CFA to induce EAE. $CD5L^{-/-}$ mice exhibited significantly more severe clinical EAE that persisted for at least 28 days, whereas WT mice began recovering 12 days post immunization (FIG. 46A). Next, the phenotype of CD4 T cells was analyzed during the course of EAE. Similar frequencies of $FoxP3^+$ Treg cells were found in WT and $CD5L^{-/-}$ mice, suggesting that the increased severity of the disease was not due to a decreased number of Tregs in Cd5l deficient mice (FIG. 50A). On the other hand, a significantly higher percentage of IL-17-producing CD4 T cells and a lower percentage of $IFN\gamma^+$ CD4 T cells in the CNS of $CD5L^{-/-}$ mice (FIGS. 46A and 51B) was observed. Moreover, in response to MOG reactivation in vitro, cells from the draining lymph node (dLN) of $CD5L^{-/-}$ mice showed higher proliferative responses and produced more IL-17 (FIG. 51C, D). This is consistent with either a direct or indirect role for CD5L in defining the function of Th17 cells.

Figure 46B:
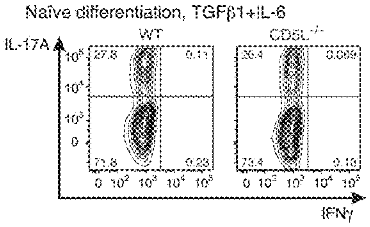
Figure 46C:
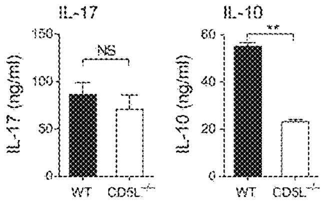
Figure 46D:
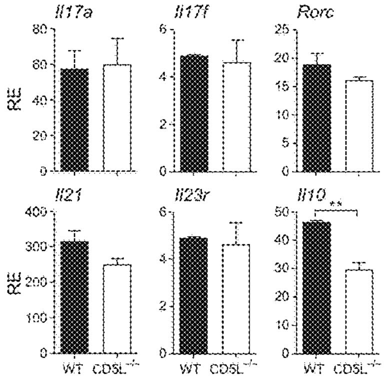

To determine whether CD5L's effect is due to a direct role in the differentiation of Th17 cells, naïve WT and $CD5L^{-/-}$ CD4 T cells were analyzed under the non-pathogenic Th17 cell condition and analyzed whether CD5L directly regulated the expression of signature Th17 genes. The loss of CD5L did not affect Th17 differentiation of naïve T cells, as measured by IL-17 expression by intracellular cytokine staining or by ELISA (FIG. 46B, C), nor that of other signature Th17 genes including Il17, Il21, Il23r or Rorc (FIG. 46D). However, under the non-pathogenic Th17 differentiation condition, WT Th17 cells produce IL-10, whereas $CD5L^{-/-}$ Th17 cells showed a decrease in the expression of IL-10 as determined by ELISA (FIG. 46C) or qPCR analysis (FIG. 46D). These observations suggest that CD5L does not regulate Th17 cell differentiation directly, that Th17 cell differentiation alone cannot explain the increased susceptibility to EAE in $CD5L^{-/-}$ mice, but that CD5L may indeed affect the internal state of differentiated Th17 cells.

Figure 46E:
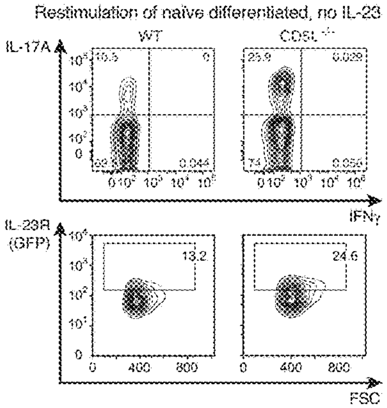
Figure 46F:
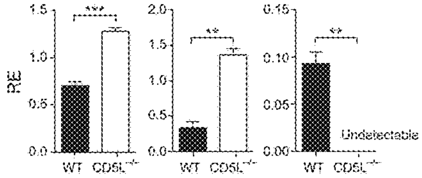
Figure 46G:
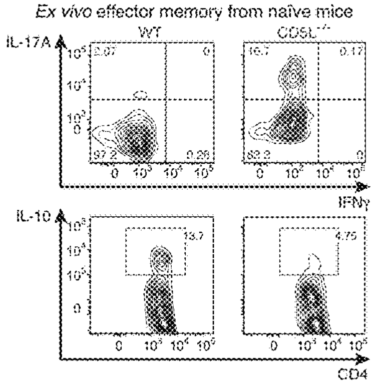
Figure 46H:
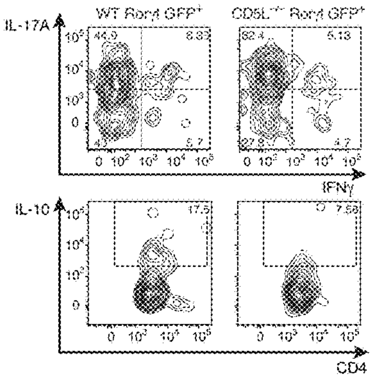

Next, it was determined whether CD5L has any role in expanding or maintaining effector/memory Th17 cells. To this end, naïve Th17 cells differentiated under the non-pathogenic conditions were washed and re-plated without IL-23. Upon restimulation, the $CD5L^{-/-}$ Th17 cells had a significantly higher percentage of $IL\text{-}17A^+$ cells and $IL\text{-}23R^+$ cells (FIG. 46E), suggesting that CD5L deficiency leads to more stably expanding Th17 cells. Consistent with this result, $CD5L^{-/-}$ Th17 cells expressed more Il17a and Il23r and less Il10 as determined by qPCR (FIG. 46F). Thus, CD5L does not regulate initial Th17 cell differentiation of the naïve T cells but does control their expansion and/or effector functions over time. Consistent with this result, effector memory cells ($CD4^+CD62L^-CD44^+$) isolated directly ex vivo from $CD5L^{-/-}$ mice expressed significantly higher IL-17 and lower IL-10 levels (FIG. 46G). This higher percentage of effector memory T cells producing IL-17 might reflect the greater stability and higher frequency of Th17 cells that persist in the repertoire of $CD5L^{-/-}$ mice. To address whether Th17 cells isolated in vivo also produced more IL-17 on a per cell basis, $ROR\gamma t^+$ ($GFP^+$) effector/memory T cells were sorted from WT and $CD5L^{-/-}$ mice, their cytokine production upon activation ex vivo was analyzed. The $ROR\gamma t.GFP^+$ T cells from the $CD5L^{-/-}$ mice showed much higher production of IL-17 and lower production of IL-10 suggesting that $ROR\gamma t^+$ cells are better IL-17 producers in the absence of CD5L (FIG. 46H).

Figure 47A:
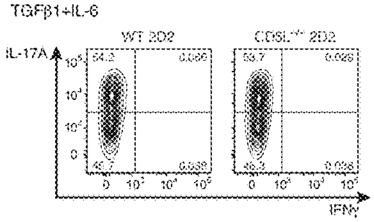
FIG. 47A-47F shows CD5L is a major switch that regulates the pathogenicity of Th17 cells. Naïve WT or CD5L$^{-/-}$ 2D2 T cells were sorted and differentiated with TGFβ1+IL-6 in the presence of irradiated APC (Jager, Dardalhon et al. 2009). Cells were rested and reactivated with plate-bound anti-CD3 and anti-CD28 antibodies for 48 h and intravenously injected into WT host. (A) Representative FACS plot are shown of cytokine profile of 2D2 T cells after differentiation and prior to in vivo transfer. (B) Weight and EAE score of recipient mice; (C) Representative histology of optic nerve (upper two panels) and CNS (lower panel). Panels are Luxol fast blue-hematoxylin and eosin stains. Demyelination is indicated by loss of normal blue staining of myelin in lower panels of CNS. (D) Representative cytokine profile of WT and CD5L$^{-/-}$ 2D2 lymphocytes isolated from CNS at day 27 post transfer. Cells were gated on Va3.2$^+$CD4$^+$. All data are representative of 3 independent mouse experiments. (E) Naïve 2D2 WT or CD5L$^{-/-}$ T cells were sorted and 100,000 cells were transferred into CD45.1 WT host. Recipients were than immunized with MOG/CFA the following day. T cells were isolated from the draining LN on day 10 following immunization and restimulated with PMA/ionomycin as described in FIG. 46. Representative FACS plots are gated on $CD45.2^{+}CD4^{+}$ cells and are of 2 independent experiments each with four mice. (F) Naïve T cells were differentiated with TGFβ1+IL-6 as in FIG. 46E and subject to RNA purification and qPCR. Data are summary of at least three independent mouse experiments.

CD5L is a major switch that regulates pathogenicity of Th17 cells: To study whether loss of CD5L can convert non-pathogenic Th17 cells into pathogenic, disease-inducing Th17 cells, $CD5L^{-/-}$ mice were crossed to 2D2 transgenic mice that express TCRs specific for MOG 35-55/$IA^b$.Naïve 2D2 transgenic T cells carrying CD5L deficiency were differentiated under the non-pathogenic (TGFβ1+IL-6) Th17 condition and then transferred into WT recipients. Prior to transfer, a similar frequency of $IL\text{-}17^+$ T cells was generated from WT and $CD5L^{-/-}$ 2D2 naïve cells (FIG. 47A), consistent with the observation that CD5L does not affect Th17 differentiation of naïve T cells.

Figure 47B:
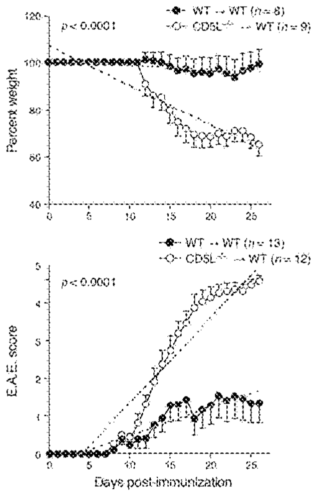
Figure 47C:
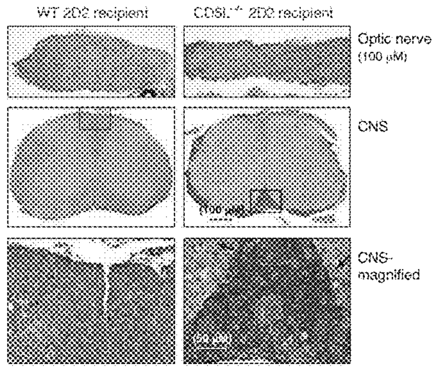
Figure 47D:
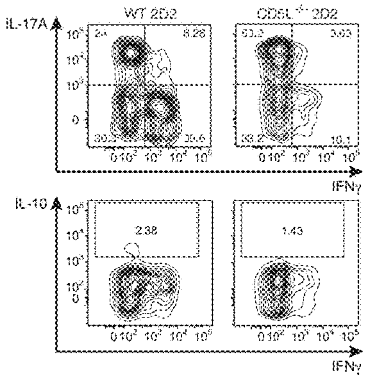
Figure 47E:
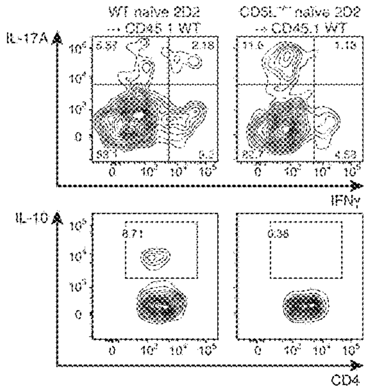

Next, clinical and histological disease progression in the recipients of WT and $CD5L^{-/-}$ 2D2 cells was compared. As expected, many recipients (6/13) of WT 2D2 Th17 cells showed very little to no signs of clinical or histological EAE. Strikingly, all (12/12) $CD5L^{-/-}$ 2D2 recipients developed severe EAE with optic neuritis. Moreover, $CD5L^{-/-}$ 2D2 recipients had significant weight loss and developed more ectopic lymphoid follicle-like structures in the CNS, a hallmark of disease induced by highly pathogenic IL-23-treated Th17 cells (FIG. 47B, C) (Peters, Pitcher et al. 2011). Thus, T cell intrinsic expression of CD5L plays a pivotal role in restraining the pathogenicity of Th17 cells. After adoptive transfer, the T cells were isolated from the CNS of mice undergoing EAE. The 2D2 $CD5L^{-/-}$ T cells retained a much higher frequency of IL-17 producing T cells and a reduced level of IL-10 as compared to the WT 2D2 T cells (FIG. 47D). Upon adoptive transfer, WT 2D2 T cells acquired production of IFNγ in vivo, whereas only a very small proportion of $CD5L^{-/-}$ 2D2 T cells produced IFNγ, suggesting that CD5L may also regulate the stability of Th17 cells. Consistent with this observation, when the naïve WT and $CD5L^{-/-}$ 2D2 T cells were transferred into WT hosts and immunized the mice with $MOG_{35-55}$/CFA without inducing EAE (no pertussis toxin was given), $CD5L^{-/-}$ 2D2 T cells accumulated a higher frequency of $IL\text{-}17A^+$ T cells compared to WT. Strikingly, while the WT T cells expressed IL-10, none of the $CD5L^{-/-}$ 2D2 T cells expressed IL-10 (FIG. 47E).

As IL-23 can suppress the expression of CD5L, and since CD5L functions to restrain Th17 cell pathogenicity, it was reasoned that sustained CD5L expression should antagonize the IL-23 driven pathogenicity of Th17 cells. To test this hypothesis, a retroviral vector for ectopic expression of CD5L in Th17 cells was generated. Naive 2D2 T cells were differentiated under pathogenic differentiation conditions (IL-1β+IL-6+IL-23), transduced with CD5L, transferred into WT recipients and followed for weight loss and the development of clinical EAE. Prior to transfer, 2D2 T cells transduced with CD5L had similar IL-17 expression and increased IL-10 expression (FIG. 51A). After transfer, ectopic expression of CD5L in Th17 cells differentiated under pathogenic conditions reduced their pathogenicity when compared to the WT control in that they led to reduced weight loss in mice and a significant decrease in the induction of EAE (FIG. 51B, C). Furthermore, CD5L overexpressing 2D2 T cells transferred in vivo, lost IL-17 production and most of the transferred cells began producing IFNγ (FIG. 51D). Therefore, CD5L does not regulate Th17 differentiation of naïve T cells, but affects the functional state of Th17 cells in that the loss of CD5L converts non-pathogenic Th17 cells into pathogenic Th17 cells that stably produce IL-17 in vivo and its sustained over-expression in pathogenic Th17 cells converts them to a less pathogenic and less stable phenotype in that these cells lose the expression of IL-17 and acquire an IFNγ producing Th1 phenotype in vivo. These two data sets unequivocally support the role of CD5L as a negative regulator of the functional pathogenic state of Th17 cells.

Figure 47F:
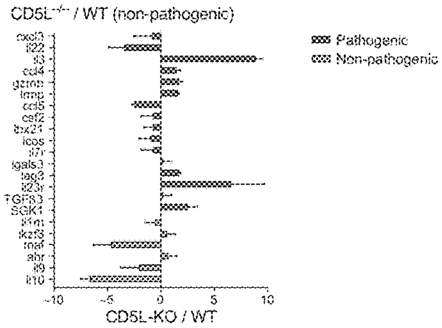

Consistent with these functional findings, CD5L also regulates the expression of the pathogenic/non-pathogenic gene signature previously defined in Th17 cells. To show this, naïve WT and $CD5L^{-/-}$ T cells were differentiated under the non-pathogenic TGFβ1+IL-6 condition and rested them in fresh media without adding any exogenous IL-23 for 48 hours followed by mRNA expression analysis by qPCR. CD5L deficient Th17 cells differentiated under the non-pathogenic condition significantly upregulated several effector molecules of the pathogenic signature, including Il23r, Il3, Ccl4, Gzmb, Lrmp, Lag3 and Sgk1, and downregulated several genes of the non-pathogenic signature, including Il10, Il19 and Maf (FIG. 47F). Several other signature genes, however, were not affected by CD5L, suggesting a more nuanced mechanism.

CD5L shifts the Th17 cell lipidome balance from saturated to unsaturated lipids, modulating Rorγt ligand availability and function: Since CD5L is known to regulate lipid metabolism, by binding to fatty acid synthase in the cytoplasm of adipocytes (Kurokawa, Arai et al. 2010), it was speculated that CD5L may also regulate Th17-cell function by specifically regulating lipid metabolites in T cells. To test this hypothesis, it was analyzed whether lipid metabolism is regulated by CD5L and is associated with the increased pathogenicity observed in Th17 cells from $CD5L^{-/-}$ mice. The lipidome of WT and $CD5L^{-/-}$ Th17 cells differentiated under the non-pathogenic (TGFβ1+IL-6) and pathogenic (TGFβ1+IL-6+IL-23) conditions was profiled. It was possible to resolve and identify around 200 lipid metabolites intracellularly or in the supernatant of differentiating Th17 cells using mass spectrometry and liquid chromatography. Of those metabolites that were differentially expressed between WT and $CD5L^{-/-}$, a striking similarity between the lipidome of $CD5L^{-/-}$ Th17 cells differentiated under the non-pathogenic condition and WT Th17 cells differentiated under the pathogenic condition (FIG. 48A) was observed. Among other metabolic changes, CD5L deficiency significantly increased the levels of saturated lipids (SFA), including metabolites that carry saturated fatty acyl and cholesterol ester (CE) as measured by liquid chromatography and mass spectrometry (FIGS. 48B and 52A), and free cholesterol as shown by microscopy (FIG. 52B). Moreover, the absence of CD5L resulted in a significant reduction in metabolites carrying polyunsaturated fatty acyls (PUFA) (FIG. 48B). Similar increase in CE and reduction in PUFA is observed in the lipidome of Th17 cells differentiated under either of two pathogenic conditions (IL-1β+IL-6+IL-23 and TGFβ3+IL-6+IL-23) compared to non-pathogenic WT cells (FIG. 48C and FIG. 51A). Thus, Th17 cell pathogenicity is associated with a shift in the balance of lipidome saturation as reflected in the increase in saturated lipids and decrease in PUFA metabolites.

Cholesterol metabolites, such as oxysterols, have been previously reported to function as agonistic ligands of Rorγt (Jin, Martynowski et al. 2010, Soroosh, Wu et al. 2014). Previous ChIP-Seq analysis (Xiao, Yosef et al. 2014) suggests that Rorγt binds at several sites in the promoter and intronic regions of Il23r and Il17 (FIG. 48D) and near CNS-9 of Il10, where other transcription factors, such as cMaf, which regulates Il10 expression, also binds. As showed above, CD5L restrains the expression of IL-23R and IL-17 and promotes IL-10 production in $Ror\gamma t^{+}$ Th17 cells, and because CD5L-deficient Th17 cells contain higher cholesterol metabolite and lower PUFA (FIG. 48A,B). Putting these data together, it was hypothesized that CD5L regulates the expression of IL-23R, IL-17 and IL-10 by affecting the binding of Rorγt to these targets, through affecting the SFA-PUFA balance.

To test this hypothesis, it was first assessed if CD5L modulates Rorγt activity by using ChIP-PCR and luciferase reporter assays. Consistent with the hypothesis, ChIP of Rorγt showed significantly higher binding of Rorγt in the Il17 and Il23r region and significantly reduced binding to the Il10 region in CD5L-deficient Th17 cells compared to WT (FIGS. 48D,E and 52C). Consistently, ectopic overexpression of CD5L is sufficient to suppress Rorγt-dependent transcription of Il17 and Il23r promoter luciferase reporters (FIGS. 48F and 52D) and to enhance the transcription of the Il10 reporter in the presence of Rorγt (FIG. 48G).

Next, it was tested whether changing the lipidome balance of WT Th17 cells with the addition of SFA or PUFA can regulate Rorγt binding to genomic regions (FIGS. 48DE and 52C), finding that in the presence of SFA, there is a significant increase in the enrichment of Rorγt-binding to Il17 and Il23r genomic elements, whereas there was a decrease in the binding of Rorγt in the presence of PUFA (FIGS. 48D and 52C). Addition of PUFA also significantly increased the enrichment of Rorγt binding to the Il10 CNS-9 region (FIG. 48E), suggesting that manipulation of the lipid content of Th17 cells can indeed modulate Rorγt DNA binding ability.

Finally, it was reasoned that if CD5L regulates Rorγt transcriptional activity by limiting Rorγt ligand(s), the addition of exogenous agonists of Rorγt would rescue the CD5L induced suppression. Indeed, addition of 7, 27 dihydroxycholesterol, previously shown as an endogenous ligand of Rorγt (Soroosh, Wu et al. 2014), rescued the CD5L-driven suppression of Il17 reporter transcription, suggesting ligand availability partly contributes to the regulation of Rorγt function by CD5L (FIG. 48H). On the other hand, the addition of PUFA decreased Rorγt driven Il17a transcription in control cells, but not in those expressing CD5L (FIG. 48I), suggesting the function of PUFA may depend on the Rorγt ligand. Indeed, while Rorγt can strongly transactivate Il23r enhancer in the presence of an agonistic ligand, the addition of PUFA to the agonist ligand almost completely inhibited Rorγt-mediated Il23r transactivation and enhanced Il10 transactivation (FIG. 48J,K). This observation suggests that PUFA may modulate Rorγt ligand binding and thus affect the ability of Rorγt to transactivate Il23r and Il10. On the other hand, while the addition of SFA by itself has little impact on Rorγt-dependent transcription, it nevertheless modified the function of the oxysterol (FIG. 48J,K). Thus, CD5L regulates the expression of Il23r and Il10, members of the pathogenic/non-pathogenic signature, by shifting lipidome balance and limiting Rorγt ligand availability as well as function.

Figure 49:
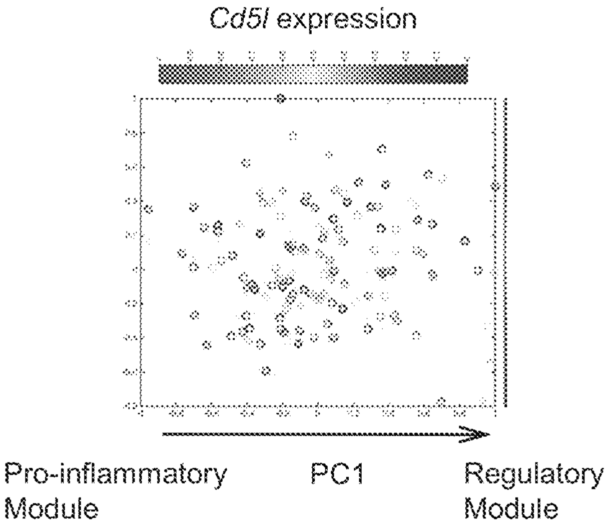
FIG. 49 CD5L expression follows the pro-inflammatory/regulatory module dichotomy across single cells. Shown is a PCA plot (first two PCs) with the cells differentiated under the TGF-β1+IL-6 condition at 48 h, where each cell is colored by an expression ranking score of CD5L (red: high, blue: low) and the first PC is marked by the pro-inflammatory/regulatory module dichotomy.

PUFA and SFA can regulate Th17 cell function and contribute to CD5L-dependent regulation of Th17 cells: As CD5L-deficient Th17 cells differentiated under the non-pathogenic condition have altered balance in lipid saturation, and since PUFA and SFA can modulate Rorγt binding and functional activity, the relevance of fatty acid moieties to Th17 cell function and its contribution to CD5L-driven Th17 cell pathogenicity was analyzed. The effect of adding PUFA and SFA on the generation of Th17 cells was first tested. WT Th17 cells were differentiated with TGFβ1+IL-6 and expanded using IL-23 in fresh media with the presence of either PUFA or SFA. PUFA suppressed the percentage of IL-$17^+$ and IL-23R.$GFP^+$ CD4 T cells (FIG. 49A), suggesting that PUFA can limit Th17 cell function under the pathogenic condition. On the other hand, addition of SFA increased the expression of both IL-17 and IL-23R expression, but this effect was not significant, possibly because the already very high levels of SFA in the pathogenic Th17 cells could not be further altered by the addition of exogenous SFA. This result is consistent with qPCR analysis of Il17 and Il23r expression and further, the effect of PUFA is abolished in $Ror\gamma t^{-/-}$ Th17 cells (FIG. 49B), suggesting the function of PUFA requires Rorγt expression. $CD5L^{-/-}$ Th17 cells differentiated under the non-pathogenic condition are also sensitive to PUFA treatment, resulting in reduced percentage of IL-$17^+$ $CD4^+$ T cells (FIG. 49C).

Next, the contribution of lipid saturation to Th17 cell pathogenicity was studied. It was speculated that if the balance of lipid saturation distinguishes non-pathogenic WT Th17 cells and pathogenic $CD5L^{-/-}$ Th17 cells, the addition of SFA to WT and PUFA to $CD5L^{-/-}$ Th17 cells (TGFβ1+IL-6) can result in reciprocal changes in transcriptional signature relevant to Th17 cell pathogenicity. Therefore (using the Nanostring nCounter) the expression of a 316 gene signature of Th17 cell differentiation and function in SFA- or control-treated WT Th17 cells and in PUFA- or control-treated $CD5L^{-/-}$ Th17 cells differentiated with TGFβ1+IL-6 was analyzed. It was found that PUFA-treated $CD5L^{-/-}$ Th17 cells resemble WT non-pathogenic Th17 cells, and SFA-treated WT non-pathogenic Th17 cells are more similar to $CD5L^{-/-}$ Th17 cells (FIG. 49D). qPCR analysis confirmed that PUFA and SFA reciprocally regulated the expression of key genes in the pathogenicity signatures, including Il10, Il23r, Ccl5, Csf2 and Lag3 (FIG. 49D). (Notably, in some cases PUFA and SFA have the same effects; for example, Il22 expression is increased following treatment by either fatty acid.) Taken together, these observations suggest that the balance of lipid saturation contributes to CD5L-dependent regulation of Th17 cells by regulating the Th17 cell transcriptome.

DISCUSSION: Th17 cells are a T helper cell lineage capable of diverse functions ranging from maintaining gut homeostasis, mounting host defense against pathogens, to inducing autoimmune diseases. How Th17 cells can mediate such diverse and opposing functions remains a critical question to be addressed. This is especially important since anti-IL-17 and Th17-based therapies have been highly efficacious in some autoimmune diseases, but have had no impact in other diseases (Genovese, Van den Bosch et al. 2010, Hueber, Sands et al. 2012, Leonardi, Matheson et al. 2012, Papp, Leonardi et al. 2012, Baeten and Kuchroo 2013, Patel, Lee et al. 2013), even when Th17 cells have been genetically linked to the disease process (Cho 2008, Lees, Barrett et al. 2011). Using single-cell genomics this issue has been addressed and identified novel functional regulators of Th17 cells have been identified.

Here, CD5L is highlighted and investigated as one of the novel regulators that affects the pathogenicity of Th17 cells. It is shown that: (1) CD5L is highly expressed only in non-pathogenic Th17 cells but in them co-varies with a pro-inflammatory module, a pattern consistent with being a negative modulator of pathogenicity; (2) CD5L does not affect Th17 differentiation but affects long-term expansion and the functional phenotype of Th17 cells; (3) CD5L-deficiency converts non-pathogenic Th17 cells into pathogenic Th17 cells; and (4) CD5L regulates lipid metabolism in Th17 cells and alters the balance between SFA and PUFA.

Seemingly paradoxically, CD5L is expressed only in non-pathogenic Th17 cells, but in co-variance with the pro-inflammatory module. This initial observation led us to hypothesize that CD5L is a negative regulator of a non-pathogenic to pathogenic transition, since such negative regulators are often known to co-vary in regulatory networks with the targets they repress, in organisms from yeast. Functional analysis bears out this hypothesis, suggesting that CD5L might indeed be expressed to restrain the pro-inflammatory module in the non-pathogenic Th17 cells. Thus, other genes with this specific pattern—exclusive expression in non-pathogenic cells but in co-variance with the pro-inflammatory module may also be repressors that quench pro-inflammatory effector functions. Thus, depending on the environmental context or trigger, non-pathogenic Th17 cells can be readily converted into pro-inflammatory or pathogenic Th17 cells, by inhibiting the expression of a single gene like CD5L. This is supported by the data, which clearly show that IL-23R signalling can suppress CD5L expression and that the persistent expression of CD5L inhibits the pro-inflammatory function of Th17 cells. In addition to suppressing the pro-inflammatory module, CD5L may also promote the function of the regulatory module, thereby acting as a switch to allow rapid responses to environmental triggers, such that Th17 cells can change their functional phenotype without having to depend on other intermediary pathways. It is also apparent that the expression of CD5L can stabilize the function of non-pathogenic Th17 cells, so that the regulatory module and proinflammatory module could co-exist in a cell population. This observation also highlights the molecular difference between the regulatory module and the proinflammatory module that are co-expressed in non-pathogenic Th17 cells, suggesting that the non-pathogenic Th17 cells that can produce both IL-17 and IL-10 have a unique role in physiological processes. This is consistent with the recent discovery that Th17 cells that can develop in the small intestine in response to gut microbiome (Esplugues, Huber et al. 2011), as well as that Th17 cells that can also co-produce IL-10 and are presumably important for protective immunity against *S. aureus* infection on the mucosal surfaces of the lung (Zielinski, Mele et al.) do not mediate autoimmunity or tissue injury.

Both pathogenic and non-pathogenic Th17 cells are present in the draining lymph nodes but pathogenic Th17 cells appear at the site of tissue inflammation (CNS) and non-pathogenic Th17 cells appear in the gut or other mucosal surfaces, where they promote mucosal barrier function and also maintain tissue homeostasis. This is mirrored in the expression of CD5L, which is highly expressed in Th17 cells in the gut at the steady state, but not in the CNS at the peak of autoimmune tissue inflammation. IL-23, which is present in the CNS during EAE, can suppress CD5L and convert non-pathogenic Th17 cells into pathogenic Th17 cells. At the steady state, it is not known what promotes CD5L expression and non-pathogenicity in the gut. TGFβ is an obvious candidate given the abundance of TGFβ in the intestine and its role in both differentiation of IL-10 producing CD4 T cells in vivo (Maynard, Harrington et al. 2007, Konkel and Chen 2011) and the differentiation of Th17 cells in vitro (Bettelli, Carrier et al. 2006, Veldhoen, Hocking et al. 2006). Specific commensal bacteria (Ivanov, Atarashi et al. 2009, Yang, Torchinsky et al. 2014) and metabolites from microbiota (Arpaia, Campbell et al. 2013) have also been implicated in regulating T cell differentiation. Notably, CD5L is reported as a secreted protein (Miyazaki, Hirokami et al. 1999) and plays a role in recognizing PAMP (Martinez V G et al. 2014). It is possible that, in vivo, CD5L expressed by non-pathogenic Th17 cells in the gut can interact with the microbiota and maintains gut tolerance and a non-pathogenic Th17 phenotype. Therefore, the two functional states of Th17 cells may be highly plastic, and depending on the milieu, either pathogenic or non-pathogenic Th17 cells can be generated by sensing changes in the tissue microenvironment. It is clear, however, the expression of CD5L in non-pathogenic Th17 cells is critical for maintaining the non-pathogenic functional state of Th17 cells and IL-23 rapidly suppresses CD5L, which renders these cells pathogenic. This hypothesis also predicts non-pathogenic Th17 cells can be easily converted into pathogenic Th17 cells by production of IL-23 locally in the gut during inflammatory bowel disease.

How does CD5L regulate the pathogenicity of Th17 cells? In this study, evidence is provided that CD5L can regulate Th17 cell function at least in part by regulating intracellular lipid metabolism in Th17 cells. CD5L was shown to inhibit the de novo synthesis of fatty acid through direct binding to fatty acid synthase (Kurokawa, Arai et al. 2010), although this has not been demonstrated in T cells. It was discovered that in Th17 cells CD5L is not a general inhibitor of fatty acid synthesis, but regulates the balance of PUFA vs. SFA. It is shown that PUFA limits ligand-dependent function for Rorγt, such that in the presence of CD5L or PUFA, Rorγt binding to the Il17a and Il23r is enhanced, along with reduced transactivation of both genes, whereas binding at and expression from the Il10 locus is enhanced. Notably, Rorγt's ability to regulate Il10 expression was not reported previously. Since CD5L does not impact overall Th17 cell differentiation, this suggests a highly nuanced effect of CD5L and lipid balance on Rorγt function, enhancing its binding to and transactivation at some loci, reducing it in others, and likely not affecting its function at other loci, such as those needed for general Th17 cell differentiation. How this is achieved mechanistically remains to be investigated. For example, the regulation of Il10 transcription is complex and depends on diverse transcription factors and epigenetic modifications. In Th17 cells, Stat3 and c-Maf can promote the expression of Il10 (Stumhofer, Silver et al. 2007, Xu, Yang et al. 2009). As Stat3, C-Maf and Rorγt can all bind to the same Il10 enhancer element, it is therefore possible that, depending on the quality and quantity of the available ligands, Rorγt may interact with other transcription factors and regulate Il10 transcription. More generally, this supports a hypothesis where the spectrum of Rorγt ligands depends—at least in part—on the CD5L-regulated PUFA vs. SFA lipid balance in the cell, and where different ligands impact distinct specificity on Rorγt, allowing it to assume a spectrum of functional states, related for example to distinct functional states. Further studies would be required to fully elucidate such a mechanism.

Several metabolic pathways have been associated with Th17 cell differentiation. HIF1α can promote Th17 cell differentiation through direct transactivation of Rorγt (Dang, Barbi et al. 2011, Shi, Wang et al. 2011) and acetyl-coA carboxylase can regulate Th17/Treg balance through the glycolytic and lipogenic pathway (Berod, Friedrich et al. 2014). Both HIF1α and acetyl-coA carboxylase are associated with obesity and mice harbouring mutations in genes that regulate Th17 cell differentiation and function have been shown to acquire an obese phenotype (Winer, Paltser et al. 2009, Ahmed and Gaffen 2010, Jhun, Yoon et al. 2012, Mathews, Wurmbrand et al. 2014). Thus, there appears to be an association between Th17 cell development and obesity. A hallmark of obesity is the accumulation of saturated fat and cholesterol. In this study, evidence is provided that at the cellular level, lipidome saturation can promote Th17 cell function by regulating Rorγt function.

In addition to regulating the pathogenicity of Th17 cells, CD5L deficient Th17 cells appeared to retain a more stable Th17 phenotype in vivo. Th17 cells from CD5L deficient naïve 2D2 T cells differentiated under non-pathogenic conditions remain mostly IL-17$^+$ and IFNγ$^-$ upon transfer into a WT host in contrast to WT 2D2 cells, which attain more IFNγ$^+$ expression. Moreover, transfer of undifferentiated naïve CD5L$^{-/-}$ CD4$^+$ 2D2 T cells resulted in higher frequency of IL-17A$^+$ cells following immunization as compared with WT 2D2 T cells. As CD5L does not regulate Th17 cell differentiation of naïve T cells, this suggests that the Th17 cellular phenotype may be more stable in the absence of CD5L. It is possible that Th17 cell stability is in part dependent on ligand availability. Therefore, sensing of the microenvironment by Th17 cells may change CD5L expression and regulate Rorγt ligand availability, which in turn may affect Th17 phenotype and function.

Thus, by using single cell genomics and computational analysis, CD5L has been identified as a novel repressor of pathogenicity of Th17 cells, highlighting the power of single cell genomics to identify molecular switches that affect Th17 cell functions, otherwise obscured by population-level genomic profiles. CD5L appears to be a molecular switch that does not affect Th17 differentiation per se but one that impacts the function (pathogenic vs. non-pathogenic phenotype) of Th17 cells, potentially by regulating the quality and/or quantity of available Rorγt ligands, allowing a single master regulator to possibly assume multiple functional states. The results connect the lipidome to essential functions of immune cells, opening new avenues for sensitive and specific therapeutic intervention.

REFERENCES

Ahmed, M. and S. L. Gaffen (2010). "IL-17 in obesity and adipogenesis." Cytokine Growth Factor Rev 21(6): 449-453.

Arpaia, N., et al. (2013). "Metabolites produced by commensal bacteria promote peripheral regulatory T-cell generation." Nature 504(7480): 451-455.

Awasthi, A., et al. (2009). "Cutting edge: IL-23 receptor gfp reporter mice reveal distinct populations of IL-17-producing cells." J Immunol 182(10): 5904-5908.

Baeten, D. L. and V. K. Kuchroo (2013). "How Cytokine networks fuel inflammation: Interleukin-17 and a tale of two autoimmune diseases." Nat Med 19(7): 824-825.

Berod, L., et al. (2014). "De novo fatty acid synthesis controls the fate between regulatory T and T helper 17 cells." Nat Med 20(11): 1327-1333.

Bettelli, E., et al. (2006). "Reciprocal developmental pathways for the generation of pathogenic effector TH17 and regulatory T cells." Nature 441(7090): 235-238.

Cho, J. H. (2008). "The genetics and immunopathogenesis of inflammatory bowel disease." Nat Rev Immunol 8(6): 458-466.

Cua, D. J., et al. (2003). "Interleukin-23 rather than interleukin-12 is the critical cytokine for autoimmune inflammation of the brain." Nature 421(6924): 744-748.

Dang, E. V., et al. (2011). "Control of T(H)17/T(reg) balance by hypoxia-inducible factor 1." Cell 146(5): 772-784.

Esplugues, E., et al. (2011). "Control of TH17 cells occurs in the small intestine." Nature 475(7357): 514-518.

Gaffen, S. L., et al. (2011). "IL-17 signaling in host defense against *Candida albicans*." Immunol Res 50(2-3): 181-187.

Genovese, M. C., et al. (2010). "LY2439821, a humanized anti-interleukin-17 monoclonal antibody, in the treatment of patients with rheumatoid arthritis: A phase I randomized, double-blind, placebo-controlled, proof-of-concept study." Arthritis Rheum 62(4): 929-939.

Ghoreschi, K., et al. (2010). "Generation of pathogenic T(H)17 cells in the absence of TGF-beta signalling." Nature 467(7318): 967-971.

Guglani, L. and S. A. Khader (2010). "Th17 cytokines in mucosal immunity and inflammation." Curr Opin HIV AIDS 5(2): 120-127.

Hueber, W., et al. (2012). "Secukinumab, a human anti-IL-17A monoclonal antibody, for moderate to severe Crohn's disease: unexpected results of a randomised, double-blind placebo-controlled trial." Gut 61(12): 1693-1700.

Ivanov, I I, et al. (2009). "Induction of intestinal Th17 cells by segmented filamentous bacteria." Cell 139(3): 485-498.

Jager, A., et al. (2009). "Th1, Th17, and Th9 effector cells induce experimental autoimmune encephalomyelitis with different pathological phenotypes." J Immunol 183(11): 7169-7177.

Jhun, J. Y., et al. (2012). "Obesity aggravates the joint inflammation in a collagen-induced arthritis model through deviation to Th17 differentiation." Exp Mol Med 44(7): 424-431.

Jin, L., et al. (2010). "Structural basis for hydroxycholesterols as natural ligands of orphan nuclear receptor ROR-gamma." Mol Endocrinol 24(5): 923-929.

Kleinewietfeld, M. and D. A. Hafler (2013). "The plasticity of human Treg and Th17 cells and its role in autoimmunity." Semin Immunol 25(4): 305-312.

Konkel, J. E. and W. Chen (2011). "Balancing acts: the role of TGF-beta in the mucosal immune system." Trends Mol Med 17(11): 668-676.

Kurokawa, J., et al. (2010). "Macrophage-derived AIM is endocytosed into adipocytes and decreases lipid droplets via inhibition of fatty acid synthase activity." Cell Metab 11(6): 479-492.

Langrish, C. L., et al. (2005). "IL-23 drives a pathogenic T cell population that induces autoimmune inflammation." J Exp Med 201(2): 233-240.

Lee, Y., et al. "Induction and molecular signature of pathogenic TH17 cells." Nat Immunol 13(10): 991-999.

Lee, Y., et al. (2014). "Unexpected targets and triggers of autoimmunity." J Clin Immunol 34 Suppl 1: S56-60.

Lees, C. W., et al. (2011). "New IBD genetics: common pathways with other diseases." Gut 60(12): 1739-1753.

Leonardi, C., et al. (2012). "Anti-interleukin-17 monoclonal antibody ixekizumab in chronic plaque psoriasis." N Engl J Med 366(13): 1190-1199.

Mathews, J. A., et al. (2014). "Induction of IL-17A Precedes Development of Airway Hyperresponsiveness during Diet-Induced Obesity and Correlates with Complement Factor D." Front Immunol 5: 440.

Maynard, C. L., et al. (2007). "Regulatory T cells expressing interleukin 10 develop from Foxp3+ and Foxp3− precursor cells in the absence of interleukin 10." Nat Immunol 8(9): 931-941.

McGeachy, M. J., et al. (2007). "TGF-beta and IL-6 drive the production of IL-17 and IL-10 by T cells and restrain T(H)-17 cell-mediated pathology." Nat Immunol 8(12): 1390-1397.

McGeachy, M. J., et al. (2009). "The interleukin 23 receptor is essential for the terminal differentiation of interleukin 17-producing effector T helper cells in vivo." Nat Immunol 10(3): 314-324.

Miyazaki, T., et al. (1999). "Increased susceptibility of thymocytes to apoptosis in mice lacking AIM, a novel murine macrophage-derived soluble factor belonging to the scavenger receptor cysteine-rich domain superfamily." J Exp Med 189(2): 413-422.

Papp, K. A., et al. (2012). "Brodalumab, an anti-interleukin-17-receptor antibody for psoriasis." N Engl J Med 366 (13): 1181-1189.

Patel, D. D., et al. (2013). "Effect of IL-17A blockade with secukinumab in autoimmune diseases." Ann Rheum Dis 72 Suppl 2: ii116-123.

Peters, A., et al. (2011). "Th17 cells induce ectopic lymphoid follicles in central nervous system tissue inflammation." Immunity 35(6): 986-996.

Romani, L. (2011). "Immunity to fungal infections." Nat Rev Immunol 11(4): 275-288.

Shi, L. Z., et al. (2011). "HIF1alpha-dependent glycolytic pathway orchestrates a metabolic checkpoint for the differentiation of TH17 and Treg cells." J Exp Med 208(7): 1367-1376.

Soroosh, P., et al. (2014). "Oxysterols are agonist ligands of RORgammat and drive Th17 cell differentiation." Proc Natl Acad Sci USA 111(33): 12163-12168.

Stumhofer, J. S., et al. (2007). "Interleukins 27 and 6 induce STAT3-mediated T cell production of interleukin 10." Nat Immunol 8(12): 1363-1371.

Veldhoen, M., et al. (2006). "TGFbeta in the context of an inflammatory cytokine milieu supports de novo differentiation of IL-17-producing T cells." Immunity 24(2): 179-189.

Winer, S., et al. (2009). "Obesity predisposes to Th17 bias." Eur J Immunol 39(9): 2629-2635.

Xiao, S., et al. (2014). "Small-molecule RORgammat antagonists inhibit T helper 17 cell transcriptional network by divergent mechanisms." Immunity 40(4): 477-489.

Xu, J., et al. (2009). "c-Maf regulates IL-10 expression during Th17 polarization." J Immunol 182(10): 6226-6236.

Yang, Y., et al. (2014). "Focused specificity of intestinal TH17 cells towards commensal bacterial antigens." Nature 510(7503): 152-156.

Zielinski, C. E., et al. "Pathogen-induced human TH17 cells produce IFN-gamma or IL-10 and are regulated by IL-1beta." Nature 484(7395): 514-518.

Example 11

GPR65 Promotes Th17 Differentiation and is Essential for EAE

GPR65, a glycosphingolipid receptor, is co-expressed with the pro-inflammatory module (FIG. 4B), suggesting that it might have a role in promoting pathogenicity. GPR65 is also highly expressed in the in vivo Th17 cells harvested from the CNS that attain a Th1-like effector/memory phenotype (FIG. 2D). Importantly, genetic variations in GPR65 are associated with multiple sclerosis (International Multiple Sclerosis Genetics et al., 2011), ankylosing spondylitis (International Genetics of Ankylosing Spondylitis et al., 2013), inflammatory bowel disease (Jostins et al., 2012), and Crohn's disease (Franke et al., 2010).

The role of GPR65 was tested in Th17 differentiation in vitro and in the development of autoimmunity in vivo. Naïve T-cells isolated from Gpr65$^{-/-}$ mice in vitro were differentiated with TGF-β1+IL-6 (non-pathogenic condition) or with IL-1β+IL-6+IL-23 (pathogenic condition) for 96 hours. In both cases, there was a ~40% reduction of IL-17a positive cells in Gpr65$^{-/-}$ cells compared to their wild type controls as measured by intracellular cytokine staining (ICC) (FIG. 5A). Memory cells from Gpr65$^{-/-}$ mice that were reactivated with IL-23 also showed a ~45% reduction in IL-17a-positive cells compared to wild type. Consistently, an enzyme-linked immunosorbent assay (ELISA) of the supernatant showed a reduced secretion of IL-17a ($p<0.01$) and IL-17f ($p<2.5\times10^{-5}$) (FIG. 5B) and increased IL-10 secretion ($p<0.01$) under pathogenic (IL-1β+IL-6+L-23) differentiation conditions.

To further validate the effect of GPR65 on Th17 function, RNA-seq profiles were measured of a bulk population of Gpr65$^{-/-}$ Th17 cells, differentiated in vitro under TGF-β1+IL-6 for 96 hours. Supporting a role for GPR65 as a driver of pathogenicity of Th17 cells, it was found that genes up-regulated (compared to wild type) in Gpr65$^{-/-}$ cells are significantly enriched ($P<18.5\times10^{-31}$, hypergeometric test) for the genes characterizing the more regulatory cells under TGF-β1+IL-6 (positive PC1, FIG. 4C) and for genes down-regulated in the pathogenicity signature (Lee et al., 2012) ($P<1.4\lambda10^{-4}$, hypergeometric test).

To determine the effect of loss of GPR65 on tissue inflammation and autoimmune disease in vivo, CD4+ lymphocytes and splenocytes derived from Gpr65$^{-/-}$ mice were transferred into RAG-1$^{-/-}$ mice followed by $MOG_{35-55}$ immunization. It was found that in the absence of GPR65-expressing T cells, mice are protected from EAE (FIG. 5D) and far fewer IL-17A and IFN-γ positive cells are recovered from the LN and spleen compared to controls transferred with wild-type cells. Furthermore, in vitro restimulation of the spleen and LN cells from the immunized mice with $MOG_{35-55}$ showed that loss of GPR65 resulted in dramatic reduction of MOG-specific IL-17A or IFN-γ positive cells compared to their wild-type controls (FIG. 5C), suggesting that GPR65 regulates the generation of encephalitogenic T cells in vivo. Taken together, the data strongly validates that GPR65 is a positive regulator of the pathogenic Th17 phenotype, and its loss results in protection from EAE.

REFERENCES

International Multiple Sclerosis Genetics, C., Wellcome Trust Case Control, C., Sawcer, S., Hellenthal, G., Pirinen, M., Spencer, C. C., Patsopoulos, N. A., Moutsianas, L., Dilthey, A., Su, Z., et al. (2011). Genetic risk and a primary role for cell-mediated immune mechanisms in multiple sclerosis. Nature 476, 214-219.

International Genetics of Ankylosing Spondylitis, C., Cortes, A., Hadler, J., Pointon, J. P., Robinson, P. C., Karaderi, T., Leo, P., Cremin, K., Pryce, K., Harris, J., et al. (2013). Identification of multiple risk variants for ankylosing spondylitis through high-density genotyping of immune-related loci. Nature genetics 45, 730-738.

Jostins, L., Ripke, S., Weersma, R. K., Duerr, R. H., McGovern, D. P., Hui, K. Y., Lee, J. C., Schumm, L. P., Sharma, Y., Anderson, C. A., et al. (2012). Host-microbe interactions have shaped the genetic architecture of inflammatory bowel disease. Nature 491, 119-124.

Franke, A., McGovern, D. P., Barrett, J. C., Wang, K., Radford-Smith, G. L., Ahmad, T., Lees, C. W., Balschun, T., Lee, J., Roberts, R., et al. (2010). Genome-wide meta-analysis increases to 71 the number of confirmed Crohn's disease susceptibility loci. Nature genetics 42, 1118-1125.

Lee, Y., Awasthi, A., Yosef, N., Quintana, F. J., Xiao, S., Peters, A., Wu, C., Kleinewietfeld, M., Kunder, S., Hafler, D. A., et al. (2012). Induction and molecular signature of pathogenic TH17 cells. Nature immunology 13, 991-999.

Example 12

MOG-Stimulated Plzp$^{-/-}$ Cells have a Defect in Generating Pathogenic Th17 Cells PLZP (ROG), a transcription factor, is a known repressor of GATA3 (Miaw et al., 2000) (Th2 master regulator), and regulates cytokine expression (Miaw et al., 2000) in T-helper cells. Since Plzp is co-expressed with the pro-inflammatory module, it was hypothesized that it may regulate pathogenicity in Th17 cells. (It was, however, not possible to undertake an EAE experiment since PLZP$^{-/-}$ mice are not available on the EAE-susceptible background.)

While in vitro differentiated Plzp$^{-/-}$ cells produced IL-17A at comparable levels to wild-type, a MOG-driven recall assay revealed that Plzp$^{-/-}$ cells have a defect in IL-17A production that becomes apparent with increasing MOG concentration during restimulation (FIG. 5H). Furthermore, Plzp$^{-/-}$ cells also produced less IL-17A than wild-type cells when reactivated in the presence of IL-23, which acts to expand previously in vivo differentiated Th17 cells. Finally, Plzp$^{-/-}$ T cells secreted less IL-17A, IL-17F (FIG. 5I), IFN-γ, IL-13 and GM-CSF. These observations suggest that PLZP regulates the expression of a wider range of inflammatory cytokines. At 48 hours into the differentiation of Plzp$^{-/-}$ cells, Irf1 (FC=5.1), Il-9 (FC=1.8) and other transcripts of the regulatory module are up regulated compared to WT (Table S10), whereas transcripts from the pro-inflammatory module, such as Ccl-20 (FC=0.38), Tnf (FC=0.10) and Il-17a (FC=0.42), are repressed.

Thus, by single cell genomics and covariance analysis, a number of novel regulators of pathogenicity of Th17 cells that affect development of Th17 cells in vitro and autoimmunity in vivo have been identified.

REFERENCES

Miaw, S. C., Choi, A., Yu, E., Kishikawa, H., and Ho, I. C. (2000). ROG, repressor of GATA, regulates the expression of cytokine genes. Immunity 12, 323-333.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

What is claimed is:

1. A method of modulating T cell balance, the method comprising:

contacting a Th17 cell or a population of T cells comprising Th17 cells with an exogenous T cell modulating agent in an amount sufficient to modify maintenance and/or function of the Th17 cell or population of T cells by altering balance between pathogenic and nonpathogenic Th17 cells as compared to maintenance and/or function of the Th17 cell or population of T cells in the absence of the T cell modulating agent, wherein the T cell modulating agent is a vector encoding for CD5L or a CRISPR-Cas9 system targeting the CD5L gene.

2. The method of claim 1, wherein the T cells are naïve T cells, partially differentiated T cells, differentiated T cells, a combination of naïve T cells and partially differentiated T cells, a combination of naïve T cells and differentiated T cells, a combination of partially differentiated T cells and differentiated T cells, or a combination of naïve T cells, partially differentiated T cells and differentiated T cells.

3. The method of claim 1, wherein the vector encoding for CD5L is a retroviral vector.

4. The method of claim 1, wherein the Th17 cell or the population of T cells is contacted in vitro or ex vivo.

* * * * *

UNITED STATES PATENT AND TRADEMARK OFFICE

CERTIFICATE OF CORRECTION

PATENT NO. : 11,209,440 B2
APPLICATION NO. : 15/245748
DATED : December 28, 2021
INVENTOR(S) : Vijay Kuchroo et al.

It is certified that error appears in the above-identified patent and that said Letters Patent is hereby corrected as shown below:

On the Title Page

Below item (72), "Inventors", in Column 1, Line 9, insert -- (73) Assignees: THE BROAD INSTITUTE, INC., Cambridge, MA (US); THE BRIGHAM AND WOMEN'S HOSPITAL, INC., Boston, MA (US); PRESIDENT AND FELLOWS OF HARVARD COLLEGE, Cambridge, MA (US); MASSACHUSETTS INSTITUTE OF TECHNOLOGY, Cambridge, MA (US) --.

On the page 3, in item (56), in Column 1, under "Other Publications", Line 18, delete "“lnterleukin-2" and insert -- "Interleukin-2 --.

On the page 3, in item (56), in Column 1, under "Other Publications", Line 36, delete "-lnducible" and insert -- -Inducible --.

On the page 4, in item (56), in Column 2, under "Other Publications", Line 13, delete "Th 17" and insert -- Th17 --.

On the page 4, in item (56), in Column 2, under "Other Publications", Line 19, delete "Mature," and insert -- Nature, --.

On the page 4, in item (56), in Column 2, under "Other Publications", Line 39, delete "anti-interieukin" and insert -- anti-interleukin --.

In the Specification

In Column 31, Line 34, delete "$Cd4^{Cre}/RF4^{fl/fl}$" and insert -- $Cd4^{Cre}IRF4^{fl/fl}$ --.

In Column 39, Line 55, delete "IL-" and insert -- IL-17 --.

Signed and Sealed this
Thirteenth Day of February, 2024

Katherine Kelly Vidal
*Director of the United States Patent and Trademark Office*

In Column 41 (TABLE 1), Line 2 (Approx.), below “Signature Genes” insert

--

| | | | |
|---|---|---|---|
| IL17A | IL21R | CCL1 | PSTPIP1 |
| IL7R | BCL3 | CD247 | IER3 |
| IRF4 | DPP4 | PROCR | FZD7 |
| CXCL10 | TGFBR1 | RELA | GLIPR1 |
| IL12RB1 | CD83 | HIF1A | AIM1 |
| TBX21 | RBPJ | PRNP | CD4 |
| ZNF281 | CXCR3 | IL17RA | LMNB1 |
| IL10RA | NOTCH2 | STAT1 | MGLL |
| CXCR4 | CCL4 | LRRFIP1 | LSP1 |
| TNFRSF13B | TAL2 | KLRD1 | GJA1 |
| ACVR1B | IL9 | RUNX1 | LGALS3BP |
| TGIF1 | FAS | ID2 | ARHGEF3 |
| ABCG2 | SPRY1 | STAT5A | BCL2L11 |
| REL | PRF1 | TNFRSF25 | TGM2 |
| ID3 | FASLG | BATF | UBIAD1 |
| ZEB1 | MT2A | KAT2B | MAP3K5 |
| MYD88 | POU2AF1 | NFATC2 | RAB33A |
| EGR2 | IFNG | CD70 | CASP1 |
| AES | PLAC8 | LITAF | FOXP1 |
| PML | IL17F | IL27RA | MTA3 |
| TGFBR3 | DDR1 | IL22 | IFIH1 |
| CCR8 | IL4 | MINA | RASGRP1 |
| ZFP161 | CD28 | XBP1 | XRCC5 |

--.

In Column 57, Line 55, delete “hematopoiesi” and insert -- hematopoiesis --.

In Column 61 (TABLE 10-continued), Line 28 (Approx.), delete “sulforafan,” and insert -- sulforaphane, --.

In Column 62 (TABLE 10-continued), Line 16 (Approx.), delete “trifluoroperazine,” and insert -- trifluoperazine, --.

In Column 62 (TABLE 10-continued), Line 56 (Approx.), delete “T5C22D3” and insert -- TSC22D3 --.

In Column 62 (TABLE 10-continued), Line 59 (Approx.), delete “chloropromazine,” and insert -- chlorpromazine, --.

In Column 63 (TABLE 10-continued), Line 38 (Approx.), delete “sulforafan,” and insert -- sulforaphane, --.

In Column 63 (TABLE 10-continued), Line 64 (Approx.), delete “beta 1,” and insert -- beta1, --.

In Column 64 (TABLE 10-continued), Line 31 (Approx.), delete “rantes,calcium,” and insert -- rantes, calcium, --.

In Column 65 (TABLE 10-continued), Line 18 (Approx.), delete “vegf” and insert -- vegf, --.

In Column 65 (TABLE 10-continued), Line 49 (Approx.), delete “dodecyl sulfate,” and insert -- dodecylsulfate, --.

In Column 69, Line 34, delete “NM’s” and insert -- NIH’s --.

In Column 73, Line 31 (Approx.), delete "RNA guided" and insert -- RNA-guided --.

In Column 76, Line 18, delete "35-45zig-" and insert -- 35-45 zig- --.

In Column 92, Line 42, delete "$Irf4^{-/-}$," and insert -- $Irf4^{fl/fl}$, --.

In Column 106 (TABLE 11-continued), Line 22 (Approx.), delete "complementati" and insert -- complementary --.

In Column 106 (TABLE 11-continued), Line 37 (Approx.), delete "FOX01" and insert -- FOXO1 --.

In Column 173-174 (TABLE S6.2-continued), Line 5 (Approx.), delete "08173" and insert -- 008173 --.

In Column 173-174 (TABLE S6.2-continued), Line 7 (Approx.), delete "08884" and insert -- 008884 --.

In Column 173-174 (TABLE S6.2-continued), Line 9 (Approx.), delete "08884" and insert -- 008884 --.

In Column 173-174 (TABLE S6.2-continued), Line 21 (Approx.), delete "P0U2AF1" and insert -- POU2AF1 --.

In Column 195, Line 49, delete "Addo" and insert -- Addo M M, --.

In Column 200, Line 43, delete "Hi Seq" and insert -- HiSeq --.

In Column 207, Line 44, delete "(IL-1□+" and insert -- (IL-1+ --.

In Column 211, Line 52, delete "polyunsaturated" and insert -- poly-unsaturated --.

In Column 215, Line 9, delete "microenvironment." and insert -- micro-environment. --.

In Column 219, Line 28, delete "(P<1.4λ10–4," and insert -- (P<1.4×10–4, --.